United States Patent
Goldberg et al.

(10) Patent No.: US 12,173,007 B2
(45) Date of Patent: Dec. 24, 2024

(54) IMIDAZOPYRIDAZINE IL-17 INHIBITOR COMPOUNDS

(71) Applicant: Janssen Pharmaceutica NV, Beerse (BE)

(72) Inventors: Steven D. Goldberg, San Diego, CA (US); Dougas C. Behenna, San Juan Capistrano, CA (US); Deane Gordon, San Diego, CA (US); Luke E. Hanna, San Diego, CA (US); Steven A. Loskot, San Diego, CA (US); Stefan McCarver, San Diego, CA (US); Steven P. Meduna, San Diego, CA (US); Timothy B. Rhorer, San Diego, CA (US); Kristen Song, San Diego, CA (US); Alexander E. Valdes, San Diego, CA (US); Xiaohua Xue, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 17/935,360

(22) Filed: Sep. 26, 2022

(65) Prior Publication Data
US 2023/0143050 A1 May 11, 2023

Related U.S. Application Data

(60) Provisional application No. 63/367,546, filed on Jul. 1, 2022, provisional application No. 63/273,422, filed on Oct. 29, 2021, provisional application No. 63/248,566, filed on Sep. 27, 2021.

(51) Int. Cl.
C07D 487/04 (2006.01)

(52) U.S. Cl.
CPC ........ *C07D 487/04* (2013.01); *C07B 2200/05* (2013.01)

(58) Field of Classification Search
CPC ........................ C07D 487/04; C07B 2200/05
See application file for complete search history.

(56) References Cited

U.S. PATENT DOCUMENTS

2022/0402922 A1   12/2022   Goldberg et al.

FOREIGN PATENT DOCUMENTS

| CN | 116143777 | 5/2023 |
|---|---|---|
| WO | 2020146194 A1 | 7/2020 |
| WO | 2020261141 A1 | 12/2020 |
| WO | 2023025783 A1 | 3/2023 |
| WO | 2023049887 A1 | 3/2023 |

OTHER PUBLICATIONS

Branisteanu. Experimental and Therapeutic Medicine 23: 201, 2022, p. 1-13 (Year: 2022).*
Abu El-Asrar A. et al., "Cytokine profiles in aqueous humor of patients with different clinical entities of endogenous uveitis", Clin. Immunol., vol. 139(2), pp. 177-184, 2011.
Adamopoulos, I.E. et al., "Alternative pathways of osteoclastogenesis in inflammatory arthritis", Nat. Rev. Rheumatol., vol. 11, pp. 189-194, 2015.
Amatya, N. et al., "IL-17 Signaling: The Yin and the Yang", Trends in Immunology, vol. 38 No. 5, pp. 310-322, 2017.
Appel, H. et al., "Analysis of IL-17+ cells in facet joints of patients with spondyloarthritis suggests that the innate immute pathway might be of greater relevance than the Th17-mediated adaptive immune response", Arthritis Research & Therapy, vol. 13, Issue 03, 9 pages, 2011.
Baeten, D. et al., "Risankizumab, an IL-23 inhibitor, for ankylosing spondylitis: results of a randomised, double-blind, placebo-controlled, proof-of-concept, dose-finding phase 2 study", Ann Rheum Dis, vol. 77 Issue 09, pp. 1295-1302, 2018.
Blauvelt et al., "The Immunologic Role of IL-17 in Psoriasis and Psoriatic Arthritis Pathogenesis", Clinical Reviews Allergy & Immunology, vol. 55 Issue 03, pp. 379-390, Aug. 14, 2018.
Camargo, LDN et al., "Effects of Anti-IL-17 Inflammation, Remodeling, and Oxidative Stress in an Experimental Model of Asthma Exacerbated by LPS", Frontiers in Immuno., vol. 8, Article 1835, 14 pages, Jan. 2018.
Chakievska, L et al., "IL-17A is functionally relevant and a potential therapeutic target in bullous pemphigoid", Journal of Autoimmunity, vol. 96, pp. 104-112, 2019.
Chakir, J. et al., "Airway remodeling-associated mediators in moderate to severe asthma: Effect of steroids on TGF-β, IL-11, IL-17, and type I and type III collagen expression", J. Allergy Clin Immunol., vol. 111 No. 06, pp. 1293-1298, Jun. 2003.
Chen, X. et al., "Plasma IL-17A Is Increased in New-Onset SLE Patients and Associated with Disease Activity", J. Clin. Immunol., vol. 30(2), pp. 221-225, 2010.
Chen, Y. et al., "The Effects of Th17 Cytokines on the inflammatory Mediator Production and Barrier Function of ARPE-19 Cells", PLoS One, vol. 6 Issue 3, Mar. 2011, 6 pages, e18139. C (Continued)

*Primary Examiner* — Kortney L. Klinkel
*Assistant Examiner* — Richard Grant Peckham
(74) *Attorney, Agent, or Firm* — Guodong Liu

(57) ABSTRACT

The present application discloses compounds having the following formula:

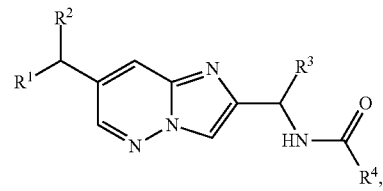

or pharmaceutically acceptable salts thereof, wherein $R^1$, $R^2$, $R^3$, and $R^4$ are defined in the specification, as well as methods of making and using the compounds disclosed herein for treating or ameliorating an IL-17 mediated syndrome, disorder and/or disease.

33 Claims, No Drawings
Specification includes a Sequence Listing.

(56) References Cited

OTHER PUBLICATIONS hristenson, S. et al., "An Airway Epithelial IL-17A Response Signature Identifies A Steroid-Unresponsive COPD Patient Subgroup", J Clin Invest., vol. 129(1), pp. 169-181, Jan. 2019.
ClinicalTrials.gov Identifier: NCT03099538, "Ixekizumab in the Treatment of Bullous Pemphigoid", Last Update Posted May 21, 2020.
ClinicalTrials.gov Identifier: NCT04586920, "A Study of LY3509754 in Healthy Non-Japanese and Japanese Participants", Last Update Posted Dec. 21, 2022.
ClinicalTrials.gov Identifier: NCT04883333, "A Single and Multiple Ascending-dose Trial of LEO 153339 in Healthy Adults", Last Update Posted Jan. 12, 2023.
Cross, et al., "Rules for the Nomenclature of Organic Chemistry", Section E: Stereochemistry, Pure and Appl. Chem., vol. 45, pp. 11-30, 1976.
Deodhar, A. et al., "Three Multicentre, Randomized, Double-Blind, Placebo-Controlled Studies Evaluating the Efficacy and Safety of Ustekinumab in Axial Spondyloarthritis", Arthritis And Rheumatology, vol. 71 No. 02, pp. 258-270, Feb. 2, 2019.
Dick, A. et al., "Secukinumab in the Treatment of Noninfectious Uveitis: Results of Three Randomized, Controlled Clinical Trials", Ophthalmology, vol. 120 No. 4, pp. 777-787, 2013.
Dolff, S. et al., "Disturbed Th1, Th2, Th17 and Treg balance in patients with systemic lupus erythematosus", Clin. Immunol., vol. 141, Issue 2, pp. 197-204, Nov. 2011.
Dos Santos TM. et al., "Effect of Anti-IL-17 Antibody Treatment Alone and in Combination With Rho-Kinase Inhibitor in a Murine Model of Asthma", Frontiers in Physiology, vol. 09, Article 1183, 19 pages, 2018.
Eby, J. et al., "Immune responses in a mouse model of vitiligo with spontaneous epidermal de- and repigmentation", Pigment Cell And Melanoma Res., vol. 27, Issue 6, pp. 1075-1085, 2014.
Gaffen, S., "Structure and signaling in the IL-17 receptor family", Nature Reviews, Immunology, vol. 09, pp. 556-567, Aug. 2009.
Havrdova, E. et al., "Activity of Secukinumab, an anti-IL-17A antibody, on brain lesions in RRMS: results from a randomised, proof-of-concept study", J Neurol., vol. 263, pp. 1287-1295, 2016.
Hawkes et al., "Psoriasis Pathogenesis and the Development of Novel Targeted Immune Therapies", J Allergy Clin Immunol., vol. 140 No. 3, pp. 645-653, 2017.
International Search Report and Written Opinion received for Application No. PCT/US2022/077001, 14 pages, dated Nov. 16, 2022.
Jansen, D. et al., "IL-17-producing CD4+ T cells are increased in early, active axial spondyloarthritis including patients without imaging abnormalities", Rheumatology, vol. 54 Issue 04, pp. 728-735, 2015.
Jawad, S. et al., "Elevated Serum Levels of Interleukin-17A in Uveitis Patients", Ocul. Immunol. Inflamm., vol. 21 No. 6, pp. 434-439, Dec. 2013.
Kelly, G. et al., "Dysregulated Cytokine Expression in Lesional and Nonlesional skin in hidradenitis suppurativa", British Journal of Dermatology, vol. 173 Issue 06, pp. 1431-1439, 2015.
Khattri, S. et al., "Efficacy and Safety of Ustekinumab treatment in adults with moderate-to-severe atopic dermatitis", Experimental Dermatology, vol. 26 Issue 01, pp. 28-35, 2017.
Koga, C. et al., "Possible Pathogenic Role of Th17 Cells for Atopic Dermatitis", Journal of Investigative Dermatology, vol. 128, pp. 2625-2630, 2008.
Koga, T. et al., "The role of IL-17 in systemic lupus erythematosus and its potential as a therapeutic target", Expert Rev. of Clin. Immunol., vol. 15, No. 6, pp. 629-637, 2019.
Kuiper, J. et al., "Intraocular Interleukin-17 and Proinflammatory Cytokines in HLA-A29—Associated Birdshot Chorioretinopathy", American J. Ophthalmol., vol. 152, No. 2, pp. 177-182, 2011.
Le Jan, S. et al., "Innate Immune Cell Produced IL-17 Sustains Inflammation in Bullous Pemphigoid", Journal Of Investigative Dermatology, vol. 134, No. 12, pp. 2908-2917, 2014.
Lemancewicz, D. et al., "The Role of Interleukin-17A and Interleukin-17E in multiple myeloma patients", Med Sci Monit., vol. 18 Issue 01, pp. 54-59, 2012.
Letko, E. et al., "Efficacy and Safety of Intravenous Secukinumab in Noninfectious Uveitis Requiring Steroid-Sparing Immunosuppressive Therapy", Ophthalmology, vol. 122, No. 5, pp. 939-948, 2015.
Lock, C. et al., "Gene-Microarray Analysis of Multiple Sclerosis lesions yields new targets validated in Autoimmune encephalomyelitis", Nature Medicine, vol. 8, No. 5, pp. 500-508, May 2002.
Ma, J. et al., "The imbalance between regulatory and IL-17-secreting CD4+ T cells in lupus patients", Clin. Rheumatol., vol. 29(11), pp. 1251-1258, 2010.
Matusevicius, D. et al., "Interleukin-17 mRNA expression in blood and CSF mononuclear cells is augmented in multiple sclerosis", Multiple Sclerosis, vol. 5, pp. 101-104, 1999.
Mease PJ, et al., "A head-to-head comparison of the efficacy and safety of ixekizumab and adalimumab in biological-naïve patients with active psoriatic arthritis: 24-week results of a randomised, open-label, blinded-assessor trial", Ann Rheum Dis., vol. 79, pp. 123-131, 2020.
Mease, P. et al., "Comparative effectiveness of Secukinumab and Etanercept in Biologic-Naïve Patients with Psoriatic Arthritis assessed by Matching-adjusted indirect Comparison", Eur J Rheumatol, vol. 6 No. 03, pp. 113-121, 2019.
Menon, B. et al., "Interleukin-17+ CD8+ T Cells are Enriched in the Joints of Patients With Psoriatic Arthritis and Correlate With Disease Activity and Joint Damage Progression", Arth Rheumatology, vol. 66, No. 5, pp. 1272-1281, May 2014.
Molet, S. et al., "IL-17 is Increased in Asthmatic Airways and Induces Human Bronchial Fibroblasts to Produce Cytokines", J Allergy Clin Immuno., vol. 108 Issue 03, pp. 430-438, Sep. 2001.
Moran, B. et al., "Hidradenitis Suppurativa Is Characterized by Dysregulation of the Th17:Treg Cell Axis, Which Is Corrected by Anti-TNF Therapy", J of Investigative Dermatology, vol. 137, Issue 11, pp. 2389-2395, 2017.
Mugheddu, C. et al., "Successful Ustekinumab Treatment of Non-infectious uveitis and Concomitant severe psoriatic Arthritis and Plaque Psoriasis", Dermatologic Therapy, vol. 30 Issue 05, pp. 1-4, 2017.
Nash, P. et al., "Secukinumab Versus Adalimumab for Psoriatic Arthritis: Comparative Effectiveness up to 48 Weeks Using a Matching-Adjusted Indirect Comparison", Rheumatol Ther., vol. 05 Issue 01, pp. 99-122, 2018.
Prabhala, R. et al., "Targeting IL-17A in Multiple Myeloma: a potential novel therapeutic approach in myeloma", Leukemia, vol. 30 Issue 02, pp. 379-389, 2016.
Prelog V. et al., "Basic Principles of the CIP-System and Proposals for a Revision", Angew. Chem. Int. Ed. Engl., vol. 21, pp. 567-583, 1982.
Prussick, L. et al., "Open-label, investigator-initiated, single-site exploratory trial evaluating secukinumab, an anti-interleukin-17A monoclonal antibody, for patients with moderate-to-severe hidradenitis suppurativa", Brit. J of Dermatology, vol. 181 Issue 03, pp. 609-611, 2019.
Robert M. et al., "IL 17 in Rheumatoid Arthritis and Precision Medicine: From Synovitis Expression to Circulating Bioactive Levels", Front. Med., vol. 05, Article 364, 10 pages, Jan. 2019.
Schlapbach, C. et al., "Expression of the IL-23/Th17 pathway in lesions of Hidradenitis Suppurativa", J. American Academy Dermatology, vol. 65, No. 04, pp. 790-798, Oct. 1, 2011.
Setiadi AF et al., "IL-17A is Associated with the breakdown of the blood-brain barrier in relapsing-remitting multiple sclerosis", J Neuroimmuno., vol. 332, pp. 147-154, 2019.
Shen, H. et al., "Frequency and Phenotype of Peripheral Blood Th17 Cells in Ankylosing Spondylitis and Rheumatoid Arthritis", Arthritis & Rheumatism, vol. 60, No. 06, pp. 1647-1656, Jun. 2009.
Singh, R. et al., "The role of IL-17 in vitiligo: A review", Autoimmun. Rev., vol. 15, pp. 397-404, 2016.
Stamp, L. et al., "Interleukin-17: the missing link between T-cell accumulation and effector cell actions in rheumatoid arthritis?", Immunol. Cell Biol., vol. 82(1), pp. 1-9, 2004.

(56) References Cited

OTHER PUBLICATIONS

Strand, V. et al., "Matching-adjusted indirect Comparison: secukinumab versus infliximab in biologic-naive patients with psoriatic arthritis", J. of Comparative Effectiveness Research, vol. 8, No. 07, pp. 497-510, 2019.

Thomi, R. et al., "Association of Hidradenitis Suppurativa With T Helper 1/ T Helper 17 Phenotypes—A Semantic Map Analysis", JAMA Derma., vol. 154, No. 05, pp. 592-595, May 2018.

Tzartos, J. et al., "Interleukin-17 Production in Central Nervous System-Infiltrating T Cells and Glial Cells Is Associated with Active Disease in Multiple Sclerosis.", American J. Of Pathology, vol. 172 No. 1, pp. 146-155, Jan. 2008.

Van Vollenhoven, R. et al., "Efficacy and safety of ustekinumab, an IL-12 and IL-23 inhibitor, in patients with active systemic lupus erythematosus: results of a multicentre, double-blind, phase 2, randomised, controlled study", Lancet, vol. 392, pp. 1330-1339, 2018.

Vargas-Rojas M. et al., "Increase of Th17 in peripheral blood of patients with chronic obstructive pulmonary disease", Respir. Med. ,vol. 105(11), pp. 1648-1654, 2011.

Wen, Z. et al., "Interleukin-17 Expression Positively Correlates with Disease Severity of Lupus Nephritis by Increasing Anti-Double-Stranded DNA Antibody Production in a Lupus Model Induced by Activated Lymphocyte Derived DNA", PLoS One., vol. 8, Issue 3, e58161, 10 pages, Mar. 2013.

Wendling, D. et al., "Serum IL-17, BMP-7, and bone turnover markers in patients with ankylosing spondylitis", Joint Bone Spine, vol. 74, pp. 304-305, 2007.

Willing A. et al., "Production of IL-17 by MAIT Cells Is Increased in Multiple Sclerosis and is Associated with IL-7 Receptor Expression", J. Of Immunology, vol. 200, No. 03, pp. 974-982, 2018.

Wong, C. et al., "Elevation of Proinflammatory Cytokine (IL-18, IL-17, IL-12) and Th2 Cytokine (IL-4) Concentrations in patients with systemic lupus Erythematosus", Lupus, vol. 9, pp. 589-593, 2000.

Wong, C. et al., "Hyperproduction of IL-23 and IL-17 in patients with systemic lupus erythematosus: Implications for Th17-mediated inflammation in auto-immunity", Clinical Immunology, vol. 127, pp. 385-393, 2008.

Xing Q. et al., "Elevated Th17 cells are accompanied by FoxP3+ Treg cells decrease in patients with lupus nephritis", Rheumatol. Int., vol. 32, pp. 949-958, 2012.

Zhang L. et al., "Increased Frequencies of Th22 Cells as well as Th17 Cells in the Peripheral Blood of Patients with Ankylosing Spondylitis and Rheumatoid Arthritis", PLoS one, vol. 7, Issue 04, 9 pages, Apr. 2012.

Zhang, R. et al., "Suppression of Experimental Autoimmune Uveoretinitis by Anti-IL-17 Antibody", Curr. Eye Res., vol. 34, No. 4, pp. 297-303, 2009.

Zhao X-F. et al., "Increased serum interleukin 17 in patients with systemic lupus erythematosus", Mol. Biol. Rep., vol. 37, pp. 81-85, 2010.

\* cited by examiner

SEQUENCE LISTING

```
Sequence total quantity: 2
SEQ ID NO: 1           moltype = AA   length = 182
FEATURE                Location/Qualifiers
source                 1..182
                       mol_type = protein
                       organism = synthetic construct
SEQUENCE: 1
MATGSRTSLL LAFGLLCLPW LQEGSAGSDY KDDDDKGSGS GSLEVLFQGP GITIPRNPGC   60
PNSEDKNFPR TVMVNLNIHN RNTNTNPKRS SDYYNRSTSP WNLHRNEDPE RYPSVIWEAQ  120
CRHLGCINAD GNVDYHMNSV PIQQEILVLR REPPHCPNSF RLEKILVSVG CTCVTPIVHH  180
VQ                                                                 182

SEQ ID NO: 2           moltype = AA   length = 323
FEATURE                Location/Qualifiers
source                 1..323
                       mol_type = protein
                       organism = synthetic construct
SEQUENCE: 2
MKFLVNVALV FMVVYISYIY ALRLLDHRAL VCSQPGLNCT VKNSTCLDDS WIHPRNLTPS   60
SPKDLQIQLH FAHTQQGDLF PVAHIEWTLQ TDASILYLEG AELSVLQLNT NERLCVRFEF  120
LSKLRHHHHRR WRFTFSHFVV DPDQEYEVTV HHLPKPIPDG DPNHQSKNFL VPDCEHARMK  180
VTTPCMSSGS LWDPNITVET LEAHQLRVSF TLWNESTHYQ ILLTSFPHME NHSCFEHMHH  240
IPAPRPEEFH QRSNVTLTLR NLKGCCRHQV QIQPFFSSCL NDCLRHSATV SCPEMPDTPE  300
PIPDYMPLWG SGGHHHHHHH HHH                                          323
```

«IMIDAZOPYRIDAZINE IL-17 INHIBITOR COMPOUNDS»

This application claims the benefit of U.S. Provisional Application 63/248,566, filed on Sep. 27, 2021, U.S. Provisional Application 63/273,422, filed on Oct. 29, 2021, and U.S. Provisional Application 63/367,546, filed on Jul. 1, 2022.

REFERENCE TO SEQUENCE LISTING SUBMITTED ELECTRONICALLY

This application contains a sequence listing, which is submitted electronically as an ST.26 XML formatted sequence listing with a file name "PRD4156WOPCT1_SL", creation date of Jul. 1, 2022 and having a size of 3 KB. The sequence listing submitted is part of the specification and is herein incorporated by reference in its entirety.

FIELD

Disclosed herein are imidazopyridazine compounds, and pharmaceutical compositions thereof, which modulate Interleukin-17A. Also disclosed herein is the therapeutic use of such compounds, for example, in treating and/or ameliorating an IL-17A mediated inflammatory syndrome, disorder, or disease.

BACKGROUND

Interleukin-17 ("IL-17"), also known as IL-17A and CTLA-8, is produced mainly by CD4+ Th17 cells, and also by other immune cells such as CD8+ T cells, γδ T cells, NK cells, NKT cells, and innate lymphoid cells (ILCs). IL-17A exists as a homodimer (A/A) or as a heterodimer (A/F) with IL-17F and signals through binding to dimeric receptor complex IL-17RA and IL-17RC. IL-17RA is ubiquitously expressed at particularly high levels by haematopoietic cell types, whereas IL-17RC is preferentially expressed by non-haematopoietic cells (Gaffen, S. Structure and signaling in the IL-17 receptor family. Nat. Rev. Immunol. 2009, 9, 556-567). IL-17A/IL-17R signaling induces de novo gene transcription by triggering NF-kB, C/EBP and MAPK pathways through ACT1-TRAF6-TRAF4. It can also stabilize target mRNA transcripts through the ACT1-TRAF2-TRAF5 complex (Amatya N. et al., Trends in Immunology, 2017, 38, 310-322). IL-17A stimulates the release of inflammatory mediators including IL-6, IL-8, G-CSF, TNF-α, and IL-1β that recruit and activate lymphocytes to the site of injury or inflammation and maintain a proinflammatory state.

As discussed below, preclinical and clinical data have demonstrated the significant pathological role of IL-17A in multiple autoimmune and inflammatory diseases.

For psoriasis: IL-17A mRNA and/or protein levels are elevated in the lesional skin and blood of patients with psoriasis and correlate with disease severity. IL-17A acts directly in synergy with other cytokines (such as TNFα, IFNγ or IL-22) on keratinocytes triggering a self-amplifying inflammatory response in the skin and leading to the formation of psoriatic plaques. The blockade of IL-17A by means of antibodies to IL-17A or IL-23 results in complete reversal of the molecular and clinical disease features in majority of psoriasis patients, manifesting the significant role of IL-17A and IL-17-producing T-cells in the immunopathogenesis of psoriasis. (Hawkes et al., Psoriasis Pathogenesis and the Development of Novel, Targeted Immune Therapies. J Allergy Clin Immunol. 2017, 140(3): 645-653).

The development and approval of IL-17 monoclonal antibodies such as secukinumab, ixekizumab, and brodalumab and their transformational efficacy for psoriasis have demonstrated IL-17A as a valid target for psoriasis treatments. (Blauvelt A. and Chiricozzi A. The Immunologic Role of IL-17 in Psoriasis and Psoriatic Arthritis Pathogenesis. Clin Rev Allergy Immunol. 2018, 55(3):379-390).

For psoriatic arthritis (PsA): IL-17A is mechanistically relevant to PsA through NFκB activation that triggers transcription of several PsA related genes including the receptor activator of nuclear factor κB ligand (RANKL). RANKL triggers the differentiation of osteoclast precursor cells into activated osteoclasts, resulting in bone resorption and subsequently joint deformity in PsA (Adamopoulos I. and Mellins E. Nature reviews Rheumatology 2015; 11:189-94). PsA joint is enriched for IL-17+CD8+ T cells, and the levels of this T cell subset are correlated with disease activity (Menon B. et al., Arthritis & Rheumatology 2014; 66: 1272-81). Synovial fibroblasts isolated from PsA patients also contain elevated IL-17R expression and secrete increased IL-6, CXCL8 and MMP3 ex vivo compared to osteoarthritis patients. Both secukinumab and ixekizumab are FDA approval drugs for PsA. In matching-adjusted indirect comparison analysis, secukinumab was associated with higher ACR 20/50/70 response rates in patients with active PsA than anti-TNFα antibodies (Mease P. et al., Eur. J. Rheumatol. 2019 Jul. 1; 6(3):113-121; Strand V. et al., J. Comp. Eff. Res. 2019, 8(7):497-510; Nash P. et al., Rheumatol. Ther. 2018, 5(1):99-122). In a recent head-to-head study, ixekizumab was superior to adalimumab in achieving simultaneous improvement of joint and skin disease (ACR50 and PASI100) in patients with PsA and inadequate response to conventional synthetic disease-modifying antirheumatic drug (Mease, P. et al. Ann Rheum Diss 2020; 79:123-131). By hitting the same target, IL-17A small molecule inhibitor compounds may exert similar or better efficacy than biologics considering that small molecules generally have better tissue penetration.

For rheumatoid arthritis (RA): IL-17A has been recognized as critical to the progression of rheumatoid arthritis. "The recognition of IL-17 as a pro-inflammatory T cell derived cytokine, and its abundance within rheumatoid joints, provides the strongest candidate mechanism to date through which T cells can capture and localize macrophage effector functions in rheumatoid arthritis" Stamp, L. et al., Immunol. Cell Biol. 2004, 82(1): 1-9. Moreover, in rheumatoid arthritis IL-17A acts locally on synoviocytes and osteoblasts contributing to synovitis and joint destruction. Robert and Miossec have proposed the use of synovial biopsies and/or biomarkers to precisely identify patients that would respond to IL-17A inhibition. Their work concludes that IL-17 inhibitors should now be considered in the development of precision medicine in RA. (Robert M. and Miossec P., Front. Med., 2019, 5:364).

For Ankylosing Spondylitis (AS): Various studies have reported elevated IL-17A and Th17 and other cells producing IL-17 in AS blood samples (Wendling D. et al., Joint Bone Spine. 2007; 74:304-305; Shen H. et al., Arthritis Rheum. 2009; 60(6):1647-56; Zhang L. et al., PLoS One. 2012; 7(4):e31000; Jansen D. et al., Rheumatology (Oxford). 2015 April; 54(4): 728-735). In situ analysis of AS spine has revealed increased IL-17A-producing cells in bone of facet (zygapophyseal) joints (Appel H. et al., Arthritis Res. Ther. 2011; 13(3):R95). Two advanced IL-17A neutralizing antibodies, secukinumab, approved by FDA for AS, and ixekizumab, have demonstrated efficacy over placebo even in anti-TNF inadequate responders. In contrast, anti- IL-23 p40 and p19 biologics failed to demonstrate beneficial effect (Deodhar A. et al., Arthritis Rheumatol. 2019, 71(2): 258-270; BaetenD. et al., Ann. Rheum. Dis. 2018, 77(9): 1295-1302), indicating the differential underling mechanism along IL-23/IL-17 pathway in AS and providing a strong evidence to support continuing developing IL-17A inhibitors.

For hidradenitis suppurativa (HS): Increased IL-17 and IL-17-producing T helper cells in the skin lesions of HS patients were reported and molecular proteomics and gene expression data indicate that the IL-23/Th17 pathway is upregulated in HS lesions (Schlapbach C. et al., J. Am. Acad. Dermatol. 2011; 65(4):790; Kelly G. et al., British J. Dermatol. 2015 December; 173(6):1431-9; Moran B. et al., J. Invest. Dermatol. 2017; 137(11):2389; Thomi R. et al., JAMA Dermatol. 2018; 154(5):592). Seven of nine (78%) patients with moderate-to-severe HS achieved HiSCR in an open-label pilot-trial with Secukinumab (Prussick L. et al., British J. Dermatol. 2019 September; 181(3):609-611), and more clinical trials with anti-IL-17 mAbs in HS are on-going.

For bullous pemphigoid (BP): IL-17 is elevated in the blister fluid and perilesional skin of BP patients. (Le Jan S. et al., J. Invest. Dermatol. 2014; 134 (12):2908-2917; Chakievska L. J Autoimmun. 2019, 96:104-112). Exome sequencing of BP patients revealed mutations in twelve IL-17-related genes in one third of patients, providing the genetic link between IL-17 pathway and BP (Chakievska L. J Autoimmun. 2019, 96:104-112). In experimental murine BP, IL-17A-/- mice are protected, and anti-IL-17A treatment significantly reduced skin lesions in wild type (Chakievska L. J Autoimmun. 2019, 96:104-112). Ixekizumab Phase 2 of treatment naive and refractory BP patients is on-going (NCT03099538).

For atopic dermatitis (AD): IL-17 was found to be elevated in peripheral blood and lesions in AD patients and Th17 cells infiltrated more markedly in acute than chronic lesions, suggesting its role in acute phase of AD (Koga C. et al., J. Invest. Dermatol. 2008, 128, 2625-2630). Molecular profile analysis from ustekinumab Phase II suggest likely contribution of IL-23/Th17/IL-17 pathway in AD (Khattri S. et al., Exp. Dermatol. 2017 January; 26(1):28-35).

For vitiligo: Many studies in vitiligo patients have demonstrated an increased frequency of Th17 cells and higher levels of IL-17 in both circulation and lesions that positively correlates with disease duration, extent, and activity (Singh R. et al., Autoimmun. Rev 2016, April; 15(4):397-404). Mouse studies demonstrated that depigmentation correlates with greater IL-17 expression/secretion, which modulates vitiligo development (Eby J. et al., Pigment Cell & Melanoma Res. 2014, November; 27(6):1075-85).

For multiple sclerosis (MS): IL-17 expression is increased in PBMCs, cerebrospinal fluid (CSF) as well as in brain lesions and cells from MS patients (Lock, C. et al., Nat. Med. 2002, 8: 500-508; Matusevicius, D. et al., Mult. Scler. 1999, 5: 101-104; Tzartos, J. et al., Am. J. Pathol. 2008, 172: 146-155). IL-17-producing T cells are enriched in active MS lesions (Tzartos, J. et al., Am. J. Pathol. 2008, 172: 146-155; Willing A. et al., J. Immunol. 2018, 200(3):974-982). IL-17A levels were elevated in the CSF of relapsing-remitting MS (RRMS) patients and correlated with the CSF/serum albumin quotient, a measure of blood-brain barrier (BBB) dysfunction, together with in vitro data that IL-17A in combination with IL-6 reduced the expression of tight junction-associated genes and disrupted monolayer integrity in a BBB cell line, highlighting the potential importance of targeting IL-17A in preserving BBB integrity in RRMS (Setiadi A F et al., J Neuroimmunol. 2019, 332:147-154). Secukinumab yielded promising first results in a proof-of-concept study in MS patients (Havrdovi, E. et al., J. Neurol. 2016, 263: 1287-1295).

For Asthma: IL-17 expression is increased in the lung, sputum, bronchoalveolar lavage fluid, and sera in patients with asthma, and the severity of airway hyperresponsiveness is positively correlated with IL-17 expression levels. (Chakir J. et al., J. Allergy Clin. Immunol. 2003,111(6):1293-8). IL-17 was reported to be increased in asthmatic airways and induce human bronchial fibroblasts to produce cytokines (Molet S. et al., J. Allergy Clin. Immunol. 2001, 108(3): 430-8). Anti-IL-17 antibody modulates airway responsiveness, inflammation, tissue remodeling, and oxidative stress in chronic mouse asthma models (Camargo LdN. et al., Front Immunol. 2018; 8:1835; dos Santos T. et al., Front. Physiol. 2018, 9:1183).

For Chronic Obstructive Pulmonary Disease (COPD): An increase in Th17 cells was observed in patients with COPD compared with current smokers without COPD and healthy subjects, and inverse correlations were found between Th17 cells with lung function (Vargas-Rojas M. et al., Respir. Med. 2011 November; 105(11):1648-54). In three recent human COPD studies, gene expression profile in bronchial epithelia showed that higher IL-17 signature expression is associated with a lack of response to inhaled corticosteroid, suggesting that there is a COPD subgroup that may benefit from IL-17 inhibitor therapy (Christenson S. et al., J. Clin. Invest. 2019; 129(1):169-181).

For Uveitis: IL-17 promotes the release of inflammatory mediators from retinal pigment epithelium cell line, disrupting the retinal pigment epithelium barrier function (Chen Y. et al., PLoS One. 2011; 6:e18139). IL-17 levels were elevated in the serum or aqueous humor of uveitis patients (El-Asrar A. et al., Clin. Immunol. 2011; 139(2):177-84; Jawad S. et al., Ocul. Immunol. Inflamm. 2013; 21(6):434-9; Kuiper J. et al., Am. J. Ophthalmol. 2011; 152(2):177-182). Anti-IL-17 antibody delayed the onset of ocular inflammation and markedly inhibited the development of experimental autoimmune uveitis in rats (Zhang R. et al., Curr. Eye Res. 2009 April; 34(4):297-303). The analysis of secondary efficacy data from subcutaneous (sc) secukinumab phase 3 trials in uveitis suggested a beneficial effect of secukinumab in reducing the use of concomitant immunosuppressive medication (Dick A. et al., Ophthalmology 2013; 120(4): 777-87). Later study of intravenous secukinumab in uveitis demonstrated greater efficacy than sc dosing, suggesting requiring optimal exposure for efficacy and confirming the therapeutic potential of IL-17A inhibition (Letko E. et al., Ophthalmology 2015, 122(5), 939-948). Ustekinumab that blocks IL-23/IL-17 pathway was also reported to successfully treat a noninfectious uveitis patient who had severe concomitant psoriasis and PsA and failed to respond to conventional immune suppressants (Mugheddu C. et al., Dermatol. Ther. 2017 September; 30(5); e12527).

For multiple myeloma (MM): IL-17A serum levels were significantly higher in MM patients and also in patients with advanced stage compared with healthy subjects (Lemancewicz D. et al., Med. Sci. Monit. 2012; 18(1): BR54-BR59). Administration of secukinumab in the SCIDhu model of human myeloma weekly for 4 weeks after the first detection of tumor in mice led to a significant inhibition of tumor growth and reduced bone damage compared to isotype control mice (Prabhala R. et al., Leukemia. 2016 February; 30(2): 379-389).

For systemic lupus erythematosus (SLE): Increased serum or plasma levels of IL-17, expansion of IL-17- producing T cells in the peripheral blood, and infiltration of Th17 cells in target organs like the kidneys was observed in SLE patients (Wong C. et al., Lupus. 2000; 9(8):589-593; Wong C. et al., Clinical Immunology. 2008; 127(3):385-393; Zhao X-F. et al., Mol. Biol. Rep. 2010 January; 37(1):81-5; Chen X. et al., J. Clin. Immunol. 2010 March; 30(2):221-5; Xing Q. et al., Rheumatol. Int. 2012 April; 32(4):949-58). Imbalance between Th17 cells and regulatory T (Treg) cells has been observed in SLE patients including quiescent stage (Ma J. et al., Clin. Rheumatol. 2010; 29(11):1251-1258; Dolff S. et al., Clin. Immunol. 2011, 141(2):197-204). Overexpression of IL-17A using adenovirus enhanced the severity of lupus nephritis, while blockade of IL-17A using neutralizing antibody resulted in decreased severity of lupus nephritis (Wen, Z. et al., PLoS One. 2013, 8: e58161). In a phase 2 study, ustekinumab, an anti-IL-12/23 p40 monoclonal antibody blocking IL-23/IL-17 pathway, has demonstrated efficacy in SLE patients (van Vollenhoven R. et al., Lancet 2018; 392: 1330-39). Human expression studies, animal models, and clinical trials indicate that IL-17 blockade may become a promising therapeutic strategy for SLE (Koga T. et al., Expert Rev. Clin. Immunol. 2019, 15 (6) 629-637).

In summary, animal and human studies have shown that IL-17A plays crucial role in pathogenesis of the multiple diseases and/or conditions discussed above. The significance of targeting IL-17A has been demonstrated by the transformational efficacy of injectable IL-17A neutralizing antibodies in patients.

Despite the advances achieved with injectable IL-17A antagonist antibodies, there is a long-felt need for the development of an oral small molecule IL-17A inhibitor as it may broaden treatment options for many patients without access to biologics. In addition, a safe and efficacious small molecule IL-17A inhibitor may offer significant benefits to patients over the injectable IL-17A neutralizing antibodies such as convenient dosing regimens and cost savings, which in turn may provide effective long-term disease management.

However, the development of an oral small molecule treatment has remained challenging. For example, no oral small molecule IL-17A inhibitor has progressed into late-stage clinical trials yet, and only two oral small molecule IL-17A inhibitors have progressed into phase I clinical trials (NCT04586920 and NCT04883333) as of Sep. 28, 2021. Additionally, as of December 2021, one of these clinical trials (NCT04586920) was suspended due to safety review. Accordingly, there is a need for new small molecule IL-17A modulators (e.g., inhibitors).

SUMMARY

The present application discloses a compound of Formula I:

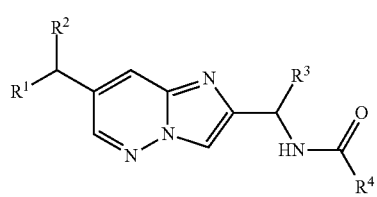

(I)

or a pharmaceutically acceptable salt thereof, wherein $R^1$, $R^2$, $R^3$, and $R^4$ are as defined herein.

The present application also discloses a pharmaceutical composition comprising a compound of Formula I, or a pharmaceutically acceptable salt thereof, and a pharmaceutically acceptable carrier.

The present application also discloses a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof. In some embodiments, the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigoid, atopic dermatitis, vitiligo, multiple sclerosis, asthma, uveitis, chronic obstructive pulmonary disorder, multiple myeloma, and systemic lupus erythematosus.

DETAILED DESCRIPTION

Definitions

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein.

It must be noted that as used herein and in the appended claims, the singular forms "a," "an," and "the" include plural reference unless the context clearly dictates otherwise.

In an attempt to help the reader of the application, the description has been separated in various paragraphs or sections, or is directed to various embodiments of the application. These separations should not be considered as disconnecting the substance of a paragraph or section or embodiments from the substance of another paragraph or section or embodiments. To the contrary, one skilled in the art will understand that the description has broad application and encompasses all the combinations of the various sections, paragraphs and sentences that can be contemplated. The discussion of any embodiment is meant only to be exemplary and is not intended to suggest that the scope of the disclosure, including the claims, is limited to these examples.

The term "administering" with respect to the methods of the invention, means a method for therapeutically or prophylactically preventing, treating or ameliorating a syndrome, disorder or disease as described herein by using a compound of the disclosure, or pharmaceutically acceptable salt thereof, composition thereof, or medicament thereof. Such methods include administering a therapeutically effective amount of a compound of the disclosure, or pharmaceutically acceptable salt thereof, composition thereof, or medicament thereof, at different times during the course of a therapy or concurrently or sequentially as a combination therapy.

The term "subject" refers to a patient, which may be an animal, preferably a mammal, most preferably a human, whom will be or has been treated by a method according to an embodiment of the application. Examples of mammals include, but are not limited to, cows, horses, sheep, pigs, cats, dogs, mice, rats, rabbits, guinea pigs, non-human primates (NHPs) such as monkeys or apes, humans, etc., more preferably a human.

The term "therapeutically effective amount" or "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, "IL-17" or "IL-17A" refers to interleukin 17A. It is also named IL17, CTLA8, CTLA-8. Interleukin 17A is a pro-inflammatory cytokine. This cytokine is produced by a group of immune cells in response to their stimulation. An exemplary amino acid sequence of human IL-17 is represented in GenBank Accession No. NP_002181.1, which can be encoded by a nucleic acid sequence such as that of GenBank Accession No. NM_002190.3.

The term "modulator" as used herein refers to any agents or molecules that can bind to IL-17, including small molecule compounds.

"Active moiety" refers to a molecule or ion responsible for a physiological or pharmacological action. A compound of formula (I), as exemplified in the Examples and also described herein, is an active moiety.

As used herein, the term "composition" is intended to encompass a product comprising the specified ingredients in the specified amounts, as well as any product which results, directly or indirectly, from combinations of the specified ingredients in the specified amounts.

As used herein, the term "treat," "treating," or "treatment" of any disease, condition, syndrome or disorder refers, in one embodiment, to ameliorating the disease, condition, syndrome or disorder (i.e., slowing or arresting or reducing the development of the disease or at least one of the clinical symptoms thereof). In another embodiment, "treat," "treating,", or "treatment" refers to alleviating or ameliorating at least one physiological or biochemical parameter associated with or causative of the disease, condition, syndrome or disorder, including those which may not be discernible by the patient. In a further embodiment, "treat," "treating," or "treatment" refers to modulating the disease, condition, syndrome or disorder either physically (e.g. stabilization of a discernible symptom), physiologically, (e.g. stabilization of a physical parameter), or both. In yet another embodiment, "treat," "treating," or "treatment" refers to preventing or delaying the onset or development or progression of the disease, condition, syndrome or disorder.

As used herein, the term "QD" means once daily.

As used herein, the term "BID" means twice daily.

The term "alkyl" is a straight or branched saturated hydrocarbon. For example, an alkyl group can have 1 to 12 carbon atoms (i.e., ($C_1$-$C_{12}$)alkyl) or 1 to 6 carbon atoms (i.e., ($C_1$-$C_6$)alkyl). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), iso-propyl (i-Pr, i-propyl, —$CH(CH_3)_2$), 1-butyl (n-bu, n-butyl, —$CH_2CH_2CH_2CH_3$), 2-butyl (s-bu, s-butyl, —$CH(CH_3)CH_2CH_3$), tert-butyl (t-bu, t-butyl, —$CH(CH_3)_3$), 1-pentyl (n-pentyl, —$CH_2CH_2CH_2CH_2CH_3$), 2-pentyl (—$CH(CH_3)CH_2CH_2CH_3$), neopentyl ($CH_2C(CH_3)_3$), 1-hexyl (—$CH_2CH_2CH_2CH_2CH_2CH_3$), 2-hexyl (—$CH(CH_3)CH_2CH_2CH_2CH_3$), heptyl (—$(CH_2)_6CH_3$), octyl (—$(CH_2)_7CH_3$), 2,2,4-trimethylpentyl (—$CH_2C(CH_3)_2CH_2CH(CH_3)_2$), nonyl (—$(CH_2)_8CH_3$), decyl (—$(CH_2)_9CH_3$), undecyl (—$(CH_2)_{10}CH_3$), and dodecyl (—$(CH_2)_{11}CH_3$). Any alkyl group may be unsubstituted or substituted.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "cycloalkyl" refers to a saturated or partially unsaturated all carbon ring system having 3 to 8 carbon atoms (i.e., $C_{(3-8)}$cycloalkyl), and preferably 3 to 6 carbon atoms (i.e., $C_{(3-6)}$cycloalkyl), wherein the cycloalkyl ring system has a single ring or multiple rings in a spirocyclic or bicyclic form. Exemplary cycloalkyls include, but are not limited to, cyclopropyl, cyclobutyl, cyclopentyl, cyclohexyl, cycloheptyl, and cyclooctyl. Unless otherwise stated specifically in the specification, a cycloalkyl group may be unsubstituted or substituted. Some cycloalkyl groups may exist as spirocycloalkyls, wherein two cycloalkyl rings are fused through a single carbon atom; for example and without limitation, an example of a spiropentyl group is

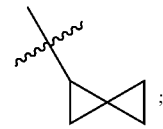 [SMILES: *C1CC12CC2]

for example and without limitation, examples of spirohexyl groups include

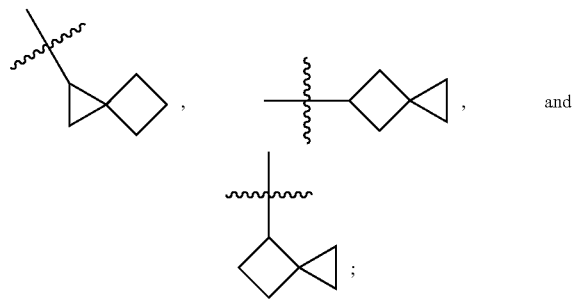

for example and without limitation examples of cycloheptyl groups include

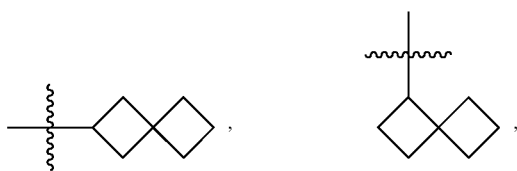

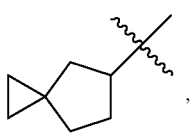 and 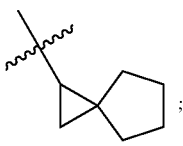;

for example and without limitation examples of cyclooctyl groups include

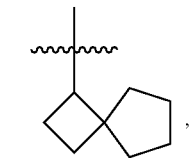, 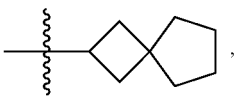,

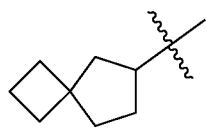, 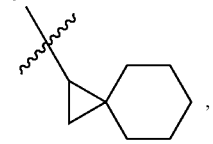,

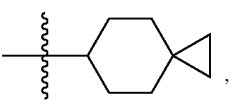, and .

Unless otherwise stated specifically in the specification, a spirocycloalkyl group may be unsubstituted or substituted. Bicyclic cycloalkyl ring systems also include

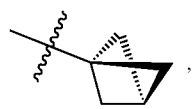, , or

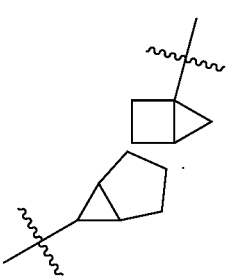.

The term "heterocycle" or "heterocyclyl" refers to a saturated or partially unsaturated ring system that has at least one atom other than carbon in the ring system, wherein the atom is selected from the group consisting of oxygen, nitrogen and sulfur. The heterocyclyl group may, for example, consist of a single ring or multiple rings (e.g., in the form of a spirocyclic or bicyclic ring system). Exemplary heterocycles include, but are not limited to oxetanyl, aziridinyl, azetidinyl, pyrrolidinyl, piperidinyl, piperazinyl, morpholinyl, tetrahydropyranyl, tetrahydrofuranyl, and thiomorpholinyl.

The term "heteroaryl" refers to a single aromatic ring that has at least one atom other than carbon in the ring, wherein the atom is selected from the group consisting of oxygen, nitrogen and sulfur. The term "heteroaryl" includes single aromatic rings of from 1 to 6 carbon atoms and 1 to 4 heteroatoms selected from the group consisting of oxygen, nitrogen and sulfur. Exemplary heteroaryl ring systems include but are not limited to pyridinyl, pyrimidinyl, pyrazinyl, pyridazinyl, pyrimidinyl, pyrazolyl, oxazolyl, oxadiazolyl, isoxazolyl, triazolyl, imidazolyl, tetrazolyl, thienyl, thiazolyl, isothiazolyl, thiadiazolyl, or furyl.

The term "halogen" or "halo" refers to bromo (—Br), chloro (—Cl), fluoro (—F) or iodo (—I).

Where the compounds disclosed herein have at least one stereocenter, they may accordingly exist as enantiomers or diastereomers. It is to be understood that all such isomers and mixtures thereof are encompassed within the scope of the present invention.

"Diastereoisomers" are stereoisomers that have at least two asymmetric atoms, but which are not mirror images of each other.

"Enantiomers" are a pair of stereoisomers that are non-superimposable mirror images of each other. A "racemic" mixture is a 1:1 mixture of a pair of enantiomers. A "scalemic" mixture of enantiomers is mixture of enantiomers at a ratio other than 1:1.

Where the processes for the preparation of the compounds according to the invention give rise to mixture of stereoisomers, these isomers may be separated by conventional techniques such as preparative chromatography. The compounds may be prepared in racemic form, a scalemic mixture, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral column vial HPLC or SFC. In some instances rotamers of compounds may exist which are observable by $^1$H NMR leading to complex multiplets and peak integration in the $^1$H NMR spectrum.

The absolute stereochemistry is specified according to the Cahn-Ingold-Prelog R-S system. Chiral centers, of which the absolute configurations are known, are labelled by prefixes R and S, assigned by the standard sequence-rule procedure, and preceded when necessary by the appropriate locants (*Pure & Appl. Chem.* 45, 1976, 11-30). Certain pairs of enantiomers and diastereomers are presented together in the Examples. These enantiomers/diastereomers may be designated in the following synthetic method and characterized as enantiomer 1 or enantiomer 2 (or, alternately, diastereomer 1 or diastereomer 2). The presentation of stereoisomers in this manner conveys the separate preparation or isolation of the compounds as pure single enantiomers or diastereomers at the identified stereocenter(s). However, unless otherwise specified, when a pure single enantiomer (or diastereomer) is presented together with the corresponding pure single enantiomer (or diastereomer) in the Examples of the present disclosure, the order in which the chemical structures/IUPAC names are presented do not necessarily correspond to the order in which the Example numbers are listed. By way of example, where R and S enantiomers of a compound are presented side-by-side under the header "Example X and Example Y," then Example X may be either the R enantiomer or the S enantiomer, and Example Y is the opposite enantiomer, regardless of the order in which the IUPAC names or chemical structures of the compounds are presented, unless otherwise specified in the method and characterization that follows.

Certain examples contain chemical structures that are depicted or labelled as an (R*) or (S*). When (R*) or (S*) is used in the name of a compound or in the chemical representation of the compound, it is intended to convey that the compound is a pure single isomer at that stereocenter; however, absolute configuration of that stereocenter has not been established. Thus, a compound designated as (R*) refers to a compound that is a pure single isomer at that stereocenter with an absolute configuration of either (R) or (S), and a compound designated as (S*) refers to a compound that is a pure single isomer at that stereocenter with an absolute configuration of either (R) or (S). For example, 4-cyclopropyl-N—((S)-(4,4-difluorocyclohexyl)(7-(((R*)-5-fluoro-5-methyl-2-oxotetrahydropyrimidin-1(2H)-yl)methyl)imidazo[1,2-b]pyridazin-2-yl)methyl)-1,2,5-oxadiazole-3-carboxamide:

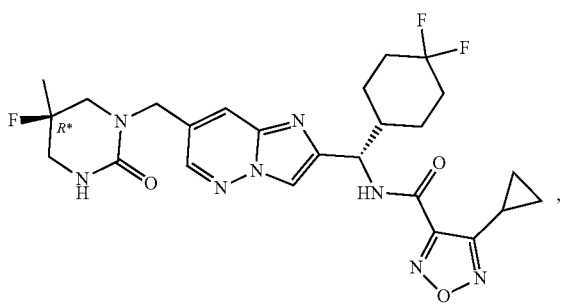 [SMILES: C[C@@]1(F)CNC(=O)N(Cc2cnn3cc([C@@H](NC(=O)c4nonc4C4CC4)C4CCC(F)(F)CC4)nc3c2)C1]

refers to a compound that is either:

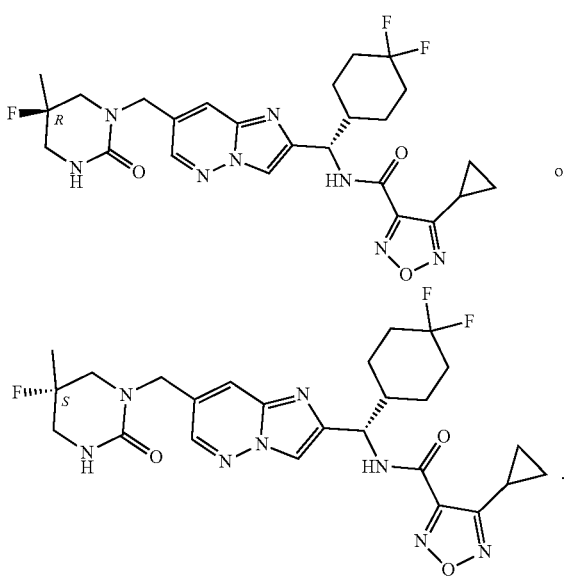

Pseudoasymmetric stereogenic centers are treated in the same way as chiral centers, but are given lower-case symbols, r or s (*Angew. Chem. Int. Ed. Engl.* 1982, 21, 567-583).

During any of the processes for preparation of the compounds disclosed herein, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

Furthermore, it is intended that within the scope of the present invention, any element, in particular when mentioned in relation to a compound of the disclosure, or pharmaceutically acceptable salt thereof, shall comprise all isotopes and isotopic mixtures of said element, either naturally occurring or synthetically produced, either with natural abundance or in an isotopically enriched form. For example, a reference to hydrogen includes within its scope $^1H$, $^2H$ (i.e., deuterium or D), and $^3H$ (i.e., tritium or T). In some embodiments, the compounds described herein include a $^2H$ (i.e., deuterium) isotope. By way of example, the group denoted —$C_{(1-6)}$alkyl includes not only —$CH_3$, but also $CD_3$; not only $CH_2CH_3$, but also $CD_2CD_3$, etc. Similarly, references to carbon and oxygen include within their scope respectively $^{12}C$, $^{13}C$ and $^{14}C$ and $^{15}O$ and $^{16}O$ and $^{17}O$ and $^{18}O$. The isotopes may be radioactive or non-radioactive. Radiolabelled compounds of the disclosure may include a radioactive isotope selected from the group comprising $^3H$, $^{11}C$, $^{18}F$, $^{35}S$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Compounds of the Disclosure

The present application discloses a compound of Formula I:

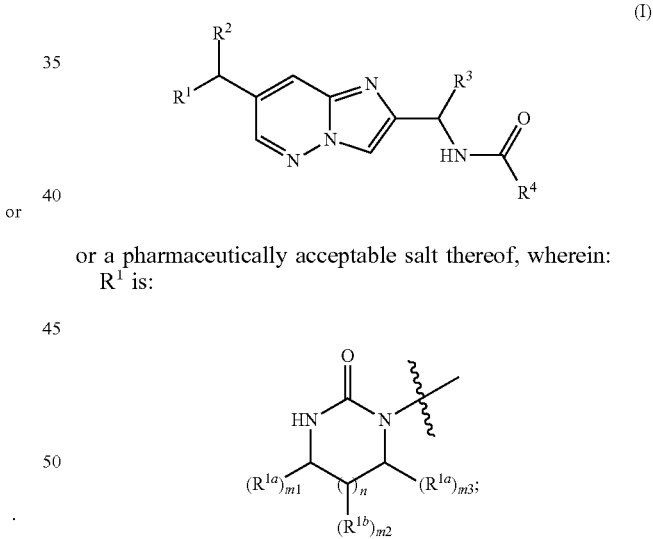

(I)

or a pharmaceutically acceptable salt thereof, wherein:
R$^1$ is:

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms, or when m1 is 2, two geminal $R^{1a}$ groups together with the carbon atom to which they are attached form a spiro $C_{(3-5)}$cycloalkyl;

$R^{1b}$ independently for each occurrence is halo or —$C_{(1-3)}$alkyl, wherein the —$C_{(1-3)}$alkyl is unsubstituted or substituted with one to five fluorine atoms, or when n is 2, two $R^{1b}$ groups together with the carbon atoms to which they are attached form a fused $C_{(3-7)}$cycloalkyl, wherein the $C_{(3-7)}$cycloalkyl is unsubstituted or substituted with one to five fluorine atoms;

n is 1 or 2;

m1, m2, and m3 are independently 0, 1, or 2;

$R^2$ is H, —$C_{(1-3)}$alkyl, —$C_{(3-5)}$cycloalkyl, —$C_{(1-3)}$alkyl-O—$C_{(1-3)}$alkyl, —$C_{(1-3)}$alkyl-O—$C_{(3-5)}$cycloalkyl, or 4- to 6-membered heterocyclyl, wherein the —$C_{(1-3)}$alkyl, —$C_{(3-5)}$cycloalkyl, —$C_{(1-3)}$alkyl-O—$C_{(1-3)}$alkyl, and —$C_{(1-3)}$alkyl-O—$C_{(3-5)}$cycloalkyl groups are unsubstituted or substituted with one to six $R^{2a}$ groups;

$R^{2a}$ independently for each occurrence is fluorine or —CN;

$R^3$ is —$C_{(1-10)}$alkyl, —$C_{(1-6)}$alkyl-O—$C_{(1-6)}$alkyl, —$C_{(1-6)}$alkyl-O—$C_{(3-5)}$cycloalkyl, —$C_{(1-6)}$alkyl-O—$C_{(3-5)}$cycloalkyl-$C_{(1-3)}$alkyl, —$C_{(3-8)}$cycloalkyl, or —$C_{(1-3)}$alkyl-($C_{(3-5)}$cycloalkyl)$_{1-2}$, each of which is unsubstituted or substituted with one to six fluorine atoms;

$R^4$ is a 5-membered heteroaryl that is unsubstituted or substituted with one to two $R^{4a}$ groups; and $R^{4a}$ is halo, —$C_{(1-6)}$alkyl, —O—$C_{(1-6)}$alkyl, —$C_{(1-6)}$alkyl-O—$C_{(1-6)}$alkyl, or —$C_{(0-2)}$alkyl-$C_{(3-6)}$cycloalkyl, wherein the —$C_{(1-6)}$alkyl, —O—$C_{(1-6)}$alkyl, —$C_{(1-6)}$alkyl-O—$C_{(1-6)}$alkyl, and —$C_{(0-2)}$alkyl-$C_{(3-6)}$cycloalkyl are unsubstituted or substituted with one to six substituents independently selected from fluorine, —CH$_3$, —CD$_3$, —CD$_2$CD$_3$, —CH$_2$F, —CHF$_2$, and —CF$_3$.

In some embodiments, disclosed herein is a compound of Formula I, or a pharmaceutically acceptable salt thereof, wherein:

$R^1$ is:

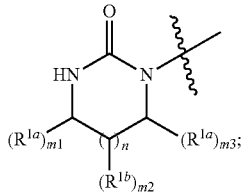

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms, or when m1 is 2, two geminal $R^{1a}$ groups together with the carbon atom to which they are attached form a spiro $C_{(3-5)}$cycloalkyl;

$R^{1b}$ independently for each occurrence is halo or —$C_{(1-3)}$alkyl, wherein the —$C_{(1-3)}$alkyl is unsubstituted or substituted with one to five fluorine atoms, or when n is 2, two $R^{1b}$ groups together with the carbon atoms to which they are attached form a fused $C_{(3-7)}$cycloalkyl, wherein the $C_{(3-7)}$cycloalkyl is unsubstituted or substituted with one to five fluorine atoms;

n is 1 or 2;

m1, m2, and m3 are independently 0, 1, or 2;

$R^2$ is H, —$C_{(1-3)}$alkyl, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl, wherein the —$C_{(1-3)}$alkyl, —$C_{(3-5)}$cycloalkyl, —$C_{(1-3)}$alkyl-O—$C_{(1-3)}$alkyl, and —$C_{(1-3)}$alkyl-O—$C_{(3-5)}$cycloalkyl groups are unsubstituted or substituted with one to six $R^{2a}$ groups;

$R^{2a}$ independently for each occurrence is fluorine or —CN;

$R^3$ is —$C_{(1-6)}$alkyl, —$C_{(1-6)}$alkyl-O—$C_{(1-6)}$alkyl, —$C_{(1-6)}$alkyl-O—$C_{(3-5)}$cycloalkyl, —$C_{(1-6)}$alkyl-O—$C_{(3-5)}$cycloalkyl-$C_{(1-3)}$alkyl, —$C_{(3-8)}$cycloalkyl, or —$C_{(1-3)}$alkyl-($C_{(3-5)}$cycloalkyl)$_{1-2}$, each of which is unsubstituted or substituted with one to six fluorine atoms;

$R^4$ is a 5-membered heteroaryl that is unsubstituted or substituted with one to two $R^{4a}$ groups; and $R^{4a}$ is halo, —$C_{(1-6)}$alkyl, —O—$C_{(1-6)}$alkyl, —$C_{(1-6)}$alkyl-O—$C_{(1-6)}$alkyl, or —$C_{(0-2)}$alkyl-$C_{(3-6)}$cycloalkyl, wherein the —$C_{(1-6)}$alkyl, —O—$C_{(1-6)}$alkyl, —$C_{(1-6)}$alkyl-O—$C_{(1-6)}$alkyl, and —$C_{(0-2)}$alkyl-$C_{(3-6)}$cycloalkyl are unsubstituted or substituted with one to six substituents independently selected from fluorine, —CH$_3$, —CD$_3$, —CD$_2$CD$_3$, —CH$_2$F, —CHF$_2$, and —CF$_3$.

In some embodiments, disclosed herein is a compound of Formula I, or a pharmaceutically acceptable salt thereof, wherein:

$R^1$ is:

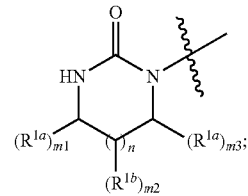

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms;

$R^{1b}$ independently for each occurrence is halo or —$C_{(1-3)}$alkyl, wherein the —$C_{(1-3)}$alkyl is unsubstituted or substituted with one to five fluorine atoms, or when n is 2, two $R^{1b}$ groups together with the carbon atoms to which they are attached form a fused $C_{(3-7)}$cycloalkyl, wherein the $C_{(3-7)}$cycloalkyl is unsubstituted or substituted with one to five fluorine atoms;

n is 1 or 2;

m1, m2, and m3 are independently 0, 1, or 2;

$R^2$ is H, —$C_{(1-3)}$alkyl, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl, wherein the —$C_{(1-3)}$alkyl, —$C_{(3-5)}$cycloalkyl, —$C_{(1-3)}$alkyl-O—$C_{(1-3)}$alkyl, and —$C_{(1-3)}$alkyl-O—$C_{(3-5)}$cycloalkyl groups are unsubstituted or substituted with one to six $R^{2a}$ groups;

$R^{2a}$ independently for each occurrence is fluorine;

$R^3$ is —$C_{(1-6)}$alkyl, —$C_{(1-6)}$alkyl-O—$C_{(1-6)}$alkyl, —$C_{(1-6)}$alkyl-O—$C_{(3-5)}$cycloalkyl, or —$C_{(3-8)}$cycloalkyl, each of which is unsubstituted or substituted with one to six fluorine atoms;

$R^4$ is a 5-membered heteroaryl that is unsubstituted or substituted with one to two $R^{4a}$ groups; and $R^{4a}$ is halo, —$C_{(1-6)}$alkyl, —O—$C_{(1-6)}$alkyl, —$C_{(1-6)}$alkyl-O—$C_{(1-6)}$alkyl, or —$C_{(0-2)}$alkyl-$C_{(3-6)}$cycloalkyl, wherein the —$C_{(1-6)}$alkyl, —O—$C_{(1-6)}$alkyl, —$C_{(1-6)}$alkyl-O—$C_{(1-6)}$alkyl, and —$C_{(0-2)}$alkyl-$C_{(3-6)}$cycloalkyl are unsubstituted or substituted with one to six substituents independently selected from fluorine, —CH$_3$, —CD$_3$, —CD$_2$CD$_3$, —CH$_2$F, —CHF$_2$, and —CF$_3$.

In some embodiments, disclosed herein is a compound of Formula I, or a pharmaceutically acceptable salt thereof, wherein:

$R^1$ is:

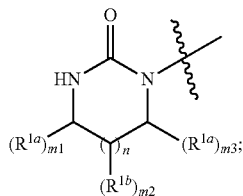

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms, or when m1 is 2, two geminal $R^{1a}$ groups together with the carbon atom to which they are attached form a spiro $C_{(3-5)}$cycloalkyl;

$R^{1b}$ independently for each occurrence is halo or —$C_{(1-3)}$alkyl, wherein the —$C_{(1-3)}$alkyl is unsubstituted or substituted with one to five fluorine atoms, or when n is 2, two $R^{1b}$ groups together with the carbon atoms to which they are attached form a fused $C_{(3-7)}$cycloalkyl, wherein the $C_{(3-7)}$cycloalkyl is unsubstituted or substituted with one to five fluorine atoms;

n is 1 or 2;

m1, m2, and m3 are independently 0, 1, or 2;

$R^2$ is H, —$C_{(1-3)}$alkyl, —$C_{(3-5)}$cycloalkyl, —$C_{(1-3)}$alkyl-O—$C_{(1-3)}$alkyl, —$C_{(1-3)}$alkyl-O—$C_{(3-5)}$cycloalkyl, or 4- to 6-membered heterocyclyl, wherein the —$C_{(1-3)}$alkyl and —$C_{(3-5)}$cycloalkyl are unsubstituted or substituted with one to six $R^{2a}$ groups;

$R^{2a}$ independently for each occurrence is fluorine or —CN;

$R^3$ is —$C_{(1-6)}$alkyl, —$C_{(1-6)}$alkyl-O—$C_{(1-6)}$alkyl, —$C_{(1-6)}$alkyl-O—$C_{(3-5)}$cycloalkyl, —$C_{(1-6)}$alkyl-O—$C_{(3-5)}$cycloalkyl-$C_{(1-3)}$alkyl, —$C_{(3-8)}$cycloalkyl, or —CH($C_{(3-5)}$cycloalkyl)$_2$, each of which is unsubstituted or substituted with one to six fluorine atoms;

$R^4$ is a 5-membered heteroaryl that is unsubstituted or substituted with one to two $R^{4a}$ groups; and $R^{4a}$ is halo, —$C_{(1-6)}$alkyl, —O—$C_{(1-6)}$alkyl, —$C_{(1-6)}$alkyl-O—$C_{(1-6)}$alkyl, or —$C_{(0-2)}$alkyl-$C_{(3-6)}$cycloalkyl, wherein the —$C_{(1-6)}$alkyl, —O—$C_{(1-6)}$alkyl, —$C_{(1-6)}$alkyl-O—$C_{(1-6)}$alkyl, and —$C_{(0-2)}$alkyl-$C_{(3-6)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein:

$R^1$ is:

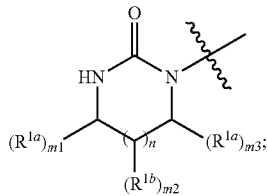

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms;

$R^{1b}$ independently for each occurrence is halo or —$C_{(1-3)}$alkyl, wherein the —$C_{(1-3)}$alkyl is unsubstituted or substituted with one to five fluorine atoms, or when n is 2, two $R^{1b}$ groups together with the carbon atoms to which they are attached form a fused $C_{(3-7)}$cycloalkyl, wherein the $C_{(3-7)}$cycloalkyl is unsubstituted or substituted with one to five fluorine atoms;

n is 1 or 2;

m1, m2, and m3 are independently 0, 1, or 2;

$R^2$ is H, —$C_{(1-3)}$alkyl, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl;

$R^3$ is —$C_{(1-6)}$alkyl, —$C_{(1-6)}$alkyl-O—$C_{(1-6)}$alkyl, —$C_{(1-6)}$alkyl-O—$C_{(3-5)}$cycloalkyl, or —$C_{(3-8)}$cycloalkyl, each of which is unsubstituted or substituted with one to six fluorine atoms;

$R^4$ is a 5-membered heteroaryl that is unsubstituted or substituted with one to two $R^{4a}$ groups; and $R^{4a}$ is halo, —$C_{(1-6)}$alkyl, —O—$C_{(1-6)}$alkyl, —$C_{(1-6)}$alkyl-O—$C_{(1-6)}$alkyl, or —$C_{(0-2)}$alkyl-$C_{(3-6)}$cycloalkyl, wherein the —$C_{(1-6)}$alkyl, —O—$C_{(1-6)}$alkyl, —$C_{(1-6)}$alkyl-O—$C_{(1-6)}$alkyl, and —$C_{(0-2)}$alkyl-$C_{(3-6)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein:

$R^1$ is:

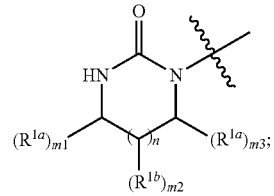

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms, or when m1 is 2, two geminal $R^{1a}$ groups together with the carbon atom to which they are attached form a spiro cyclopropyl;

$R^{1b}$ independently for each occurrence is halo or —$C_{(1-3)}$alkyl, wherein the —$C_{(1-3)}$alkyl is unsubstituted or substituted with one to five fluorine atoms, or when n is 2, two $R^{1b}$ groups together with the carbon atoms to which they are attached form a fused $C_{(3-5)}$cycloalkyl, wherein the $C_{(3-5)}$cycloalkyl is unsubstituted or substituted with one to five fluorine atoms;

n is 1 or 2;

m1, m2, and m3 are independently 0, 1, or 2;

$R^2$ is H, —$C_{(1-3)}$alkyl, —$C_{(3-5)}$cycloalkyl, —$C_{(1-3)}$alkyl-O—$C_{(1-3)}$alkyl, —$C_{(1-3)}$alkyl-O—$C_{(3-5)}$cycloalkyl, or 4- to 6-membered heterocyclyl, wherein the —$C_{(1-3)}$alkyl is unsubstituted or substituted with one to six fluorine atoms, and wherein the —$C_{(3-5)}$cycloalkyl is unsubstituted or substituted with one —CN group;

$R^3$ is —$C_{(1-6)}$alkyl, —$C_{(1-4)}$alkyl-O—$C_{(1-4)}$alkyl, —$C_{(1-3)}$alkyl-O—$C_{(3-5)}$cycloalkyl, —$C_{(1-3)}$alkyl-O—$C_{(3-5)}$cycloalkyl-$CH_3$, —$C_{(5-6)}$cycloalkyl, or —CH($C_{(3-5)}$cycloalkyl)$_2$, each of which is unsubstituted or substituted with one to six fluorine atoms;

R⁴ is a 5-membered heteroaryl that is unsubstituted or substituted with one to two R⁴ᵃ groups; and R⁴ᵃ is —C$_{(1-4)}$alkyl, —O—C$_{(1-4)}$alkyl, —C$_{(1-4)}$alkyl-O—C$_{(1-4)}$alkyl, or —C$_{(0-2)}$alkyl-C$_{(3-4)}$cycloalkyl, wherein the —C$_{(1-4)}$alkyl, —O—C$_{(1-4)}$alkyl, —C$_{(1-4)}$alkyl-O—C$_{(1-4)}$alkyl, and —C$_{(0-2)}$alkyl-C$_{(3-4)}$cycloalkyl are unsubstituted or substituted with one to six substituents independently selected from fluorine, —CH₃, —CD₃, —CD₂CD₃, —CH₂F, —CHF₂, and —CF₃.

In some embodiments, disclosed herein is a compound of Formula I, or a pharmaceutically acceptable salt thereof, wherein:

R¹ is:

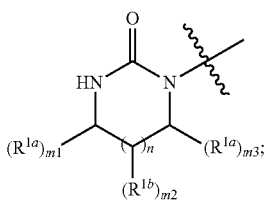

R¹ᵃ independently for each occurrence is —C$_{(1-3)}$alkyl or —C$_{(3-5)}$cycloalkyl, wherein the —C$_{(1-3)}$alkyl is unsubstituted or substituted with one to five fluorine atoms;

R¹ᵇ independently for each occurrence is halo or —C$_{(1-3)}$alkyl, wherein the —C$_{(1-3)}$alkyl is unsubstituted or substituted with one to five fluorine atoms, or when n is 2, two R¹ᵇ groups together with the carbon atoms to which they are attached form a fused C$_{(3-5)}$cycloalkyl, wherein the C$_{(3-5)}$cycloalkyl is unsubstituted or substituted with one to five fluorine atoms;

n is 1 or 2;

m1, m2, and m3 are independently 0, 1, or 2;

R² is H, —C$_{(3-5)}$cycloalkyl, —C$_{(1-3)}$alkyl-O—C$_{(1-3)}$alkyl, or —C$_{(1-3)}$alkyl-O—C$_{(3-5)}$cycloalkyl;

R³ is —C$_{(1-6)}$alkyl, —C$_{(1-4)}$alkyl-O—C$_{(1-4)}$alkyl, —C$_{(1-3)}$alkyl-O—C$_{(3-5)}$cycloalkyl, or cyclohexyl, each of which is substituted or substituted with one to six fluorine atoms;

R⁴ is a 5-membered heteroaryl that is unsubstituted or substituted with one to two R⁴ᵃ groups; and R⁴ᵃ is —C$_{(1-4)}$alkyl, —O—C$_{(1-4)}$alkyl, —C$_{(1-4)}$alkyl-O—C$_{(1-4)}$alkyl, or —C$_{(0-2)}$alkyl-C$_{(3-4)}$cycloalkyl, wherein the —C$_{(1-4)}$alkyl, —O—C$_{(1-4)}$alkyl, —C$_{(1-4)}$alkyl-O—C$_{(1-4)}$alkyl, and —C$_{(0-2)}$alkyl-C$_{(3-4)}$cycloalkyl are unsubstituted or substituted with one to six substituents independently selected from fluorine, —CH₃, —CD₃, —CD₂CD₃, —CH₂F, —CHF₂, and —CF₃.

In some embodiments, disclosed herein is a compound of Formula I, or a pharmaceutically acceptable salt thereof, wherein:

R¹ is:

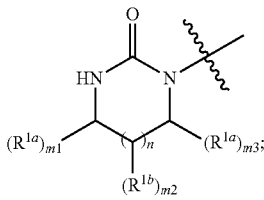

R¹ᵃ independently for each occurrence is —C$_{(1-3)}$alkyl or —C$_{(3-5)}$cycloalkyl, wherein the —C$_{(1-3)}$alkyl is unsubstituted or substituted with one to five fluorine atoms, or when m1 is 2, two geminal R¹ᵃ groups together with the carbon atom to which they are attached form a spiro cyclopropyl;

R¹ᵇ independently for each occurrence is halo or —C$_{(1-3)}$alkyl, wherein the —C$_{(1-3)}$alkyl is unsubstituted or substituted with one to five fluorine atoms, or when n is 2, two R¹ᵇ groups together with the carbon atoms to which they are attached form a fused C$_{(3-5)}$cycloalkyl, wherein the C$_{(3-5)}$cycloalkyl is unsubstituted or substituted with one to five fluorine atoms;

n is 1 or 2;

m1, m2, and m3 are independently 0, 1, or 2;

R² is H, —C$_{(1-3)}$alkyl, —C$_{(3-5)}$cycloalkyl, —C$_{(1-3)}$alkyl-O—C$_{(1-3)}$alkyl, —C$_{(1-3)}$alkyl-O—C$_{(3-5)}$cycloalkyl, or tetrahydropyranyl, wherein the —C$_{(1-3)}$alkyl is unsubstituted or substituted with one to six fluorine atoms, and wherein the —C$_{(3-5)}$cycloalkyl is unsubstituted or substituted with one —CN groups;

R³ is —C$_{(5-6)}$alkyl substituted with two to three fluorine atoms, —C$_{(5-6)}$cycloalkyl substituted with two fluorine atoms,

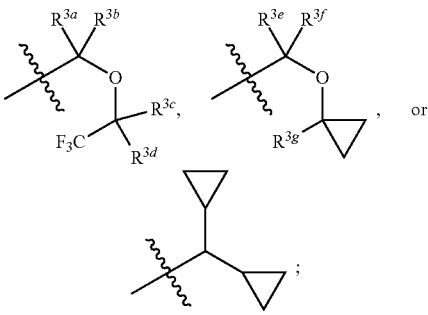

R³ᵃ, R³ᵇ, R³ᶜ, and R³ᵈ are each independently H or —CH₃;

R³ᵉ and R³ᶠ are each independently H or —CH₃;

R³ᵍ is H or —CF₃;

R⁴ is a 5-membered heteroaryl that is unsubstituted or substituted with one to two R⁴ᵃ groups; and R⁴ᵃ is —C$_{(1-4)}$alkyl, —O—C$_{(1-4)}$alkyl, —C$_{(1-4)}$alkyl-O—C$_{(1-4)}$alkyl, or —C$_{(0-2)}$alkyl-C$_{(3-4)}$cycloalkyl, wherein the —C$_{(1-4)}$alkyl, —O—C$_{(1-4)}$alkyl, —C$_{(1-4)}$alkyl-O—C$_{(1-4)}$alkyl, and —C$_{(0-2)}$alkyl-C$_{(3-4)}$cycloalkyl are unsubstituted or substituted with one to six substituents independently selected from fluorine, —CH₃, —CD₃, —CD₂CD₃, —CH₂F, —CHF₂, and —CF₃.

In some embodiments, disclosed herein is a compound of Formula I, or a pharmaceutically acceptable salt thereof, wherein:

R¹ is:

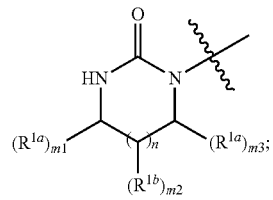

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms;

$R^{1b}$ independently for each occurrence is halo or —$C_{(1-3)}$alkyl, wherein the —$C_{(1-3)}$alkyl is unsubstituted or substituted with one to five fluorine atoms, or when n is 2, two $R^{1b}$ groups together with the carbon atoms to which they are attached form a fused $C_{(3-5)}$cycloalkyl, wherein the $C_{(3-5)}$cycloalkyl is unsubstituted or substituted with one to five fluorine atoms;

n is 1 or 2;

m1, m2, and m3 are independently 0, 1, or 2;

$R^2$ is H, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl;

$R^3$ is —$C_{(1-5)}$alkyl substituted with one —$CF_3$,

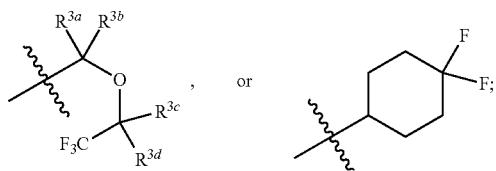

$R^{3a}$, $R^{3b}$, $R^{3c}$, and $R^{3d}$ are each independently H or —$CH_3$;

$R^4$ is a 5-membered heteroaryl that is unsubstituted or substituted with one to two $R^{4a}$ groups; and $R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein:

$R^1$ is:

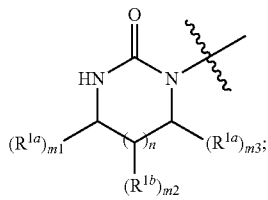

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms;

$R^{1b}$ independently for each occurrence is halo or —$C_{(1-3)}$alkyl, wherein the —$C_{(1-3)}$alkyl is unsubstituted or substituted with one to five fluorine atoms, or when n is 2, two $R^{1b}$ groups together with the carbon atoms to which they are attached form a fused $C_{(3-5)}$cycloalkyl, wherein the $C_{(3-5)}$cycloalkyl is unsubstituted or substituted with one to five fluorine atoms;

n is 1 or 2;

m1, m2, and m3 are independently 0, 1, or 2;

$R^2$ is H, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl;

$R^3$ is:

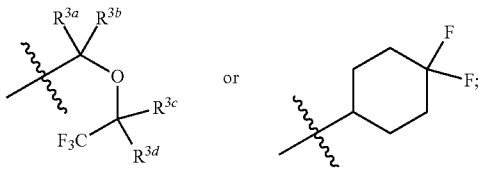

$R^{3a}$, $R^{3b}$, $R^{3c}$, and $R^{3d}$ are each independently H or —$CH_3$;

$R^4$ is a 5-membered heteroaryl that is unsubstituted or substituted with one to two $R^{4a}$ groups; and $R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein:

$R^1$ is:

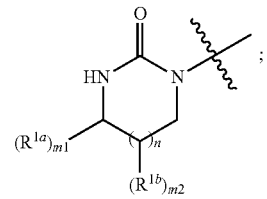

$R^{1a}$ independently for each occurrence is —$CH_3$, —$CH_2F$, —$CHF_2$, —$CF_3$, or —$C_{(3-4)}$cycloalkyl, or when m1 is 2, two geminal $R^{1a}$ groups together with the carbon atom to which they are attached form a spiro cyclopropyl;

$R^{1b}$ independently for each occurrence is fluoro, —$CH_3$, —$CH_2F$, —$CHF_2$, —$CF_3$, or when n is 2, two $R^{1b}$ groups together with the carbon atoms to which they are attached form a fused $C_{(3-5)}$cycloalkyl, wherein the $C_{(3-5)}$cycloalkyl is unsubstituted or substituted with one to five fluorine atoms n is 1 or 2;

m1 and m2 are independently 0, 1, or 2;

$R^2$ is H, —$C_{(1-3)}$alkyl, —$C_{(3-5)}$cycloalkyl, —$C_{(1-3)}$alkyl-O—$C_{(1-3)}$alkyl, —$C_{(1-3)}$alkyl-O—$C_{(3-5)}$cycloalkyl, or tetrahydropyranyl, wherein the —$C_{(1-3)}$alkyl is unsubstituted or substituted with one to six fluorine atoms, and wherein the —$C_{(3-5)}$cycloalkyl is unsubstituted or substituted with one —CN groups;

$R^3$ is —$C_{(5-6)}$alkyl substituted with two to three fluorine atoms, —$C_{(5-6)}$cycloalkyl substituted with two fluorine atoms,

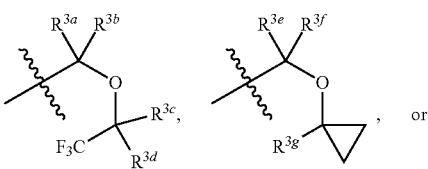

-continued

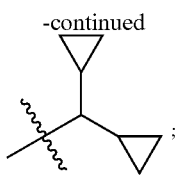

$R^{3a}$, $R^{3b}$, $R^{3c}$, and $R^{3d}$ are each independently H or —CH$_3$;
$R^{3e}$ and $R^{3f}$ are each independently H or —CH$_3$;
$R^{3g}$ is H or —CF$_3$;
$R^4$ is a 5-membered heteroaryl that is unsubstituted or substituted with one to two $R^{4a}$ groups; and
$R^{4a}$ is —C$_{(1-4)}$alkyl, —O—C$_{(1-4)}$alkyl, —C$_{(1-4)}$alkyl-O—C$_{(1-4)}$alkyl, or —C$_{(0-2)}$alkyl-C$_{(3-4)}$cycloalkyl, wherein the —C$_{(1-4)}$alkyl, —O—C$_{(1-4)}$alkyl, —C$_{(1-4)}$alkyl-O—C$_{(1-4)}$alkyl, and —C$_{(0-2)}$alkyl-C$_{(3-4)}$cycloalkyl are unsubstituted or substituted with one to six substituents independently selected from fluorine, —CH$_3$, —CD$_3$, —CD$_2$CD$_3$, —CH$_2$F, —CHF$_2$, and —CF$_3$.

In some embodiments, disclosed herein is a compound of Formula I, or a pharmaceutically acceptable salt thereof, wherein:
$R^1$ is:

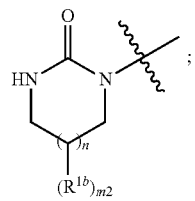

$R^{1b}$ independently for each occurrence is fluoro, —CH$_3$, —CH$_2$F, —CHF$_2$, —CF$_3$, or when n is 2, two $R^{1b}$ groups together with the carbon atoms to which they are attached form a fused C$_{(3-5)}$cycloalkyl, wherein the C$_{(3-5)}$cycloalkyl is unsubstituted or substituted with one to five fluorine atoms;
n is 1 or 2;
m2 is 0, 1, or 2;
$R^2$ is H, —C$_{(3-5)}$cycloalkyl, —C$_{(1-3)}$alkyl-O—C$_{(1-3)}$alkyl, or —C$_{(1-3)}$alkyl-O—C$_{(3-5)}$cycloalkyl;
$R^3$ is —C$_{(1-5)}$alkyl substituted with one —CF$_3$,

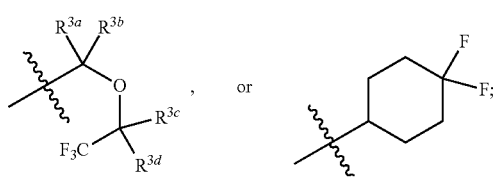

$R^{3a}$, $R^{3b}$, $R^{3c}$, and $R^{3d}$ are each independently H or —CH$_3$;
$R^4$ is a 5-membered heteroaryl that is unsubstituted or substituted with one to two $R^{4a}$ groups; and
$R^{4a}$ is —C$_{(1-4)}$alkyl, —O—C$_{(1-4)}$alkyl, —C$_{(1-4)}$alkyl-O—C$_{(1-4)}$alkyl, or —C$_{(0-2)}$alkyl-C$_{(3-4)}$cycloalkyl, wherein the —C$_{(1-4)}$alkyl, —O—C$_{(1-4)}$alkyl, —C$_{(1-4)}$alkyl-O—C$_{(1-4)}$alkyl, and —C$_{(0-2)}$alkyl-C$_{(3-4)}$cycloalkyl are unsubstituted or substituted with one to six substituents independently selected from fluorine, —CH$_3$, —CD$_3$, —CD$_2$CD$_3$, —CH$_2$F, —CHF$_2$, and —CF$_3$.

In some embodiments, disclosed herein is a compound of Formula I, or a pharmaceutically acceptable salt thereof, wherein:
$R^1$ is:

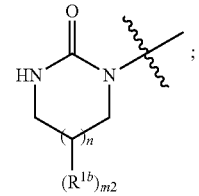

$R^{1b}$ independently for each occurrence is fluoro, —CH$_3$, —CH$_2$F, —CHF$_2$, —CF$_3$, or when n is 2, two $R^{1b}$ groups together with the carbon atoms to which they are attached form a fused C$_{(3-5)}$cycloalkyl, wherein the C$_{(3-5)}$cycloalkyl is unsubstituted or substituted with one to five fluorine atoms;
n is 1 or 2;
m2 is 0, 1, or 2;
$R^2$ is H, —C$_{(3-5)}$cycloalkyl, —C$_{(1-3)}$alkyl-O—C$_{(1-3)}$alkyl, or —C$_{(1-3)}$alkyl-O—C$_{(3-5)}$cycloalkyl;
$R^3$ is:

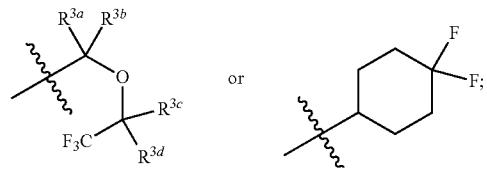

$R^{3a}$, $R^{3b}$, $R^{3c}$, and $R^{3d}$ are each independently H or —CH$_3$;
$R^4$ is a 5-membered heteroaryl that is unsubstituted or substituted with one to two $R^{4a}$ groups; and
$R^{4a}$ is —C$_{(1-4)}$alkyl, —O—C$_{(1-4)}$alkyl, —C$_{(1-4)}$alkyl-O—C$_{(1-4)}$alkyl, or —C$_{(0-2)}$alkyl-C$_{(3-4)}$cycloalkyl, wherein the —C$_{(1-4)}$alkyl, —O—C$_{(1-4)}$alkyl, —C$_{(1-4)}$alkyl-O—C$_{(1-4)}$alkyl, and —C$_{(0-2)}$alkyl-C$_{(3-4)}$cycloalkyl are unsubstituted or substituted with one to six substituents independently selected from fluorine, —CH$_3$, —CD$_3$, —CD$_2$CD$_3$, —CH$_2$F, —CHF$_2$, and —CF$_3$.

In some embodiments, disclosed herein is a compound of Formula I, or a pharmaceutically acceptable salt thereof, wherein:
$R^1$ is:

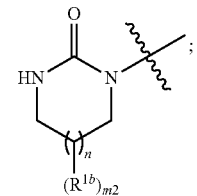

$R^{1b}$ independently for each occurrence is fluoro, or when n is 2, two $R^{1b}$ groups together with the carbon atoms to which they are attached form a fused C$_{(3)}$cycloalkyl, wherein the $C_{(3)}$cycloalkyl is unsubstituted or substituted with one to two fluorine atoms;
n is 1 or 2;
m2 is 0, 1, or 2;
$R^2$ is H, —$C_{(3-5)}$cycloalkyl, —$C_{(1-3)}$alkyl-O—$C_{(1-3)}$alkyl, or —$C_{(1-3)}$alkyl-O—$C_{(3-5)}$cycloalkyl;
$R^3$ is —$C_{(5-6)}$alkyl substituted with two to three fluorine atoms, —$C_{(5-6)}$cycloalkyl substituted with two fluorine atoms,

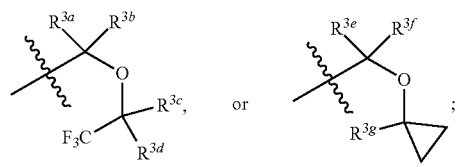

$R^{3a}$, $R^{3b}$, $R^{3c}$, and $R^{3d}$ are each independently H or —$CH_3$;
$R^{3e}$ and $R^{3f}$ are each independently H or —$CH_3$;
$R^{3g}$ is H or —$CF_3$;
$R^4$ is

and
$R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein:
$R^1$ is:

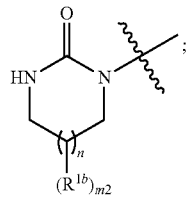

$R^{1b}$ independently for each occurrence is fluoro, or when n is 2, two $R^{1b}$ groups together with the carbon atoms to which they are attached form a fused $C_{(3)}$cycloalkyl, wherein the $C_{(3)}$cycloalkyl is unsubstituted or substituted with one to two fluorine atoms;
n is 1 or 2;
m2 is 0, 1, or 2;
$R^2$ is H, cyclopropyl, —$CH_2OCH_3$, or —$CH_2$—O—cyclopropyl;
$R^3$ is —$C_{(5-6)}$alkyl substituted with two to three fluorine atoms, —$C_{(5-6)}$cycloalkyl substituted with two fluorine atoms, or

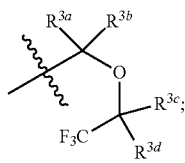

$R^{3a}$, $R^{3b}$, $R^{3c}$, and $R^{3d}$ are each independently H or —$CH_3$;
$R^4$ is

and
$R^{4a}$ is methyl, ethyl, isopropyl, —$CD_2CD_3$, —$CHF_2$, —$CF_3$, —$CH_2CH_2CF_3$, —$OCH_3$, —$OCH_2CHF_2$, —$CH_2OCHF_2$, cyclopropyl, or —$CH_2$-cyclopropyl.

In some embodiments, disclosed herein is a compound of Formula I, or a pharmaceutically acceptable salt thereof, wherein $R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms, or when m1 is 2, two geminal $R^{1a}$ groups together with the carbon atom to which they are attached form a spiro cyclopropyl.

In some embodiments, disclosed herein is a compound of Formula I, or a pharmaceutically acceptable salt thereof, wherein $R^{1a}$ independently for each occurrence is —$C_{(1-3)}$alkyl that is unsubstituted or substituted with one to five fluorine atoms, or when m1 is 2, two geminal $R^{1a}$ groups together with the carbon atom to which they are attached form a spiro cyclopropyl.

In some embodiments, disclosed herein is a compound of Formula I, or a pharmaceutically acceptable salt thereof, wherein $R^{1a}$ independently for each occurrence is —$CH_3$, —$CH_2F$, —$CHF_2$, —$CF_3$, or —$C_{(3-4)}$cycloalkyl, or when m1 is 2, two geminal $R^{1a}$ groups together with the carbon atom to which they are attached form a spiro cyclopropyl.

In some embodiments, disclosed herein is a compound of Formula I, or a pharmaceutically acceptable salt thereof, wherein $R^{1a}$ independently for each occurrence is —$CH_3$, —$CH_2F$, —$CHF_2$, or —$CF_3$, or when m1 is 2, two geminal $R^{1a}$ groups together with the carbon atom to which they are attached form a spiro cyclopropyl.

In some embodiments, disclosed herein is a compound of Formula I, or a pharmaceutically acceptable salt thereof, wherein $R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms.

In some embodiments, disclosed herein is a compound of Formula I, or a pharmaceutically acceptable salt thereof, wherein $R^{1a}$ independently for each occurrence is —$C_{(1-3)}$alkyl or —$C_{(3-5)}$cycloalkyl.

In some embodiments, disclosed herein is a compound of Formula I, or a pharmaceutically acceptable salt thereof, wherein $R^{1a}$ independently for each occurrence is —$CH_3$, —$CH_2F$, —$CHF_2$, —$CF_3$, or —$C_{(3-4)}$cycloalkyl.

In some embodiments, disclosed herein is a compound of Formula I, or a pharmaceutically acceptable salt thereof, wherein $R^{1a}$ independently for each occurrence is —$C_{(1-3)}$ alkyl that is unsubstituted or substituted with one to five fluorine atoms. In some embodiments, disclosed herein is a compound of Formula I, or a pharmaceutically acceptable salt thereof, wherein R$^{1a}$ independently for each occurrence is —C$_{(3-5)}$cycloalkyl. In some embodiments, disclosed herein is a compound of Formula I, or a pharmaceutically acceptable salt thereof, wherein m1 is 2, and two geminal R$^{1a}$ groups together with the carbon atom to which they are attached form a spiro cyclopropyl.

In some embodiments, disclosed herein is a compound of Formula I, or a pharmaceutically acceptable salt thereof, wherein R$^{1b}$ independently for each occurrence is halo or —C$_{(1-3)}$alkyl, or when n is 2, two R$^{1b}$ groups together with the carbon atoms to which they are attached form a fused C$_{(3-5)}$cycloalkyl, wherein the C$_{(3-5)}$cycloalkyl is unsubstituted or substituted with one to five fluorine.

In some embodiments, disclosed herein is a compound of Formula I, or a pharmaceutically acceptable salt thereof, wherein R$^{1b}$ independently for each occurrence is halo or —C$_{(1-3)}$alkyl, wherein the —C$_{(1-3)}$alkyl is unsubstituted or substituted with one to five fluorine atoms, or when n is 2, two R$^{1b}$ groups together with the carbon atoms to which they are attached form a fused C$_{(3-5)}$cycloalkyl, wherein the C$_{(3-5)}$cycloalkyl is unsubstituted or substituted with one to five fluorine atoms.

In some embodiments, disclosed herein is a compound of Formula I, or a pharmaceutically acceptable salt thereof, wherein R$^{1b}$ independently for each occurrence is fluoro, —CH$_3$, —CH$_2$F, —CHF$_2$, —CF$_3$, or when n is 2, two R$^{1b}$ groups together with the carbon atoms to which they are attached form a fused C$_{(3-5)}$cycloalkyl, wherein the C$_{(3-5)}$ cycloalkyl is unsubstituted or substituted with one to five fluorine atoms.

In some embodiments, disclosed herein is a compound of Formula I, or a pharmaceutically acceptable salt thereof, wherein R$^{1b}$ independently for each occurrence is fluoro, —CH$_3$, —CH$_2$F, —CHF$_2$, —CF$_3$, or when n is 2, two R$^{1b}$ groups together with the carbon atoms to which they are attached form a fused C$_{(3)}$cycloalkyl, wherein the C$_{(3)}$ cycloalkyl is unsubstituted or substituted with one to two fluorine atoms.

In some embodiments, disclosed herein is a compound of Formula I, or a pharmaceutically acceptable salt thereof, wherein R$^{1b}$ independently for each occurrence is fluoro, or when n is 2, two R$^{1b}$ groups together with the carbon atoms to which they are attached form a fused C$_{(3)}$cycloalkyl, wherein the C$_{(3)}$cycloalkyl is unsubstituted or substituted with one to two fluorine atoms In some embodiments, disclosed herein is a compound of Formula I, or a pharmaceutically acceptable salt thereof, wherein n is 1. In some embodiments, disclosed herein is a compound of Formula I, or a pharmaceutically acceptable salt thereof, wherein n is 2.

In some embodiments, disclosed herein is a compound of Formula I, or a pharmaceutically acceptable salt thereof, wherein m1 is 0, 1, or 2. In some embodiments, disclosed herein is a compound of Formula I, or a pharmaceutically acceptable salt thereof, wherein m1 is 0. In some embodiments, disclosed herein is a compound of Formula I, or a pharmaceutically acceptable salt thereof, wherein m2 is 0, 1, or 2. In some embodiments, disclosed herein is a compound of Formula I, or a pharmaceutically acceptable salt thereof, wherein m3 is 0.

In some embodiments, disclosed herein is a compound of Formula I, or a pharmaceutically acceptable salt thereof, wherein m1 is 0, 1, or 2; m2 is 0, 1, or 2; and m3 is 0. In some embodiments, disclosed herein is a compound of Formula I, or a pharmaceutically acceptable salt thereof, wherein m1 is 0; m2 is 0, 1, or 2; and m3 is 0.

In some embodiments, disclosed herein is a compound of Formula I, or a pharmaceutically acceptable salt thereof, wherein:
R$^1$ is:

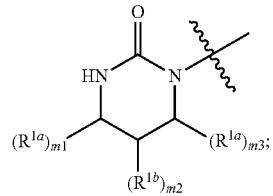

R$^{1a}$ independently for each occurrence is —C$_{(1-3)}$alkyl or —C$_{(3-5)}$cycloalkyl, wherein the —C$_{(1-3)}$alkyl is unsubstituted or substituted with one to five fluorine atoms, or when m1 is 2, two geminal R$^{1a}$ groups together with the carbon atom to which they are attached form a spiro C$_{(3-5)}$cycloalkyl;
R$^{1b}$ independently for each occurrence is halo or —C$_{(1-3)}$alkyl, wherein the —C$_{(1-3)}$alkyl is unsubstituted or substituted with one to five fluorine atoms; and
m1, m2, and m3 are independently 0, 1, or 2.

In some embodiments, disclosed herein is a compound of Formula I, or a pharmaceutically acceptable salt thereof, wherein:
R$^1$ is:

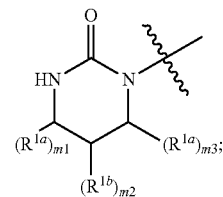

R$^{1a}$ independently for each occurrence is —CH$_3$, —CH$_2$F, —CHF$_2$, or —CF$_3$, or when m1 is 2, two geminal R$^{1a}$ groups together with the carbon atom to which they are attached form a spiro cyclopropyl;
R$^{1b}$ independently for each occurrence is fluoro, —CH$_3$, —CH$_2$F, —CHF$_2$, —CF$_3$; and
m1, m2, and m3 are independently 0, 1, or 2.

In some embodiments, disclosed herein is a compound of Formula I, or a pharmaceutically acceptable salt thereof, wherein:
R$^1$ is:

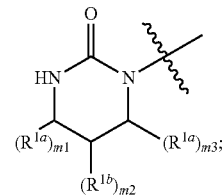

R$^{1a}$ independently for each occurrence is —C$_{(1-3)}$alkyl or —C$_{(3-5)}$cycloalkyl, wherein the —C$_{(1-3)}$alkyl is unsubstituted or substituted with one to five fluorine atoms;

$R^{1b}$ independently for each occurrence is halo or —$C_{(1-3)}$alkyl, wherein the —$C_{(1-3)}$alkyl is unsubstituted or substituted with one to five fluorine atoms; and m1, m2, and m3 are independently 0, 1, or 2.

In some embodiments, disclosed herein is a compound of Formula I, or a pharmaceutically acceptable salt thereof, wherein:

$R^1$ is:

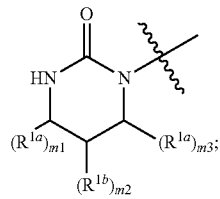

$R^{1a}$ independently for each occurrence is —$CH_3$, —$CH_2F$, —$CHF_2$, —$CF_3$, or —$C_{(3-4)}$cycloalkyl;

$R^{1b}$ independently for each occurrence is fluoro, —$CH_3$, —$CH_2F$, —$CHF_2$, or —$CF_3$; and m1, m2, and m3 are independently 0, 1, or 2.

In some embodiments, disclosed herein is a compound of Formula I, or a pharmaceutically acceptable salt thereof, wherein:

$R^1$ is:

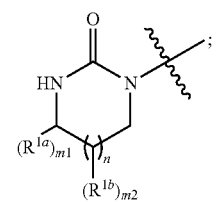

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms, or when m1 is 2, two geminal $R^{1a}$ groups together with the carbon atom to which they are attached form a spiro $C_{(3-5)}$cycloalkyl;

$R^{1b}$ independently for each occurrence is halo or —$C_{(1-3)}$alkyl, wherein the —$C_{(1-3)}$alkyl is unsubstituted or substituted with one to five fluorine atoms; and m1 and m2 are independently 0, 1, or 2.

In some embodiments, disclosed herein is a compound of Formula I, or a pharmaceutically acceptable salt thereof, wherein:

$R^1$ is:

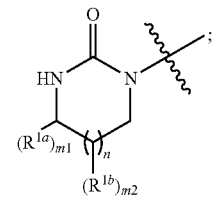

$R^{1a}$ independently for each occurrence is —$CH_3$, —$CH_2F$, —$CHF_2$, or —$CF_3$, or when m1 is 2, two geminal $R^{1a}$ groups together with the carbon atom to which they are attached form a spiro cyclopropyl;

$R^{1b}$ independently for each occurrence is fluoro, —$CH_3$, —$CH_2F$, —$CHF_2$, —$CF_3$; and m1 and m3 are independently 0, 1, or 2.

In some embodiments, disclosed herein is a compound of Formula I, or a pharmaceutically acceptable salt thereof, wherein:

$R^1$ is:

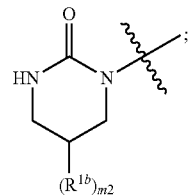

$R^{1b}$ independently for each occurrence is fluoro, —$CH_3$, —$CH_2F$, —$CHF_2$, —$CF_3$; and m2 is 0, 1, or 2.

In some embodiments, disclosed herein is a compound of Formula I, or a pharmaceutically acceptable salt thereof, wherein:

$R^1$ is:

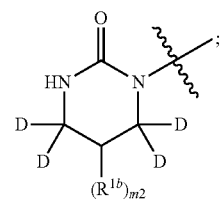

$R^{1b}$ independently for each occurrence is fluoro, —$CH_3$, —$CH_2F$, —$CHF_2$, —$CF_3$; and m2 is 0, 1, or 2.

In some embodiments, disclosed herein is a compound of Formula I, or a pharmaceutically acceptable salt thereof, wherein:

$R^1$ is:

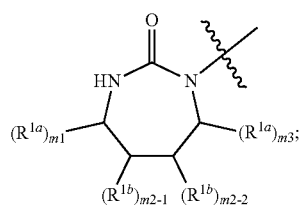

$R^{1a}$ independently for each occurrence is —$C_{(1-3)}$alkyl or —$C_{(3-5)}$cycloalkyl, wherein the —$C_{(1-3)}$alkyl is unsubstituted or substituted with one to five fluorine atoms;

$R^{1b}$ independently for each occurrence is halo or —$C_{(1-3)}$alkyl, wherein the —$C_{(1-3)}$alkyl is unsubstituted or substituted with one to five fluorine atoms, or two vicinal $R^{1b}$ groups together with the carbon atoms to which they are attached form a fused $C_{(3-7)}$cycloalkyl, wherein the $C_{(3-7)}$cycloalkyl is unsubstituted or substituted with one to five fluorine atoms; and m1, m2-1, m2-2, and m3 are independently 0, 1, or 2.

In some embodiments, disclosed herein is a compound of Formula I, or a pharmaceutically acceptable salt thereof, wherein:

R¹ is:

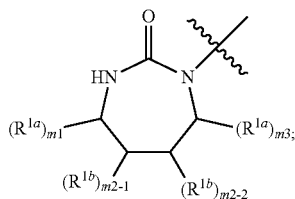

R$^{1a}$ independently for each occurrence is —CH$_3$, —CH$_2$F, —CHF$_2$, —CF$_3$, or —C$_{(3-4)}$cycloalkyl;
R$^{1b}$ independently for each occurrence is fluoro, —CH$_3$, —CH$_2$F, —CHF$_2$, —CF$_3$, or two vicinal R$^{1b}$ groups together with the carbon atoms to which they are attached form a fused C$_{(3-5)}$cycloalkyl, wherein the C$_{(3-5)}$cycloalkyl is unsubstituted or substituted with one to five fluorine atoms; and
m1, m2-1, m2-2, and m3 are independently 0, 1, or 2.

In some embodiments, disclosed herein is a compound of Formula I, or a pharmaceutically acceptable salt thereof, wherein:
R¹ is:

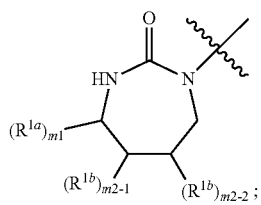

R$^{1a}$ independently for each occurrence is —C$_{(1-3)}$alkyl or —C$_{(3-5)}$cycloalkyl, wherein the —C$_{(1-3)}$alkyl is unsubstituted or substituted with one to five fluorine atoms;
R$^{1b}$ independently for each occurrence is halo or —C$_{(1-3)}$alkyl, wherein the —C$_{(1-3)}$alkyl is unsubstituted or substituted with one to five fluorine atoms, or two vicinal R$^{1b}$ groups together with the carbon atoms to which they are attached form a fused C$_{(3-7)}$cycloalkyl, wherein the C$_{(3-7)}$cycloalkyl is unsubstituted or substituted with one to five fluorine atoms; and
m1, m2-1, and m2-2 are independently 0, 1, or 2.

In some embodiments, disclosed herein is a compound of Formula I, or a pharmaceutically acceptable salt thereof, wherein:
R¹ is:

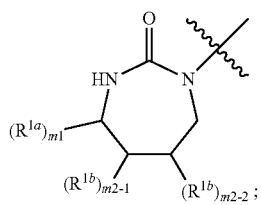

R$^{1a}$ independently for each occurrence is —CH$_3$, —CH$_2$F, —CHF$_2$, —CF$_3$, or —C$_{(3-4)}$cycloalkyl;
R$^{1b}$ independently for each occurrence is fluoro, —CH$_3$, —CH$_2$F, —CHF$_2$, —CF$_3$, or two vicinal R$^{1b}$ groups together with the carbon atoms to which they are attached form a fused C$_{(3-5)}$cycloalkyl, wherein the C$_{(3-5)}$cycloalkyl is unsubstituted or substituted with one to five fluorine atoms; and
m1, m2-1, and m2-2 are independently 0, 1, or 2.

In some embodiments, disclosed herein is a compound of Formula I, or a pharmaceutically acceptable salt thereof, wherein:
R¹ is:

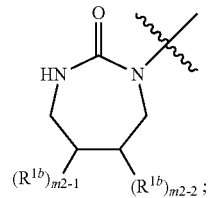

R$^{1b}$ independently for each occurrence is fluoro, —CH$_3$, —CH$_2$F, —CHF$_2$, —CF$_3$, or two vicinal R$^{1b}$ groups together with the carbon atoms to which they are attached form a fused C$_{(3-5)}$cycloalkyl, wherein the C$_{(3-5)}$cycloalkyl is unsubstituted or substituted with one to five fluorine atoms; and
m2-1 and m2-2 are independently 0, 1, or 2.

In some embodiments, disclosed herein is a compound of Formula I, or a pharmaceutically acceptable salt thereof, wherein R¹ is:

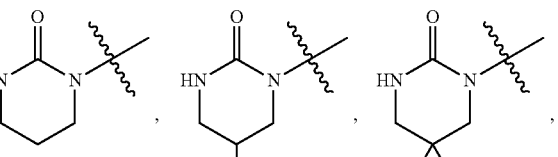

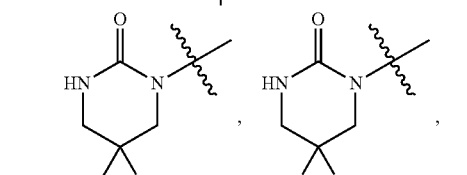

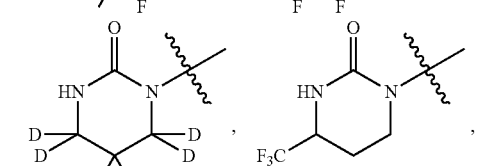

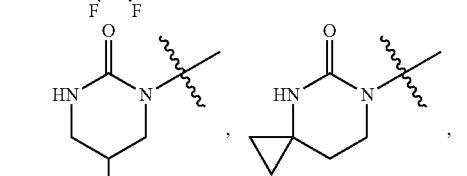

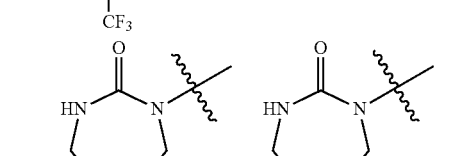

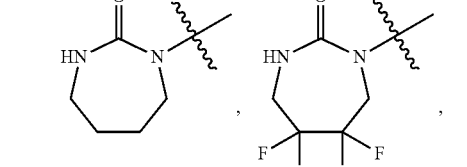

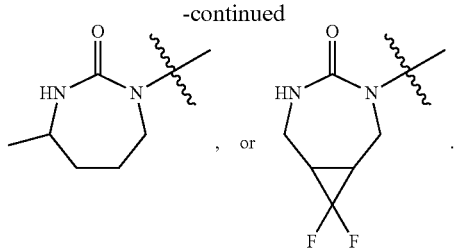

, or .

In some embodiments, disclosed herein is a compound of Formula I, or a pharmaceutically acceptable salt thereof, wherein R¹ is:

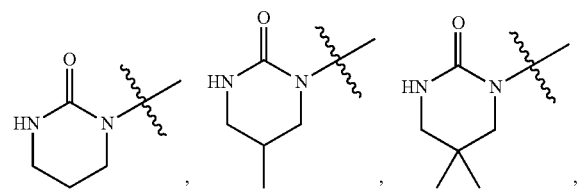

,

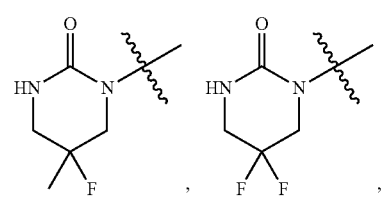

,

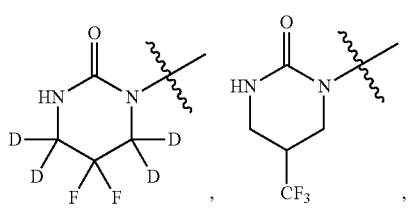

, or 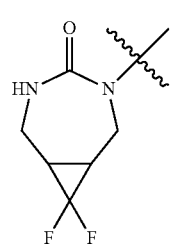 .

In some embodiments, disclosed herein is a compound of Formula I, or a pharmaceutically acceptable salt thereof, wherein R¹ is:

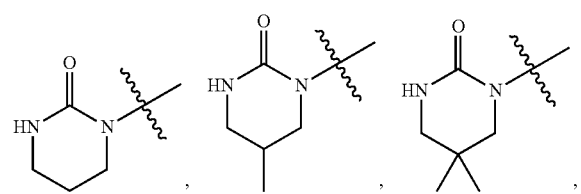

,

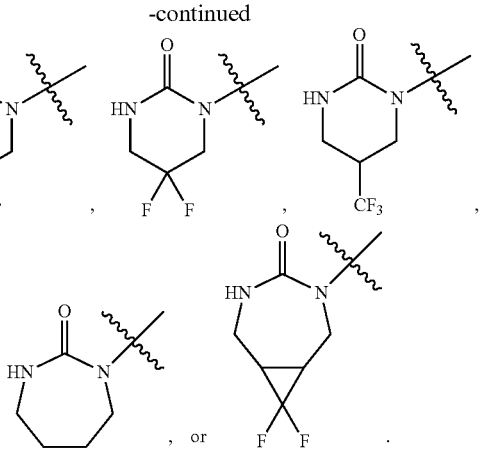

, or .

In some embodiments, disclosed herein is a compound of Formula I, or a pharmaceutically acceptable salt thereof, wherein R¹ is:

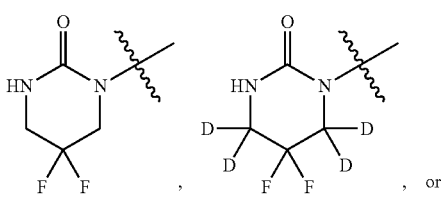

, or .

In some embodiments, disclosed herein is a compound of Formula I, or a pharmaceutically acceptable salt thereof, wherein R¹ is:

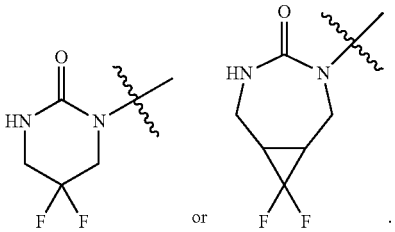 [SMILES: *N1CC(F)(F)CNC1=O ; *N1CC2C(CNC1=O)C2(F)F]

.

In some embodiments, disclosed herein is a compound of Formula I, or a pharmaceutically acceptable salt thereof, wherein R¹ is

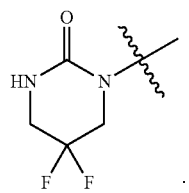 [SMILES: *N1CC(F)(F)CNC1=O]

In some embodiments, disclosed herein is a compound of Formula I, or a pharmaceutically acceptable salt thereof, wherein R¹ is

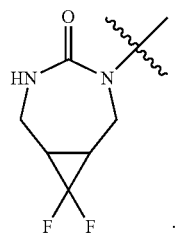

In some embodiments, disclosed herein is a compound of Formula I, or a pharmaceutically acceptable salt thereof, wherein R¹ is

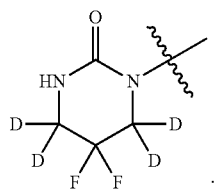 [SMILES: *N1C(=O)NC([2H])([2H])C(F)(F)C1([2H])[2H]]

In some embodiments, disclosed herein is a compound of Formula I, or a pharmaceutically acceptable salt thereof, wherein R² is H, —C$_{(1-3)}$alkyl, —C$_{(3-5)}$cycloalkyl, —C$_{(1-3)}$alkyl-O—C$_{(1-3)}$alkyl, or —C$_{(1-3)}$alkyl-O—C$_{(3-5)}$cycloalkyl, wherein the —C$_{(1-3)}$alkyl, —C$_{(3-5)}$cycloalkyl, —C$_{(1-3)}$alkyl-O—C$_{(1-3)}$alkyl, and —C$_{(1-3)}$alkyl-O—C$_{(3-5)}$cycloalkyl groups are unsubstituted or substituted with one to six R$^{2a}$ groups.

In some embodiments, disclosed herein is a compound of Formula I, or a pharmaceutically acceptable salt thereof, wherein R² is H, —C$_{(1-3)}$alkyl, —C$_{(3-5)}$cycloalkyl, —C$_{(1-3)}$alkyl-O—C$_{(1-3)}$alkyl, —C$_{(1-3)}$alkyl-O—C$_{(3-5)}$cycloalkyl, or 4- to 6-membered heterocyclyl, wherein the —C$_{(1-3)}$alkyl and —C$_{(3-5)}$cycloalkyl are unsubstituted or substituted with one to six R$^{2a}$ groups.

In some embodiments, disclosed herein is a compound of Formula I, or a pharmaceutically acceptable salt thereof, wherein R² is H, —C$_{(1-3)}$alkyl, —C$_{(3-5)}$cycloalkyl, —C$_{(1-3)}$alkyl-O—C$_{(1-3)}$alkyl, —C$_{(1-3)}$alkyl-O—C$_{(3-5)}$cycloalkyl, or 4- to 6-membered heterocyclyl, wherein the —C$_{(1-3)}$alkyl is unsubstituted or substituted with one to six fluorine atoms, and wherein the —C$_{(3-5)}$cycloalkyl is unsubstituted or substituted with one —CN group.

In some embodiments, disclosed herein is a compound of Formula I, or a pharmaceutically acceptable salt thereof, wherein R² is H, —C$_{(1-3)}$alkyl, —C$_{(3-5)}$cycloalkyl, —C$_{(1-3)}$alkyl-O—C$_{(1-3)}$alkyl, —C$_{(1-3)}$alkyl-O—C$_{(3-5)}$cycloalkyl, or tetrahydropyranyl, wherein the —C$_{(1-3)}$alkyl is unsubstituted or substituted with one to six fluorine atoms, and wherein the —C$_{(3-5)}$cycloalkyl is unsubstituted or substituted with one —CN groups.

In some embodiments, disclosed herein is a compound of Formula I, or a pharmaceutically acceptable salt thereof, wherein R² is H, —C$_{(3-5)}$cycloalkyl, —C$_{(1-3)}$alkyl-O—C$_{(1-3)}$alkyl, or —C$_{(1-3)}$alkyl-O—C$_{(3-5)}$cycloalkyl.

In some embodiments, disclosed herein is a compound of Formula I, or a pharmaceutically acceptable salt thereof, wherein R² is H. In some embodiments, disclosed herein is a compound of Formula I, or a pharmaceutically acceptable salt thereof, wherein R² is —C$_{(1-3)}$alkyl that is unsubstituted or substituted with one to six fluorine atoms. In some embodiments, disclosed herein is a compound of Formula I, or a pharmaceutically acceptable salt thereof, wherein R² is —C$_{(3-5)}$cycloalkyl that is unsubstituted or substituted with one —CN group. In some embodiments, disclosed herein is a compound of Formula I, or a pharmaceutically acceptable salt thereof, wherein R² is —C$_{(1-3)}$alkyl-O—C$_{(1-3)}$alkyl. In some embodiments, disclosed herein is a compound of Formula I, or a pharmaceutically acceptable salt thereof, wherein R² is —C$_{(1-3)}$alkyl-O—C$_{(3-5)}$cycloalkyl. In some embodiments, disclosed herein is a compound of Formula I, or a pharmaceutically acceptable salt thereof, wherein R² is 4- to 6-membered heterocyclyl.

In some embodiments, disclosed herein is a compound of Formula I, or a pharmaceutically acceptable salt thereof, wherein R² is:

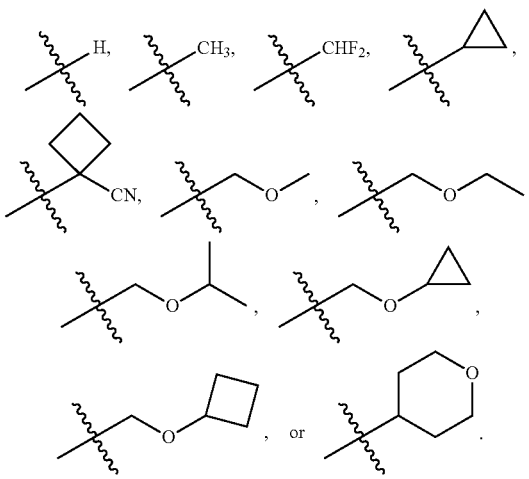

In some embodiments, disclosed herein is a compound of Formula I, or a pharmaceutically acceptable salt thereof, wherein R² is H, cyclopropyl, —CH$_2$OCH$_2$CH$_3$, —CH$_2$OCH$_3$, or —CH$_2$—O-cyclopropyl.

In some embodiments, disclosed herein is a compound of Formula I, or a pharmaceutically acceptable salt thereof, wherein R² is H, cyclopropyl, —CH$_2$OCH$_3$, or —CH$_2$—O-cyclopropyl.

In some embodiments, disclosed herein is a compound of Formula I, or a pharmaceutically acceptable salt thereof, wherein R² is H. In some embodiments, disclosed herein is a compound of Formula I, or a pharmaceutically acceptable salt thereof, wherein R² is —CH$_3$. In some embodiments, disclosed herein is a compound of Formula I, or a pharmaceutically acceptable salt thereof, wherein R² is —CHF$_2$. In some embodiments, disclosed herein is a compound of Formula I, or a pharmaceutically acceptable salt thereof, wherein $R^2$ is cyclopropyl. In some embodiments, disclosed herein is a compound of Formula I, or a pharmaceutically acceptable salt thereof, wherein $R^2$ is cyanocyclobutyl. In some embodiments, disclosed herein is a compound of Formula I, or a pharmaceutically acceptable salt thereof, wherein $R^2$ is —CH$_2$OCH$_3$. In some embodiments, disclosed herein is a compound of Formula I, or a pharmaceutically acceptable salt thereof, wherein $R^2$ is —CH$_2$OCH$_2$CH$_3$. In some embodiments, disclosed herein is a compound of Formula I, or a pharmaceutically acceptable salt thereof, wherein $R^2$ is —CH$_2$OCH(CH$_3$)$_2$. In some embodiments, disclosed herein is a compound of Formula I, or a pharmaceutically acceptable salt thereof, wherein $R^2$ is —CH$_2$—O-cyclopropyl. In some embodiments, disclosed herein is a compound of Formula I, or a pharmaceutically acceptable salt thereof, wherein $R^2$ is —CH$_2$—O-cyclobutyl. In some embodiments, disclosed herein is a compound of Formula I, or a pharmaceutically acceptable salt thereof, wherein $R^2$ is tetrahydropyranyl.

In some embodiments, disclosed herein is a compound of Formula I, or a pharmaceutically acceptable salt thereof, which is a compound of Formula Ia:

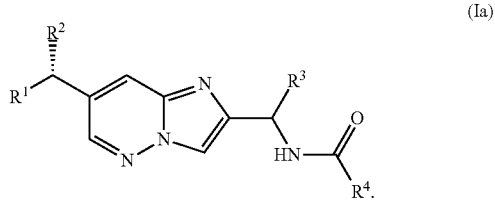

(Ia)

In some embodiments, disclosed herein is a compound of Formula I, or a pharmaceutically acceptable salt thereof, wherein $R^{2a}$ is fluorine. In some embodiments, disclosed herein is a compound of Formula I, or a pharmaceutically acceptable salt thereof, wherein $R^{2a}$ is —CN.

In some embodiments, disclosed herein is a compound of Formula I, or a pharmaceutically acceptable salt thereof, wherein $R^3$ is —C$_{(1-10)}$alkyl, —C$_{(1-6)}$alkyl-O—C$_{(1-6)}$alkyl, —C$_{(1-6)}$alkyl-O—C$_{(3-5)}$cycloalkyl, —C$_{(1-6)}$alkyl-O—C$_{(3-5)}$cycloalkyl-C$_{(1-3)}$alkyl, —C$_{(3-8)}$cycloalkyl, or —CH(C$_{(3-5)}$cycloalkyl)$_2$, each of which is unsubstituted or substituted with one to six fluorine atoms.

In some embodiments, disclosed herein is a compound of Formula I, or a pharmaceutically acceptable salt thereof, wherein $R^3$ is —C$_{(1-8)}$alkyl, —C$_{(1-6)}$alkyl-O—C$_{(1-6)}$alkyl, —C$_{(1-6)}$alkyl-O—C$_{(3-5)}$cycloalkyl, —C$_{(1-6)}$alkyl-O—C$_{(3-5)}$cycloalkyl-C$_{(1-3)}$alkyl, —C$_{(3-8)}$cycloalkyl, or —CH(C$_{(3-5)}$cycloalkyl)$_2$, each of which is unsubstituted or substituted with one to six fluorine atoms.

In some embodiments, disclosed herein is a compound of Formula I, or a pharmaceutically acceptable salt thereof, wherein $R^3$ is —C$_{(1-7)}$alkyl, —C$_{(1-6)}$alkyl-O—C$_{(1-6)}$alkyl, —C$_{(1-6)}$alkyl-O—C$_{(3-5)}$cycloalkyl, —C$_{(1-6)}$alkyl-O—C$_{(3-5)}$cycloalkyl-C$_{(1-3)}$alkyl, —C$_{(3-8)}$cycloalkyl, or —CH(C$_{(3-5)}$cycloalkyl)$_2$, each of which is unsubstituted or substituted with one to six fluorine atoms.

In some embodiments, disclosed herein is a compound of Formula I, or a pharmaceutically acceptable salt thereof, wherein $R^3$ is —C$_{(1-6)}$alkyl, —C$_{(1-6)}$alkyl-O—C$_{(1-6)}$alkyl, —C$_{(1-6)}$alkyl-O—C$_{(3-5)}$cycloalkyl, —C$_{(1-6)}$alkyl-O—C$_{(3-5)}$cycloalkyl-C$_{(1-3)}$alkyl, —C$_{(3-8)}$cycloalkyl, or —CH(C$_{(3-5)}$cycloalkyl)$_2$, each of which is unsubstituted or substituted with one to six fluorine atoms.

In some embodiments, disclosed herein is a compound of Formula I, or a pharmaceutically acceptable salt thereof, wherein $R^3$ is —C$_{(5-6)}$alkyl, —C$_{(1-4)}$alkyl-O—C$_{(1-4)}$alkyl, —C$_{(1-3)}$alkyl-O—C$_{(3-5)}$cycloalkyl, —C$_{(1-3)}$alkyl-O—C$_{(3-5)}$cycloalkyl-CH$_3$, —C$_{(5-6)}$cycloalkyl, or —CH(C$_{(3-5)}$cycloalkyl)$_2$, each of which is unsubstituted or substituted with one to six fluorine atoms.

In some embodiments, disclosed herein is a compound of Formula I, or a pharmaceutically acceptable salt thereof, wherein $R^3$ is —C$_{(5-6)}$alkyl substituted with two to three fluorine atoms, —C$_{(1-6)}$alkyl-O—C$_{(1-5)}$alkyl-CF$_3$, —C$_{(1-6)}$alkyl-O—C$_{(3-5)}$cycloalkyl, —C$_{(1-6)}$alkyl-O—C$_{(3-5)}$cycloalkyl-CF$_3$, —C$_{(5-6)}$cycloalkyl substituted with two fluorine atoms, or —CH(C$_{(3-5)}$cycloalkyl)$_2$.

In some embodiments, disclosed herein is a compound of Formula I, or a pharmaceutically acceptable salt thereof, wherein $R^3$ is —C$_{(5-7)}$alkyl substituted with two to three fluorine atoms, —C$_{(1-6)}$alkyl-O—C$_{(1-5)}$alkyl-CF$_3$, —C$_{(1-6)}$alkyl-O—C$_{(3-5)}$cycloalkyl, —C$_{(1-6)}$alkyl-O—C$_{(3-5)}$cycloalkyl-CF$_3$, —C$_{(5-6)}$cycloalkyl substituted with two fluorine atoms, or —CH(C$_{(3-5)}$cycloalkyl)$_2$.

In some embodiments, disclosed herein is a compound of Formula I, or a pharmaceutically acceptable salt thereof, wherein $R^3$ is —C$_{(1-6)}$alkyl, —C$_{(1-6)}$alkyl-O—C$_{(1-6)}$alkyl, —C$_{(1-6)}$alkyl-O—C$_{(3-5)}$cycloalkyl, or —C$_{(3-8)}$cycloalkyl, each of which is unsubstituted or substituted with one to six fluorine atoms.

In some embodiments, disclosed herein is a compound of Formula I, or a pharmaceutically acceptable salt thereof, wherein $R^3$ is —C$_{(1-6)}$alkyl, —C$_{(1-6)}$alkyl-O—C$_{(1-6)}$alkyl, or —C$_{(1-6)}$alkyl-O—C$_{(3-5)}$cycloalkyl, each of which is unsubstituted or substituted with one to six fluorine atoms.

In some embodiments, disclosed herein is a compound of Formula I, or a pharmaceutically acceptable salt thereof, wherein $R^3$ is —C$_{(1-6)}$alkyl, —C$_{(1-4)}$alkyl-O—C$_{(1-4)}$alkyl, —C$_{(1-3)}$alkyl-O—C$_{(3-5)}$cycloalkyl, or cyclohexyl, each of which is substituted or unsubstituted with one to six fluorine atoms.

In some embodiments, disclosed herein is a compound of Formula I, or a pharmaceutically acceptable salt thereof, wherein $R^3$ is —C$_{(1-6)}$alkyl, —C$_{(1-4)}$alkyl-O—C$_{(1-4)}$alkyl, or cyclohexyl, each of which is substituted or unsubstituted with one to six fluorine atoms.

In some embodiments, disclosed herein is a compound of Formula I, or a pharmaceutically acceptable salt thereof, wherein $R^3$ is —C$_{(1-6)}$alkyl, —C$_{(1-6)}$alkyl-O—C$_{(1-5)}$alkyl-CF$_3$, or cyclohexyl, wherein the —C$_{(1-6)}$alkyl is substituted with one to three fluorine atoms and wherein the cyclohexyl is substituted with two fluorine atoms.

In some embodiments, disclosed herein is a compound of Formula I, or a pharmaceutically acceptable salt thereof, wherein $R^3$ is —C$_{(1-5)}$alkyl, —C$_{(1-6)}$alkyl-O—C$_{(1-5)}$alkyl-CF$_3$, or cyclohexyl, wherein the —C$_{(1-5)}$alkyl is substituted with one —CF$_3$ and wherein the cyclohexyl is substituted with two fluorine atoms.

In some embodiments, disclosed herein is a compound of Formula I, or a pharmaceutically acceptable salt thereof, wherein $R^3$ is —C$_{(1-6)}$alkyl-O—C$_{(1-5)}$alkyl-CF$_3$ or cyclohexyl, wherein the cyclohexyl is substituted with two fluorine atoms.

In some embodiments, disclosed herein is a compound of Formula I, or a pharmaceutically acceptable salt thereof, wherein $R^3$ is —C$_{(1-6)}$alkyl that is unsubstituted or substituted with one to six fluorine atoms. In some embodiments, disclosed herein is a compound of Formula I, or a pharmaceutically acceptable salt thereof, wherein $R^3$ is —C$_{(5-6)}$alkyl substituted with two to three fluorine atoms. In some embodiments, disclosed herein is a compound of Formula I, or a pharmaceutically acceptable salt thereof, wherein $R^3$ is —$C_{(1-5)}$alkyl substituted with one —$CF_3$. In some embodiments, disclosed herein is a compound of Formula I, or a pharmaceutically acceptable salt thereof, wherein $R^3$ is —$C_{(5)}$alkyl substituted with one —$CF_3$.

In some embodiments, disclosed herein is a compound of Formula I, or a pharmaceutically acceptable salt thereof, wherein $R^3$ is —$C_{(1-6)}$alkyl-O—$C_{(1-6)}$alkyl that is unsubstituted or substituted with one to six fluorine atoms. In some embodiments, disclosed herein is a compound of Formula I, or a pharmaceutically acceptable salt thereof, wherein $R^3$ is —$C_{(1-6)}$alkyl-O—$C_{(1-5)}$alkyl-$CF_3$.

In some embodiments, disclosed herein is a compound of Formula I, or a pharmaceutically acceptable salt thereof, wherein $R^3$ is —$C_{(1-6)}$alkyl-O—$C_{(3-5)}$cycloalkyl that is unsubstituted or substituted with one to six fluorine atoms. In some embodiments, disclosed herein is a compound of Formula I, or a pharmaceutically acceptable salt thereof, wherein $R^3$ is —$C_{(1-6)}$alkyl-O—$C_{(3-5)}$cycloalkyl-$C_{(1-3)}$alkyl that is unsubstituted or substituted with one to six fluorine atoms. In some embodiments, disclosed herein is a compound of Formula I, or a pharmaceutically acceptable salt thereof, wherein $R^3$ is —$C_{(1-6)}$alkyl-O—$C_{(3-5)}$cycloalkyl-$CF_3$.

In some embodiments, disclosed herein is a compound of Formula I, or a pharmaceutically acceptable salt thereof, wherein $R^3$ is —$C_{(3-8)}$cycloalkyl that is unsubstituted or substituted with one to six fluorine atoms. In some embodiments, disclosed herein is a compound of Formula I, or a pharmaceutically acceptable salt thereof, wherein $R^3$ is —$C_{(5-6)}$cycloalkyl substituted with two fluorine atoms. In some embodiments, disclosed herein is a compound of Formula I, or a pharmaceutically acceptable salt thereof, wherein $R^3$ is cyclohexyl substituted with two fluorine atoms.

In some embodiments, disclosed herein is a compound of Formula I, or a pharmaceutically acceptable salt thereof, wherein $R^3$ is —$C_{(1-3)}$alkyl-($C_{(3-5)}$cycloalkyl)$_{1-2}$ that is unsubstituted or substituted with one to six fluorine atoms. In some embodiments, disclosed herein is a compound of Formula I, or a pharmaceutically acceptable salt thereof, wherein $R^3$ is —$CH(C_{(3-5)}$cycloalkyl)$_2$.

In some embodiments, disclosed herein is a compound of Formula I, or a pharmaceutically acceptable salt thereof, wherein $R^3$ is —$C_{(5-6)}$alkyl substituted with two to three fluorine atoms, —$C_{(5-6)}$cycloalkyl substituted with two fluorine atoms,

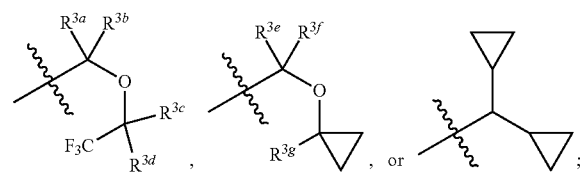

$R^{3a}$, $R^{3b}$, $R^{3c}$, and $R^{3d}$ are each independently H or —$CH_3$;
$R^{3e}$ and $R^{3f}$ are each independently H or —$CH_3$; and
$R^{3g}$ is H or —$CF_3$.

In some embodiments, disclosed herein is a compound of Formula I, or a pharmaceutically acceptable salt thereof, wherein $R^3$ is —$C_{(5-6)}$alkyl substituted with two to three fluorine atoms, —$C_{(5-6)}$cycloalkyl substituted with two fluorine atoms, or

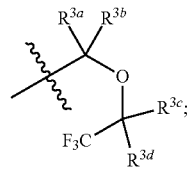

and
$R^{3a}$, $R^{3b}$, $R^{3c}$, and $R^{3d}$ are each independently H or —$CH_3$.

In some embodiments, disclosed herein is a compound of Formula I, or a pharmaceutically acceptable salt thereof, wherein $R^3$ is —$C_{(1-5)}$alkyl substituted with one —$CF_3$,

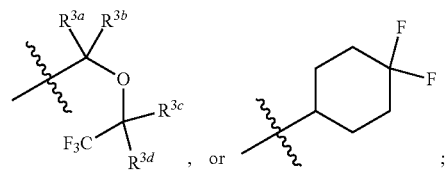

$R^{3a}$, $R^{3b}$, $R^{3c}$, and $R^{3d}$ are each independently H or —$CH_3$.

In some embodiments, disclosed herein is a compound of Formula I, or a pharmaceutically acceptable salt thereof, wherein $R^3$ is —$C_{(1-5)}$alkyl substituted with one —$CF_3$ or

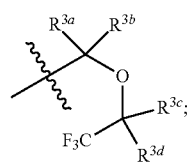

$R^{3a}$, $R^{3b}$, $R^{3c}$, and $R^{3d}$ are each independently H or —$CH_3$.

In some embodiments, disclosed herein is a compound of Formula I, or a pharmaceutically acceptable salt thereof, wherein $R^3$ is:

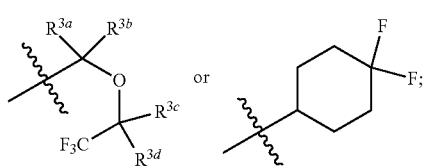

$R^{3a}$, $R^{3b}$, $R^{3c}$, and $R^{3d}$ are each independently H or —$CH_3$.

In some embodiments, disclosed herein is a compound of Formula I, or a pharmaceutically acceptable salt thereof, wherein $R^3$ is:

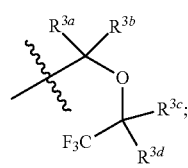

$R^{3a}$, $R^{3b}$, $R^{3c}$, and $R^{3d}$ are each independently H or —CH$_3$.

In some embodiments, disclosed herein is a compound of Formula I, or a pharmaceutically acceptable salt thereof, wherein $R^3$ is:

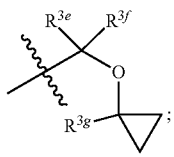

$R^{3e}$ and $R^{3f}$ are each independently H or —CH$_3$; and $R^{3g}$ is H or —CF$_3$.

In some embodiments, disclosed herein is a compound of Formula I, or a pharmaceutically acceptable salt thereof, wherein $R^3$ is —C$_{(1-5)}$alkyl substituted with one —CF$_3$.

In some embodiments, disclosed herein is a compound of Formula I, or a pharmaceutically acceptable salt thereof, wherein $R^3$ is:

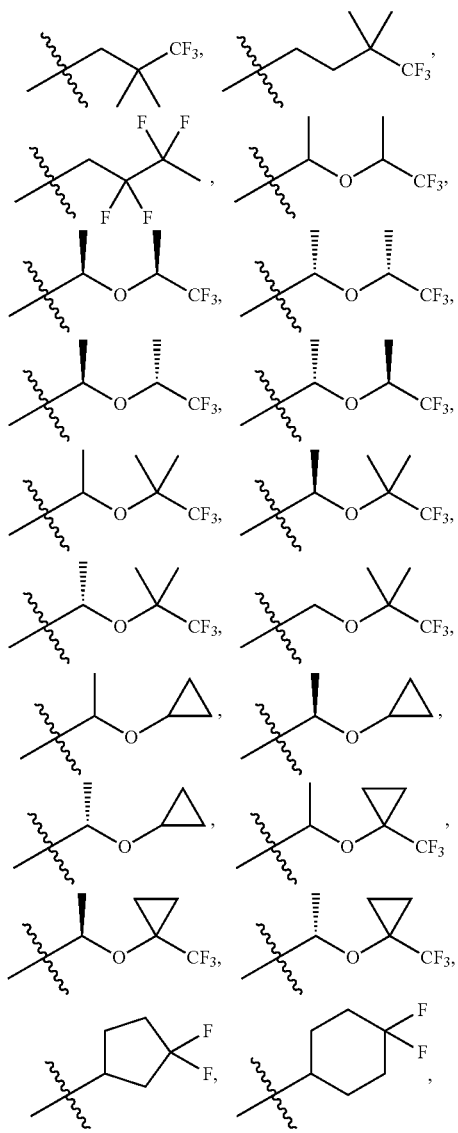

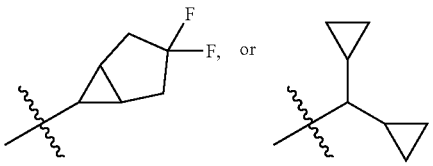

In some embodiments, disclosed herein is a compound of Formula I, or a pharmaceutically acceptable salt thereof, wherein $R^3$ is:

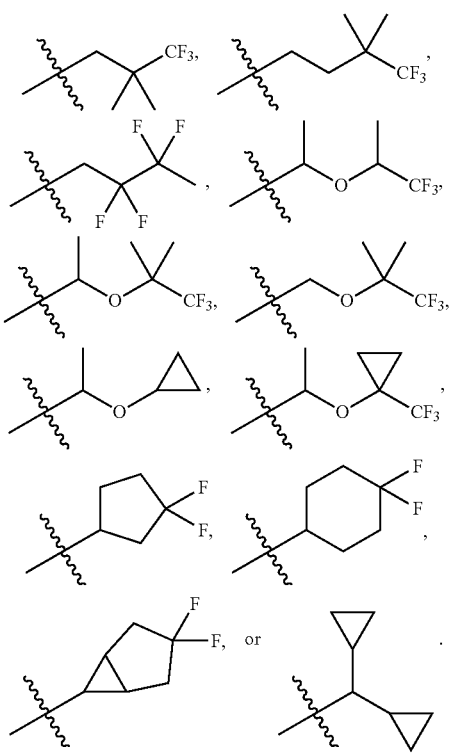

In some embodiments, disclosed herein is a compound of Formula I, or a pharmaceutically acceptable salt thereof, wherein $R^3$ is:

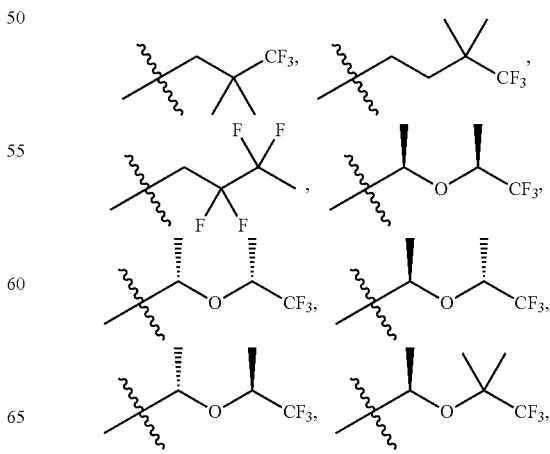

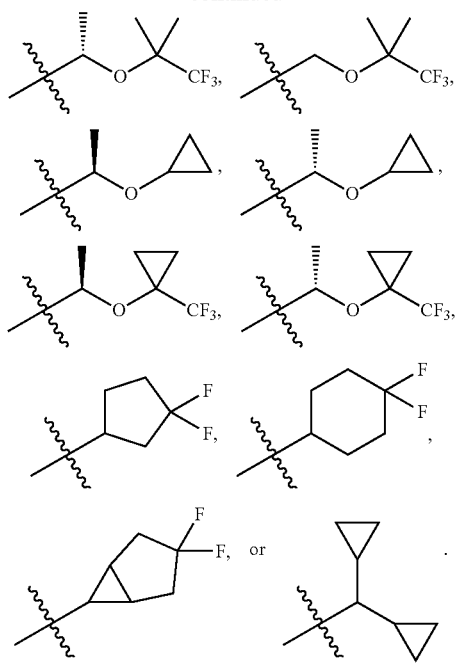

In some embodiments, disclosed herein is a compound of Formula I, or a pharmaceutically acceptable salt thereof, wherein R³ is:

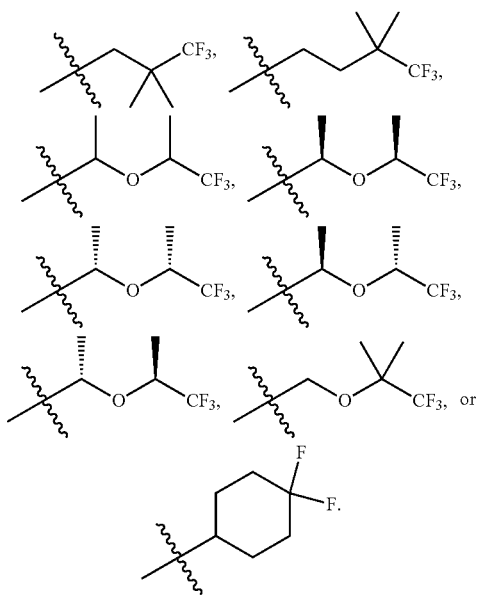

In some embodiments, disclosed herein is a compound of Formula I, or a pharmaceutically acceptable salt thereof, wherein R³ is:

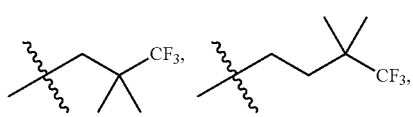

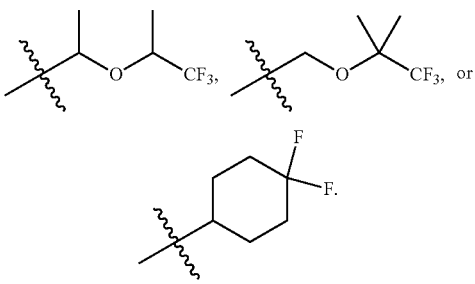

In some embodiments, disclosed herein is a compound of Formula I, or a pharmaceutically acceptable salt thereof, wherein R³ is:

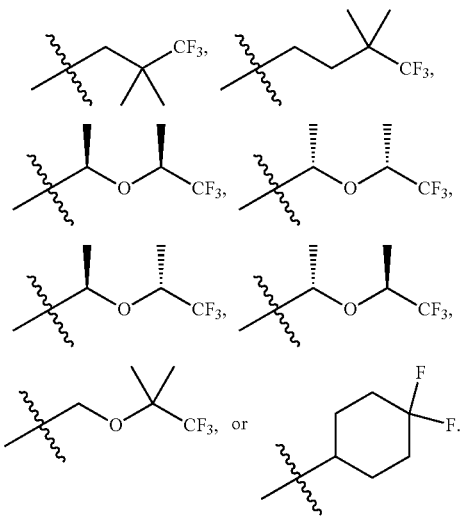

In some embodiments, disclosed herein is a compound of Formula I, or a pharmaceutically acceptable salt thereof, wherein R³ is:

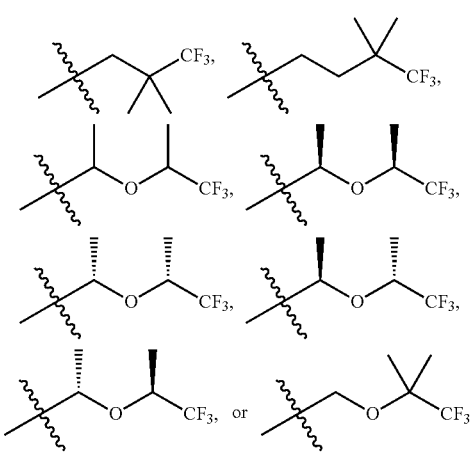

In some embodiments, disclosed herein is a compound of Formula I, or a pharmaceutically acceptable salt thereof, wherein R³ is:

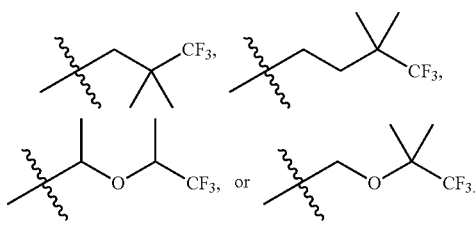

In some embodiments, disclosed herein is a compound of Formula I, or a pharmaceutically acceptable salt thereof, wherein $R^3$ is:

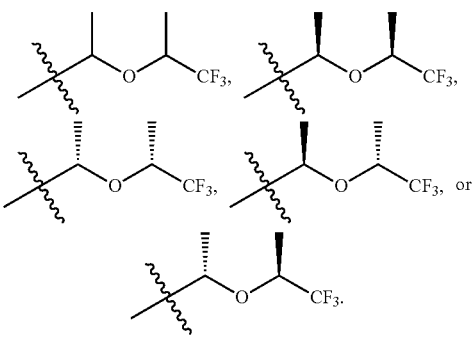

In some embodiments, disclosed herein is a compound of Formula I, or a pharmaceutically acceptable salt thereof, wherein $R^3$ is

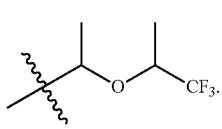 [SMILES: *C(C)OC(C)C(F)(F)F]

In some embodiments, disclosed herein is a compound of Formula I, or a pharmaceutically acceptable salt thereof, wherein $R^3$ is

In some embodiments, disclosed herein is a compound of Formula I, or a pharmaceutically acceptable salt thereof, wherein $R^3$ is

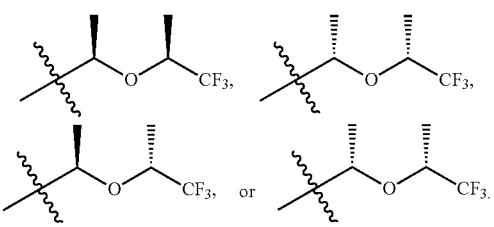

In some embodiments, disclosed herein is a compound of Formula I, or a pharmaceutically acceptable salt thereof, wherein $R^3$ is

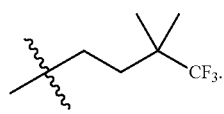

In some embodiments, disclosed herein is a compound of Formula I, or a pharmaceutically acceptable salt thereof, wherein $R^3$ is

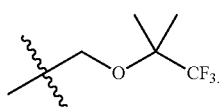 [SMILES: *COC(C)(C)C(F)(F)F]

In some embodiments, disclosed herein is a compound of Formula I, or a pharmaceutically acceptable salt thereof, wherein $R^3$ is

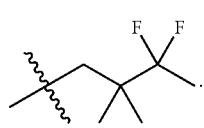

In some embodiments, disclosed herein is a compound of Formula I, or a pharmaceutically acceptable salt thereof, wherein $R^3$ is

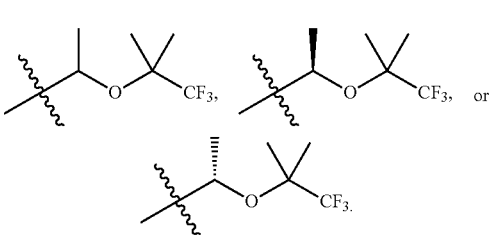

In some embodiments, disclosed herein is a compound of Formula I, or a pharmaceutically acceptable salt thereof, wherein $R^3$ is

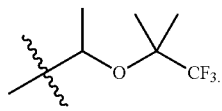 [SMILES: *C(C)OC(C)(C)C(F)(F)F]

In some embodiments, disclosed herein is a compound of Formula I, or a pharmaceutically acceptable salt thereof, wherein $R^3$ is

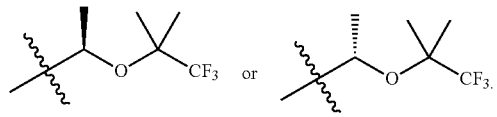 [SMILES: *[C@@H](C)OC(C)(C)C(F)(F)F ; *[C@H](C)OC(C)(C)C(F)(F)F]

In some embodiments, disclosed herein is a compound of Formula I, or a pharmaceutically acceptable salt thereof, wherein $R^3$ is

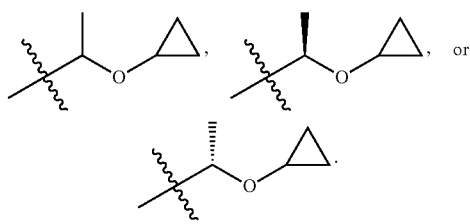

In some embodiments, disclosed herein is a compound of Formula I, or a pharmaceutically acceptable salt thereof, wherein $R^3$ is

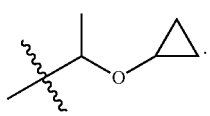 [SMILES: *C(C)OC1CC1]

In some embodiments, disclosed herein is a compound of Formula I, or a pharmaceutically acceptable salt thereof, wherein $R^3$ is

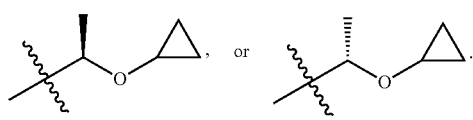

In some embodiments, disclosed herein is a compound of Formula I, or a pharmaceutically acceptable salt thereof, wherein $R^3$ is

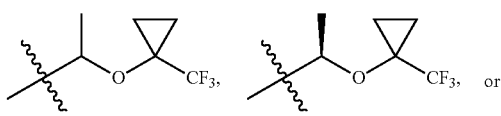

-continued

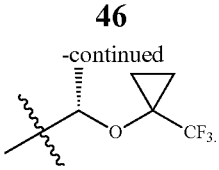

In some embodiments, disclosed herein is a compound of Formula I, or a pharmaceutically acceptable salt thereof, wherein $R^3$ is

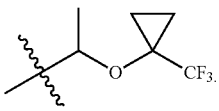 [SMILES: *C(C)OC1(C(F)(F)F)CC1]

In some embodiments, disclosed herein is a compound of Formula I, or a pharmaceutically acceptable salt thereof, wherein $R^3$ is

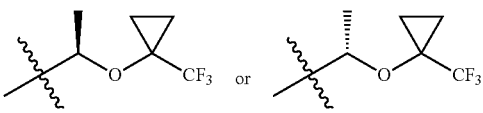

In some embodiments, disclosed herein is a compound of Formula I, or a pharmaceutically acceptable salt thereof, wherein $R^3$ is

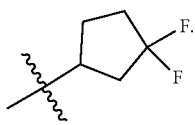 [SMILES: *C1CCC(F)(F)C1]

In some embodiments, disclosed herein is a compound of Formula I, or a pharmaceutically acceptable salt thereof, wherein $R^3$ is

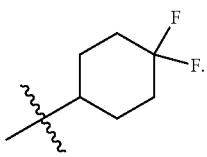 [SMILES: *C1CCC(F)(F)CC1]

In some embodiments, disclosed herein is a compound of Formula I, or a pharmaceutically acceptable salt thereof, wherein $R^3$ is

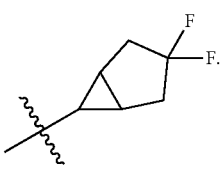 [SMILES: *C1C2CC(F)(F)CC12]

In some embodiments, disclosed herein is a compound of Formula I, or a pharmaceutically acceptable salt thereof, wherein $R^3$ is

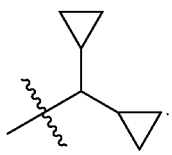 [SMILES: *C(C1CC1)C1CC1]

In some embodiments, disclosed herein is a compound of Formula I, or a pharmaceutically acceptable salt thereof, which is a compound of Formula Ib:

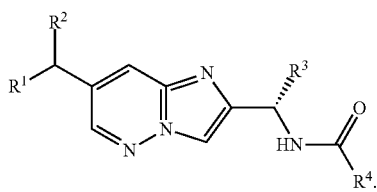

(Ib)

In some embodiments, disclosed herein is a compound of Formula I, or a pharmaceutically acceptable salt thereof, which is a compound of Formula Ib-1:

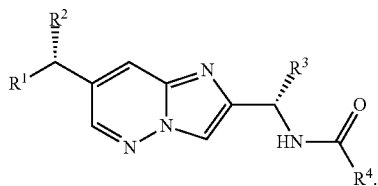

(Ib-1)

In some embodiments, disclosed herein is a compound of Formula I, or a pharmaceutically acceptable salt thereof, which is a compound of Formula Ic:

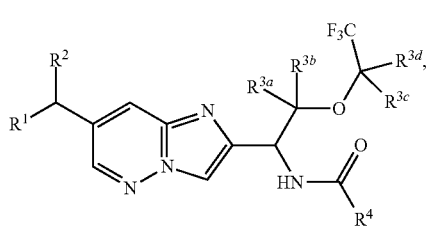

(Ic)

wherein $R^{3a}$, $R^{3b}$, $R^{3c}$, and $R^{3d}$ are each independently H or —CH$_3$.

In some embodiments, disclosed herein is a compound of Formula I, or a pharmaceutically acceptable salt thereof, which is a compound of Formula Ic-1:

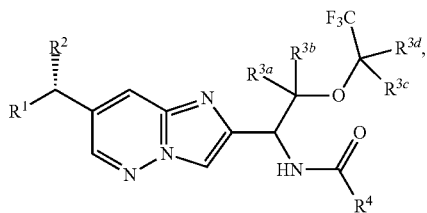

(Ic-1)

wherein $R^{3a}$, $R^{3b}$, $R^{3c}$, and $R^{3d}$ are each independently H or —CH$_3$.

In some embodiments, disclosed herein is a compound of Formula I, or a pharmaceutically acceptable salt thereof, which is a compound of Formula Ic-2:

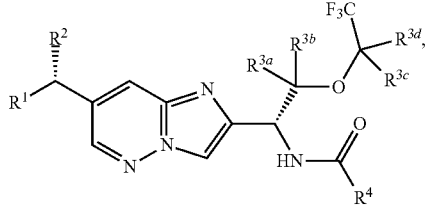

(Ic-2)

wherein $R^{3a}$, $R^{3b}$, $R^{3c}$, and $R^{3d}$ are each independently H or —CH$_3$.

In some embodiments, disclosed herein is a compound of Formula I, or a pharmaceutically acceptable salt thereof, which is a compound of Formula Id:

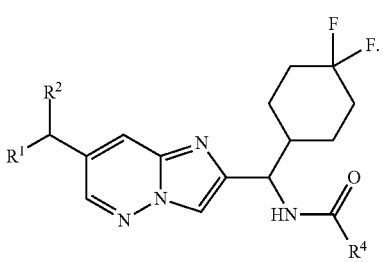

(Id)

In some embodiments, disclosed herein is a compound of Formula I, or a pharmaceutically acceptable salt thereof, which is a compound of Formula Id-1:

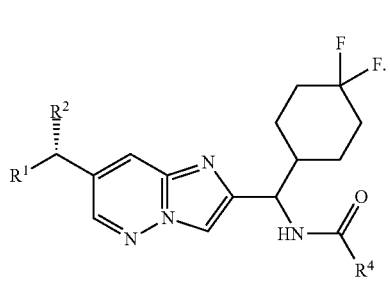

(Id-1)

In some embodiments, disclosed herein is a compound of Formula I, or a pharmaceutically acceptable salt thereof, which is a compound of Formula Id-2:

(Id-2)

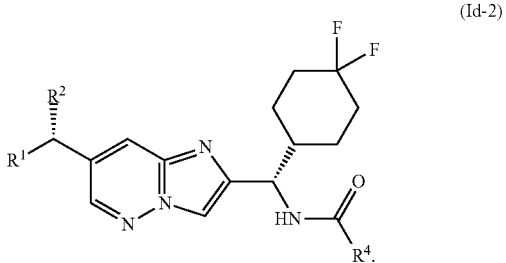

In some embodiments, disclosed herein is a compound of Formula I, or a pharmaceutically acceptable salt thereof, wherein $R^4$ is a 5-membered heteroaryl that is substituted with one or two $R^{4a}$ groups.

In some embodiments, disclosed herein is a compound of Formula I, or a pharmaceutically acceptable salt thereof, wherein $R^4$ is a 5-membered heteroaryl comprising one to three heteroatoms selected from O and N, wherein the 5-membered heteroaryl is unsubstituted or substituted with one to two $R^{4a}$ groups.

In some embodiments, disclosed herein is a compound of Formula I, or a pharmaceutically acceptable salt thereof, wherein $R^4$ is pyrrolyl, pyrazolyl, imidazolyl, triazolyl, oxazolyl, isoxazolyl, or oxadiazolyl, each of which is unsubstituted or substituted with one to two $R^{4a}$ groups. In some embodiments, disclosed herein is a compound of Formula I, or a pharmaceutically acceptable salt thereof, wherein $R^4$ is pyrazolyl, triazolyl, isoxazolyl, or oxadiazolyl, each of which is unsubstituted or substituted with one to two $R^{4a}$ groups. In some embodiments, disclosed herein is a compound of Formula I, or a pharmaceutically acceptable salt thereof, wherein $R^4$ is pyrazolyl or oxadiazolyl, each of which is unsubstituted or substituted with one to two $R^{4a}$ groups.

In some embodiments, disclosed herein is a compound of Formula I, or a pharmaceutically acceptable salt thereof, wherein $R^4$ is pyrrolyl, pyrazolyl, imidazolyl, 1,2,3-triazolyl, 1,2,4-triazolyl, oxazolyl, isoxazolyl, 1,2,3-oxadiazolyl, 1,2,4-oxadiazolyl, 1,2,5-oxadiazolyl, or 1,3,4-oxadiazolyl, each of which is unsubstituted or substituted with one to two $R^{4a}$ groups. In some embodiments, disclosed herein is a compound of Formula I, or a pharmaceutically acceptable salt thereof, wherein $R^4$ is pyrazolyl, 1,2,3-triazolyl, 1,2,4-triazolyl, isoxazolyl, or 1,2,5-oxadiazolyl, each of which is unsubstituted or substituted with one to two $R^{4a}$ groups. In some embodiments, disclosed herein is a compound of Formula I, or a pharmaceutically acceptable salt thereof, wherein $R^4$ is pyrazolyl or 1,2,5-oxadiazolyl, each of which is unsubstituted or substituted with one to two $R^{4a}$ groups.

In some embodiments, disclosed herein is a compound of Formula I, or a pharmaceutically acceptable salt thereof, wherein $R^4$ is:

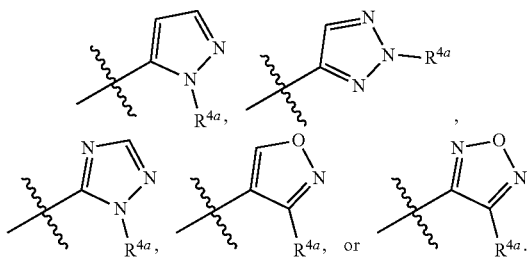

In some embodiments, disclosed herein is a compound of Formula I, or a pharmaceutically acceptable salt thereof, wherein $R^4$ is:

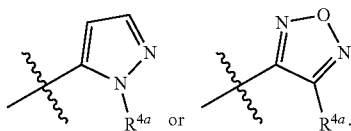

In some embodiments, disclosed herein is a compound of Formula I, or a pharmaceutically acceptable salt thereof, wherein $R^4$ is

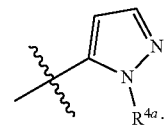

In some embodiments, disclosed herein is a compound of Formula I, or a pharmaceutically acceptable salt thereof, wherein $R^4$ is

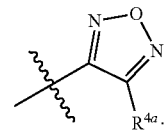

In some embodiments, disclosed herein is a compound of Formula I, or a pharmaceutically acceptable salt thereof, wherein $R^{4a}$ is —$C_{(1-4)}$alkyl, —O—$C_{(1-4)}$alkyl, —$C_{(1-4)}$alkyl-O—$C_{(1-4)}$alkyl, or —$C_{(0-2)}$alkyl-$C_{(3-4)}$cycloalkyl, wherein the —$C_{(1-4)}$alkyl, —O—$C_{(1-4)}$alkyl, —$C_{(1-4)}$alkyl-O—$C_{(1-4)}$alkyl, and —$C_{(0-2)}$alkyl-$C_{(3-4)}$cycloalkyl are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein $R^{4a}$ is —$C_{(1-6)}$alkyl, —O—$C_{(1-6)}$alkyl, or —$C_{(0-2)}$alkyl-$C_{(3-6)}$cycloalkyl, each of which are unsubstituted or substituted with one to six substituents independently selected from fluorine, —$CH_3$, —$CD_3$, —$CD_2CD_3$, —$CH_2F$, —$CHF_2$, and —$CF_3$. In some embodiments, disclosed herein is a compound of Formula I, or a pharmaceutically acceptable salt thereof, wherein $R^{4a}$ is —$C_{(1-4)}$alkyl, —O—$C_{(1-4)}$alkyl, or —$C_{(0-2)}$alkyl-$C_{(3-4)}$cycloalkyl, each of which are unsubstituted or substituted with one to six substituents independently selected from fluorine, —$CH_3$, —$CD_3$, —$CD_2CD_3$, —$CH_2F$, —$CHF_2$, and —$CF_3$.

In some embodiments, disclosed herein is a compound of Formula I, or a pharmaceutically acceptable salt thereof, wherein $R^{4a}$ is —$C_{(1-6)}$alkyl or —$C_{(0-2)}$alkyl-$C_{(3-6)}$cycloalkyl, each of which are unsubstituted or substituted with one to six substituents independently selected from fluorine, —$CH_3$, —$CD_3$, —$CD_2CD_3$, —$CH_2F$, —$CHF_2$, and —$CF_3$. In some embodiments, disclosed herein is a compound of Formula I, or a pharmaceutically acceptable salt thereof, wherein $R^{4a}$ is —$C_{(1-4)}$alkyl or —$C_{(0-2)}$alkyl-$C_{(3-4)}$cycloalkyl, each of which are unsubstituted or substituted with one to six substituents independently selected from fluorine, —CH₃, —CD₃, —CD₂CD₃, —CH₂F, —CHF₂, and —CF₃.

In some embodiments, disclosed herein is a compound of Formula I, or a pharmaceutically acceptable salt thereof, wherein $R^{4a}$ is methyl, ethyl, isopropyl, —CD₂CD₃, —CHF₂, —CF₃, —CH₂CH₂CF₃, —OCH₃, —OCH₂CHF₂, —CH₂OCHF₂, cyclopropyl, or —CH₂-cyclopropyl.

In some embodiments, disclosed herein is a compound of Formula I, or a pharmaceutically acceptable salt thereof, wherein $R^{4a}$ is methyl, isopropyl, —CD₂CD₃, —CH₂CH₂CF₃, —OCH₂CHF₂, —CH₂OCHF₂, cyclopropyl, or —CH₂-cyclopropyl.

In some embodiments, disclosed herein is a compound of Formula I, or a pharmaceutically acceptable salt thereof, wherein $R^{4a}$ is methyl, ethyl, isopropyl, —CHF₂, —CF₃, —OCH₃, or cyclopropyl.

In some embodiments, disclosed herein is a compound of Formula I, or a pharmaceutically acceptable salt thereof, wherein $R^{4a}$ is methyl, isopropyl, or cyclopropyl.

In some embodiments, disclosed herein is a compound of Formula I, or a pharmaceutically acceptable salt thereof, wherein $R^4$ is:

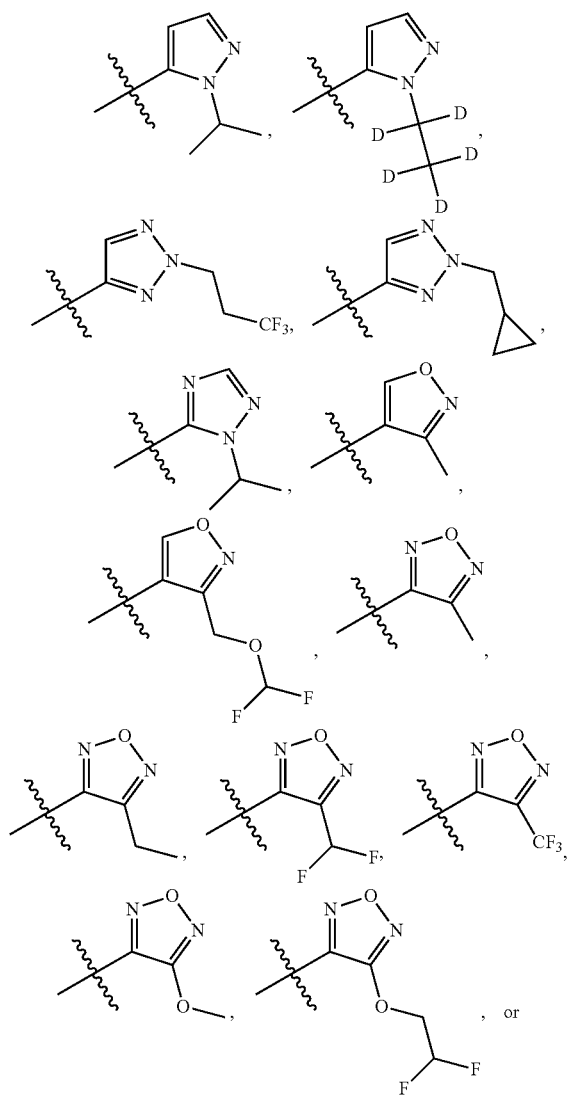

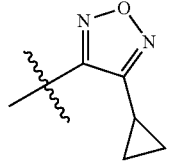

In some embodiments, disclosed herein is a compound of Formula I, or a pharmaceutically acceptable salt thereof, wherein $R^4$ is:

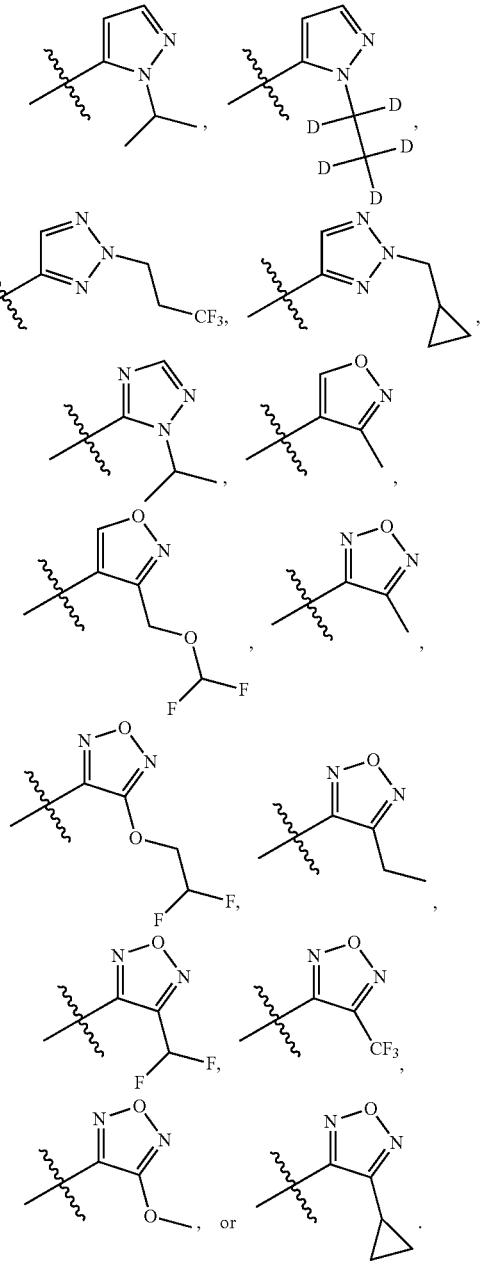

In some embodiments, disclosed herein is a compound of Formula I, or a pharmaceutically acceptable salt thereof, wherein $R^4$ is:

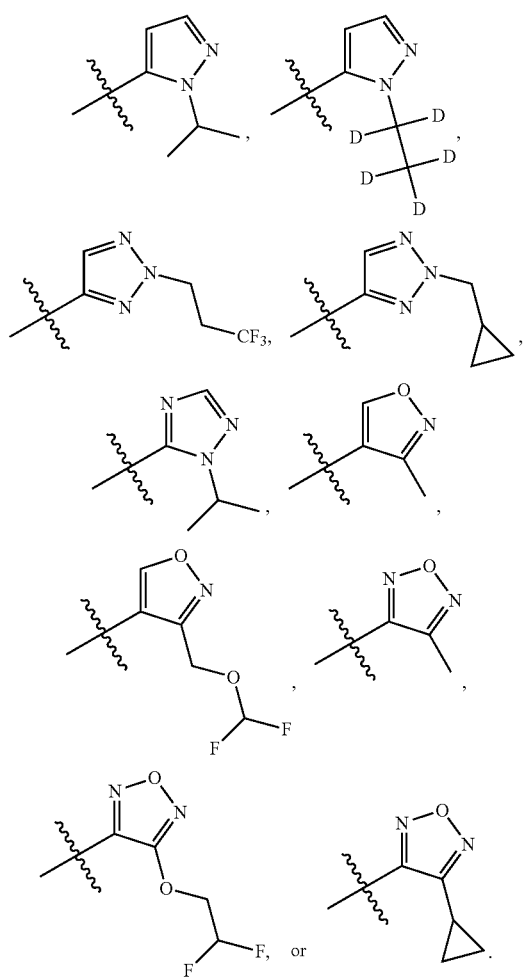
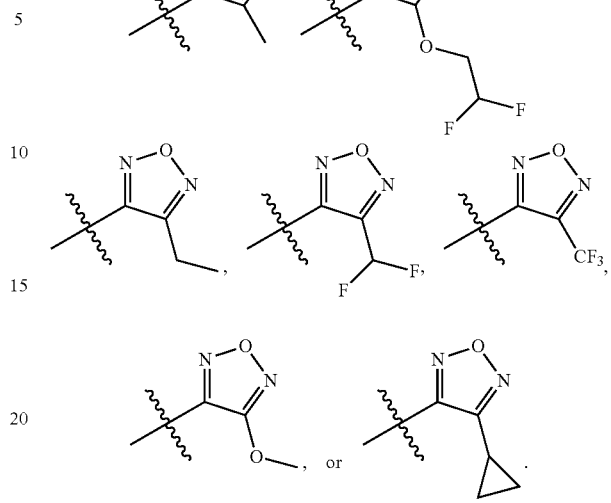
In some embodiments, disclosed herein is a compound of Formula I, or a pharmaceutically acceptable salt thereof, wherein R⁴ is:
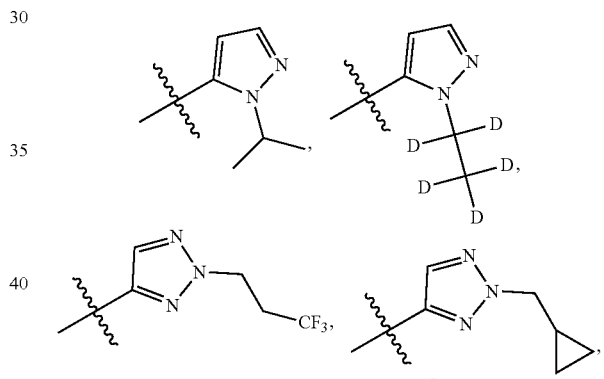
In some embodiments, disclosed herein is a compound of Formula I, or a pharmaceutically acceptable salt thereof, wherein R⁴ is:
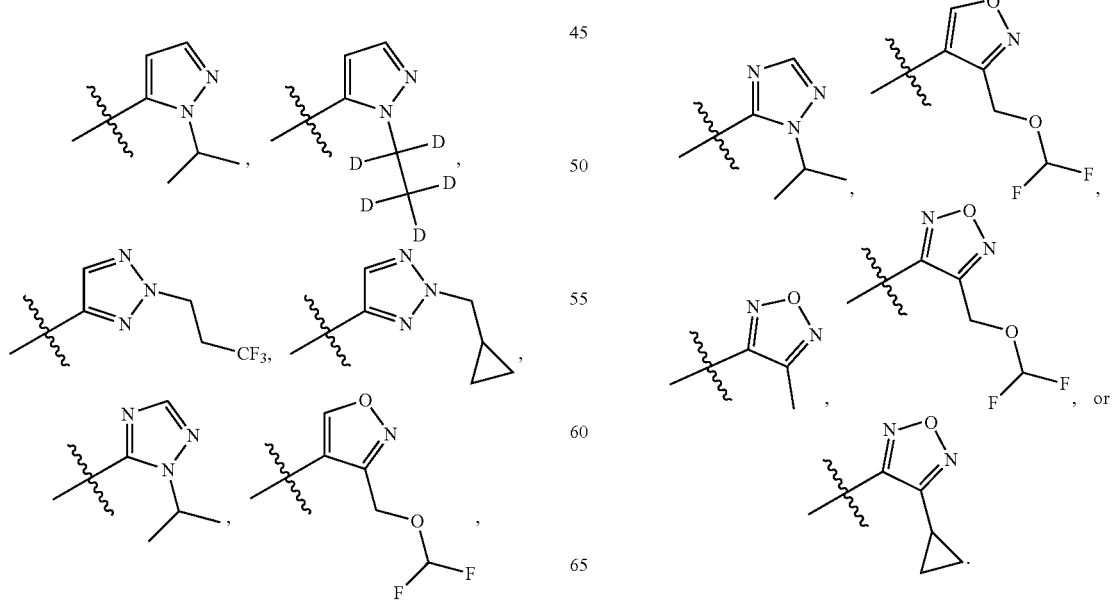

In some embodiments, disclosed herein is a compound of Formula I, or a pharmaceutically acceptable salt thereof, wherein R⁴ is

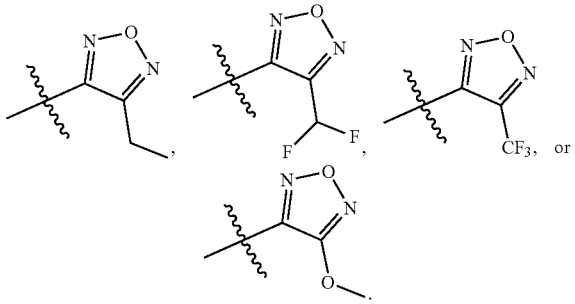

In some embodiments, disclosed herein is a compound of Formula I, or a pharmaceutically acceptable salt thereof, wherein R⁴ is

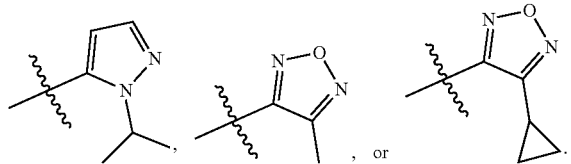

In some embodiments, disclosed herein is a compound of Formula I, or a pharmaceutically acceptable salt thereof, wherein R⁴ is

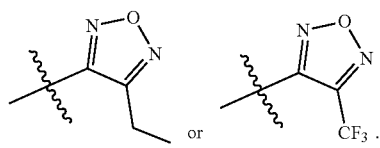

In some embodiments, disclosed herein is a compound of Formula I, or a pharmaceutically acceptable salt thereof, wherein R⁴ is

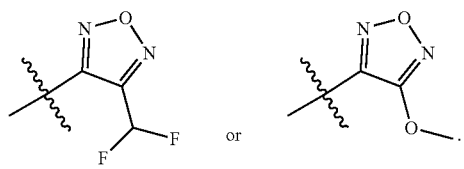

In some embodiments, disclosed herein is a compound of Formula I, or a pharmaceutically acceptable salt thereof, wherein R⁴ is

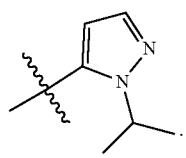 [SMILES: *c1ccnn1C(C)C]

In some embodiments, disclosed herein is a compound of Formula I, or a pharmaceutically acceptable salt thereof, wherein R⁴ is

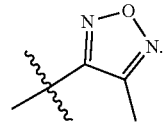 [SMILES: *c1nonc1C]

In some embodiments, disclosed herein is a compound of Formula I, or a pharmaceutically acceptable salt thereof, wherein R⁴ is

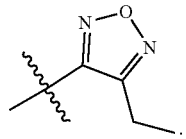 [SMILES: *c1nonc1CC]

In some embodiments, disclosed herein is a compound of Formula I, or a pharmaceutically acceptable salt thereof, wherein R⁴ is

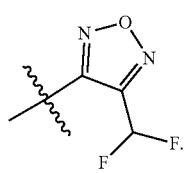 [SMILES: *c1nonc1C(F)F]

In some embodiments, disclosed herein is a compound of Formula I, or a pharmaceutically acceptable salt thereof, wherein R⁴ is

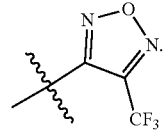

In some embodiments, disclosed herein is a compound of Formula I, or a pharmaceutically acceptable salt thereof, wherein R⁴ is

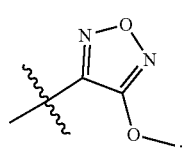 [SMILES: *c1nonc1OC]

In some embodiments, disclosed herein is a compound of Formula I, or a pharmaceutically acceptable salt thereof, wherein R⁴ is

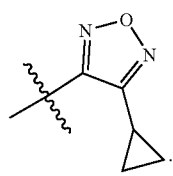 [SMILES: *c1nonc1C1CC1]

In some embodiments, disclosed herein is a compound of Formula I, or a pharmaceutically acceptable salt thereof, that is a deuterated isotope comprising one to thirty deuterium atoms. In some embodiments, disclosed herein is a compound of Formula I, or a pharmaceutically acceptable salt thereof, that is a deuterated isotope comprising one to fifteen deuterium atoms. In some embodiments, disclosed herein is a compound of Formula I, or a pharmaceutically acceptable salt thereof, that is a deuterated isotope comprising one to seven deuterium atoms.

In some embodiments, disclosed herein is a compound of Formula I, or a pharmaceutically acceptable salt thereof, having a structure as shown in Tables 1A, 1B, 1C, 1D, 1E, and 1F.

TABLE 1A

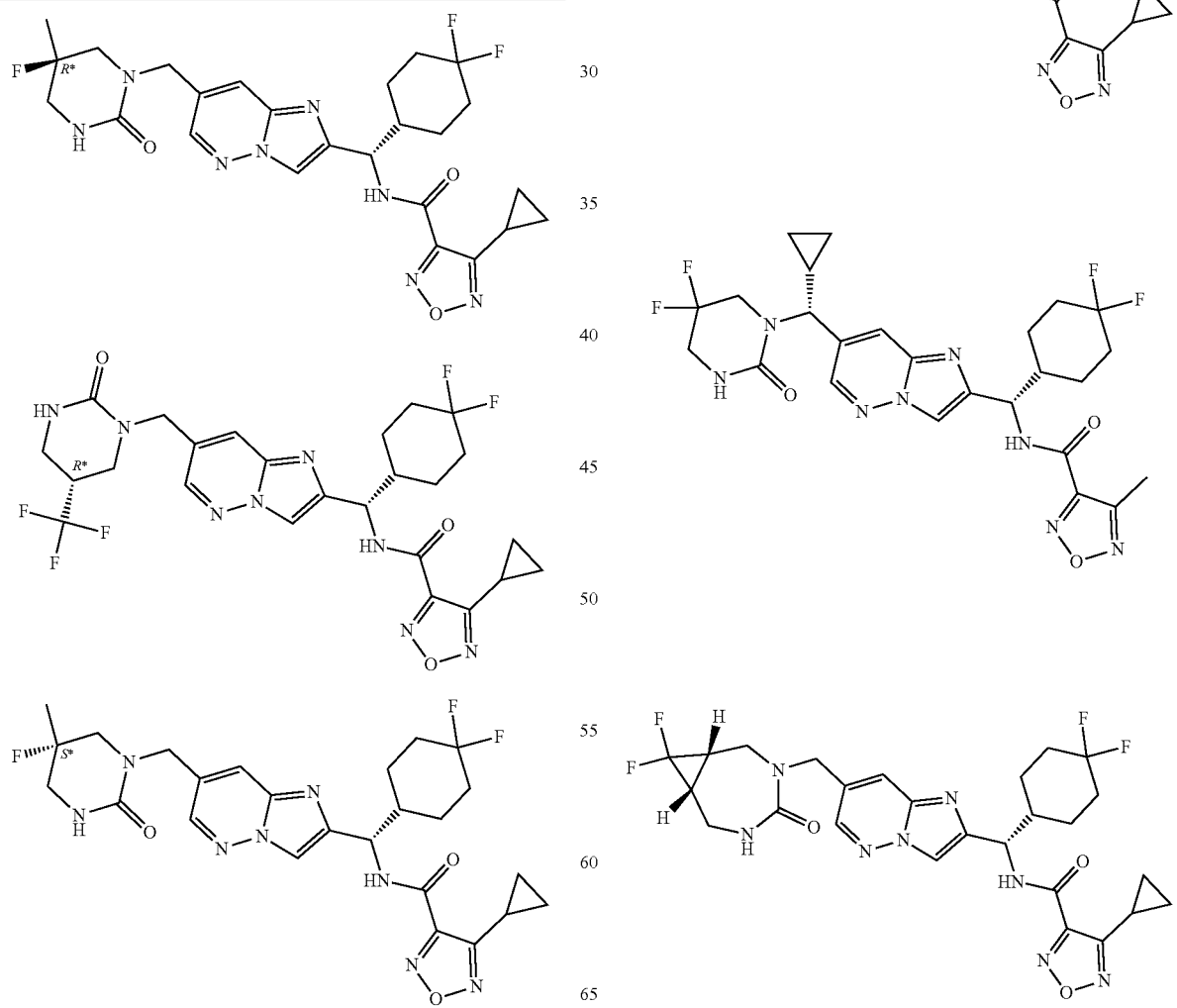

TABLE 1A-continued

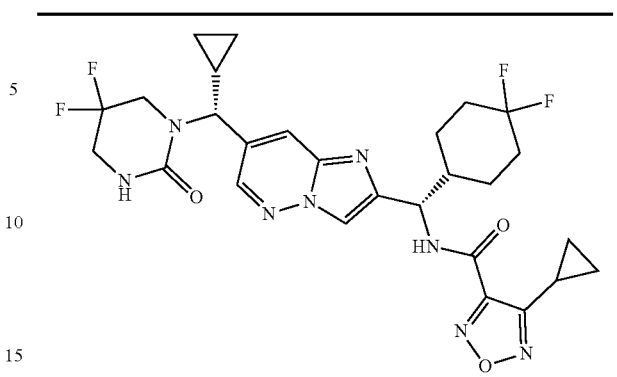

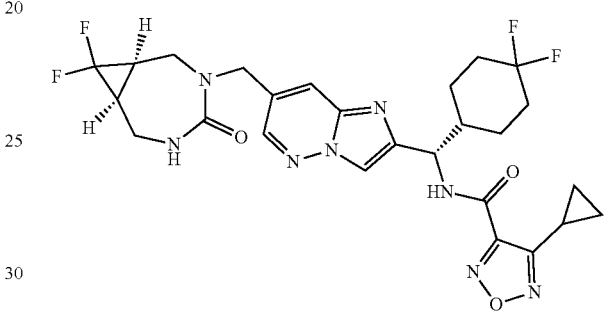

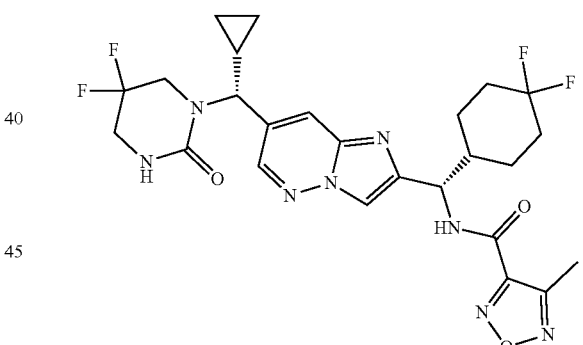

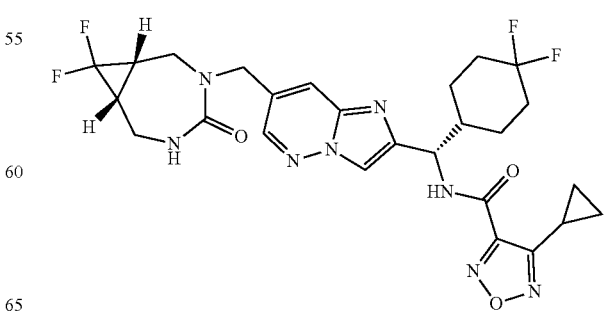

TABLE 1A-continued
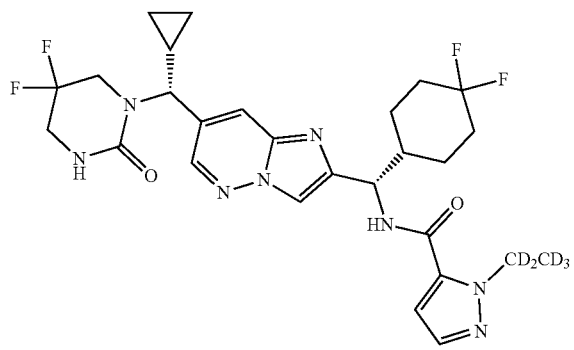
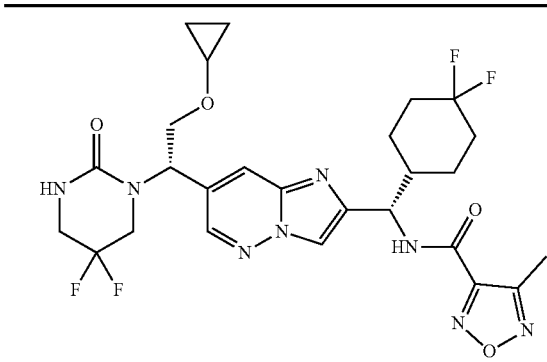
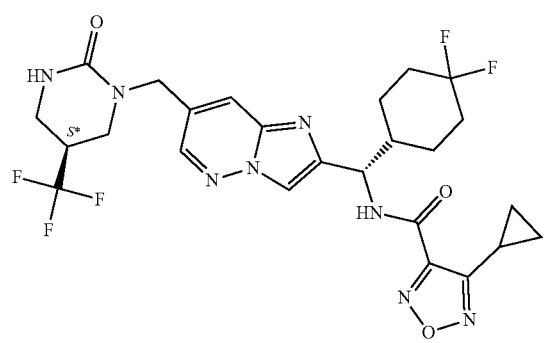 [SMILES: O=C(N[C@H](c1cn2ncc(CN3C[C@@H](C(F)(F)F)CNC3=O)cc2n1)C1CCC(F)(F)CC1)c1nonc1C1CC1]
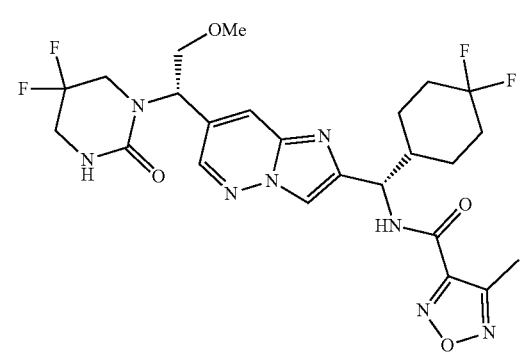
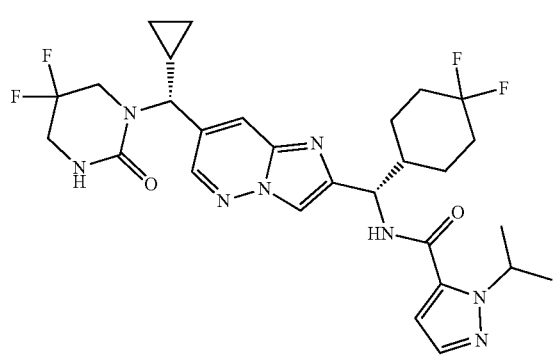 [SMILES: CC(C)n1nccc1C(=O)N[C@H](c1cn2ncc([C@@H](C3CC3)N3CC(F)(F)CNC3=O)cc2n1)C1CCC(F)(F)CC1]
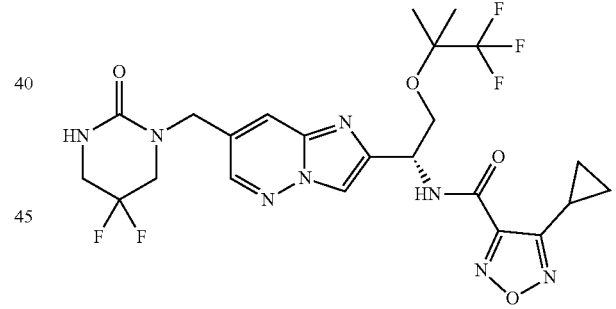
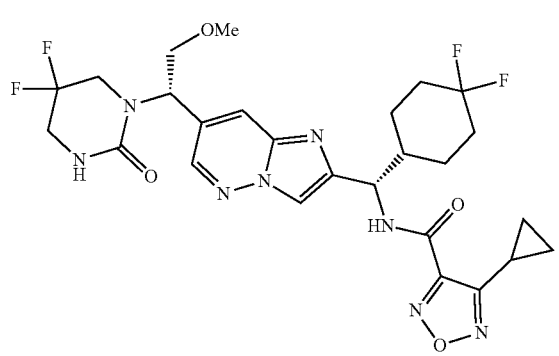 [SMILES: COC[C@H](c1cnn2cc([C@@H](NC(=O)c3nonc3C3CC3)C3CCC(F)(F)CC3)nc2c1)N1CC(F)(F)CNC1=O]
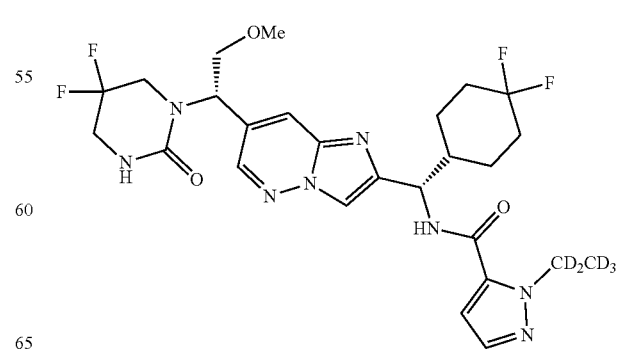

TABLE 1A-continued
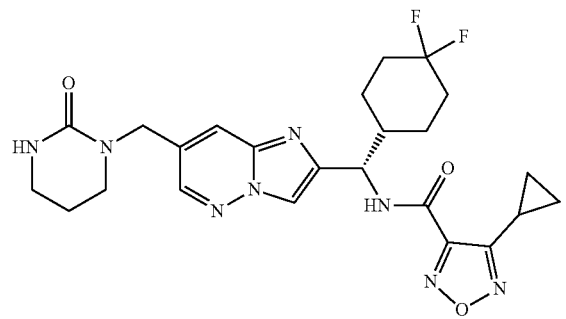 [SMILES: O=C(N[C@H](c1cn2ncc(CN3CCCNC3=O)cc2n1)C1CCC(F)(F)CC1)c1nonc1C1CC1]
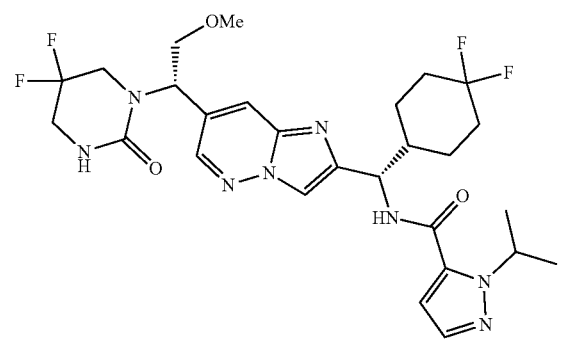 [SMILES: COC[C@H](c1cnn2cc([C@@H](NC(=O)c3ccnn3C(C)C)C3CCC(F)(F)CC3)nc2c1)N1CC(F)(F)CNC1=O]
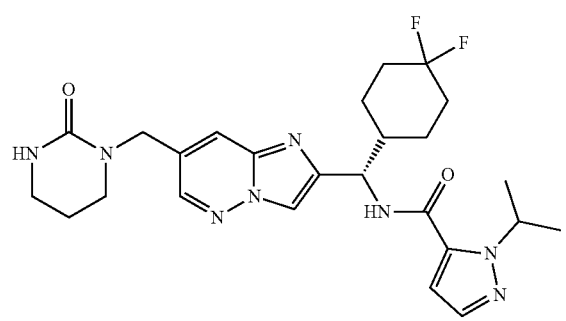 [SMILES: CC(C)n1nccc1C(=O)N[C@H](c1cn2ncc(CN3CCCNC3=O)cc2n1)C1CCC(F)(F)CC1]
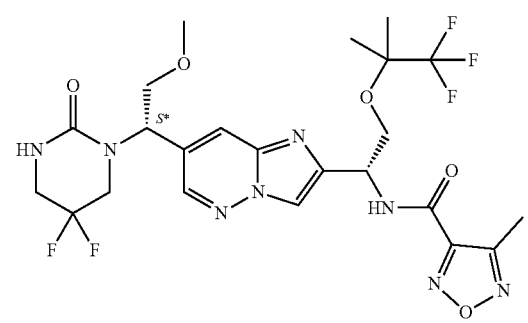 [SMILES: COC[C@H](c1cnn2cc([C@H](COC(C)(C)C(F)(F)F)NC(=O)c3nonc3C)nc2c1)N1CC(F)(F)CNC1=O]
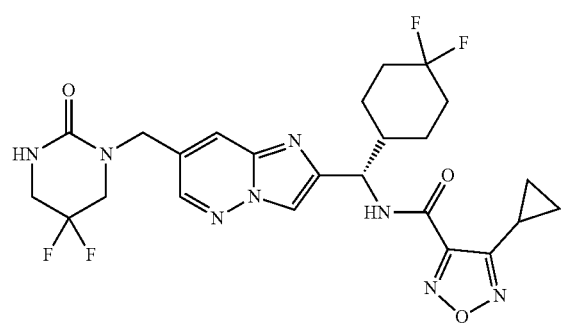 [SMILES: O=C(N[C@H](c1cn2ncc(CN3CC(F)(F)CNC3=O)cc2n1)C1CCC(F)(F)CC1)c1nonc1C1CC1]
TABLE 1B
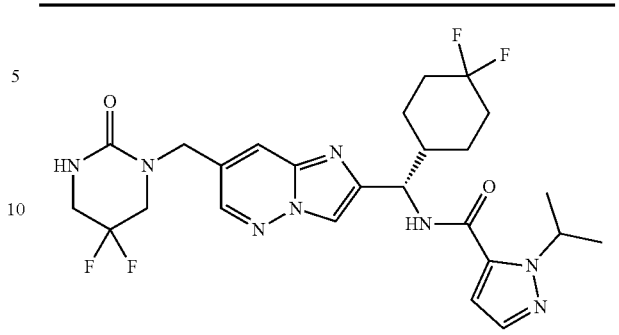
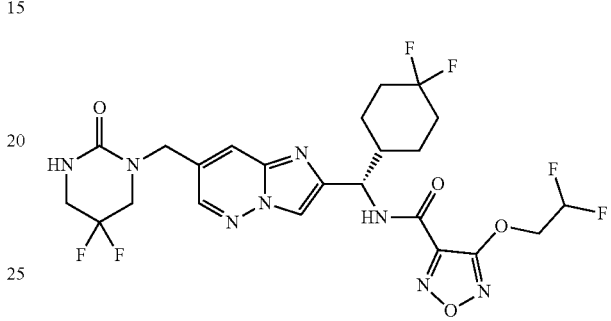
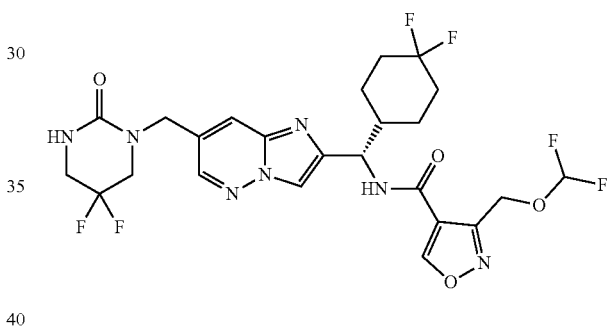
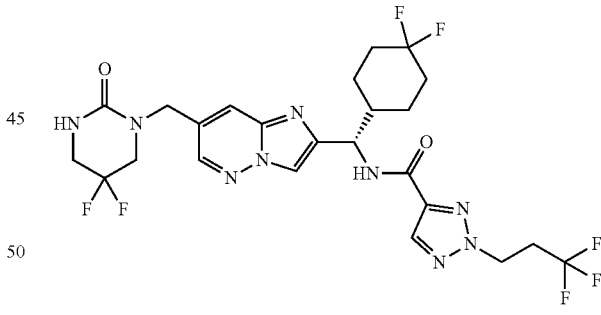
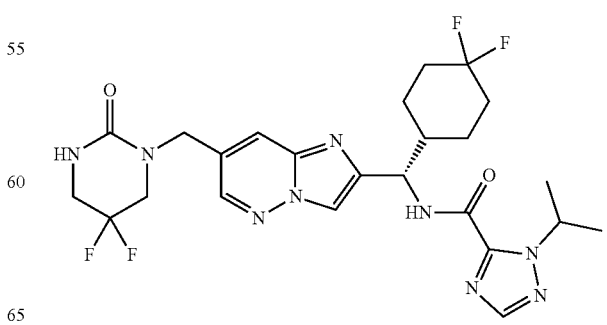

TABLE 1B-continued
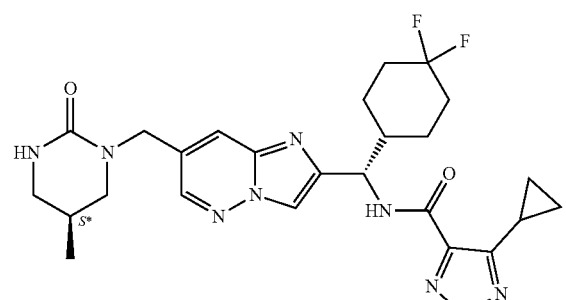
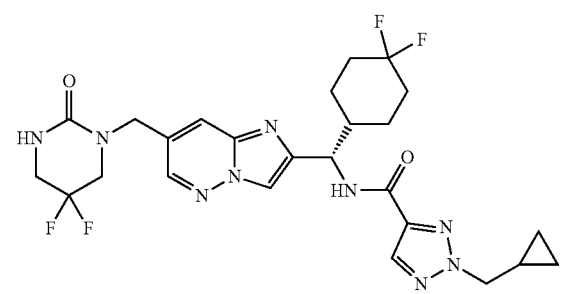
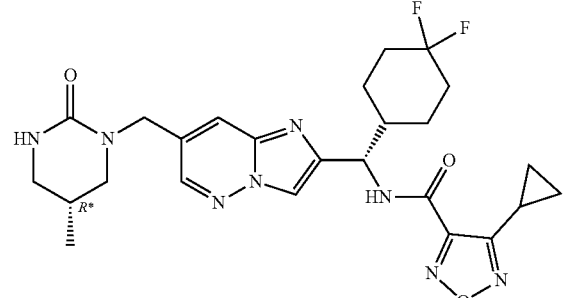
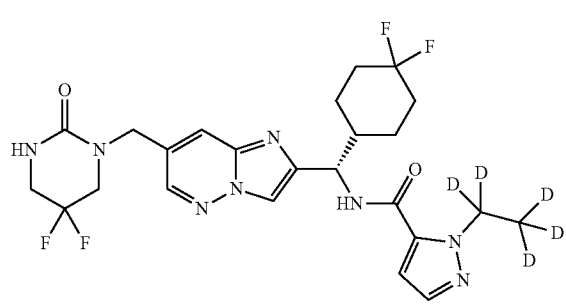 [SMILES: [2H]C([2H])([2H])C([2H])([2H])n1nccc1C(=O)N[C@H](c1cn2ncc(CN3CC(F)(F)CNC3=O)cc2n1)C1CCC(F)(F)CC1]
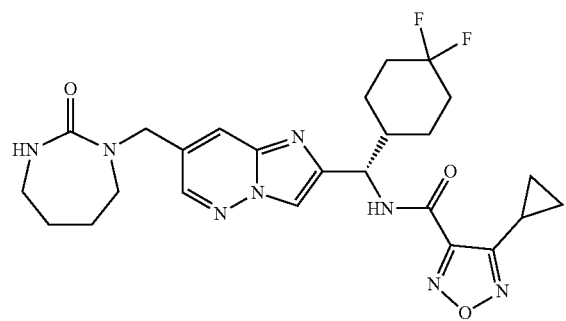 [SMILES: O=C(N[C@H](c1cn2ncc(CN3CCCCNC3=O)cc2n1)C1CCC(F)(F)CC1)c1nonc1C1CC1]
TABLE 1B-continued
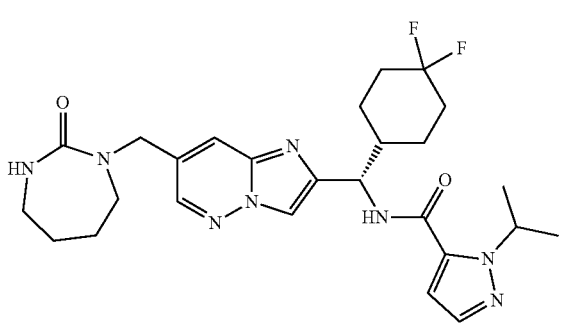 [SMILES: CC(C)n1nccc1C(=O)N[C@H](c1cn2ncc(CN3CCCCNC3=O)cc2n1)C1CCC(F)(F)CC1]
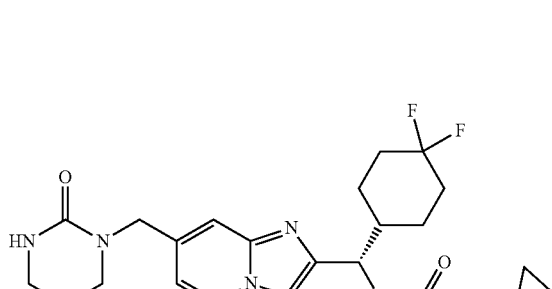
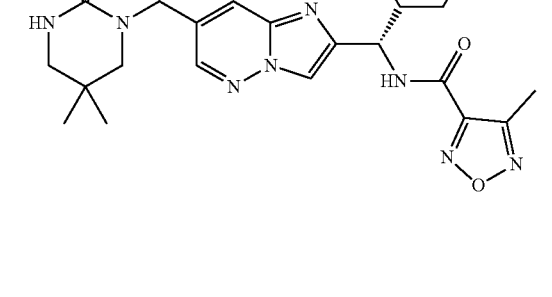
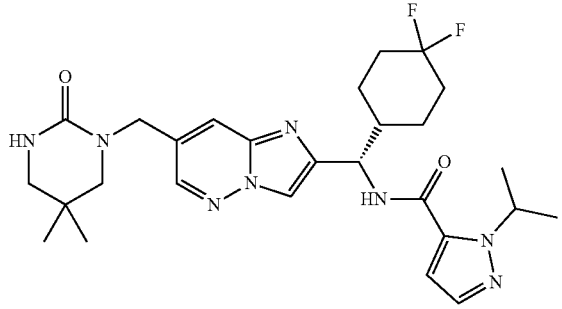 [SMILES: CC(C)n1nccc1C(=O)N[C@H](c1cn2ncc(CN3CC(C)(C)CNC3=O)cc2n1)C1CCC(F)(F)CC1]

TABLE 1C

TABLE 1C-continued
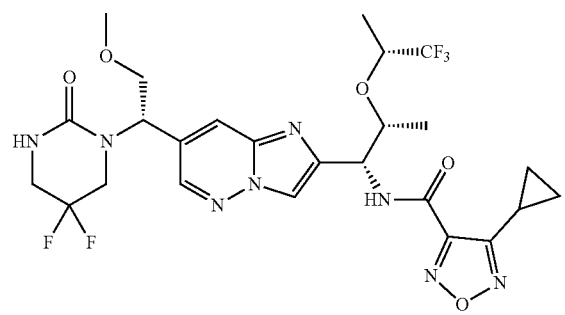 [SMILES: COC[C@H](c1cnn2cc([C@@H](NC(=O)c3nonc3C3CC3)[C@@H](C)O[C@H](C)C(F)(F)F)nc2c1)N1CC(F)(F)CNC1=O]
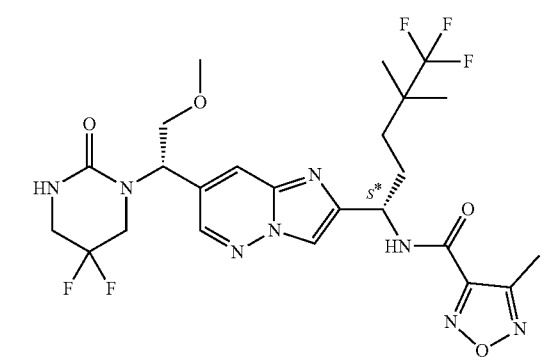 [SMILES: COC[C@H](c1cnn2cc([C@H](CCC(C)(C)C(F)(F)F)NC(=O)c3nonc3C)nc2c1)N1CC(F)(F)CNC1=O]
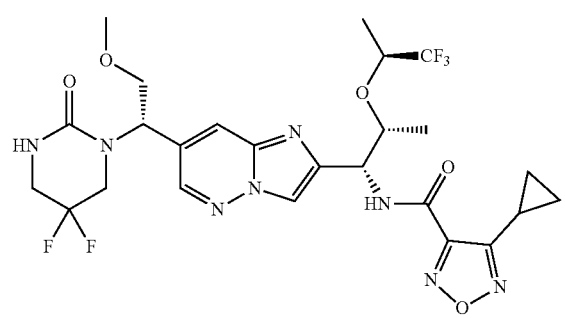 [SMILES: COC[C@H](c1cnn2cc([C@@H](NC(=O)c3nonc3C3CC3)[C@@H](C)O[C@@H](C)C(F)(F)F)nc2c1)N1CC(F)(F)CNC1=O]
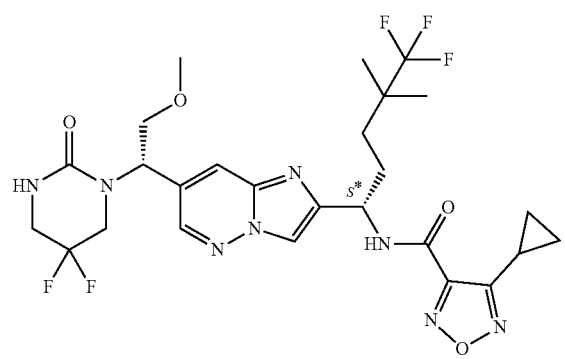 [SMILES: COC[C@H](c1cnn2cc([C@H](CCC(C)(C)C(F)(F)F)NC(=O)c3nonc3C3CC3)nc2c1)N1CC(F)(F)CNC1=O]
TABLE 1D
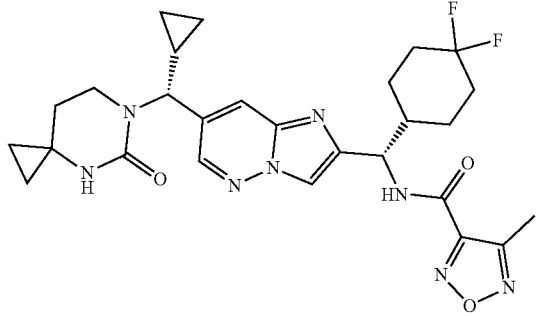 [SMILES: Cc1nonc1C(=O)N[C@H](c1cn2ncc([C@@H](C3CC3)N3CCC4(CC4)NC3=O)cc2n1)C1CCC(F)(F)CC1]
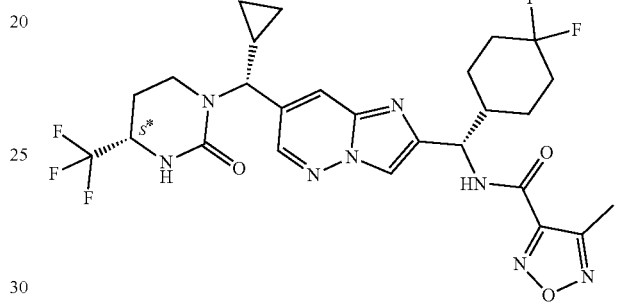
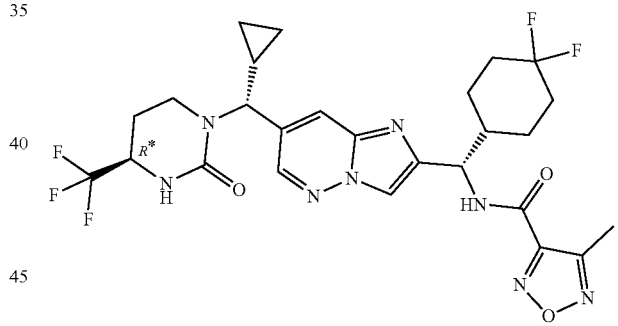
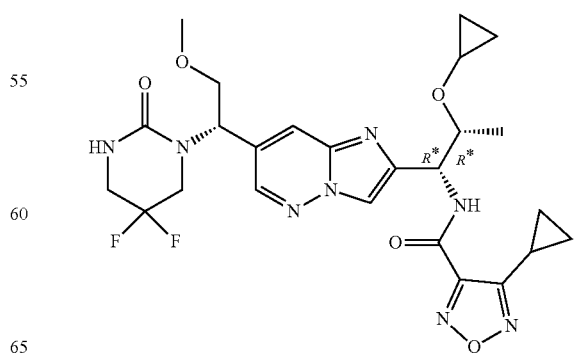

TABLE 1D-continued
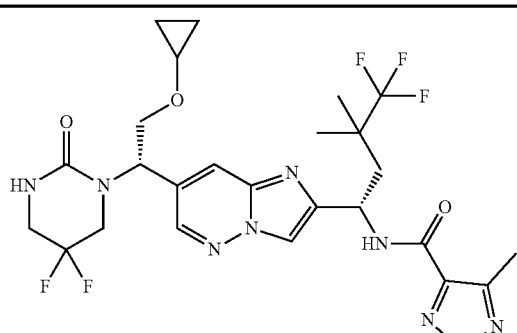
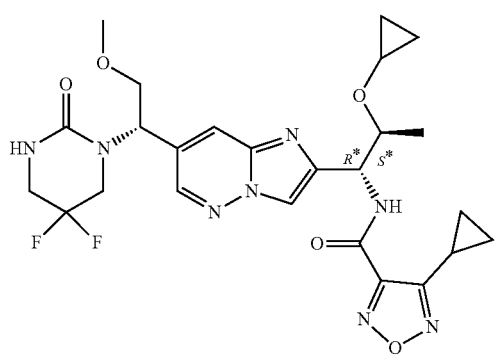 [SMILES: COC[C@H](c1cnn2cc([C@@H](NC(=O)c3nonc3C3CC3)[C@H](C)OC3CC3)nc2c1)N1CC(F)(F)CNC1=O]
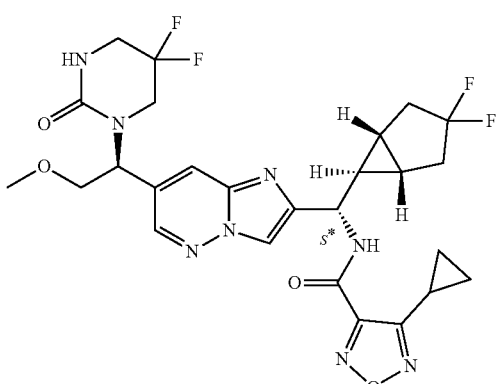
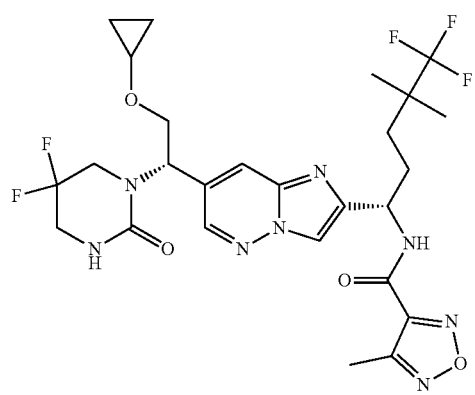 [SMILES: Cc1nonc1C(=O)N[C@@H](CCC(C)(C)C(F)(F)F)c1cn2ncc([C@@H](COC3CC3)N3CC(F)(F)CNC3=O)cc2n1]
TABLE 1D-continued
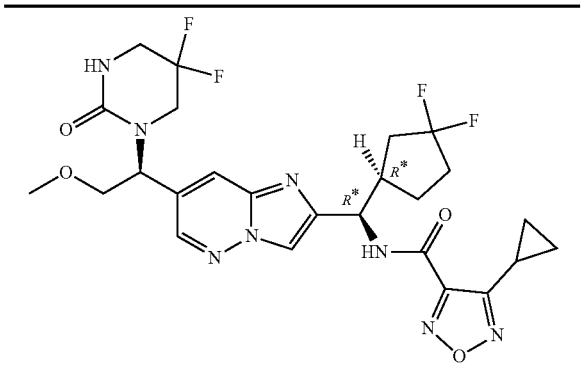
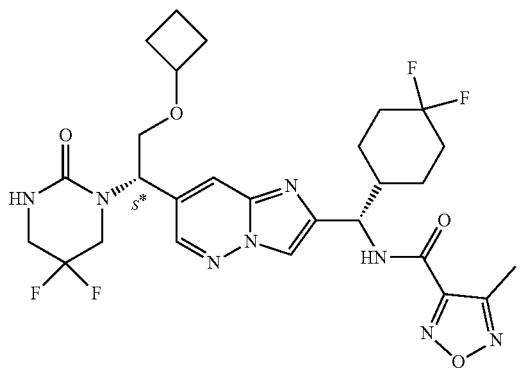 [SMILES: Cc1nonc1C(=O)N[C@H](c1cn2ncc([C@@H](COC3CCC3)N3CC(F)(F)CNC3=O)cc2n1)C1CCC(F)(F)CC1]
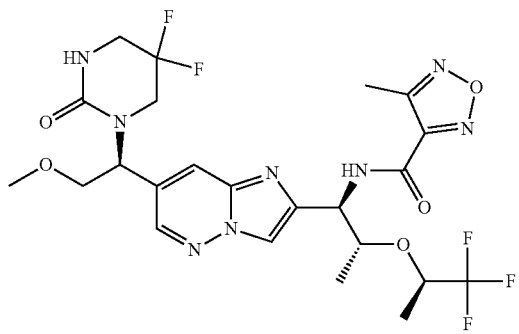 [SMILES: COC[C@H](c1cnn2cc([C@@H](NC(=O)c3nonc3C)[C@@H](C)O[C@H](C)C(F)(F)F)nc2c1)N1CC(F)(F)CNC1=O]
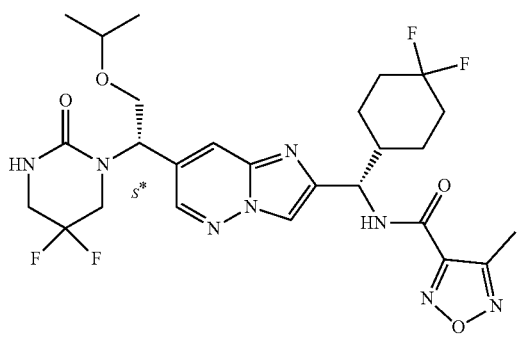 [SMILES: Cc1nonc1C(=O)N[C@H](c1cn2ncc([C@@H](COC(C)C)N3CC(F)(F)CNC3=O)cc2n1)C1CCC(F)(F)CC1]

TABLE 1D-continued
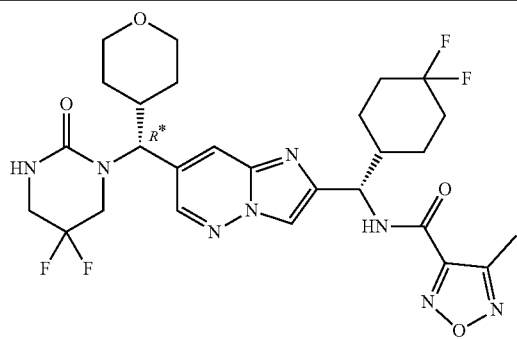
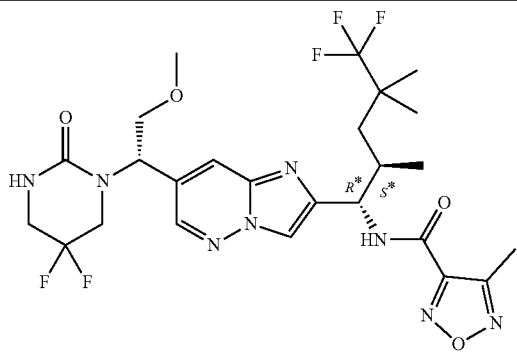
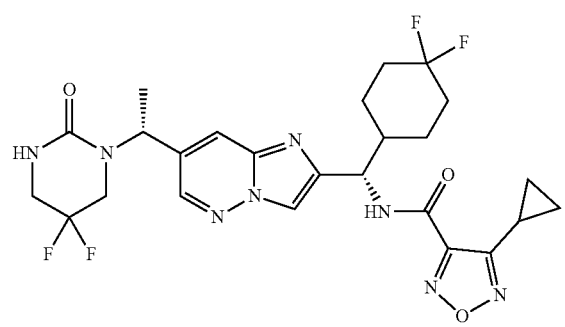 [SMILES: C[C@H](c1cnn2cc([C@@H](NC(=O)c3nonc3C3CC3)C3CCC(F)(F)CC3)nc2c1)N1CC(F)(F)CNC1=O]
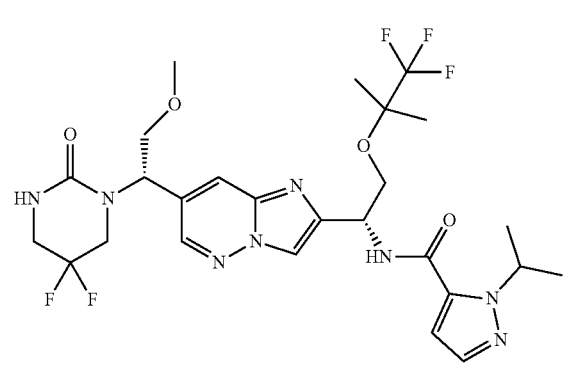
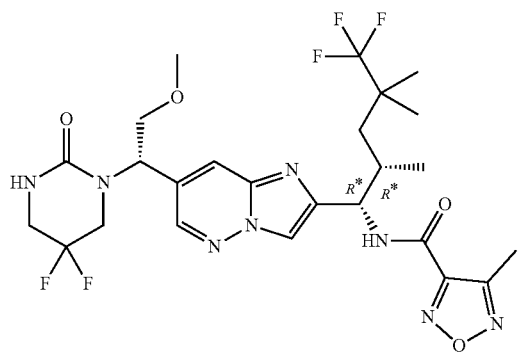 [SMILES: COC[C@H](c1cnn2cc([C@@H](NC(=O)c3nonc3C)[C@@H](C)CC(C)(C)C(F)(F)F)nc2c1)N1CC(F)(F)CNC1=O]
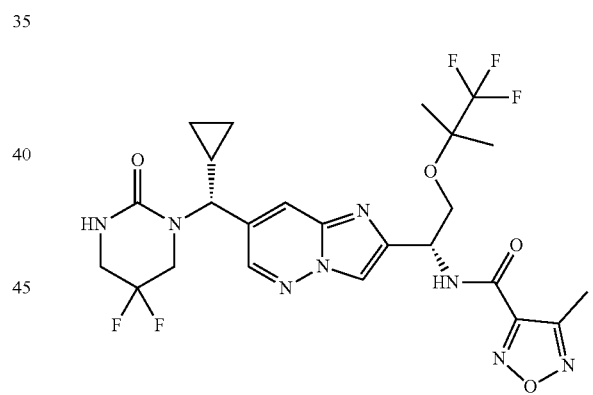
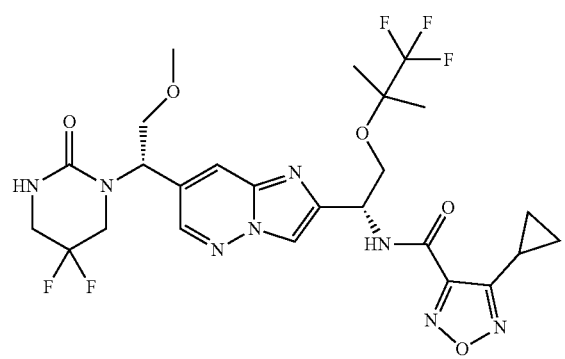 [SMILES: COC[C@H](c1cnn2cc([C@H](COC(C)(C)C(F)(F)F)NC(=O)c3nonc3C3CC3)nc2c1)N1CC(F)(F)CNC1=O]
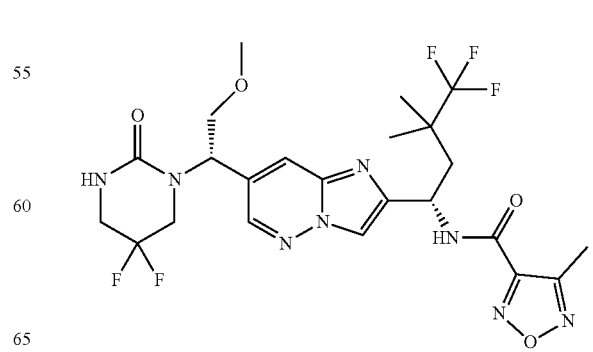

TABLE 1E
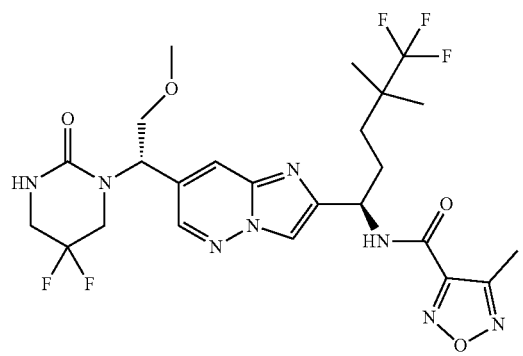 [SMILES: COC[C@H](c1cnn2cc([C@@H](CCC(C)(C)C(F)(F)F)NC(=O)c3nonc3C)nc2c1)N1CC(F)(F)CNC1=O]
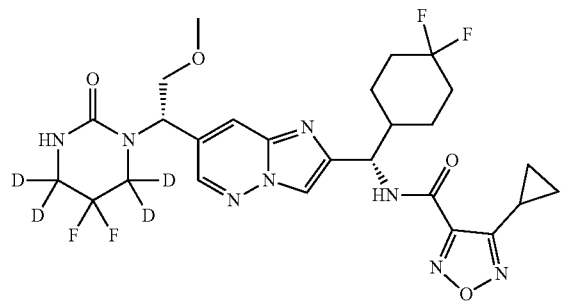 [SMILES: [2H]C1([2H])NC(=O)N([C@H](COC)c2cnn3cc([C@@H](NC(=O)c4nonc4C4CC4)C4CCC(F)(F)CC4)nc3c2)C([2H])([2H])C1(F)F]
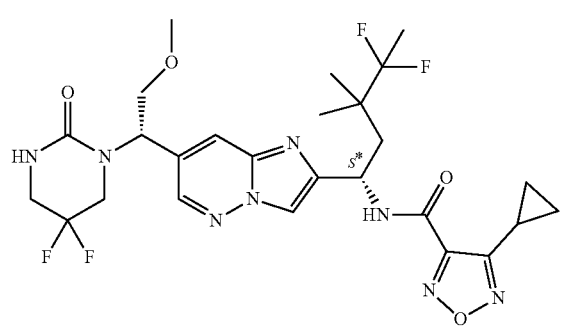 [SMILES: COC[C@H](c1cnn2cc([C@H](CC(C)(C)C(C)(F)F)NC(=O)c3nonc3C3CC3)nc2c1)N1CC(F)(F)CNC1=O]
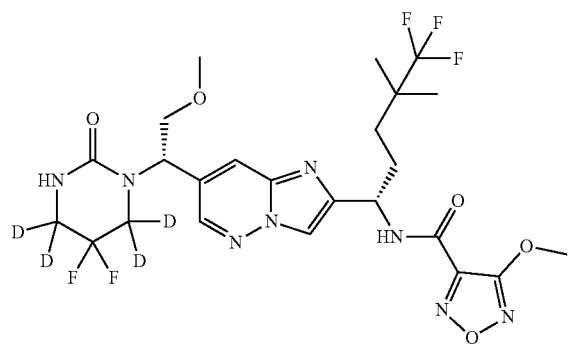 [SMILES: [2H]C1([2H])NC(=O)N([C@H](COC)c2cnn3cc([C@H](CCC(C)(C)C(F)(F)F)NC(=O)c4nonc4OC)nc3c2)C([2H])([2H])C1(F)F]
TABLE 1E-continued
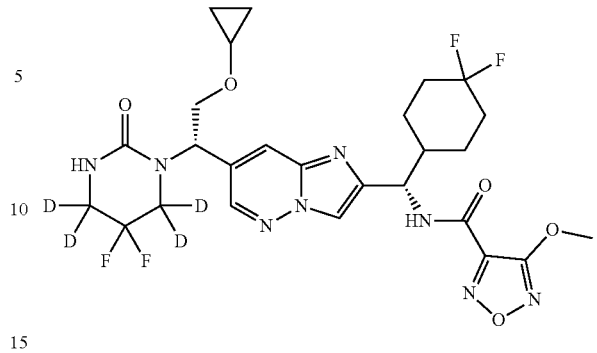
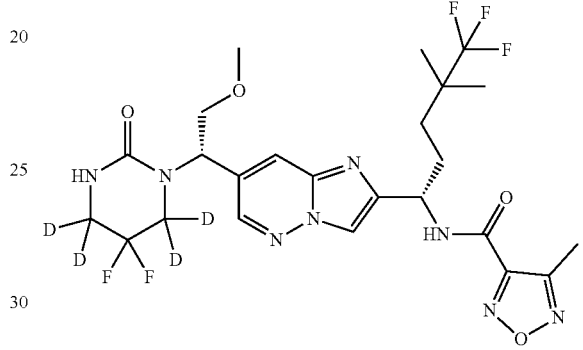
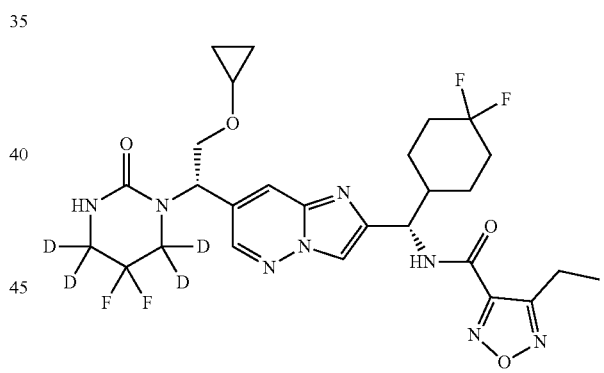
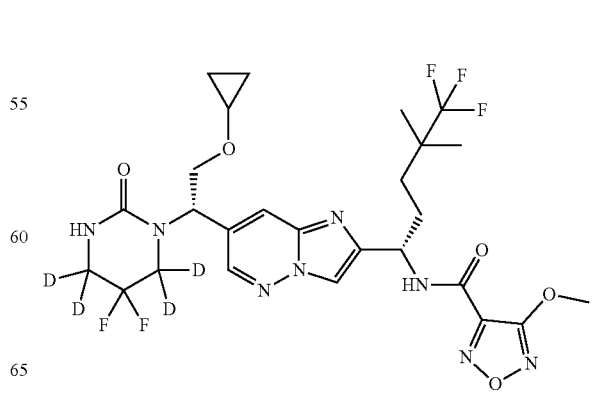

TABLE 1E-continued
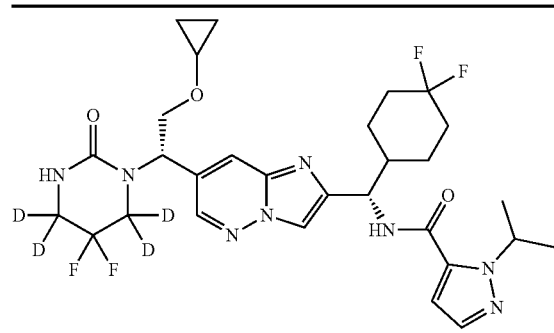
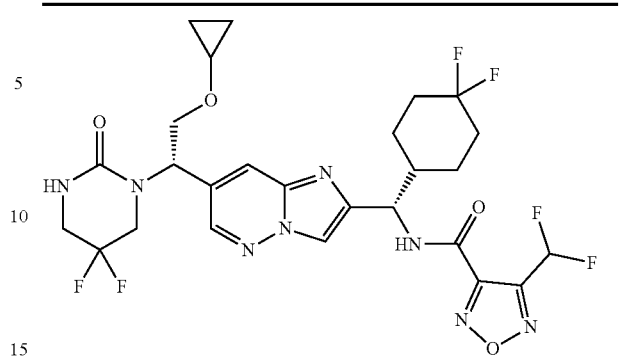
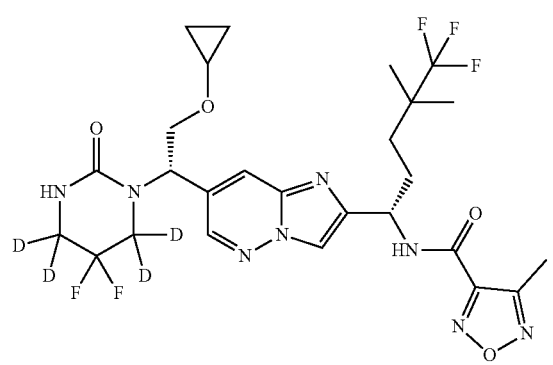
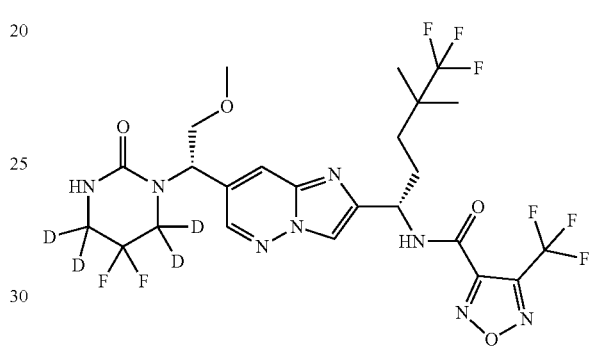
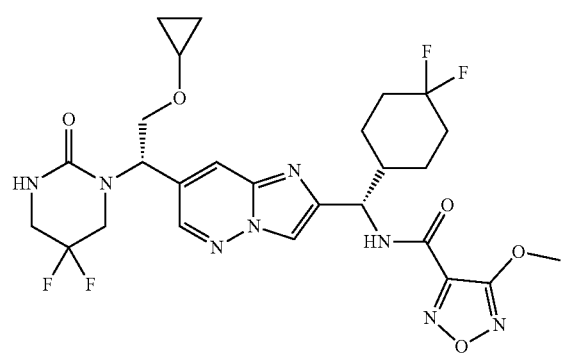 [SMILES: COc1nonc1C(=O)N[C@H](c1cn2ncc([C@@H](COC3CC3)N3CC(F)(F)CNC3=O)cc2n1)C1CCC(F)(F)CC1]
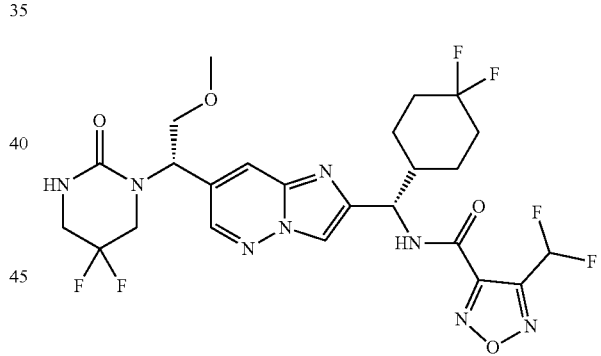
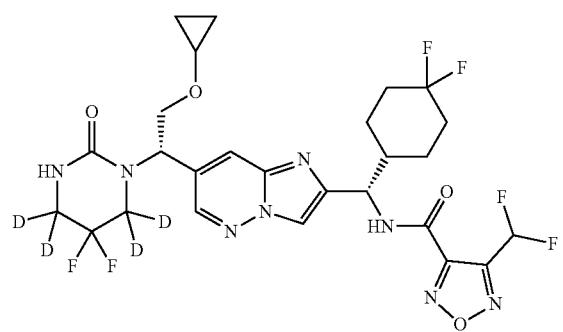 [SMILES: [2H]C1([2H])NC(=O)N([C@H](COC2CC2)c2cnn3cc([C@@H](NC(=O)c4nonc4C(F)F)C4CCC(F)(F)CC4)nc3c2)C([2H])([2H])C1(F)F]
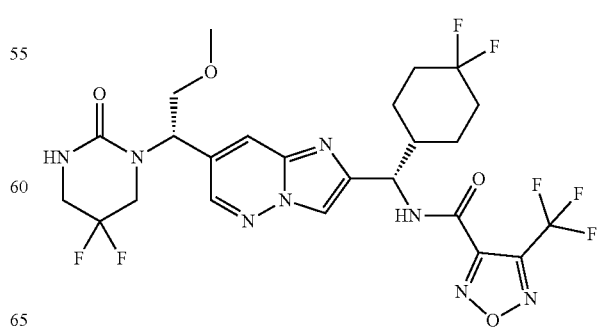

TABLE 1E-continued
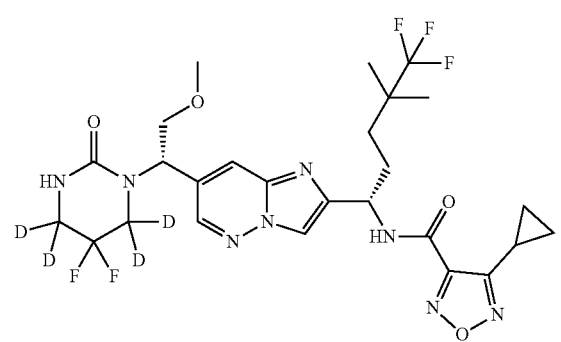
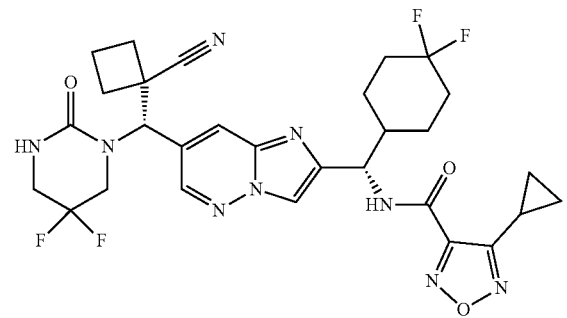
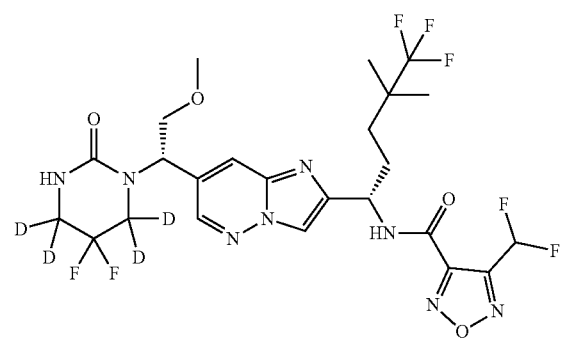
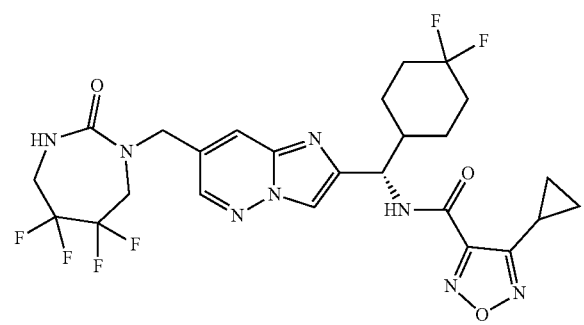 [SMILES: O=C(N[C@H](c1cn2ncc(CN3CC(F)(F)C(F)(F)CNC3=O)cc2n1)C1CCC(F)(F)CC1)c1nonc1C1CC1]
TABLE 1F
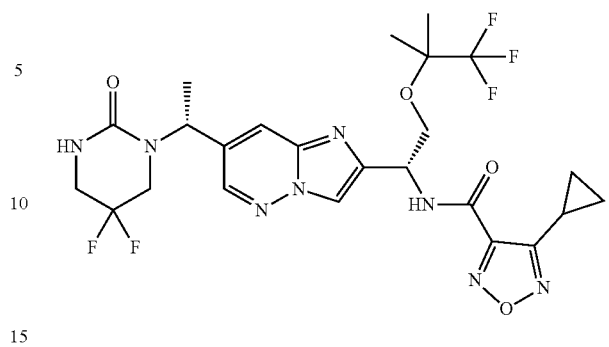
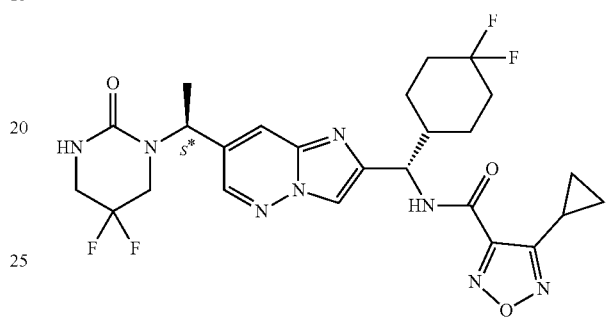
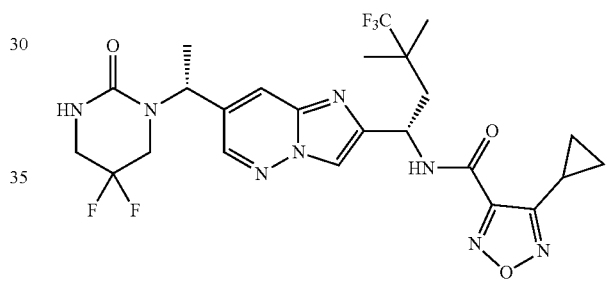
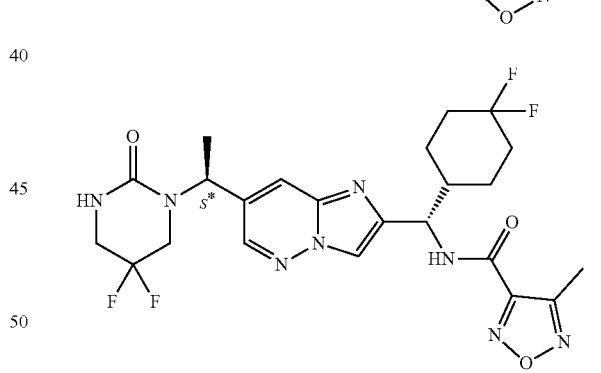
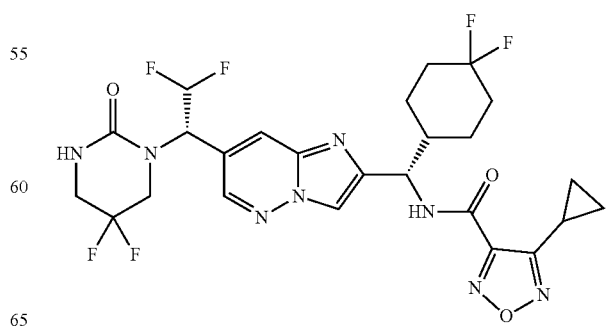

TABLE 1F-continued
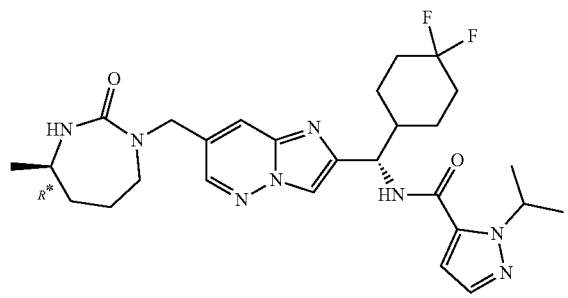 [SMILES: CC(C)n1nccc1C(=O)N[C@H](c1cn2ncc(CN3CCC[C@@H](C)NC3=O)cc2n1)C1CCC(F)(F)CC1]
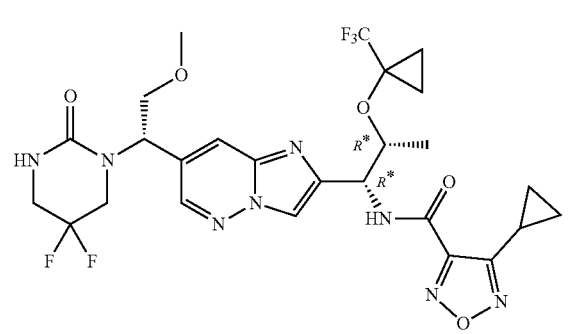 [SMILES: COC[C@H](c1cnn2cc([C@@H](NC(=O)c3nonc3C3CC3)[C@@H](C)OC3(C(F)(F)F)CC3)nc2c1)N1CC(F)(F)CNC1=O]
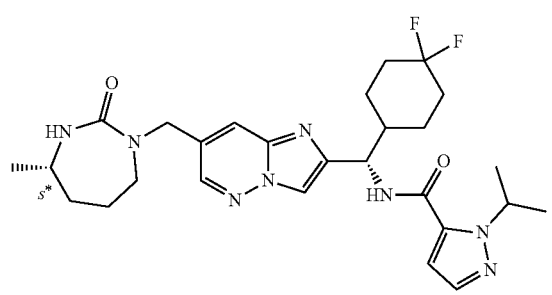
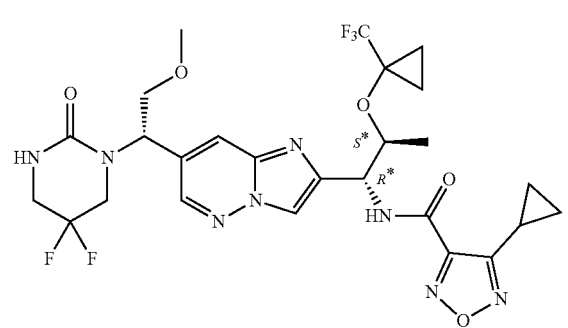 [SMILES: COC[C@H](c1cnn2cc([C@@H](NC(=O)c3nonc3C3CC3)[C@H](C)OC3(C(F)(F)F)CC3)nc2c1)N1CC(F)(F)CNC1=O]
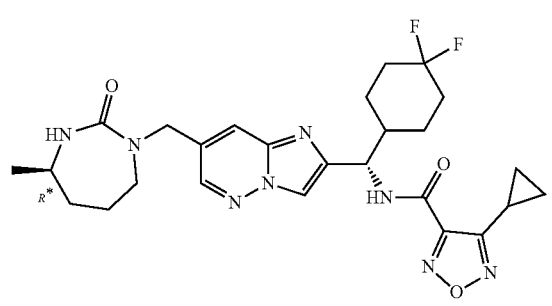 [SMILES: C[C@@H]1CCCN(Cc2cnn3cc([C@@H](NC(=O)c4nonc4C4CC4)C4CCC(F)(F)CC4)nc3c2)C(=O)N1]
TABLE 1F-continued
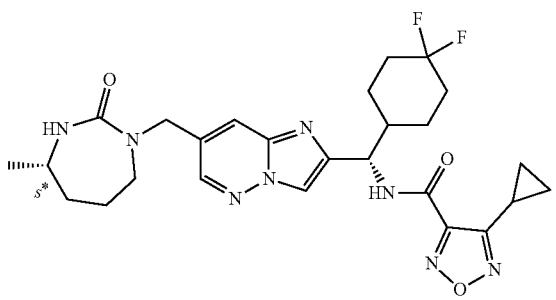 [SMILES: C[C@H]1CCCN(Cc2cnn3cc([C@@H](NC(=O)c4nonc4C4CC4)C4CCC(F)(F)CC4)nc3c2)C(=O)N1]
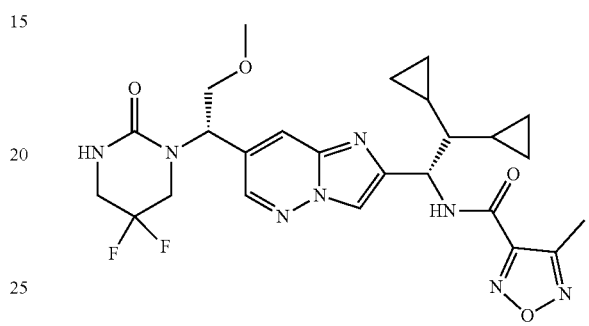
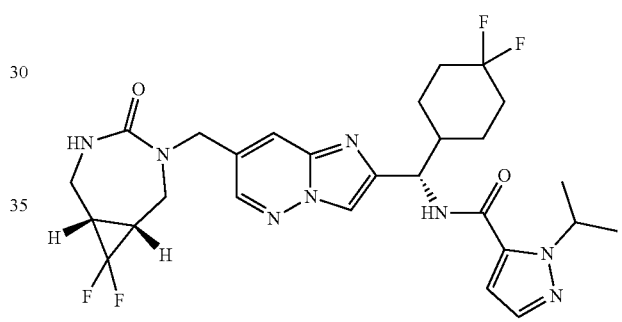
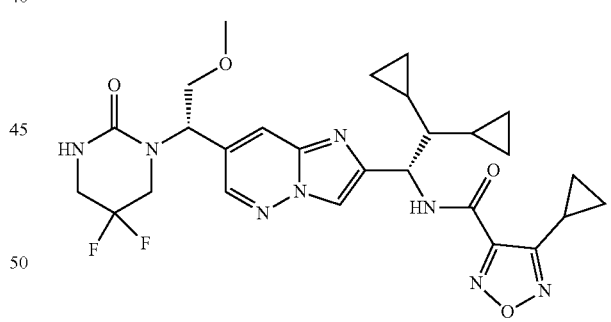
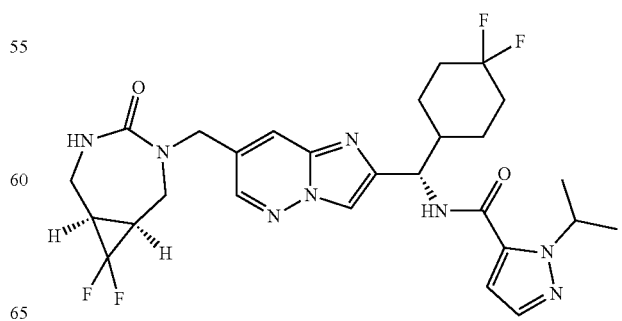

TABLE 1F-continued
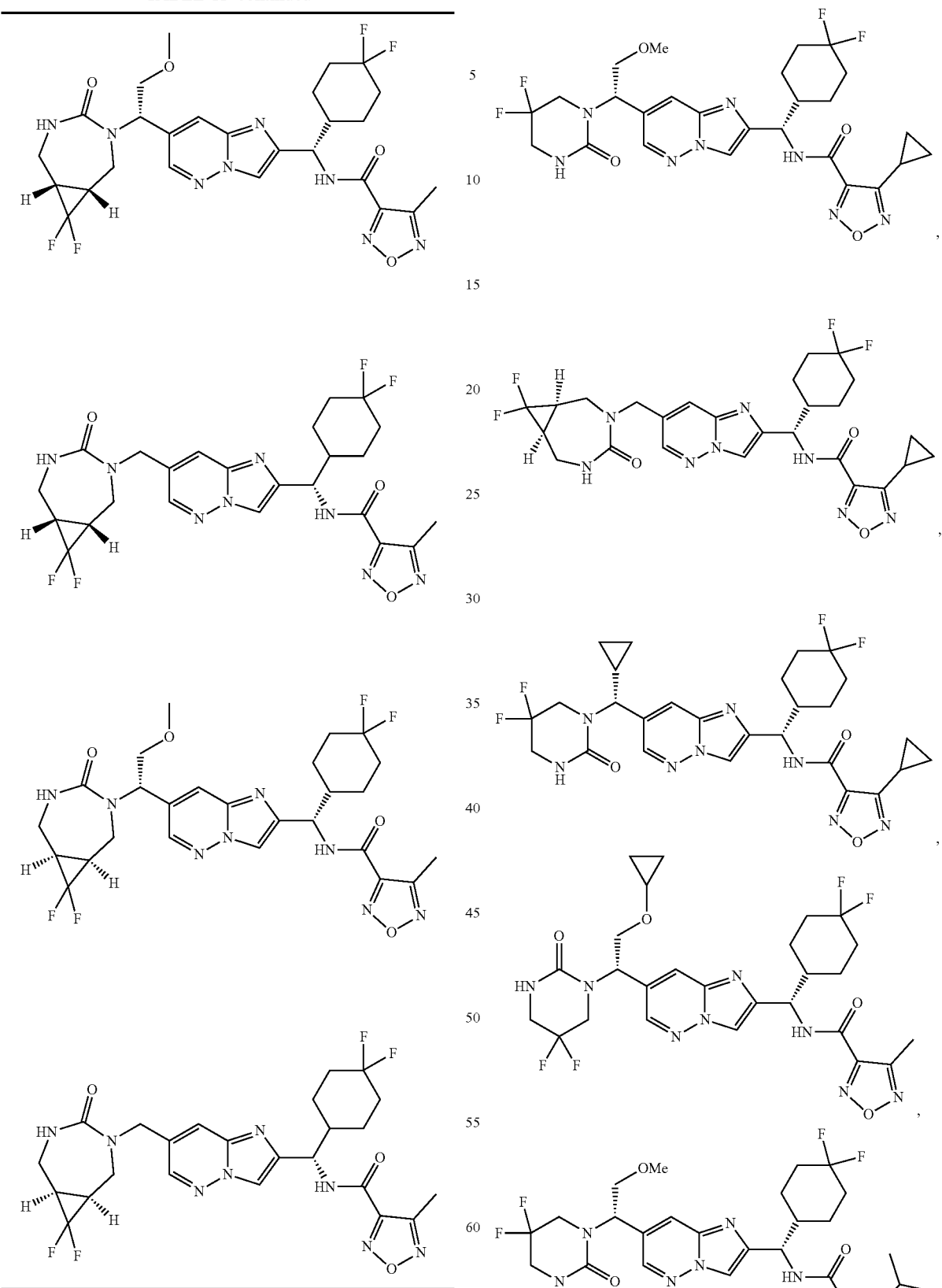
In some embodiments, disclosed herein is a compound of Formula I, or a pharmaceutically acceptable salt thereof, selected from the group consisting of:

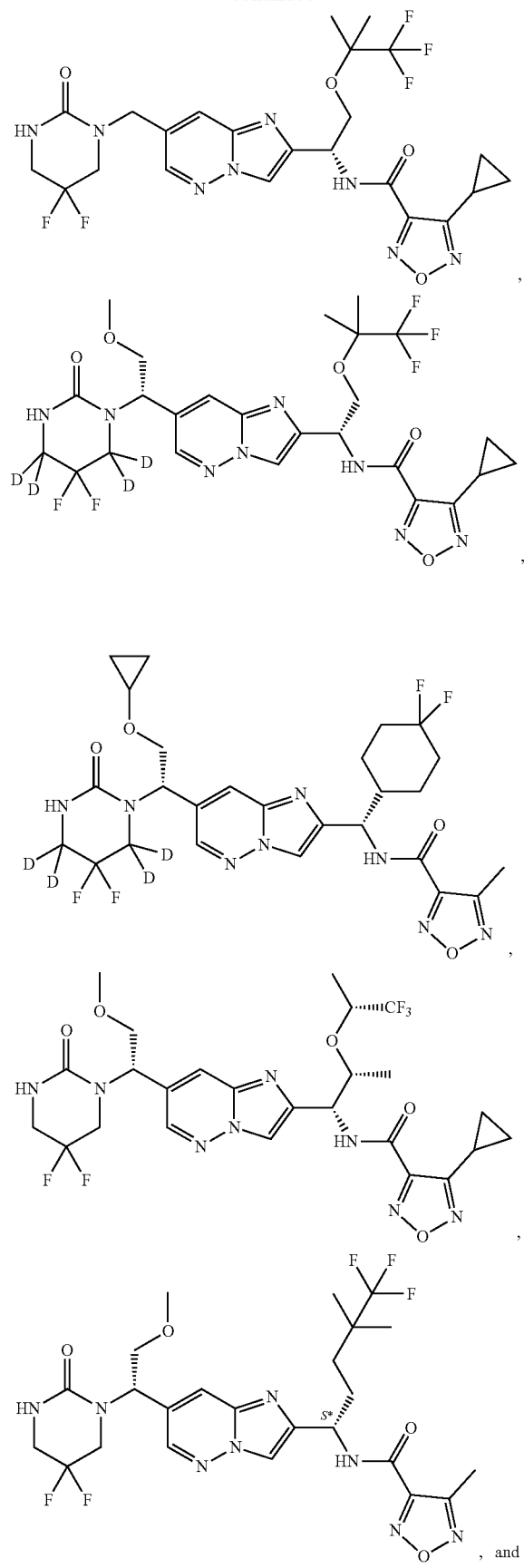
,
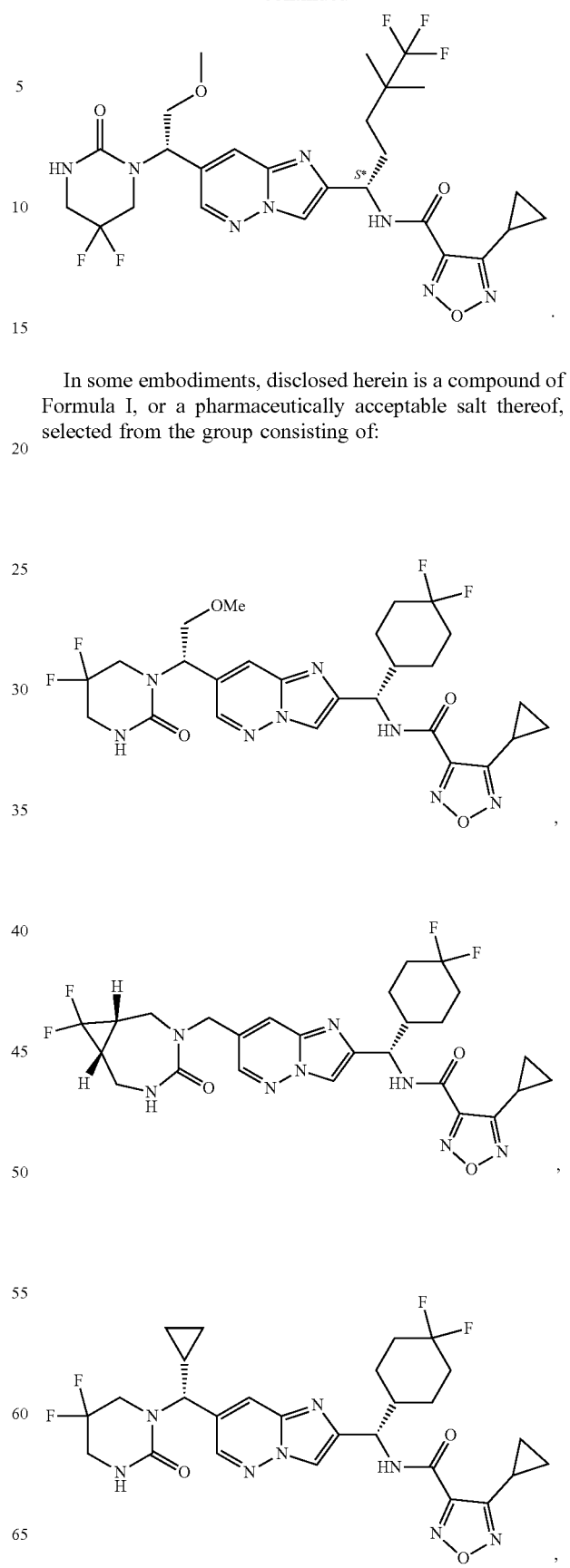
In some embodiments, disclosed herein is a compound of Formula I, or a pharmaceutically acceptable salt thereof, selected from the group consisting of:

85
-continued
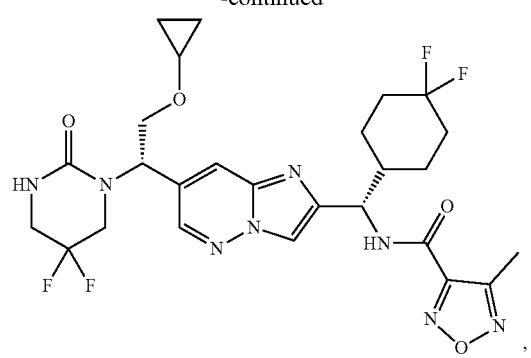
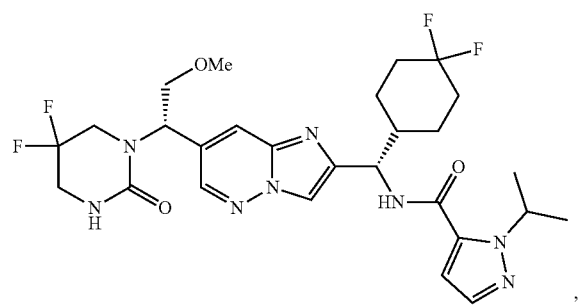
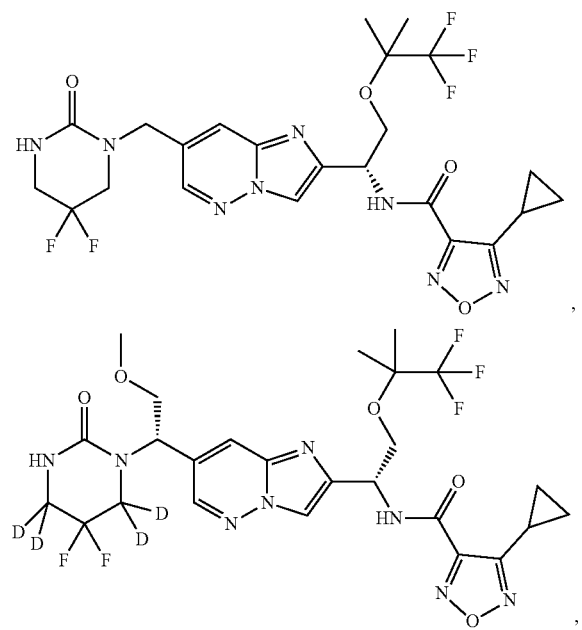
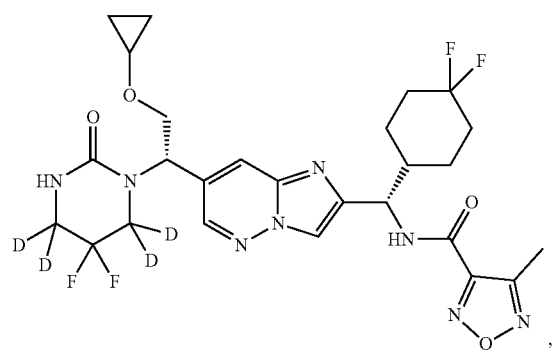
86
-continued
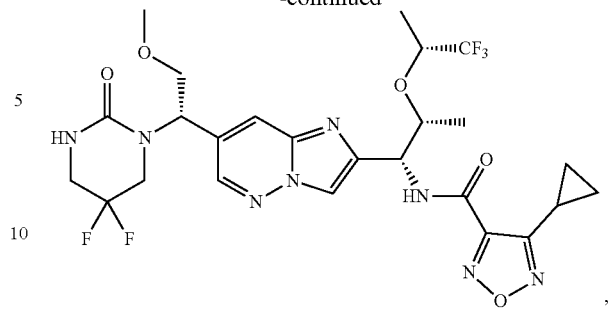
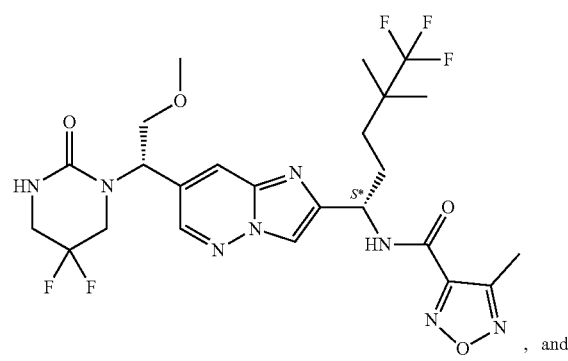
, and
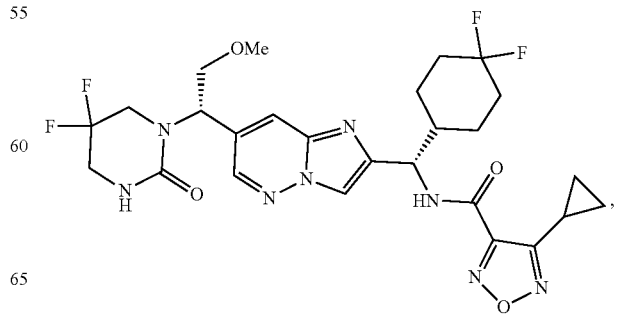
In some embodiments, disclosed herein is a compound of Formula I, or a pharmaceutically acceptable salt thereof, selected from the group consisting of:

-continued
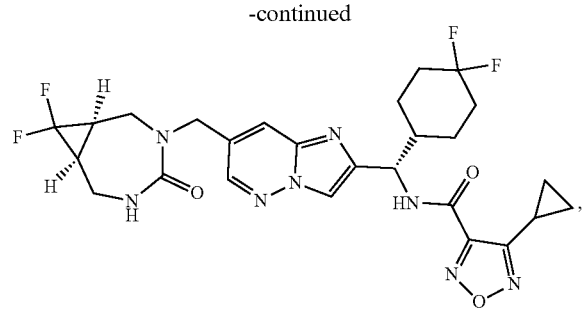
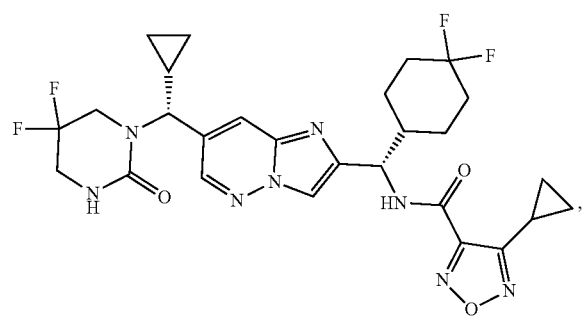 [SMILES: O=C(N[C@H](c1cn2ncc([C@@H](C3CC3)N3CC(F)(F)CNC3=O)cc2n1)C1CCC(F)(F)CC1)c1nonc1C1CC1]
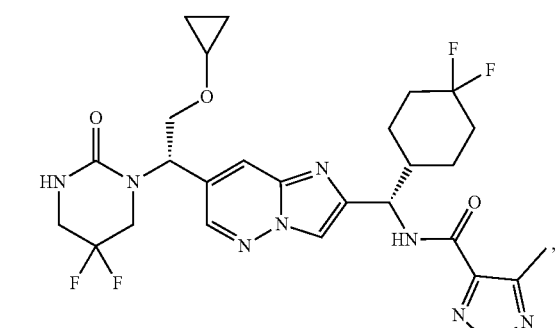
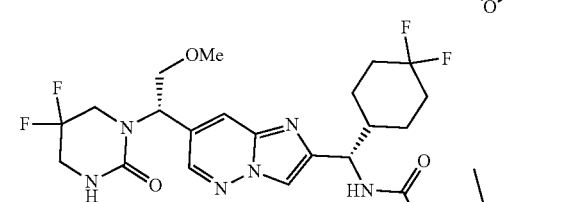
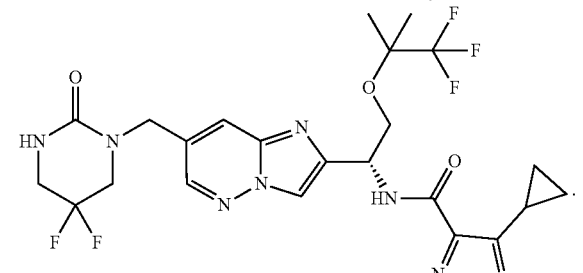
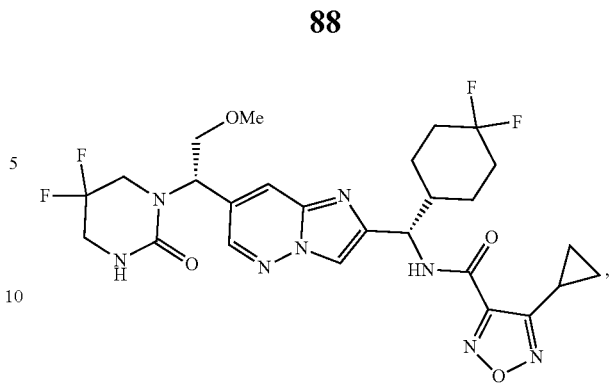
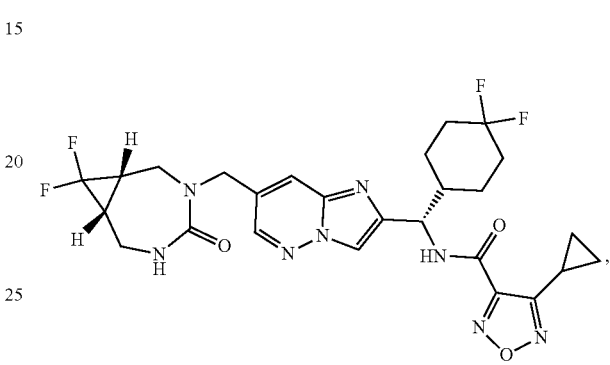
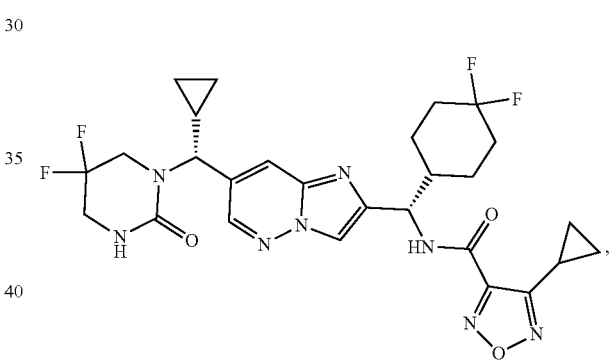
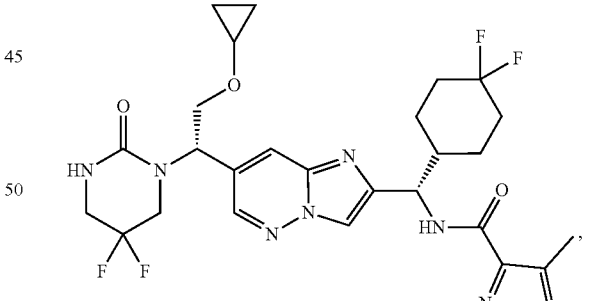
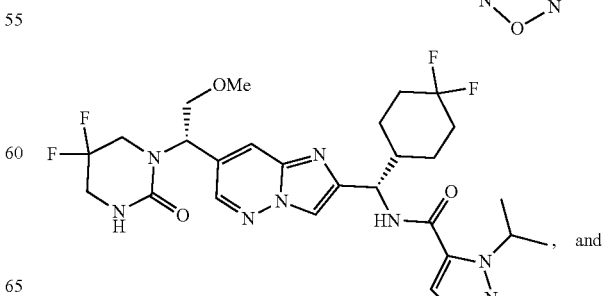
In some embodiments, disclosed herein is a compound of Formula I, or a pharmaceutically acceptable salt thereof, selected from the group consisting of:

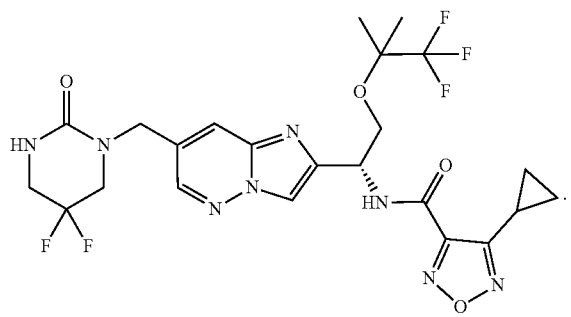
In some embodiments, disclosed herein is a compound of Formula I, or a pharmaceutically acceptable salt thereof, selected from the group consisting of:
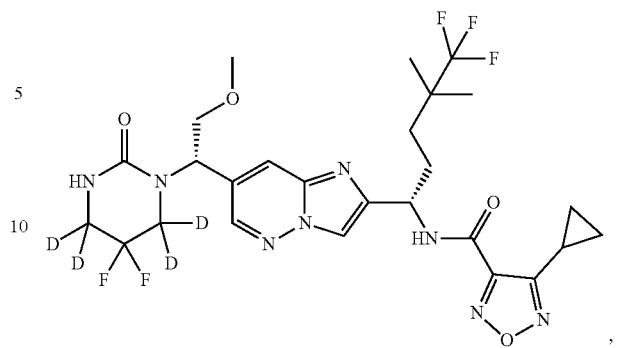
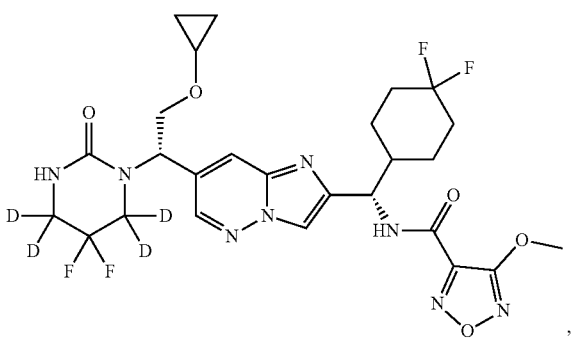
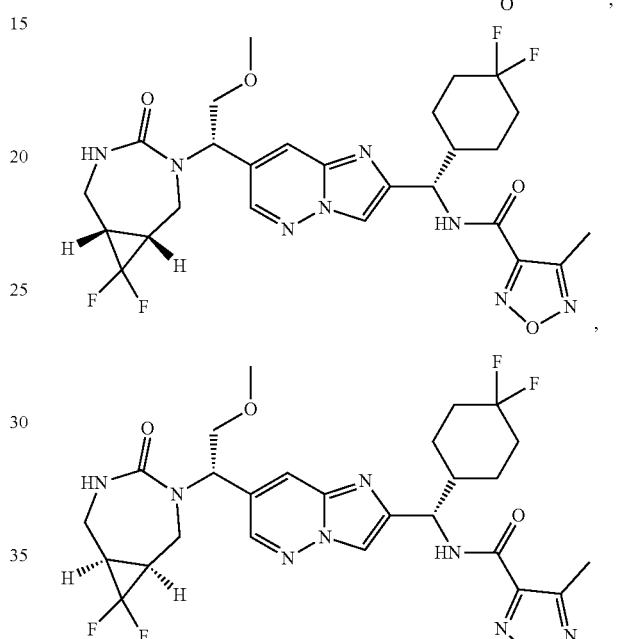
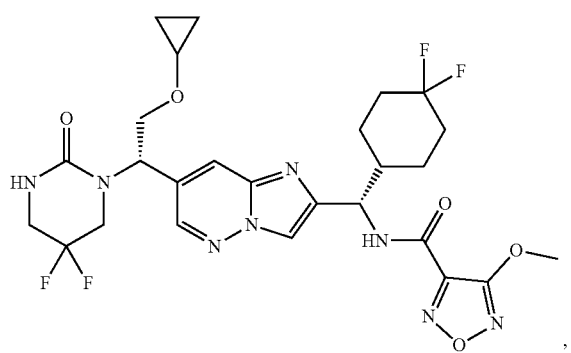
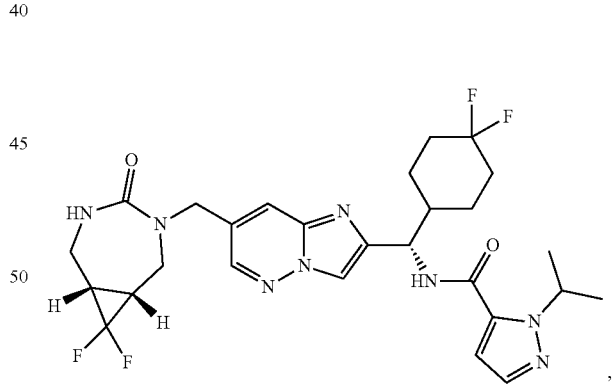
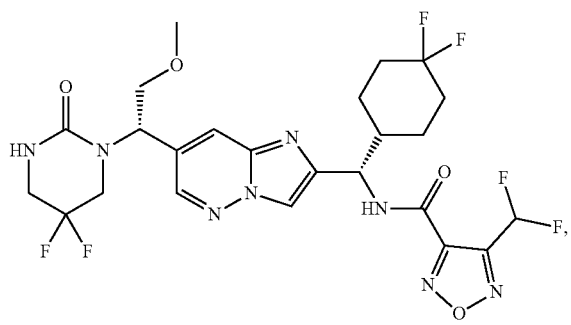
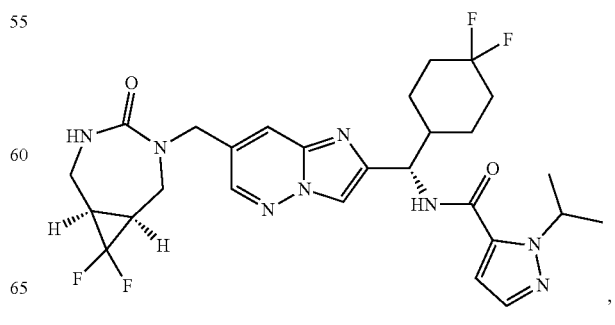

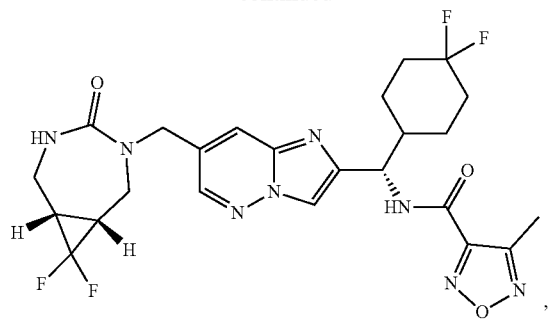

,

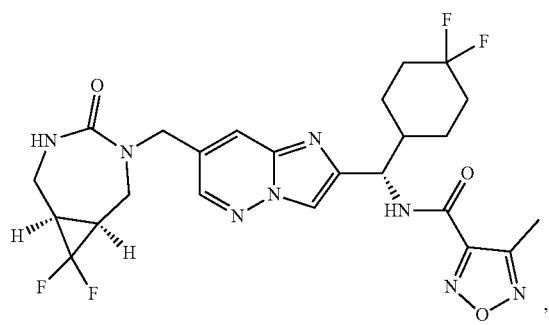

,

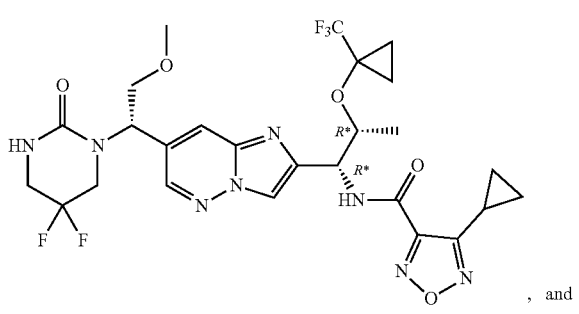

, and

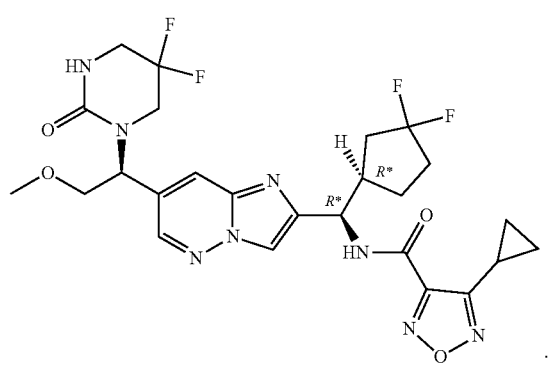

.

In some embodiments, disclosed herein is a compound of Formula I, or a pharmaceutically acceptable salt thereof, having the following structure:

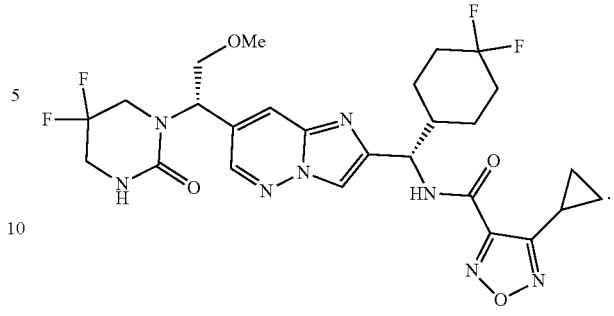

In some embodiments, disclosed herein is a compound of Formula I, or a pharmaceutically acceptable salt thereof, having the following structure:

In some embodiments, disclosed herein is a compound of Formula I, or a pharmaceutically acceptable salt thereof, having the following structure:

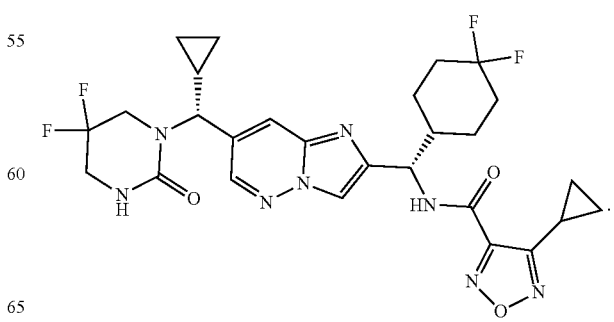

.

In some embodiments, disclosed herein is a compound of Formula I, or a pharmaceutically acceptable salt thereof, having the following structure:

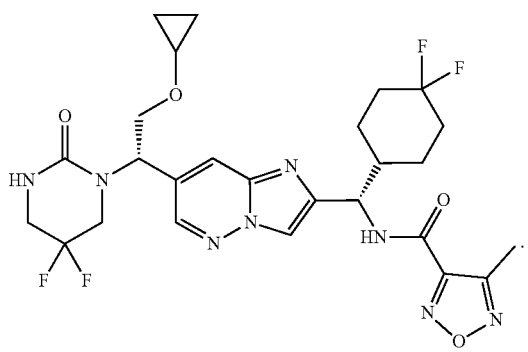 [SMILES: Cc1nonc1C(=O)N[C@H](c1cn2ncc([C@@H](COC3CC3)N3CC(F)(F)CNC3=O)cc2n1)C1CCC(F)(F)CC1]

In some embodiments, disclosed herein is a compound of Formula I, or a pharmaceutically acceptable salt thereof, having the following structure:

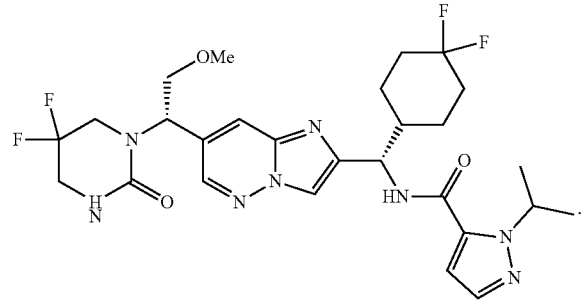 [SMILES: COC[C@H](c1cnn2cc([C@@H](NC(=O)c3ccnn3C(C)C)C3CCC(F)(F)CC3)nc2c1)N1CC(F)(F)CNC1=O]

In some embodiments, disclosed herein is a compound of Formula I, or a pharmaceutically acceptable salt thereof, having the following structure:

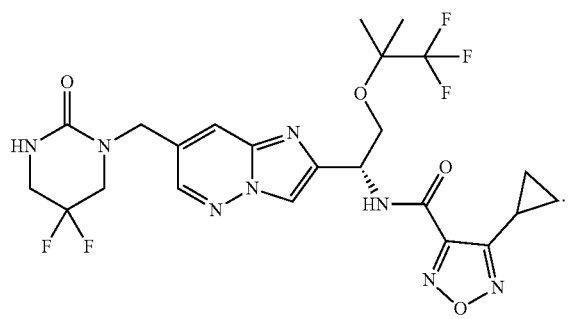 [SMILES: CC(C)(OC[C@H](NC(=O)c1nonc1C1CC1)c1cn2ncc(CN3CC(F)(F)CNC3=O)cc2n1)C(F)(F)F]

In some embodiments, disclosed herein is a compound of Formula I, or a pharmaceutically acceptable salt thereof, having the following structure:

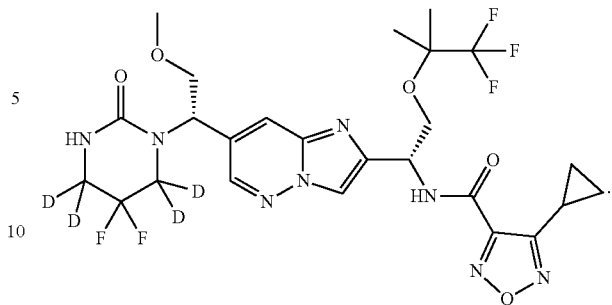

In some embodiments, disclosed herein is a compound of Formula I, or a pharmaceutically acceptable salt thereof, having the following structure:

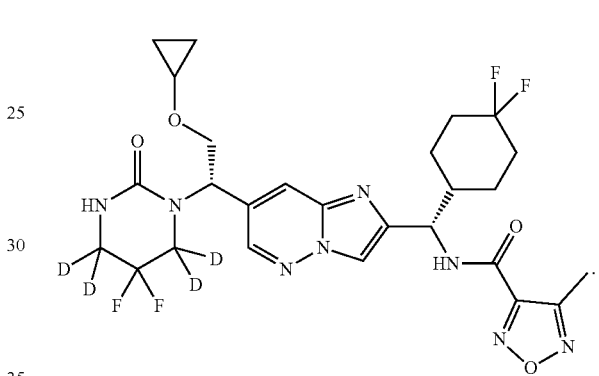

In some embodiments, disclosed herein is a compound of Formula I, or a pharmaceutically acceptable salt thereof, having the following structure:

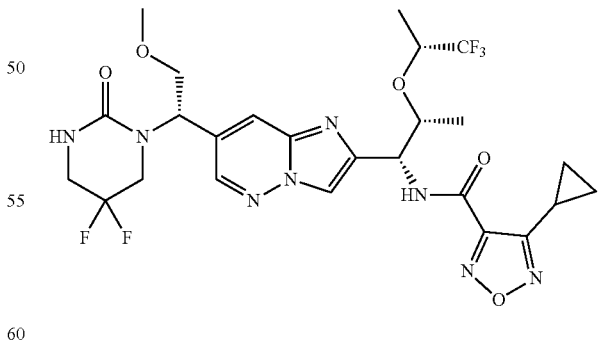

In some embodiments, disclosed herein is a compound of Formula I, or a pharmaceutically acceptable salt thereof, having the following structure:

In some embodiments, disclosed herein is a compound of Formula I, or a pharmaceutically acceptable salt thereof, having the following structure:

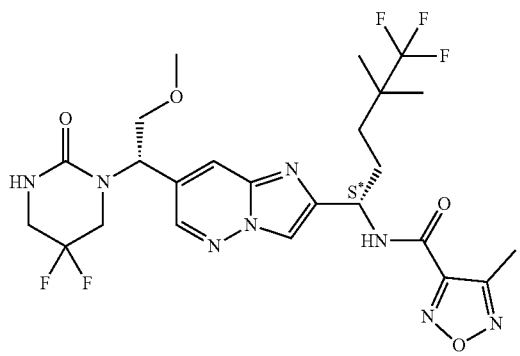

In some embodiments, disclosed herein is a compound of Formula I, or a pharmaceutically acceptable salt thereof, having the following structure:

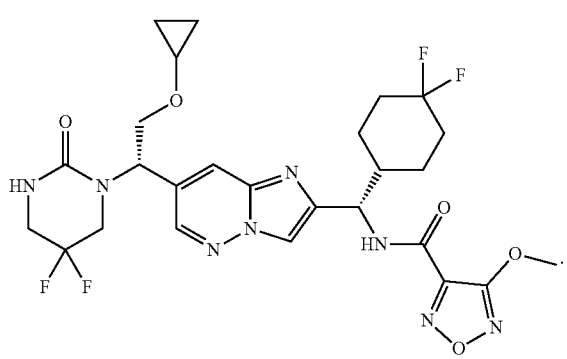

In some embodiments, disclosed herein is a compound of Formula I, or a pharmaceutically acceptable salt thereof, having the following structure:

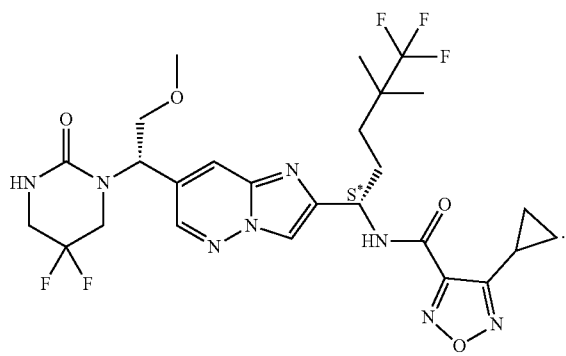

In some embodiments, disclosed herein is a compound of Formula I, or a pharmaceutically acceptable salt thereof, having the following structure:

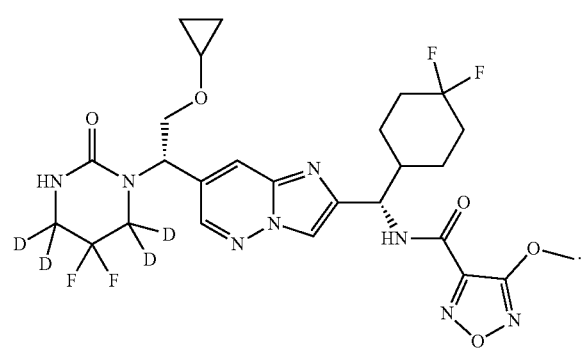 [SMILES: [2H]C1([2H])NC(=O)N([C@H](COC2CC2)c2cnn3cc([C@@H](NC(=O)c4nonc4OC)C4CCC(F)(F)CC4)nc3c2)C([2H])([2H])C1(F)F]

In some embodiments, disclosed herein is a compound of Formula I, or a pharmaceutically acceptable salt thereof, having the following structure:

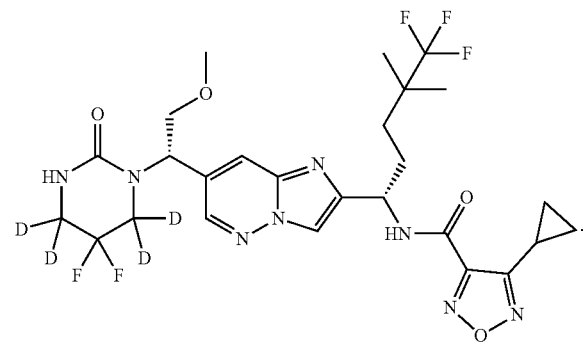 [SMILES: [2H]C1([2H])NC(=O)N([C@H](COC)c2cnn3cc([C@H](CCC(C)(C)C(F)(F)F)NC(=O)c4nonc4C4CC4)nc3c2)C([2H])([2H])C1(F)F]

In some embodiments, disclosed herein is a compound of Formula I, or a pharmaceutically acceptable salt thereof, having the following structure:

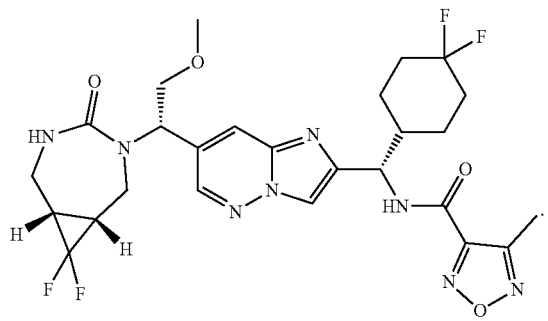 [SMILES: COC[C@H](c1cnn2cc([C@@H](NC(=O)c3nonc3C)C3CCC(F)(F)CC3)nc2c1)N1C[C@H]2[C@@H](CNC1=O)C2(F)F]

In some embodiments, disclosed herein is a compound of Formula I, or a pharmaceutically acceptable salt thereof, having the following structure:

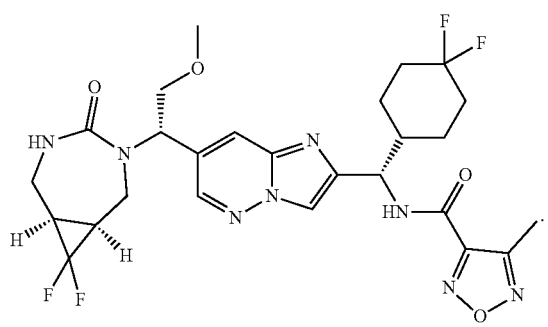 [SMILES: COC[C@H](c1cnn2cc([C@@H](NC(=O)c3nonc3C)C3CCC(F)(F)CC3)nc2c1)N1C[C@@H]2[C@H](CNC1=O)C2(F)F]

In some embodiments, disclosed herein is a compound of Formula I, or a pharmaceutically acceptable salt thereof, having the following structure:

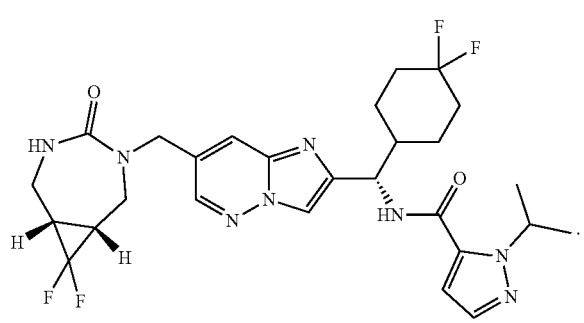 [SMILES: CC(C)n1nccc1C(=O)N[C@H](c1cn2ncc(CN3C[C@H]4[C@@H](CNC3=O)C4(F)F)cc2n1)C1CCC(F)(F)CC1]

In some embodiments, disclosed herein is a compound of Formula I, or a pharmaceutically acceptable salt thereof, having the following structure:

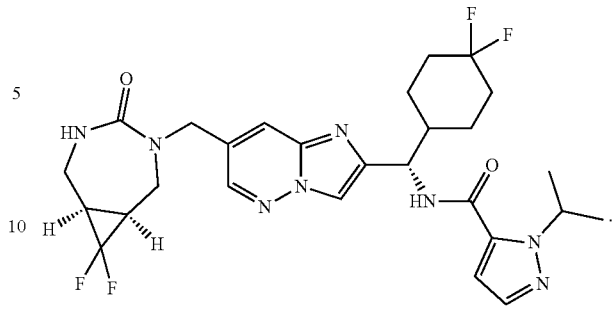

In some embodiments, disclosed herein is a compound of Formula I, or a pharmaceutically acceptable salt thereof, having the following structure:

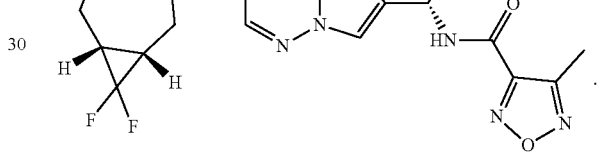

In some embodiments, disclosed herein is a compound of Formula I, or a pharmaceutically acceptable salt thereof, having the following structure:

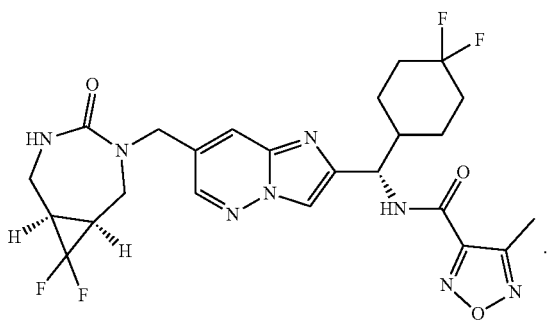 [SMILES: Cc1nonc1C(=O)N[C@H](c1cn2ncc(CN3C[C@@H]4[C@H](CNC3=O)C4(F)F)cc2n1)C1CCC(F)(F)CC1]

In some embodiments, disclosed herein is a compound of Formula I, or a pharmaceutically acceptable salt thereof, having the following structure:

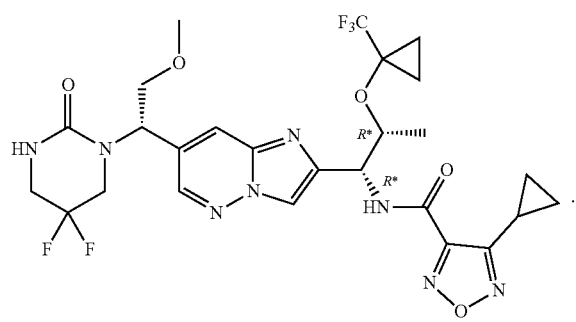 [SMILES: COC[C@H](c1cnn2cc([C@@H](NC(=O)c3nonc3C3CC3)[C@@H](C)OC3(C(F)(F)F)CC3)nc2c1)N1CC(F)(F)CNC1=O]
In some embodiments, disclosed herein is a compound of Formula I, or a pharmaceutically acceptable salt thereof, having the following structure:
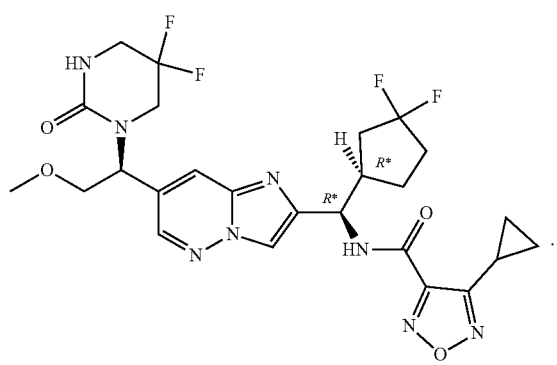 [SMILES: COC[C@H](c1cnn2cc([C@H](NC(=O)c3nonc3C3CC3)[C@@H]3CCC(F)(F)C3)nc2c1)N1CC(F)(F)CNC1=O]
In some embodiments, disclosed herein is a compound of Formula I, or a pharmaceutically acceptable salt thereof, having a structure as shown in Tables 2A, 2B, 2C, 2D, and 2E.
TABLE 2A
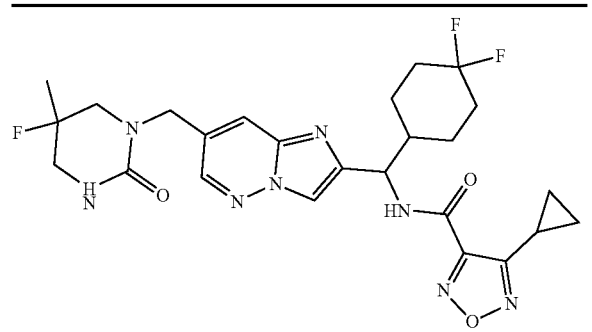
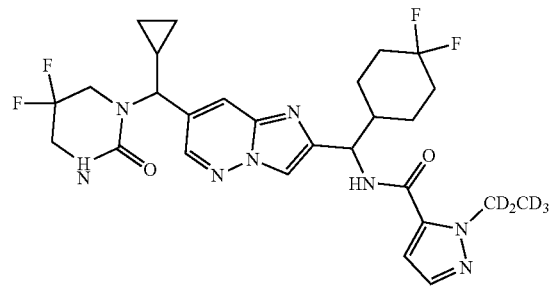
TABLE 2A-continued
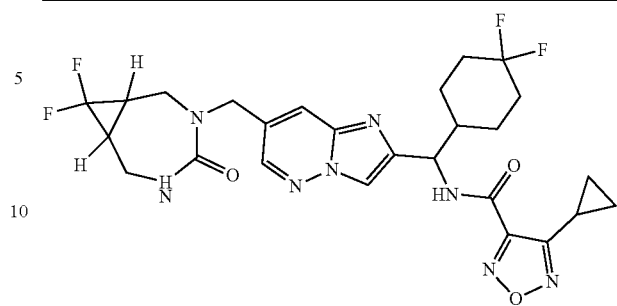
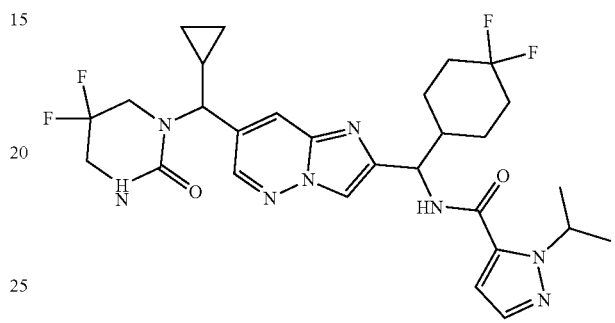
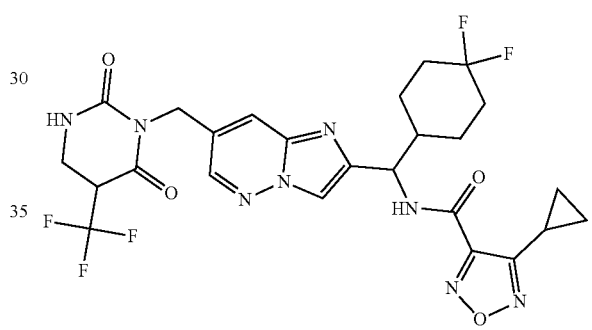
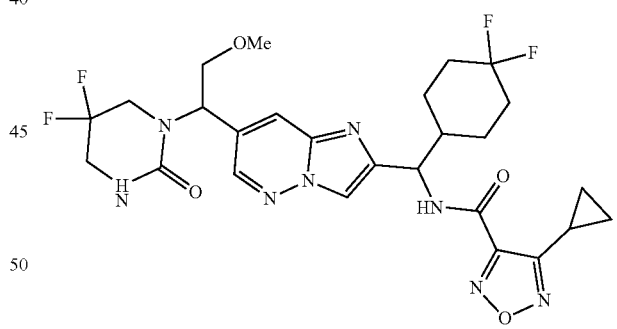
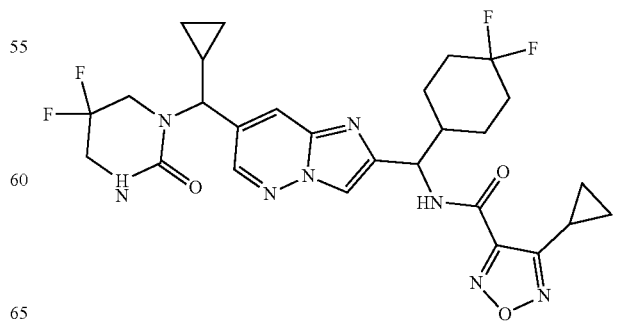

TABLE 2A-continued
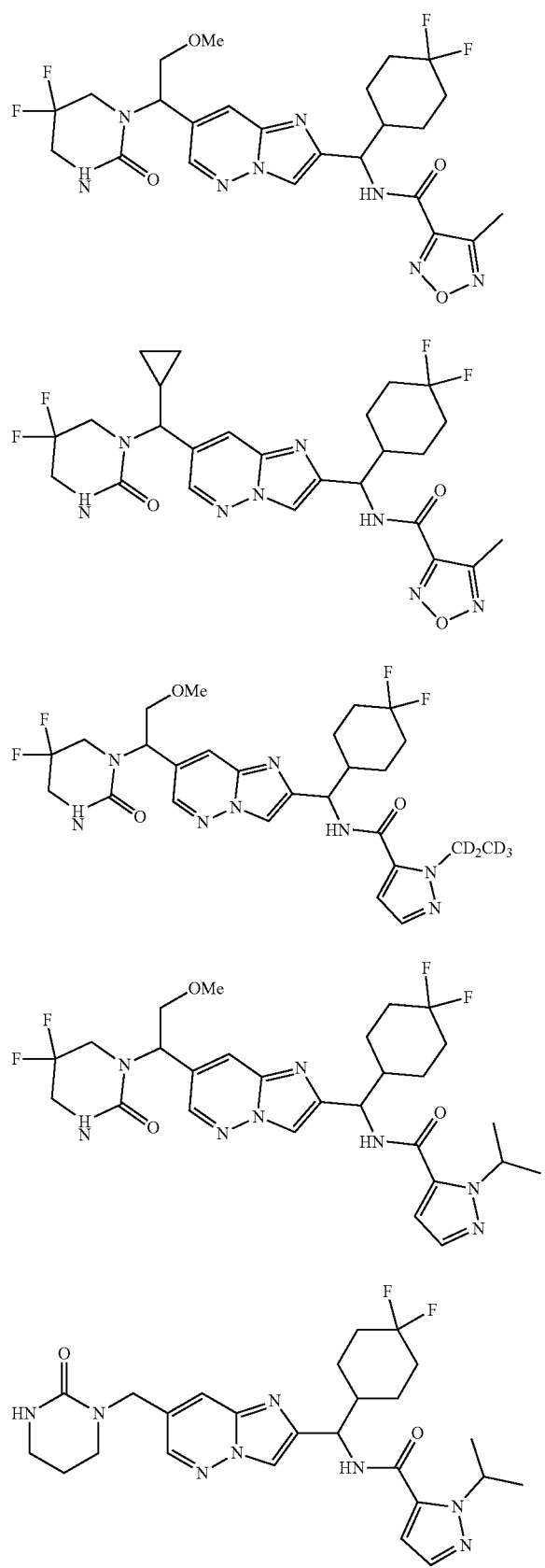
TABLE 2A-continued
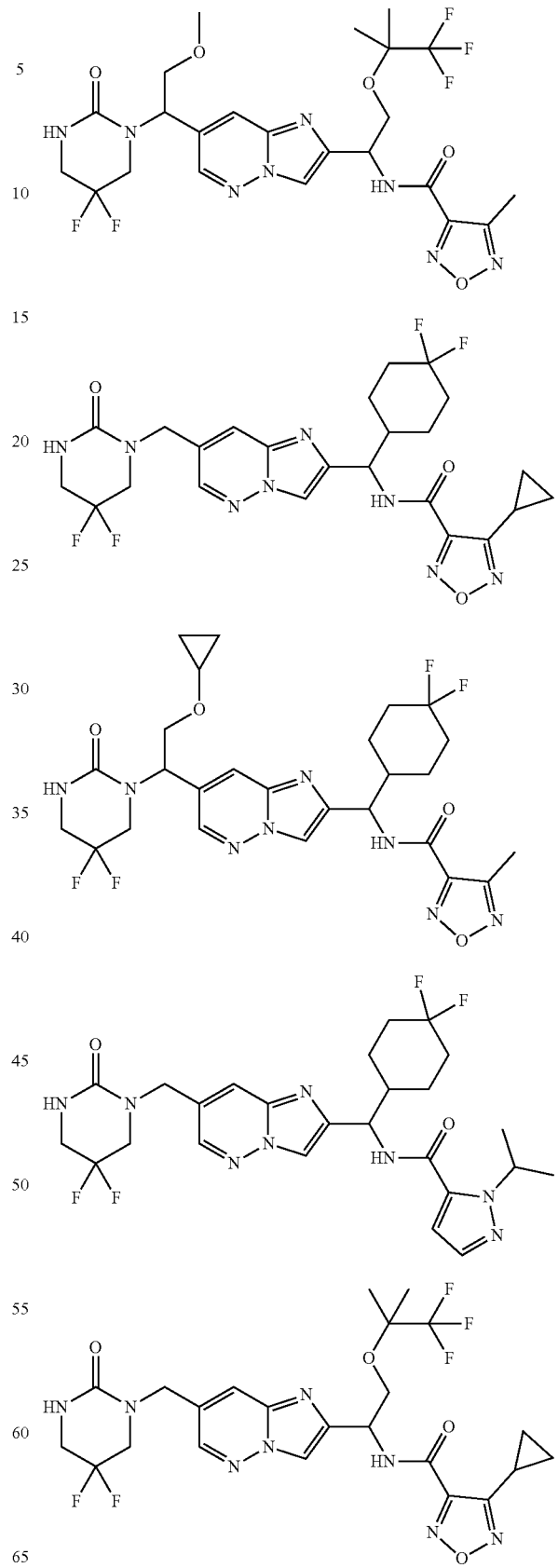

| TABLE 2A-continued |
|---|
| 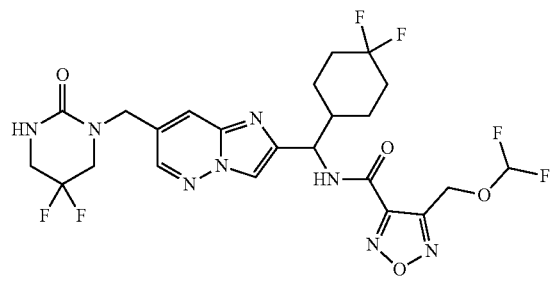 [SMILES: O=C(NC(c1cn2ncc(CN3CC(F)(F)CNC3=O)cc2n1)C1CCC(F)(F)CC1)c1nonc1COC(F)F] |
| 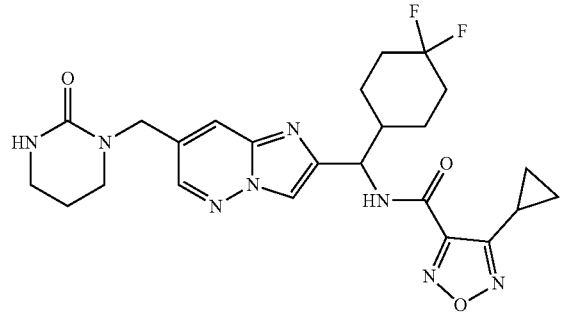 |
| 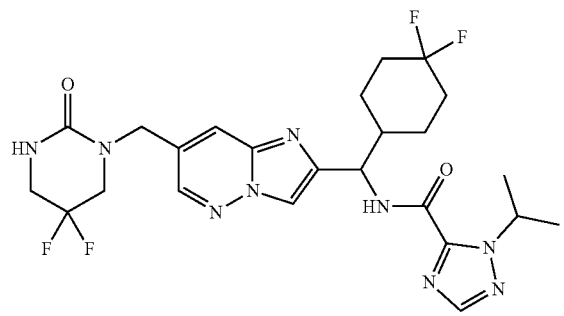 |
| TABLE 2B |
|---|
| 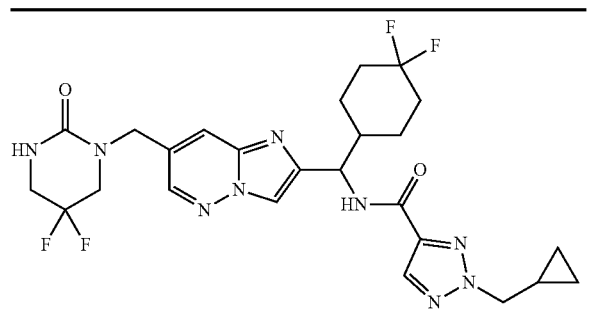 |
| 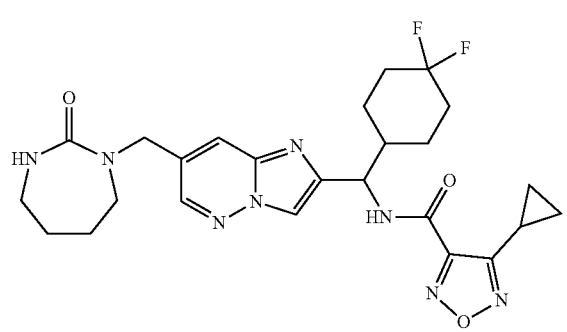 [SMILES: O=C(NC(c1cn2ncc(CN3CCCCNC3=O)cc2n1)C1CCC(F)(F)CC1)c1nonc1C1CC1] |
| TABLE 2B-continued |
|---|
| 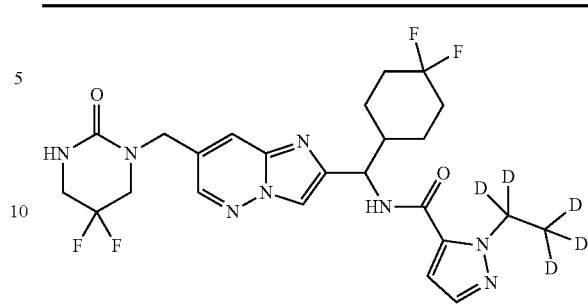 |
| 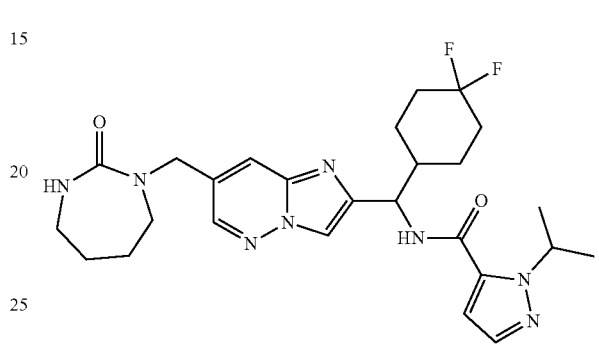 |
| 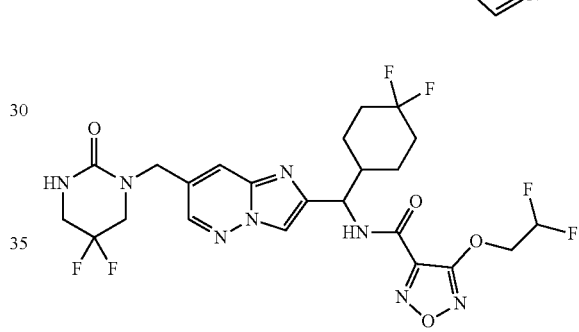 |
| 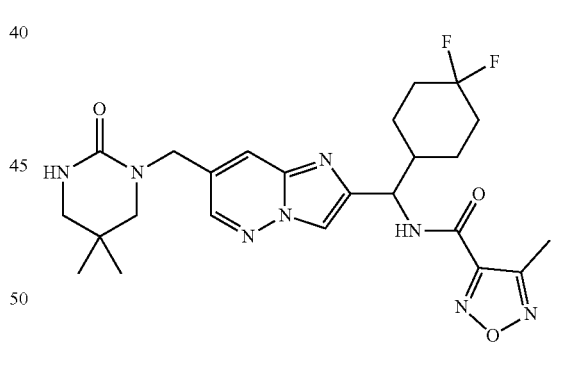 |
| 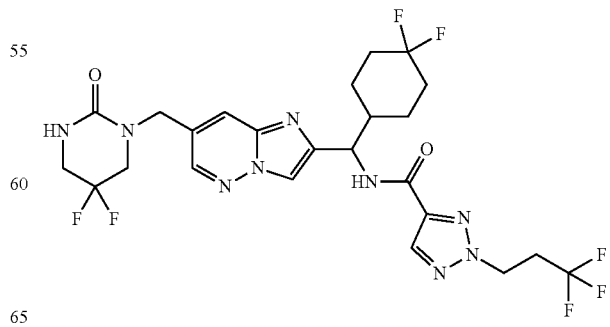 |

TABLE 2B-continued
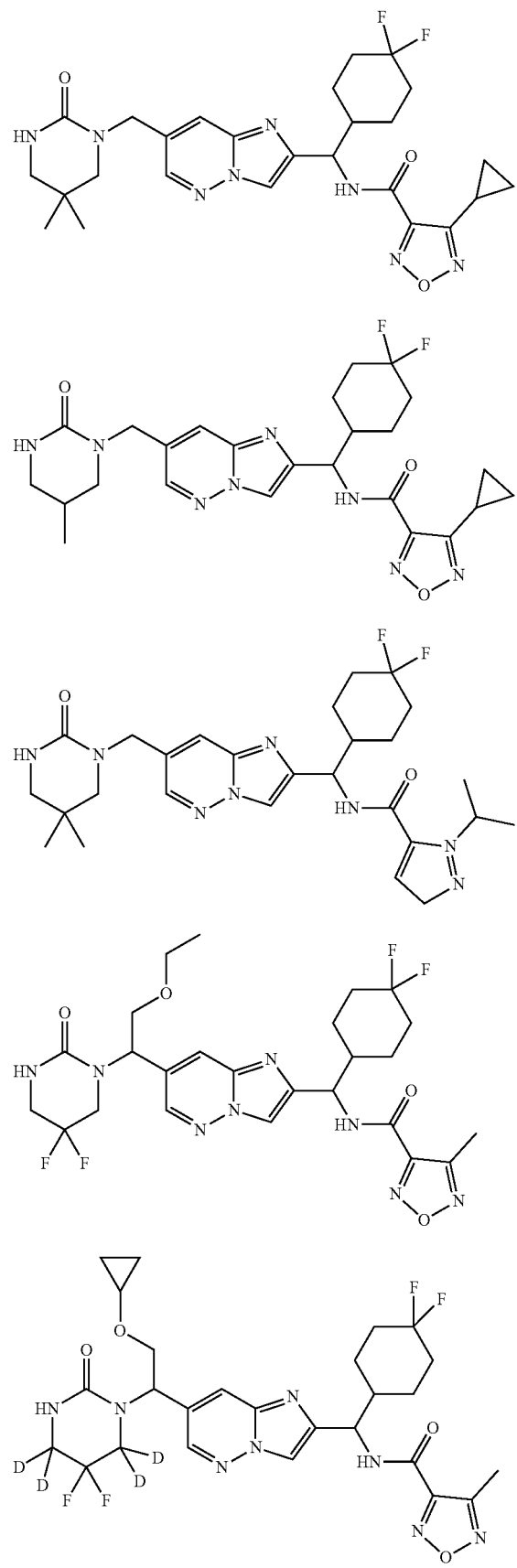
TABLE 2B-continued
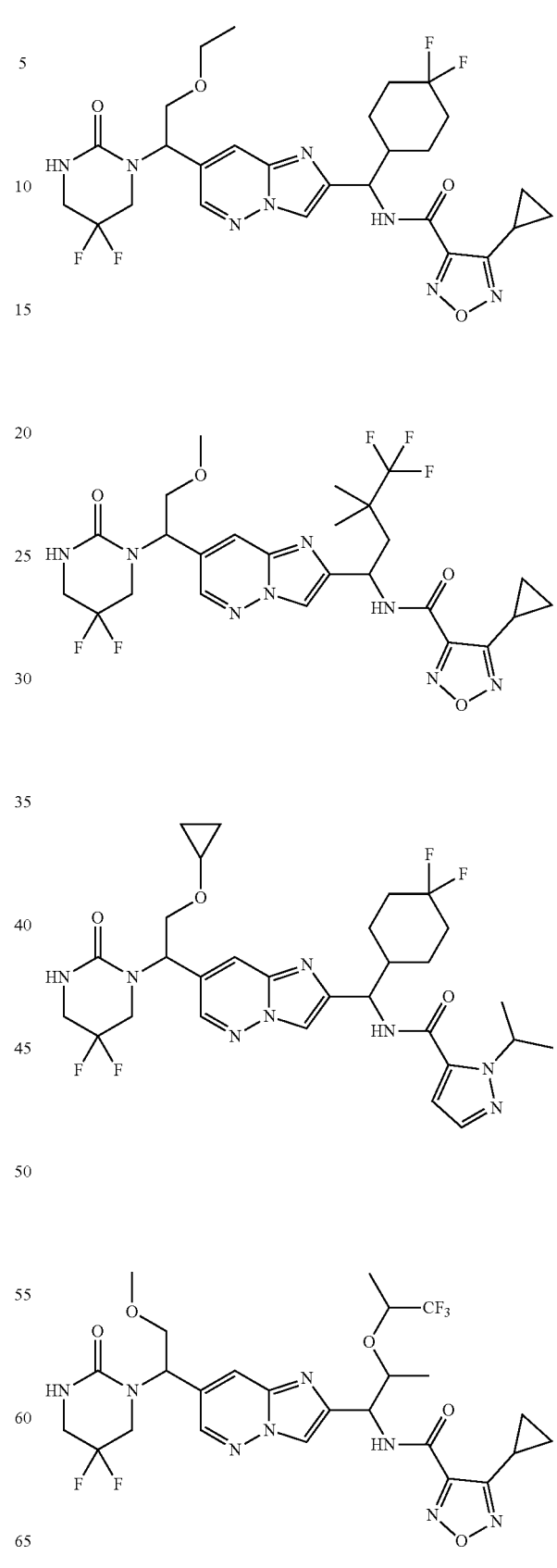

TABLE 2B-continued
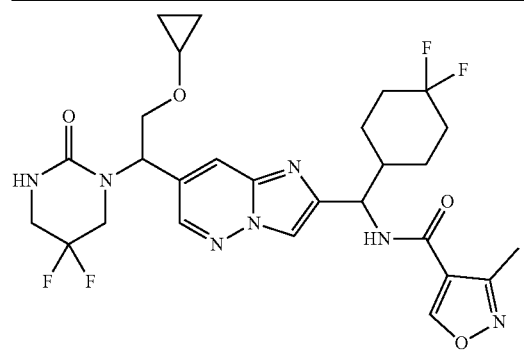
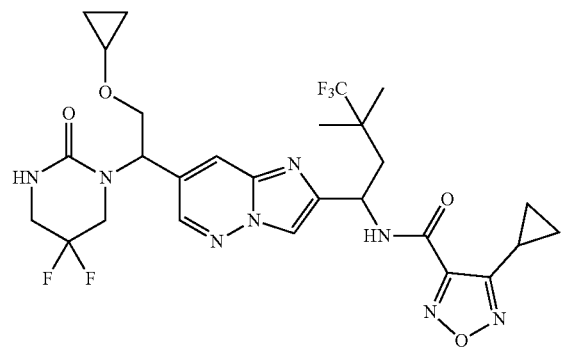
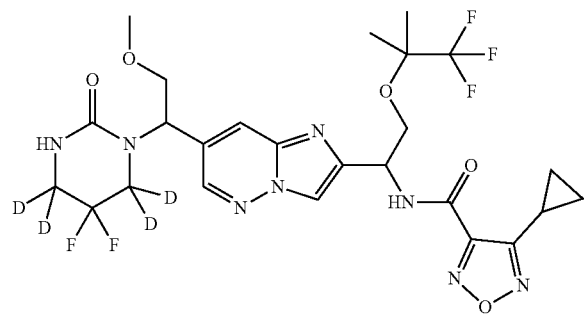 [SMILES: [2H]C1([2H])NC(=O)N(C(COC)c2cnn3cc(C(COC(C)(C)C(F)(F)F)NC(=O)c4nonc4C4CC4)nc3c2)C([2H])([2H])C1(F)F]
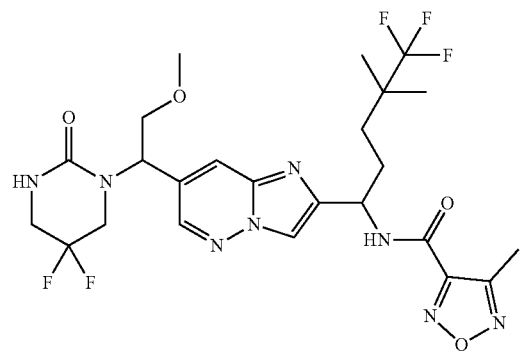 [SMILES: COCC(c1cnn2cc(C(CCC(C)(C)C(F)(F)F)NC(=O)c3nonc3C)nc2c1)N1CC(F)(F)CNC1=O]
TABLE 2C
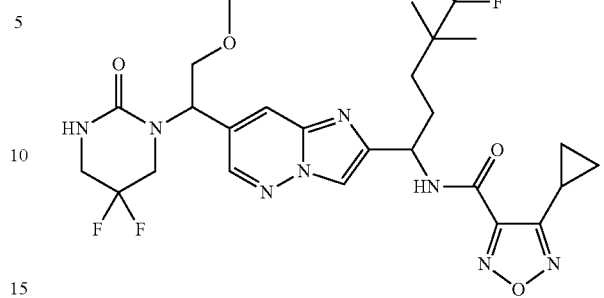
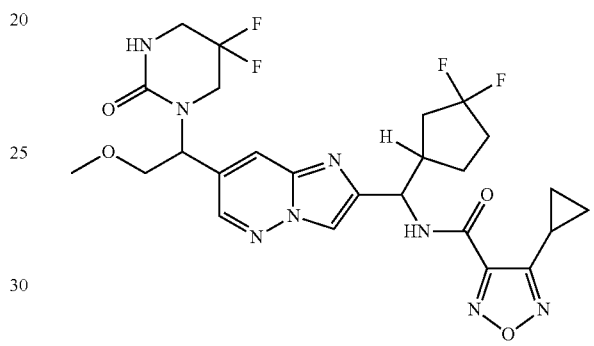
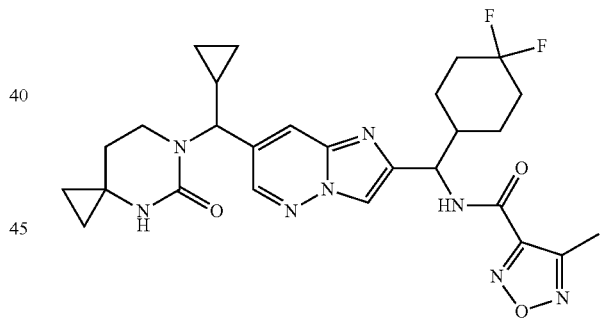
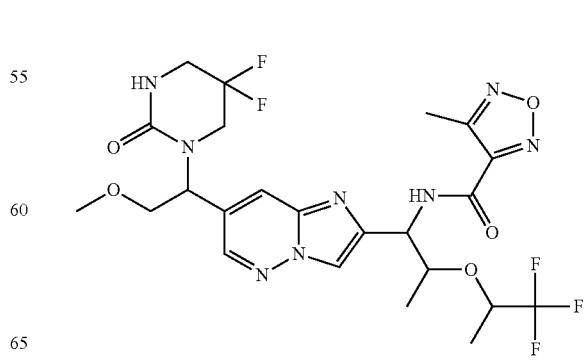

TABLE 2C-continued
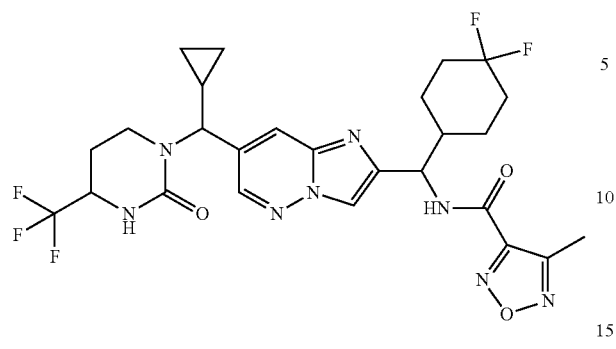
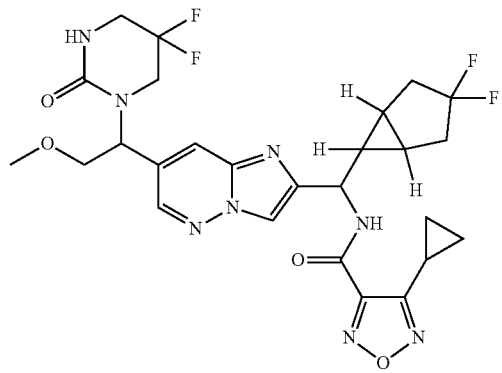
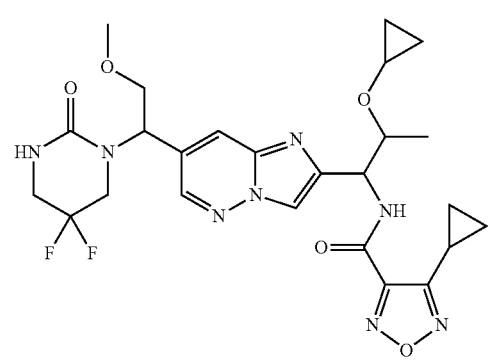 [SMILES: COCC(c1cnn2cc(C(NC(=O)c3nonc3C3CC3)C(C)OC3CC3)nc2c1)N1CC(F)(F)CNC1=O]
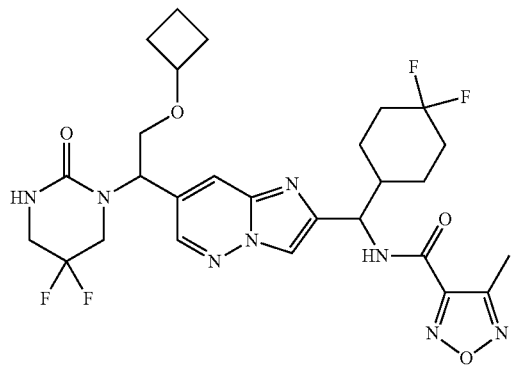
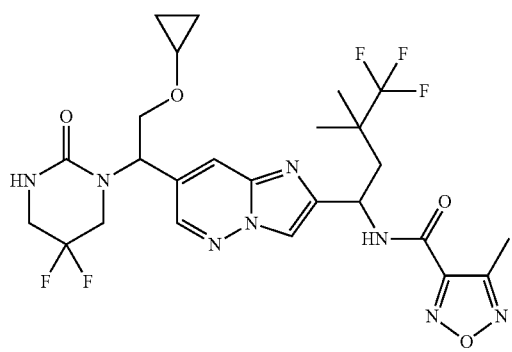 [SMILES: Cc1nonc1C(=O)NC(CC(C)(C)C(F)(F)F)c1cn2ncc(C(COC3CC3)N3CC(F)(F)CNC3=O)cc2n1]
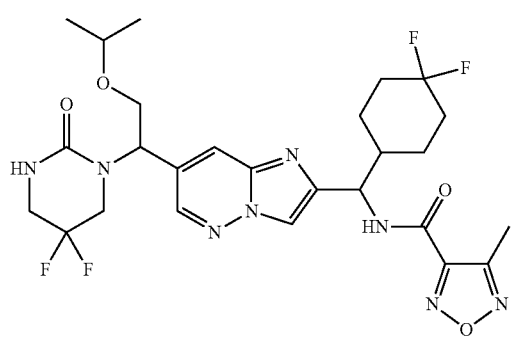
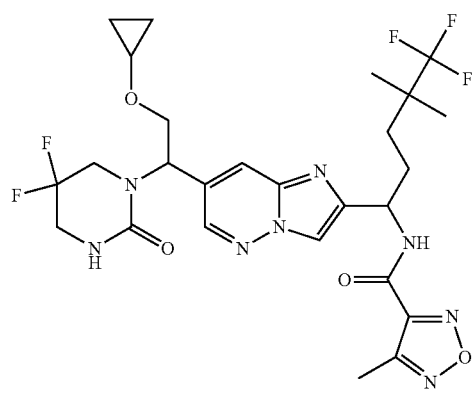 [SMILES: Cc1nonc1C(=O)NC(CCC(C)(C)C(F)(F)F)c1cn2ncc(C(COC3CC3)N3CC(F)(F)CNC3=O)cc2n1]
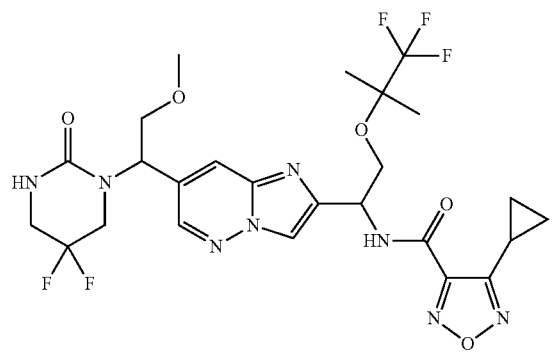 [SMILES: COCC(c1cnn2cc(C(COC(C)(C)C(F)(F)F)NC(=O)c3nonc3C3CC3)nc2c1)N1CC(F)(F)CNC1=O]

TABLE 2C-continued
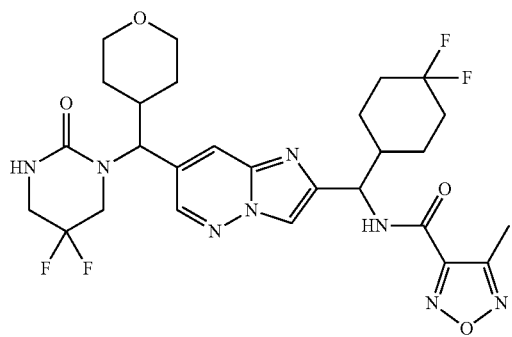 [SMILES: Cc1nonc1C(=O)NC(c1cn2ncc(C(C3CCOCC3)N3CC(F)(F)CNC3=O)cc2n1)C1CCC(F)(F)CC1]
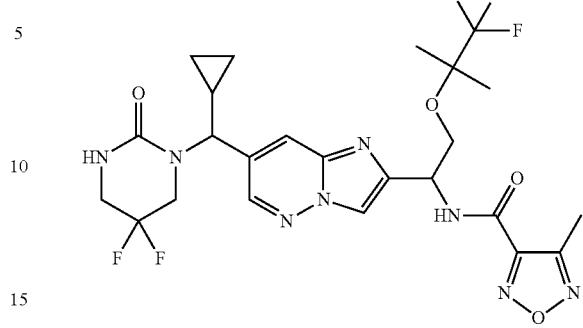
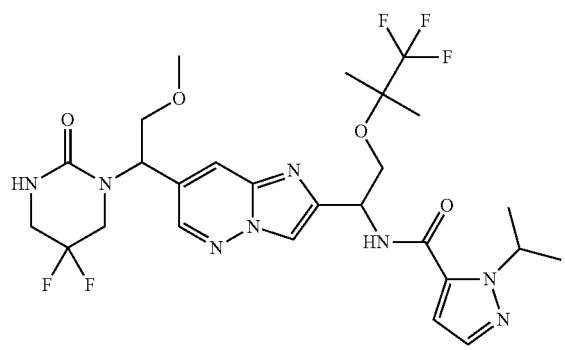 [SMILES: COCC(c1cnn2cc(C(COC(C)(C)C(F)(F)F)NC(=O)c3ccnn3C(C)C)nc2c1)N1CC(F)(F)CNC1=O]
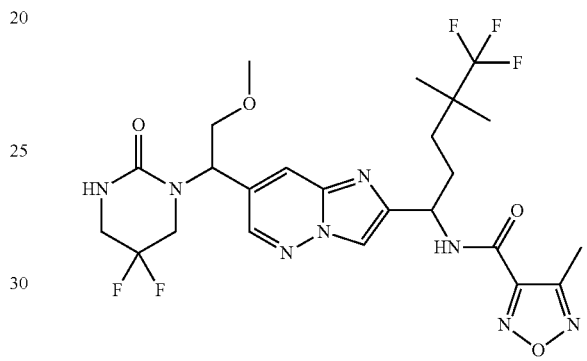
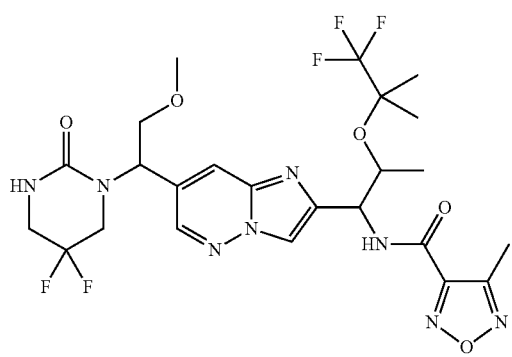 [SMILES: COCC(c1cnn2cc(C(NC(=O)c3nonc3C)C(C)OC(C)(C)C(F)(F)F)nc2c1)N1CC(F)(F)CNC1=O]
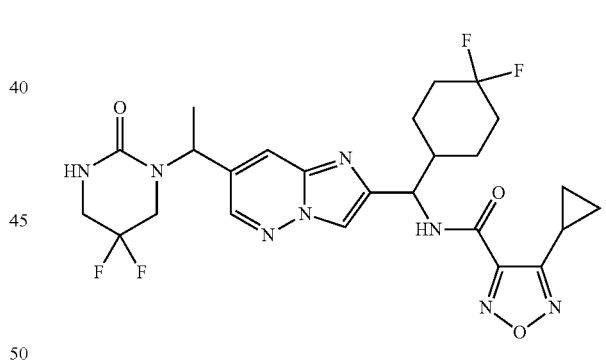
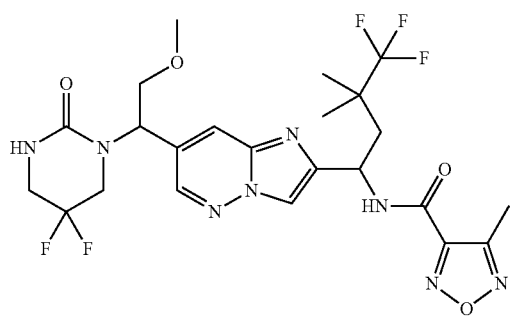 [SMILES: COCC(c1cnn2cc(C(CC(C)(C)C(F)(F)F)NC(=O)c3nonc3C)nc2c1)N1CC(F)(F)CNC1=O]
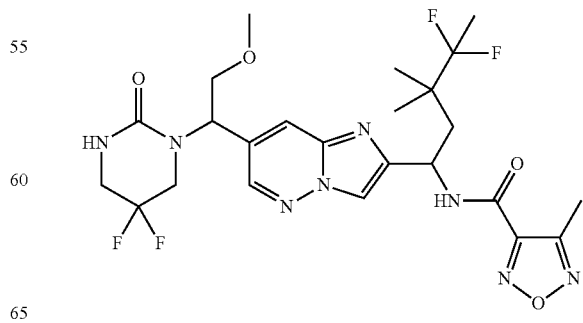

TABLE 2D
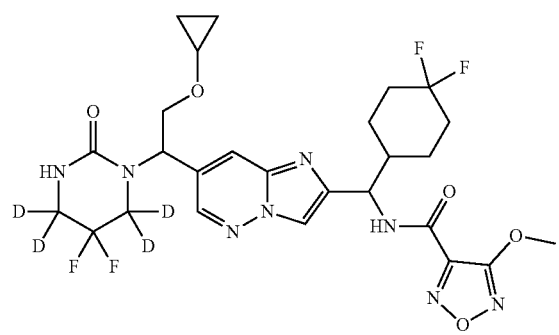
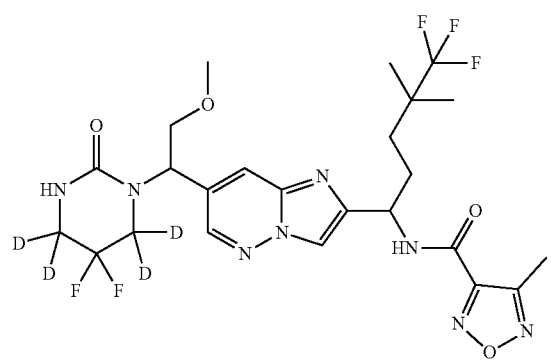
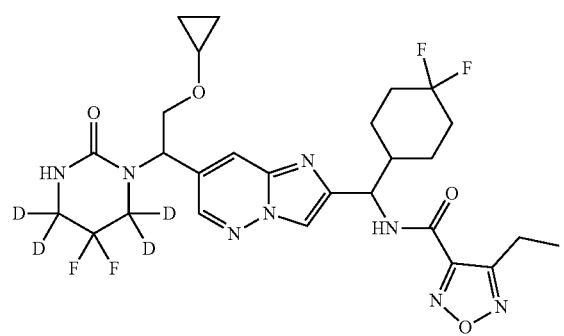 [SMILES: [2H]C1([2H])NC(=O)N(C(COC2CC2)c2cnn3cc(C(NC(=O)c4nonc4OC)C4CCC(F)(F)CC4)nc3c2)C([2H])([2H])C1(F)F]
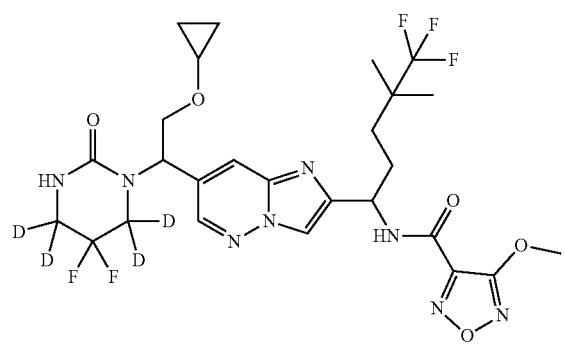
TABLE 2D-continued
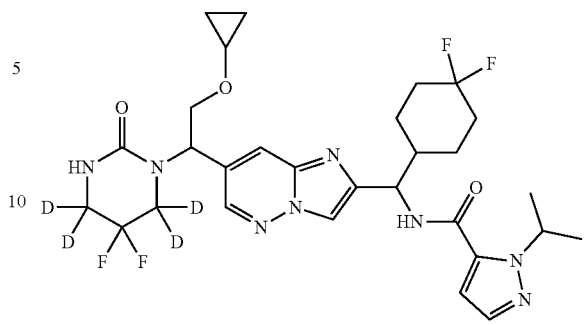
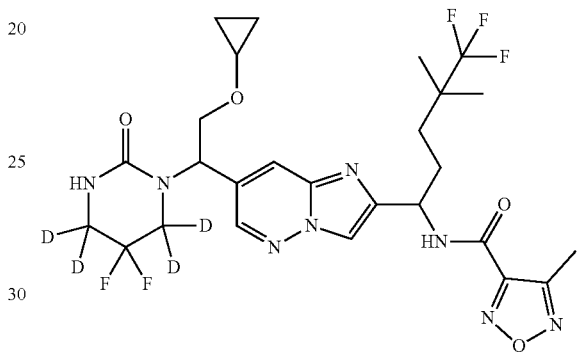
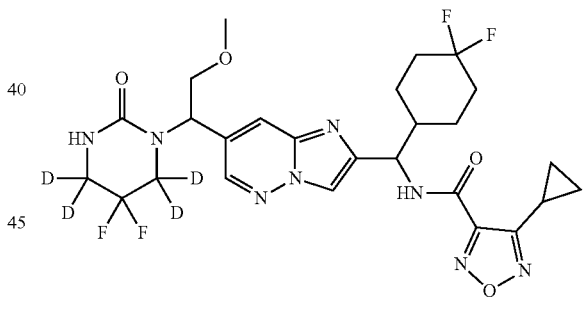
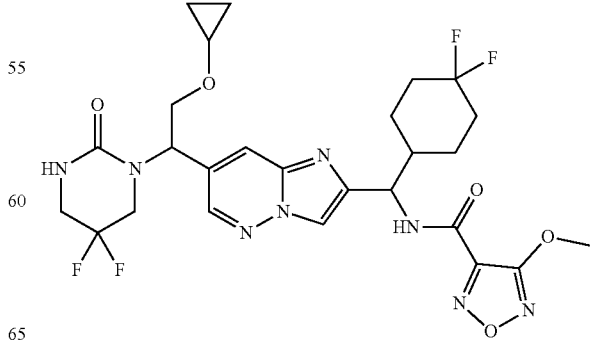

TABLE 2D-continued
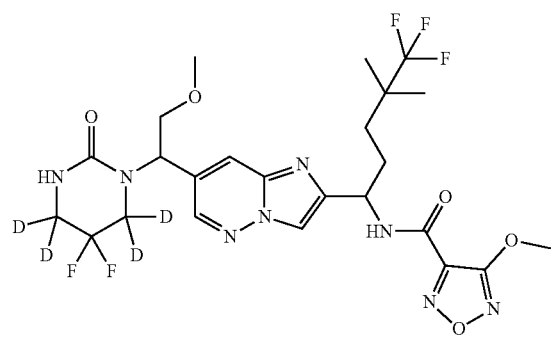
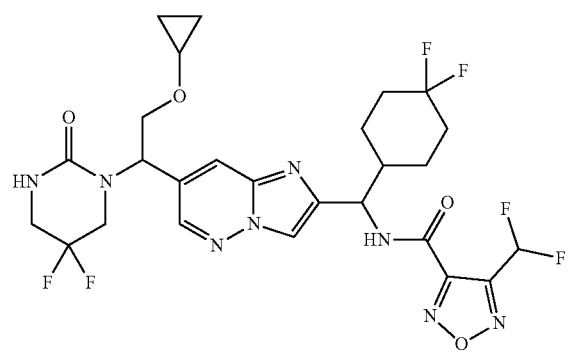
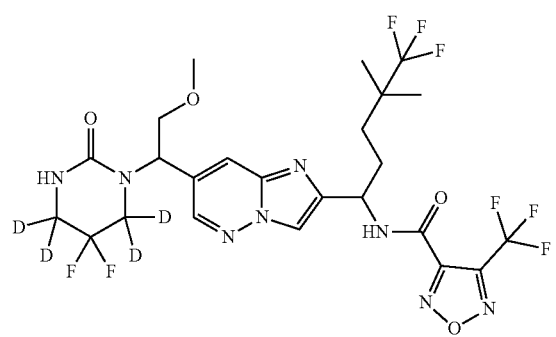 [SMILES: [2H]C1([2H])NC(=O)N(C(COC)c2cnn3cc(C(CCC(C)(C)C(F)(F)F)NC(=O)c4nonc4C(F)(F)F)nc3c2)C([2H])([2H])C1(F)F]
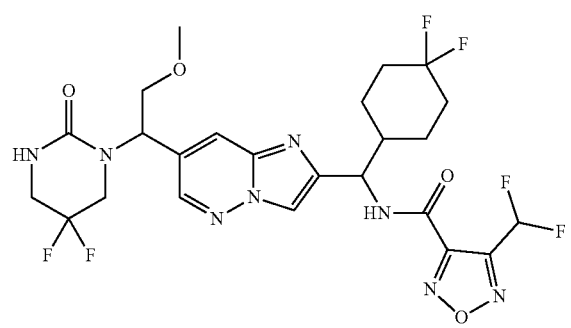
TABLE 2D-continued
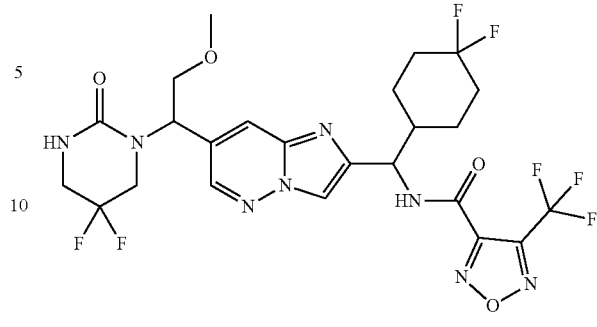
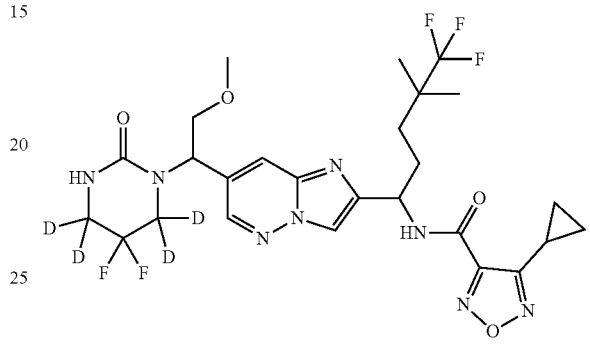
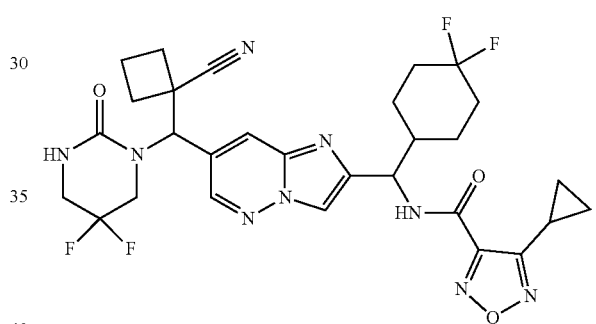
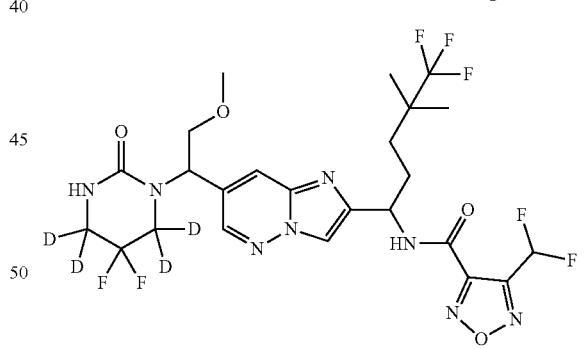
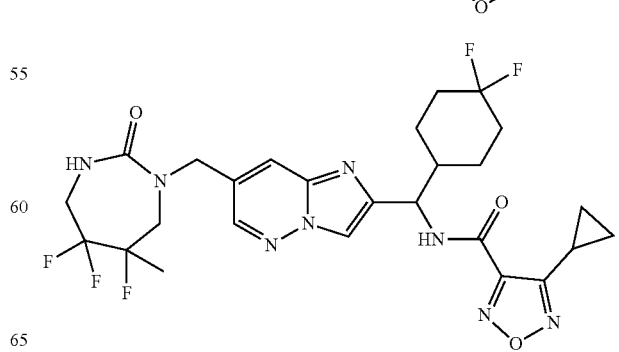

TABLE 2D-continued
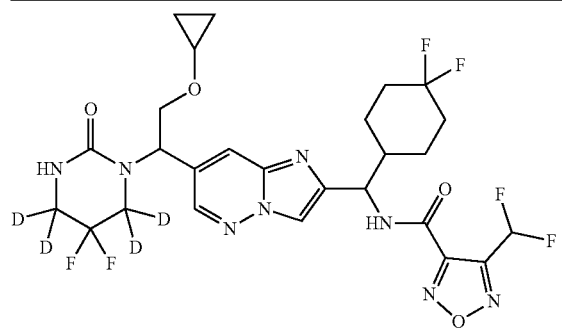
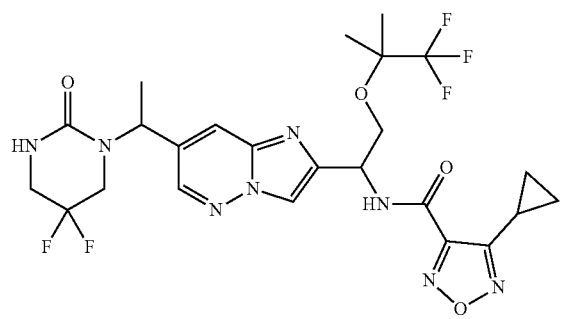 [SMILES: CC(c1cnn2cc(C(COC(C)(C)C(F)(F)F)NC(=O)c3nonc3C3CC3)nc2c1)N1CC(F)(F)CNC1=O]
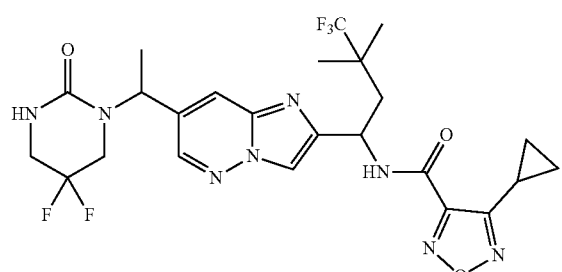
TABLE 2E
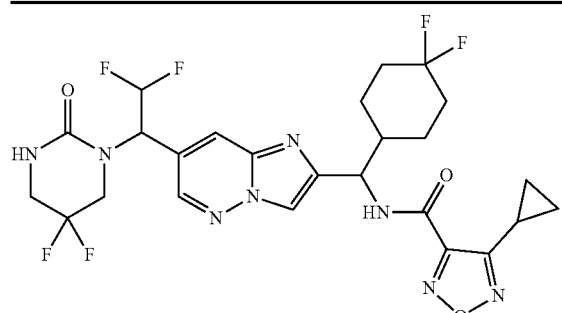
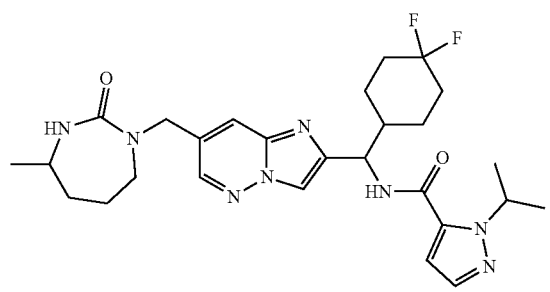 [SMILES: CC1CCCN(Cc2cnn3cc(C(NC(=O)c4ccnn4C(C)C)C4CCC(F)(F)CC4)nc3c2)C(=O)N1]
TABLE 2E-continued
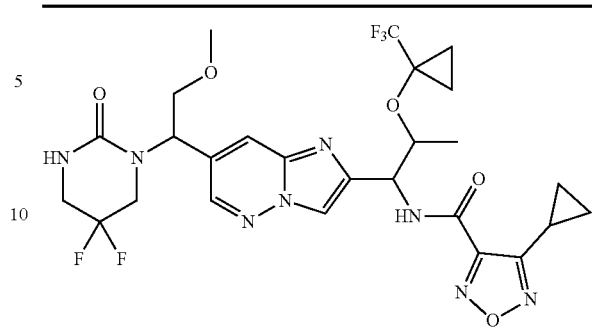
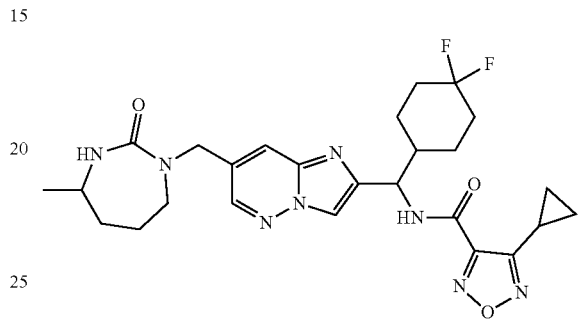
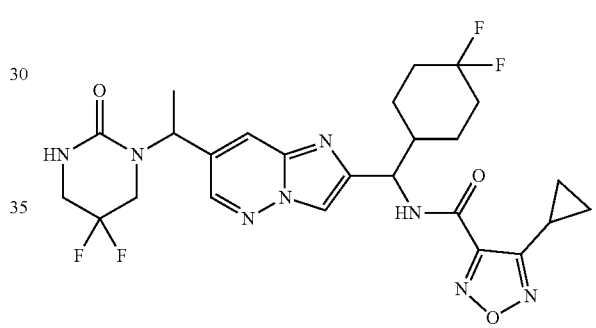
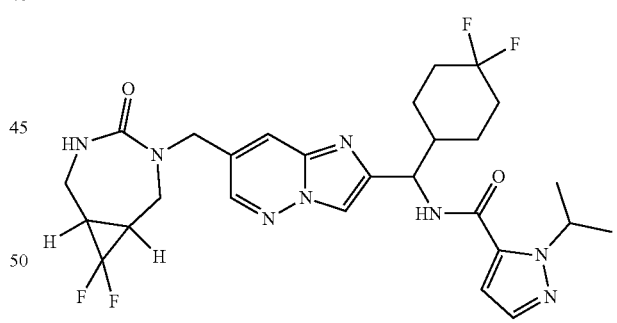
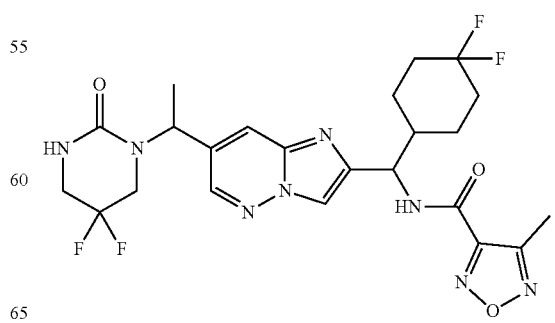

TABLE 2E-continued

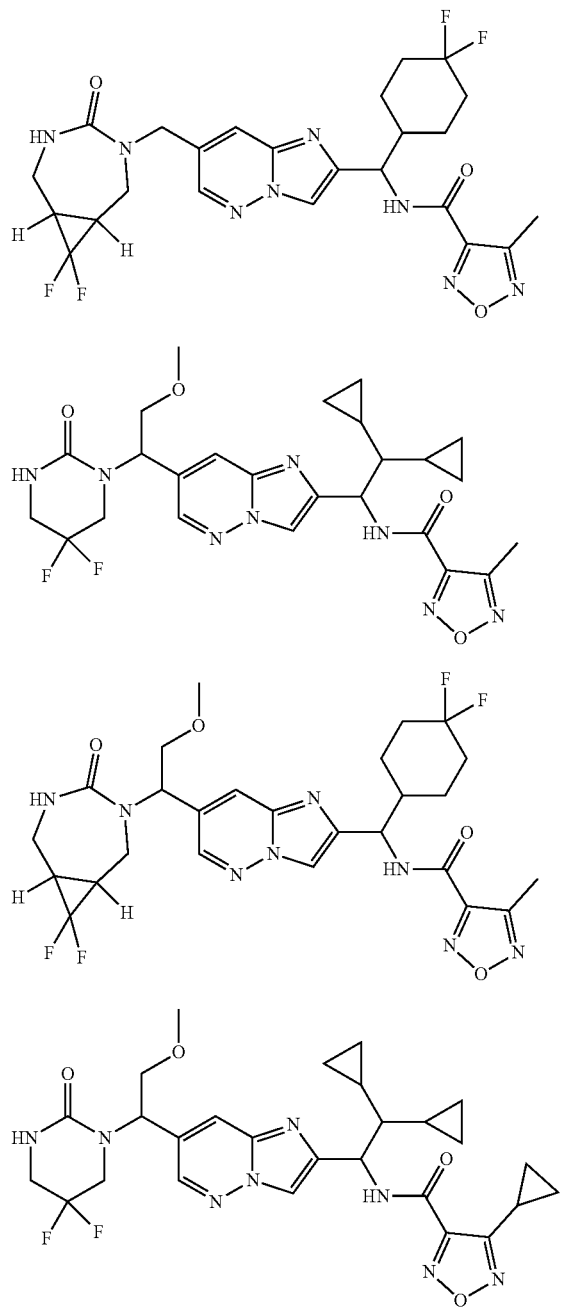

In some embodiments, disclosed herein is a pharmaceutical composition, comprising a compound of Formula I, or a pharmaceutically acceptable salt thereof, and a pharmaceutically acceptable carrier. In some embodiments, the pharmaceutical composition is formulated for oral administration (e.g., a tablet or capsule).

In some embodiments, disclosed herein is a pharmaceutical composition made by mixing a compound of Formula I, or a pharmaceutically acceptable salt thereof, and a pharmaceutically acceptable carrier.

In some embodiments, disclosed herein is a process for making a pharmaceutical composition comprising mixing a compound of Formula I, or a pharmaceutically acceptable salt thereof, and a pharmaceutically acceptable carrier.

III. Therapeutic Use

The present application is also directed to a method for treating and/or ameliorating a IL-17 mediated inflammatory syndrome, disorder or disease comprising administering to a subject in need thereof an effective amount of a compound of Formula I, or pharmaceutically acceptable salt thereof, composition thereof, or medicament thereof.

In some embodiments, disclosed herein is a method for treating or ameliorating an IL-17A mediated inflammatory syndrome, disorder, or disease comprising administering to a subject in need thereof a therapeutically effective amount of a compound of Formula I, or a pharmaceutically acceptable salt thereof.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigoid, atopic dermatitis, vitiligo, multiple sclerosis, asthma, uveitis, chronic obstructive pulmonary disorder, multiple myeloma, and systemic lupus erythematosus.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is psoriasis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is psoriatic arthritis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is rheumatoid arthritis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is ankylosing spondylitis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is hidradenitis suppurativa.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is bullous pemphigoid.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is atopic dermatitis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is vitiligo.

In some embodiments, disclosed herein is a method for treating or ameliorating and/an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is multiple sclerosis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is systemic lupus erythematosus.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is asthma.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is uveitis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is chronic obstructive pulmonary disorder.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is multiple myeloma.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigoid, atopic dermatitis, vitiligo, multiple sclerosis, asthma, uveitis, chronic obstructive pulmonary disorder, multiple myeloma, and systemic lupus erythematosus, wherein the compound of Formula I or the pharmaceutically acceptable salt thereof is administered orally (e.g., as a tablet or capsule).

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigoid, atopic dermatitis, vitiligo, multiple sclerosis, asthma, uveitis, chronic obstructive pulmonary disorder, multiple myeloma, and systemic lupus erythematosus, wherein the therapeutically effective amount is a dose of about 10 mg to 300 mg QD. In some embodiments, the therapeutically effective amount is a dose of about 20 mg to 200 mg QD. In some embodiments, the therapeutically effective amount is a dose of about 50 mg to 100 mg QD.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigoid, atopic dermatitis, vitiligo, multiple sclerosis, asthma, uveitis, chronic obstructive pulmonary disorder, multiple myeloma, and systemic lupus erythematosus, wherein the therapeutically effective amount is a dose of about 10 mg to 300 mg BID. In some embodiments, the therapeutically effective amount is a dose of about 20 mg to 200 mg BID. In some embodiments, the therapeutically effective amount is a dose of about 50 mg to 100 mg BID.

In some embodiments, disclosed herein is the use of a therapeutically effective amount of compound of Formula I, or a pharmaceutically acceptable salt thereof, for treating and/or ameliorating an IL-17A mediated inflammatory syndrome, disorder, or disease selected from the group consisting of: psoriasis, psoriatic arthritis, rheumatoid arthritis, ankylosing spondylitis, hidradenitis suppurativa, bullous pemphigoid, atopic dermatitis, vitiligo, multiple sclerosis, asthma, uveitis, chronic obstructive pulmonary disorder, multiple myeloma, and systemic lupus erythematosus.

In some embodiments, disclosed herein is the use of a compound of Formula I, or pharmaceutically acceptable salt thereof, in the manufacture of a medicament for treating and/or ameliorating an IL-17A mediated inflammatory syndrome, disorder, or disease selected from the group consisting of: psoriasis, psoriatic arthritis, rheumatoid arthritis, ankylosing spondylitis, hidradenitis suppurativa, bullous pemphigoid, atopic dermatitis, vitiligo, multiple sclerosis, asthma, uveitis, chronic obstructive pulmonary disorder, multiple myeloma, and systemic lupus erythematosus.

In some embodiments, disclosed herein is a method for treating and/or ameliorating an IL-17 mediated inflammatory syndrome, disorder or disease comprising administering to a subject in need thereof a therapeutically effective amount of a compound of Formula I, or pharmaceutically acceptable salt thereof, a composition thereof, or a medicament thereof.

In some embodiments, disclosed herein is a method of treating and/or ameliorating an IL-17 mediated inflammatory syndrome, disorder or disease, wherein the syndrome, disorder or disease is selected from the group consisting of: psoriasis, psoriatic arthritis, rheumatoid arthritis, ankylosing spondylitis, hidradenitis suppurativa, atopic dermatitis, vitiligo, multiple sclerosis, asthma, allergic asthma, steroid resistant asthma, neutrophilic asthma, chronic obstructive pulmonary disease, uveitis, multiple myeloma, and systemic lupus erythematosus, comprising administering to a subject in need thereof a therapeutically effective amount of a compound of Formula I, or pharmaceutically acceptable salt thereof, a composition thereof, or a medicament thereof.

In some embodiments, disclosed herein is a method of treating or ameliorating an IL-17 mediated inflammatory syndrome, disorder or disease, wherein the syndrome, disorder or disease is selected from the group consisting of: psoriasis, psoriatic arthritis, and ankylosing spondylitis, comprising administering to a subject in need thereof a therapeutically effective amount of a compound of Formula I, or pharmaceutically acceptable salt thereof, a composition thereof, or a medicament thereof.

In some embodiments, disclosed herein are methods of modulating IL-17 activity in a mammal by administration of a therapeutically effective amount of at least one compound of Formula I, or pharmaceutically acceptable salt thereof.

Also disclosed herein is a method of inhibiting production of interleukin-17, comprising administering to a subject in need thereof a therapeutically effective amount of a compound of Formula I, or pharmaceutically acceptable salt thereof.

IV. Combination Therapy

A compound of Formula I, or pharmaceutically acceptable salt thereof, a composition thereof, or a medicament thereof may also be used in combination with one or more additional therapeutic agents.

In some embodiments, the one or more additional therapeutic agents is selected from the group consisting of anti-inflammatory agents, immunomodulatory agents, and immunosuppressive agents.

In some embodiments, the one or more additional therapeutic agents is selected from the group consisting of: anti-TNFalpha agents such as infliximab (Remicade®), adalimumab (Humira®), certolizumab pegol (Cimzia®), golimumab (Simponi®), etanercept (Enbrel®), thalidomide (Immunoprin®), lenalidomide (Revlimid®), and pomalidomide (Pomalyst®/Imnovid®); anti-p40 antibody agents such as ustekinumab (Stelara®); and anti-p19 antibody agents such as guselkumab (Tremfya®), tildrakizumab (Ilumya™/Ilumetri), risankizumab (Skyrizi®), and mirikizumab.

In some embodiments, disclosed herein is a method of treating and/or ameliorating an IL-17 mediated inflammatory syndrome, disorder or disease, in a subject in need thereof comprising administering to the subject a therapeutically effective amount of the compound of Formula I, or pharmaceutically acceptable salt thereof, composition thereof, or medicament thereof in a combination therapy with one or more additional therapeutic agents, such as anti-inflammatory agents, immunomodulatory agents, or immunosuppressive agents, wherein said syndrome, disorder or disease is selected from the group consisting of psoriasis, psoriatic arthritis, rheumatoid arthritis, ankylosing spondylitis, hidradenitis suppurativa, atopic dermatitis, vitiligo, multiple sclerosis, asthma, allergic asthma, steroid resistant asthma, neutrophilic asthma, chronic obstructive pulmonary disease, uveitis, multiple myeloma, and systemic lupus erythematosus.

In some embodiments, disclosed herein is a method of treating and/or ameliorating an IL-17 mediated inflammatory syndrome, disorder or disease, in a subject in need thereof comprising administering to the subject a therapeutically effective amount of the compound of Formula I, or pharmaceutically acceptable salt thereof, composition thereof, or medicament thereof in a combination therapy with one or more additional therapeutic agents, such as anti-inflammatory agents, or immunosuppressive agents, wherein said syndrome, disorder or disease is psoriasis, psoriatic arthritis, ankylosing spondylitis. In some embodiments, the IL-17 mediated inflammatory syndrome, disorder or disease is psoriasis. In some embodiments, the IL-17 mediated inflammatory syndrome, disorder or disease is psoriatic arthritis. In some embodiments, the IL-17 mediated inflammatory syndrome, disorder or disease is ankylosing spondylitis.

Dosage Regimen

When employed as IL-17A modulators, the compounds disclosed herein may be administered in an effective amount within the dosage range of about 0.5 mg to about 1 g, preferably between about 0.5 mg to about 500 mg, in single or divided daily doses. In some embodiments, the dosage amount is about 5 mg to 400 mg. In some embodiments, the dosage amount is about 10 mg to 300 mg. In some embodiments, the dosage amount is about 0.5, 1, 5, 10, 15, 20, 25, 30, 35, 40, 45, 50, 55, 60, 65, 70, 75, 80, 85, 90, 95, or 100 mg of a compound of Formula I, or pharmaceutically acceptable salt thereof. In some embodiments, the dosage amount is about 100, 105, 110, 115, 120, 125, 130, 135, 140, 145, 150, 155, 160, 165, 170, 175, 180, 185, 190, 195, or 200 mg of a compound of Formula I, or pharmaceutically acceptable salt thereof. In some embodiments, the dosage amount is about 200, 205, 210, 215, 220, 225, 230, 235, 240, 245, 250, 255, 260, 265, 270, 275, 280, 285, 290, 295, or 300 mg of a compound of Formula I, or pharmaceutically acceptable salt thereof. In some embodiments, the dosage amount is about 300, 315, 320, 325, 330, 335, 340, 345, 350, 355, 360, 365, 370, 375, 380, 385, 390, 395, or 400 mg of a compound of Formula I, or pharmaceutically acceptable salt thereof. In some embodiments, the dosage amount is about 400, 405, 410, 415, 420, 425, 430, 435, 440, 445, 450, 455, 460, 465, 470, 475, 480, 485, 490, 495, or 500 mg of a compound of Formula I, or pharmaceutically acceptable salt thereof.

In some embodiments, a compound of Formula I, or pharmaceutically acceptable salt thereof, may be administered in an effective amount within the dosage range of about 10 mg to 300 mg QD. In some embodiments, a compound of Formula I, or pharmaceutically acceptable salt thereof, may be administered in an effective amount within the dosage range of about 20 mg to 200 mg QD. In some embodiments, a compound of Formula I, or pharmaceutically acceptable salt thereof, may be administered in an effective amount within the dosage range of about 50 mg to 100 mg QD.

In some embodiments, a compound of Formula I, or pharmaceutically acceptable salt thereof, may be administered in an effective amount within the dosage range of about 10 mg to 300 mg BID. In some embodiments, a compound of Formula I, or pharmaceutically acceptable salt thereof, may be administered in an effective amount within the dosage range of about 20 mg to 200 mg BID. In some embodiments, a compound of Formula I, or pharmaceutically acceptable salt thereof, may be administered in an effective amount within the dosage range of about 50 mg to 100 mg BID.

The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine, or zinc.

Pharmaceutical Compositions

The compounds of Formula I, or pharmaceutically acceptable salt thereof, may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, topical, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

Also disclosed herein is a method of making a pharmaceutical composition comprising mixing a pharmaceutically acceptable carrier with any of the compounds of Formula I, or pharmaceutically acceptable salt thereof. Additionally, the present application includes pharmaceutical compositions made by mixing a pharmaceutically acceptable carrier with any of the compounds of the present invention.

EXAMPLES

Abbreviations

Herein and throughout the application, the following abbreviations may be used.

Å Angstrom
Ac acetyl
ACN acetonitrile
atm atmosphere
Boc tert-butoxycarbonyl
br broad
Bu butyl
CDI 1,1'-carbonyldiimidazole
Cp cyclopentadienyl
δ NMR chemical shift in parts per million downfield from a standard
d doublet
d day(s)
DCC N,N-dicyclohexylcarbodiimide DCM dichloromethane
DCE dichloroethane
Dess-Martin Periodinane 1,1,1-tris(acetyloxy)-1,1-dihydro-1,2-benziodoxol-3-(1H)-one
DIBAL diisobutylaluminum hydride
DIPA diisopropylamine
DIPEA N,N-diisopropylethylamine (Hünig's base)
DMAP 4-(dimethylamino)pyridine
DMSO dimethyl sulfoxide
EDCI 1-ethyl-3-(3-dimethylaminopropyl) carbodiimide hydrochloride
ESI electrospray ionization
Et ethyl
EtOAc ethyl acetate
g gram(s)
h hour(s)
Hantzsch ester diethyl 1,4-dihydro-2,6-dimethyl-3,5-pyridinedicarboxylate
HOBt 1-hydroxybenzotriazole
HPLC high pressure liquid chromatography
Hz Hertz
IPA isopropanol
J coupling constant (NMR spectroscopy)
L liter(s)
LC liquid chromatography
LED light emitting diode
m milli or multiplet
m/z mass-to-charge ratio
M+ parent molecular ion
M molar (moles/liter)
Me methyl
MeCN acetonitrile
min minute(s)
MOM methoxymethyl
μ micro
MS mass spectrometry
N normal (equivalent concentration)
NMP 1-methyl-2-pyrrolidone
NMR nuclear magnetic resonance
PPTS pyridinium p-toluenesulfonate
Rochelle salt potassium sodium tartrate tetrahydrate
rt room temperature
RuPhos Pd G3 (2-Dicyclohexylphosphino-2',6'-diisopropoxy-1,1'-biphenyl)[2-(2'-amino-1,1'-biphenyl)]palladium(II) methanesulfonate
s singlet
SFC supercritical fluid chromatography
spt septet
t triplet
T3P 1-propanephosphonic anhydride
TEA triethylamine
Tf trifluoromethanesulfonate
TFA trifluoroacetic acid
TFE 2,2,2-trifluoroethan-1-ol
THF tetrahydrofuran
TLC thin layer chromatography
TMP 2,2,6,6-tetramethylpiperidine
TMS trimethylsilyl In some embodiments, provided herein are processes and intermediates disclosed herein that are useful for preparing a compound of the disclosure or pharmaceutically acceptable salts thereof.

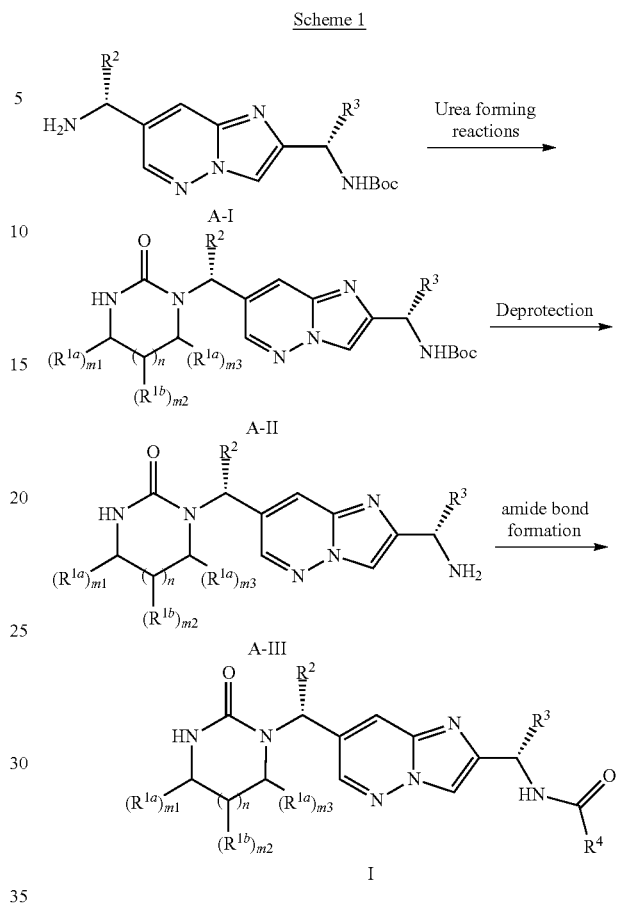

Scheme 1

Compounds of Formula I can be prepared according to Scheme 1. Compounds A-I can be converted to compounds A-II through a sequence of reactions which will be known as "urea formation conditions". This can be achieved by reacting an amine as present in compounds A-I with an activated amino alcohol precursor, such as 3-(1,3-dioxoisoindolin-2-yl)-2,2-difluoropropyl trifluoromethanesulfonate. The adduct formed from this reaction is then subjected to hydrazine in a solvent such as ethanol. The resulting diamine can then be cyclized using CDI or triphosgene and DIPEA in a solvent such as THF or DCM to afford compounds A-II. Alternatively, compounds A-II can be prepared by reacting an amine as present in compounds A-I via a three-step process. Initial reaction of compounds A-I with a suitably protected amino aldehyde such as 2-(1-(1,3-dioxoisoindolin-2-yl)cyclopropyl)acetaldehyde, in the presence of a reducing agent such as NaCNBH3 in a solvent such as methanol in the presence or absence of additives such as acetic acid provides a secondary amine adduct (structure not shown). In step 2, this adduct is then subjected to hydrazine in a solvent such as ethanol to afford a diamine (structure not shown). Finally in step 3, this diamine can then be treated with CDI or triphosgene and DIPEA in a solvent such as THF or DCM to afford compounds A-II. Compounds A-II are treated with an acid such as TFA in a solvent such as DCM to afford compounds A-III. These conditions are herein known as "Boc deprotection conditions". Amide bond formation between amines A-III and carboxylic acids (R4CO2H) can be achieved through the use of a coupling agent, such as HATU, EDCI or 2-chloro-1-methylpyridinium iodide in the presence of a base, such as DIPEA or TEA, in a solvent, such as DMF, MeCN, or DCM, with or without an additive, such as HOBt, to yield compounds of Formula I. Alternatively, amide bond formation can be achieved by treatment of amines A-III with a reagent such as a carboxylic acid chloride (R⁴CO₂Cl) in the presence or absence of additives such as DIPEA or DMAP in solvents such as ACN, DCM or THF to yield compounds of Formula I. In addition, amines A-III can be treated with N-hydroxysuccinate esters in the presence of reagents such as DIPEA in a solvent such as acetonitrile to provide compounds of Formula I. Alternatively, amide bond formation can be achieved by treatment of amines A-III with a reagent such as an ester ($R^4CO_2R^{4a}$ wherein $R^{4aa}$ is —$C_{(1-6)}$alkyl) with or without an additive, such as TEA, in a solvent such as ACN to afford compounds of Formula I.

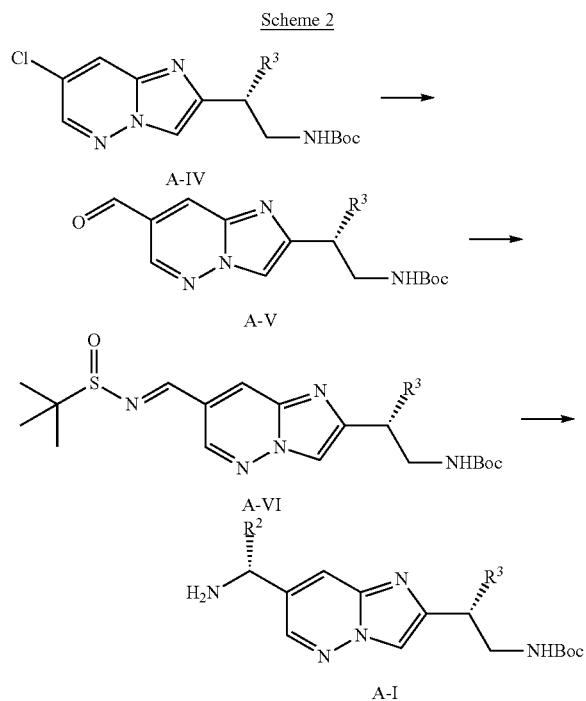

A-IV

A-V

A-VI

A-I

Amines A-I can also be prepared as shown in Scheme 2. Halogenated intermediates A-IV can be converted to compounds A-V via a two step sequence of 1) vinylation with a reagent such as potassium trifluoro(vinyl)boranide, and a catalyst such RuPhos Pd G3 in a solvent such as 1,4-dioxane, and 2) oxidative cleavage of the olefin prepared in the previous step with reagents such as K₂OsO₄·2H₂O and NaIO₄ in solvents such as 1,4-dioxane and water. Sulfinimine formation may be achieved using a reagent such as 2-methylpropane-2-sulfinamide in the presence of CuSO₄ or Cs₂CO₃ in a solvent such as DCM to afford compounds A-VI. Addition of suitable nucleophiles, such as R²M where M is Li, MgCl, or MgBr to sulfinimines A-VI then affords the corresponding sulfinamines (structure not shown) that upon deprotection of the sulfinamine with a reagent such as HCl in a solvent such as 1,4-dioxane then affords amines A-I.

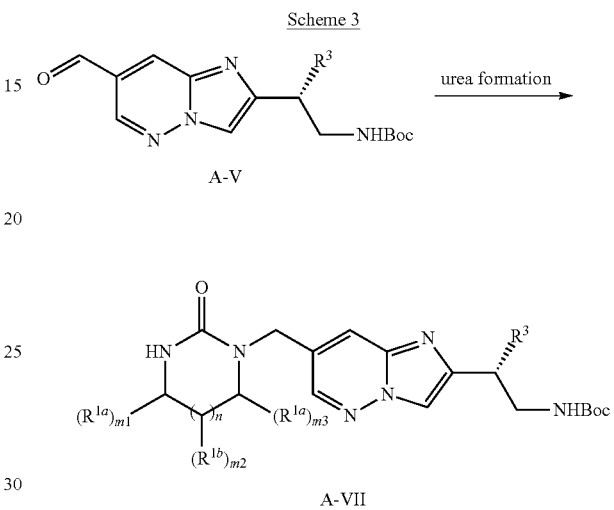

Scheme 3

A-V

A-VII

Ureas A-VII may be prepared by several methods, two of such methods are described in Scheme 3. Method 1: Aldehydes A-V can be treated with diamines such as 2,2-difluoropropane-1,3-diamine dihydrochloride under reductive amination conditions such as NaCNBH₃ in a solvent such as methanol in the presence of additives such as acetic acid, followed by treatment with a reagent such as triphosgene or CDI in a solvent such as DCM or THF to afford the corresponding cyclic ureas A-VII. Method 2: In a two-step method, aldehydes A-V are subjected to reductive amination conditions with a mono-protected diamine, such as tert-butyl (S)-(1-aminopropan-2-yl)carbamate, using NaCNBH₃ in a solvent such as methanol in the presence of additives such as acetic acid. In the second step, the adduct formed in the first step is treated with reagents such as potassium tert-pentoxide in solvents such as tert-amyl alcohol to afford ureas A-VII. Compounds A-VII can be converted to compounds of Formula I using the methods described in Scheme 1 for the conversion of compounds A-II to compounds of Formula I.

Scheme 4

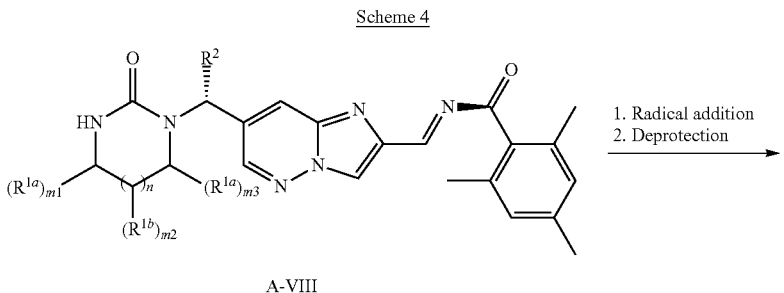

1. Radical addition
2. Deprotection

A-VIII

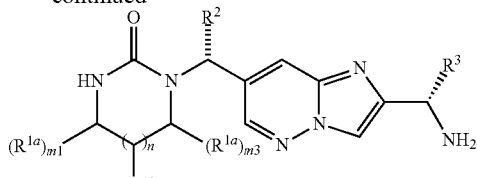

A-III

Intermediates A-III may also be prepared as shown in Scheme 4. Treatment of sulfinimides A-VIII with diethyl 1,4-dihydro-2,6-dimethyl-3,5-pyridinedicarboxylate and an appropriate radical precursor such as 1,3-dioxoisoindolin-2-yl 2-cyclopropoxypropanoate in a solvent such as DMSO in the presence of an amine base such as DIPEA, with 450 nm light affords the corresponding sulfinamides (structure not shown). Subsequent deprotection of the sulfinamide with a reagent such as HCl in a solvent such as 1,4-dioxane then affords amines A-III.

and a solvent such as DCM provides the corresponding sulfinimines (structure not shown). Subsequent reaction of the sulfinimines with a reagent, such as 3-[1-(trifluoromethyl)cyclopropyl]propanoic acid and a base, such as LDA in a solvent, such as THF affords compounds B-II. Compounds B-II can be converted to compounds B-III by a two-step process. Initially, compounds B-II are treated with N-hydroxyphthalimide in the presence of a reagent such as DCC, with an additive, such as DMAP, in a solvent, such as DCM. The second step of this process is reduction of the

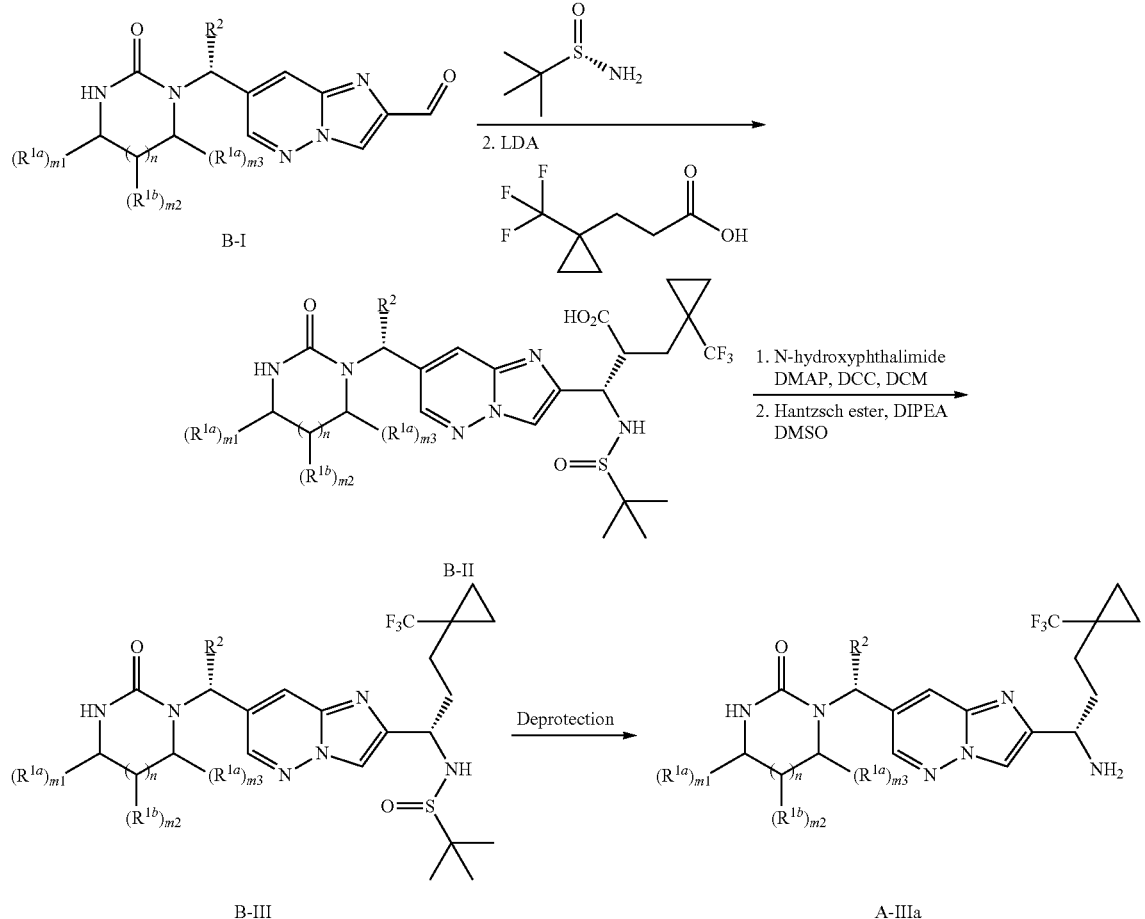

Amines A-IIIa may be prepared as shown in Scheme 5. Treatment of aldehydes B-I with (S)-(-)-2-methyl-2-propanesulfinamide in the presence of a reagent such as CuSO$_4$ dioxoisoindoline substituent using a reagent, such as Hantzsch ester, in the presence of a base, such as DIPEA, in a solvent, such as DMSO. Deprotection of sulfinamines B-III with a reagent such as HCl in a solvent such as 1,4-dioxane then affords amines A-IIIa.

Intermediate 1:
2-Fluoro-2-methylpropane-1,3-diamine dihydrochloride

Step A: 2-Fluoro-2-methylmalonamide. Diethyl 2-fluoromalonate (2.00 g, 11.2 mmol) and anhydrous THF (40 mL) were added in one portion to a nitrogen-purged 250 mL three-neck round-bottomed flask, which was charged with t-BuOK (13.5 mL, 13.5 mmol, 1 M in THF) and the resulting mixture stirred for 0.5 h at rt. The mixture was treated with MeI (0.840 mL, 13.5 mmol), via syringe over 1 min and the resulting mixture stirred for another 1 h at rt. The mixture was then treated with ammonia (60 mL, 7 M in MeOH) in one portion and the reaction mixture was stirred for another 16 h at rt. The reaction mixture was then concentrated to dryness to provide a white solid. The solid was washed with $H_2O$ (40 mL) and dried under vacuum to afford 2-fluoro-2-methylmalonamide (80% yield) as a white solid.

Step B: 2-Fluoro-2-methylpropane-1,3-diamine dihydrochloride. 2-Fluoro-2-methylmalonamide (1.2 g, 9.0 mmol, Step A) and THF (15 mL) were added to an oven-dried and nitrogen-purged 100 mL three-neck round-bottomed flask, which was subsequently cooled to 0° C. in an ice/water bath. The mixture was treated with $BH_3 \cdot THF$ (45 mL, 45 mmol) dropwise via constant pressure dropping funnel over 10 min. The reaction mixture was stirred for 3 h at 50° C. before treating with MeOH (5.0 mL), portion-wise over 5 min. The resulting mixture was stirred for another 1 h at rt. The reaction mixture was then concentrated to dryness and the residue dissolved in MeOH (20 mL) and HCl (5 mL, 4 M in MeOH). The resulting mixture was stirred for another 0.5 h at rt, filtered and the filter cake was dried under vacuum to afford 2-fluoro-2-methylpropane-1,3-diamine dihydrochloride (62% yield) as a white solid.

Intermediate 2: 1-((R)-(2-((S)-Amino(4,4-difluorocyclohexyl)methyl)imidazo[1,2-b]pyridazin-7-yl)(cyclopropyl)methyl)-5,5-difluorotetrahydropyrimidin-2(1H)-one

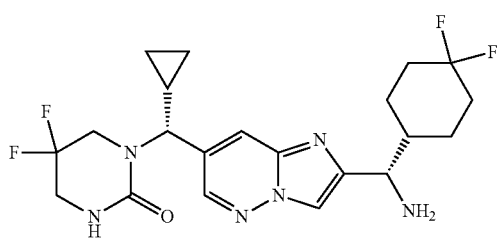 [SMILES: N[C@H](c1cn2ncc([C@@H](C3CC3)N3CC(F)(F)CNC3=O)cc2n1)C1CCC(F)(F)CC1]

Step A: tert-Butyl ((S)-(7-((R)-cyclopropyl((3-(1,3-dioxoisoindolin-2-yl)-2,2-difluoropropyl)amino)methyl)imidazo[1,2-b]pyridazin-2-yl)(4,4-difluorocyclohexyl)methyl)carbamate. To tert-butyl ((S)-(7-((R)-amino(cyclopropyl)methyl)imidazo[1,2-b]pyridazin-2-yl)(4,4-difluorocyclohexyl)methyl)carbamate (100 mg, 0.23 mmol), and 3-(1,3-dioxoisoindolin-2-yl)-2,2-difluoropropyl trifluoromethanesulfonate (172 mg, 0.46 mmol) in acetonitrile (1.2 mL) was added DIPEA (44 µL, 0.25 mmol) and the reaction mixture was heated at 50° C. for 18 h. The reaction mixture was cooled to rt, concentrated under vacuum, and purified by silica gel chromatography (0-100% EtOAc (with 10% MeOH)/hexanes) to provide the title compound (81% yield).

Step B: tert-Butyl ((S)-(7-((R)-((3-amino-2,2-difluoropropyl)amino)(cyclopropyl)methyl)imidazo[1,2-b]pyridazin-2-yl)(4,4-difluorocyclohexyl)methyl)carbamate. To tert-butyl ((S)-(7-((R)-cyclopropyl((3-(1,3-dioxoisoindolin-2-yl)-2,2-difluoropropyl)amino)methyl)imidazo[1,2-b]pyridazin-2-yl)(4,4-difluorocyclohexyl)methyl)carbamate (500 mg, 0.76 mmol, Step A) in EtOH (3.8 mL) was added hydrazine monohydrate (110 µL, 2.28 mmol). The reaction mixture was warmed to 35° C. and stirred for 18 h, at which time a thick slurry had formed. The reaction mixture was cooled in an ice bath, filtered, washed with 10 mL of ice cold EtOH, and the filtrate concentrated to give the title compound which was used without further purification in the next step (assume 100% yield).

Step C: tert-Butyl ((S)-(7-((R)-cyclopropyl(5,5-difluoro-2-oxotetrahydropyrimidin-1(2H)-yl)methyl)imidazo[1,2-b]pyridazin-2-yl)(4,4-difluorocyclohexyl)methyl)carbamate. To a stirred solution of tert-butyl ((S)-(7-((R)-((3-amino-2,2-difluoropropyl)amino)(cyclopropyl)methyl)imidazo[1,2-b]pyridazin-2-yl)(4,4-difluorocyclohexyl)methyl)carbamate (0.76 mmol, theoretical, Step B) in THF (12 mL) was added CDI (185 mg, 1.14 mmol) and the reaction mixture was stirred at 60° C. for 18 h. The reaction mixture was cooled to rt, treated with aqueous 3 M NaOH (2 mL) while stirring for 10 min, then diluted with brine, and the layers separated. The organic layer was washed with brine, dried over anhydrous $Na_2SO_4$, filtered and concentrated. This material was purified by silica gel chromatography (0-100% EtOAc (with 10% MeOH)/hexanes) to provide the title compound (77% yield).

Step D: 1-((R)-(2-((S)-Amino(4,4-difluorocyclohexyl)methyl)imidazo[1,2-b]pyridazin-7-yl)(cyclopropyl)methyl)-5,5-difluorotetrahydropyrimidin-2(1H)-one. A vial was charged with tert-butyl ((S)-(7-((R)-cyclopropyl(5,5-difluoro-2-oxotetrahydropyrimidin-1(2H)-yl)methyl)imidazo[1,2-b]pyridazin-2-yl)(4,4-difluorocyclohexyl)methyl)carbamate (153 mg, 0.28 mmol, Step C) and TFA (2 mL, 26.13 mmol). The reaction was stirred for 2 h at rt and then concentrated. The resulting oil was dissolved in DCM and carefully quenched by the addition of 0.5 M aqueous NaOH until the pH of the solution was >pH 7. The water layer was washed with DCM. The combined organic phases were washed with brine, dried over anhydrous $Na_2SO_4$, filtered and concentrated to give the title compound which was used without further purification (assume 100% yield).

Intermediate 3: 1-((S)-1-(2-((S)-Amino(4,4-difluorocyclohexyl)methyl)imidazo[1,2-b]pyridazin-7-yl)-2-methoxyethyl)-5,5-difluorotetrahydropyrimidin-2(1H)-one

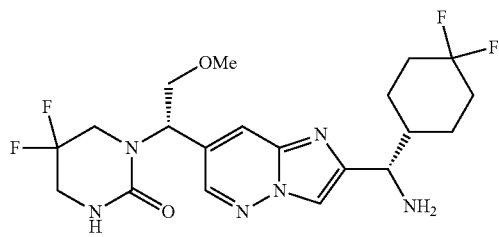 [SMILES: COC[C@H](c1cnn2cc([C@@H](N)C3CCC(F)(F)CC3)nc2c1)N1CC(F)(F)CNC1=O]

Step A: tert-Butyl ((S)-(7-((S)-1-(((R)-tert-butylsulfinyl)amino)-2-methoxyethyl)imidazo[1,2-b]pyridazin-2-yl)(4,4-difluorocyclohexyl)methyl)carbamate. To an oven-dried, $N_2$ flushed flask was added tributyl(methoxymethyl)stannane (1.41 g, 4.22 mmol) and THF (20.1 mL). The flask was cooled (−78° C.) and n-butyllithium (1.76 mL, 4.22 mmol, 2.4 M in hexanes) was added in a dropwise manner. After a further 15 min at −78° C., the reaction mixture was treated with a solution of tert-butyl ((S)-(7-((E)-(((R)-tert-butylsulfinyl)imino)methyl)imidazo[1,2-b]pyridazin-2-yl)(4,4-difluorocyclohexyl)methyl)carbamate (1.00 g, 2.01 mmol) in THF (5 mL) in a dropwise manner. Upon stirring at −78° C. for an additional 2 h, the reaction mixture was quenched with EtOH (0.35 mL), allowed to warm to rt, and diluted with saturated aqueous $NaHCO_3$ and EtOAc. The layers were separated and the aqueous layer was further extracted with EtOAc. The combined organic layers were dried over anhydrous $Na_2SO_4$, filtered, and concentrated to dryness. The residue was purified by silica gel chromatography (40-100% acetone/hexanes) to give the title compound (39% yield) as the second eluting isomer.

Step B: tert-Butyl ((S)-(7-((S)-1-amino-2-methoxyethyl)imidazo[1,2-b]pyridazin-2-yl)(4,4-difluorocyclohexyl)methyl)carbamate. The title compound was prepared as described for the synthesis of Intermediate 9, using tert-butyl ((S)-(7-((S)-1-(((R)-tert-butylsulfinyl)amino)-2-methoxyethyl)imidazo[1,2-b]pyridazin-2-yl)(4,4-difluorocyclohexyl)methyl)carbamate (Step A) in place of tert-butyl ((R)-1-(7-((S*)-1-(((R)-tert-butylsulfinyl)amino)-2-methoxyethyl)imidazo[1,2-b]pyridazin-2-yl)-2-((1,1,1-trifluoro-2-methylpropan-2-yl)oxy)ethyl)carbamate to afford the title compound as a white foam (100% yield).

Step C: tert-Butyl ((S)-(4,4-difluorocyclohexyl)(7-((S)-1-((3-(1,3-dioxoisoindolin-2-yl)-2,2-difluoropropyl)amino)-2-methoxyethyl)imidazo[1,2-b]pyridazin-2-yl)methyl)carbamate. The title compound was prepared as described for the synthesis of Intermediate 2, Step A, using tert-butyl ((S)-(7-((S)-1-amino-2-methoxyethyl)imidazo[1,2-b]pyridazin-2-yl)(4,4-difluorocyclohexyl)methyl)carbamate (Step B) in place of tert-butyl ((S)-(7-((R)-amino(cyclopropyl)methyl)imidazo[1,2-b]pyridazin-2-yl)(4,4-difluorocyclohexyl)methyl)carbamate to afford the title compound (84% yield).

Step D: tert-Butyl ((S)-(7-((S)-1-((3-amino-2,2-difluoropropyl)amino)-2-methoxyethyl)imidazo[1,2-b]pyridazin-2-yl)(4,4-difluorocyclohexyl)methyl)carbamate. The title compound was prepared as described for the synthesis of Intermediate 2, Step B, using tert-butyl ((S)-(4,4-difluorocyclohexyl)(7-((S)-1-((3-(1,3-dioxoisoindolin-2-yl)-2,2-difluoropropyl)amino)-2-methoxyethyl)imidazo[1,2-b]pyridazin-2-yl)methyl)carbamate (Step C) in place of tert-butyl ((S)-(7-((R)-cyclopropyl((3-(1,3-dioxoisoindolin-2-yl)-2,2-difluoropropyl)amino)methyl)imidazo[1,2-b]pyridazin-2-yl)(4,4-difluorocyclohexyl)methyl)carbamate to afford the title compound (86% yield).

Step E: tert-Butyl ((S)-(7-((S)-1-(5,5-difluoro-2-oxotetrahydropyrimidin-1(2H)-yl)-2-methoxyethyl)imidazo[1,2-b]pyridazin-2-yl)(4,4-difluorocyclohexyl)methyl)carbamate. The title compound was prepared as described for the synthesis of Intermediate 2, Step C, using tert-butyl ((S)-(7-((S)-1-((3-amino-2,2-difluoropropyl)amino)-2-methoxyethyl)imidazo[1,2-b]pyridazin-2-yl)(4,4-difluorocyclohexyl)methyl)carbamate (Step D) in place of tert-butyl ((S)-(7-((R)-((3-amino-2,2-difluoropropyl)amino)(cyclopropyl)methyl)imidazo[1,2-b]pyridazin-2-yl)(4,4-difluorocyclohexyl)methyl)carbamate to afford the title compound (100% yield).

Step F: 1-((S)-1-(2-((S)-Amino(4,4-difluorocyclohexyl)methyl)imidazo[1,2-b]pyridazin-7-yl)-2-methoxyethyl)-5,5-difluorotetrahydropyrimidin-2(1H)-one. The title compound was prepared as described for the synthesis of Intermediate 2, Step D, using tert-butyl ((S)-(7-((S)-1-(5,5-difluoro-2-oxotetrahydropyrimidin-1(2H)-yl)-2-methoxyethyl)imidazo[1,2-b]pyridazin-2-yl)(4,4-difluorocyclohexyl)methyl)carbamate (Step E) in place of tert-butyl ((S)-(7-((R)-cyclopropyl(5,5-difluoro-2-oxotetrahydropyrimidin-1(2H)-yl)methyl)imidazo[1,2-b]pyridazin-2-yl)(4,4-difluorocyclohexyl)methyl)carbamate and adding DCM (2 mL) as a co-solvent to afford the title compound that was used without further purification (93% yield).

Intermediate 4: tert-Butyl (R)-(1-(7-chloroimidazo[1,2-b]pyridazin-2-yl)-2-((1,1,1-trifluoro-2-methylpropan-2-yl)oxy)ethyl)carbamate

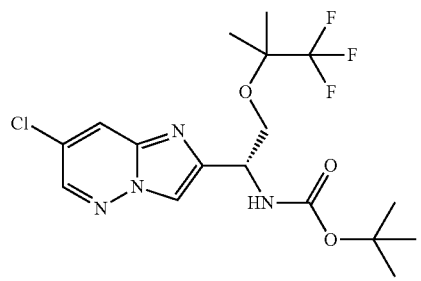 [SMILES: CC(C)(C)OC(=O)N[C@@H](COC(C)(C)C(F)(F)F)c1cn2ncc(Cl)cc2n1]

An oven dried round-bottom flask was charged with 5-chloropyridazin-3-amine (4.45 g, 34.3 mmol), tert-butyl (S)-(4-(dimethyl(oxo)-$\lambda^6$-sulfaneylidene)-3-oxo-1-((1,1,1-trifluoro-2-methylpropan-2-yl)oxy)butan-2-yl)carbamate (12.7 g, 32.6 mmol), chlorocyclopentadienylbis(triphenylphosphine)ruthenium (II) (630 mg, 0.868 mmol), sodium trifluoromethanesulfonate (313 mg, 1.82 mmol) and 4 Å molecular sieves (8.9 g). Anhydrous toluene (110 mL) was added under an atmosphere of $N_2$ and then the reaction was heated to 90° C. for 24 h. The mixture was allowed to cool to rt then filtered through diatomaceous earth (e.g., Celite®). The filter cake was washed with EtOAc and then the filtrate was concentrated under reduced pressure. The residue was purified by silica gel chromatography (0-40% EtOAc/hexanes) to provide the title compound in 28% yield.

Intermediate 5: tert-Butyl (R)-(2-((1,1,1-trifluoro-2-methylpropan-2-yl)oxy)-1-(7-vinylimidazo[1,2-b]pyridazin-2-yl)ethyl)carbamate

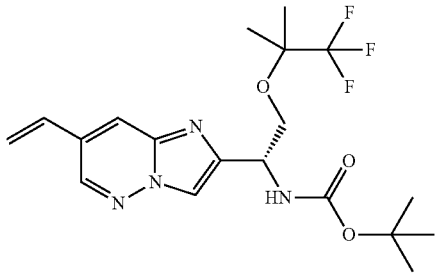 [SMILES: C=Cc1cnn2cc([C@H](COC(C)(C)C(F)(F)F)NC(=O)OC(C)(C)C)nc2c1]

To a solution of tert-butyl (R)-(1-(7-chloroimidazo[1,2-b]pyridazin-2-yl)-2-((1,1,1-trifluoro-2-methylpropan-2-yl)oxy)ethyl)carbamate (4.05 g, 9.58 mmol, Intermediate 4) and potassium vinyltrifluoroborate (1.93 g, 14.4 mmol) in 1,4-dioxane (33 mL) was added a solution of potassium phosphate tribasic (6.10 g, 28.7 mmol) in H$_2$O (5 mL). The mixture was degassed by N$_2$ sparging for 10 min then RuPhos Pd G3 (200 mg, 0.239 mmol) was added, the vessel sealed with a Teflon septum, and the reaction mixture was heated to 100° C. for 2 h. After this time, the mixture was concentrated under reduced pressure, diluted with H$_2$O and extracted three times with EtOAc. The combined organic extracts were washed with brine, dried over anhydrous Na$_2$SO$_4$, filtered, and concentrated under reduced pressure to afford the title compound that was used without further purification.

Intermediate 6: tert-Butyl (R)-(1-(7-formylimidazo[1,2-b]pyridazin-2-yl)-2-((1,1,1-trifluoro-2-methylpropan-2-yl)oxy)ethyl)carbamate

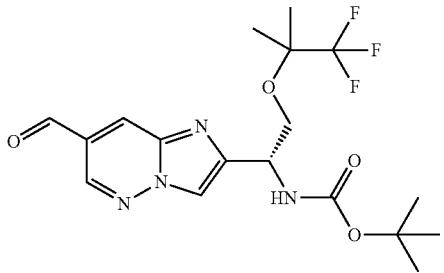 [SMILES: CC(C)(C)OC(=O)N[C@@H](COC(C)(C)C(F)(F)F)c1cn2ncc(C=O)cc2n1]

To a well-stirred mixture of tert-butyl (R)-(2-((1,1,1-trifluoro-2-methylpropan-2-yl)oxy)-1-(7-vinylimidazo[1,2-b]pyridazin-2-yl)ethyl)carbamate (3.97 g, 9.58 mmol, Intermediate 5) and potassium osmate(VI) dihydrate (88 mg, 0.24 mmol) in 1,4-dioxane (12 mL) was added a suspension of sodium periodate (8.20 g, 38.3 mmol) in H$_2$O (11 mL). The reaction was stirred at rt for 3 h then filtered through diatomaceous earth (e.g., Celite®). The filter cake was washed with EtOAc and then the filtrate was concentrated under reduced pressure. The residue was purified by silica gel chromatography (10-100% EtOAc/hexanes) to provide the title compound in 69% yield.

Intermediate 7: tert-Butyl ((R)-1-(7-((E)-(((R)-tert-butylsulfinyl)imino)methyl)imidazo[1,2-b]pyridazin-2-yl)-2-((1,1,1-trifluoro-2-methylpropan-2-yl)oxy)ethyl)carbamate

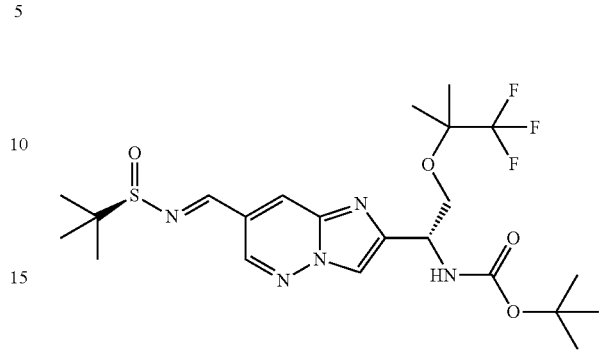

A mixture of tert-butyl (R)-(1-(7-formylimidazo[1,2-b]pyridazin-2-yl)-2-((1,1,1-trifluoro-2-methylpropan-2-yl)oxy)ethyl)carbamate (2.75 g, 6.60 mmol, Intermediate 6), (R)-2-methylpropane-2-sulfinamide (1.12 g, 9.25 mmol), and Cs$_2$CO$_3$ (3.01 g, 9.25 mmol) in CH$_2$C$_2$ (21 mL) was stirred for 16 h at rt then filtered through diatomaceous earth (e.g., Celite®) and the filtrate was concentrated under reduced pressure. The residue was purified by silica gel chromatography (10-100% EtOAc/hexanes) to provide the title compound in 87% yield.

Intermediate 8: tert-Butyl ((R)-1-(7-((S*)-1-(((R)-tert-butylsulfinyl)amino)-2-methoxyethyl)imidazo[1,2-b]pyridazin-2-yl)-2-((1,1,1-trifluoro-2-methylpropan-2-yl)oxy)ethyl)carbamate

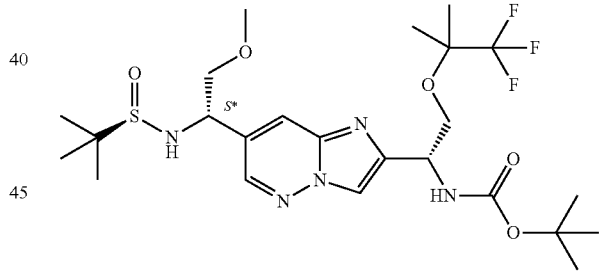

A solution of tributyl(methoxymethyl)stannane (948 mg, 2.83 mmol) in THE (10 mL) was cooled to −78° C. then n-butyllithium (1.8 mL, 1.6 M in hexanes, 2.8 mmol) was added dropwise. The reaction was stirred for 20 min then a solution of tert-butyl ((R)-1-(7-((E)-(((R)-tert-butylsulfinyl)imino)methyl)imidazo[1,2-b]pyridazin-2-yl)-2-((1,1,1-trifluoro-2-methylpropan-2-yl)oxy)ethyl)carbamate (700 mg, 1.35 mmol, Intermediate 7) in THE (5 mL) was added slowly over a period of 10 min. The reaction was stirred at −78° C. for 2.5 h then quenched with EtOH (0.24 mL) and allowed to warm to rt. To this mixture was added saturated aqueous NaHCO$_3$ (1.5 mL) and potassium fluoride (1.3 g, 11 mmol, 50% w/w on diatomaceous earth (e.g., Celite®)). The resulting suspension was stirred for 16 h then the solids were removed by filtration and the filtrate was concentrated under reduced pressure. Purification by silica gel chromatography (10-100% EtOAc/hexanes) provided the title compound in 17% yield.

Intermediate 9: tert-Butyl ((R)-1-(7-((S*)-1-amino-2-methoxyethyl)imidazo[1,2-b]pyridazin-2-yl)-2-((1,1,1-trifluoro-2-methylpropan-2-yl)oxy)ethyl)carbamate

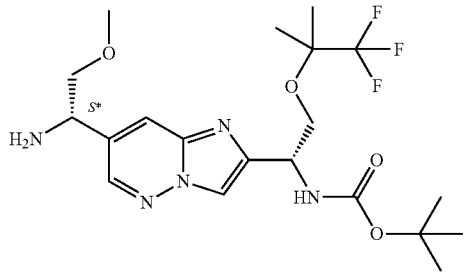 [SMILES: COC[C@@H](N)c1cnn2cc([C@H](COC(C)(C)C(F)(F)F)NC(=O)OC(C)(C)C)nc2c1]

To a solution of tert-butyl ((R)-1-(7-((S*)-1-(((R)-tert-butylsulfinyl)amino)-2-methoxyethyl)imidazo[1,2-b]pyridazin-2-yl)-2-((1,1,1-trifluoro-2-methylpropan-2-yl)oxy)ethyl)carbamate (126 mg, 0.223 mmol, Intermediate 8) in EtOAc (1 mL) was added HCl (0.11 mL, 0.45 mmol, 4 M in 1,4-dioxane). The reaction was stirred at rt for 4.5 h then HCl (0.055 mL, 0.23 mmol, 4 M in 1,4-dioxane) was added. The reaction was stirred at rt for 30 min then diluted with H₂O (5 mL). The resulting solution was washed twice with 3:2 hexanes/EtOAc and these extracts were discarded. The pH of the aqueous mixture was adjusted by the addition of Na₂CO₃ (71 mg). The resulting solution was extracted three times with EtOAc. The combined organic layers were dried over anhydrous Na₂SO₄, filtered, and concentrated under reduced pressure to provide the title compound in 68% yield.

Intermediate 10: tert-Butyl ((R)-1-(7-((S*)-1-(5,5-difluoro-2-oxotetrahydropyrimidin-1(2H)-yl)-2-methoxyethyl)imidazo[1,2-b]pyridazin-2-yl)-2-((1,1,1-trifluoro-2-methylpropan-2-yl)oxy)ethyl)carbamate

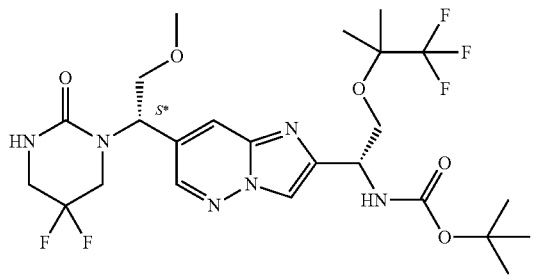 [SMILES: COC[C@H](c1cnn2cc([C@H](COC(C)(C)C(F)(F)F)NC(=O)OC(C)(C)C)nc2c1)N1CC(F)(F)CNC1=O]

Step A: tert-Butyl ((R)-1-(7-((S*)-1-((3-(1,3-dioxoisoindolin-2-yl)-2,2-difluoropropyl)amino)-2-methoxyethyl)imidazo[1,2-b]pyridazin-2-yl)-2-((1,1,1-trifluoro-2-methylpropan-2-yl)oxy)ethyl)carbamate. To a stirred solution of tert-butyl ((R)-1-(7-((S*)-1-amino-2-methoxyethyl)imidazo[1,2-b]pyridazin-2-yl)-2-((1,1,1-trifluoro-2-methylpropan-2-yl)oxy)ethyl)carbamate (70 mg, 0.15 mmol, Intermediate 9), and 3-(1,3-dioxoisoindolin-2-yl)-2,2-difluoropropyl trifluoromethanesulfonate (113 mg, 0.303 mmol) in acetonitrile (0.8 mL) was added DIPEA (29 µL, 0.17 mmol). The reaction mixture was heated at 50° C. for 36 h. The reaction mixture was then cooled to rt, concentrated under reduced pressure, and diluted with H₂O. The mixture was extracted twice with EtOAc then the combined organic extracts were washed with saturated aqueous NH₄Cl and brine, dried over anhydrous Na₂SO₄, filtered and concentrated under reduced pressure to afford the title compound that was used without further purification.

Step B: tert-Butyl ((R)-1-(7-((S*)-1-((3-amino-2,2-difluoropropyl)amino)-2-methoxyethyl)imidazo[1,2-b]pyridazin-2-yl)-2-((1,1,1-trifluoro-2-methylpropan-2-yl)oxy)ethyl)carbamate. To a solution of tert-butyl ((R)-1-(7-((S*)-1-((3-(1,3-dioxoisoindolin-2-yl)-2,2-difluoropropyl)amino)-2-methoxyethyl)imidazo[1,2-b]pyridazin-2-yl)-2-((1,1,1-trifluoro-2-methylpropan-2-yl)oxy)ethyl)carbamate (104 mg, 0.152 mmol, Step A) in EtOH (1.5 mL) was added hydrazine monohydrate (120 µL, 1.85 mmol). The reaction mixture was heated to 50° C. and stirred for 2 h, at which time a thick slurry had formed. The reaction mixture was diluted with H₂O and extracted twice with EtOAc. The combined organic extracts were washed with water and brine, dried over anhydrous Na₂SO₄, filtered and concentrated under reduced pressure to afford the title compound that was used without further purification.

Step C: tert-Butyl ((R)-1-(7-((S*)-1-(5,5-difluoro-2-oxotetrahydropyrimidin-1(2H)-yl)-2-methoxyethyl)imidazo[1,2-b]pyridazin-2-yl)-2-((1,1,1-trifluoro-2-methylpropan-2-yl)oxy)ethyl)carbamate. To a stirred solution of tert-butyl ((R)-1-(7-((S*)-1-((3-amino-2,2-difluoropropyl)amino)-2-methoxyethyl)imidazo[1,2-b]pyridazin-2-yl)-2-((1,1,1-trifluoro-2-methylpropan-2-yl)oxy)ethyl)carbamate (84 mg, 0.15 mmol, Step B) in THF (3 mL) was added CDI (74 mg, 0.46 mmol) and the reaction mixture was heated to 60° C. for 1 h. The reaction mixture was then cooled to rt then quenched with H₂O. The mixture was diluted with EtOAc, washed with 0.05 M aqueous HCl and brine, dried over anhydrous Na₂SO₄, filtered and concentrated under reduced pressure to provide the title compound that was used without further purification.

Intermediate 11: 1-((S*)-1-(2-((R)-1-Amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one hydrochloride

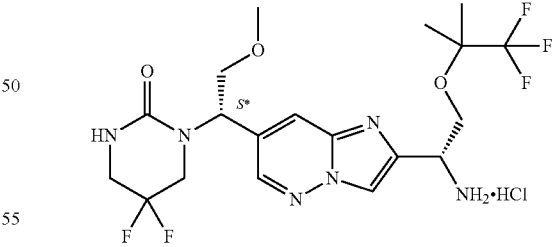

HCl (0.76 mL, 3.0 mmol, 4 M in 1,4-dioxane) was added to tert-butyl ((R)-1-(7-((S*)-1-(5,5-difluoro-2-oxotetrahydropyrimidin-1(2H)-yl)-2-methoxyethyl)imidazo[1,2-b]pyridazin-2-yl)-2-((1,1,1-trifluoro-2-methylpropan-2-yl)oxy)ethyl)carbamate (84 mg, 0.15 mmol, Intermediate 10). The reaction was stirred at rt for 45 min then diluted with MeOH and concentrated under reduced pressure. The residue was dissolved in MeCN then concentrated under reduced pressure to provide the title compound that was used without further purification.

Intermediate 12: Tributyl(cyclopropoxymethyl)stannane

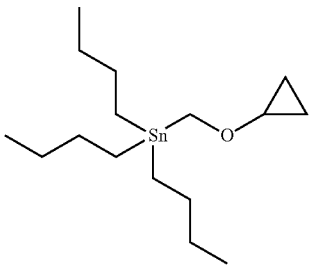 [SMILES: CCC[CH2][Sn]([CH2]CCC)([CH2]CCC)[CH2]OC1CC1]

To a reaction vial containing NaH (0.500 g, 12.5 mmol, 60% in mineral oil) under N₂ was added DMF (40 mL). The resulting suspension was cooled to 0° C. then cyclopropanol (0.789 mL, 12.5 mmol) was added dropwise. The reaction was stirred at this temperature for 10 min then tributyl (iodomethyl)stannane (3.32 mL, 10.0 mmol) was added. The reaction was allowed to warm to rt and stirred for 1 h then quenched with H₂O and diluted with aqueous 5% LiCl. The resulting mixture was extracted with CH₂Cl₂ (3×25 mL) then the combined organics were washed with brine, dried over anhydrous Na₂SO₄, filtered and concentrated under reduced pressure. Purification by silica gel chromatography (0-20% EtOAc/hexanes) provided the title compound in 100% yield.

Intermediate 13: tert-Butyl ((S)-(7-((S)-1-(((R)-tert-butylsulfinyl)amino)-2-cyclopropoxyethyl)imidazo[1,2-b]pyridazin-2-yl)(4,4-difluorocyclohexyl)methyl)carbamate

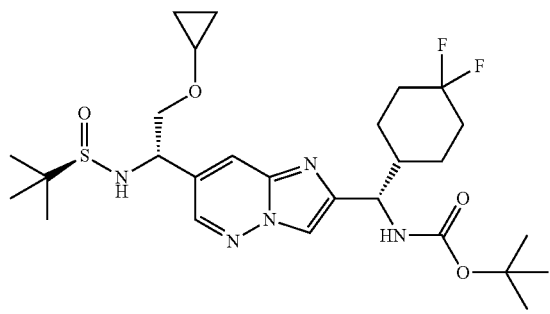 [SMILES: CC(C)(C)OC(=O)N[C@H](c1cn2ncc([C@@H](COC3CC3)N[S@](=O)C(C)(C)C)cc2n1)C1CCC(F)(F)CC1]

A solution of tributyl(cyclopropoxymethyl)stannane (800 mg, 2.22 mmol, Intermediate 12) in THF (10 mL) was cooled to −78° C. then n-butyllithium (1.4 mL, 1.6 M in hexanes, 2.2 mmol) was added dropwise. The reaction was stirred for 20 min then a solution of tert-butyl ((S)-(7-((E)-(((R)-tert-butylsulfinyl)imino)methyl)imidazo[1,2-b]pyridazin-2-yl)(4,4-difluorocyclohexyl)methyl)carbamate (525 mg, 1.06 mmol) in THF (5 mL) was added slowly over a period of 10 min. The reaction was stirred at −78° C. for 30 min then quenched with EtOH (0.19 mL) and allowed to warm to rt. The resulting mixture was diluted with EtOAc, washed with saturated aqueous NaHCO₃ and brine, dried over anhydrous Na₂SO₄, filtered and concentrated under reduced pressure. The residue was purified by silica gel chromatography (10-60% acetone/(hexanes with 0.1% TEA)) to provide the title compound in 48% yield. The stereochemistry was assigned by Mosher ester analysis of Intermediate 14.

Intermediate 14: tert-Butyl ((S)-(7-((S)-1-amino-2-cyclopropoxyethyl)imidazo[1,2-b]pyridazin-2-yl)(4,4-difluorocyclohexyl)methyl)carbamate

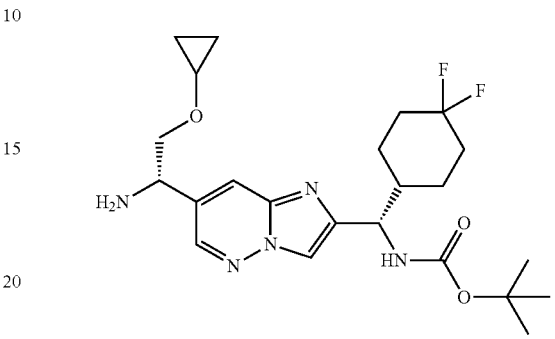

To a solution of tert-butyl ((S)-(7-((S)-1-(((R)-tert-butylsulfinyl)amino)-2-cyclopropoxyethyl)imidazo[1,2-b]pyridazin-2-yl)(4,4-difluorocyclohexyl)methyl)carbamate (300 mg, 0.527 mmol, Intermediate 13) in EtOAc (3.5 mL) was added HCl (0.33 mL, 1.3 mmol, 4 M in 1,4-dioxane). The reaction was stirred at rt for 1 h then diluted with H₂O. The resulting solution was washed twice with hexanes and these extracts were discarded. The pH of the aqueous mixture was adjusted by the addition of 3 M aqueous NaOH (0.7 mL) then extracted three times with EtOAc. The combined organic layers were dried over anhydrous Na₂SO₄, filtered, and concentrated under reduced pressure to provide the title compound that was used without further purification. The stereochemistry was assigned by Mosher ester analysis.

Intermediate 15: tert-Butyl ((S)-(7-((S)-2-cyclopropoxy-1-(5,5-difluoro-2-oxotetrahydropyrimidin-1(2H)-yl)ethyl)imidazo[1,2-b]pyridazin-2-yl)(4,4-difluorocyclohexyl)methyl)carbamate

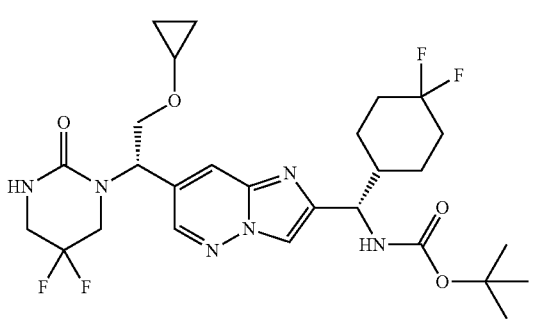 [SMILES: CC(C)(C)OC(=O)N[C@H](c1cn2ncc([C@@H](COC3CC3)N3CC(F)(F)CNC3=O)cc2n1)C1CCC(F)(F)CC1]

Step A: tert-Butyl ((S)-(7-((S)-2-cyclopropoxy-1-((3-(1,3-dioxoisoindolin-2-yl)-2,2-difluoropropyl)amino)ethyl)imidazo[1,2-b]pyridazin-2-yl)(4,4-difluorocyclohexyl)methyl)carbamate. To a stirred solution of tert-butyl ((S)-(7-((S)-1-amino-2-cyclopropoxyethyl)imidazo[1,2-b]pyridazin-2-yl)(4,4-difluorocyclohexyl)methyl)carbamate (245 mg, 0.527 mmol, Intermediate 14), and 3-(1,3-dioxoisoindolin-2-yl)-2,2-difluoropropyl trifluoromethanesulfonate (354 mg, 0.949 mmol) in acetonitrile (2.6 mL) was added DIPEA (138 µL, 0.791 mmol). The reaction mixture was heated at 55° C. for 16 h. The reaction was cooled to rt and concentrated under reduced pressure. Purification by silica gel chromatography (10-100% (10% MeOH in EtOAc)/hexanes) provided the title compound in 55% yield.

Step B: tert-Butyl ((S)-(7-((S)-1-((3-amino-2,2-difluoropropyl)amino)-2-cyclopropoxyethyl)imidazo[1,2-b]pyridazin-2-yl)(4,4-difluorocyclohexyl)methyl)carbamate. To a solution of tert-butyl ((S)-(7-((S)-2-cyclopropoxy-1-((3-(1,3-dioxoisoindolin-2-yl)-2,2-difluoropropyl)amino)ethyl)imidazo[1,2-b]pyridazin-2-yl)(4,4-difluorocyclohexyl)methyl)carbamate (0.20 g, 0.29 mmol, Step A) in EtOH (3 mL) was added hydrazine monohydrate (220 µL, 2.9 mmol). The reaction mixture was heated to 50° C. and stirred for 2 h, at which time a thick slurry had formed. The reaction mixture was diluted with EtOAc then washed with aqueous 5% LiCl and brine, dried over anhydrous $Na_2SO_4$, filtered and concentrated under reduced pressure to afford the title compound in 92% yield.

Step C: tert-Butyl ((S)-(7-((S)-2-cyclopropoxy-1-(5,5-difluoro-2-oxotetrahydropyrimidin-1(2H)-yl)ethyl)imidazo[1,2-b]pyridazin-2-yl)(4,4-difluorocyclohexyl)methyl)carbamate. A stirred solution of tert-butyl ((S)-(7-((S)-1-((3-amino-2,2-difluoropropyl)amino)-2-cyclopropoxyethyl)imidazo[1,2-b]pyridazin-2-yl)(4,4-difluorocyclohexyl)methyl)carbamate (150 mg, 0.27 mmol, Step B) and DIPEA. (116 µL, 0.671 mmol) in $CH_2Cl_2$ (5 mL) was cooled to 0° C. then a solution of triphosgene (32 mg, 0.11 mmol) in $CH_2Cl_2$ (0.5 mL) was added. The reaction was stirred for 15 min at 0° C. then quenched with $H_2O$ and 2 M aqueous HCl (0.67 mL, 1.3 mmol). The resulting mixture was extracted three times with $CH_2Cl_2$ then the combined organic layers were dried over anhydrous $Na_2SO_4$, filtered and concentrated under reduced pressure to provide the title compound that was used without further purification.

Intermediate 16: 1-((S)-1-(2-((S)-Amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride

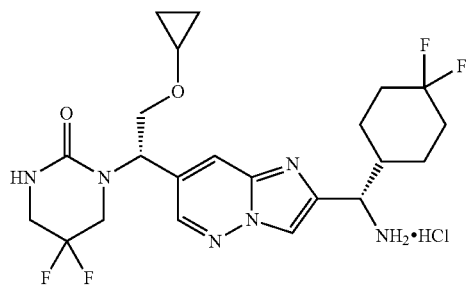

The title compound was prepared as described for the synthesis of Intermediate 11, using tert-butyl ((S)-(7-((S)-2-cyclopropoxy-1-(5,5-difluoro-2-oxotetrahydropyrimidin-1(2H)-yl)ethyl)imidazo[1,2-b]pyridazin-2-yl)(4,4-difluorocyclohexyl)methyl)carbamate (Intermediate 15) in place of tert-butyl ((R)-1-(7-((S*)-1-(5,5-difluoro-2-oxotetrahydropyrimidin-1(2H)-yl)-2-methoxyethyl)imidazo[1,2-b]pyridazin-2-yl)-2-((1,1,1-trifluoro-2-methylpropan-2-yl)oxy)ethyl)carbamate. 1-((S)-1-(2-((S)-Amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride was converted to 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one (hereafter known as Intermediate 16A) by dissolving 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride (1.12 g, 1.87 mmol) in EtOAc (50 mL) and saturated aqueous $NaHCO_3$ (30 mL) and then adjusting the pH of the solution to pH 11 by the addition of 3 M aqueous NaOH. The layers were separated and the aqueous layer further extracted with EtOAc (4×25 mL). The organic layers were combined, washed with brine, dried over anhydrous $Na_2SO_4$, filtered, and concentrated to dryness to provide Intermediate 16A as a white solid (99% yield).

Intermediate 17: tert-Butyl (R)-(1-(7-(((3-amino-2,2-difluoropropyl)amino)methyl)imidazo[1,2-b]pyridazin-2-yl)-2-((1,1,1-trifluoro-2-methylpropan-2-yl)oxy)ethyl)carbamate

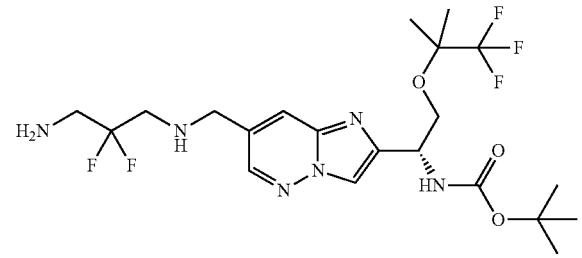 [SMILES: CC(C)(C)OC(=O)N[C@@H](COC(C)(C)C(F)(F)F)c1cn2ncc(CNCC(F)(F)CN)cc2n1]

To a flask charged with tert-butyl (R)-(1-(7-formylimidazo[1,2-b]pyridazin-2-yl)-2-((1,1,1-trifluoro-2-methylpropan-2-yl)oxy)ethyl)carbamate (72 mg, 0.173 mmol, Intermediate 6) and 2,2-difluoropropane-1,3-diamine dihydrochloride (63.3 mg, 0.346 mmol) in DCM (6 mL) was added triethylamine (0.121 mL, 0.865 mmol). The reaction was stirred at rt until the solids dissolved and then heated to 40° C. After 1 h, reaction was cooled to rt and MeOH (1 mL), sodium cyanoborohydride (65.2 mg, 1.04 mmol), and AcOH (0.040 mL, 0.692 mmol) were added and the resulting mixture stirred at rt. After 1 h, LCMS analysis indicated that all of the tert-butyl (R)-(1-(7-formylimidazo[1,2-b]pyridazin-2-yl)-2-((1,1,1-trifluoro-2-methylpropan-2-yl)oxy)ethyl)carbamate had been consumed. The mixture was concentrated under reduced pressure and diluted with saturated aqueous $NaHCO_3$ and $CH_2Cl_2$. The resulting mixture was extracted twice with $CH_2Cl_2$. The combined organic layers were washed with brine, dried over anhydrous $MgSO_4$, filtered, and concentrated under reduced pressure to provide the title compound that was used without further purification.

Intermediate 18: tert-Butyl (R)-(1-(7-((5,5-difluoro-2-oxotetrahydropyrimidin-1(2H)-yl)methyl)imidazo[1,2-b]pyridazin-2-yl)-2-((1,1,1-trifluoro-2-methylpropan-2-yl)oxy)ethyl)carbamate

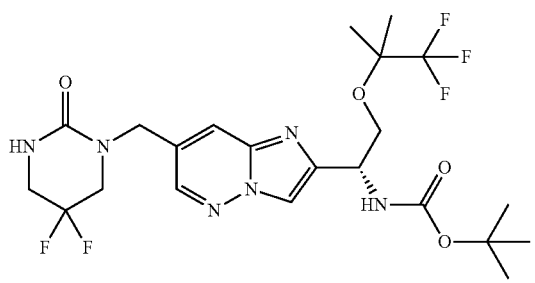 [SMILES: CC(C)(C)OC(=O)N[C@@H](COC(C)(C)C(F)(F)F)c1cn2ncc(CN3CC(F)(F)CNC3=O)cc2n1]

To tert-butyl (R)-(1-(7-(((3-amino-2,2-difluoropropyl)amino)methyl)imidazo[1,2-b]pyridazin-2-yl)-2-((1,1,1-trifluoro-2-methylpropan-2-yl)oxy)ethyl)carbamate (84.1 mg, 0.165 mmol, Intermediate 17) in THF (4.3 mL) was added CDI (84.1 mg, 0.519 mmol). The resulting mixture was heated to 65° C. After 75 min, LCMS analysis indicated that all of the tert-butyl (R)-(1-(7-(((3-amino-2,2-difluoropropyl)amino)methyl)imidazo[1,2-b]pyridazin-2-yl)-2-((1,1,1-trifluoro-2-methylpropan-2-yl)oxy)ethyl)carbamate had been consumed. The mixture was cooled to rt and quenched with 1 M aqueous NaOH (1.5 mL). The mixture was then concentrated under reduced pressure and partitioned between saturated aqueous NaHCO$_3$ and EtOAc. The aqueous layer was further extracted (twice) with EtOAc. The combined organic layers were washed with brine, dried over anhydrous Na$_2$SO$_4$, filtered, and concentrated under reduced pressure. Purification by silica gel chromatography (10-100% (10% MeOH in EtOAc)/hexanes) provided the title compound in 67% yield (62.4 mg).

Intermediate 19: (R)-1-((2-(1-Amino-2-((1,1,1-trifluoro-2-methylpropan-2-yl)oxy)ethyl)imidazo[1,2-b]pyridazin-7-yl)methyl)-5,5-difluorotetrahydropyrimidin-2(1H)-one

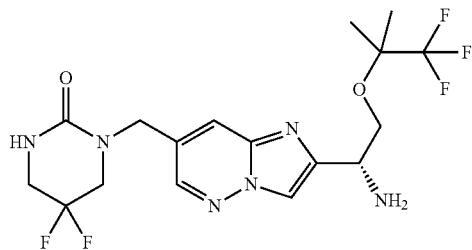 [SMILES: CC(C)(OC[C@H](N)c1cn2ncc(CN3CC(F)(F)CNC3=O)cc2n1)C(F)(F)F]

To a mixture of tert-butyl (R)-(1-(7-((5,5-difluoro-2-oxotetrahydropyrimidin-1(2H)-yl)methyl)imidazo[1,2-b]pyridazin-2-yl)-2-((1,1,1-trifluoro-2-methylpropan-2-yl)oxy)ethyl)carbamate (62.4 mg, 0.116 mmol, Intermediate 18) in CH$_2$Cl$_2$ (21 mL) was added 2,2,2-trifluoroacetic acid (0.18 mL, 2.33 mmol) and the resulting mixture was stirred at rt. After 20 min, LCMS analysis indicated that all of of tert-butyl (R)-(1-(7-((5,5-difluoro-2-oxotetrahydropyrimidin-1(2H)-yl)methyl)imidazo[1,2-b]pyridazin-2-yl)-2-((1,1,1-trifluoro-2-methylpropan-2-yl)oxy)ethyl)carbamate had been consumed. The mixture was diluted with EtOAc (2 mL) and washed twice with saturated aqueous NaHCO$_3$. The aqueous layer was then washed with 4:1 DCM/IPA mixture. The combined organic layers were washed with brine, dried over anhydrous Na$_2$SO$_4$, filtered, and concentrated under reduced pressure to provide the title compound that was used without further purification.

Intermediate 20: (S)-1-((2-(Amino(4,4-difluorocyclohexyl)methyl)imidazo[1,2-b]pyridazin-7-yl)methyl)-5,5-difluorotetrahydropyrimidin-2(1H)-one

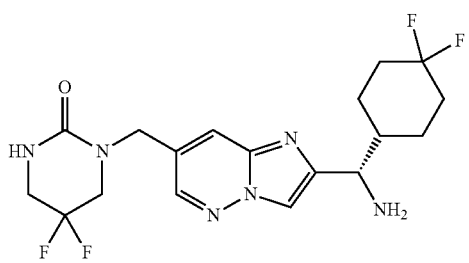 [SMILES: N[C@H](c1cn2ncc(CN3CC(F)(F)CNC3=O)cc2n1)C1CCC(F)(F)CC1]

Step A: tert-Butyl (S)-((7-(((3-amino-2,2-difluoropropyl)amino)methyl)imidazo[1,2-b]pyridazin-2-yl)(4,4-difluorocyclohexyl)methyl)carbamate. A solution of tert-butyl (S)-((4,4-difluorocyclohexyl)(7-formylimidazo[1,2-b]pyridazin-2-yl)methyl)carbamate (300 mg, 0.761 mmol), 2,2-difluoropropane-1,3-diamine dihydrochloride (418 mg, 2.28 mmol), and triethylamine (0.742 mL, 5.32 mmol) in DCM (8.6 mL) was stirred at rt. After 2 h, acetic acid (0.261 mL, 4.56 mmol) and MeOH (1.5 mL) were added. After a further 5 min, sodium cyanoborohydride (167 mg, 2.65 mmol) was added and the heterogenous reaction mixture was stirred for 16 h at rt. The reaction mixture was diluted with DCM (30 mL), saturated aqueous sodium bicarbonate (30 mL), and aqueous 3 M sodium hydroxide (30 mL) were added. The layers were separated, and the aqueous layer was extracted with DCM (3×20 mL). The combined organic layers were dried over anhydrous Na$_2$SO$_4$, filtered and concentrated to a gum that was used directly in the next step without further purification.

Step B: tert-Butyl (S)-((7-((5,5-difluoro-2-oxotetrahydropyrimidin-1(2H)-yl)methyl)imidazo[1,2-b]pyridazin-2-yl)(4,4-difluorocyclohexyl)methyl)carbamate. The tert-butyl (S)-((7-(((3-amino-2,2-difluoropropyl)amino)methyl)imidazo[1,2-b]pyridazin-2-yl)(4,4-difluorocyclohexyl)methyl)carbamate (0.76 mmol, theoretical) prepared in Step A was diluted with THF (10 mL) and treated with CDI (370 mg, 2.28 mmol). The resulting mixture was stirred at rt for 45 min. The reaction mixture was then diluted with THF (90 mL) and warmed to 60° C. for 45 min. The reaction mixture was cooled to rt and treated with aqueous 3 M sodium hydroxide (3 mL). After stirring for 1 h at rt, the reaction mixture was diluted with brine (20 mL) and the layers were separated. The organic layer was washed with aqueous 0.1 M HCl (2×10 mL) and brine (2×10 mL), dried over anhydrous MgSO$_4$, filtered and concentrated to a gum that was used directly in the next step without further purification.

Step C: (S)-1-((2-(Amino(4,4-difluorocyclohexyl)methyl)imidazo[1,2-b]pyridazin-7-yl)methyl)-5,5-difluorotetrahydropyrimidin-2(1H)-one. To a cooled (0° C.) solution of tert-butyl (S)-((7-((5,5-difluoro-2-oxotetrahydropyrimidin-1(2H)-yl)methyl)imidazo[1,2-b]pyridazin-2-yl)(4,4-difluorocyclohexyl)methyl)carbamate (500 mg) prepared in Step B in DCM (3.7 mL) was added TFA (3.7 mL, 48 mmol). After stirring at 0° C. for 1.5 h, the reaction mixture was concentrated to dryness, and then diluted with EtOAc (20 mL), brine (30 mL), aqueous 3 M sodium hydroxide (5 mL), and saturated aqueous sodium bicarbonate (3 mL). The layers were separated, and the aqueous layer was extracted with EtOAc (2×20 mL) and DCM (6×15 mL). The combined organic extracts were dried over anhydrous Na$_2$SO$_4$, filtered and concentrated to dryness to provide the title compound as a yellow film (88.3% yield over 3 steps) that was used without further purification.

Intermediate 21: 1-((2-((S)-Amino(4,4-difluorocyclohexyl)methyl)imidazo[1,2-b]pyridazin-7-yl)methyl)-5-methyltetrahydropyrimidin-2(1H)-one

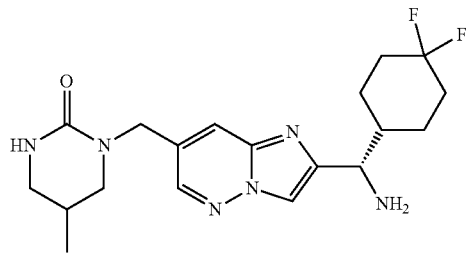 [SMILES: CC1CNC(=O)N(Cc2cnn3cc([C@@H](N)C4CCC(F)(F)CC4)nc3c2)C1]

Step A: tert-Butyl ((1S)-(7-(((3-((tert-butoxycarbonyl)amino)-2-methylpropyl)amino)methyl)imidazo[1,2-b]pyridazin-2-yl)(4,4-difluorocyclohexyl)methyl)carbamate. The title compound was synthesized in a manner analogous to Intermediate 20 Step A using tert-butyl (3-amino-2-methylpropyl)carbamate) in place of 2,2-difluoropropane-1,3-diamine dihydrochloride.

Step B: tert-Butyl ((1S)-(4,4-difluorocyclohexyl)(7-((5-methyl-2-oxotetrahydropyrimidin-1(2H)-yl)methyl)imidazo[1,2-b]pyridazin-2-yl)methyl)carbamate. tert-Butyl ((1S)-(7-(((3-((tert-butoxycarbonyl)amino)-2-methylpropyl)amino)methyl)imidazo[1,2-b]pyridazin-2-yl)(4,4-difluorocyclohexyl)methyl)carbamate (0.76 mmol, theoretical, Step A) was diluted with THF (10 mL), treated with potassium tert-pentoxide (1.5 mL, 2 M in tert-amyl alcohol), and warmed to 60° C. After 2.5 h the reaction mixture was cooled to rt, treated with aqueous 1 M HCl (5 mL), and diluted with EtOAc (30 mL), brine (30 mL) and saturated aqueous NaHCO$_3$ (30 mL). The layers were separated, and the aqueous layer was extracted with EtOAc (3×20 mL). The combined organics were dried over anhydrous Na$_2$SO$_4$, filtered, and concentrated to dryness to give an oil that was used in the next step without further purification.

Step C: 1-((2-((S)-Amino(4,4-difluorocyclohexyl)methyl)imidazo[1,2-b]pyridazin-7-yl)methyl)-5-methyltetrahydropyrimidin-2(1H)-one. The title compound was prepared as described for the synthesis of Intermediate 20 Step C using tert-butyl ((1S)-(4,4-difluorocyclohexyl)(7-((5-methyl-2-oxotetrahydropyrimidin-1(2H)-yl)methyl)imidazo[1,2-b]pyridazin-2-yl)methyl)carbamate (Step B) in place of tert-butyl (S)-((7-(((5,5-difluoro-2-oxotetrahydropyrimidin-1(2H)-yl)methyl)imidazo[1,2-b]pyridazin-2-yl)(4,4-difluorocyclohexyl)methyl)carbamate to provide the title compound (312 mg,) that was used without further purification.

Intermediate 22: (S)-1-((2-(Amino(4,4-difluorocyclohexyl)methyl)imidazo[1,2-b]pyridazin-7-yl)methyl)-1,3-diazepan-2-one

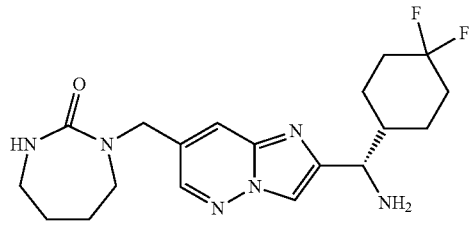 [SMILES: N[C@H](c1cn2ncc(CN3CCCCNC3=O)cc2n1)C1CCC(F)(F)CC1]

Step A: tert-Butyl (S)-((7-(((4-aminobutyl)amino)methyl)imidazo[1,2-b]pyridazin-2-yl)(4,4-difluorocyclohexyl)methyl)carbamate. The title compound was synthesized in a manner analogous to Intermediate 20 Step A using 1,4-diaminobutane in place of 2,2-difluoropropane-1,3-diamine dihydrochloride.

Step B: tert-Butyl (S)-((4,4-difluorocyclohexyl)(7-((2-oxo-1,3-diazepan-1-yl)methyl)imidazo[1,2-b]pyridazin-2-yl)methyl)carbamate. The title compound was synthesized in a manner analogous to Intermediate 20 Step B using tert-butyl (S)-((7-(((4-aminobutyl)amino)methyl)imidazo[1,2-b]pyridazin-2-yl)(4,4-difluorocyclohexyl)methyl)carbamate (Step A) in place of tert-butyl (S)-((7-(((3-amino-2,2-difluoropropyl)amino)methyl)imidazo[1,2-b]pyridazin-2-yl)(4,4-difluorocyclohexyl)methyl)carbamate.

Step C: (S)-1-((2-(Amino(4,4-difluorocyclohexyl)methyl)imidazo[1,2-b]pyridazin-7-yl)methyl)-1,3-diazepan-2-one. The title compound was synthesized in a manner analogous to Intermediate 20 Step C using tert-butyl (S)-((4,4-difluorocyclohexyl)(7-((2-oxo-1,3-diazepan-1-yl)methyl)imidazo[1,2-b]pyridazin-2-yl)methyl)carbamate (Step B) in place of (S)-1-((2-(amino(4,4-difluorocyclohexyl)methyl)imidazo[1,2-b]pyridazin-7-yl)methyl)-5,5-difluorotetrahydropyrimidin-2(1H)-one to give the title compound that was used without further purification.

Intermediate 23: (S)-1-((2-(Amino(4,4-difluorocyclohexyl)methyl)imidazo[1,2-b]pyridazin-7-yl)methyl)-5,5-dimethyltetrahydropyrimidin-2(1H)-one

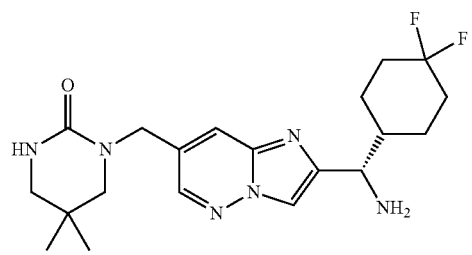 [SMILES: CC1(C)CNC(=O)N(Cc2cnn3cc([C@@H](N)C4CCC(F)(F)CC4)nc3c2)C1]

Step A: tert-Butyl (S)-((7-(((3-amino-2,2-dimethylpropyl)amino)methyl)imidazo[1,2-b]pyridazin-2-yl)(4,4-difluorocyclohexyl)methyl)carbamate. The title compound was synthesized in a manner analogous to Intermediate 20 Step A using 2,2-dimethylpropane-1,3-diamine in place of 2,2-difluoropropane-1,3-diamine dihydrochloride.

Step B: tert-Butyl (S)-((4,4-difluorocyclohexyl)(7-((5,5-dimethyl-2-oxotetrahydropyrimidin-1(2H)-yl)methyl)imidazo[1,2-b]pyridazin-2-yl)methyl)carbamate. The title compound was synthesized in a manner analogous to Intermediate 20 Step B using tert-butyl (S)-((7-(((3-amino-2,2-dimethylpropyl)amino)methyl)imidazo[1,2-b] pyridazin-2-yl)(4,4-difluorocyclohexyl)methyl)carbamate (Step A) in place of tert-butyl (S)-((7-(((3-amino-2,2-difluoropropyl)amino)methyl)imidazo[1,2-b]pyridazin-2-yl)(4,4-difluorocyclohexyl)methyl)carbamate.

Step C: (S)-1-((2-(Amino(4,4-difluorocyclohexyl) methyl)imidazo[1,2-b]pyridazin-7-yl)methyl)-5,5-dimethyltetrahydropyrimidin-2(1H)-one. The title compound was synthesized in a manner analogous to Intermediate 20, Step C using tert-butyl (S)-((4,4-difluorocyclohexyl)(7-((5,5-dimethyl-2-oxotetrahydropyrimidin-1(2H)-yl)methyl)imidazo [1,2-b]pyridazin-2-yl)methyl)carbamate (Step B) in place of tert-butyl (S)-((7-((5,5-difluoro-2-oxotetrahydropyrimidin-1 (2H)-yl)methyl)imidazo[1,2-b]pyridazin-2-yl)(4,4-difluorocyclohexyl)methyl)carbamate to give the title compound that was used without further purification.

Intermediate 24: (S)-1-((2-(Amino(4,4-difluorocyclohexyl)methyl)imidazo[1,2-b]pyridazin-7-yl) methyl)tetrahydropyrimidin-2(1H)-one

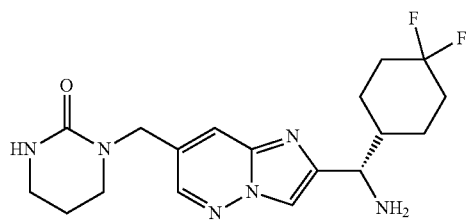 [SMILES: N[C@H](c1cn2ncc(CN3CCCNC3=O)cc2n1)C1CCC(F)(F)CC1]

Step A: tert-Butyl (S)-((7-(((3-aminopropyl)amino) methyl)imidazo[1,2-b]pyridazin-2-yl)(4,4-difluorocyclohexyl)methyl)carbamate. The title compound was synthesized in a manner analogous to Intermediate 20 Step A using 1,3-diaminopropane in place of 2,2-difluoropropane-1,3-diamine dihydrochloride.

Step B: tert-Butyl (S)-((4,4-difluorocyclohexyl)(7-((2-oxotetrahydropyrimidin-1(2H)-yl)methyl)imidazo[1,2-b] pyridazin-2-yl)methyl)carbamate. The title compound was synthesized in a manner analogous to Intermediate 20 Step B using tert-butyl (S)-((7-(((3-aminopropyl)amino)methyl) imidazo[1,2-b]pyridazin-2-yl)(4,4-difluorocyclohexyl) methyl)carbamate (Step A) in place of tert-butyl (S)-((7-(((3-amino-2,2-difluoropropyl)amino)methyl)imidazo[1,2-b]pyridazin-2-yl)(4,4-difluorocyclohexyl)methyl) carbamate.

Step C: (S)-1-((2-(Amino(4,4-difluorocyclohexyl) methyl)imidazo[1,2-b]pyridazin-7-yl)methyl)tetrahydropyrimidin-2(1H)-one. The title compound was synthesized in a manner analogous to Intermediate 20 Step C using tert-butyl (S)-((4,4-difluorocyclohexyl)(7-((2-oxotetrahydropyrimidin-1(2H)-yl)methyl)imidazo[1,2-b]pyridazin-2-yl)methyl) carbamate (Step B) in place of tert-butyl (S)-((7-((5,5-difluoro-2-oxotetrahydropyrimidin-1(2H)-yl)methyl) imidazo[1,2-b]pyridazin-2-yl)(4,4-difluorocyclohexyl) methyl)carbamate to give the title compound that was used without further purification.

Intermediate 25: 1-((S*)-1-(2-((S)-Amino(4,4-difluorocyclohexyl)methyl)imidazo[1,2-b]pyridazin-7-yl)-2-ethoxyethyl)-5,5-difluorotetrahydropyrimidin-2(1H)-one hydrochloride

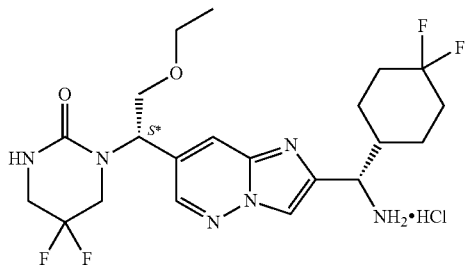

Step A. Tributyl(ethoxymethyl)stannane. The title compound was prepared as described for the synthesis of Intermediate 12, using ethanol in place of cyclopropanol in 86% yield.

Step B. tert-Butyl ((S)-(7-((S*)-1-(((R)-tert-butylsulfinyl) amino)-2-ethoxyethyl)imidazo[1,2-b]pyridazin-2-yl)(4,4-difluorocyclohexyl)methyl)carbamate. The title compound was prepared in a manner analogous to the synthesis of Intermediate 13, using tributyl(ethoxymethyl)stannane (Step A) in place of tributyl(cyclopropoxymethyl)stannane in 56% yield.

Step C. tert-Butyl ((S)-(7-((S*)-1-amino-2-ethoxyethyl) imidazo[1,2-b]pyridazin-2-yl)(4,4-difluorocyclohexyl) methyl)carbamate. The title compound was prepared as described for the synthesis of Intermediate 14, using tert-butyl ((S)-(7-((S*)-1-(((R)-tert-butylsulfinyl)amino)-2-ethoxyethyl)imidazo[1,2-b]pyridazin-2-yl)(4,4-difluorocyclohexyl)methyl)carbamate (Step B) in place of tert-butyl ((S)-(7-((S-1-(((R)-tert-butylsulfinyl)amino)-2-cyclopropoxyethyl)imidazo[1,2-b]pyridazin-2-yl)(4,4-difluorocyclohexyl)methyl)carbamate and was used without further purification.

Step D. tert-Butyl ((S)-(7-((S*)-1-(5,5-difluoro-2-oxotetrahydropyrimidin-1(2H)-yl)-2-ethoxyethyl)imidazo[1,2-b] pyridazin-2-yl)(4,4-difluorocyclohexyl)methyl)carbamate. The title compound was prepared as described for the synthesis of Intermediate 15, using tert-butyl ((S)-(7-((S*)-1-amino-2-ethoxyethyl)imidazo[1,2-b]pyridazin-2-yl)(4,4-difluorocyclohexyl)methyl)carbamate (Step C) in place of tert-butyl ((S)-(7-((S)-1-amino-2-cyclopropoxyethyl)imidazo[1,2-b]pyridazin-2-yl)(4,4-difluorocyclohexyl)methyl) carbamate in 60% yield.

Step E. 1-((S*)-1-(2-((S)-Amino(4,4-difluorocyclohexyl) methyl)imidazo[1,2-b]pyridazin-7-yl)-2-ethoxyethyl)-5,5-difluorotetrahydropyrimidin-2(1H)-one hydrochloride. The title compound was prepared as described for the synthesis of Intermediate 11, using tert-butyl ((S)-(7-((S*)-1-(5,5-difluoro-2-oxotetrahydropyrimidin-1(2H)-yl)-2-ethoxyethyl)imidazo[1,2-b]pyridazin-2-yl)(4,4-difluorocyclohexyl)methyl)carbamate (Step D) in place of tert-butyl ((R)-1-(7-((S*)-1-(5,5-difluoro-2-oxotetrahydropyrimidin-1 (2H)-yl)-2-methoxyethyl)imidazo[1,2-b]pyridazin-2-yl)-2-((1,1,1-trifluoro-2-methylpropan-2-yl)oxy)ethyl)carbamate in 92% yield.

Intermediate 26: 2,5-Dioxopyrrolidin-1-yl 1-isopropyl-1H-pyrazole-5-carboxylate

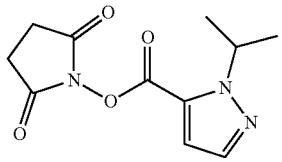 [SMILES: CC(C)n1nccc1C(=O)ON1C(=O)CCC1=O]

Step A. 1-Isopropyl-1H-pyrazole-5-carbonyl chloride. A round bottom flask was charged with 1-isopropyl-1H-pyrazole-5-carboxylic acid (1 g, 6.5 mmol) and DCM (13 mL) and was cooled to 0° C. under a nitrogen atmosphere. To the solution was added oxalyl chloride (1.1 mL, 13.0 mmol) followed by DMF (0.05 mL, 0.65 mmol) dropwise. The reaction was stirred as it slowly warmed to rt. Once the gas evolution ceased the reaction was concentrated under reduced pressure into a yellow oil that was then dissolved in 12 mL of dry DCM and stored as a 2 M solution.

Step B. 2,5-Dioxopyrrolidin-1-yl 1-isopropyl-1H-pyrazole-5-carboxylate. A round bottom flask was charged with N-hydroxysuccinimide (1.1 g, 9.7 mmol), DCM (25 mL), and DIPEA (16 mL, 6.5 mmol), and cooled to 0° C. under a nitrogen atmosphere. To the solution was added a solution of 1-isopropyl-1H-pyrazole-5-carbonyl chloride (13 mL, 6.5 mmol, 2 M in DCM, Step A). The solution was allowed to warm to rt as it stirred for 1 h. The solution was washed with water and then with brine, dried over anhydrous MgSO$_4$, filtered, and concentrated. The isolated material was purified by silica gel chromatography (0-100% EtOAc (with 10% MeOH)/hexanes) to afford the title compound as an off white solid.

Intermediate 27: 3-(1,3-Dioxoisoindolin-2-yl)-2,2-difluoropropyl-1,1,3,3-d$_4$ trifluoromethanesulfonate

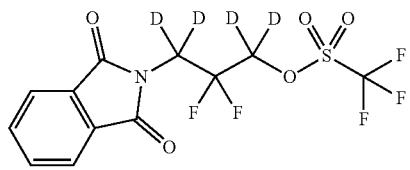 [SMILES: [2H]C([2H])(OS(=O)(=O)C(F)(F)F)C(F)(F)C([2H])([2H])N1C(=O)c2ccccc2C1=O]

Step A. N-benzyl-2,2-difluoro-3,3-d$_2$-3-hydroxypropanamide. A flask was charged with methyl 3-(benzylamino)-2,2-difluoro-3-oxopropanoate (2 g, 8.2 mmol), MeOH (42 mL), and cooled to 0° C. To the cold solution was added sodium borodeuteride (860 mg, 20.6 mmol) portionwise. The reaction was stirred for an hour at 0° C. then quenched by the addition of water (15 mL). The reaction was concentrated to remove the MeOH. The resulting solution was further diluted with water and extracted with ethyl acetate (3×50 mL). The combined organics were washed with brine, dried over anhydrous MgSO4, filtered and concentrated to yield N-benzyl-2,2-difluoro-3,3-d$_2$-3-hydroxypropanamide:

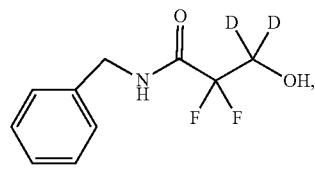 [SMILES: [2H]C([2H])(O)C(F)(F)C(=O)NCc1ccccc1]

as a white solid (100% yield) that was used without further purification.

Step B. 3-(Benzylamino)-2,2-difluoropropan-1,1,3,3-d$_4$-1-ol. A flask was charged with N-Benzyl-2,2-difluoro-3,3-d$_2$-3-hydroxypropanamide (7.7 g, 35.5 mmol, Step A), and THF (230 mL). To the reaction was added boron trifluoride diethyletherate (18.8 mL, 46.5 wt %, 70.9 mmol) portionwise. The reaction mixture was then heated to reflux and stirred for 1 h. The reaction mixture was cooled to room temperature and quenched by the careful addition of MeOH (50 mL). The resulting mixture was stirred for 30 minutes then concentrated to dryness. Ethyl acetate was added to the resulting white solid and the remaining solids were removed by filtration. The filtrate was concentrated to yield the title compound, which was used without further purification.

Step C. 3-Amino-2,2-difluoropropan-1,1,3,3-d$_4$-1-ol. A flask was charged with a 3-(benzylamino)-2,2-difluoropropan-1,1,3,3-d$_4$-1-ol (7.1 g, 34.3 mmol, Step B), MeOH (690 mL), Pd/C (3.7 g, 3.4 mmol, 10 wt % Pd), and ammonium formate (21.7 g, 343.9 mmol). The reaction was warmed to 60° C. and stirred for 3 h. The reaction was cooled to room temperature, filtered through a pad of diatomaceous earth (e.g., Celite®), and the solids were washed with ethyl acetate. The combined organic layers were concentrated to an off white solid that was used directly in the next step.

Step D. 2-(2,2-Difluoro-3-hydroxypropyl-1,1,3,3-d$_4$) isoindoline-1,3-dione. A flask was charged with 3-amino-2,2-difluoropropan-1,1,3,3-d$_4$-1-ol (3.6 g, 34.4 mmol, Step C), N-carbethoxyphthalimide (8.7 g, 39.6 mmol), THF (86 mL), and DIPEA (23.7 mL, 137 mmol). The reaction mixture was then heated to 60° C. for 12 h. The reaction mixture was cooled to room temperature, and concentrated to dryness. Water (250 mL) was added to the resulting residue and stirred for 30 min during which time a solid formed. The solid was collected by filtration, dried overnight under reduced pressure to yield the title compound as a white powder (59% yield over steps B, C and D).

Step E: 3-(1,3-Dioxoisoindolin-2-yl)-2,2-difluoropropyl-1,1,3,3-d$_4$ trifluoromethanesulfonate. A flask was charged with, 2-(2,2-difluoro-3-hydroxypropyl-1,1,3,3-d$_4$)isoindoline-1,3-dione (1.5 g, 5.9 mmol, Step D), DCM (20 mL), and pyridine (0.53 mL, 6.6 mmol), and trifluoromethanesulfonic anhydride (1.1 mL, 6.3 mmol) was added dropwise. The reaction mixture was stirred for 30 min at rt then quenched by the addition of water (5 mL). The resulting layers were separated and the aqueous layer was further extracted with DCM (2×5 mL). The combined organic layers were washed with brine, dried over anhydrous MgSO$_4$, filtered and concentrated to afford an off white solid in 50% yield.

Intermediate 28: 1-((S)-1-(2-((R)-1-Amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one-4,4,6,6-d$_4$

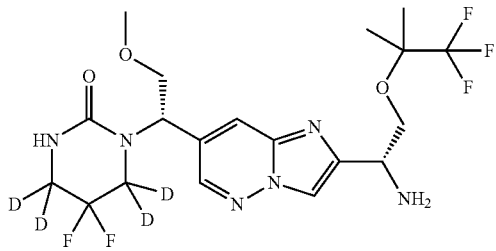 [SMILES: [2H]C1([2H])NC(=O)N([C@H](COC)c2cnn3cc([C@@H](N)COC(C)(C)C(F)(F)F)nc3c2)C([2H])([2H])C1(F)F]

Step A: tert-Butyl ((R)-1-(6-chloro-7-((S)-1-((3-(1,3-dioxoisoindolin-2-yl)-2,2-difluoropropyl-1,1,3,3-d$_4$)amino)-2-methoxyethyl)imidazo[1,2-b]pyridazin-2-yl)-2-((1,1,1-trifluoro-2-methylpropan-2-yl)oxy)ethyl)carbamate. A flask was charged with tert-butyl ((R)-1-(7-((S)-1-amino-2-methoxyethyl)-6-chloroimidazo[1,2-b]pyridazin-2-yl)-2-((1,1,1-trifluoro-2-methylpropan-2-yl)oxy)ethyl)carbamate (484 mg, 0.98 mmol, Intermediate 48), 3-(1,3-dioxoisoindolin-2-yl)-2,2-difluoropropyl-1,1,3,3-d$_4$ trifluoromethanesulfonate (458 mg, 1.2 mmol, Intermediate 27), MeCN (3.5 mL), and DIPEA (0.33 mL, 1.9 mmol). The resulting reaction mixture was stirred at 60° C. for 48 h. The reaction was cooled to rt and partitioned between water and ethyl acetate. The aqueous layer was further extracted with ethyl acetate (2×). The combined organic layers were washed with brine, dried over anhydrous MgSO$_4$, filtered, concentrated, and purified by silica gel chromatography (0-100% ethyl acetate (w/10% MeOH): hexanes) to afford the title compound as a white solid (71%).

Step B: tert-Butyl ((R)-1-(7-((S)-1-((3-(1,3-dioxoisoindolin-2-yl)-2,2-difluoropropyl-1,1,3,3-d$_4$)amino)-2-methoxyethyl)imidazo[1,2-b]pyridazin-2-yl)-2-((1,1,1-trifluoro-2-methylpropan-2-yl)oxy)ethyl)carbamate. A vial was charged with tert-butyl ((R)-1-(6-chloro-7-((S)-1-((3-(1,3-dioxoisoindolin-2-yl)-2,2-difluoropropyl-1,1,3,3-d$_4$)amino)-2-methoxyethyl)imidazo[1,2-b]pyridazin-2-yl)-2-((1,1,1-trifluoro-2-methylpropan-2-yl)oxy)ethyl)carbamate (450 mg, 0.62 mmol, Step A), 2-methyl-2-butanol (20 mL), 2,2,2-trifluoroethanol (10 mL), Pd/C (381 mg, 10 wt % Pd), and ammonium formate (1.3 g, 21.7 mmol). The vial was warmed to 90° C., stirred for 1 h, then cooled to rt. The reaction mixture was filtered through a pad of diatomaceous earth (e.g., Celite®), and the solids were washed with ethanol. The combined organic layers were concentrated to yield the title compound as a yellow solid (100%).

Step C: tert-Butyl ((R)-1-(7-((S)-1-((3-amino-2,2-difluoropropyl-1,1,3,3-d$_4$)amino)-2-methoxyethyl)imidazo[1,2-b]pyridazin-2-yl)-2-((1,1,1-trifluoro-2-methylpropan-2-yl)oxy)ethyl)carbamate. A flask was charged with a stir bar, tert-butyl ((R)-1-(7-((S)-1-((3-(1,3-dioxoisoindolin-2-yl)-2,2-difluoropropyl-1,1,3,3-d$_4$)amino)-2-methoxyethyl)imidazo[1,2-b]pyridazin-2-yl)-2-((1,1,1-trifluoro-2-methylpropan-2-yl)oxy)ethyl)carbamate (435 mg, 0.63 mmol, Step B), ethanol (3.3 mL), and hydrazine monohydrate (0.42 mL, 6.3 mmol). The reaction was stirred at rt for 2 h. The reaction was then partitioned between water and ethyl acetate, the layers were separated, and the aqueous layer was further extracted with ethyl acetate (2×). The combined organic layers were washed with brine, dried over anhydrous MgSO$_4$, filtered, and concentrated to a glassy solid (71%).

Step D: tert-Butyl ((R)-1-(7-((S)-1-(5,5-difluoro-2-oxotetrahydropyrimidin-1(2H)-yl-4,4,6,6-d$_4$)-2-methoxyethyl)imidazo[1,2-b]pyridazin-2-yl)-2-((1,1,1-trifluoro-2-methylpropan-2-yl)oxy)ethyl)carbamate. A flask was charged with tert-butyl ((R)-1-(7-((S)-1-((3-amino-2,2-difluoropropyl-1,1,3,3-d$_4$)amino)-2-methoxyethyl)imidazo[1,2-b]pyridazin-2-yl)-2-((1,1,1-trifluoro-2-methylpropan-2-yl)oxy)ethyl)carbamate (241 mg, 0.43 mmol, Step C), THF (8.6 mL), CDI (209 mg, 1.3 mmol), and DIPEA (0.22 mL, 1.3 mmol). The reaction was warmed to 60° C. and stirred for 1 h. The reaction was cooled to rt and partitioned between water and ethyl acetate. The layers were separated, and the aqueous phase was further extracted with ethyl acetate (2×). The combined organic layers were washed with brine, dried over anhydrous MgSO$_4$, filtered, concentrated, and purified by silica gel chromatography (0-100% ethyl acetate (w/10% MeOH): hexanes) to afford the title compound as a glassy solid (45%).

Step E: 1-((S)-1-(2-((R)-1-Amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one-4,4,6,6-d$_4$. A flask was charged with tert-butyl ((R)-1-(7-((S)-1-(5,5-difluoro-2-oxotetrahydropyrimidin-1(2H)-yl-4,4,6,6-d$_4$)-2-methoxyethyl)imidazo[1,2-b]pyridazin-2-yl)-2-((1,1,1-trifluoro-2-methylpropan-2-yl)oxy)ethyl)carbamate (105 mg, 0.18 mmol, Step D), and TFA (1 mL). The reaction was stirred at rt for 5 min then concentrated. The residue was partitioned between saturated aqueous NaHCO$_3$ and ethyl acetate. The organic layer was washed with brine, dried over anhydrous MgSO$_4$, filtered, and concentrated to give a yellow solid (100%).

Intermediate 29: tert-Butyl ((S)-(7-((S)-2-cyclopropoxy-1-(5,5-difluoro-2-oxotetrahydropyrimidin-1(2H)-yl-4,4,6,6-d$_4$)ethyl)imidazo[1,2-b]pyridazin-2-yl)(4,4-difluorocyclohexyl)methyl)carbamate

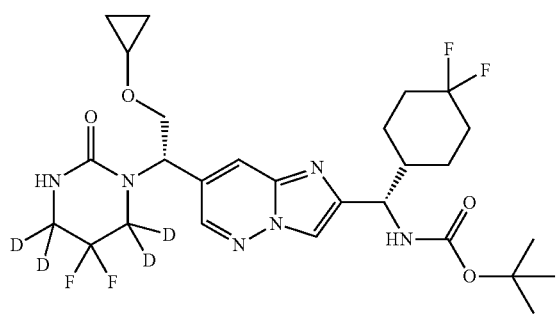 [SMILES: [2H]C1([2H])NC(=O)N([C@H](COC2CC2)c2cnn3cc([C@@H](NC(=O)OC(C)(C)C)C4CCC(F)(F)CC4)nc3c2)C([2H])([2H])C1(F)F]

The title compound was prepared as described for Intermediate 10 using 3-(1,3-dioxoisoindolin-2-yl)-2,2-difluoropropyl-1,1,3,3-d$_4$ trifluoromethanesulfonate (Intermediate 27) in place of 3-(1,3-dioxoisoindolin-2-yl)-2,2-difluoropropyl trifluoromethanesulfonate, and tert-butyl ((S)-(7-((S)-1-amino-2-cyclopropoxyethyl)imidazo[1,2-b]pyridazin-2-yl)(4,4-difluorocyclohexyl)methyl)carbamate (Intermediate 14) in place of tert-butyl ((R)-1-(7-((S*)-1-amino-2-methoxyethyl)imidazo[1,2-b]pyridazin-2-yl)-2-((1,1,1-trifluoro-2-methylpropan-2-yl)oxy)ethyl)carbamate (30% yield).

Intermediate 30: 1-((S)-1-(2-((S)-Amino(4,4-difluorocyclohexyl)methyl)imidazo[1,2-b]pyridazin-7-yl)-2-cyclopropoxyethyl)-5,5-difluorotetrahydropyrimidin-2(1H)-one-4,4,6,6-d$_4$

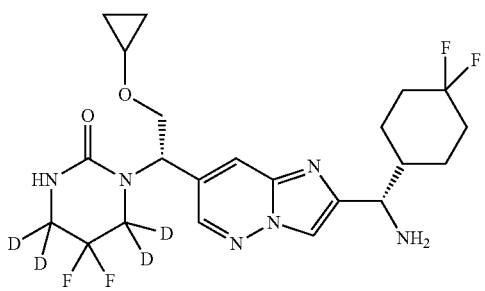 [SMILES: [2H]C1([2H])NC(=O)N([C@H](COC2CC2)c2cnn3cc([C@@H](N)C4CCC(F)(F)CC4)nc3c2)C([2H])([2H])C1(F)F]

The title compound was prepared as described for Intermediate 28, Step B using tert-butyl ((S)-(7-((S)-2-cyclopropoxy-1-(5,5-difluoro-2-oxotetrahydropyrimidin-1(2H)-yl-4,4,6,6-d$_4$)ethyl)imidazo[1,2-b]pyridazin-2-yl)(4,4-difluorocyclohexyl)methyl)carbamate (Intermediate 29) in place of tert-butyl ((R)-1-(7-((S)-1-(5,5-difluoro-2-oxotetrahydropyrimidin-1(2H)-yl-4,4,6,6-d$_4$)-2-methoxyethyl)imidazo[1,2-b]pyridazin-2-yl)-2-((1,1,1-trifluoro-2-methylpropan-2-yl)oxy)ethyl)carbamate (71% yield).

Intermediate 31: 2,5-Dioxopyrrolidin-1-yl 4-cyclopropyl-1,2,5-oxadiazole-3-carboxylate

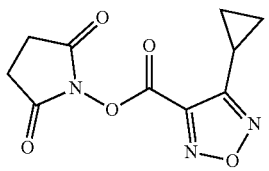 [SMILES: O=C(ON1C(=O)CCC1=O)c1nonc1C1CC1]

Step A: 4-Cyclopropyl-1,2,5-oxadiazole-3-carbonyl chloride. A flask was charged with 4-cyclopropyl-1,2,5-oxadiazole-3-carboxylic acid (200 mg, 1.3 mmol) and DCM (2.5 mL), and cooled to 0° C. Then, oxalyl chloride (0.22 mL, 2.6 mmol) and one drop of DMF were added. The resulting mixture was stirred for 1 h as it warmed to rt. The mixture was concentrated to a yellow oil and was used without further purification.

Step B: 2,5-Dioxopyrrolidin-1-yl 4-cyclopropyl-1,2,5-oxadiazole-3-carboxylate. The residue from Step A was dissolved in DCM (3.2 mL) and cooled to 0° C. To the solution was added N-hydroxysuccinimide (231 mg, 1.9 mmol), and DIPEA (0.34 mL, 1.9 mmol). The reaction was stirred for 1 h as it warmed to rt. The reaction was quenched by the addition of water (3 mL), the layers were separated. The organic layer was washed with brine, dried over anhydrous MgSO$_4$, filtered and concentrated to dryness. This material was purified by silica gel chromatography (0-100% ethyl acetate (with 10% MeOH)/hexanes) to afford the title compound as a clear oil (40% yield).

Intermediate 32: (R,E)-N-(5-(((tert-Butylsulfinyl)imino)methyl)-6-chloropyridazin-3-yl)pivalamide

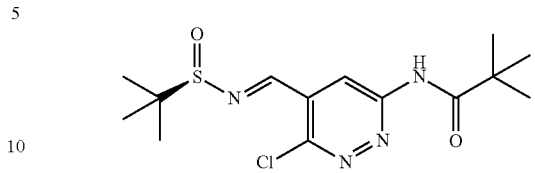

Step A: N-(6-Chloropyridazin-3-yl)pivalamide. To a stirred solution of 6-chloropyridazin-3-amine (350 g, 2.70 mol) and pyridine (427 g, 5.40 mol) in DCM (5000 mL) was added 2,2-dimethylpropanoyl chloride (814 g, 6.75 mol) dropwise at 0° C. under nitrogen atmosphere. The resulting mixture was stirred for 2 h at rt under a nitrogen atmosphere. The mixture was basified to pH 7~8 using saturated aqueous NaHCO$_3$ (aq.) and the resulting mixture was extracted with DCM (3×3 L). The combined organic layers were washed with brine (1×2 L) and water (1×2 L), dried over anhydrous Na$_2$SO$_4$. After filtration, the filtrate was concentrated under reduced pressure and the residue was purified by trituration with petroleum ether (2 L). The precipitated solids were collected by filtration affording the title compound in 87% yield.

Step B: N-(6-Chloro-5-iodopyridazin-3-yl)pivalamide. To a stirred solution of TMPMgCl·LiCl (6.8 L, 6.8 mol) was added N-(6-chloropyridazin-3-yl)pivalamide (560 g, 2.62 mol, Step A) in THF (5.0 L) dropwise at −60° C. under nitrogen atmosphere. The resulting mixture was stirred for 2.5 h at −55° C. under nitrogen atmosphere, then iodine (998 g, 3.93 mol) in THF (3.0 L) dropwise at −60° C. The resulting mixture was stirred for an additional 1 h at −55° C. and the reaction was then quenched by the addition of sat. NH$_4$Cl (aq.) (2 L) at −40° C. The resulting mixture was extracted with EtOAc (3×3 L) and the combined organic layers were washed with sat. aqueous Na$_2$S$_3$O$_4$ (1×2 L) and brine (1×2 L), dried over anhydrous Na$_2$SO$_4$, and filtered. The filtrate was concentrated under reduced pressure and the residue was purified by silica gel column chromatography (33% EtOAc/petroleum ether) to afford the title compound in 69% yield.

Step C: N-(6-Chloro-5-formylpyridazin-3-yl)pivalamide. To a stirred solution of N-(6-chloro-5-iodopyridazin-3-yl)pivalamide (607 g, 1.79 mol, Step B) in THF (6.0 L) was added a 60% dispersion of NaH in mineral oil (93.0 g, 2.32 mol) in portions at 0° C. under nitrogen atmosphere. The resulting mixture was stirred for 30 min at rt under a nitrogen atmosphere and isopropylmagnesium chloride lithium chloride complex (1.99 L, 2.59 mol) was added dropwise at −60° C. The resulting mixture was stirred for additional 1.5 h at −55° C. and then dimethylformamide (653 g, 8.94 mol) in THF (700 mL) was added dropwise at −60° C. The resulting mixture was stirred for additional 1 h at rt and then quenched by the addition of saturated aqueous NH$_4$Cl (2 L) at 0° C. The resulting mixture was extracted with EtOAc (3×3 L). The combined organic layers were washed with brine (1×2 L) and water (1×2 L), dried over anhydrous Na$_2$SO$_4$, and filtered. The filtrate was concentrated under reduced pressure to afford the title compound that was used without further purification.

Step D: (R,E)-N-(5-(((tert-Butylsulfinyl)imino)methyl)-6-chloropyridazin-3-yl)pivalamide. To a stirred solution of N-(6-chloro-5-formylpyridazin-3-yl)pivalamide (372 g, 1.54 mol, Step C) and (R)-2-methylpropane-2-sulfinamide (243 g, 2.00 mol) in DCM (2.20 L) was added potassium bisulfate (272 g, 2.00 mol) in portions at rt. The resulting mixture was stirred overnight at rt and then quenched with water (2 L) at rt. The mixture was extracted with DCM (3×1.5 L), and the combined organic layers were washed with water (1×1 L), dried over anhydrous Na₂SO₄, and filtered. The filtrate was concentrated under reduced pressure and purified by silica gel column chromatography (25% EtOAc/petroleum ether) to afford the title compound in 60% yield over 2 steps.

Intermediate 33: N-(5-((S)-1-(((R)-tert-Butylsulfinyl)amino)-2-methoxyethyl)-6-chloropyridazin-3-yl)pivalamide

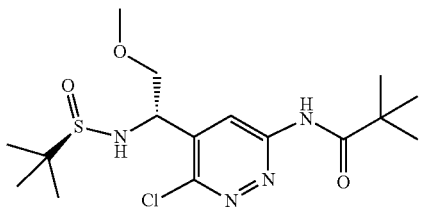 [SMILES: COC[C@@H](N[S@](=O)C(C)(C)C)c1cc(NC(=O)C(C)(C)C)nnc1Cl]

To a stirred solution of magnesium (47.4 g, 1.95 mol) in THF (360 mL) was added dibromoethane (13.7 g, 74.0 mmol) dropwise at rt under a nitrogen atmosphere. The resulting mixture was stirred for 30 min at rt under a nitrogen atmosphere and additional dibromoethane (60.0 g, 222 mmol) was added. Then the reaction mixture was heated to 40° C., mercuric chloride (4.72 g, 17.4 hmmol) was added in portions and the reaction mixture was stirred for an additional 20 min at rt. MOMBr (22.1 g, 177 mmol) in toluene (30 mL) was then added dropwise at rt and stirred for an additional 20 min. The reaction mixture was then cooled to −15° C. followed by the addition of more MOMBr (200 g, 1.60 mol) in toluene (270 mL) dropwise and the resulting mixture was stirred for 40 min at −15° C. To the mixture was added LiCl (74.0 g, 1.74 mol) in portions and the resulting mixture was stirred for 30 min at −15° C. To the mixture was added (R,E)-N-(5-(((tert-butylsulfinyl)imino)methyl)-6-chloropyridazin-3-yl)pivalamide (60.0 g, 174 mmol, Intermediate 32) in THF (360 mL) dropwise at −20° C. The resulting mixture was stirred for additional 30 min at −10° C. The reaction was quenched by the addition of sat. NH₄Cl (aq.) (5 L) at 0° C. The mixture was extracted with EtOAc (3×2 L) and the combined organic layers were washed with water (1×2 L), dried over anhydrous Na₂SO₄, and filtered. The filtrate was concentrated under reduced pressure and purified sequentially by silica gel column chromatography (50% EtOAc/petroleum ether), reverse phase flash chromatography (40%) MeCN/water (0.1% NH₄HCO₃), and chiral SFC (CHIRAL ART Cellulose-SC, 5 μm, 5×25 cm, 30% MeOH/CO₂) to afford the title compound as the second eluting isomer in 21% yield.

Intermediate 34: N-(5-((S)-1-(((R)-tert-Butylsulfinyl)amino)-2-cyclopropoxyethyl)-6-chloropyridazin-3-yl)pivalamide

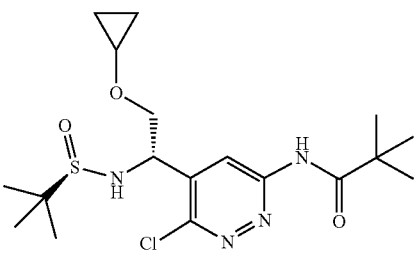 [SMILES: CC(C)(C)C(=O)Nc1cc([C@@H](COC2CC2)N[S@](=O)C(C)(C)C)c(Cl)nn1]

The title compound was synthesized in a manner analogous to Intermediate 13 using (R,E)-N-(5-(((tert-butylsulfinyl)imino)methyl)-6-chloropyridazin-3-yl)pivalamide (Intermediate 32) in place of tert-butyl ((S)-(7-((E)-(((R)-tert-butylsulfinyl)imino)methyl)imidazo[1,2-b]pyridazin-2-yl)(4,4-difluorocyclohexyl)methyl)carbamate. The product was purified by silica gel chromatography (0-80% EtOAc/petroleum ether), preparative HPLC (Xtimate C18, 10 μm, 40×150 mm, 35-65% MeCN/water (0.05% aqueous NH₃ with 10 mM NH₄HCO₃)), and chiral SFC (DAICEL CHIRALPAK AD, 10 μm, 30×250 mm, 10% EtOH (with 0.1% aqueous ammonia)/CO₂) to afford the title compound as the second eluting fraction in 6% yield.

Intermediate 35: (S)-1-(1-(6-Amino-3-chloropyridazin-4-yl)-2-methoxyethyl)-5,5-difluorotetrahydropyrimidin-2(1H)-one

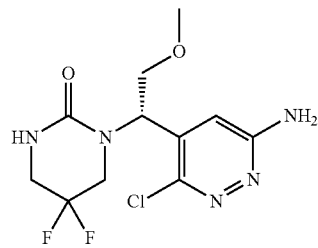 [SMILES: COC[C@H](c1cc(N)nnc1Cl)N1CC(F)(F)CNC1=O]

Step A: (S)—N-(5-(1-Amino-2-methoxyethyl)-6-chloropyridazin-3-yl)pivalamide. To a stirred solution of N-(5-((S)-1-(((R)-tert-butylsulfinyl)amino)-2-methoxyethyl)-6-chloropyridazin-3-yl)pivalamide (Intermediate 33, 8.00 g, 20.5 mmol) in EtOAc (102 mL) at room temperature was added a solution of HCl in 1,4-dioxane (4 M, 20.5 mL, 81.9 mmol). After 5 h, the reaction mixture was diluted with hexanes (150 mL) and water (200 mL). The layers were separated, and the organic layer was extracted with aqueous HCl (0.05 M, 2×50 mL). The combined aqueous layers were diluted with EtOAc (50 mL) and brought to pH 11 with aqueous 3 M NaOH. The layers were separated, and the aqueous layers were extracted with EtOAc (4×50 mL). The combined organic layers were dried over anhydrous Na₂SO₄ and concentrated to give the title compound as a solid (>99% yield, heavy with trace EtOAc), which was used without further purification.

Step B: (S)—N-(6-Chloro-5-(1-((3-(1,3-dioxoisoindolin-2-yl)-2,2-difluoropropyl)amino)-2-methoxyethyl)pyridazin-3-yl)pivalamide. To a stirred solution of (S)—N-(5-(1-amino-2-methoxyethyl)-6-chloropyridazin-3-yl)pivalamide (5.87 g, 20.6 mmol, Step A) in ACN (68.8 mL) under an $N_2$ atmosphere was added DIPEA (5.75 mL, 33.0 mmol) and 3-(1,3-dioxoisoindolin-2-yl)-2,2-difluoropropyl trifluoromethanesulfonate (10.8 g, 28.9 mmol) and the reaction mixture was heated to 55° C. After 23 h, additional portions of DIPEA (0.90 mL, 5.22 mmol) and 3-(1,3-dioxoisoindolin-2-yl)-2,2-difluoropropyl trifluoromethanesulfonate (1.60 g, 4.29 mmol) were added and heating was continued for an additional 72 h. The reaction mixture was concentrated and purified by silica gel chromatography (10 to 50% acetone in hexanes with 0.1% TEA V/V) to give the title compound (80%).

Step C: (S)-2-(3-((1-(6-Amino-3-chloropyridazin-4-yl)-2-methoxyethyl)amino)-2,2-difluoropropyl)isoindoline-1,3-dione. To a stirred solution of (S)—N-(6-chloro-5-(1-((3-(1,3-dioxoisoindolin-2-yl)-2,2-difluoropropyl)amino)-2-methoxyethyl)pyridazin-3-yl)pivalamide (4.11 g, 8.06 mmol, Step B) in 1,4-dioxane (40 mL) was added aqueous $H_2SO_4$ (3 M, 80.6 mL, 242 mmol) and the reaction mixture was heated to 60° C. for 6 h. The reaction mixture was cooled to rt, diluted with EtOAc (80 mL) and water (80 mL), cooled to 0° C. and treated with $NaHCO_3$ (40 g) in a portion wise manner with stirring (gas evolution). The reaction mixture was diluted with saturated aqueous $NaHCO_3$ (100 mL), and the layers were separated. The aqueous layer was extracted with EtOAc (4×100 mL), and the combined organic layers were dried over anhydrous $Na_2SO_4$ and concentrated to give the title compound as a solid (>99% yield, heavy with trace EtOAc), which was used without further purification.

Step D: (S)—$N^1$-(1-(6-Amino-3-chloropyridazin-4-yl)-2-methoxyethyl)-2,2-difluoropropane-1,3-diamine. To a stirred suspension of (S)-2-(3-((1-(6-amino-3-chloropyridazin-4-yl)-2-methoxyethyl)amino)-2,2-difluoropropyl)isoindoline-1,3-dione (3.43 g, 8.06 mmol, Step C) in EtOH (115 mL) was added hydrazine hydrate (1.20 mL, 24.2 mmol) and the reaction mixture was heated to 40° C. for 56 h. The reaction mixture was cooled to 0° C., filtered and the filter cake was washed with ice cold EtOH (3×5 mL). The filtrate was evaporated to dryness to give the title compound (98%), which was used without further purification.

Step E: (S)-1-(1-(6-Amino-3-chloropyridazin-4-yl)-2-methoxyethyl)-5,5-difluorotetrahydropyrimidin-2(1H)-one. To a cooled (0° C.) stirred solution of CDI (1.40 g, 8.63 mmol) in THF (200 mL) was added a suspension of (S)—$N^1$-(1-(6-amino-3-chloropyridazin-4-yl)-2-methoxyethyl)-2,2-difluoropropane-1,3-diamine (2.22 g, 7.51 mmol, Step D) in THF (50 mL) in a dropwise manner over 5 min. After 2 h, the reaction mixture was allowed to warm to rt and was stirred for 12 h. The reaction mixture was then heated to 60° C. for 6 h. The reaction mixture was cooled to rt, evaporated to dryness, and purified by reverse phase basic HPLC (X-Bridge Prep C18 5 μm column 50×250 mm, 5-100% acetonitrile/water (with 20 nM $NH_4OH$). The product containing fractions were lyophilized to give the title compound (71% yield) as a white solid.

Intermediate 36: (S)-1-(1-(6-Amino-3-chloropyridazin-4-yl)-2-cyclopropoxyethyl)-5,5-difluoro-tetrahydropyrimidin-2(1H)-one

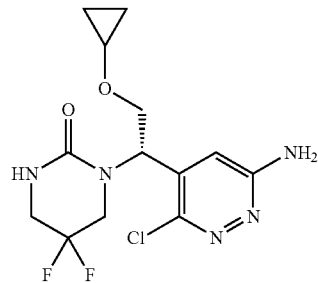 [SMILES: Nc1cc([C@@H](COC2CC2)N2CC(F)(F)CNC2=O)c(Cl)nn1]

Step A: (S)—N-(5-(1-Amino-2-cyclopropoxyethyl)-6-chloropyridazin-3-yl)pivalamide. The title compound was synthesized in a manner analogous to Intermediate 35 Step A using N-(5-((S)-1-(((R)-tert-butylsulfinyl)amino)-2-cyclopropoxyethyl)-6-chloropyridazin-3-yl)pivalamide (Intermediate 34) in place of N-(5-((S)-1-(((R)-tert-butylsulfinyl)amino)-2-methoxyethyl)-6-chloropyridazin-3-yl)pivalamide (99% yield) that was used without further purification.

Step B: (S)—N-(6-Chloro-5-(2-cyclopropoxy-1-((3-(1,3-dioxoisoindolin-2-yl)-2,2-difluoropropyl)amino)ethyl)pyridazin-3-yl)pivalamide. The title compound was synthesized in a manner analogous to Intermediate 35 Step B using (S)—N-(5-(1-amino-2-cyclopropoxyethyl)-6-chloropyridazin-3-yl)pivalamide (Step A) in place of (S)—N-(5-(1-amino-2-methoxyethyl)-6-chloropyridazin-3-yl)pivalamide (78% yield).

Step C: (S)-2-(3-((1-(6-Amino-3-chloropyridazin-4-yl)-2-cyclopropoxyethyl)amino)-2,2-difluoropropyl)isoindoline-1,3-dione. The title compound was synthesized in a manner analogous to Intermediate 35 Step C using (S)—N-(6-chloro-5-(2-cyclopropoxy-1-((3-(1,3-dioxoisoindolin-2-yl)-2,2-difluoropropyl)amino)ethyl)pyridazin-3-yl)pivalamide (Step B) in place of (S)—N-(6-chloro-5-(1-((3-(1,3-dioxoisoindolin-2-yl)-2,2-difluoropropyl)amino)-2-methoxyethyl)pyridazin-3-yl)pivalamide (99% yield that was used without further purification).

Step D: (S)—$N^1$-(1-(6-Amino-3-chloropyridazin-4-yl)-2-cyclopropoxyethyl)-2,2-difluoropropane-1,3-diamine. The title compound was synthesized in a manner analogous to Intermediate 35 Step D using (S)-2-(3-((1-(6-amino-3-chloropyridazin-4-yl)-2-cyclopropoxyethyl)amino)-2,2-difluoropropyl)isoindoline-1,3-dione (Step C) in place (S)-2-(3-((1-(6-amino-3-chloropyridazin-4-yl)-2-methoxyethyl)amino)-2,2-difluoropropyl)isoindoline-1,3-dione (99% yield that was used without further purification).

Step E: (S)-1-(1-(6-Amino-3-chloropyridazin-4-yl)-2-cyclopropoxyethyl)-5,5-difluorotetrahydropyrimidin-2(1H)-one. The title compound was synthesized in a manner analogous to Intermediate 35 Step E using (S)—$N^1$-(1-(6-amino-3-chloropyridazin-4-yl)-2-cyclopropoxyethyl)-2,2-difluoropropane-1,3-diamine (Step D) in place of (S)—$N^1$-(1-(6-amino-3-chloropyridazin-4-yl)-2-methoxyethyl)-2,2-difluoropropane-1,3-diamine (18% yield).

Intermediate 37: tert-Butyl ((3S,4R)-1-(dimethyl (oxo)-λ⁶-sulfaneylidene)-2-oxo-4-(((R)-1,1,1-trifluoropropan-2-yl)oxy)pentan-3-yl)carbamate

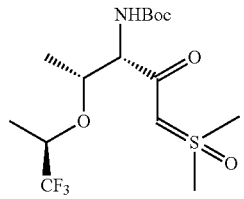 [SMILES: C[C@@H](O[C@H](C)C(F)(F)F)[C@H](NC(=O)OC(C)(C)C)C(=O)C=S(C)(C)=O]

Step A: (R)-2-(((R)-1,1,1-Trifluoropropan-2-yl)oxy)propanoic acid. Sodium hydride (3.5 g, 88 mmol, 60% dispersion in mineral oil) was added in portions to a solution of (R)-1,1,1-trifluoropropan-2-ol (5.0 g, 44 mmol) in DMF (70 mL) at 0° C. The resultant mixture was stirred for 30 min at rt before recooling to 0° C. A separate solution of (S)-2-bromopropanoic acid (6.0 g, 40 mmol) in DMF (5 mL) was added at 0° C. and the resulting mixture was allowed to warm to rt and stir for 12 h. After this time, the reaction mixture was poured into ice chilled water (100 mL) and extracted with MTBE (25 mL). The pH of the aqueous layer was adjusted by the addition of 2 N aqueous HCl (15 mL) until the pH of the mixture was pH=5-6. This aqueous layer was extracted with MTBE (80 mL×3). The combined organic layers were washed with brine, dried over anhydrous Na$_2$SO$_4$, filtered, and concentrated under reduced pressure to afford the title compound in 93% yield as a yellow oil that was used without further purification.

Step B: (R)—N-Methoxy-N-methyl-2-(((R)-1,1,1-trifluoropropan-2-yl)oxy)propanamide. A round-bottom flask was charged with (R)-2-(((R)-1,1,1-trifluoropropan-2-yl)oxy) propanoic acid (7.6 g, 41 mmol, Step A), DMF (70 mL), HATU (20 g, 53 mmol), and DIPEA (18 mL, 102 mmol). The mixture was stirred for 5 min before the addition of N,O-dimethylhydroxylamine hydrochloride (6.0 g, 61 mmol). The resulting solution stirred for 12 h, after which time, the reaction was quenched with water (30 mL) and diluted with MTBE (50 mL). The organic layer was separated, and the aqueous layer was extracted with MTBE (80 mL×2). The combined organic layers were washed with water and brine, dried over anhydrous Na$_2$SO$_4$, filtered, and concentrated under reduced pressure. The product was purified by silica gel chromatography (9-17% EtOAc/petroleum ether) to afford the title compound in 58% yield as a yellow oil.

Step C: (R)-2-(((R)-1,1,1-Trifluoropropan-2-yl)oxy)propanal. A round-bottom flask was charged with (R)—N-methoxy-N-methyl-2-(((R)-1,1,1-trifluoropropan-2-yl)oxy) propanamide (5.4 g, 24 mmol, Step B) and THF (300 mL), cooled to −78° C. and LAH (4.5 g, 120 mmol) was added portion wise. The resulting mixture was stirred for about 1 h at −78° C. and was subsequently quenched with water (20 mL) dropwise at −78° C. A saturated aqueous solution of sodium potassium tartrate (120 mL) was added, and the solution was stirred for 30 min and then extracted with MTBE (120 mL×3). The combined organic layers were washed with brine, dried over anhydrous Na$_2$SO$_4$, filtered, and concentrated under reduced pressure to afford the title compound in 100% yield that was used without further purification.

Step D: (S)-2-Methyl-N—((R,E)-2-(((R)-1,1,1-trifluoropropan-2-yl)oxy)propylidene)propane-2-sulfinamide. A round-bottom flask was charged with (R)-2-(((R)-1,1,1-trifluoropropan-2-yl)oxy)propanal (7.4 g, 44 mmol, Step C), THF (250 mL), CuSO$_4$ (28 g, 174 mmol), (S)-2-methylpropane-2-sulfinamide (7.9 g, 65 mmol), and PPTS (2.2 g, 8.7 mmol), and the resulting mixture was stirred at 30° C. for 16 h. The suspension was filtered through diatomaceous earth (e.g., Celite®), and the filtrate was concentrated under reduced pressure. This product was purified by silica gel chromatography (0-50% EtOAc/petroleum ether) to afford the title compound in 73% yield as a colorless oil.

Step E: (S)—N-((1R,2R)-1-Cyano-2-(((R)-1,1,1-trifluoropropan-2-yl)oxy)propyl)-2-methylpropane-2-sulfinamide. A mixture of (S)-2-methyl-N—((R,E)-2-(((R)-1,1,1-trifluoropropan-2-yl)oxy)propylidene)propane-2-sulfinamide (8.7 g, 32 mmol, Step D), TMSCN (5.5 mL, 44 mmol), Sc(OTf)$_3$ (3.1 g, 6.4 mmol), and 4 Å molecular sieves (5 g) in DCM (100 mL) was stirred at rt for 16 h. The reaction was then filtered and concentrated under reduced pressure. Purification by silica gel chromatography (0-60 EtOAc/petroleum ether) provided the title compound as a colorless oil in 79% yield.

Step F: O—((R)-1,1,1-Trifluoropropan-2-yl)-L-threonine hydrogen chloride. (S)—N-((1R,2R)-1-Cyano-2-(((R)-1,1,1-trifluoropropan-2-yl)oxy)propyl)-2-methylpropane-2-sulfinamide (7.6 g, 25 mmol, Step E) was dissolved in 4M HCl in 1,4-dioxane (120 mL) and water (20 mL). The resulting mixture was stirred for 16 h at 80° C. The reaction was then cooled to rt and concentrated to dryness to afford the title compound as a brown oil, which was used without further purification assuming 100% yield.

Step G: N-(tert-Butoxycarbonyl)-O—((R)-1,1,1-trifluoropropan-2-yl)-L-threonine. A round bottom flask was charged with O—((R)-1,1,1-trifluoropropan-2-yl)-L-threonine hydrogen chloride (7.3 g, 25 mmol, Step F), THF (100 mL), and 1 M aqueous NaOH (101 mL) and allowed to stir at rt for 0.5 h. Boc$_2$O (5.5 g, 25 mmol) was then added in one portion and the reaction was allowed to stir for 16 h at rt. The reaction mixture was poured into water (100 mL) and the biphasic mixture was extracted with EtOAc (3×100 mL). The aqueous layer was then acidified with citric acid to pH 3-4. The acidic aqueous layer was then extracted with EtOAc (3×100 mL) and the combined organic layers were washed with brine, dried over anhydrous MgSO$_4$, filtered, and concentrated under reduced pressure to afford the title compound in 88% yield, which was used without further purification.

Step H: tert-Butyl ((3S,4R)-1-(dimethyl(oxo)-λ⁶-sulfaneylidene)-2-oxo-4-(((R)-1,1,1-trifluoropropan-2-yl)oxy) pentan-3-yl)carbamate. To a suspension of trimethylsulfoxonium iodide (15.5 g, 49.2 mmol) in THF (250 mL) was added 1 M THF solution of potassium tert-butoxide (73.7 mL, 73.7 mmol). The mixture was stirred at rt for 2 h. In a separate flask a solution of N-(tert-butoxycarbonyl)-O—((R)-1,1,1-trifluoropropan-2-yl)-L-threonine (15.5 g, 49.2 mmol, Step G) in THF (250 mL) was cooled to 0° C., charged with CDI (9.57 g, 59.0 mmol) in one portion, and stirred for 2 h at 0° C. This solution was then added dropwise to the previously prepared solution and allowed to stir for 2 h at 25° C. The reaction mixture was then poured into water (200 mL) and extracted with EtOAc (100 mL×3). The combined organic layers were washed with brine, dried over anhydrous MgSO$_4$, filtered, and concentrated to dryness. The product was purified by silica gel chromatography (0-100% EtOAc/petroleum ether) and chiral SFC (DAICEL CHRALPAK AD, 10 μm, 50×250 mm, 20% EtOH (with 0.1% of 25% aqueous NH$_3$)/CO$_2$) to afford the title compound in 21% yield as the first eluting fraction.

Intermediate 38: tert-Butyl ((3S,4R)-1-(dimethyl(oxo)-λ⁶-sulfaneylidene)-2-oxo-4-(((S)-1,1,1-trifluoropropan-2-yl)oxy)pentan-3-yl)carbamate

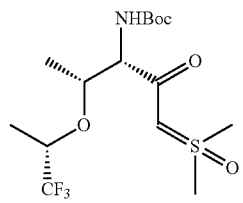

Step A: (R)—(((S)-1,1,1-Trifluoropropan-2-yl)oxy)propanoic acid. The title compound was synthesized in a manner analogous to Intermediate 37 Step A using (S)-1,1,1-trifluoropropan-2-ol in place of (R)-1,1,1-trifluoropropan-2-ol in 80% yield.

Step B: (R)—N-Methoxy-N-methyl-2-(((S)-1,1,1-trifluoropropan-2-yl)oxy)propanamide. The title compound was synthesized in a manner analogous to Intermediate 37 Step B using (R)—(((S)-1,1,1-trifluoropropan-2-yl)oxy)propanoic acid (Step A) in place of (R)-2-(((R)-1,1,1-trifluoropropan-2-yl)oxy)propanoic acid in 46% yield.

Step C: (R)-2-(((S)-1,1,1-Trifluoropropan-2-yl)oxy)propanal. The title compound was synthesized in a manner analogous to Intermediate 37 Step C using (R)—N-methoxy-N-methyl-2-(((S)-1,1,1-trifluoropropan-2-yl)oxy)propanamide (Step B) in place of (R)—N-methoxy-N-methyl-2-(((R)-1,1,1-trifluoropropan-2-yl)oxy)propanamide in 80% yield.

Step D: (S)-2-Methyl-N—((R,E)-2-(((S)-1,1,1-trifluoropropan-2-yl)oxy)propylidene)propane-2-sulfinamide. The title compound was synthesized in a manner analogous to Intermediate 37 Step D using (R)-2-(((S)-1,1,1-trifluoropropan-2-yl)oxy)propanal (Step C) in place of (R)-2-(((R)-1,1,1-trifluoropropan-2-yl)oxy)propanal in 55% yield.

Step E: (S)—N-((1R,2R)-1-Cyano-2-(((S)-1,1,1-trifluoropropan-2-yl)oxy)propyl)-2-methylpropane-2-sulfinamide. The title compound was synthesized in a manner analogous to Intermediate 37 Step E using (S)-2-methyl-N—((R,E)-2-(((S)-1,1,1-trifluoropropan-2-yl)oxy)propylidene)propane-2-sulfinamide (Step D) in place of (S)-2-methyl-N—((R,E)-2-(((R)-1,1,1-trifluoropropan-2-yl)oxy)propylidene)propane-2-sulfinamide in 91% yield.

Step F: O—((S)-1,1,1-Trifluoropropan-2-yl)-L-threonine hydrogen chloride. The title compound was synthesized in a manner analogous to Intermediate 37 Step F using (S)—N-((1R,2R)-1-cyano-2-(((S)-1,1,1-trifluoropropan-2-yl)oxy)propyl)-2-methylpropane-2-sulfinamide (Step E) in place of (S)—N-((1R,2R)-1-cyano-2-(((R)-1,1,1-trifluoropropan-2-yl)oxy)propyl)-2-methylpropane-2-sulfinamide assuming 100% yield.

Step G: N-(tert-Butoxycarbonyl)-O—((S)-1,1,1-trifluoropropan-2-yl)-L-threonine. The title compound was synthesized in a manner analogous to Intermediate 37 Step G using O—((S)-1,1,1-trifluoropropan-2-yl)-L-threonine hydrogen chloride (Step F) in place of O—((R)-1,1,1-trifluoropropan-2-yl)-L-threonine hydrogen chloride and was used without further purification.

Step H: tert-Butyl ((3S,4R)-1-(dimethyl(oxo)-λ⁶-sulfaneylidene)-2-oxo-4-(((S)-1,1,1-trifluoropropan-2-yl)oxy)pentan-3-yl)carbamate. The title compound was synthesized in a manner analogous to Intermediate 37 Step H using N-(tert-butoxycarbonyl)-O—((S)-1,1,1-trifluoropropan-2-yl)-L-threonine (Step G) in place of N-(tert-butoxycarbonyl)-O—((R)-1,1,1-trifluoropropan-2-yl)-L-threonine. The product was purified by silica gel chromatography (0-100% EtOAc/petroleum ether) and chiral SFC (DAICEL CHRALPAK AD, 10 μm, 50×250 mm, 15% EtOH (with 0.1% of 25% aqueous NH₃)/CO₂) to afford the title compound as the first eluting fraction in 19% yield.

Intermediate 39: tert-Butyl ((3S,4R)-1-iodo-2-oxo-4-(((R)-1,1,1-trifluoropropan-2-yl)oxy)pentan-3-yl)carbamate

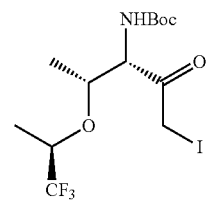 [SMILES: C[C@@H](O[C@H](C)C(F)(F)F)[C@H](NC(=O)OC(C)(C)C)C(=O)CI]

Step A: tert-Butyl ((3S,4R)-1-chloro-2-oxo-4-(((R)-1,1,1-trifluoropropan-2-yl)oxy)pentan-3-yl)carbamate. An oven dried round bottom flask was charged with anhydrous lithium chloride (120 mg, 2.85 mmol) and tert-butyl ((3S,4R)-1-(dimethyl(oxo)-λ⁶-sulfaneylidene)-2-oxo-4-(((R)-1,1,1-trifluoropropan-2-yl)oxy)pentan-3-yl)carbamate (400 mg, 1.03 mmol, Intermediate 37) under an N₂ atmosphere. Anhydrous THF (7.2 mL) was added, the reaction was cooled to 0° C., then methanesulfonic acid (71.5 μL, 1.01 mmol) was added dropwise. The reaction was maintained at 0° C. for 10 min then heated to 60° C. for 3 h. After this time the mixture was cooled to rt, diluted with H₂O, and extracted with 1:1 EtOAc:hexanes. The organic extracts were washed with brine, dried over anhydrous Na₂SO₄, filtered, and concentrated to provide the title compound that was used without further purification.

Step B: tert-Butyl ((3S,4R)-1-iodo-2-oxo-4-(((R)-1,1,1-trifluoropropan-2-yl)oxy)pentan-3-yl)carbamate. A mixture of tert-butyl ((3S,4R)-1-chloro-2-oxo-4-(((R)-1,1,1-trifluoropropan-2-yl)oxy)pentan-3-yl)carbamate (354 mg, 1.02 mmol, Step A) and NaI (1.53 g, 10.2 mmol) in acetone was stirred at rt for 1 h then diluted with EtOAc and filtered. The filtrate was washed with saturated aqueous sodium thiosulfate then dried over anhydrous Na₂SO₄, filtered, and concentrated to afford the title compound that was used without further purification.

Intermediate 40: tert-Butyl ((3S,4R)-1-iodo-2-oxo-4-(((S)-1,1,1-trifluoropropan-2-yl)oxy)pentan-3-yl)carbamate

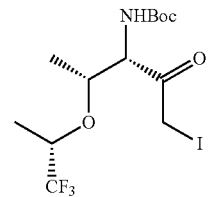 [SMILES: C[C@H](O[C@H](C)[C@H](NC(=O)OC(C)(C)C)C(=O)CI)C(F)(F)F]

Step A: tert-Butyl ((3S,4R)-1-chloro-2-oxo-4-(((S)-1,1,1-trifluoropropan-2-yl)oxy)pentan-3-yl)carbamate. The title compound was synthesized in a manner analogous to Intermediate 39 Step A using tert-butyl ((3S,4R)-1-(dimethyl(oxo)-λ⁶-sulfaneylidene)-2-oxo-4-(((S)-1,1,1-trifluoropropan-2-yl)oxy)pentan-3-yl)carbamate (Intermediate 38) in place of tert-butyl ((3S,4R)-1-(dimethyl(oxo)-λ⁶-sulfaneylidene)-2-oxo-4-(((R)-1,1,1-trifluoropropan-2-yl)oxy)pentan-3-yl)carbamate and was used without further purification.

Step B: tert-Butyl ((3S,4R)-1-iodo-2-oxo-4-(((S)-1,1,1-trifluoropropan-2-yl)oxy)pentan-3-yl)carbamate. The title compound was synthesized in a manner analogous to Intermediate 39 Step B using tert-butyl ((3S,4R)-1-chloro-2-oxo-4-(((S)-1,1,1-trifluoropropan-2-yl)oxy)pentan-3-yl)carbamate (Step A) in place of tert-butyl ((3S,4R)-1-chloro-2-oxo-4-(((R)-1,1,1-trifluoropropan-2-yl)oxy)pentan-3-yl)carbamate that was used without further purification.

Intermediate 41: (1R,2R)-1-(7-((S)-1-(5,5-Difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propan-1-aminium trifluoroacetate

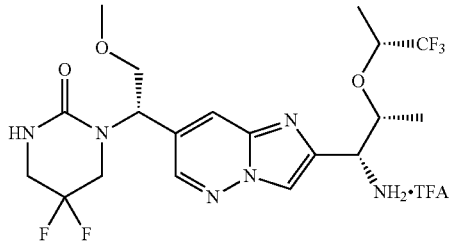

Step A: tert-Butyl ((1R,2R)-1-(6-chloro-7-((S)-1-(5,5-difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propyl)carbamate. An oven dried round bottom flask was charged with (S)-1-(1-(6-amino-3-chloropyridazin-4-yl)-2-methoxyethyl)-5,5-difluorotetrahydropyrimidin-2(1H)-one (80 mg, 0.25 mmol, Intermediate 35) and activated 4 Å mol sieves and DMA (3.3 mL). A separate solution of tert-butyl ((3S,4R)-1-iodo-2-oxo-4-(((R)-1,1,1-trifluoropropan-2-yl)oxy)pentan-3-yl)carbamate (273 mg, 0.62 mmol, Intermediate 39) in DMA (2 mL) was added and the reaction was heated to 50° C. for 16 h under an a N₂ atmosphere. After this time, the reaction was cooled to rt and filtered over diatomaceous earth (e.g., Celite®). The filtrate was then diluted with 5% LiCl solution and the aqueous layer was extracted with EtOAc (3×). The combined organic layers were washed with brine, dried over anhydrous MgSO₄, filtered, and concentrated under reduced pressure. The product was purified by silica gel chromatography (0-100% Acetone/hexanes (0.1% TEA)) to afford the title compound in 82% yield.

Step B: tert-Butyl ((1R,2R)-1-(7-((S)-1-(5,5-difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propyl)carbamate. tert-Butyl ((1R,2R)-1-(6-chloro-7-((S)-1-(5,5-difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propyl)carbamate (125 mg, 0.203 mmol, Step A) was dissolved in EtOH (15.6 mL) and TFE (10 mL) and ammonium formate (192 mg, 3.05 mmol) and 10% wt Pd/C (124 mg) were sequentially added. The resulting heterogenous solution was heated to 85° C. for 1 h under N₂ atmosphere. The reaction mixture was then filtered through diatomaceous earth (e.g., Celite®), concentrated under reduced pressure, and used without further purification.

Step C: (1R,2R)-1-(7-((S)-1-(5,5-Difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propan-1-aminium trifluoroacetate. tert-Butyl ((1R,2R)-1-(7-((S)-1-(5,5-difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propyl)carbamate (118 mg, 0.203 mmol, Step B) was dissolved in DCM (6.6 mL) and cooled to 0° C. TFA (6.5 mL) was then added dropwise, and the resulting mixture was allowed to stir for 40 min. After this time, the reaction was concentrated under reduced pressure to afford the title compound, which was used without further purification.

Intermediate 42: (1R,2R)-1-(7-((S)-1-(5,5-Difluoro-2-oxotetrahydropyrimidin-1(2H)-yl)-2-methoxyethyl)imidazo[1,2-b]pyridazin-2-yl)-2-(((S)-1,1,1-trifluoropropan-2-yl)oxy)propan-1-aminium trifluoroacetate

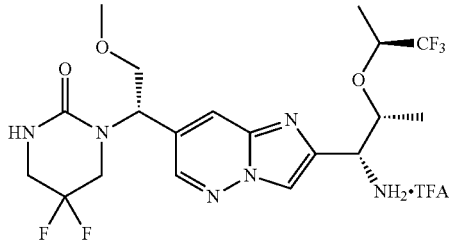

Step A: tert-Butyl ((1R,2R)-1-(6-chloro-7-((S)-1-(5,5-difluoro-2-oxotetrahydropyrimidin-1(2H)-yl)-2-methoxyethyl)imidazo[1,2-b]pyridazin-2-yl)-2-(((S)-1,1,1-trifluoropropan-2-yl)oxy)propyl)carbamate. The title compound was synthesized in a manner analogous to Intermediate 41, Step A using tert-butyl ((3S,4R)-1-iodo-2-oxo-4-(((S)-1,1,1-trifluoropropan-2-yl)oxy)pentan-3-yl)carbamate (Intermediate 40) in place of tert-butyl ((3S,4R)-1-iodo-2-oxo-4-(((R)-1,1,1-trifluoropropan-2-yl)oxy)pentan-3-yl)carbamate to afford the title compound after silica gel chromatography (0-100% Acetone/hexanes (0.1% TEA)) in 68% yield.

Step B: tert-Butyl ((1R,2R)-1-(7-((S)-1-(5,5-difluoro-2-oxotetrahydropyrimidin-1(2H)-yl)-2-methoxyethyl)imidazo[1,2-b]pyridazin-2-yl)-2-(((S)-1,1,1-trifluoropropan-2-yl)oxy)propyl)carbamate. The title compound was synthesized in a manner analogous to Intermediate 41, Step B using tert-butyl ((1R,2R)-1-(6-chloro-7-((S)-1-(5,5-difluoro-2-oxotetrahydropyrimidin-1(2H)-yl)-2-methoxyethyl)imidazo[1,2-b]pyridazin-2-yl)-2-(((S)-1,1,1-trifluoropropan-2-yl)oxy)propyl)carbamate (Step A) in place of tert-butyl ((1R,2R)-1-(6-chloro-7-((S)-1-(5,5-difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propyl)carbamate to afford the title compound after silica gel chromatography (0-100% Acetone/hexanes (0.1% TEA)) in 74% yield.

Step C: (1R,2R)-1-(7-((S)-1-(5,5-Difluoro-2-oxotetrahydropyrimidin-1(2H)-yl)-2-methoxyethyl)imidazo[1,2-b]pyridazin-2-yl)-2-(((S)-1,1,1-trifluoropropan-2-yl)oxy)propan-1-aminium trifluoroacetate. The title compound was synthesized in a manner analogous to Intermediate 41, Step C using tert-butyl ((1R,2R)-1-(7-((S)-1-(5,5-difluoro-2-oxotetrahydropyrimidin-1(2H)-yl)-2-methoxyethyl)imidazo[1,2-b]pyridazin-2-yl)-2-(((S)-1,1,1-trifluoropropan-2-yl)oxy)propyl)carbamate (Step B) in place of tert-butyl ((1R,2R)-1-(7-((S)-1-(5,5-difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propyl)carbamate to afford the title compound that was used without further purification.

Intermediate 43: (S)-1-(7-((S)-2-Cyclopropoxy-1-(5,5-difluoro-2-oxotetrahydropyrimidin-1(2H)-yl)ethyl)imidazo[1,2-b]pyridazin-2-yl)-4,4,4-trifluoro-3,3-dimethylbutan-1-aminium trifluoroacetate

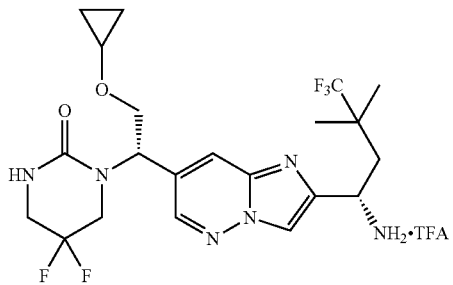

Step A: tert-Butyl ((S)-1-(6-chloro-7-((S)-2-cyclopropoxy-1-(5,5-difluoro-2-oxotetrahydropyrimidin-1(2H)-yl)ethyl)imidazo[1,2-b]pyridazin-2-yl)-4,4,4-trifluoro-3,3-dimethylbutyl)carbamate. The title compound was synthesized in a manner analogous to Intermediate 41, Step A using (S)-1-(1-(6-amino-3-chloropyridazin-4-yl)-2-cyclopropoxyethyl)-5,5-difluorotetrahydropyrimidin-2(1H)-one (Intermediate 36) in place of (S)-1-(1-(6-amino-3-chloropyridazin-4-yl)-2-methoxyethyl)-5,5-difluorotetrahydropyrimidin-2(1H)-one and tert-butyl (S)-(6,6,6-trifluoro-1-iodo-5,5-dimethyl-2-oxohexan-3-yl)carbamate in place of tert-butyl ((3S,4R)-1-iodo-2-oxo-4-(((R)-1,1,1-trifluoropropan-2-yl)oxy)pentan-3-yl)carbamate to afford the title compound after silica gel chromatography (0-100% Acetone/hexanes (0.1% TEA)) in >99% yield.

Step B: tert-Butyl ((S)-1-(7-((S)-2-cyclopropoxy-1-(5,5-difluoro-2-oxotetrahydropyrimidin-1(2H)-yl)ethyl)imidazo[1,2-b]pyridazin-2-yl)-4,4,4-trifluoro-3,3-dimethylbutyl)carbamate. The title compound was synthesized in a manner analogous to Intermediate 41, Step B using tert-butyl ((S)-1-(6-chloro-7-((S)-2-cyclopropoxy-1-(5,5-difluoro-2-oxotetrahydropyrimidin-1(2H)-yl)ethyl)imidazo[1,2-b]pyridazin-2-yl)-4,4,4-trifluoro-3,3-dimethylbutyl)carbamate (Step A) in place of tert-butyl ((1R,2R)-1-(6-chloro-7-((S)-1-(5,5-difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propyl)carbamate to afford the title compound that was used without further purification.

Step C: (S)-1-(7-((S)-2-Cyclopropoxy-1-(5,5-difluoro-2-oxotetrahydropyrimidin-1(2H)-yl)ethyl)imidazo[1,2-b]pyridazin-2-yl)-4,4,4-trifluoro-3,3-dimethylbutan-1-aminium trifluoroacetate. The title compound was synthesized in a manner analogous to Intermediate 41, Step C using tert-butyl ((S)-1-(7-((S)-2-cyclopropoxy-1-(5,5-difluoro-2-oxotetrahydropyrimidin-1(2H)-yl)ethyl)imidazo[1,2-b]pyridazin-2-yl)-4,4,4-trifluoro-3,3-dimethylbutyl)carbamate (Step B) in place of tert-butyl ((1R,2R)-1-(7-((S)-1-(5,5-difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propyl)carbamate to afford the title compound that was used without further purification.

Intermediate 44: 1-((S)-1-(2-((S)-1-Amino-4,4,4-trifluoro-3,3-dimethylbutyl)imidazo[1,2-b]pyridazin-7-yl)-2-methoxyethyl)-5,5-difluorotetrahydropyrimidin-2(1H)-one

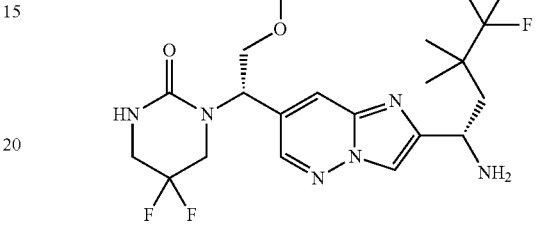

Step A. tert-Butyl ((S)-1-(6-chloro-7-((S)-1-(5,5-difluoro-2-oxotetrahydropyrimidin-1(2H)-yl)-2-methoxyethyl)imidazo[1,2-b]pyridazin-2-yl)-4,4,4-trifluoro-3,3-dimethylbutyl)carbamate. To an oven dried N$_2$ flushed vial was added oven dried 4 Å molecular sieves (3.5 g), (S)-1-(1-(6-amino-3-chloropyridazin-4-yl)-2-methoxyethyl)-5,5-difluorotetrahydropyrimidin-2(1H)-one (Intermediate 35, 138 mg, 0.43 mmol), tert-butyl (S)-(6,6,6-trifluoro-1-iodo-5,5-dimethyl-2-oxohexan-3-yl)carbamate (910 mg, 2.15 mmol) and dimethyl acetamide (9 mL). The reaction mixture was heated (50° C.) and stirred for 72 h, at which time an additional portion of tert-butyl (S)-(6,6,6-trifluoro-1-iodo-5,5-dimethyl-2-oxohexan-3-yl)carbamate (1.27 g, 3.00 mmol) was added. After a further 36 h, a final portion of tert-butyl (S)-(6,6,6-trifluoro-1-iodo-5,5-dimethyl-2-oxohexan-3-yl)carbamate (280 mg, 0.66 mmol) was added and heating continued for an additional 36 h. The reaction mixture was cooled to rt, filtered, and the solids were washed with EtOAc (10 mL) and DCM (10 mL). The filtrate was diluted with brine (50 mL), and the layers were separated. The aqueous layer was extracted with EtOAc (3×20 mL) and the combined organic layers were washed with brine (2×30 mL), saturated aqueous NaS$_2$O$_3$ (1×20 mL), and brine (1×20 mL). The combined organic layers were dried over anhydrous Na$_2$SO$_4$, concentrated, and purified by silica gel chromatography (5 to 60% acetone in hexanes with 0.1% TEA V/V) to give the title compound (48%).

Step B. tert-Butyl ((S)-1-(7-((S)-1-(5,5-difluoro-2-oxotetrahydropyrimidin-1(2H)-yl)-2-methoxyethyl)imidazo[1,2-b]pyridazin-2-yl)-4,4,4-trifluoro-3,3-dimethylbutyl)carbamate. To a suspension of ammonium formate (194 mg, 3.08 mmol) and 10% Pd/C (126 mg, dry) in EtOH (20 mL) was added tert-butyl ((S)-1-(6-chloro-7-((S)-1-(5,5-difluoro-2-oxotetrahydropyrimidin-1(2H)-yl)-2-methoxyethyl)imidazo[1,2-b]pyridazin-2-yl)-4,4,4-trifluoro-3,3-dimethylbutyl)carbamate (123 mg, 0.21 mmol, Step A). The reaction mixture was attached to a nitrogen bubbler, heated (80° C.) and stirred for 70 minutes. The reaction mixture was cooled to room temperature, filtered over diatomaceous earth (e.g., Celite®), and washed with EtOH (20 mL). Filtrate was evaporated to dryness and partitioned between saturated aqueous NaHCO$_3$ (15 mL) and DCM (20 mL). The layers were separated and the aqueous layer was extracted with DCM (1×20 mL). The combined organic layers were dried over anhydrous Na$_2$SO$_4$, and concentrated to give the title compound (99%), which was used without further purification.

Step C. 1-((S)-1-(2-((S)-1-Amino-4,4,4-trifluoro-3,3-dimethylbutyl)imidazo[1,2-b]pyridazin-7-yl)-2-methoxyethyl)-5,5-difluorotetrahydropyrimidin-2(1H)-one. The title compound was prepared as described for the synthesis of Intermediate 20 Step C using tert-butyl ((S)-1-(7-((S)-1-(5,5-difluoro-2-oxotetrahydropyrimidin-1(2H)-yl)-2-methoxyethyl)imidazo[1,2-b]pyridazin-2-yl)-4,4,4-trifluoro-3,3-dimethylbutyl)carbamate (Step B) in place of tert-butyl (S)-((7-((5,5-difluoro-2-oxotetrahydropyrimidin-1(2H)-yl)methyl)imidazo[1,2-b]pyridazin-2-yl)(4,4-difluorocyclohexyl)methyl)carbamate to provide the title compound (100%) that was used without further purification.

Intermediate 45: tert-Butyl (S)-(1-(dimethyl(oxo)-λ$^6$-sulfaneylidene)-7,7,7-trifluoro-6,6-dimethyl-2-oxoheptan-3-yl)carbamate

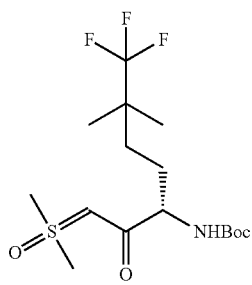 [SMILES: CC(C)(C)OC(=O)N[C@@H](CCC(C)(C)C(F)(F)F)C(=O)C=S(C)(C)=O]

Step A: 1,1,1-Trifluoro-4-iodo-2,2-dimethylbutane. To a stirring solution of 4,4,4-trifluoro-3,3-dimethylbutan-1-ol (9.75 g, 62.5 mmol) in DCM (125 mL) was added triphenylphosphine (24.6 g, 93.7 mmol) and imidazole (5.53 g, 81.2 mmol), and the resulting mixture was cooled to 0° C. Iodine (23.8 g, 93.7 mmol) was then added portion-wise and the mixture was stirred for 24 h at which time it was quenched with saturated aqueous NaHCO$_3$ and stirred for 15 min. The organic layer was removed and washed sequentially with half-saturated aqueous NaHCO$_3$ and brine, dried over anhydrous MgSO$_4$, filtered, and concentrated to a residue. To the residue was added chilled hexanes (50 mL), and the mixture was stirred vigorously for 10 min at which time a white precipitated formed. The white solid was removed by filtration through a pad of silica and the solids were washed with a second portion of chilled hexanes. The filtrates were concentrated to afford the title compound as a clear, colorless oil (66% yield) that was used without further purification.

Step B: (2R, 5S)-2-Isopropyl-3,6-dimethoxy-5-(4,4,4-trifluoro-3,3-dimethylbutyl)-2,5-dihydropyrazine. To a stirred solution of (R)-2-isopropyl-3,6-dimethoxy-2,5-dihydropyrazine (0.66 g, 3.59 mmol) in THF (7 mL) at −78° C. was added t-BuLi (2.33 mL, 3.95 mmol, 1.7 M in pentane), and the reaction was allowed to stir at −78° C. After 1 hour, a solution of 1,1,1-trifluoro-4-iodo-2,2-dimethylbutane (1.05 g, 3.95 mmol, Step A) in THF (6 mL) was added dropwise, and the reaction was stirred for 24 h at room temperature. The reaction was quenched by the addition of aqueous phosphate buffer (50 mL, 0.1 M, pH 7) and was diluted with diethyl ether. The organic layer was removed, and the aqueous layer was extracted with diethyl ether (2×50 mL). The combined organic layers were dried over anhydrous MgSO$_4$, filtered and concentrated to give an oil. LC/MS of this oil revealed a mixture of diastereomers in ~1.5:1 ratio. This mixture was separated by silica gel chromatography (0-30% ethyl acetate in hexanes) to afford the first-eluting isomer (50% yield), which was designated as the R,S diastereomer, as a yellow oil. The second-eluting isomer, designated as the R,R diastereomer, (2R,5R)-2-isopropyl-3,6-dimethoxy-5-(4,4,4-trifluoro-3,3-dimethylbutyl)-2,5-dihydropyrazine, was isolated in 28% yield.

Step C: Methyl (S)-2-amino-6,6,6-trifluoro-5,5-dimethylhexanoate. To a stirred solution of (2R, 5S)-2-isopropyl-3,6-dimethoxy-5-(4,4,4-trifluoro-3,3-dimethylbutyl)-2,5-dihydropyrazine (1.15 g, 3.57 mmol, Step B first-eluting isomer) in ACN (14.3 mL) at room temperature was added aqueous HCl (14.3 mL, 1 M). After stirring for 2 h, the reaction mixture was poured onto saturated aqueous NaHCO$_3$ at 0° C. and was then extracted with EtOAc (3×150 mL). The combined organic layers were washed with brine, dried over anhydrous MgSO$_4$, filtered, and concentrated to give an oil that was used without further purification.

Step D: Methyl (S)-2-((tert-butoxycarbonyl)amino)-6,6,6-trifluoro-5,5-dimethylhexanoate. To a stirred solution of methyl (S)-2-amino-6,6,6-trifluoro-5,5-dimethylhexanoate (810.6 mg, 3.57 mmol, Step C) in DCM (15.1 mL) was added Boc$_2$O (1.56 g, 7.14 mmol). After 24 h, the reaction was quenched with aq. HCl (10 mL, 1 M), and the layers were separated. The organic layer was washed with aq. HCl (10 mL, 1 M), water, brine, dried over anhydrous MgSO$_4$, filtered, and concentrated to give an oil that was used in the next step without further purification.

Step E: (S)-2-((tert-Butoxycarbonyl)amino)-6,6,6-trifluoro-5,5-dimethylhexanoic acid. To a stirred solution of methyl (S)-2-((tert-butoxycarbonyl)amino)-6,6,6-trifluoro-5,5-dimethylhexanoate (925 mg, 2.83 mmol, Step D) in THF (22.4 mL) at 0° C. was added aq. LiOH (8.50 mL, 1 M) and the resulting mixture was stirred for 2 h. The reaction mixture was then acidified to pH 2 using aq. HCl (1 M). The mixture was extracted with EtOAc (3×60 mL). The combined organic layers were washed with brine, dried over anhydrous MgSO$_4$, filtered, and concentrated to give a clear oil that was used in the next step without further purification.

Step F: tert-Butyl (S)-(1-(dimethyl(oxo)-λ$^6$-sulfaneylidene)-7,7,7-trifluoro-6,6-dimethyl-2-oxoheptan-3-yl)carbamate. To a suspension of trimethylsulfoxonium chloride (0.581 g, 4.52 mmol) in THF (7 mL) was added a solution of t-BuOK (4.24 mL, 4.24 mmol, 1 M in THF) and the resulting solution was allowed to stir for 2 h. Separately, to a solution of (S)-2-((tert-butoxycarbonyl)amino)-6,6,6-trifluoro-5,5-dimethylhexanoic acid (885 mg, 2.83 mmol, Step E) in THF (7 mL) cooled to 0° C. was added CDI (550 mg, 3.39 mmol) and the resulting mixture was stirred for 2 h at 0° C. This mixture was then added via cannula to the trimethylsulfoxonium derived suspension, and the resulting mixture was stirred at rt. After 2 h, the reaction mixture was filtered through diatomaceous earth (e.g., Celite®), concentrated, and purified via silica gel chromatography (0-100% ethyl acetate in hexanes) to afford the title compound (56% yield) as a white foam.

Intermediate 46: tert-Butyl (S)-(7,7,7-trifluoro-1-iodo-6,6-dimethyl-2-oxoheptan-3-yl)carbamate

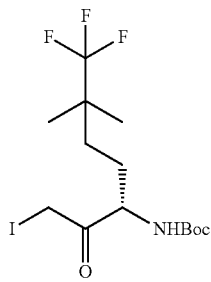 [SMILES: CC(C)(C)OC(=O)N[C@@H](CCC(C)(C)C(F)(F)F)C(=O)CI]

Step A: tert-Butyl (S)-(1-chloro-7,7,7-trifluoro-6,6-dimethyl-2-oxoheptan-3-yl)carbamate. The title compound was synthesized in a manner analogous to Intermediate 39 Step A, using tert-butyl (S)-(1-(dimethyl(oxo)-λ⁶-sulfaneylidene)-7,7,7-trifluoro-6,6-dimethyl-2-oxoheptan-3-yl)carbamate (Intermediate 45) in place of tert-butyl ((3S,4R)-1-(dimethyl(oxo)-λ⁶-sulfaneylidene)-2-oxo-4-(((R)-1,1,1-trifluoropropan-2-yl)oxy)pentan-3-yl)carbamate and was used without further purification.

Step B: tert-Butyl (S)-(7,7,7-trifluoro-1-iodo-6,6-dimethyl-2-oxoheptan-3-yl)carbamate. The title compound was synthesized in a manner analogous to Intermediate 39 Step B, using tert-butyl (S)-(1-chloro-7,7,7-trifluoro-6,6-dimethyl-2-oxoheptan-3-yl)carbamate (Step A) in place of tert-butyl ((3S,4R)-1-chloro-2-oxo-4-(((R)-1,1,1-trifluoropropan-2-yl)oxy)pentan-3-yl)carbamate and was used without further purification.

Intermediate 47: 1-((S)-1-(2-((S)-1-Amino-5,5,5-trifluoro-4,4-dimethylpentyl)imidazo[1,2-b]pyridazin-7-yl)-2-methoxyethyl)-5,5-difluorotetrahydropyrimidin-2(1H)-one

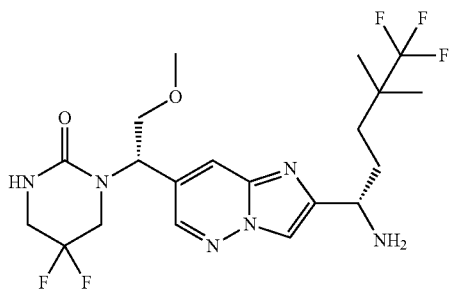 [SMILES: COC[C@H](c1cnn2cc([C@@H](N)CCC(C)(C)C(F)(F)F)nc2c1)N1CC(F)(F)CNC1=O]

Step A: tert-Butyl ((S)-1-(6-chloro-7-((S)-1-(5,5-difluoro-2-oxotetrahydropyrimidin-1(2H)-yl)-2-methoxyethyl)imidazo[1,2-b]pyridazin-2-yl)-5,5,5-trifluoro-4,4-dimethylpentyl)carbamate. The title compound was synthesized in a manner analogous to Intermediate 44 Step A, using tert-butyl (S)-(7,7,7-trifluoro-1-iodo-6,6-dimethyl-2-oxoheptan-3-yl)carbamate (Intermediate 46) in place of tert-butyl (S)-(6,6,6-trifluoro-1-iodo-5,5-dimethyl-2-oxohexan-3-yl)carbamate to provide the title compound (20% yield) as a brown oil.

Step B: tert-Butyl ((S)-1-(7-((S)-1-(5,5-difluoro-2-oxotetrahydropyrimidin-1(2H)-yl)-2-methoxyethyl)imidazo[1,2-b]pyridazin-2-yl)-5,5,5-trifluoro-4,4-dimethylpentyl)carbamate. The title compound was synthesized in a manner analogous to Intermediate 44 Step B, using tert-butyl ((S)-1-(6-chloro-7-((S)-1-(5,5-difluoro-2-oxotetrahydropyrimidin-1(2H)-yl)-2-methoxyethyl)imidazo[1,2-b]pyridazin-2-yl)-5,5,5-trifluoro-4,4-dimethylpentyl)carbamate (Step A) in place of tert-butyl ((S)-1-(6-chloro-7-((S)-1-(5,5-difluoro-2-oxotetrahydropyrimidin-1(2H)-yl)-2-methoxyethyl)imidazo[1,2-b]pyridazin-2-yl)-4,4,4-trifluoro-3,3-dimethylbutyl)carbamate to provide the title compound as a brown oil that was used without further purification.

Step C: 1-((S)-1-(2-((S)-1-Amino-5,5,5-trifluoro-4,4-dimethylpentyl)imidazo[1,2-b]pyridazin-7-yl)-2-methoxyethyl)-5,5-difluorotetrahydropyrimidin-2(1H)-one. The title compound was synthesized in a manner analogous to Intermediate 44 Step C, using tert-butyl ((S)-1-(7-((S)-1-(5,5-difluoro-2-oxotetrahydropyrimidin-1(2H)-yl)-2-methoxyethyl)imidazo[1,2-b]pyridazin-2-yl)-5,5,5-trifluoro-4,4-dimethylpentyl)carbamate (Step B) in place of tert-butyl ((S)-1-(7-((S)-1-(5,5-difluoro-2-oxotetrahydropyrimidin-1(2H)-yl)-2-methoxyethyl)imidazo[1,2-b]pyridazin-2-yl)-4,4,4-trifluoro-3,3-dimethylbutyl)carbamate to afford the title compound as a yellow oil that was used without further purification.

Intermediate 48: tert-Butyl ((R)-1-(7-((S)-1-amino-2-methoxyethyl)-6-chloroimidazo[1,2-b]pyridazin-2-yl)-2-((1,1,1-trifluoro-2-methylpropan-2-yl)oxy)ethyl)carbamate

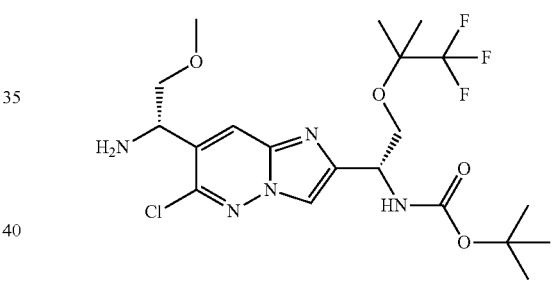

Step A: (S)—N-(5-(1-Amino-2-methoxyethyl)-6-chloropyridazin-3-yl)pivalamide. To a stirred solution of N-(5-(((S)-1-(((R)-tert-butylsulfinyl)amino)-2-methoxyethyl)-6-chloropyridazin-3-yl)pivalamide (8.00 g, 20.5 mmol, Intermediate 33) in EtOAc (102 mL) at rt was added a solution of HCl in 1,4-dioxane (4 M, 20.5 mL, 81.9 mmol). After 5 h, the reaction mixture was diluted with hexanes (150 mL) and water (200 mL). The layers were separated, and the organic layer was extracted with aqueous HCl (0.05 M, 2×50 mL). The combined aqueous layers were diluted with EtOAc (50 mL) and the pH of the solution was adjusted to pH 11 with aqueous 3 M NaOH. The layers were separated, and the aqueous layers were extracted with EtOAc (4×50 mL). The combined organic layers were dried over anhydrous Na₂SO₄ and concentrated to give the title compound as a solid (>99% yield, trace EtOAc was present), which was used without further purification.

Step B: (S)—N-(6-Chloro-5-(1-(1,3-dioxoisoindolin-2-yl)-2-methoxyethyl)pyridazin-3-yl)pivalamide. To a stirred solution of (S)—N-(5-(1-amino-2-methoxyethyl)-6-chloropyridazin-3-yl)pivalamide (1.17 g, 4.07 mmol, Step A) and isobenzofuran-1,3-dione (0.81 g, 5.48 mmol) in toluene (25 mL) was added DIPEA (1.1 mL, 6.3 mmol) and the resulting solution was heated at 100° C. for 17 h. The reaction mixture was cooled to rt and concentrated to a residue, then purified by silica gel chromatography (0-100% EtOAc in hexanes) to give the title compound (89.5%).

Step C: (S)-2-(1-(6-Amino-3-chloropyridazin-4-yl)-2-methoxyethyl)isoindoline-1,3-dione. To a 50 mL pear shaped flask charged with (S)—N-(6-chloro-5-(1-(1,3-dioxoisoindolin-2-yl)-2-methoxyethyl)pyridazin-3-yl)pivalamide (1.2 g, 2.9 mmol, Step B), 1,4-dioxane (7.2 mL) then 6 M H$_2$SO$_4$ (4.8 mL, 28.8 mmol) were added and the resulting yellow solution was heated at 60° C. for 11 h. Then this solution was cooled to 0° C. and the pH was adjusted to pH 8 by the slow addition of 58.7 mL of saturated aqueous sodium bicarbonate. The aqueous portion of this mixture was extracted with EtOAc (3×25 mL). The combined organic layers were dried over anhydrous Na$_2$SO$_4$, filtered, and concentrated to give a brown oil. The product was purified by silica gel chromatography (0-100% EtOAc in hexanes) to give the title compound as a white foam (74.1%).

Step D: tert-Butyl ((R)-1-(6-chloro-7-((S)-1-(1,3-dioxoisoindolin-2-yl)-2-methoxyethyl)imidazo[1,2-b]pyridazin-2-yl)-2-((1,1,1-trifluoro-2-methylpropan-2-yl)oxy)ethyl)carbamate. The title compound was prepared as described for the synthesis of Intermediate 41 Step A using (S)-2-(1-(6-amino-3-chloropyridazin-4-yl)-2-methoxyethyl)isoindoline-1,3-dione (Step C) in place of (S)-1-(1-(6-amino-3-chloropyridazin-4-yl)-2-methoxyethyl)-5,5-difluorotetrahydropyrimidin-2(1H)-one and tert-butyl (S)-(4-iodo-3-oxo-1-((1,1,1-trifluoro-2-methylpropan-2-yl)oxy)butan-2-yl)carbamate in place of tert-butyl ((3S,4R)-1-iodo-2-oxo-4-(((R)-1,1,1-trifluoropropan-2-yl)oxy)pentan-3-yl)carbamate to provide the title compound (65%) as a brown oil.

Step E: tert-Butyl ((R)-1-(7-((S)-1-amino-2-methoxyethyl)-6-chloroimidazo[1,2-b]pyridazin-2-yl)-2-((1,1,1-trifluoro-2-methylpropan-2-yl)oxy)ethyl)carbamate. To tert-butyl ((R)-1-(6-chloro-7-((S)-1-(1,3-dioxoisoindolin-2-yl)-2-methoxyethyl)imidazo[1,2-b]pyridazin-2-yl)-2-((1,1,1-trifluoro-2-methylpropan-2-yl)oxy)ethyl)carbamate (473 mg, 0.756 mmol, Step D) in EtOH (5 mL) was added hydrazine monohydrate (565 µL, 7.56 mmol) and the resulting red-brown solution was stirred at rt for 4 h. The mixture was concentrated to a residue that was then diluted with H$_2$O (5 mL) and was extracted with EtOAc (3×5 mL). NaCl (solid) was added to this mixture to facilitate separation of the aqueous and organic layers. The organic layer was dried over anhydrous MgSO$_4$, filtered, concentrated, and purified by silica gel chromatography (0-5% (2 M NH$_3$ in MeOH)/DCM) to give the title compound (95%) as a brown oil.

Intermediate 49: 2-(1-(1,3-Dioxoisoindolin-2-yl)cyclopropyl)acetaldehyde

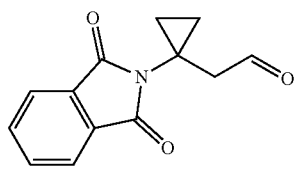 [SMILES: O=CCC1(N2C(=O)c3ccccc3C2=O)CC1]

Step A. 2-(1-(2-Hydroxyethyl)cyclopropyl)isoindoline-1,3-dione. To a mixture of 2-(1-aminocyclopropyl)ethan-1-ol hydrochloride (3.40 g, 24.7 mmol), ethyl 1,3-dioxoisoindoline-2-carboxylate (6.04 g, 27.6 mmol) and anhydrous THF (60 mL) under N$_2$ was added DIPEA (14.4 mL, 82.4 mmol) dropwise over 1 min. The resulting mixture was heated at 75° C. for 2 d. The mixture was diluted with water (100 mL) and extracted with DCM (3×100 mL). The organic layers were combined, washed with brine (100 mL), dried over anhydrous Na$_2$SO$_4$, filtered, and concentrated to dryness to provide a light-yellow oil. The oil was purified by silica gel chromatography (0-30% EtOAc/petroleum ether) to provide the title compound as a white solid (34% yield).

Step B. 2-(1-(1,3-Dioxoisoindolin-2-yl)cyclopropyl)acetaldehyde. A mixture of 2-(1-(2-hydroxyethyl)cyclopropyl)isoindoline-1,3-dione (100 mg, 0.430 mmol, Step A), Dess-Martin periodinane (367 mg, 0.860 mmol), NaHCO$_3$ (254 mg, 3.03 mmol), 4 Å molecular sieves (200 mg) and anhydrous DCM (10 mL) was stirred at rt for 1 h. The mixture was then filtered and concentrated to dryness to provide a light-yellow oil. The oil was purified by silica gel chromatography (0-30% EtOAc/petroleum ether) to afford the title compound as a white solid (61% yield).

Intermediate 50: 3-(1,3-Dioxoisoindolin-2-yl)-4,4,4-trifluorobutanal

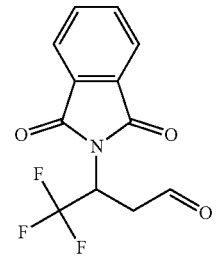 [SMILES: O=CCC(N1C(=O)c2ccccc2C1=O)C(F)(F)F]

Step A. 2-(1,1,1-Trifluoro-4-hydroxybutan-2-yl)isoindoline-1,3-dione. To a mixture of 3-amino-4,4,4-trifluorobutan-1-ol (5.04 g, 35.2 mmol), ethyl 1,3-dioxoisoindoline-2-carboxylate (8.50 g, 38.8 mmol) and anhydrous THF (100 mL) under N$_2$ was added DIPEA (20.3 mL, 116 mmol). The resulting mixture was heated at 75° C. for 40 h. The mixture was concentrated to dryness and then dissolved in DCM (100 mL) and washed with 2 M aqueous HCl (2×50 mL). The organic layer was dried over anhydrous Na$_2$SO$_4$, filtered and concentrated to dryness to provide a yellow gum. The gum was initially purified by silica gel chromatography (0-50% EtOAc/petroleum ether) and then further purified by preparative HPLC (Welch Xtimate C18, 5 µm, 30×150 mm, 31-61% MeCN/water (formic acid)) to provide the title compound as a yellow oil (31% yield).

Step B. 3-(1,3-Dioxoisoindolin-2-yl)-4,4,4-trifluorobutanal. A mixture of 2-(1,1,1-trifluoro-4-hydroxybutan-2-yl)isoindoline-1,3-dione (500 mg, 1.83 mmol, Step A), NaHCO$_3$ (769 mg, 9.15 mmol) and anhydrous DCM (15 mL) was cooled to 0° C. in an ice bath and then Dess-Martin periodinane (1.16 g, 2.75 mmol) was added in one portion and the resulting mixture was stirred at rt for 1 h. After that time, the mixture was treated with saturated aqueous Na$_2$S$_2$O$_3$ (100 mL) dropwise over 30 min and then extracted with EtOAc (2×50 mL). The organic layers were combined, washed with brine (100 mL), dried over anhydrous Na$_2$SO$_4$, filtered, and concentrated to dryness to provide a white solid. The solid was purified by silica gel chromatography (20-50% EtOAc/petroleum ether) to afford the title compound as a yellow oil (66% yield).

Intermediate 51: (S*)-(7-((S)-1-(5,5-Difluoro-2-oxotetrahydropyrimidin-1(2H)-yl)-2-methoxyethyl)imidazo[1,2-b]pyridazin-2-yl)((1R,5S,6r)-3,3-difluorobicyclo[3.1.0]hexan-6-yl)methanaminium 2,2,2-trifluoroacetate

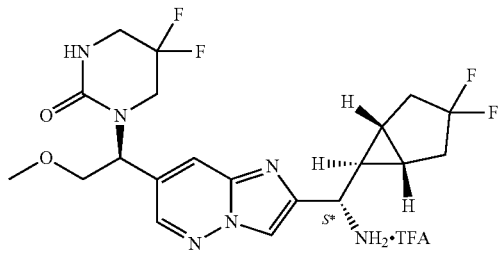

Step A: tert-Butyl ((S*)-(6-chloro-7-((S)-1-(5,5-difluoro-2-oxotetrahydropyrimidin-1(2H)-yl)-2-methoxyethyl)imidazo[1,2-b]pyridazin-2-yl)((1R,5S,6r)-3,3-difluorobicyclo[3.1.0]hexan-6-yl)methyl)carbamate. The title compound was synthesized in a manner analogous to Intermediate 41 Step A using tert-butyl ((S*)-1-((1R,3s,5S)-6,6-difluorobicyclo[3.1.0]hexan-3-yl)-3-iodo-2-oxopropyl)carbamate in place of tert-butyl ((3S,4R)-1-iodo-2-oxo-4-(((R)-1,1,1-trifluoropropan-2-yl)oxy)pentan-3-yl)carbamate. The title compound (70% yield) was purified by silica gel chromatography (0-100% acetone/hexanes (0.1% TEA)).

Step B: tert-Butyl ((S*)-(7-((S)-1-(5,5-difluoro-2-oxotetrahydropyrimidin-1(2H)-yl)-2-methoxyethyl)imidazo[1,2-b]pyridazin-2-yl)((1R,5S,6r)-3,3-difluorobicyclo[3.1.0]hexan-6-yl)methyl)carbamate. The title compound was synthesized in a manner analogous to Intermediate 41 Step B using tert-butyl ((S*)-(6-chloro-7-((S)-1-(5,5-difluoro-2-oxotetrahydropyrimidin-1(2H)-yl)-2-methoxyethyl)imidazo[1,2-b]pyridazin-2-yl)((1R,5S,6r)-3,3-difluorobicyclo[3.1.0]hexan-6-yl)methyl)carbamate (Step A) in place of tert-butyl ((1R,2R)-1-(6-chloro-7-((S)-1-(5,5-difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propyl)carbamate. The title compound (68% yield) was purified via silica gel chromatography (0-100% acetone/hexanes (0.1% TEA)).

Step C: (S*)-(7-((S)-1-(5,5-Difluoro-2-oxotetrahydropyrimidin-1(2H)-yl)-2-methoxyethyl)imidazo[1,2-b]pyridazin-2-yl)((1R,5S,6r)-3,3-difluorobicyclo[3.1.0]hexan-6-yl)methanaminium 2,2,2-trifluoroacetate. The title compound was synthesized in a manner analogous to Intermediate 41 Step C using tert-butyl ((S*)-(7-((S)-1-(5,5-difluoro-2-oxotetrahydropyrimidin-1(2H)-yl)-2-methoxyethyl)imidazo[1,2-b]pyridazin-2-yl)((1R,5S,6r)-3,3-difluorobicyclo[3.1.0]hexan-6-yl)methyl)carbamate (Step B) in place of tert-butyl ((1R,2R)-1-(7-((S)-1-(5,5-difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propyl)carbamate. The title compound was used without further purification assuming a quantitative yield.

Intermediate 52: tert-Butyl ((R*)-1-((R*)-3,3-difluorocyclopentyl)-3-(dimethyl(oxo)-λ⁶-sulfaneylidene)-2-oxopropyl)carbamate

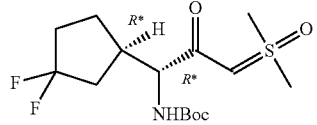 [SMILES: CC(C)(C)OC(=O)N[C@@H](C(=O)C=S(C)(C)=O)[C@@H]1CCC(F)(F)C1]

Step A: (S)—N-((E)-(3,3-Difluorocyclopentyl)methylene)-2-methylpropane-2-sulfinamide. The title compound was synthesized in a manner analogous to Intermediate 37 Step D using 3,3-difluorocyclopentane-1-carbaldehyde in place of (R)-2-(((R)-1,1,1-trifluoropropan-2-yl)oxy)propanal in 43% yield. This material was found to epimerize over time and was used in Step B.

Step B: (S)—N-(Cyano(3,3-difluorocyclopentyl)methyl)-2-methylpropane-2-sulfinamide. The title compound (90% yield) was synthesized in a manner analogous to Intermediate 37 Step E using (S)—N-((E)-(3,3-difluorocyclopentyl)methylene)-2-methylpropane-2-sulfinamide (Step A) in place of (S)-2-methyl-N—((R,E)-2-(((R)-1,1,1-trifluoropropan-2-yl)oxy)propylidene)propane-2-sulfinamide.

Step C: Carboxy(3,3-difluorocyclopentyl)methanaminium chloride. The title compound was synthesized in a manner analogous to Intermediate 37 Step F using (S)—N-(cyano(3,3-difluorocyclopentyl)methyl)-2-methylpropane-2-sulfinamide (Step B) in place of (S)—N-((1R,2R)-1-cyano-2-(((R)-1,1,1-trifluoropropan-2-yl)oxy)propyl)-2-methylpropane-2-sulfinamide and used without further purification.

Step D: 2-((tert-Butoxycarbonyl)amino)-2-(3,3-difluorocyclopentyl)acetic acid. The title compound was synthesized in a manner analogous to Intermediate 37 Step G using carboxy(3,3-difluorocyclopentyl)methanaminium chloride (Step C) in place of O—((R)-1,1,1-trifluoropropan-2-yl)-L-threonine hydrogen chloride and was used without further purification.

Step E: tert-Butyl ((R*)-1-((R*)-3,3-difluorocyclopentyl)-3-(dimethyl(oxo)-λ⁶-sulfaneylidene)-2-oxopropyl)carbamate. The title compound was synthesized in a manner analogous to Intermediate 37, Step H using 2-((tert-butoxycarbonyl)amino)-2-(3,3-difluorocyclopentyl)acetic acid (Step D) in place of N-(tert-butoxycarbonyl)-O—((R)-1,1,1-trifluoropropan-2-yl)-L-threonine. Because of the epimerization of the product of Step A, four diastereomers were formed. These diastereomers were first purified by silica gel chromatography (0-100% EtOAc/hexanes) and then subsequently purified by preparative acidic HPLC (YMC-Triart Prep C18 10 µm column, 50×250 mm, 10-50% acetonitrile/water (0.225% formic acid)). The four diastereomers were then separated using SFC. The compounds were first separated by (DAICEL CHIRALPAK IG, 10 µm, 50×250 mm, 35% EtOH (with 0.1% of 25% aqueous NH₃)/CO₂) followed by two additional separations by (DAICEL CHIRALPAK IG, 10 µm, 50×250 mm, 30% MeOH (with 0.1% of 25% aqueous NH₃)/CO₂) to obtain the pure title compound after lyophilization in a 10% yield. Additional analysis of the title compound provided the following data: analytical SFC using (DAICEL CHIRALPAK IG, 3 µm, 5×100 mm, 5 to 40% MeOH (0.05% DEA)/CO₂ over 4.5 min) retention time 3.82 min and optical rotation of $[\alpha]_D^{23}=-28.6$ (MeOH, c=0.29).

Intermediate 53: tert-Butyl ((R*)-1-((R*)-3,3-difluorocyclopentyl)-3-iodo-2-oxopropyl)carbamate

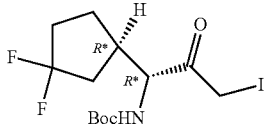 [SMILES: CC(C)(C)OC(=O)N[C@@H](C(=O)CI)[C@@H]1CCC(F)(F)C1]

Step A: tert-Butyl ((R*)-3-chloro-1-((R*)-3,3-difluorocyclopentyl)-2-oxopropyl)carbamate. The title compound was synthesized in a manner analogous to Intermediate 39 Step A using tert-butyl ((R*)-1-((R*)-3,3-difluorocyclopentyl)-3-(dimethyl(oxo)-$\lambda^6$-sulfaneylidene)-2-oxopropyl)carbamate (Intermediate 52) in place of tert-butyl ((3S,4R)-1-(dimethyl(oxo)-$\lambda^6$-sulfaneylidene)-2-oxo-4-(((R)-1,1,1-trifluoropropan-2-yl)oxy)pentan-3-yl)carbamate and was used without further purification (100% yield).

Step B: tert-Butyl ((R*)-1-((R*)-3,3-difluorocyclopentyl)-3-iodo-2-oxopropyl)carbamate. The title compound was synthesized in a manner analogous to Intermediate 39 Step B using tert-butyl ((R*)-3-chloro-1-((R*)-3,3-difluorocyclopentyl)-2-oxopropyl)carbamate (Step A) in place of tert-butyl ((3S,4R)-1-chloro-2-oxo-4-(((R)-1,1,1-trifluoropropan-2-yl)oxy)pentan-3-yl)carbamate and was used without further purification (100% yield).

Intermediate 54: (R*)-(7-((S)-1-(5,5-Difluoro-2-oxotetrahydropyrimidin-1(2H)-yl)-2-methoxyethyl)imidazo[1,2-b]pyridazin-2-yl)((R*)-3,3-difluorocyclopentyl)methanaminium 2,2,2-trifluoroacetate

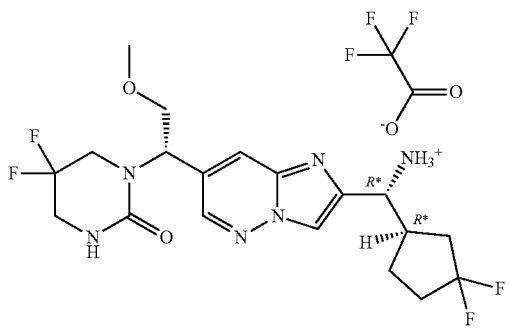

Step A: tert-Butyl ((R*)-(6-chloro-7-((S)-1-(5,5-difluoro-2-oxotetrahydropyrimidin-1(2H)-yl)-2-methoxyethyl)imidazo[1,2-b]pyridazin-2-yl)((R*)-3,3-difluorocyclopentyl)methyl)carbamate. The title compound was synthesized in a manner analogous to Intermediate 41 Step A using tert-butyl ((R*)-1-((R*)-3,3-difluorocyclopentyl)-3-iodo-2-oxopropyl)carbamate (Intermediate 53) in place of tert-butyl ((3S,4R)-1-iodo-2-oxo-4-(((R)-1,1,1-trifluoropropan-2-yl)oxy)pentan-3-yl)carbamate. The title compound (61% yield) was purified by silica gel chromatography (0-100% acetone/hexanes (0.1% TEA)).

Step B: tert-Butyl ((R*)-(7-((S)-1-(5,5-difluoro-2-oxotetrahydropyrimidin-1(2H)-yl)-2-methoxyethyl)imidazo[1,2-b]pyridazin-2-yl)((R*)-3,3-difluorocyclopentyl)methyl)carbamate. The title compound was synthesized in a manner analogous to Intermediate 41 Step B using tert-butyl ((R*)-(6-chloro-7-((S)-1-(5,5-difluoro-2-oxotetrahydropyrimidin-1(2H)-yl)-2-methoxyethyl)imidazo[1,2-b]pyridazin-2-yl)((R*)-3,3-difluorocyclopentyl)methyl)carbamate (Step A) in place of tert-butyl ((1R,2R)-1-(6-chloro-7-((S)-1-(5,5-difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propyl)carbamate. The title compound (>99% yield) was purified by silica gel chromatography (0-100% acetone/hexanes (0.1% TEA)).

Step C: (R*)-(7-((S)-1-(5,5-Difluoro-2-oxotetrahydropyrimidin-1(2H)-yl)-2-methoxyethyl)imidazo[1,2-b]pyridazin-2-yl)((R*)-3,3-difluorocyclopentyl)methanaminium 2,2,2-trifluoroacetate. The title compound was synthesized in a manner analogous to Intermediate 41 Step C using tert-butyl ((R*)-(7-((S)-1-(5,5-difluoro-2-oxotetrahydropyrimidin-1(2H)-yl)-2-methoxyethyl)imidazo[1,2-b]pyridazin-2-yl)((R*)-3,3-difluorocyclopentyl)methyl)carbamate (Step B) in place of tert-butyl ((1R,2R)-1-(7-((S)-1-(5,5-difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propyl)carbamate and was used without further purification.

Intermediate 55: 1,3-Dioxoisoindolin-2-yl 2-cyclopropoxypropanoate

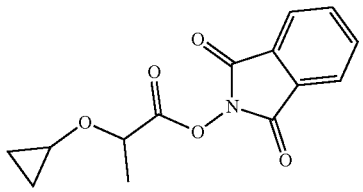 [SMILES: CC(OC1CC1)C(=O)ON1C(=O)c2ccccc2C1=O]

Step A: 2-Cyclopropoxypropanoic acid. The title compound was synthesized in a manner analogous to Intermediate 37 Step A using cyclopropanol in place of (R)-1,1,1-trifluoropropan-2-ol and 2-bromopropanoic acid in place of (S)-2-bromopropanoic acid and was used without further purification.

Step B: 1,3-Dioxoisoindolin-2-yl 2-cyclopropoxypropanoate. 2-Cyclopropoxypropanoic acid (3.2 g, 25 mmol, Step A), DMAP (310 mg, 2.50 mmol), and 2-hydroxyisoindoline-1,3-dione (6.3 g, 37 mmol) was dissolved in DCM (90 mL) at 0° C. Separately, DCC (5.7 g, 27 mmol) was dissolved in DCM (35 mL) and this DCC solution was then added dropwise to the reaction mixture. The reaction was then warmed to rt and allowed to stir overnight. The reaction mixture was then filtered through diatomaceous earth (e.g., Celite®), concentrated to dryness, and purified by silica gel chromatography (0-70% EtOAc/hexanes) to afford the title compound in 65% yield.

Intermediate 56: (S)—N-((E)-(7-((S)-1-(5,5-Difluoro-2-oxotetrahydropyrimidin-1(2H)-yl)-2-methoxyethyl)imidazo[1,2-b]pyridazin-2-yl)methylene)-2,4,6-trimethylbenzenesulfinamide

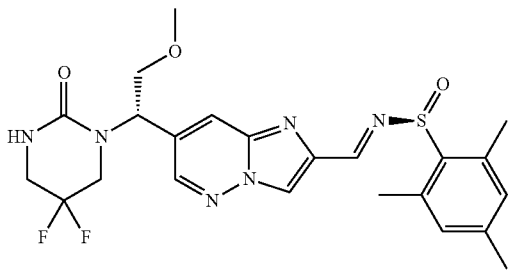 [SMILES: COC[C@H](c1cnn2cc(/C=N/[S@@](=O)c3c(C)cc(C)cc3C)nc2c1)N1CC(F)(F)CNC1=O]

Step A: Ethyl (S)-6-chloro-7-(1-(5,5-difluoro-2-oxotetrahydropyrimidin-1(2H)-yl)-2-methoxyethyl)imidazo[1,2-b]pyridazine-2-carboxylate. (S)-1-(1-(6-Amino-3-chloropyridazin-4-yl)-2-methoxyethyl)-5,5-difluorotetrahydropyrimidin-2(1H)-one (4.0 g, 12 mmol, Intermediate 35) was dissolved in EtOH (83 mL). 4 Å Molecular sieves (5 g) and ethyl bromopyruvate (3.5 mL, 25 mmol) were added sequentially, and the resulting reaction mixture was heated to 70° C. overnight. The reaction mixture was then filtered through diatomaceous earth (e.g., Celite®) and washed with EtOH. The solution was than partitioned between DCM (50 mL), a saturated aqueous solution of NaHCO₃ (80 mL) and aqueous NaS₂O₃ (40 mL, 0.5 M). The aqueous layer was further extracted with DCM (4×30 mL). The combined organic layers were dried over anhydrous $Na_2SO_4$, filtered, concentrated to dryness and purified by silica gel chromatography (15-90% acetone/hexanes (0.1% TEA)) to afford the title compound as a tan foam in 78% yield.

Step B: Ethyl (S)-7-(1-(5,5-difluoro-2-oxotetrahydropyrimidin-1(2H)-yl)-2-methoxyethyl)imidazo[1,2-b]pyridazine-2-carboxylate. Ethyl (S)-6-chloro-7-(1-(5,5-difluoro-2-oxotetrahydropyrimidin-1(2H)-yl)-2-methoxyethyl)imidazo[1,2-b]pyridazine-2-carboxylate (4.0 g, 9.7 mmol, Step A), 10% Pd/C (1.2 g, 9.7 mmol), and 28% NH₄OH (2.0 mL, 29 mmol) were added sequentially to a Parr shaker containing MeOH (195 mL). The vessel was then pressurized to 20 psi of H₂ and shaken for about 1 h. After this time, the reaction vessel was depressurized, and the reaction mixture was filtered and concentrated to dryness. The residue was partitioned between EtOAc (40 mL) and saturated aqueous NaHCO₃ (40 mL). The aqueous layer was further extracted with DCM (3×20 mL). The combined organic layers were dried over anhydrous Na₂SO₄, filtered, and concentrated to dryness to afford the title compound, which was used without further purification in 90% yield.

Step C: (S)-7-(1-(5,5-Difluoro-2-oxotetrahydropyrimidin-1(2H)-yl)-2-methoxyethyl)imidazo[1,2-b]pyridazine-2-carbaldehyde. Ethyl (S)-7-(1-(5,5-difluoro-2-oxotetrahydropyrimidin-1(2H)-yl)-2-methoxyethyl)imidazo[1,2-b]pyridazine-2-carboxylate (3.4 g, 8.8 mmol, Step B) was dissolved in THF (88 mL) and the reaction mixture was cooled to −78° C. A DIBAL solution (24 mL, 24 mmol, 1 M in DCM) was then added dropwise over 5 min. The reaction mixture was allowed to stir at −78° C. for 1.5 h and then quenched with Rochelle salt (10 g), a saturated aqueous solution of Rochelle salt (25 mL), and EtOAc (75 mL). The solution was allowed to warm to rt and stir overnight. After that time, the solution was diluted with EtOAc (75 mL), brine (30 mL), and 0.1 M aqueous HCl (40 mL). The layers were separated and the aqueous layer was further extracted with EtOAc (4×40 mL). The combined organic layers were washed with brine, dried over anhydrous Na₂SO₄, filtered, and concentrated to dryness to afford the title compound that was used without further purification in 99% yield.

Step D: (S)—N-((E)-(7-((S)-1-(5,5-Difluoro-2-oxotetrahydropyrimidin-1(2H)-yl)-2-methoxyethyl)imidazo[1,2-b]pyridazin-2-yl)methylene)-2,4,6-trimethylbenzenesulfinamide. (S)-7-(1-(5,5-Difluoro-2-oxotetrahydropyrimidin-1(2H)-yl)-2-methoxyethyl)imidazo[1,2-b]pyridazine-2-carbaldehyde (2.9 g, 8.7 mmol, Step C) and Cs₂CO₃ (20 g, 61 mmol) were added to DCM (115 mL). (S)-2,4,6-Trimethylbenzenesulfinamide (1.7 g, 9.5 mmol) was then added and the reaction was allowed to stir at rt for 4 h. The reaction was filtered and washed with DCM. The solution was concentrated to dryness and then triturated with hexanes (45 mL) and DCM (16 mL). The turbid solution was filtered and the solid was dried to afford the title compound in 92% yield.

Intermediate 57: 1-((1S)-1-(2-((1R*)-1-Amino-2-cyclopropoxypropyl)imidazo[1,2-b]pyridazin-7-yl)-2-methoxyethyl)-5,5-difluorotetrahydropyrimidin-2(1H)-one

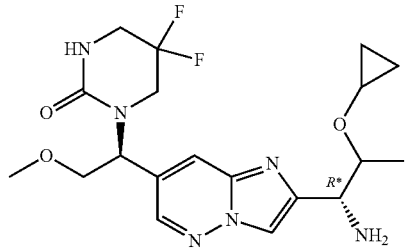 [SMILES: COC[C@H](c1cnn2cc([C@@H](N)C(C)OC3CC3)nc2c1)N1CC(F)(F)CNC1=O]

Step A: (S)—N-((1R*)-2-Cyclopropoxy-1-(7-((S)-1-(5,5-difluoro-2-oxotetrahydropyrimidin-1(2H)-yl)-2-methoxyethyl)imidazo[1,2-b]pyridazin-2-yl)propyl)-2,4,6-trimethylbenzenesulfinamide. (S)—N-((E)-(7-((S)-1-(5,5-Difluoro-2-oxotetrahydropyrimidin-1(2H)-yl)-2-methoxyethyl)imidazo[1,2-b]pyridazin-2-yl)methylene)-2,4,6-trimethylbenzenesulfinamide (160 mg, 0.32 mmol, Intermediate 56) was dissolved in DMSO (4.9 mL) and then DIPEA (0.14 mL, 0.79 mmol), diethyl 1,4-dihydro-2,6-dimethyl-3,5-pyridinedicarboxylate (160 mg, 0.63 mmol), and 1,3-dioxoisoindolin-2-yl 2-cyclopropoxypropanoate (180 mg, 0.63 mmol, Intermediate 55) were added sequentially. The reaction mixture was sparged with N₂ for 15 min and then irradiated with 450 nm light (40% LED intensity, max rpm fan, 1000 rpm stir) for 3 h. After this time DIPEA (30 μL, 0.16 mmol), diethyl 1,4-dihydro-2,6-dimethyl-3,5-pyridinedicarboxylate (32 mg, 0.13 mmol), and 1,3-dioxoisoindolin-2-yl 2-cyclopropoxypropanoate (34 mg, 0.13 mmol) were added. The reaction mixture was re-sparged for 5 min, and irradiated for an additional 30 min (450 nm light (40% LED intensity, max rpm fan, 1000 rpm stir)). The reaction mixture was than diluted with brine (30 mL), saturated aqueous NaHCO₃ (15 mL), water (15 mL), and EtOAc (30 mL). The layers were separated and the aqueous layer was extracted with EtOAc (4×20 mL). The combined organic layers were dried over anhydrous Na₂SO₄, filtered, and concentrated to dryness. The residue was then purified by silica gel chromatography (0-100% of (25% EtOH and 0.1% TEA in EtOAc)/EtOAc) to afford the title compound in 52% yield.

Step B: 1-((1S)-1-(2-((1R*)-1-Amino-2-cyclopropoxypropyl)imidazo[1,2-b]pyridazin-7-yl)-2-methoxyethyl)-5,5-difluorotetrahydropyrimidin-2(1H)-one. The title compound was synthesized in a manner analogous to Intermediate 9 using (S)—N-((1R*)-2-cyclopropoxy-1-(7-((S)-1-(5,5-difluoro-2-oxotetrahydropyrimidin-1(2H)-yl)-2-methoxyethyl)imidazo[1,2-b]pyridazin-2-yl)propyl)-2,4,6-trimethylbenzenesulfinamide (Step A) in place of tert-butyl ((R)-1-(7-((S*)-1-(((R)-tert-butylsulfinyl)amino)-2-methoxyethyl)imidazo[1,2-b]pyridazin-2-yl)-2-((1,1,1-trifluoro-2-methylpropan-2-yl)oxy)ethyl)carbamate and was used without further purification (100% yield).

Intermediate 58: (S)-1-(7-((S)-2-Cyclopropoxy-1-(5,5-difluoro-2-oxotetrahydropyrimidin-1(2H)-yl)ethyl)imidazo[1,2-b]pyridazin-2-yl)-5,5,5-trifluoro-4,4-dimethylpentan-1-aminium 2,2,2-trifluoroacetate

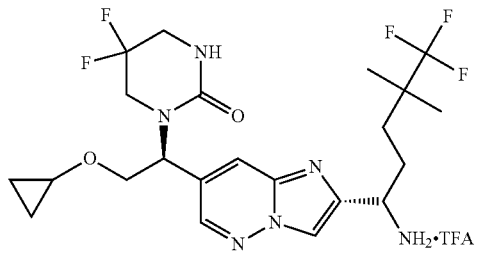

Step A: tert-Butyl ((S)-1-(6-chloro-7-((S)-2-cyclopropoxy-1-(5,5-difluoro-2-oxotetrahydropyrimidin-1(2H)-yl)ethyl)imidazo[1,2-b]pyridazin-2-yl)-5,5,5-trifluoro-4,4-dimethylpentyl)carbamate. tert-Butyl (S)-(7,7,7-trifluoro-1-iodo-6,6-dimethyl-2-oxoheptan-3-yl)carbamate (150 mg, 0.33 mmol, Intermediate 46) was added to a solution of (S)-1-(1-(6-amino-3-chloropyridazin-4-yl)-2-cyclopropoxyethyl)-5,5-difluorotetrahydropyrimidin-2(1H)-one (77 mg, 0.22 mmol, Intermediate 36) and sodium phosphate dibasic (41 mg, 0.29 mmol) in NMP (0.16 mL) and the reaction mixture was heated to 40° C. for 18 h. After this time an additional aliquot of tert-butyl (S)-(7,7,7-trifluoro-1-iodo-6,6-dimethyl-2-oxoheptan-3-yl)carbamate (100 mg, 0.22 mmol, Intermediate 46) and sodium phosphate dibasic (40 mg, 0.28 mmol) were added and the mixture was heated at 40° C. for an additional 8 h. The reaction mixture was then poured into water and was extracted with EtOAc (3×). The combined organic layers were washed with brine twice, dried over anhydrous MgSO₄, filtered, and concentrated to dryness. The residue was the purified by silica gel chromatography (0-100% acetone/hexanes (0.1% TEA)) to afford the title compound in 99% yield.

Step B: tert-Butyl ((S)-1-(7-((S)-2-cyclopropoxy-1-(5,5-difluoro-2-oxotetrahydropyrimidin-1(2H)-yl)ethyl)imidazo[1,2-b]pyridazin-2-yl)-5,5,5-trifluoro-4,4-dimethylpentyl)carbamate. The title compound was synthesized in a manner analogous to Intermediate 41 Step B, using tert-butyl ((S)-1-(6-chloro-7-((S)-2-cyclopropoxy-1-(5,5-difluoro-2-oxotetrahydropyrimidin-1(2H)-yl)ethyl)imidazo[1,2-b]pyridazin-2-yl)-5,5,5-trifluoro-4,4-dimethylpentyl)carbamate (Step A) in place of tert-butyl ((1R,2R)-1-(6-chloro-7-((S)-1-(5,5-difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propyl)carbamate. The material was purified by silica gel chromatography (0-100% acetone/hexanes (0.1% TEA)) to provide the title compound in 55% yield.

Step C: (S)-1-(7-((S)-2-Cyclopropoxy-1-(5,5-difluoro-2-oxotetrahydropyrimidin-1(2H)-yl)ethyl)imidazo[1,2-b]pyridazin-2-yl)-5,5,5-trifluoro-4,4-dimethylpentan-1-aminium 2,2,2-trifluoroacetate. The title compound was synthesized in a manner analogous to Intermediate 41 Step C using tert-butyl ((S)-1-(7-((S)-2-cyclopropoxy-1-(5,5-difluoro-2-oxotetrahydropyrimidin-1(2H)-yl)ethyl)imidazo[1,2-b]pyridazin-2-yl)-5,5,5-trifluoro-4,4-dimethylpentyl)carbamate (Step B) in place of tert-butyl ((1R,2R)-1-(7-((S)-1-(5,5-difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propyl)carbamate and was used without further purification (100% yield).

Intermediate 59:
Tributyl(isopropoxymethyl)stannane

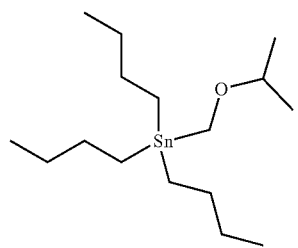 [SMILES: CCC[CH2][Sn]([CH2]CCC)([CH2]CCC)[CH2]OC(C)C]

Under dry conditions, sodium hydride (250 mg, 6.25 mmol, 60% dispersion in mineral oil) was dissolved in DMF (20 mL) and cooled to 0° C. Propan-2-ol (478 μL, 6.25 mmol) was added dropwise and stirred for 5 min before adding tributyl(iodomethyl)stannane (1.66 mL, 5.00 mmol) dropwise. The ice bath was removed and after stirring for 1 h, the reaction was quenched with H₂O (15 mL), diluted with aqueous 5% LiCl (10 mL) and extracted with DCM (2×20 mL). The combined organic layers were washed with aqueous 5% LiCl, dried over anhydrous Na₂SO₄, filtered, and concentrated to dryness. The residue was purified by silica gel chromatography (10% EtOAc/hexanes) to provide the title compound in 95% yield.

Intermediate 60:
Tributyl(cyclobutoxymethyl)stannane

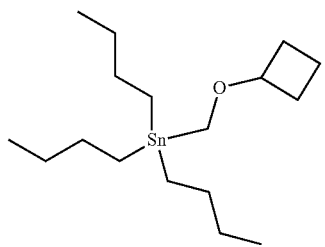 [SMILES: CCC[CH2][Sn]([CH2]CCC)([CH2]CCC)[CH2]OC1CCC1]

The title compound (100% yield) was prepared as described for the synthesis of Intermediate 59 using cyclobutanol in place of propan-2-ol.

Intermediate 61: 1-((S*)-1-(2-((S)-Amino(4,4-difluorocyclohexyl)methyl)imidazo[1,2-b]pyridazin-7-yl)-2-cyclobutoxyethyl)-5,5-difluorotetrahydropyrimidin-2(1H)-one

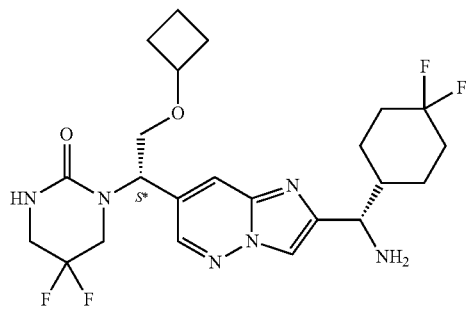 [SMILES: N[C@H](c1cn2ncc([C@@H](COC3CCC3)N3CC(F)(F)CNC3=O)cc2n1)C1CCC(F)(F)CC1]

Step A: tert-Butyl ((S)-(7-((S*)-1-(((R)-tert-butylsulfinyl)amino)-2-cyclobutoxyethyl)imidazo[1,2-b]pyridazin-2-yl)(4,4-difluorocyclohexyl)methyl)carbamate. The title compound (50% yield) was synthesized in a manner analogous to Intermediate 3 Step A using tributyl(cyclobutoxymethyl)stannane (Intermediate 60) in place of tributyl(methoxymethyl)stannane.

Step B: tert-Butyl ((S)-(7-((S*)-1-amino-2-cyclobutoxyethyl)imidazo[1,2-b]pyridazin-2-yl)(4,4-difluorocyclohexyl)methyl)carbamate. The title compound (94% yield) was prepared as described for the synthesis of Intermediate 9 using tert-butyl ((S)-(7-((S*)-1-(((R)-tert-butylsulfinyl)amino)-2-cyclobutoxyethyl)imidazo[1,2-b]pyridazin-2-yl)(4,4-difluorocyclohexyl)methyl)carbamate (Step A) in place of tert-butyl ((R)-1-(7-((S*)-1-(((R)-tert-butylsulfinyl)amino)-2-methoxyethyl)imidazo[1,2-b]pyridazin-2-yl)-2-((1,1,1-trifluoro-2-methylpropan-2-yl)oxy)ethyl)carbamate.

Step C: tert-Butyl ((S)-(7-((S*)-2-cyclobutoxy-1-((3-(1,3-dioxoisoindolin-2-yl)-2,2-difluoropropyl)amino)ethyl)imidazo[1,2-b]pyridazin-2-yl)(4,4-difluorocyclohexyl)methyl)carbamate. The title compound (78% yield) was prepared as described for the synthesis of Intermediate 2 Step A using tert-butyl ((S)-(7-((S*)-1-amino-2-cyclobutoxyethyl)imidazo[1,2-b]pyridazin-2-yl)(4,4-difluorocyclohexyl)methyl)carbamate (Step B) in place of tert-butyl ((S)-(7-((R)-amino(cyclopropyl)methyl)imidazo[1,2-b]pyridazin-2-yl)(4,4-difluorocyclohexyl)methyl)carbamate.

Step D: tert-Butyl ((S)-(7-((S*)-1-((3-amino-2,2-difluoropropyl)amino)-2-cyclobutoxyethyl)imidazo[1,2-b]pyridazin-2-yl)(4,4-difluorocyclohexyl)methyl)carbamate. The title compound (90% yield) was prepared as described for the synthesis of Intermediate 2 Step B using tert-butyl ((S)-(7-((S*)-2-cyclobutoxy-1-((3-(1,3-dioxoisoindolin-2-yl)-2,2-difluoropropyl)amino)ethyl)imidazo[1,2-b]pyridazin-2-yl)(4,4-difluorocyclohexyl)methyl)carbamate (Step C) in place of tert-butyl ((S)-(7-((R)-cyclopropyl((3-(1,3-dioxoisoindolin-2-yl)-2,2-difluoropropyl)amino)methyl)imidazo[1,2-b]pyridazin-2-yl)(4,4-difluorocyclohexyl)methyl)carbamate.

Step E: tert-Butyl ((S)-(7-((S*)-2-cyclobutoxy-1-(5,5-difluoro-2-oxotetrahydropyrimidin-1(2H)-yl)ethyl)imidazo[1,2-b]pyridazin-2-yl)(4,4-difluorocyclohexyl)methyl)carbamate. The title compound (66% yield) was prepared as described for the synthesis of Intermediate 2 Step C using tert-butyl ((S)-(7-((S*)-1-((3-amino-2,2-difluoropropyl)amino)-2-cyclobutoxyethyl)imidazo[1,2-b]pyridazin-2-yl)(4,4-difluorocyclohexyl)methyl)carbamate (Step D) in place of tert-butyl ((S)-(7-((R)-((3-amino-2,2-difluoropropyl)amino)(cyclopropyl)methyl)imidazo[1,2-b]pyridazin-2-yl)(4,4-difluorocyclohexyl)methyl)carbamate.

Step F: 1-((S*)-1-(2-((S)-Amino(4,4-difluorocyclohexyl)methyl)imidazo[1,2-b]pyridazin-7-yl)-2-cyclobutoxyethyl)-5,5-difluorotetrahydropyrimidin-2(1H)-one. The title compound was prepared as described for the synthesis of Intermediate 2 Step D using tert-butyl ((S)-(7-((S*)-2-cyclobutoxy-1-(5,5-difluoro-2-oxotetrahydropyrimidin-1(2H)-yl)ethyl)imidazo[1,2-b]pyridazin-2-yl)(4,4-difluorocyclohexyl)methyl)carbamate (Step E) in place of tert-butyl ((S)-(7-((R)-cyclopropyl(5,5-difluoro-2-oxotetrahydropyrimidin-1(2H)-yl)methyl)imidazo[1,2-b]pyridazin-2-yl)(4,4-difluorocyclohexyl)methyl)carbamate and adding DCM (2 mL) as a co-solvent, and the residue was used without further purification (82% yield).

Intermediate 62: 1-((S*)-1-(2-((S)-Amino(4,4-difluorocyclohexyl)methyl)imidazo[1,2-b]pyridazin-7-yl)-2-isopropoxyethyl)-5,5-difluorotetrahydropyrimidin-2(1H)-one

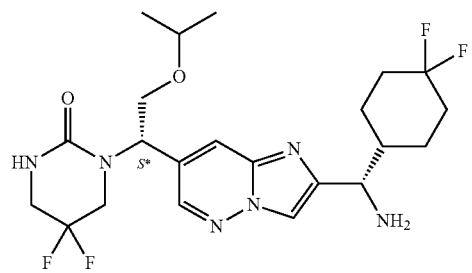 [SMILES: CC(C)OC[C@H](c1cnn2cc([C@@H](N)C3CCC(F)(F)CC3)nc2c1)N1CC(F)(F)CNC1=O]

The title compound (27% yield) was prepared as described for the synthesis of Intermediate 61 using tributyl(isopropoxymethyl)stannane (Intermediate 59) in place of tributyl(cyclobutoxymethyl)stannane.

Intermediate 63: 1-((R*)-(2-((S)-Amino(4,4-difluorocyclohexyl)methyl)imidazo[1,2-b]pyridazin-7-yl)(tetrahydro-2H-pyran-4-yl)methyl)-5,5-difluorotetrahydropyrimidin-2(1H)-one

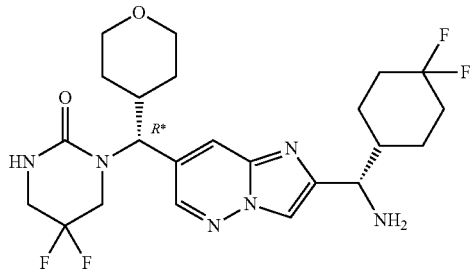 [SMILES: N[C@H](c1cn2ncc([C@@H](C3CCOCC3)N3CC(F)(F)CNC3=O)cc2n1)C1CCC(F)(F)CC1]

185

Step A: tert-Butyl ((S)-(7-((R*)—(((S)-tert-butylsulfinyl)amino)(tetrahydro-2H-pyran-4-yl)methyl)imidazo[1,2-b]pyridazin-2-yl)(4,4-difluorocyclohexyl)methyl)carbamate. A solution of tert-butyl ((S)-(7-((E)-(((S)-tert-butylsulfinyl)imino)methyl)imidazo[1,2-b]pyridazin-2-yl)(4,4-difluorocyclohexyl)methyl)carbamate (3.00 g, 6.03 mmol) in CH$_2$Cl$_2$ (60 mL) was cooled to −78° C. then tetrahydropyran-4-yl magnesium bromide (25 mL, 0.5 M in THF, 13 mmol) was added dropwise. The reaction was stirred for 20 min then warmed to 0° C. The reaction was stirred at this temperature for 30 min then another portion of tetrahydropyran-4-yl magnesium bromide (12 mL, 0.5 M in THF, 6.0 mmol) was added. The reaction was stirred at 0° C. for 1 h then another portion of tetrahydropyran-4-yl magnesium bromide (6.0 mL, 0.5 M in THF, 3.0 mmol) was added. The reaction was stirred at 0° C. for 1 h then quenched with acetic acid (1.4 mL, 24 mmol), diluted with saturated aqueous NaHCO$_3$, and the layers were separated. The aqueous phase was extracted with CH$_2$Cl$_2$ then the combined organic layers were washed with brine, dried over anhydrous Na$_2$SO$_4$, filtered, and concentrated under reduced pressure. The two diastereoisomers that resulted were purified and separated by silica gel chromatography (30-60% acetone/hexanes). The major diastereomer (second eluting peak) was further purified by silica gel chromatography (50-60% acetone/hexanes with 0.1% TEA) (21% yield) and was designated as the R* isomer.

Step B: tert-Butyl ((S)-(7-((R*)-amino(tetrahydro-2H-pyran-4-yl)methyl)imidazo[1,2-b]pyridazin-2-yl)(4,4-difluorocyclohexyl)methyl)carbamate. The title compound (86% yield) was prepared in a manner analogous to Intermediate 9 using tert-butyl ((S)-(7-((R*)—(((S)-tert-butylsulfinyl)amino)(tetrahydro-2H-pyran-4-yl)methyl)imidazo[1,2-b]pyridazin-2-yl)(4,4-difluorocyclohexyl)methyl)carbamate (Step A) in place of tert-butyl ((R)-1-(7-((S*)-1-(((R)-tert-butylsulfinyl)amino)-2-methoxyethyl)imidazo[1,2-b]pyridazin-2-yl)-2-((1,1,1-trifluoro-2-methylpropan-2-yl)oxy)ethyl)carbamate.

Step C: tert-Butyl ((S)-(7-((R*)-(5,5-difluoro-2-oxotetrahydropyrimidin-1(2H)-yl)(tetrahydro-2H-pyran-4-yl)methyl)imidazo[1,2-b]pyridazin-2-yl)(4,4-difluorocyclohexyl)methyl)carbamate. The title compound was prepared in a manner analogous to Intermediate 10 using tert-butyl ((S)-(7-((R*)-amino(tetrahydro-2H-pyran-4-yl)methyl)imidazo[1,2-b]pyridazin-2-yl)(4,4-difluorocyclohexyl)methyl)carbamate (Step B) in place of tert-butyl ((R)-1-(7-((S*)-1-amino-2-methoxyethyl)imidazo[1,2-b]pyridazin-2-yl)-2-((1,1,1-trifluoro-2-methylpropan-2-yl)oxy)ethyl)carbamate. Purification by silica gel chromatography (20-100% (10% MeOH/EtOAc)/(0.1% TEA/hexanes)) afforded the title compound in 29% yield.

Step D: 1-((R*)-2-((S)-Amino(4,4-difluorocyclohexyl)methyl)imidazo[1,2-b]pyridazin-7-yl)(tetrahydro-2H-pyran-4-yl)methyl)-5,5-difluorotetrahydropyrimidin-2(1H)-one. To a solution of tert-butyl ((S)-(7-((R*)-(5,5-difluoro-2-oxotetrahydropyrimidin-1(2H)-yl)(tetrahydro-2H-pyran-4-yl)methyl)imidazo[1,2-b]pyridazin-2-yl)(4,4-difluorocyclohexyl)methyl)carbamate (0.21 g, 0.32 mmol, Step C) in CH$_2$Cl$_2$ (0.2 mL) was added TFA (1.0 mL, 13 mmol). The reaction mixture was stirred at rt for 10 min then diluted with H$_2$O and Na$_2$CO$_3$ was added until the pH of the mixture was pH 10. The mixture was extracted with 4:1 CH$_2$Cl$_2$:IPA, then the combined organics were dried over anhydrous Na$_2$SO$_4$, filtered, and concentrated under reduced pressure to afford the title compound in 57% yield.

186

Intermediate 64: 1,3-Dioxoisoindolin-2-yl 2-((1,1,1-trifluoro-2-methylpropan-2-yl)oxy)propanoate

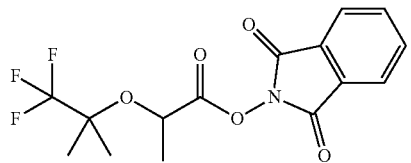 [SMILES: CC(OC(C)(C)C(F)(F)F)C(=O)ON1C(=O)c2ccccc2C1=O]

Step A: 2-((1,1,1-Trifluoro-2-methylpropan-2-yl)oxy)propanoic acid. The title compound was synthesized in a manner analogous to Intermediate 37 Step A using 1,1,1-trifluoro-2-methylpropan-2-ol in place of (R)-1,1,1-trifluoropropan-2-ol and 2-bromopropanoic acid in place of (S)-2-bromopropanoic acid and was used without further purification.

Step B: 1,3-Dioxoisoindolin-2-yl 2-((1,1,1-trifluoro-2-methylpropan-2-yl)oxy)propanoate. The title compound (18% yield) was synthesized in a manner analogous to Intermediate 55 Step B using 2-((1,1,1-trifluoro-2-methylpropan-2-yl)oxy)propanoic acid (Step A) in place of 2-cyclopropoxypropanoic acid.

Intermediate 65: 1-((1S)-1-(2-((1R*)-1-Amino-2-((1,1,1-trifluoro-2-methylpropan-2-yl)oxy)propyl)imidazo[1,2-b]pyridazin-7-yl)-2-methoxyethyl)-5,5-difluorotetrahydropyrimidin-2(1H)-one

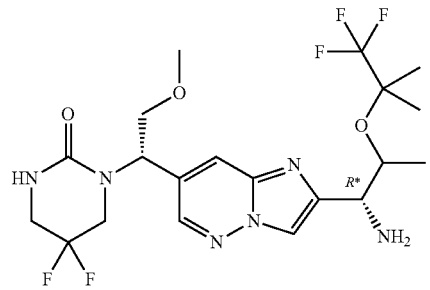 [SMILES: COC[C@H](c1cnn2cc([C@@H](N)C(C)OC(C)(C)C(F)(F)F)nc2c1)N1CC(F)(F)CNC1=O]

Step A: (S)—N-((1R*)-1-(7-((S)-1-(5,5-Difluoro-2-oxotetrahydropyrimidin-1(2H)-yl)-2-methoxyethyl)imidazo[1,2-b]pyridazin-2-yl)-2-((1,1,1-trifluoro-2-methylpropan-2-yl)oxy)propyl)-2,4,6-trimethylbenzenesulfinamide. The title compound (45% yield) was synthesized in a manner analogous to Intermediate 57 Step A using 1,3-dioxoisoindolin-2-yl 2-((1,1,1-trifluoro-2-methylpropan-2-yl)oxy)propanoate (Intermediate 64) in place of 1,3-dioxoisoindolin-2-yl 2-cyclopropoxypropanoate.

Step B: 1-((1S)-1-(2-((1R*)-1-Amino-2-((1,1,1-trifluoro-2-methylpropan-2-yl)oxy)propyl)imidazo[1,2-b]pyridazin-7-yl)-2-methoxyethyl)-5,5-difluorotetrahydropyrimidin-2(1H)-one. The title compound was synthesized in a manner analogous to Intermediate 9 using (S)—N-((1R*)-1-(7-((S)-1-(5,5-difluoro-2-oxotetrahydropyrimidin-1(2H)-yl)-2-methoxyethyl)imidazo[1,2-b]pyridazin-2-yl)-2-((1,1,1-trifluoro-2-methylpropan-2-yl)oxy)propyl)-2,4,6-trimethylbenzenesulfinamide (Step A) in place of tert-butyl ((R)-1-(7-((S*)-1-(((R)-tert-butylsulfinyl)amino)-2-methoxyethyl)imidazo[1,2-b]pyridazin-2-yl)-2-((1,1,1-trifluoro-2-methylpropan-2-yl)oxy)ethyl)carbamate and was used without further purification (100% yield).

Intermediate 66: 1-((R)-(2-((R)-1-Amino-2-((1,1,1-trifluoro-2-methylpropan-2-yl)oxy)ethyl)imidazo[1,2-b]pyridazin-7-yl)(cyclopropyl)methyl)-5,5-difluorotetrahydropyrimidin-2(1H)-one

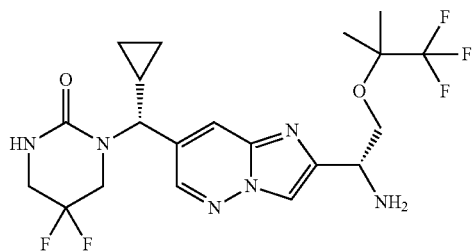 [SMILES: CC(C)(OC[C@H](N)c1cn2ncc([C@@H](C3CC3)N3CC(F)(F)CNC3=O)cc2n1)C(F)(F)F]

Step A: (S,E)-N-(Cyclopropylmethylene)-2-methylpropane-2-sulfinamide. To a mixture of cyclopropanecarboxaldehyde (23.7 mL, 317.7 mmol) and (S)-2-methylpropane-2-sulfinamide (35 g, 289 mmol) in DCM (271 mL) were added $CuSO_4$ (138 g, 866 mmol) and PPTS (3.63 g, 14.4 mmol) and the resulting mixture stirred at rt for 40 h. Then, additional cyclopropanecarboxaldehyde (2.15 mL, 28.9 mmol) and $CuSO_4$ (23 g, 140 mmol) were added. The mixture was stirred for 2.5 d at rt and then filtered through diatomaceous earth (e.g., Celite®), and the filtrate was concentrated under reduced pressure. The concentrate was filtered through a pad of silica gel, rinsing with 40% EtOAc/hexanes. The filtrate was concentrated to dryness to provide the title compound as a pale-yellow oil (86% yield).

Step B: N-(5-((R)—(((S)-tert-Butylsulfinyl)amino)(cyclopropyl)methyl)-6-chloropyridazin-3-yl)pivalamide. To a solution of 2,2,6,6-tetramethylpiperidinylmagnesium chloride lithium chloride complex in THF/toluene (75 mL, 61 mmol, 0.82 M) at −40° C. was added a solution of N-(6-chloropyridazin-3-yl)pivalamide (5.00 g, 23.4 mmol, Intermediate 32, Step A) in THF (50 mL) dropwise over 20 min via an addition funnel. The residue in the addition funnel was rinsed into the reaction mixture using an additional aliquot of THF (10 mL). The resulting solution was stirred at −40° C. for 3 h, then (S,E)-N-(cyclopropylmethylene)-2-methylpropane-2-sulfinamide (5.12 g, 28.1 mmol, Step A) was added. The solution was removed from the cold bath and allowed to warm to rt. After 1 h, additional (S,E)-N-(cyclopropylmethylene)-2-methylpropane-2-sulfinamide (1.28 g, 7.02 mmol, Step A) was added and the mixture was stirred at rt overnight. After that time, saturated aqueous $NH_4Cl$ was added and the mixture was extracted with EtOAc (3×). The organic layers were combined, washed with brine, dried over anhydrous $MgSO_4$, filtered, and concentrated to dryness. The residue was purified by silica gel chromatography (20-50% acetone/hexanes) to provide the title compound as a light-yellow foam (65% yield).

Step C: (R)—N-(5-(Amino(cyclopropyl)methyl)-6-chloropyridazin-3-yl)pivalamide. To a mixture of N-(5-((R)—(((S)-tert-butylsulfinyl)amino)(cyclopropyl)methyl)-6-chloropyridazin-3-yl)pivalamide (6.00 g, 15.5 mmol, Step B) in EtOAc (77.5 mL) was added 4 M HCl in 1,4-dioxane (15.5 mL, 62 mmol) and the resulting mixture stirred at rt for 3 d. The mixture was then poured into water (200 mL) and diluted with hexanes (150 mL). The layers were separated and the organic layer was extracted with 0.05 M aqueous HCl (50 mL). The aqueous layers were combined and washed with hexanes (50 mL). Then, the aqueous layers were poured into a flask with EtOAc (100 mL) and the pH of the solution was adjusted to pH 10 by the addition of 3 M aqueous NaOH. The layers were separated and the aqueous layer was further extracted with EtOAc (4×50 mL). The EtOAc layers were combined, dried over anhydrous $Na_2SO_4$, filtered, and concentrated to dryness to provide the title compound as a foam (86% yield).

Step D: (R)—N-(6-Chloro-5-(cyclopropyl((3-(1,3-dioxoisoindolin-2-yl)-2,2-difluoropropyl)amino)methyl)pyridazin-3-yl)pivalamide. A mixture of (R)—N-(5-(amino(cyclopropyl)methyl)-6-chloropyridazin-3-yl)pivalamide (2.0 g, 7.1 mmol, Step C), 3-(1,3-dioxoisoindolin-2-yl)-2,2-difluoropropyl trifluoromethanesulfonate (4.22 g, 11.3 mmol), DIPEA (1.85 mL, 10.6 mmol) and ACN (24 mL) was heated at 55° C. for 2.5 d. The mixture was cooled to rt and concentrated to dryness. The residue was purified by silica gel chromatography (10-50% acetone/hexanes (0.1% TEA)) to provide the title compound as a white solid (78% yield).

Step E: (R)-2-(3-(((6-Amino-3-chloropyridazin-4-yl)(cyclopropyl)methyl)amino)-2,2-difluoropropyl)isoindoline-1,3-dione. To a solution of (R)—N-(6-chloro-5-(cyclopropyl ((3-(1,3-dioxoisoindolin-2-yl)-2,2-difluoropropyl)amino) methyl)pyridazin-3-yl)pivalamide (1 g, 2 mmol, Step D) in MeOH (15 mL) was added $H_2SO_4$ (15 mL, 45 mmol, 3 M in water) and the resulting solution was heated at 55° C. for 8 h. The mixture was cooled to rt and diluted with half-saturated brine (50 mL) and EtOAc, and then the pH of the mixture was adjusted to pH 12 by the addition of 3 M aqueous NaOH. The layers were separated and the aqueous layer was further extracted with EtOAc (50 mL) followed by DCM (2×30 mL). The organic layers were combined, dried over anhydrous $Na_2SO_4$, filtered, and concentrated to dryness to provide the title compound (68% yield).

Step F: (R)—$N^1$-((6-Amino-3-chloropyridazin-4-yl)(cyclopropyl)methyl)-2,2-difluoropropane-1,3-diamine. The title compound was prepared as described for Intermediate 2 Step B using (R)-2-(3-(((6-amino-3-chloropyridazin-4-yl)(cyclopropyl)methyl)amino)-2,2-difluoropropyl)isoindoline-1,3-dione (Step E) in place of tert-butyl ((S)-(7-((R)-cyclopropyl((3-(1,3-dioxoisoindolin-2-yl)-2,2-difluoropropyl)amino)methyl)imidazo[1,2-b]pyridazin-2-yl)(4,4-difluorocyclohexyl)methyl)carbamate and was used without further purification.

Step G: (R)-1-((6-Amino-3-chloropyridazin-4-yl)(cyclopropyl)methyl)-5,5-difluorotetrahydropyrimidin-2(1H)-one. The title compound (69% yield) was prepared as described for Intermediate 15 Step C using (R)—$N^1$-((6-amino-3-chloropyridazin-4-yl)(cyclopropyl)methyl)-2,2-difluoropropane-1,3-diamine (Step F) in place of tert-butyl ((S)-(7-((S)-1-((3-amino-2,2-difluoropropyl)amino)-2-cyclopropoxyethyl)imidazo[1,2-b]pyridazin-2-yl)(4,4-difluorocyclohexyl)methyl)carbamate.

Step H: tert-Butyl ((R)-1-(6-chloro-7-((R)-cyclopropyl(5,5-difluoro-2-oxotetrahydropyrimidin-1(2H)-yl)methyl)imidazo[1,2-b]pyridazin-2-yl)-2-((1,1,1-trifluoro-2-methylpropan-2-yl)oxy)ethyl)carbamate. The title compound was prepared as described for Intermediate 41 Step A using (R)-1-((6-amino-3-chloropyridazin-4-yl)(cyclopropyl) methyl)-5,5-difluorotetrahydropyrimidin-2(1H)-one (Step G) in place of (S)-1-(1-(6-amino-3-chloropyridazin-4-yl)-2-methoxyethyl)-5,5-difluorotetrahydropyrimidin-2(1H)-one and tert-butyl (S)-(4-iodo-3-oxo-1-((1,1,1-trifluoro-2-methylpropan-2-yl)oxy)butan-2-yl)carbamate in place of tert-butyl ((3S,4R)-1-iodo-2-oxo-4-(((R)-1,1,1-trifluoropropan- 2-yl)oxy)pentan-3-yl)carbamate. In addition, the reaction mixture was heated at 50° C. for 48 h instead of 16 h and purified by silica gel chromatography (5-60% acetone/hexanes (0.1% TEA)) to provide the title compound in 79% yield.

Step I: tert-Butyl ((R)-1-(7-((R)-cyclopropyl(5,5-difluoro-2-oxotetrahydropyrimidin-1(2H)-yl)methyl)imidazo[1,2-b]pyridazin-2-yl)-2-((1,1,1-trifluoro-2-methylpropan-2-yl)oxy)ethyl)carbamate. To a Parr shaker bottle was added 10% Pd/C (469 mg, 3.83 mmol) and MeOH (10 mL). Then, a solution of tert-butyl ((R)-1-(6-chloro-7-((R)-cyclopropyl(5,5-difluoro-2-oxotetrahydropyrimidin-1(2H)-yl)methyl)imidazo[1,2-b]pyridazin-2-yl)-2-((1,1,1-trifluoro-2-methylpropan-2-yl)oxy)ethyl)carbamate (385 mg, 0.63 mmol, Step H) in MeOH (20 mL) was added and the bottle was placed under 50 psi H₂ on the Parr shaker for 17 h. The bottle was sparged with air, filtered through diatomaceous earth (e.g., Celite®), and the filtrate was concentrated under reduced pressure. The residue was purified by silica gel chromatography (5-50% acetone/hexanes (0.1% TEA)) to provide the title compound as a light-yellow oil (5% yield).

Step J: 1-((R)-(2-((R)-1-Amino-2-((1,1,1-trifluoro-2-methylpropan-2-yl)oxy)ethyl)imidazo[1,2-b]pyridazin-7-yl)(cyclopropyl)methyl)-5,5-difluorotetrahydropyrimidin-2(1H)-one. The title compound (100% yield) was prepared as described in Intermediate 20 Step C using tert-butyl ((R)-1-(7-((R)-cyclopropyl(5,5-difluoro-2-oxotetrahydropyrimidin-1(2H)-yl)methyl)imidazo[1,2-b]pyridazin-2-yl)-2-((1,1,1-trifluoro-2-methylpropan-2-yl)oxy)ethyl)carbamate (Step I) in place of tert-butyl (S)-((7-((5,5-difluoro-2-oxotetrahydropyrimidin-1(2H)-yl)methyl)imidazo[1,2-b]pyridazin-2-yl)(4,4-difluorocyclohexyl)methyl)carbamate.

Intermediate 67: 1-((R)-1-(2-((S)-Amino(4,4-difluorocyclohexyl)methyl)imidazo[1,2-b]pyridazin-7-yl)ethyl)-5,5-difluorotetrahydropyrimidin-2(1H)-one

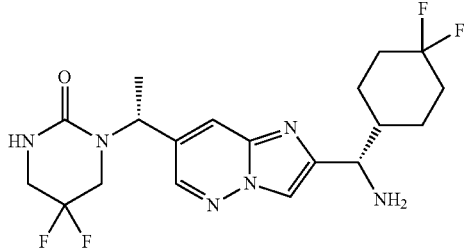 [SMILES: C[C@H](c1cnn2cc([C@@H](N)C3CCC(F)(F)CC3)nc2c1)N1CC(F)(F)CNC1=O]

Step A: tert-Butyl ((S)-(6-chloro-7-((R)-1-(5,5-difluoro-2-oxotetrahydropyrimidin-1(2H)-yl)ethyl)imidazo[1,2-b]pyridazin-2-yl)(4,4-difluorocyclohexyl)methyl)carbamate. An oven dried vial was charged with (R)-1-(1-(6-amino-3-chloropyridazin-4-yl)ethyl)-5,5-difluorotetrahydropyrimidin-2(1H)-one (79 mg, 0.27 mmol, Intermediate 84), activated 4 Å mol sieves and DMA (1.2 mL). A separate solution of tert-butyl (S)-(1-(4,4-difluorocyclohexyl)-3-iodo-2-oxopropyl)carbamate (451 mg, 1.08 mmol) in DMA (6 mL) was added and the reaction mixture was heated to 50° C. for 2.5 d under an a N₂ atmosphere. After this time, an additional aliquot of tert-butyl (S)-(1-(4,4-difluorocyclohexyl)-3-iodo-2-oxopropyl)carbamate (451 mg, 1.08 mmol) in DMA (3 mL) was added and the reaction mixture was heated at 50° C. for 1 h. The reaction mixture was then cooled to rt, diluted with EtOAc, filtered, and the collected solids were rinsed with EtOAc and DCM. To the filtrate was added ¼ saturated brine (50 mL) and the layers were separated. The aqueous layer was further extracted with EtOAc (20 mL), then the organic layers were combined, dried over anhydrous Na₂SO₄, filtered, and concentrated to dryness. The residue was purified by silica gel chromatography (5-60% acetone/hexanes (0.1% TEA)) to provide the title compound (100% yield).

Step B: 1-((R)-1-(2-((S)-Amino(4,4-difluorocyclohexyl)methyl)imidazo[1,2-b]pyridazin-7-yl)ethyl)-5,5-difluorotetrahydropyrimidin-2(1H)-one. To a Parr shaker bottle was added 10% Pd/C (250 mg, 2.04 mmol) and MeOH (10 mL). Then, a solution of tert-butyl ((S)-(6-chloro-7-((R)-1-(5,5-difluoro-2-oxotetrahydropyrimidin-1(2H)-yl)ethyl)imidazo[1,2-b]pyridazin-2-yl)(4,4-difluorocyclohexyl)methyl)carbamate (189 mg, 0.34 mmol, Step A) in MeOH (15 mL) was added followed by NH₄OH (0.28 mL, 2.12 mmol, 28-30% in water) and the bottle was placed under 50 psi H₂ on the Parr shaker for 3.5 h. The bottle was sparged with air and concentrated to dryness. The residue was dissolved in DCM (6 mL), cooled to 0° C. in an ice-bath and then TFA (2 mL, 26 mmol) was added. The resulting mixture was stirred at rt for 75 min, then concentrated to dryness to provide the title compound (99% yield), which was used without further purification.

Intermediate 68: 1-((S)-1-(2-((R)-1-Amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one

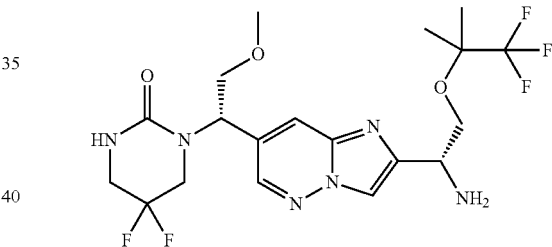

Step A: tert-Butyl ((R)-1-(6-chloro-7-((S)-1-(5,5-difluoro-2-oxotetrahydropyrimidin-1(2H)-yl)-2-methoxyethyl)imidazo[1,2-b]pyridazin-2-yl)-2-((1,1,1-trifluoro-2-methylpropan-2-yl)oxy)ethyl)carbamate. The title compound (50% yield) was prepared as described in Intermediate 67 Step A using (S)-1-(1-(6-amino-3-chloropyridazin-4-yl)-2-methoxyethyl)-5,5-difluorotetrahydropyrimidin-2(1H)-one (Intermediate 35) in place of (R)-1-(1-(6-amino-3-chloropyridazin-4-yl)ethyl)-5,5-difluorotetrahydropyrimidin-2(1H)-one and tert-butyl (S)-(4-iodo-3-oxo-1-((1,1,1-trifluoro-2-methylpropan-2-yl)oxy)butan-2-yl)carbamate in place of tert-butyl (S)-(1-(4,4-difluorocyclohexyl)-3-iodo-2-oxopropyl)carbamate.

Step B: tert-Butyl ((R)-1-(7-((S)-1-(5,5-difluoro-2-oxotetrahydropyrimidin-1(2H)-yl)-2-methoxyethyl)imidazo[1,2-b]pyridazin-2-yl)-2-((1,1,1-trifluoro-2-methylpropan-2-yl)oxy)ethyl)carbamate. A vial was charged with tert-butyl ((R)-1-(6-chloro-7-((S)-1-(5,5-difluoro-2-oxotetrahydropyrimidin-1(2H)-yl)-2-methoxyethyl)imidazo[1,2-b]pyridazin-2-yl)-2-((1,1,1-trifluoro-2-methylpropan-2-yl)oxy)ethyl)carbamate (127 mg, 0.21 mmol, Step A), EtOH (20 mL), Pd/C (63 mg, 0.52 mmol, 10 wt % Pd) and ammonium formate (130 mg, 2.07 mmol). The vial was heated to 80° C., stirred for 6 h, then stirred at rt overnight.

The reaction mixture was filtered through a pad of diatomaceous earth (e.g., Celite®), and the solids were washed with EtOH. The combined organic layers were concentrated to dryness, then partitioned between DCM (20 mL) and saturated aqueous NaHCO₃ (15 mL). The aqueous layer was further extracted with DCM (20 mL), then the organic layers were combined, dried over anhydrous Na₂SO₄, filtered and concentrated to dryness to provide the title compound (100% yield) that was used without further purification.

Step C: 1-((S)-1-(2-((R)-1-Amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2 (1H)-one. To a mixture of tert-butyl ((R)-1-(7-((S)-1-(5,5-difluoro-2-oxotetrahydropyrimidin-1(2H)-yl)-2-methoxyethyl)imidazo[1,2-b]pyridazin-2-yl)-2-((1,1,1-trifluoro-2-methylpropan-2-yl)oxy)ethyl)carbamate (120 mg, 0.21 mmol, Step B) in DCM (6.7 mL) at 0° C. was added TFA (6 mL) and the resulting solution was stirred at 0° C. for 1.5 h. The mixture was concentrated to dryness and azeotroped with toluene to provide the title compound in 100% yield, which was used without further purification.

Intermediate 69: tert-Butyl (R)-(1-(dimethyl(oxo)-λ⁶-sulfaneylidene)-7,7,7-trifluoro-6,6-dimethyl-2-oxoheptan-3-yl)carbamate

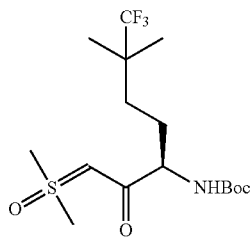 [SMILES: CC(C)(C)OC(=O)N[C@H](CCC(C)(C)C(F)(F)F)C(=O)C=S(C)(C)=O]

The title compound (59% yield) was prepared as described for the synthesis of Intermediate 45 Steps C-F using (2R,5R)-2-isopropyl-3,6-dimethoxy-5-(4,4,4-trifluoro-3,3-dimethylbutyl)-2,5-dihydropyrazine (Intermediate 45, Step B second-eluting isomer) in place of (2R,5S)-2-isopropyl-3,6-dimethoxy-5-(4,4,4-trifluoro-3,3-dimethylbutyl)-2,5-dihydropyrazine in Step C.

Intermediate 70: tert-Butyl (R)-(7,7,7-trifluoro-1-iodo-6,6-dimethyl-2-oxoheptan-3-yl)carbamate

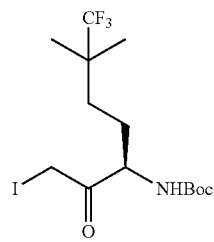 [SMILES: CC(C)(C)OC(=O)N[C@H](CCC(C)(C)C(F)(F)F)C(=O)CI]

The title compound was prepared as described for the synthesis of Intermediate 46 using tert-butyl (R)-(1-(dimethyl(oxo)-λ⁶-sulfaneylidene)-7,7,7-trifluoro-6,6-dimethyl-2-oxoheptan-3-yl)carbamate (Intermediate 69) in place of tert-butyl (S)-(1-(dimethyl(oxo)-λ⁶-sulfaneylidene)-7,7,7-trifluoro-6,6-dimethyl-2-oxoheptan-3-yl)carbamate in Step A.

Intermediate 71: 1-((S)-1-(2-((R)-1-Amino-5,5,5-trifluoro-4,4-dimethylpentyl)imidazo[1,2-b]pyridazin-7-yl)-2-methoxyethyl)-5,5-difluorotetrahydropyrimidin-2(1H)-one

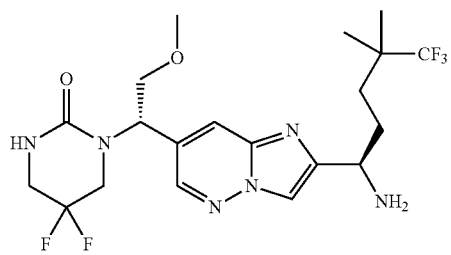 [SMILES: COC[C@H](c1cnn2cc([C@H](N)CCC(C)(C)C(F)(F)F)nc2c1)N1CC(F)(F)CNC1=O]

The title compound was prepared as described for the synthesis of Intermediate 44, using tert-butyl (R)-(7,7,7-trifluoro-1-iodo-6,6-dimethyl-2-oxoheptan-3-yl)carbamate (Intermediate 70) in place of tert-butyl (S)-(6,6,6-trifluoro-1-iodo-5,5-dimethyl-2-oxohexan-3-yl)carbamate in Step A. In step B, instead of an aqueous extraction, the residue was directly purified by silica gel chromatography (5-70% acetone/hexanes (with 0.1% TEA)), and in step C, the mixture was concentrated to dryness and used directly without aqueous workup or further purification.

Intermediate 72: 1,3-Dioxoisoindolin-2-yl 4,4-difluoro-3,3-dimethylpentanoate

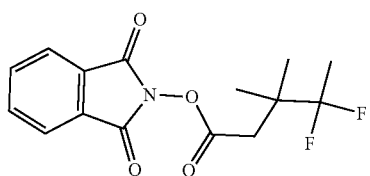 [SMILES: CC(F)(F)C(C)(C)CC(=O)ON1C(=O)c2ccccc2C1=O]

A mixture of 4,4-difluoro-3,3-dimethylpentanoic acid (1 g, 6.02 mmol), N-hydroxyphthalimide (1.11 g, 6.62 mmol), EDCI (1.27 g, 6.62 mmol) and DMAP (74 mg, 0.6 mmol) in DCM (17 mL) was stirred at rt overnight. After that time, the mixture was concentrated to dryness and the residue was purified by silica gel chromatography (10-90% EtOAc/hexanes) to provide the title compound as a white solid (44% yield).

Intermediate 73: 1-((S)-1-(2-((S)-1-Amino-5,5,5-trifluoro-4,4-dimethylpentyl)imidazo[1,2-b]pyridazin-7-yl)-2-methoxyethyl)-5,5-difluorotetrahydropyrimidin-2(1H)-one-4,4,6,6-$d_4$

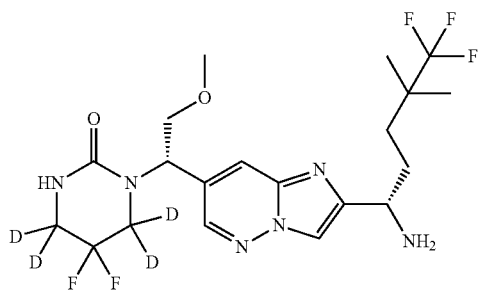 [SMILES: [2H]C1([2H])NC(=O)N([C@H](COC)c2cnn3cc([C@@H](N)CCC(C)(C)C(F)(F)F)nc3c2)C([2H])([2H])C1(F)F]

Step A: (S)—N-(6-Chloro-5-(1-((3-(1,3-dioxoisoindolin-2-yl)-2,2-difluoropropyl-1,1,3,3-$d_4$)amino)-2-methoxyethyl)pyridazin-3-yl)pivalamide. The title compound was prepared as described in Intermediate 35 Step B using 3-(1,3-dioxoisoindolin-2-yl)-2,2-difluoropropyl-1,1,3,3-$d_4$ trifluoromethanesulfonate (Intermediate 27) in place of 3-(1,3-dioxoisoindolin-2-yl)-2,2-difluoropropyl trifluoromethanesulfonate. The reaction was heated at 55° C. for 45 h and subsequently heated at 60° C. for 54 h with no additional aliquots of starting materials added to provide the title compound as a white foam (79% yield).

Step B: (S)-2-(3-((1-(6-Amino-3-chloropyridazin-4-yl)-2-methoxyethyl)amino)-2,2-difluoropropyl-1,1,3,3-$d_4$)isoindoline-1,3-dione. The title compound was prepared as described in Intermediate 35 Step C using (S)—N-(6-chloro-5-(1-((3-(1,3-dioxoisoindolin-2-yl)-2,2-difluoropropyl-1,1,3,3-$d_4$)amino)-2-methoxyethyl)pyridazin-3-yl)pivalamide (Step A) in place of (S)—N-(6-chloro-5-(1-((3-(1,3-dioxoisoindolin-2-yl)-2,2-difluoropropyl)amino)-2-methoxyethyl)pyridazin-3-yl)pivalamide and was used without further purification.

Step C: (S)—$N^1$-(1-(6-Amino-3-chloropyridazin-4-yl)-2-methoxyethyl)-2,2-difluoropropane-1,1,3,3-$d_4$-1,3-diamine. The title compound was prepared as described in Intermediate 35 Step D using (S)-2-(3-((1-(6-amino-3-chloropyridazin-4-yl)-2-methoxyethyl)amino)-2,2-difluoropropyl-1,1,3,3-$d_4$)isoindoline-1,3-dione (Step B) in place of (S)-2-(3-((1-(6-amino-3-chloropyridazin-4-yl)-2-methoxyethyl)amino)-2,2-difluoropropyl)isoindoline-1,3-dione. The reaction mixture was stirred at rt for 1.5 h and then heated at 35° C. for 40 h to provide the title compound as a yellow oil that was used without further purification.

Step D: (S)-1-(1-(6-Amino-3-chloropyridazin-4-yl)-2-methoxyethyl)-5,5-difluorotetrahydropyrimidin-2(1H)-one-4,4,6,6-$d_4$. The title compound was prepared as described in Intermediate 35 Step E using (S)—$N^1$-(1-(6-amino-3-chloropyridazin-4-yl)-2-methoxyethyl)-2,2-difluoropropane-1,1,3,3-$d_4$-1,3-diamine (Step C) in place of (S)—$N^1$-(1-(6-amino-3-chloropyridazin-4-yl)-2-methoxyethyl)-2,2-difluoropropane-1,3-diamine, and the reaction mixture was heated at 55° C. for 3 h to provide the title compound in 5% yield.

Step E: tert-Butyl ((S)-1-(6-chloro-7-((S)-1-(5,5-difluoro-2-oxotetrahydropyrimidin-1(2H)-yl-4,4,6,6-$d_4$)-2-methoxyethyl)imidazo[1,2-b]pyridazin-2-yl)-5,5,5-trifluoro-4,4-dimethylpentyl)carbamate. The title compound was prepared as described in Intermediate 44 Step A using (S)-1-(1-(6-amino-3-chloropyridazin-4-yl)-2-methoxyethyl)-5,5-difluorotetrahydropyrimidin-2(1H)-one-4,4,6,6-$d_4$ (Step D) in place of (S)-1-(1-(6-amino-3-chloropyridazin-4-yl)-2-methoxyethyl)-5,5-difluorotetrahydropyrimidin-2(1H)-one and tert-butyl (S)-(7,7,7-trifluoro-1-iodo-6,6-dimethyl-2-oxoheptan-3-yl)carbamate (Intermediate 46) in place of tert-butyl (S)-(6,6,6-trifluoro-1-iodo-5,5-dimethyl-2-oxohexan-3-yl)carbamate. The reaction mixture was heated at 50° C. for 4.5 h to provide the title compound in 54% yield.

Step F: tert-Butyl ((5)-1-(7-((S)-1-(5,5-difluoro-2-oxotetrahydropyrimidin-1(2H)-yl-4,4,6,6-$d_4$)-2-methoxyethyl)imidazo[1,2-b]pyridazin-2-yl)-5,5,5-trifluoro-4,4-dimethylpentyl)carbamate. To a Parr shaker bottle was added 10% Pd/C (250 mg, 2.04 mmol) and tert-butyl ((5)-1-(6-chloro-7-((5)-1-(5,5-difluoro-2-oxotetrahydropyrimidin-1(2H)-yl-4,4,6,6-$d_4$)-2-methoxyethyl)imidazo[1,2-b]pyridazin-2-yl)-5,5,5-trifluoro-4,4-dimethylpentyl)carbamate (174 mg, 0.28 mmol, Step E) in MeOH (25 mL) followed by NH$_4$OH (0.11 mL, 0.85 mmol, 28-30% in water) and the bottle was placed under 50 psi H$_2$ on the Parr shaker for 3 h. The bottle was sparged with air, then the mixture was filtered, rinsed with MeOH, and the filtrate was concentrated to dryness to provide the title compound that was used without further purification.

Step G: 1-((S)-1-(2-((S)-1-Amino-5,5,5-trifluoro-4,4-dimethylpentyl)imidazo[1,2-b]pyridazin-7-yl)-2-methoxyethyl)-5,5-difluorotetrahydropyrimidin-2(1H)-one-4,4,6,6-$d_4$. A solution of tert-butyl ((S)-1-(7-((S)-1-(5,5-difluoro-2-oxotetrahydropyrimidin-1(2H)-yl-4,4,6,6-$d_4$)-2-methoxyethyl)imidazo[1,2-b]pyridazin-2-yl)-5,5,5-trifluoro-4,4-dimethylpentyl)carbamate (164 mg, 0.28 mmol, Step F) in DCM (9.4 mL) was cooled to 0° C. Then, TFA (3 mL, 39 mmol) was added and the resulting mixture stirred at rt for 4.5 h. The mixture was concentrated to dryness and the residue diluted with EtOAc (50 mL) and saturated aqueous NaHCO$_3$ (50 mL). The pH of the mixture was adjusted to pH 11 by the addition of 3 M aqueous NaOH and brine (15 mL). The layers were separated and the aqueous portion was further extracted with EtOAc (4×30 mL). The organic layers were combined, dried over anhydrous Na$_2$SO$_4$, filtered, and concentrated to dryness to provide the title compound as a light-yellow foam that was used without further purification.

Intermediate 74: 1-((S)-1-(2-((S)-1-Amino-5,5,5-trifluoro-4,4-dimethylpentyl)imidazo[1,2-b]pyridazin-7-yl)-2-cyclopropoxyethyl)-5,5-difluorotetrahydropyrimidin-2(1H)-one-4,4,6,6-$d_4$

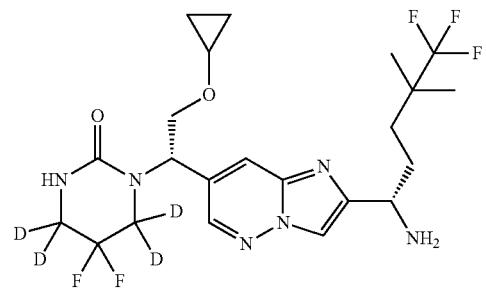 [SMILES: [2H]C1([2H])NC(=O)N([C@H](COC2CC2)c2cnn3cc([C@@H](N)CCC(C)(C)C(F)(F)F)nc3c2)C([2H])([2H])C1(F)F]

Step A: (S)—N-(6-Chloro-5-(2-cyclopropoxy-1-((3-(1,3-dioxoisoindolin-2-yl)-2,2-difluoropropyl-1,1,3,3-$d_4$)amino)ethyl)pyridazin-3-yl)pivalamide. The title compound was prepared as described in Intermediate 35 Step B using (S)—N-(5-(1-amino-2-cyclopropoxyethyl)-6-chloro-pyridazin-3-yl)pivalamide (Intermediate 36, Step A) in place of (S)—N-(5-(1-amino-2-methoxyethyl)-6-chloropyridazin-3-yl)pivalamide and 3-(1,3-dioxoisoindolin-2-yl)-2,2-difluoropropyl-1,1,3,3-d$_4$ trifluoromethanesulfonate (Intermediate 27) in place of 3-(1,3-dioxoisoindolin-2-yl)-2,2-difluoropropyl trifluoromethanesulfonate. The reaction mixture was heated at 55° C. for 46 h and then heated at 60° C. for 54 h with no additional aliquots of starting materials added to provide the title compound as a white foam (82% yield).

Step B: (S)-2-(3-((1-(6-Amino-3-chloropyridazin-4-yl)-2-cyclopropoxyethyl)amino)-2,2-difluoropropyl-1,1,3,3-d$_4$) isoindoline-1,3-dione. The title compound was prepared as described in Intermediate 35 Step C using (S)—N-(6-chloro-5-(2-cyclopropoxy-1-((3-(1,3-dioxoisoindolin-2-yl)-2,2-difluoropropyl-1,1,3,3-d$_4$)amino)ethyl)pyridazin-3-yl)pivalamide (Step A) in place of (S)—N-(6-chloro-5-(1-((3-(1,3-dioxoisoindolin-2-yl)-2,2-difluoropropyl)amino)-2-methoxyethyl)pyridazin-3-yl)pivalamide and was used without further purification.

Step C: (S)—N$^1$-(1-(6-Amino-3-chloropyridazin-4-yl)-2-cyclopropoxyethyl)-2,2-difluoropropane-1,1,3,3-d$_4$-1,3-diamine. The title compound was prepared as described in Intermediate 35 Step D using (S)-2-(3-((1-(6-amino-3-chloropyridazin-4-yl)-2-cyclopropoxyethyl)amino)-2,2-difluoropropyl-1,1,3,3-d$_4$)isoindoline-1,3-dione (Step B) in place of (S)-2-(3-((1-(6-amino-3-chloropyridazin-4-yl)-2-methoxyethyl)amino)-2,2-difluoropropyl)isoindoline-1,3-dione. The reaction mixture was heated at rt for 1.5 h followed by 35° C. for 39.5 h to provide the title compound as a gummy solid that was used without further purification.

Step D: (S)-1-(1-(6-Amino-3-chloropyridazin-4-yl)-2-cyclopropoxyethyl)-5,5-difluorotetrahydropyrimidin-2(1H)-one-4,4,6,6-d$_4$. The title compound (73% yield) was prepared as described in Intermediate 35 Step E using (S)—N$^1$-(1-(6-amino-3-chloropyridazin-4-yl)-2-cyclopropoxyethyl)-2,2-difluoropropane-1,1,3,3-d$_4$-1,3-diamine (Step C) in place of (S)—N$^1$-(1-(6-amino-3-chloropyridazin-4-yl)-2-methoxyethyl)-2,2-difluoropropane-1,3-diamine.

Step E: tert-Butyl ((S)-1-(6-chloro-7-((S)-2-cyclopropoxy-1-(5,5-difluoro-2-oxotetrahydropyrimidin-1(2H)-yl-4,4,6,6-d$_4$)ethyl)imidazo[1,2-b]pyridazin-2-yl)-5,5,5-trifluoro-4,4-dimethylpentyl)carbamate. The title compound was prepared as described in Intermediate 44 Step A using (S)-1-(1-(6-amino-3-chloropyridazin-4-yl)-2-cyclopropoxyethyl)-5,5-difluorotetrahydropyrimidin-2(1H)-one-4,4,6,6-d$_4$ (Step D) in place of (S)-1-(1-(6-amino-3-chloropyridazin-4-yl)-2-methoxyethyl)-5,5-difluorotetrahydropyrimidin-2(1H)-one and tert-butyl (S)-(7,7,7-trifluoro-1-iodo-6,6-dimethyl-2-oxoheptan-3-yl)carbamate (Intermediate 46) in place of tert-butyl (S)-(6,6,6-trifluoro-1-iodo-5,5-dimethyl-2-oxohexan-3-yl)carbamate. The reaction mixture was heated at 50° C. for 16.5 h and no additional iodide was added to provide the title compound in 84% yield.

Step F: tert-Butyl ((S)-1-(7-((S)-2-cyclopropoxy-1-(5,5-difluoro-2-oxotetrahydropyrimidin-1(2H)-yl-4,4,6,6-d$_4$) ethyl)imidazo[1,2-b]pyridazin-2-yl)-5,5,5-trifluoro-4,4-dimethylpentyl)carbamate. The title compound was prepared as described in Intermediate 73 Step F using tert-butyl ((S)-1-(6-chloro-7-((S)-2-cyclopropoxy-1-(5,5-difluoro-2-oxotetrahydropyrimidin-1(2H)-yl-4,4,6,6-d$_4$)ethyl)imidazo[1,2-b]pyridazin-2-yl)-5,5,5-trifluoro-4,4-dimethylpentyl)carbamate (Step E) in place of tert-butyl ((S)-1-(6-chloro-7-((S)-1-(5,5-difluoro-2-oxotetrahydropyrimidin-1(2H)-yl-4,4,6,6-d$_4$)-2-methoxyethyl)imidazo[1,2-b]pyridazin-2-yl)-5,5,5-trifluoro-4,4-dimethylpentyl)carbamate and was used without further purification.

Step G: 1-((S)-1-(2-((S)-1-Amino-5,5,5-trifluoro-4,4-dimethylpentyl)imidazo[1,2-b]pyridazin-7-yl)-2-cyclopropoxyethyl)-5,5-difluorotetrahydropyrimidin-2(1H)-one-4,4,6,6-d$_4$. The title compound was prepared as described in Intermediate 73 Step G using tert-butyl ((S)-1-(7-((S)-2-cyclopropoxy-1-(5,5-difluoro-2-oxotetrahydropyrimidin-1(2H)-yl-4,4,6,6-d$_4$)ethyl)imidazo[1,2-b]pyridazin-2-yl)-5,5,5-trifluoro-4,4-dimethylpentyl)carbamate (Step F) in place of tert-butyl ((S)-1-(7-((S)-1-(5,5-difluoro-2-oxotetrahydropyrimidin-1(2H)-yl-4,4,6,6-d$_4$)-2-methoxyethyl)imidazo[1,2-b]pyridazin-2-yl)-5,5,5-trifluoro-4,4-dimethylpentyl)carbamate and was used without further purification.

Intermediate 75: Ethyl 4-(difluoromethyl)-1,2,5-oxadiazole-3-carboxylate

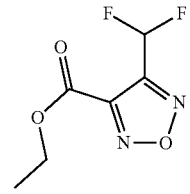

Step A: Ethyl (E)-4,4-difluoro-2-(hydroxyimino)-3-oxobutanoate. To a solution of ethyl 4,4-difluoro-3-oxobutanoate (24 mL, 181 mmol) in acetic acid (181 mL, 3.16 mol) was added a solution of sodium nitrite (18.8 g, 271.8 mmol) in water (60 mL) dropwise over 10 min. The resulting solution was stirred at 0° C. for 1.5 h. The mixture was then diluted with water (250 mL) and extracted with EtOAc (3×200 mL). The organic layers were combined and washed with saturated aqueous NaHCO$_3$ (4×100 mL). Then, the pH of the aqueous layer was adjusted to pH 6 by the addition of solid NaHCO$_3$, EtOAc (200 mL) was added and the mixture stirred vigorously for 1 h. The layers were separated and the aqueous layer was further extracted with EtOAc (3×100 mL). The EtOAc layers were combined, dried over anhydrous Na$_2$SO$_4$, filtered, and concentrated to dryness to provide the title compound as a brown oil (92% yield), which was used without further purification.

Step B: Ethyl (2E,3E)-4,4-difluoro-2,3-bis(hydroxyimino)butanoate. To a mixture of ethyl (E)-4,4-difluoro-2-(hydroxyimino)-3-oxobutanoate (22.4 g, 114.7 mmol, Step A) in EtOH (114 mL) were added hydroxylamine hydrochloride (36.2 g, 516 mmol) and HCl (114 mL, 457 mmol, 4 M in 1,4-dioxane) and the resulting mixture was heated at 50° C. for 25 h. The reaction was cooled to rt, filtered, and the solids rinsed with DCM. The filtrate was concentrated to dryness and the residue was diluted with saturated aqueous NaHCO$_3$ (150 mL). The mixture was extracted with EtOAc (100 mL followed by 2×50 mL). The organic layers were combined, dried over anhydrous Na$_2$SO$_4$, filtered, and concentrated to dryness. DCM (40 mL) was added to the residue and the mixture was stirred at rt for 2 h. A white precipitate formed and was removed by filtration, washing with DCM. The filtrate was concentrated to dryness and the residue purified by silica gel chromatography (0-100 EtOAc/hexanes) to provide the title compound as a pink solid (43% yield).

Step C: Ethyl 4-(difluoromethyl)-1,2,5-oxadiazole-3-carboxylate. To a solution of ethyl (2E,3E)-4,4-difluoro-2,3-bis(hydroxyimino)butanoate (1.5 g, 7.1 mmol, Step B) in THF (29 mL) at 0° C. was added CDI (1.45 g, 8.92 mmol). The mixture was stirred at 0° C. for 5 min and then heated to 45° C. for 4.5 h. The mixture was cooled to rt and concentrated to dryness. The residue was purified by silica gel chromatography (0-100% EtOAc/hexanes) to provide the title compound as a colorless oil (42% yield).

Intermediate 76:
4-(Difluoromethyl)-1,2,5-oxadiazole-3-carboxylic acid

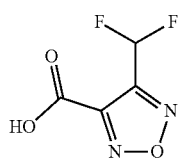

To a mixture of ethyl 4-(difluoromethyl)-1,2,5-oxadiazole-3-carboxylate (550 mg, 2.86 mmol, Intermediate 75) in water (5.7 mL) and 1,4-dioxane (5.7 mL) was added HCl (2.39 mL, 28.6 mmol, concentrated) and the resulting mixture was heated at 100° C. for 4 h. The reaction was cooled to rt, diluted with water (20 mL) and brine (15 mL) and extracted with diethyl ether (5×25 mL). The organic layers were combined, dried over anhydrous MgSO$_4$ overnight, filtered, and concentrated to dryness to provide the title compound as a colorless oil (approximately 52% yield, title compound contained approximately 10% 1,4-dioxane) that was used without further purification.

Intermediate 77: Ethyl 4-(trifluoromethyl)-1,2,5-oxadiazole-3-carboxylate

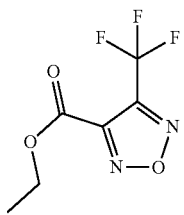

Step A: Ethyl (E)-4,4,4-trifluoro-2-(hydroxyimino)-3-oxobutanoate. The title compound was prepared as described in Intermediate 75 Step A using ethyl 4,4,4-trifluoroacetoacetate in place of ethyl 4,4-difluoro-3-oxobutanoate to provide the title compound as a colorless oil (74% yield).

Step B: Ethyl (2E,3E)-4,4,4-trifluoro-2,3-bis(hydroxyimino)butanoate. To a mixture of ethyl (E)-4,4,4-trifluoro-2-(hydroxyimino)-3-oxobutanoate (8.45 g, 39.7 mmol, Step A) in EtOH (200 mL) was added hydroxylamine hydrochloride (11.1 g, 159 mmol) followed by sodium acetate (9.76 g, 119 mmol) and the resulting mixture was heated at 80° C. for 7 h followed by rt for 9 h. The mixture was filtered and the filtrate concentrated to dryness. The residue was suspended in diethyl ether (300 mL) and sonicated. The remaining solids were filtered and rinsed with diethyl ether. The diethyl ether layers were combined, washed with saturated aqueous NaHCO$_3$ (100 mL) then by brine (100 mL), and dried over anhydrous Na$_2$SO$_4$. The mixture was filtered, concentrated to dryness and purified by silica gel chromatography (0-100% EtOAc/hexanes) to provide the title compound as a light orange-red oil (20% yield).

Step C: Ethyl 4-(trifluoromethyl)-1,2,5-oxadiazole-3-carboxylate. The title compound (15% yield) was prepared as described in Intermediate 75 Step C using ethyl (2E,3E)-4,4,4-trifluoro-2,3-bis(hydroxyimino)butanoate (Step B) in place of ethyl (2E,3E)-4,4-difluoro-2,3-bis(hydroxyimino)butanoate and heated at 45° C. for 2 d and then stirred at rt for 1 d.

Intermediate 78: tert-Butyl ((S)-(7-((S)-amino(1-cyanocyclobutyl)methyl)imidazo[1,2-b]pyridazin-2-yl)(4,4-difluorocyclohexyl)methyl)carbamate

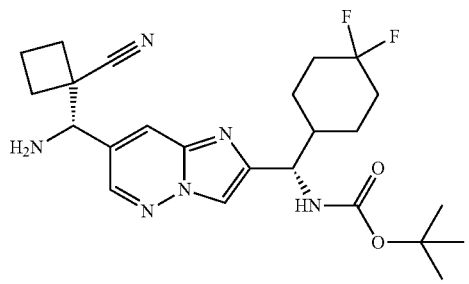 [SMILES: CC(C)(C)OC(=O)N[C@H](c1cn2ncc([C@H](N)C3(C#N)CCC3)cc2n1)C1CCC(F)(F)CC1]

The title compound (96% yield) was prepared as described for the synthesis of Intermediate 14 using tert-butyl ((S)-(7-((S)—(((R)-tert-butylsulfinyl)amino)(1-cyanocyclobutyl)methyl)imidazo[1,2-b]pyridazin-2-yl)(4,4-difluorocyclohexyl)methyl)carbamate in place of ((S)-(7-((S)-1-(((R)-tert-butylsulfinyl)amino)-2-cyclopropoxyethyl) imidazo[1,2-b]pyridazin-2-yl)(4,4-difluorocyclohexyl) methyl)carbamate.

Intermediate 79: tert-Butyl ((S)-(7-((S)-(1-cyanocyclobutyl)(5,5-difluoro-2-oxotetrahydropyrimidin-1(2H)-yl)methyl)imidazo[1,2-b]pyridazin-2-yl)(4,4-difluorocyclohexyl)methyl)carbamate

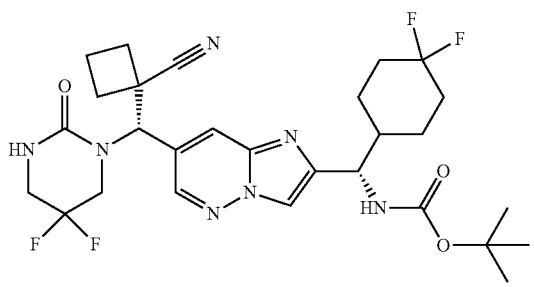 [SMILES: CC(C)(C)OC(=O)N[C@H](c1cn2ncc([C@H](N3CC(F)(F)CNC3=O)C3(C#N)CCC3)cc2n1)C1CCC(F)(F)CC1]

Step A: tert-Butyl ((S)-(7-((S)-(1-cyanocyclobutyl)((3-(1,3-dioxoisoindolin-2-yl)-2,2-difluoropropyl)amino)methyl) imidazo[1,2-b]pyridazin-2-yl)(4,4-difluorocyclohexyl) methyl)carbamate. The title compound (45% yield) was prepared as described for the synthesis of Intermediate 15 Step A using tert-butyl ((S)-(7-((S)-amino(1-cyanocyclobutyl)methyl)imidazo[1,2-b]pyridazin-2-yl)(4,4-difluorocyclohexyl)methyl)carbamate (Intermediate 78) in place of tert-butyl ((S)-(7-((S)-1-amino-2-cyclopropoxyethyl)imidazo[1,2-b]pyridazin-2-yl)(4,4-difluorocyclohexyl)methyl)carbamate.

Step B: tert-Butyl ((S)-(7-((S)-((3-amino-2,2-difluoropropyl)amino)(1-cyanocyclobutyl)methyl)imidazo[1,2-b]pyridazin-2-yl)(4,4-difluorocyclohexyl)methyl)carbamate. The title compound (91% yield) was prepared as described for the synthesis of Intermediate 15 Step B using tert-butyl ((S)-(7-((S)-(1-cyanocyclobutyl)((3-(1,3-dioxoisoindolin-2-yl)-2,2-difluoropropyl)amino)methyl)imidazo[1,2-b]pyridazin-2-yl)(4,4-difluorocyclohexyl)methyl)carbamate (Step A) in place of tert-butyl ((S)-(7-((S)-2-cyclopropoxy-1-((3-(1,3-dioxoisoindolin-2-yl)-2,2-difluoropropyl)amino)ethyl)imidazo[1,2-b]pyridazin-2-yl)(4,4-difluorocyclohexyl)methyl)carbamate.

Step C: tert-Butyl ((S)-(7-((S)-(1-cyanocyclobutyl)(5,5-difluoro-2-oxotetrahydropyrimidin-1(2H)-yl)methyl)imidazo[1,2-b]pyridazin-2-yl)(4,4-difluorocyclohexyl)methyl)carbamate. The title compound (22% yield) was prepared as described for the synthesis of Intermediate 15 Step C using tert-butyl ((S)-(7-((S)-((3-amino-2,2-difluoropropyl)amino)(1-cyanocyclobutyl)methyl)imidazo[1,2-b]pyridazin-2-yl)(4,4-difluorocyclohexyl)methyl)carbamate (Step B) in place of tert-butyl ((S)-(7-((S)-1-((3-amino-2,2-difluoropropyl)amino)-2-cyclopropoxyethyl)imidazo[1,2-b]pyridazin-2-yl)(4,4-difluorocyclohexyl)methyl)carbamate.

Intermediate 80: 1-((S)-(2-((S)-Amino(4,4-difluorocyclohexyl)methyl)imidazo[1,2-b]pyridazin-7-yl)(5,5-difluoro-2-oxotetrahydropyrimidin-1(2H)-yl)methyl)cyclobutane-1-carbonitrile

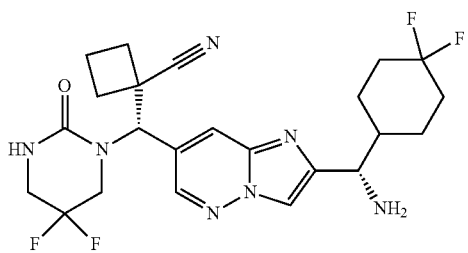 [SMILES: N#CC1([C@H](c2cnn3cc([C@@H](N)C4CCC(F)(F)CC4)nc3c2)N2CC(F)(F)CNC2=O)CCC1]

The title compound was prepared as described for the synthesis of Intermediate 20 Step C using tert-butyl ((S)-(7-((S)-(1-cyanocyclobutyl)(5,5-difluoro-2-oxotetrahydropyrimidin-1(2H)-yl)methyl)imidazo[1,2-b]pyridazin-2-yl)(4,4-difluorocyclohexyl)methyl)carbamate (Intermediate 79) in place of tert-butyl ((R)-1-(7-((S*)-1-(5,5-difluoro-2-oxotetrahydropyrimidin-1(2H)-yl)-2-methoxyethyl)imidazo[1,2-b]pyridazin-2-yl)-2-((1,1,1-trifluoro-2-methylpropan-2-yl)oxy)ethyl)carbamate and was used without further purification.

Intermediate 81: (S)-1-((2-(Amino(4,4-difluorocyclohexyl)methyl)imidazo[1,2-b]pyridazin-7-yl)methyl)-5,5,6,6-tetrafluoro-1,3-diazepan-2-one

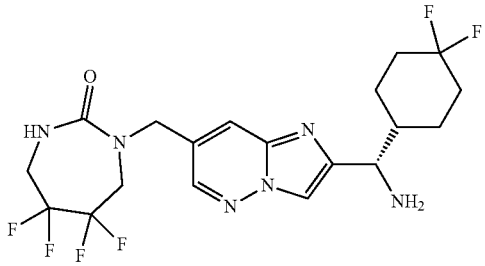 [SMILES: N[C@H](c1cn2ncc(CN3CC(F)(F)C(F)(F)CNC3=O)cc2n1)C1CCC(F)(F)CC1]

Step A: tert-Butyl (S)-((7-(((4-amino-2,2,3,3-tetrafluorobutyl)amino)methyl)imidazo[1,2-b]pyridazin-2-yl)(4,4-difluorocyclohexyl)methyl)carbamate. The title compound was synthesized in a manner analogous to Intermediate 20 Step A using 2,2,3,3-tetrafluorobutane-1,4-diamine in place of 2,2-difluoropropane-1,3-diamine dihydrochloride and was used without further purification.

Step B: tert-Butyl ((1S)-(4,4-difluorocyclohexyl)(7-((5-methyl-2-oxotetrahydropyrimidin-1(2H)-yl)methyl)imidazo[1,2-b]pyridazin-2-yl)methyl)carbamate. The title compound was synthesized in a manner analogous to Intermediate 20 Step B using tert-butyl (S)-((7-(((4-amino-2,2,3,3-tetrafluorobutyl)amino)methyl)imidazo[1,2-b]pyridazin-2-yl)(4,4-difluorocyclohexyl)methyl)carbamate (Step A) in place of tert-butyl (S)-((7-(((3-amino-2,2-difluoropropyl)amino)methyl)imidazo[1,2-b]pyridazin-2-yl)(4,4-difluorocyclohexyl)methyl)carbamate to afford the title compound in 30% yield over the two steps.

Step C: (S)-1-((2-(Amino(4,4-difluorocyclohexyl)methyl)imidazo[1,2-b]pyridazin-7-yl)methyl)-5,5,6,6-tetrafluoro-1,3-diazepan-2-one. The title compound (93% yield) was prepared as described for the synthesis of Intermediate 20 Step C using tert-butyl ((1S)-(4,4-difluorocyclohexyl)(7-((5-methyl-2-oxotetrahydropyrimidin-1(2H)-yl)methyl)imidazo[1,2-b]pyridazin-2-yl)methyl)carbamate (Step B) in place of tert-butyl (S)-((7-((5,5-difluoro-2-oxotetrahydropyrimidin-1(2H)-yl)methyl)imidazo[1,2-b]pyridazin-2-yl)(4,4-difluorocyclohexyl)methyl)carbamate.

Intermediate 82: (S,E)-N-Ethylidene-2-methylpropane-2-sulfinamide

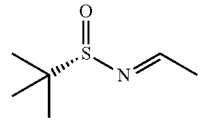

To a stirred solution of (S)-(−)-2-methyl-2-propanesulfinamide (10.0 g, 80.9 mmol) in DCM (40.4 mL) was added acetaldehyde (32.1 g, 728 mmol), anhydrous MgSO$_4$ (29.2 g, 243 mmol), and PPTS (1.02 g, 4.04 mmol). The reaction mixture was stirred at rt for 12 h, at which point the reaction mixture was filtered through diatomaceous earth (e.g., Celite®) and the filter cake washed with DCM. The filtrate was transferred to a separatory funnel and washed with water (100 mL), half-saturated brine (100 mL), and saturated brine (100 mL). The organic layer was collected, dried over anhydrous MgSO₄, filtered, and concentrated to afford the title compound in 94% yield.

Intermediate 83: N-(5-((R)-1-(((S)-tert-Butylsulfinyl)amino)ethyl)-6-chloropyridazin-3-yl)pivalamide

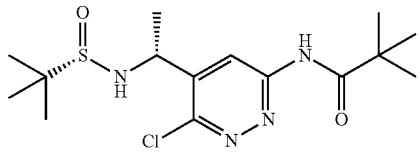 [SMILES: C[C@@H](N[S@@](=O)C(C)(C)C)c1cc(NC(=O)C(C)(C)C)nnc1Cl]

To a stirred solution of TMPMgCl·LiCl (128.1 mL, 121.7 mmol, 1.0 M in THF/toluene) was added N-(6-chloropyridazin-3-yl)pivalamide (10 g, 46.8 mmol, Intermediate 32 Step A) in THF (100 mL) dropwise at −40° C. under a nitrogen atmosphere. The resulting mixture was stirred for 2.5 h at −40° C. under nitrogen atmosphere, then (S,E)-N-ethylidene-2-methylpropane-2-sulfinamide (11.2 g, 76.1 mmol, Intermediate 82) was added dropwise over 5 min. The reaction mixture was stirred at −40° C. for 20 min at which point the cooling bath was removed and then the reaction mixture was allowed to warm to rt. After 24 h, the reaction mixture was cooled to 0° C. and quenched by the addition of saturated aqueous NH₄Cl (30 mL). The resulting mixture was extracted with EtOAc (3×200 mL) and the combined organic layers were dried over anhydrous Na₂SO₄, and filtered. The filtrate was concentrated to dryness and the residue was initially purified by silica gel chromatography (10-45% acetone/hexanes (with 0.1% TEA)) and then further purified by SFC (Whelk O1 SS 3 μm, 50×3 mm, Mobile phase: 20% MeOH, 80% CO₂) to afford the title compound in 30% yield.

Intermediate 84: (R)-1-(1-(6-Amino-3-chloropyridazin-4-yl)ethyl)-5,5-difluorotetrahydropyrimidin-2(1H)-one

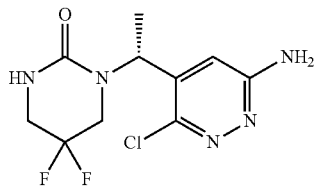 [SMILES: C[C@H](c1cc(N)nnc1Cl)N1CC(F)(F)CNC1=O]

Step A: (R)—N-(5-(1-Aminoethyl)-6-chloropyridazin-3-yl)pivalamide. The title compound (92% yield) was prepared as described for the synthesis of Intermediate 35 Step A using N-(5-((R)-1-(((S)-tert-butylsulfinyl)amino)ethyl)-6-chloropyridazin-3-yl)pivalamide (Intermediate 83) in place of N-(5-((S)-1-(((R)-tert-butylsulfinyl)amino)-2-methoxyethyl)-6-chloropyridazin-3-yl)pivalamide.

Step B: (R)—N-(6-Chloro-5-(1-((3-(1,3-dioxoisoindolin-2-yl)-2,2-difluoropropyl)amino)ethyl)pyridazin-3-yl)pivalamide. The title compound (79% yield) was prepared as described for the synthesis of Intermediate 35 Step B using (R)—N-(5-(1-aminoethyl)-6-chloropyridazin-3-yl)pivalamide (Step A) in place of (S)—N-(5-(1-amino-2-methoxyethyl)-6-chloropyridazin-3-yl)pivalamide.

Step C: (R)-2-(3-((1-(6-Amino-3-chloropyridazin-4-yl)ethyl)amino)-2,2-difluoropropyl)isoindoline-1,3-dione. The title compound (63% yield) was prepared as described for the synthesis of Intermediate 35 Step C using (R)—N-(6-chloro-5-(1-((3-(1,3-dioxoisoindolin-2-yl)-2,2-difluoropropyl)amino)ethyl)pyridazin-3-yl)pivalamide (Step B) in place of (S)—N-(6-chloro-5-(1-((3-(1,3-dioxoisoindolin-2-yl)-2,2-difluoropropyl)amino)-2-methoxyethyl)pyridazin-3-yl)pivalamide.

Step D: (R)—N¹-(1-(6-Amino-3-chloropyridazin-4-yl)ethyl)-2,2-difluoropropane-1,3-diamine. The title compound was prepared as described for the synthesis of Intermediate 35 Step D using (R)-2-(3-((1-(6-amino-3-chloropyridazin-4-yl)ethyl)amino)-2,2-difluoropropyl)isoindoline-1,3-dione (Step C) in place of (S)-2-(3-((1-(6-amino-3-chloropyridazin-4-yl)-2-methoxyethyl)amino)-2,2-difluoropropyl)isoindoline-1,3-dione and was used without further purification.

Step E: (R)-1-(1-(6-Amino-3-chloropyridazin-4-yl)ethyl)-5,5-difluorotetrahydropyrimidin-2(1H)-one. The title compound (100% yield over Step D and Step E) was prepared as described for the synthesis of Intermediate 35 Step E using (R)—N¹-(1-(6-amino-3-chloropyridazin-4-yl)ethyl)-2,2-difluoropropane-1,3-diamine (Step D) in place of (S)—N¹-(1-(6-amino-3-chloropyridazin-4-yl)-2-methoxyethyl)-2,2-difluoropropane-1,3-diamine.

Intermediate 85: 1-((R)-1-(2-((R)-1-Amino-2-((1,1,1-trifluoro-2-methylpropan-2-yl)oxy)ethyl)imidazo[1,2-b]pyridazin-7-yl)ethyl)-5,5-difluorotetrahydropyrimidin-2(1H)-one

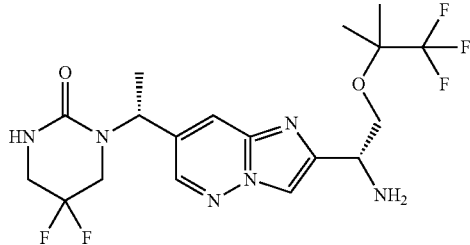

Step A: tert-Butyl ((R)-1-(6-chloro-7-((R)-1-(5,5-difluoro-2-oxotetrahydropyrimidin-1(2H)-yl)ethyl)imidazo[1,2-b]pyridazin-2-yl)-2-((1,1,1-trifluoro-2-methylpropan-2-yl)oxy)ethyl)carbamate. The title compound (42% yield) was synthesized in a manner analogous to Intermediate 41 Step A using (R)-1-(1-(6-amino-3-chloropyridazin-4-yl)ethyl)-5,5-difluorotetrahydropyrimidin-2(1H)-one (Intermediate 84) in place of (S)-1-(1-(6-amino-3-chloropyridazin-4-yl)-2-methoxyethyl)-5,5-difluorotetrahydropyrimidin-2(1H)-one and tert-butyl (S)-(4-iodo-3-oxo-1-((1,1,1-trifluoro-2-methylpropan-2-yl)oxy)butan-2-yl)carbamate in place of tert-butyl ((3S,4R)-1-iodo-2-oxo-4-(((R)-1,1,1-trifluoropropan-2-yl)oxy)pentan-3-yl)carbamate.

Step B: tert-Butyl ((R)-1-(7-((R)-1-(5,5-difluoro-2-oxotetrahydropyrimidin-1(2H)-yl)ethyl)imidazo[1,2-b]pyridazin-2-yl)-2-((1,1,1-trifluoro-2-methylpropan-2-yl)oxy)ethyl)carbamate. To a solution of tert-butyl ((R)-1-(6-chloro-7-((R)-1-(5,5-difluoro-2-oxotetrahydropyrimidin-1(2H)-yl)ethyl)imidazo[1,2-b]pyridazin-2-yl)-2-((1,1,1-trifluoro-2-methylpropan-2-yl)oxy)ethyl)carbamate (133.4 mg, 0.228 mmol, Step A) in MeOH (9.1 mL) in a Parr shaker was added 10% wt Pd/C (97.1 mg, 0.09 mmol). To the vessel was attached a vacuum line and the vessel was purged and backfilled with 1 atm $N_2$ three times. The vessel was then purged and backfilled with 3 atm of $H_2$ (three times) and was shaken at this pressure for 5 h. After 5 h, the reaction mixture was filtered through diatomaceous earth (e.g., Celite®) and the pad was washed with MeOH. The filtrate was concentrated to dryness and the residue was purified by silica gel chromatography (0-100% EtOAc/hexanes) to afford the title compound in 31% yield.

Step C: 1-((R)-1-(2-((R)-1-Amino-2-((1,1,1-trifluoro-2-methylpropan-2-yl)oxy)ethyl)imidazo[1,2-b]pyridazin-7-yl)ethyl)-5,5-difluorotetrahydropyrimidin-2(1H)-one. The title compound (100% yield) was synthesized in a manner analogous to Intermediate 41 Step C using tert-butyl ((R)-1-(7-((R)-1-(5,5-difluoro-2-oxotetrahydropyrimidin-1(2H)-yl)ethyl)imidazo[1,2-b]pyridazin-2-yl)-2-((1,1,1-trifluoro-2-methylpropan-2-yl)oxy)ethyl)carbamate (Step B) in place of tert-butyl ((1R,2R)-1-(7-((S)-1-(5,5-difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propyl)carbamate.

Intermediate 86: 1-((R)-1-(2-((S)-1-Amino-4,4,4-trifluoro-3,3-dimethylbutyl)imidazo[1,2-b]pyridazin-7-yl)ethyl)-5,5-difluorotetrahydropyrimidin-2(1H)-one

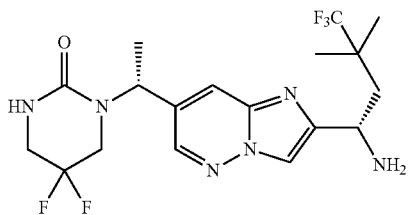 [SMILES: C[C@H](c1cnn2cc([C@@H](N)CC(C)(C)C(F)(F)F)nc2c1)N1CC(F)(F)CNC1=O]

Step A: tert-Butyl ((S)-1-(6-chloro-7-((S)-2-cyclopropoxy-1-(5,5-difluoro-2-oxotetrahydropyrimidin-1(2H)-yl)ethyl)imidazo[1,2-b]pyridazin-2-yl)-4,4,4-trifluoro-3,3-dimethylbutyl)carbamate. The title compound (34% yield) was synthesized in a manner analogous to Intermediate 44 Step A using (R)-1-(1-(6-amino-3-chloropyridazin-4-yl)ethyl)-5,5-difluorotetrahydropyrimidin-2(1H)-one (Intermediate 84) in place of (S)-1-(1-(6-amino-3-chloropyridazin-4-yl)-2-methoxyethyl)-5,5-difluorotetrahydropyrimidin-2(1H)-one.

Step B: tert-Butyl ((S)-1-(7-((R)-1-(5,5-difluoro-2-oxotetrahydropyrimidin-1(2H)-yl)ethyl)imidazo[1,2-b]pyridazin-2-yl)-4,4,4-trifluoro-3,3-dimethylbutyl)carbamate. The title compound (31% yield) was synthesized in a manner analogous to Intermediate 85 Step B using tert-butyl ((S)-1-(6-chloro-7-((S)-2-cyclopropoxy-1-(5,5-difluoro-2-oxotetrahydropyrimidin-1(2H)-yl)ethyl)imidazo[1,2-b]pyridazin-2-yl)-4,4,4-trifluoro-3,3-dimethylbutyl)carbamate (Step A) in place of tert-butyl ((R)-1-(6-chloro-7-((R)-1-(5,5-difluoro-2-oxotetrahydropyrimidin-1(2H)-yl)ethyl)imidazo[1,2-b]pyridazin-2-yl)-2-((1,1,1-trifluoro-2-methylpropan-2-yl)oxy)ethyl)carbamate.

Step C: 1-((R)-1-(2-((S)-1-Amino-4,4,4-trifluoro-3,3-dimethylbutyl)imidazo[1,2-b]pyridazin-7-yl)ethyl)-5,5-difluorotetrahydropyrimidin-2(1H)-one. The title compound (100% yield) was prepared in a manner analogous to Intermediate 20 Step C using tert-butyl ((S)-1-(7-((R)-1-(5,5-difluoro-2-oxotetrahydropyrimidin-1(2H)-yl)ethyl)imidazo[1,2-b]pyridazin-2-yl)-4,4,4-trifluoro-3,3-dimethylbutyl)carbamate (Step B) in place of tert-butyl (S)-((7-((5,5-difluoro-2-oxotetrahydropyrimidin-1(2H)-yl)methyl)imidazo[1,2-b]pyridazin-2-yl)(4,4-difluorocyclohexyl)methyl)carbamate.

Intermediate 87: 1-((S)-1-(2-((S)-Amino(4,4-difluorocyclohexyl)methyl)imidazo[1,2-b]pyridazin-7-yl)-2,2-difluoroethyl)-5,5-difluorotetrahydropyrimidin-2(1H)-one

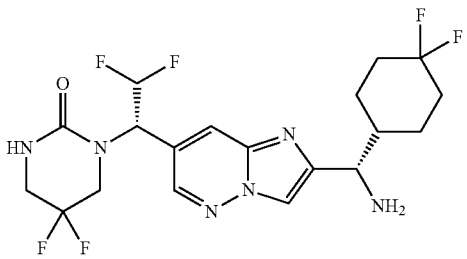 [SMILES: N[C@H](c1cn2ncc([C@@H](C(F)F)N3CC(F)(F)CNC3=O)cc2n1)C1CCC(F)(F)CC1]

Step A: tert-Butyl ((S)-(7-((S)-1-(((R)-tert-butylsulfinyl)amino)-2,2-difluoroethyl)imidazo[1,2-b]pyridazin-2-yl)(4,4-difluorocyclohexyl)methyl)carbamate. To a stirred solution of tert-butyl ((S)-(7-((E)-(((R)-tert-butylsulfinyl)imino)methyl)imidazo[1,2-b]pyridazin-2-yl)(4,4-difluorocyclohexyl)methyl)carbamate (1.89 g, 3.81 mmol) and (difluoromethyl)trimethylsilane (1.51 mL, 11.0 mmol) in THF (30 mL) was added t-BuOK (1 M in THF, 11.3 mL, 11.3 mmol) at −78° C. After stirring for 1.5 h at −78° C., the reaction was quenched at −78° C. via the addition of saturated aqueous $NH_4Cl$ (20 mL) and allowed to warm to rt. The reaction was then diluted with water (150 mL) and $Et_2O$ (150 mL) and transferred to a separatory funnel where the layers were separated. The aqueous layer was then washed with $Et_2O$ (3×100 mL). The combined organic layers were washed with brine, dried over anhydrous $MgSO_4$, filtered, concentrated to dryness, and purified by silica gel chromatography (10-50% acetone/hexanes) to afford the title compound in 17% yield.

Step B: tert-Butyl ((S)-(7-((S)-1-amino-2,2-difluoroethyl)imidazo[1,2-b]pyridazin-2-yl)(4,4-difluorocyclohexyl)methyl)carbamate. The title compound (88% yield) was prepared as described for the synthesis of Intermediate 9 using tert-butyl ((S)-(7-((S)-1-(((R)-tert-butylsulfinyl)amino)-2,2-difluoroethyl)imidazo[1,2-b]pyridazin-2-yl)(4,4-difluorocyclohexyl)methyl)carbamate (Step A) in place of tert-butyl ((R)-1-(7-((S*)-1-(((R)-tert-butylsulfinyl)amino)-2-methoxyethyl)imidazo[1,2-b]pyridazin-2-yl)-2-((1,1,1-trifluoro-2-methylpropan-2-yl)oxy)ethyl)carbamate.

Step C: tert-Butyl ((S)-(4,4-difluorocyclohexyl)(7-((S)-1-((3-(1,3-dioxoisoindolin-2-yl)-2,2-difluoropropyl)amino)-2,2-difluoroethyl)imidazo[1,2-b]pyridazin-2-yl)methyl)carbamate. The title compound (59% yield) was prepared as described for the synthesis of Intermediate 2 Step A using tert-butyl ((S)-(7-((S)-1-amino-2,2-difluoroethyl)imidazo[1,2-b]pyridazin-2-yl)(4,4-difluorocyclohexyl)methyl)carbamate (Step B) in place of tert-butyl ((S)-(7-((R)-amino(cyclopropyl)methyl)imidazo[1,2-b]pyridazin-2-yl)(4,4-difluorocyclohexyl)methyl)carbamate.

Step D: tert-Butyl ((S)-(7-((S)-1-((3-amino-2,2-difluoropropyl)amino)-2,2-difluoroethyl)imidazo[1,2-b]pyridazin-2-yl)(4,4-difluorocyclohexyl)methyl)carbamate. The title compound was prepared as described for the synthesis of Intermediate 2 Step B tert-butyl ((S)-(4,4-difluorocyclohexyl)(7-((S)-1-((3-(1,3-dioxoisoindolin-2-yl)-2,2-difluoropropyl)amino)-2,2-difluoroethyl)imidazo[1,2-b]pyridazin-2-yl)methyl)carbamate (Step C) in place of tert-butyl ((S)-(7-((R)-cyclopropyl((3-(1,3-dioxoisoindolin-2-yl)-2,2-difluoropropyl)amino)methyl)imidazo[1,2-b]pyridazin-2-yl)(4,4-difluorocyclohexyl)methyl)carbamate and was used without further purification.

Step E: tert-Butyl ((S)-(7-((S)-1-(5,5-difluoro-2-oxotetrahydropyrimidin-1(2H)-yl)-2,2-difluoroethyl)imidazo[1,2-b]pyridazin-2-yl)(4,4-difluorocyclohexyl)methyl)carbamate. The title compound (60% yield over Step D and Step E) was prepared as described for the synthesis of Intermediate 2, Step C, using tert-butyl ((S)-(7-((S)-1-((3-amino-2,2-difluoropropyl)amino)-2,2-difluoroethyl)imidazo[1,2-b]pyridazin-2-yl)(4,4-difluorocyclohexyl)methyl)carbamate (Step D) in place of tert-butyl ((S)-(7-((R)-((3-amino-2,2-difluoropropyl)amino)(cyclopropyl)methyl)imidazo[1,2-b]pyridazin-2-yl)(4,4-difluorocyclohexyl)methyl)carbamate.

Step F: 1-((S)-1-(2-((S)-Amino(4,4-difluorocyclohexyl)methyl)imidazo[1,2-b]pyridazin-7-yl)-2,2-difluoroethyl)-5,5-difluorotetrahydropyrimidin-2(1H)-one. The title compound (100% yield) was prepared as described for the synthesis of Intermediate 2 Step D tert-butyl ((S)-(7-((S)-1-(5,5-difluoro-2-oxotetrahydropyrimidin-1(2H)-yl)-2,2-difluoroethyl)imidazo[1,2-b]pyridazin-2-yl)(4,4-difluorocyclohexyl)methyl)carbamate (Step E) in place of tert-butyl ((S)-(7-((R)-cyclopropyl(5,5-difluoro-2-oxotetrahydropyrimidin-1(2H)-yl)methyl)imidazo[1,2-b]pyridazin-2-yl)(4,4-difluorocyclohexyl)methyl)carbamate and adding DCM (2 mL) as a co-solvent.

Intermediate 88: 1,3-Dioxoisoindolin-2-yl 2-(1-(trifluoromethyl)cyclopropoxy)propanoate

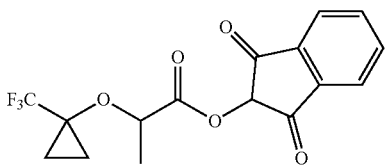 [SMILES: CC(OC1(C(F)(F)F)CC1)C(=O)OC1C(=O)c2ccccc2C1=O]

The title compound (68% yield) was prepared in a manner analogous to Intermediate 55 Step B using 2-[1-(trifluoromethyl)cyclopropoxy]propanoic acid in place of 2-cyclopropoxypropanoic acid.

Intermediate 89: 1-((1S)-1-(2-((1R*)-1-Amino-2-(1-(trifluoromethyl)cyclopropoxy)propyl)imidazo[1,2-b]pyridazin-7-yl)-2-methoxyethyl)-5,5-difluorotetrahydropyrimidin-2(1H)-one

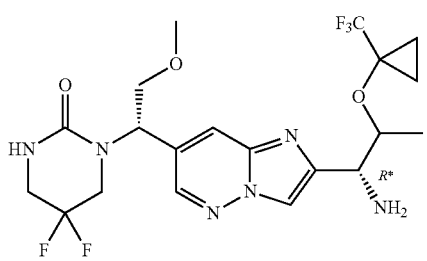 [SMILES: COC[C@H](c1cnn2cc([C@@H](N)C(C)OC3(C(F)(F)F)CC3)nc2c1)N1CC(F)(F)CNC1=O]

Step A: (S)—N-((1R*)-1-(7-((S)-1-(5,5-Difluoro-2-oxotetrahydropyrimidin-1(2H)-yl)-2-methoxyethyl)imidazo[1,2-b]pyridazin-2-yl)-2-(1-(trifluoromethyl)cyclopropoxy)propyl)-2,4,6-trimethylbenzenesulfinamide.

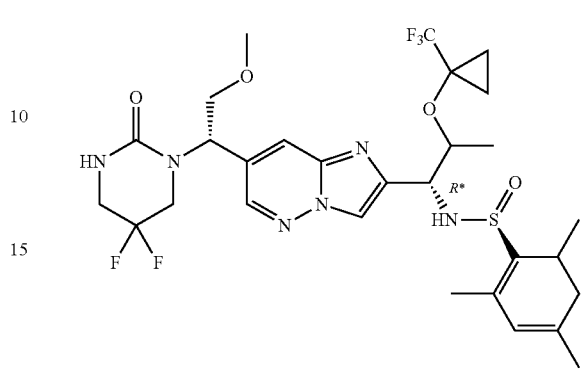

The title compound (32% yield) was prepared in a manner analogous to Intermediate 57 Step A using 1,3-dioxoisoindolin-2-yl 2-(1-(trifluoromethyl)cyclopropoxy)propanoate (Intermediate 88) in place of 1,3-dioxoisoindolin-2-yl 2-cyclopropoxypropanoate.

Step B: 1-((1S)-1-(2-((1R*)-1-Amino-2-(1-(trifluoromethyl)cyclopropoxy)propyl)imidazo[1,2-b]pyridazin-7-yl)-2-methoxyethyl)-5,5-difluorotetrahydropyrimidin-2(1H)-one. The title compound (100% yield) was prepared in a manner analogous to Intermediate 57 Step B using (S)—N-((1R*)-1-(7-((S)-1-(5,5-difluoro-2-oxotetrahydropyrimidin-1(2H)-yl)-2-methoxyethyl)imidazo[1,2-b]pyridazin-2-yl)-2-(1-(trifluoromethyl)cyclopropoxy)propyl)-2,4,6-trimethylbenzenesulfinamide (Step A) in place of (S)—N-((1R*)-2-cyclopropoxy-1-(7-((S)-1-(5,5-difluoro-2-oxotetrahydropyrimidin-1(2H)-yl)-2-methoxyethyl)imidazo[1,2-b]pyridazin-2-yl)propyl)-2,4,6-trimethylbenzenesulfinamide.

Intermediate 90: 1-((S*)-1-(2-((S)-Amino(4,4-difluorocyclohexyl)methyl)imidazo[1,2-b]pyridazin-7-yl)ethyl)-5,5-difluorotetrahydropyrimidin-2(1H)-one

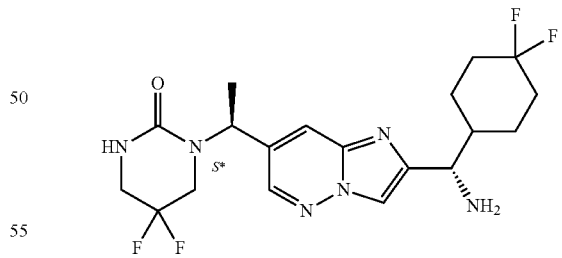

Step A: tert-Butyl ((S)-(7-((S*)-1-(((S)-tert-butylsulfinyl)amino)ethyl)imidazo[1,2-b]pyridazin-2-yl)(4,4-difluorocyclohexyl)methyl)carbamate. To a stirred solution of tert-butyl ((S)-(7-((E)-(((S)-tert-butylsulfinyl)imino)methyl)imidazo[1,2-b]pyridazin-2-yl)(4,4-difluorocyclohexyl)methyl)carbamate (6.07 g, 12.2 mmol) in THF (165 mL) was added methylmagnesium bromide (3 M in THF, 9.36 mL, 28.1 mmol) at −78° C. After 3 h, the reaction was quenched by addition of saturated aqueous NH₄Cl (100 mL) at −78° C. and allowed to slowly warm to rt over time. The reaction mixture was diluted with water (100 mL) and EtOAc (150 mL) and transferred to a separatory funnel where the layers were separated. The aqueous layer was washed with EtOAc (3×100 mL), and the combined organic layers were washed with brine, dried over anhydrous MgSO₄, filtered and concentrated to dryness. The material was initially purified by silica gel chromatography (10-70% acetone/hexanes) and then further purified by chiral SFC (Whelk O1 SS 5 μm, 250×21 mm, Mobile phase: 25% methanol, 75% CO₂) to afford the title compound in 33% yield.

Step B: tert-Butyl ((S)-(7-((S*)-1-aminoethyl)imidazo[1,2-b]pyridazin-2-yl)(4,4-difluorocyclohexyl)methyl)carbamate. The title compound (82% yield) was prepared as described for the synthesis of Intermediate 9 using tert-butyl ((S)-(7-((S*)-1-(((S)-tert-butylsulfinyl)amino)ethyl)imidazo[1,2-b]pyridazin-2-yl)(4,4-difluorocyclohexyl)methyl)carbamate (Step A) in place of tert-butyl ((R)-1-(7-((S*)-1-(((R)-tert-butylsulfinyl)amino)-2-methoxyethyl)imidazo[1,2-b]pyridazin-2-yl)-2-((1,1,1-trifluoro-2-methylpropan-2-yl)oxy)ethyl)carbamate.

Step C: tert-Butyl ((S)-(4,4-difluorocyclohexyl)(7-((S*)-1-((3-(1,3-dioxoisoindolin-2-yl)-2,2-difluoropropyl)amino)ethyl)imidazo[1,2-b]pyridazin-2-yl)methyl)carbamate. The title compound (95% yield) was prepared as described for the synthesis of Intermediate 2 Step A using tert-butyl ((S)-(7-((S*)-1-aminoethyl)imidazo[1,2-b]pyridazin-2-yl)(4,4-difluorocyclohexyl)methyl)carbamate (Step B) in place of tert-butyl ((S)-(7-((R)-amino(cyclopropyl)methyl)imidazo[1,2-b]pyridazin-2-yl)(4,4-difluorocyclohexyl)methyl)carbamate.

Step D: tert-Butyl ((S)-(7-((S*)-1-((3-amino-2,2-difluoropropyl)amino)ethyl)imidazo[1,2-b]pyridazin-2-yl)(4,4-difluorocyclohexyl)methyl)carbamate. The title compound was prepared as described for the synthesis of Intermediate 2 Step B using tert-butyl ((S)-(4,4-difluorocyclohexyl)(7-((S*)-1-((3-(1,3-dioxoisoindolin-2-yl)-2,2-difluoropropyl)amino)ethyl)imidazo[1,2-b]pyridazin-2-yl)methyl)carbamate (Step C) in place of tert-butyl ((S)-(7-((R)-cyclopropyl((3-(1,3-dioxoisoindolin-2-yl)-2,2-difluoropropyl)amino)methyl)imidazo[1,2-b]pyridazin-2-yl)(4,4-difluorocyclohexyl)methyl)carbamate and was used without further purification.

Step E: tert-Butyl ((S)-(7-((S*)-1-(5,5-difluoro-2-oxotetrahydropyrimidin-1(2H)-yl)ethyl)imidazo[1,2-b]pyridazin-2-yl)(4,4-difluorocyclohexyl)methyl)carbamate. The title compound was prepared as described for the synthesis of Intermediate 2 Step C using tert-butyl ((S)-(7-((S*)-1-((3-amino-2,2-difluoropropyl)amino)ethyl)imidazo[1,2-b]pyridazin-2-yl)(4,4-difluorocyclohexyl)methyl)carbamate (Step D) in place of tert-butyl ((S)-(7-((R)-((3-amino-2,2-difluoropropyl)amino)(cyclopropyl)methyl)imidazo[1,2-b]pyridazin-2-yl)(4,4-difluorocyclohexyl)methyl)carbamate and was used without further purification.

Step F: 1-((S*)-1-(2-((S)-Amino(4,4-difluorocyclohexyl)methyl)imidazo[1,2-b]pyridazin-7-yl)ethyl)-5,5-difluorotetrahydropyrimidin-2(1H)-one. The title compound (84% yield over Steps D-F) was prepared as described for the synthesis of Intermediate 2 Step D using tert-butyl ((S)-(7-((S*)-1-(5,5-difluoro-2-oxotetrahydropyrimidin-1(2H)-yl)ethyl)imidazo[1,2-b]pyridazin-2-yl)(4,4-difluorocyclohexyl)methyl)carbamate (Step E) in place of tert-butyl ((S)-(7-((R)-cyclopropyl(5,5-difluoro-2-oxotetrahydropyrimidin-1(2H)-yl)methyl)imidazo[1,2-b]pyridazin-2-yl)(4,4-difluorocyclohexyl)methyl)carbamate and adding DCM (2 mL) as a co-solvent.

Intermediate 91: 1-((2-((S)-Amino(4,4-difluorocyclohexyl)methyl)imidazo[1,2-b]pyridazin-7-yl)methyl)-4-methyl-1,3-diazepan-2-one

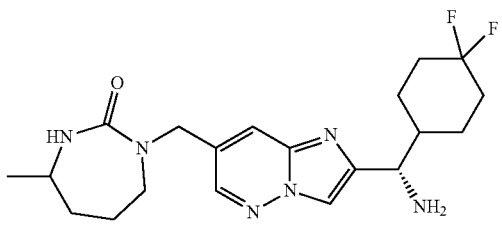 [SMILES: CC1CCCN(Cc2cnn3cc([C@@H](N)C4CCC(F)(F)CC4)nc3c2)C(=O)N1]

Step A: tert-Butyl ((1S)-(7-(((4-(((benzyloxy)carbonyl)amino)pentyl)amino)methyl)imidazo[1,2-b]pyridazin-2-yl)(4,4-difluorocyclohexyl)methyl)carbamate. The title compound was synthesized in a manner analogous to Intermediate 20 Step A using benzyl (5-aminopentan-2-yl)carbamate in place of 2,2-difluoropropane-1,3-diamine dihydrochloride and was used without further purification.

Step B: tert-Butyl ((1S)-(4,4-difluorocyclohexyl)(7-((4-methyl-2-oxo-1,3-diazepan-1-yl)methyl)imidazo[1,2-b]pyridazin-2-yl)methyl)carbamate. The title compound (59% yield over two steps) was synthesized in a manner analogous to Intermediate 21 Step B using ((1S)-(7-(((4-(((benzyloxy)carbonyl)amino)pentyl)amino)methyl)imidazo[1,2-b]pyridazin-2-yl)(4,4-difluorocyclohexyl)methyl)carbamate (Step A) in place of tert-butyl ((1S)-(7-(((3-((tert-butoxycarbonyl)amino)-2-methylpropyl)amino)methyl)imidazo[1,2-b]pyridazin-2-yl)(4,4-difluorocyclohexyl)methyl)carbamate.

Step C: 1-((2-((S)-Amino(4,4-difluorocyclohexyl)methyl)imidazo[1,2-b]pyridazin-7-yl)methyl)-4-methyl-1,3-diazepan-2-one. The title compound (77% yield) was prepared as described for the synthesis of Intermediate 20 Step C using tert-butyl ((1S)-(4,4-difluorocyclohexyl)(7-((4-methyl-2-oxo-1,3-diazepan-1-yl)methyl)imidazo[1,2-b]pyridazin-2-yl)methyl)carbamate (Step B) in place of tert-butyl (S)-((7-((5,5-difluoro-2-oxotetrahydropyrimidin-1(2H)-yl)methyl)imidazo[1,2-b]pyridazin-2-yl)(4,4-difluorocyclohexyl)methyl)carbamate.

Intermediate 92: Diastereomeric Mixture of (1R,7S)-3-((2-((S)-amino(4,4-difluorocyclohexyl)methyl)imidazo[1,2-b]pyridazin-7-yl)methyl)-8,8-difluoro-3,5-diazabicyclo[5.1.0]octan-4-one and (1S,7R)-3-((2-((S)-amino(4,4-difluorocyclohexyl)methyl)imidazo[1,2-b]pyridazin-7-yl)methyl)-8,8-difluoro-3,5-diazabicyclo[5.1.0]octan-4-one

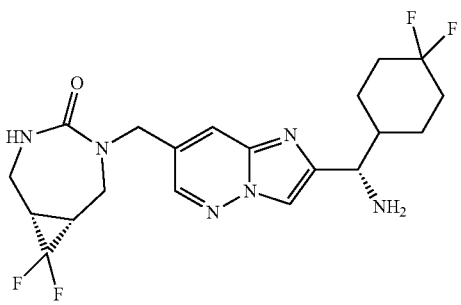

-continued

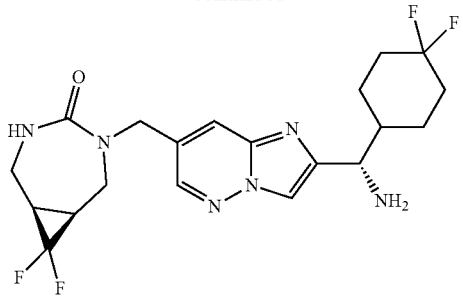

Step A: Diastereomeric mixture of tert-butyl ((S)-(7-(((((1S,3R)-3-(aminomethyl)-2,2-difluorocyclopropyl)methyl)amino)methyl)imidazo[1,2-b]pyridazin-2-yl)(4,4-difluorocyclohexyl)methyl)carbamate and tert-butyl ((S)-(7-(((((1R,3S)-3-(aminomethyl)-2,2-difluorocyclopropyl)methyl)amino)methyl)imidazo[1,2-b]pyridazin-2-yl)(4,4-difluorocyclohexyl)methyl)carbamate. The title compounds were synthesized in a manner analogous to Intermediate 20 Step A using ((1S,2R)-3,3-difluorocyclopropane-1,2-diyl)dimethanamine dihydrochloride in place of 2,2-difluoropropane-1,3-diamine dihydrochloride and were used without further purification.

Step B: Diastereomeric mixture of tert-butyl ((S)-(7-(((1S,7R)-8,8-difluoro-4-oxo-3,5-diazabicyclo[5.1.0]octan-3-yl)methyl)imidazo[1,2-b]pyridazin-2-yl)(4,4-difluorocyclohexyl)methyl)carbamate and tert-butyl ((S)-(7-(((1R,7S)-8,8-difluoro-4-oxo-3,5-diazabicyclo[5.1.0]octan-3-yl)methyl)imidazo[1,2-b]pyridazin-2-yl)(4,4-difluorocyclohexyl)methyl)carbamate. The title compounds (62% yield over two steps) were synthesized in a manner analogous to Intermediate 20 Step B using the diastereomeric mixture made in Step A in place of tert-butyl (S)-((7-(((3-amino-2,2-difluoropropyl)amino)methyl)imidazo[1,2-b]pyridazin-2-yl)(4,4-difluorocyclohexyl)methyl)carbamate.

Step C: Diastereomeric mixture of (1R,7S)-3-((2-((S)-amino(4,4-difluorocyclohexyl)methyl)imidazo[1,2-b]pyridazin-7-yl)methyl)-8,8-difluoro-3,5-diazabicyclo[5.1.0]octan-4-one and (1S,7R)-3-((2-((S)-amino(4,4-difluorocyclohexyl)methyl)imidazo[1,2-b]pyridazin-7-yl)methyl)-8,8-difluoro-3,5-diazabicyclo[5.1.0]octan-4-one. The title compounds (100% yield) were prepared as described for the synthesis of Intermediate 20 Step C using the diastereomeric mixture made in Step B in place of tert-butyl (S)-((7-((5,5-difluoro-2-oxotetrahydropyrimidin-1(2H)-yl)methyl)imidazo[1,2-b]pyridazin-2-yl)(4,4-difluorocyclohexyl)methyl)carbamate.

Intermediate 93: 1-((S)-1-(2-((S)-1-Amino-2,2-dicyclopropylethyl)imidazo[1,2-b]pyridazin-7-yl)-2-methoxyethyl)-5,5-difluorotetrahydropyrimidin-2(1H)-one

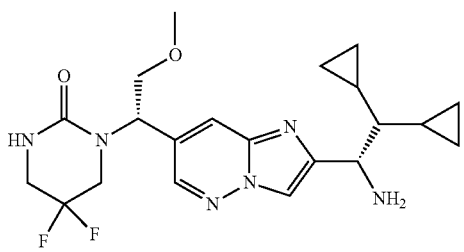 [SMILES: COC[C@H](c1cnn2cc([C@@H](N)C(C3CC3)C3CC3)nc2c1)N1CC(F)(F)CNC1=O]

Step A: (2-Methoxyethene-1,1-diyl)dicyclopropane. To a solution of methoxymethyl)triphenylphosphonium (67.0 g, 218 mmol) in THF (100 mL) that had been cooled to 0° C. was added lithium bis(trimethylsilyl)amide (218 mL, 218 mmol, 1 M in THF) dropwise while stirring for 45 min at 0° C. Then a solution of dicyclopropylmethanone (20.0 g, 182 mmol) in THF (100 mL) was added dropwise over 10 min to the reaction mixture. The resulting mixture was stirred for 3 h at rt. The reaction mixture was diluted with n-hexane (100 mL) and then filtered to remove the precipitate. The filtrate was diluted with $H_2O$ (200 mL) and extracted with EtOAc (200 mL×3). The organic extracts were dried over anhydrous $Na_2SO_4$, filtered, and concentrated to dryness to give the title compound as a light-yellow oil (100% yield) that was used without further purification.

Step B: 2,2-Dicyclopropylacetaldehyde. To a solution of (2-methoxyethene-1,1-diyl)dicyclopropane (25.0 g, 181 mmol, Step A) in anhydrous THF (150 mL) was added HCl (150 mL, 10% in water) and the resulting mixture was heated for 16 h at 75° C. The mixture was diluted with $H_2O$ (100 mL) and extracted with EtOAc (100 mL×3). The combined organic layers were dried over anhydrous $Na_2SO_4$, filtered, and concentrated to dryness to give the title compound (98% yield) as a light-yellow oil, which was used without further purification.

Step C: (S,E)-N-(2,2-Dicyclopropylethylidene)-2-methylpropane-2-sulfinamide. To a solution of 2,2-dicyclopropylacetaldehyde (22.0 g, 177 mmol, Step B) in anhydrous DCM (300 mL) were added (S)-2-methylpropane-2-sulfinamide (25.8 g, 213 mmol), anhydrous $CuSO_4$ (113 g, 709 mmol) and PPTS (6.68 g, 26.6 mmol) and the resulting mixture was stirred at rt for 16 h. The reaction mixture was filtered and the filtrate was washed with $H_2O$ (100 mL×2) and brine (100 mL). The organic layer was dried over anhydrous $Na_2SO_4$, filtered, and concentrated to dryness to give a light-yellow oil that was purified by silica gel chromatography (0-10% EtOAc/petroleum ether) to give the title compound as a light-yellow oil (62% yield).

Step D: (S)—N—((S)-1-Cyano-2,2-dicyclopropylethyl)-2-methylpropane-2-sulfinamide. To a solution of (S,E)-N-(2,2-dicyclopropylethylidene)-2-methylpropane-2-sulfinamide (25.0 g, 110 mmol, Step C) in anhydrous DCM (300 mL) were added TMSCN (29.5 mL, 220 mmol), $Sc(OTf)_3$ (10.8 g, 22.0 mmol) and 4 Å molecular sieves (20 g). The resulting mixture was stirred for 16 h at rt. The reaction mixture was filtered and the filtrate was concentrated to dryness to give a light-yellow oil that was purified by silica gel chromatography (0-60% EtOAc/petroleum ether) to give the title compound as a light-yellow oil (44% yield).

Step E: Methyl (S)-2-amino-3,3-dicyclopropylpropanoate. To MeOH (50 mL) cooled to 0° C. was added MeCOCl (37.7 mL, 531 mmol) dropwise via syringe over 40 min. The reaction mixture was stirred for 30 min at 0° C. Then, a solution of (S)—N—((S)-1-cyano-2,2-dicyclopropylethyl)-2-methylpropane-2-sulfinamide (5.00 g, 19.7 mmol, Step D) in MeOH (50 mL) was added and the resulting mixture was heated for 22 h at 65° C. After that time, the mixture was cooled to 0° C. and another portion of MeCOCl (25.2 mL, 353 mmol) was added dropwise via syringe over 40 min. The mixture was stirred for 30 min at 0° C. The reaction mixture was heated for 16 h at 65° C. and then the mixture was cooled to 0° C. and MeCOCl (12.6 mL, 177 mmol) was added dropwise via syringe over 40 min. The reaction mixture was stirred for 30 min at 0° C. Then the reaction mixture was heated for 16 h at 65° C. After that time, the mixture was cooled to rt and concentrated to dryness to give the title compound as a light-yellow oil (92% yield) that was used without further purification.

Step F: Methyl (S)-2-((tert-butoxycarbonyl)amino)-3,3-dicyclopropylpropanoate. To a solution of methyl (S)-2-amino-3,3-dicyclopropylpropanoate (6.60 g, 30.0 mmol, Step E) in THF (150 mL) were added $K_2CO_3$ (16.6 g, 120 mmol) and $H_2O$ (50 mL) and the resulting mixture was stirred for 30 min followed by the addition of $(Boc)_2O$ (6.98 mL, 30.0 mmol) in one portion. The reaction mixture was stirred for 2 h at rt. The reaction mixture was then poured into water (200 mL) and extracted with EtOAc (200 mL×3). The combined organic layers were dried over anhydrous $Na_2SO_4$, filtered, and concentrated to dryness to give a yellow oil that was purified by silica gel chromatography (0-10% EtOAc/petroleum ether) to give the title compound as a light-yellow oil (47% yield).

Step G: (S)-2-((tert-Butoxycarbonyl)amino)-3,3-dicyclopropylpropanoic acid. To a solution of methyl (S)-2-((tert-butoxycarbonyl)amino)-3,3-dicyclopropylpropanoate (4.00 g, 14.1 mmol, Step F) in MeOH (15 mL) were added $H_2O$ (5 mL) and LiOH·$H_2O$ (2.96 g, 70.6 mmol) and the resulting mixture was heated for 16 h at 60° C. After that time, the mixture was concentrated to dryness to give a light-yellow solid that was poured into $H_2O$ (50 mL) and washed with EtOAc (50 mL×2). The organic and aqueous layers were separated and the pH of the aqueous solution was adjusted to pH 5-6 by the addition of saturated aqueous $KHSO_4$. Then, the aqueous portion was extracted with EtOAc (50 mL×3) and the organic and aqueous layers were separated. The combined organic layers were dried over anhydrous $Na_2SO_4$, filtered, and concentrated to dryness to give the title compound as a light-yellow solid (100% yield) that was used without further purification.

Step H: tert-Butyl (S)-(1,1-dicyclopropyl-4-(dimethyl(oxo)-$\lambda^6$-sulfaneylidene)-3-oxobutan-2-yl)carbamate. To a solution of (S)-2-((tert-butoxycarbonyl)amino)-3,3-dicyclopropylpropanoic acid (10.0 g, 37.1 mmol, Step G) in anhydrous THF (50 mL) was added CDI (7.22 g, 44.6 mmol) and the resulting mixture was stirred for 2 h at 0° C. to form a yellow liquid designated mixture A. In a separate vessel, to a solution of $Me_3SOI$ (13.1 g, 59.4 mmol) in anhydrous THF (50 mL) was added t-BuOK (55.7 mL, 55.7 mmol) and this mixture, designated mixture B, was stirred for 2 h at rt. Then mixture A was added to mixture B by syringe over 2 min at rt. The culminating mixture was stirred for 2 h at 25° C., then diluted with $H_2O$ (200 mL) and extracted with EtOAc (200 mL×2). The combined organic layers were washed with brine (100 mL), dried over anhydrous $Na_2SO_4$, filtered, and concentrated to dryness to give a yellow solid that was initially purified by silica gel chromatography (0-100% EtOAc/petroleum ether) to give the title compound as a light-yellow oil. This oil was further purified by chiral SFC (DAICEL CHIRALPAK IG column, 10 μm, 250×50 mm; 35-35% (v/v) EtOH (containing 0.1% of 25% aqueous $NH_3$)/$CO_2$)) to give the title compound as an off-white solid (24% yield).

Step I. tert-Butyl ((S)-1-(6-chloro-7-((S)-1-(5,5-difluoro-2-oxotetrahydropyrimidin-1(2H)-yl)-2-methoxyethyl)imidazo[1,2-b]pyridazin-2-yl)-2,2-dicyclopropylethyl)carbamate. To a vial were added (S)-1-(1-(6-amino-3-chloropyridazin-4-yl)-2-methoxyethyl)-5,5-difluorotetrahydropyrimidin-2(1H)-one (150 mg, 0.466 mmol, Intermediate 35), tert-butyl (S)-(1,1-dicyclopropyl-4-(dimethyl(oxo)-$\lambda^6$-sulfaneylidene)-3-oxobutan-2-yl)carbamate (192 mg, 0.560 mmol, Step H), RuCl(Cp)(PPh$_3$)$_2$ (16.9 mg, 0.0233 mmol), sodium trifluoromethanesulfonate (4.0 mg, 0.023 mol), dried 3 Å molecular sieves (121 mg) and toluene (1.5 mL) under an atmosphere of $N_2$ and the resulting brown mixture was heated at 85° C. for 2 h. The reaction mixture was filtered through diatomaceous earth (e.g., Celite®) and washed with EtOAc (3×5 mL). Concentration of the filtrate gave a brown gel that was purified by silica gel chromatography (0-100% EtOAc/DCM) to give a brown gel that was further purified by preparative HPLC (20 mM $NH_4OH$ in $H_2O$/$CH_3CN$) to provide the title compound as a white gel (59% yield). SFC analysis was performed by SFC (Stationary phase: Whelk O1 SS, 3 μm, 50×3.0 mm, Mobile phase: gradient 5% to 60% methanol, 40% $CO_2$), showing 88.9% of tert-butyl ((S)-1-(6-chloro-7-((S)-1-(5,5-difluoro-2-oxotetrahydropyrimidin-1(2H)-yl)-2-methoxyethyl)imidazo[1,2-b]pyridazin-2-yl)-2,2-dicyclopropylethyl)carbamate and 11.1% of a diastereomeric product.

Step J: tert-Butyl ((S)-2,2-dicyclopropyl-1-(7-((S)-1-(5,5-difluoro-2-oxotetrahydropyrimidin-1(2H)-yl)-2-methoxyethyl)imidazo[1,2-b]pyridazin-2-yl)ethyl)carbamate. To a solution of tert-butyl ((S)-1-(6-chloro-7-((S)-1-(5,5-difluoro-2-oxotetrahydropyrimidin-1(2H)-yl)-2-methoxyethyl)imidazo[1,2-b]pyridazin-2-yl)-2,2-dicyclopropylethyl)carbamate (an 88.9/11.1 diastereomeric mixture, 104 mg, 0.183 mmol, Step I) in MeOH (9.6 mL) were added Pd/C (10%, 78 mg, 0.073 mmol) and Hunig's base (63.0 mL, 0.366 mmol). The reaction vessel was evacuated and $H_2$ was bubbled through the solution three times. The reaction mixture was stirred under an atmosphere of $H_2$ at rt for 40 min. Then the reaction mixture was filtered through diatomaceous earth (e.g., Celite®), the solids were rinsed with MeOH and the filtrate was concentrated under reduced pressure to give a colorless gel. This colorless gel was subjected to SFC (Stationary phase: Whelk O1 SS 5 mm, 250×30 mm, Mobile phase: 25% methanol, 75% $CO_2$) to afford two diastereomers. The first eluting isomer was the title compound, which was isolated as a colorless gel (75%, >99% ee).

Step K: 1-((S)-1-(2-((S)-1-Amino-2,2-dicyclopropylethyl)imidazo[1,2-b]pyridazin-7-yl)-2-methoxyethyl)-5,5-difluorotetrahydropyrimidin-2(1H)-one. To a solution of tert-butyl ((S)-2,2-dicyclopropyl-1-(7-((S)-1-(5,5-difluoro-2-oxotetrahydropyrimidin-1(2H)-yl)-2-methoxyethyl)imidazo[1,2-b]pyridazin-2-yl)ethyl)carbamate (106 mg, 0.197 mmol, Step J, first eluting isomer) in DCM (1.9 mL) cooled to 0° C. was added TFA (0.48 mL, 6.2 mmol) and the resulting solution was stirred at 0° C. for 1.5 h. Then the mixture was concentrated and to it was added 2 M $NH_3$ in MeOH (1.0 mL, 2.0 mmol) at 0° C. to adjust the pH to pH 9. Then $H_2O$ (5 mL) was added and the mixture was extracted with DCM/IPA (4/1, 3×5 mL). The combined organic layers were dried over anhydrous $Na_2SO_4$, filtered, and concentrated to dryness to give the title compound as a colorless film (100% yield) that was used without further purification.

Intermediate 94: Diastereomeric Mixture of ((1R*, 3S*)-3-((1,3-dioxoisoindolin-2-yl)methyl)-2,2-difluorocyclopropyl)methyl trifluoromethanesulfonate and ((1S*,3R*)-3-((1,3-dioxoisoindolin-2-yl) methyl)-2,2-difluorocyclopropyl)methyl trifluoromethanesulfonate

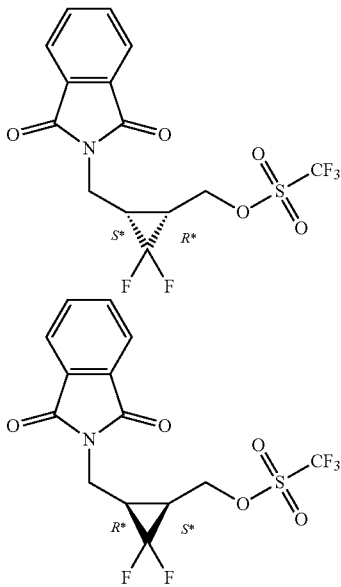

Step A: Diastereomeric mixture of ((1S*,3R*)-3-(aminomethyl)-2,2-difluorocyclopropyl)methanol and ((1R*, 3S*)-3-(aminomethyl)-2,2-difluorocyclopropyl)methanol. To a stirred solution of a diastereomeric mixture of methyl (1S*,3R*)-3-(aminomethyl)-2,2-difluorocyclopropane-1-carboxylate hydrochloride and methyl (1R*,3S*)-3-(aminomethyl)-2,2-difluorocyclopropane-1-carboxylate hydrochloride (293 mg, 1.45 mmol) in THF (7.26 mL) at 0° C. was added lithium borohydride (316.4 mg, 14.5 mmol) portionwise. The reaction mixture was then warmed to 65° C. and allowed to stir for 30 min at which point the reaction vessel was cooled to 0° C. and MeOH (4.78 mL) was added slowly. The reaction mixture was then warmed to 65° C. for 30 min. The mixture was allowed to cool to rt and then concentrated. To the residue was added 1 M aqueous HCl (10 mL) and the solution was allowed to stir at rt for 2 h. The pH of the solution was adjusted to pH 10.0 by the addition of 3 M aqueous NaOH. The aqueous solution was transferred to a separatory funnel and extracted with DCM (4×50 mL), and chloroform:IPA (3:1, 3×50 mL). The combined organic layers were dried with anhydrous MgSO₄, filtered, and concentrated to give the title compounds in 78% yield.

Step B: Diastereomeric mixture of 2-(((1R*,3S*)-2,2-difluoro-3-(hydroxymethyl)cyclopropyl)methyl)isoindoline-1,3-dione and 2-(((1S*,3R*)-2,2-difluoro-3-(hydroxymethyl)cyclopropyl)methyl)isoindoline-1,3-dione. To a stirred solution of the diastereomeric mixture made in Step A (156 mg, 1.14 mmol) in THF (3.79 mL) at rt was added DIPEA (0.78 mL, 4.55 mmol) and the mixture was allowed to stir for 5 min. Then, N-carbethoxyphthalimide (287 mg, 1.31 mmol) was added, a reflux condenser was attached to the flask and the resulting mixture was heated at 75° C. for 16 h. The mixture was concentrated to approximately one-third of the reaction volume and transferred to a separatory funnel containing EtOAc and water. The layers were separated and the mixture further extracted with EtOAc (2×100 mL). The combined organic layers were then washed with water (50 mL) and brine (50 mL), dried over anhydrous MgSO₄, filtered, and concentrated to give an oil. This oil was purified by silica gel chromatography (10-90% EtOAc/hexanes) to afford the title compounds in 61% yield.

Step C: Diastereomeric mixture of ((1S*,3R*)-3-((1,3-dioxoisoindolin-2-yl)methyl)-2,2-difluorocyclopropyl) methyl trifluoromethanesulfonate and ((1R*,3S*)-3-((1,3-dioxoisoindolin-2-yl)methyl)-2,2-difluorocyclopropyl) methyl trifluoromethanesulfonate. To a stirred solution of the diastereomeric mixture made in Step B (93.3 mg, 0.35 mmol) in DCM (1.2 mL) at 0° C. was added pyridine (31.1 µL, 0.38 mmol) and the mixture was allowed to stir for 5 min before the dropwise addition of trifluoromethanesulfonic anhydride (62.1 µL, 0.367 mmol). The resulting mixture was stirred at 0° C. for 1 h. The reaction was quenched by the addition of water (5 mL) then diluted with DCM (10 mL). The layers were separated and the aqueous layer was extracted with DCM (2×20 mL). The combined organic layers were washed with brine (20 mL), dried over anhydrous MgSO₄, filtered, and concentrated to afford the title compounds in quantitative yield.

Intermediate 95: Diastereomeric Mixture of (1S*, 7R*)-3-((S)-1-(2-((S)-amino(4,4-difluorocyclohexyl) methyl)imidazo[1,2-b]pyridazin-7-yl)-2-methoxyethyl)-8,8-difluoro-3,5-diazabicyclo[5.1.0]octan-4-one and (1R*,7S*)-3-((S)-1-(2-((S)-amino(4,4-difluorocyclohexyl)methyl)imidazo[1,2-b]pyridazin-7-yl)-2-methoxyethyl)-8,8-difluoro-3,5-diazabicyclo[5.1.0]octan-4-one

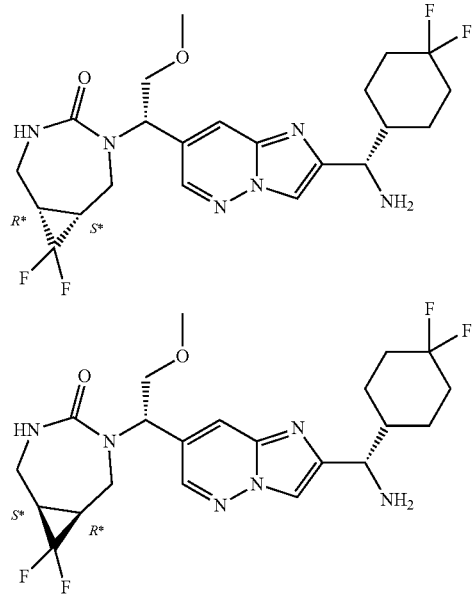

Step A: Diastereomeric mixture of tert-butyl ((S)-(4,4-difluorocyclohexyl)(7-((S)-1-((((1R*,3S*)-3-((1,3-dioxoisoindolin-2-yl)methyl)-2,2-difluorocyclopropyl)methyl) amino)-2-methoxyethyl)imidazo[1,2-b]pyridazin-2-yl) methyl)carbamate and tert-butyl ((S)-(4,4-difluorocyclohexyl)(7-((S)-1-((((1S*,3R*)-3-((1,3-dioxoisoindolin-2-yl)methyl)-2,2-difluorocyclopropyl)

methyl)amino)-2-methoxyethyl)imidazo[1,2-b]pyridazin-2-yl)methyl)carbamate. The title compounds (38% yield) were prepared as described for the synthesis of Intermediate 2 Step A using tert-butyl ((S)-(7-((S)-1-amino-2-methoxyethyl)imidazo[1,2-b]pyridazin-2-yl)(4,4-difluorocyclohexyl)methyl)carbamate (Intermediate 3 Step B) in place of tert-butyl ((S)-(7-((R)-amino(cyclopropyl)methyl)imidazo[1,2-b]pyridazin-2-yl)(4,4-difluorocyclohexyl)methyl)carbamate and the diastereomeric mixture made in Intermediate 94 in place of 3-(1,3-dioxoisoindolin-2-yl)-2,2-difluoropropyl trifluoromethanesulfonate.

Step B: Diastereomeric mixture of tert-butyl ((S)-(7-((S)-1-((((1S*,3R*)-3-(aminomethyl)-2,2-difluorocyclopropyl)methyl)amino)-2-methoxyethyl)imidazo[1,2-b]pyridazin-2-yl)(4,4-difluorocyclohexyl)methyl)carbamate and tert-butyl ((S)-(7-((S)-1-((((1R*,3S*)-3-(aminomethyl)-2,2-difluorocyclopropyl)methyl)amino)-2-methoxyethyl)imidazo[1,2-b]pyridazin-2-yl)(4,4-difluorocyclohexyl)methyl)carbamate. The title compounds (60% yield) were prepared as described for the synthesis of Intermediate 2 Step B using the diastereomeric mixture made in Step A in place of tert-butyl ((S)-(7-((R)-cyclopropyl((3-(1,3-dioxoisoindolin-2-yl)-2,2-difluoropropyl)amino)methyl)imidazo[1,2-b]pyridazin-2-yl)(4,4-difluorocyclohexyl)methyl)carbamate.

Step C: Diastereomeric mixture of tert-butyl ((S)-(7-((S)-1-((1S*,7R*)-8,8-difluoro-4-oxo-3,5-diazabicyclo[5.1.0]octan-3-yl)-2-methoxyethyl)imidazo[1,2-b]pyridazin-2-yl)(4,4-difluorocyclohexyl)methyl)carbamate and tert-butyl ((S)-(7-((S)-1-((1R*,7S*)-8,8-difluoro-4-oxo-3,5-diazabicyclo[5.1.0]octan-3-yl)-2-methoxyethyl)imidazo[1,2-b]pyridazin-2-yl)(4,4-difluorocyclohexyl)methyl)carbamate. The title compounds (22% yield) were prepared as described for Intermediate 15 Step C using the diastereomeric mixture made in Step B in place of tert-butyl ((S)-(7-((S)-1-((3-amino-2,2-difluoropropyl)amino)-2-cyclopropoxyethyl)imidazo[1,2-b]pyridazin-2-yl)(4,4-difluorocyclohexyl)methyl)carbamate.

Step D: Diastereomeric mixture of (1S*,7R*)-3-((S)-1-(2-((S)-amino(4,4-difluorocyclohexyl)methyl)imidazo[1,2-b]pyridazin-7-yl)-2-methoxyethyl)-8,8-difluoro-3,5-diazabicyclo[5.1.0]octan-4-one and (1R*,7S*)-3-((S)-1-(2-((S)-amino(4,4-difluorocyclohexyl)methyl)imidazo[1,2-b]pyridazin-7-yl)-2-methoxyethyl)-8,8-difluoro-3,5-diazabicyclo[5.1.0]octan-4-one. The title compounds (100% yield) were prepared as described for the synthesis of Intermediate 2 Step D using the diastereomeric mixture made in Step C in place of tert-butyl ((S)-(7-((R)-cyclopropyl(5,5-difluoro-2-oxotetrahydropyrimidin-1(2H)-yl)methyl)imidazo[1,2-b]pyridazin-2-yl)(4,4-difluorocyclohexyl)methyl)carbamate.

Intermediate 96: tert-Butyl (S)-(5,5,5-trifluoro-1-(7-formylimidazo[1,2-b]pyridazin-2-yl)-4,4-dimethylpentyl)carbamate Step A: tert-Butyl (S)-(1-(7-chloroimidazo[1,2-b]pyridazin-2-yl)-5,5,5-trifluoro-4,4-dimethylpentyl)carbamate. 5-Chloropyridazin-3-amine (1.00 g, 7.72 mmol) and tert-butyl (S)-(1-(dimethyl(oxo)-$\lambda^6$-sulfaneylidene)-7,7,7-trifluoro-6,6-dimethyl-2-oxoheptan-3-yl)carbamate (3.29 g, 8.49 mmol, Intermediate 45) were dissolved in toluene (21 mL). 4 Å Molecular sieves (2.00 g), NaOTf (66.4 mg, 0.386 mmol), and chloro(cyclopentadienyl)bis(triphenylphosphine)ruthenium(II) (141 mg, 0.193 mmol) were added sequentially, and the resulting mixture was heated at 85° C. for 16 h. The reaction mixture was concentrated onto diatomaceous earth (e.g., Celite®), and purified by silica gel chromatography (0-100% EtOAc/hexanes) to afford the title compound in 30% yield.

Step B: tert-Butyl (S)-(5,5,5-trifluoro-4,4-dimethyl-1-(7-vinylimidazo[1,2-b]pyridazin-2-yl)pentyl)carbamate. tert-Butyl (S)-(1-(7-chloroimidazo[1,2-b]pyridazin-2-yl)-5,5,5-trifluoro-4,4-dimethylpentyl)carbamate (0.960 mg, 2.28 mmol, Step A), potassium trifluoro(vinyl)borate (0.460 g, 3.43 mmol), and $K_3PO_4$ (1.46 g, 6.90 mmol) were added under a positive pressure of nitrogen gas to a reactor containing 1,4-dioxane and water (24 mL, 5:1 v/v, sparged with $N_2$ before use). The mixture was heated at reflux temperature (85° C.), and then RuPhos Pd G3 (49.7 mg, 60.0 mmol) was added. The resulting mixture was stirred at 85° C. for 6 h. After this time, the mixture was allowed to cool to rt and then concentrated to remove most of the 1,4-dioxane. The residue was then diluted with EtOAc and water, the layers were separated, and the aqueous layer was extracted twice with EtOAc. The organic layers were combined, washed with brine, dried over anhydrous $MgSO_4$, filtered, and concentrated to dryness to afford the title compound as a brown foam, which was used without further purification.

Step C: tert-Butyl (S)-(5,5,5-trifluoro-1-(7-formylimidazo[1,2-b]pyridazin-2-yl)-4,4-dimethylpentyl)carbamate. A solution of $NaIO_4$ (2.43 g, 11.4 mmol) in water (55 mL) was added to a solution of tert-butyl (S)-(5,5,5-trifluoro-4,4-dimethyl-1-(7-vinylimidazo[1,2-b]pyridazin-2-yl)pentyl)carbamate (8.81 g, 22.5 mmol, Step B) in 1,4-dioxane (55 mL). The resulting mixture was then cooled with an ice bath to just above freezing and $K_2OsO_4 \cdot 2H_2O$ (42.0 mg, 0.114 mmol) was added. The reaction mixture was then removed from the ice bath and stirred for 1 h. The resulting thick suspension was diluted with water and the solution was extracted with EtOAc (4×). The combined organic layers were washed with brine, dried over anhydrous $Na_2SO_4$, filtered, concentrated onto diatomaceous earth (e.g., Celite®), and purified by silica gel chromatography (0-50% acetone/hexanes) to afford the title compound in 64% yield.

Intermediate 97: (S)-1-((2-(1-Amino-5,5,5-trifluoro-4,4-dimethylpentyl)imidazo[1,2-b]pyridazin-7-yl)methyl)-5,5-difluorotetrahydropyrimidin-2(1H)-one

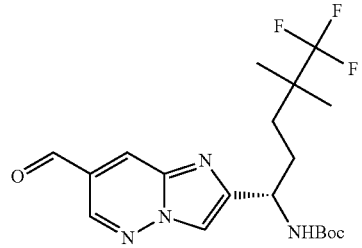 [SMILES: CC(C)(C)OC(=O)N[C@@H](CCC(C)(C)C(F)(F)F)c1cn2ncc(C=O)cc2n1]

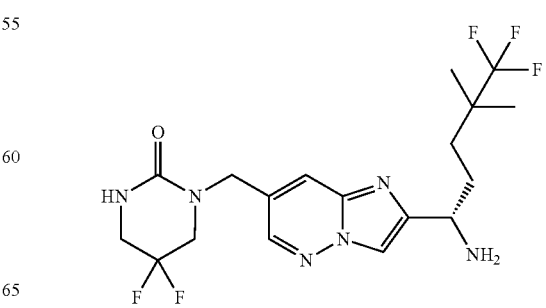

Step A: tert-Butyl (S)-(1-(7-(((3-amino-2,2-difluoropropyl)amino)methyl)imidazo[1,2-b]pyridazin-2-yl)-5,5,5-trifluoro-4,4-dimethylpentyl)carbamate. The title compound was synthesized in a manner analogous to Intermediate 20 Step A using tert-butyl (S)-(5,5,5-trifluoro-1-(7-formylimidazo[1,2-b]pyridazin-2-yl)-4,4-dimethylpentyl)carbamate (Intermediate 96) in place of tert-butyl (S)-((4,4-difluorocyclohexyl)(7-formylimidazo[1,2-b]pyridazin-2-yl)methyl)carbamate and was used without further purification.

Step B: tert-Butyl (S)-(1-(7-((5,5-difluoro-2-oxotetrahydropyrimidin-1(2H)-yl)methyl)imidazo[1,2-b]pyridazin-2-yl)-5,5,5-trifluoro-4,4-dimethylpentyl)carbamate. The title compound was synthesized in a manner analogous to Intermediate 20 Step B using tert-butyl (S)-(1-(7-(((3-amino-2,2-difluoropropyl)amino)methyl)imidazo[1,2-b]pyridazin-2-yl)-5,5,5-trifluoro-4,4-dimethylpentyl)carbamate (Step A) in place of tert-butyl (S)-((7-(((3-amino-2,2-difluoropropyl)amino)methyl)imidazo[1,2-b]pyridazin-2-yl)(4,4-difluorocyclohexyl)methyl)carbamate. The material was purified by silica gel chromatography (0-100% acetone/hexanes) to afford the title compound in 37% yield over steps A and B.

Step C: (S)-1-((2-(1-Amino-5,5,5-trifluoro-4,4-dimethylpentyl)imidazo[1,2-b]pyridazin-7-yl)methyl)-5,5-difluorotetrahydropyrimidin-2(1H)-one. The title compound was synthesized in a manner analogous to Intermediate 20 Step C using tert-butyl (S)-(1-(7-((5,5-difluoro-2-oxotetrahydropyrimidin-1(2H)-yl)methyl)imidazo[1,2-b]pyridazin-2-yl)-5,5,5-trifluoro-4,4-dimethylpentyl)carbamate (Step B) in place of tert-butyl (S)-((7-((5,5-difluoro-2-oxotetrahydropyrimidin-1(2H)-yl)methyl)imidazo[1,2-b]pyridazin-2-yl)(4,4-difluorocyclohexyl)methyl)carbamate and was used without further purification.

Intermediate 98: Diastereomeric Mixture of (1S*,7R*)-3-((2-((S)-1-amino-5,5,5-trifluoro-4,4-dimethylpentyl)imidazo[1,2-b]pyridazin-7-yl)methyl)-8,8-difluoro-3,5-diazabicyclo[5.1.0]octan-4-one and (1R*,7S*)-3-((2-((S)-1-amino-5,5,5-trifluoro-4,4-dimethylpentyl)imidazo[1,2-b]pyridazin-7-yl)methyl)-8,8-difluoro-3,5-diazabicyclo[5.1.0]octan-4-one

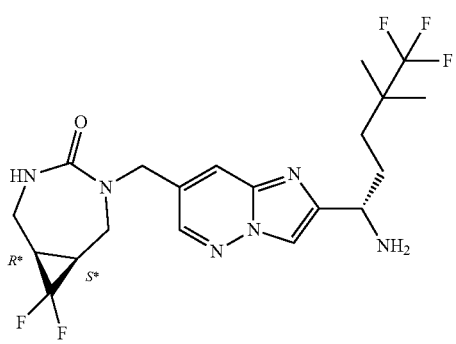

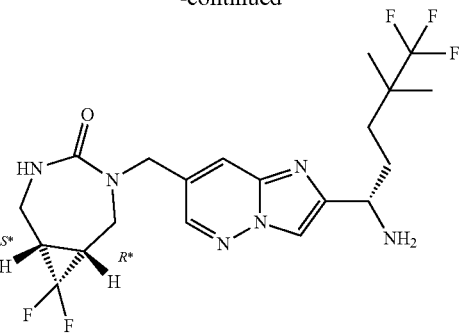

The title compounds were synthesized in a manner analogous to Intermediate 20 Steps A, B and C using tert-butyl (S)-(5,5,5-trifluoro-1-(7-formylimidazo[1,2-b]pyridazin-2-yl)-4,4-dimethylpentyl)carbamate (Intermediate 96) in place of tert-butyl (S)-((4,4-difluorocyclohexyl)(7-formylimidazo[1,2-b]pyridazin-2-yl)methyl)carbamate and ((1S,2R)-3,3-difluorocyclopropane-1,2-diyl)dimethanamine dihydrochloride in place of 2,2-difluoropropane-1,3-diamine dihydrochloride in Step A. In Step B, the residue was purified by silica gel chromatography (0-100% acetone/hexanes).

Intermediate 99: 4-(1,3-Dioxoisoindolin-2-yl)-2,2,3,3-tetrafluorobutyl trifluoromethanesulfonate

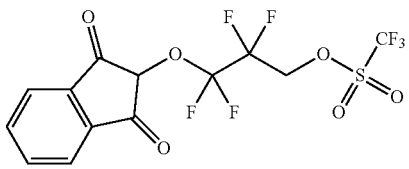 [SMILES: O=C1c2ccccc2C(=O)C1OC(F)(F)C(F)(F)COS(=O)(=O)C(F)(F)F]

Step A: 4-(Benzyloxy)-2,2,3,3-tetrafluorobutan-1-ol. 2,2,3,3-Tetrafluorobutane-1,4-diol (5.00 g, 30.8 mmol), $K_2CO_3$ (8.53 g, 61.7 mmol) and MeCN (60 mL) were added to a three-neck round-bottomed flask, and a solution of BnBr (5.28 g, 30.8 mmol) in MeCN (10 mL) in one portion was added. The resulting mixture was stirred at 85° C. for 16 h. The reaction mixture was cooled to rt, filtered through a pad of diatomaceous earth (e.g., Celite®), and the pad was rinsed with MeCN. The combined filtrates were concentrated to dryness to give an oil that was subjected to silica gel chromatography (0-19% EtOAc/petroleum ether) to provide the title compound as a colorless oil (95% yield).

Step B: 4-(Benzyloxy)-2,2,3,3-tetrafluorobutyl trifluoromethanesulfonate. A round-bottom flask was charged with 4-(benzyloxy)-2,2,3,3-tetrafluorobutan-1-ol (8.00 g, 31.7 mmol, Step A) followed by the dropwise addition of DCM (10 mL) and pyridine (5.04 mL, 62.6 mmol). The resulting mixture was stirred at 25° C. for 5 min, then trifluoromethanesulfonic anhydride (5.34 mL, 31.7 mmol) was added to the mixture dropwise. The resulting mixture was stirred at 25° C. for 3 h. The reaction mixture was then partitioned between DCM (20 mL) and water (20 mL), and the aqueous layer further extracted with DCM (2×20 mL). The organic layers were combined, washed with $H_2O$ (20 mL) and brine (20 mL), dried over anhydrous $Na_2SO_4$, filtered, and concentrated to dryness to give a liquid. The liquid was then subjected to silica gel chromatography (0-9% EtOAc/petroleum ether) to afford the title compound as a colorless liquid (97% yield).

Step C: 2-(4-(Benzyloxy)-2,2,3,3-tetrafluorobutyl)isoindoline-1,3-dione. A mixture of 4-(benzyloxy)-2,2,3,3-tetrafluorobutyl trifluoromethanesulfonate (5.00 g, 13.0 mmol, Step B) and potassium 1,3-dioxoisoindolin-2-ide (4.82 g, 26.0 mmol) in DMF (32 mL) was heated at 85° C. overnight under nitrogen. The reaction mixture was cooled to rt then partitioned between EtOAc (50 mL) and water (50 mL), and the aqueous layer was further extracted with EtOAc (50 mL×2). The organic layers were combined, washed with water (50 mL×3), and brine (50 mL), dried over anhydrous $Na_2SO_4$, filtered, and concentrated to dryness to give a colorless oil. The oil was subjected to silica gel chromatography (0-20% EtOAc/petroleum ether) to afford the title compound as a white solid (89% yield).

Step D: 2-(2,2,3,3-Tetrafluoro-4-hydroxybutyl)isoindoline-1,3-dione. To a mixture of 2-(4-(benzyloxy)-2,2,3,3-tetrafluorobutyl)isoindoline-1,3-dione (2.80 g, 7.34 mmol, Step C) in DCM (5 mL) at −78° C. was added $BCl_3$ (18.4 mL, 1.0 M in DCM, 18.4 mmol) dropwise over 20 min. The reaction mixture was allowed to warm gradually to 20° C., and then stirred at 20° C. for an additional 2 h. The reaction mixture was quenched with saturated aqueous $NaHCO_3$ (10 mL) and extracted with EtOAc (3×10 mL). The combined organic layers were dried over anhydrous $Na_2SO_4$, filtered, and concentrated to dryness to give a yellow solid. The yellow solid was purified by silica gel chromatography (0-25% EtOAc/petroleum ether) to afford the title compound as a white solid, which was used without further purification.

Step E: 4-(1,3-Dioxoisoindolin-2-yl)-2,2,3,3-tetrafluorobutyl trifluoromethanesulfonate. A round-bottom flask was charged with 2-(2,2,3,3-tetrafluoro-4-hydroxybutyl) isoindoline-1,3-dione (10.0 g, 34.3 mmol, Step D), DCM (100 mL) and pyridine (5.46 mL, 67.8 mmol) and the resulting mixture was stirred at 25° C. for 5 min. Then, trifluoromethanesulfonic anhydride (5.78 mL, 34.3 mmol) was added dropwise over 10 min and the resulting mixture was stirred at 25° C. for 3 h. The reaction mixture was then partitioned between DCM (100 mL) and water (100 mL), and the aqueous layer further extracted with DCM (2×100 mL). The organic layers were combined, washed with $H_2O$ (100 mL), and brine (100 mL), dried over anhydrous $Na_2SO_4$, filtered, and concentrated to dryness to give a yellow solid. The yellow solid was triturated with 100 mL of n-hexanes to afford the title compound as a pink solid (15% yield over Steps D and E).

Intermediate 100: 1-((S)-1-(2-((S)-Amino(4,4-difluorocyclohexyl)methyl)imidazo[1,2-b]pyridazin-7-yl)-2-methoxyethyl)-5,5,6,6-tetrafluoro-1,3-diazepan-2-one Step A: tert-Butyl ((S)-(4,4-difluorocyclohexyl)(7-((S)-1-((4-(1,3-dioxoisoindolin-2-yl)-2,2,3,3-tetrafluorobutyl)amino)-2-methoxyethyl)imidazo[1,2-b]pyridazin-2-yl)methyl)carbamate. The title compound (84% yield) was prepared as described for the synthesis of Intermediate 2 Step A using tert-butyl ((S)-(7-((S)-1-amino-2-methoxyethyl)imidazo[1,2-b]pyridazin-2-yl)(4,4-difluorocyclohexyl)methyl)carbamate (Intermediate 3 Step B) in place of tert-butyl ((S)-(7-((R)-amino(cyclopropyl)methyl)imidazo[1,2-b]pyridazin-2-yl)(4,4-difluorocyclohexyl)methyl)carbamate and 4-(1,3-dioxoisoindolin-2-yl)-2,2,3,3-tetrafluorobutyl trifluoromethanesulfonate (Intermediate 99) in place of 3-(1,3-dioxoisoindolin-2-yl)-2,2-difluoropropyl trifluoromethanesulfonate.

Step B: tert-Butyl ((S)-(7-((S)-1-((4-amino-2,2,3,3-tetrafluorobutyl)amino)-2-methoxyethyl)imidazo[1,2-b]pyridazin-2-yl)(4,4-difluorocyclohexyl)methyl)carbamate. The title compound (73% yield) was prepared as described for the synthesis of Intermediate 2 Step B using tert-butyl ((S)-(4,4-difluorocyclohexyl)(7-((S)-1-((4-(1,3-dioxoisoindolin-2-yl)-2,2,3,3-tetrafluorobutyl)amino)-2-methoxyethyl)imidazo[1,2-b]pyridazin-2-yl)methyl)carbamate (Step A) in place of tert-butyl ((S)-(7-((R)-cyclopropyl((3-(1,3-dioxoisoindolin-2-yl)-2,2-difluoropropyl)amino)methyl) imidazo[1,2-b]pyridazin-2-yl)(4,4-difluorocyclohexyl) methyl)carbamate.

Step C: tert-Butyl ((S)-(4,4-difluorocyclohexyl)(7-((S)-2-methoxy-1-(5,5,6,6-tetrafluoro-2-oxo-1,3-diazepan-1-yl) ethyl)imidazo[1,2-b]pyridazin-2-yl)methyl)carbamate. The title compound (41% yield) was prepared as described for the synthesis of Intermediate 2 Step C using tert-butyl ((S)-(7-((S)-1-((4-amino-2,2,3,3-tetrafluorobutyl)amino)-2-methoxyethyl)imidazo[1,2-b]pyridazin-2-yl)(4,4-difluorocyclohexyl)methyl)carbamate (Step B) in place of tert-butyl ((S)-(7-((R)-((3-amino-2,2-difluoropropyl)amino)(cyclopropyl)methyl)imidazo[1,2-b]pyridazin-2-yl)(4,4-difluorocyclohexyl)methyl)carbamate.

Step D: 1-((S)-1-(2-((S)-Amino(4,4-difluorocyclohexyl) methyl)imidazo[1,2-b]pyridazin-7-yl)-2-methoxyethyl)-5,5, 6,6-tetrafluoro-1,3-diazepan-2-one. The title compound (99% yield) was prepared as described for the synthesis of Intermediate 2 Step D using tert-butyl ((S)-(4,4-difluorocyclohexyl)(7-((S)-2-methoxy-1-(5,5,6,6-tetrafluoro-2-oxo-1, 3-diazepan-1-yl)ethyl)imidazo[1,2-b]pyridazin-2-yl) methyl)carbamate (Step C) in place of tert-butyl ((S)-(7-((R)-cyclopropyl(5,5-difluoro-2-oxotetrahydropyrimidin-1 (2H)-yl)methyl)imidazo[1,2-b]pyridazin-2-yl)(4,4-difluorocyclohexyl)methyl)carbamate.

Intermediate 101: 1-((S)-1-(2-((S*)-1-Amino-3-(1-(trifluoromethyl)cyclopropyl)propyl)imidazo[1,2-b]pyridazin-7-yl)-2-methoxyethyl)-5,5-difluorotetrahydropyrimidin-2(1H)-one

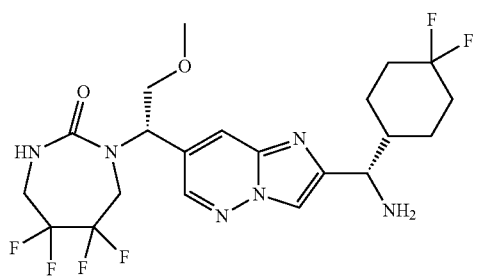 [SMILES: COC[C@H](c1cnn2cc([C@@H](N)C3CCC(F)(F)CC3)nc2c1)N1CC(F)(F)C(F)(F)CNC1=O]

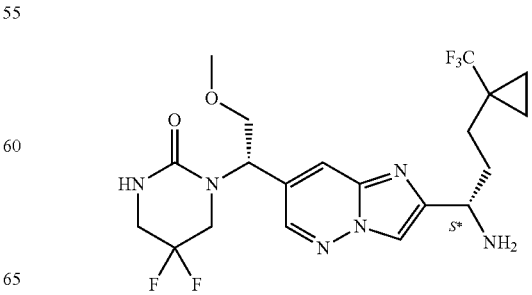

Step A: (S)—N-((E)-(7-((S)-1-(5,5-Difluoro-2-oxotetrahydropyrimidin-1(2H)-yl)-2-methoxyethyl)imidazo[1,2-b]pyridazin-2-yl)methylene)-2-methylpropane-2-sulfinamide. A mixture of (S)-(−)-2-methyl-2-propanesulfinamide (0.51 g, 4.2 mmol), (S)-7-(1-(5,5-difluoro-2-oxotetrahydropyrimidin-1(2H)-yl)-2-methoxyethyl)imidazo[1,2-b]pyridazine-2-carbaldehyde (1.50 g, 4.42 mmol, Intermediate 56 Step C) and CuSO₄ (2.16 g, 13.3 mmol) in DCM (15 mL) was stirred at rt for 2 h. The reaction mixture was then filtered through a pad of diatomaceous earth (e.g., Celite®), which was rinsed with DCM. The filtrate was concentrated to dryness and purified via silica gel chromatography (0-100% acetone/hexanes) to afford the title compound in 77% yield.

Step B: (2S*,3S*)-3-(((S)-tert-Butylsulfinyl)amino)-3-(7-((R)-1-(5,5-difluoro-2-oxotetrahydropyrimidin-1(2H)-yl)-2-methoxyethyl)imidazo[1,2-b]pyridazin-2-yl)-2-((1-(trifluoromethyl)cyclopropyl)methyl)propanoic acid. To a solution of DIPA (0.70 mL, 5.0 mmol) in THF (10 mL) at 0° C. was added n-BuLi (2 mL, 2.5 M in hexanes, 5 mmol). After stirring for 30 min at 0° C., the solution was cooled to −78° C. and then 3-[1-(trifluoromethyl)cyclopropyl]propanoic acid (455 mg, 2.50 mmol) was added dropwise. The resulting mixture was stirred at −78° C. for 1 h, then a solution of (S)—N-((E)-(7-((S)-1-(5,5-difluoro-2-oxotetrahydropyrimidin-1(2H)-yl)-2-methoxyethyl)imidazo[1,2-b]pyridazin-2-yl)methylene)-2-methylpropane-2-sulfinamide (443 mg, 1.00 mmol, Step A) in THF (20 mL) was added via cannula. The reaction mixture was stirred at −78° C. for 30 min and then allowed to warm to 0° C. and stirred at 0° C. for 30 min. The reaction mixture was then quenched with distilled water (60 mL) and washed with EtOAc (20 mL). The pH of the aqueous layer was adjusted to pH ~1 by the addition of 1 M aqueous KHSO₄ and then the aqueous layer was extracted with DCM (2×30 mL). The combined organic layers were dried over anhydrous MgSO₄, filtered, and concentrated to dryness to afford the title compound that was used without further purification.

Step C: 1,3-Dioxoisoindolin-2-yl (2S*,3S*)-3-(((S)-tert-butylsulfinyl)amino)-3-(7-((R)-1-(5,5-difluoro-2-oxotetrahydropyrimidin-1(2H)-yl)-2-methoxyethyl)imidazo[1,2-b]pyridazin-2-yl)-2-((1-(trifluoromethyl)cyclopropyl)methyl)propanoate. To a solution of (2S*,3S*)-3-(((S)-tert-butylsulfinyl)amino)-3-(7-((R)-1-(5,5-difluoro-2-oxotetrahydropyrimidin-1(2H)-yl)-2-methoxyethyl)imidazo[1,2-b]pyridazin-2-yl)-2-((1-(trifluoromethyl)cyclopropyl)methyl)propanoic acid (540 mg, 0.865 mmol, Step B) in DCM (12.9 mL) at 0° C. were added N-hydroxyphthalimide (262 mg, 1.56 mmol), DMAP (10.6 mg, 0.087 mmol) and DCC (321 mg, 1.56 mmol). The resulting mixture was allowed to warm to rt and stir for 18 h. Then, the reaction mixture was cooled to 0° C., filtered through a pad of diatomaceous earth (e.g., Celite®), and the pad rinsed with cold DCM. The combined filtrate was concentrated to dryness and subjected to silica gel chromatography (50-100% acetone/hexanes) to afford the title compound that was used without further purification.

Step D: (S)—N—((S*)-1-(7-((S)-1-(5,5-Difluoro-2-oxotetrahydropyrimidin-1(2H)-yl)-2-methoxyethyl)imidazo[1,2-b]pyridazin-2-yl)-3-(1-(trifluoromethyl)cyclopropyl)propyl)-2-methylpropane-2-sulfinamide. To a solution of 1,3-dioxoisoindolin-2-yl (2S*,3S*)-3-(((S)-tert-butylsulfinyl)amino)-3-(7-((R)-1-(5,5-difluoro-2-oxotetrahydropyrimidin-1(2H)-yl)-2-methoxyethyl)imidazo[1,2-b]pyridazin-2-yl)-2-((1-(trifluoromethyl)cyclopropyl)methyl)propanoate (80.7 mg, 0.105 mmol, Step C) and Hantzsch ester (19.9 mg, 0.079 mmol) in DMSO (0.78 mL) under N₂ was added DIPEA (0.054 mL, 0.32 mmol and the resulting mixture was irradiated with 450 nm light (max rpm fan, 40% LED intensity) for 1 h. The reaction mixture was then diluted with EtOAc (50 mL) and washed with brine (3×30 mL). The organic layer was dried over anhydrous MgSO₄, filtered and concentrated to dryness. The material was purified via silica gel chromatography (50-100% acetone/hexanes) to afford the title compound in 5% yield over steps B, C, and D.

Step E: 1-((S)-1-(2-((S*)-1-Amino-3-(1-(trifluoromethyl)cyclopropyl)propyl)imidazo[1,2-b]pyridazin-7-yl)-2-methoxyethyl)-5,5-difluorotetrahydropyrimidin-2(1H)-one. To a solution of (S)—N—((S*)-1-(7-((S)-1-(5,5-difluoro-2-oxotetrahydropyrimidin-1(2H)-yl)-2-methoxyethyl)imidazo[1,2-b]pyridazin-2-yl)-3-(1-(trifluoromethyl)cyclopropyl)propyl)-2-methylpropane-2-sulfinamide (30 mg, 0.052 mmol, Step D) in 1,4-dioxane (0.52 mL) and MeOH (0.26 mL) was added HCl (0.82 mL, 3.27 mmol, 4 M in 1,4-dioxane) and the resulting mixture was stirred at rt for 30 min. Then, the reaction mixture was diluted with water and washed with hexanes. The pH of the aqueous layer was adjusted to pH 10 by the addition of 10% aqueous K₂CO₃ solution. The aqueous layer was extracted with EtOAc (5×20 mL). The combined organic layers were washed with brine, dried over anhydrous MgSO₄, filtered, and concentrated to dryness to afford the title compound that was used without further purification.

Intermediate 102: 4-(2,2,2-Trifluoroethyl)-1,2,5-oxadiazole-3-carboxylic acid

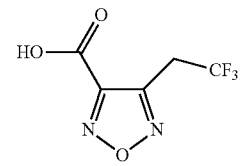 [SMILES: O=C(O)c1nonc1CC(F)(F)F]

Step A: Methyl 5,5,5-trifluoro-2-(hydroxyimino)-3-oxopentanoate. A solution of sodium nitrite (6.75 g, 97.8 mmol) in water (27 mL) was added dropwise to a solution of methyl 5,5,5-trifluoro-3-oxopentanoate (15.0 g, 81.5 mmol) in AcOH (36 mL) that had been cooled to 0° C., and the resulting mixture was allowed to slowly warm to rt and then stirred at rt for 3 h. The reaction mixture was quenched with water (100 mL) and extracted with Et₂O (2×100 mL). The combined organic layers were washed with brine, dried over anhydrous Na₂SO₄, filtered, and concentrated to dryness to afford the title compound in 69% yield as a yellow oil.

Step B: Methyl 5,5,5-trifluoro-2,3-bis(hydroxyimino)pentanoate. Hydroxylamine hydrochloride (10.2 g, 146 mmol) and NaOAc (8.31 g, 101 mmol) were added to a solution of methyl 5,5,5-trifluoro-2-(hydroxyimino)-3-oxopentanoate (12.0 g, 56.3 mmol, Step A) in EtOH (240 mL). The resulting mixture was heated at 80° C. for 5 h. The mixture was cooled to rt, filtered, and the filtrate was concentrated to dryness. The residue was purified by silica gel chromatography (0-10% EtOAc/petroleum ether) to afford the title compound in 78% yield.

Step C: Methyl 4-(2,2,2-trifluoroethyl)-1,2,5-oxadiazole-3-carboxylate. To a solution of methyl 5,5,5-trifluoro-2,3-bis(hydroxyimino)pentanoate (10.0 g, 43.8 mmol, Step B) in THF (100 mL) at 0° C. was added CDI (10.7 g, 65.8 mmol) in portions and the resulting mixture was stirred at 0° C. for 1 h. After that time, the mixture was heated at 45° C. for 16 h then cooled to rt and quenched by the addition of water (100 mL). The mixture was extracted with Et$_2$O (2×100 mL) and the combined organic layers were washed with brine, dried over anhydrous Na$_2$SO$_4$, filtered, and concentrated to dryness. The residue was purified by silica gel chromatography (0-10% EtOAc/petroleum ether) to afford the title compound in 34% yield as a light-yellow oil.

Step D: 4-(2,2,2-Trifluoroethyl)-1,2,5-oxadiazole-3-carboxylic acid. To a solution of methyl 4-(2,2,2-trifluoroethyl)-1,2,5-oxadiazole-3-carboxylate (500 mg, 2.38 mmol, Step C) in THF (7.9 mL) was added LiOH (1.19 mL, 2 M in H$_2$O, 2.38 mmol). The resulting mixture was stirred at rt for 1 h, then was diluted with water (10 mL) and extracted with EtOAc. The organic layer was discarded, and the pH of the aqueous layer was adjusted to pH 1 by the addition of 6 N aqueous HCl and then extracted with EtOAc (3×). The combined organic layers were washed with brine, dried over anhydrous MgSO$_4$, filtered, and concentrated to dryness to afford the title compound that was used without further purification.

Intermediate 103:1-((S)-1-(2-((S*)-1-Amino-5,5-difluoro-4,4-dimethylhexyl)imidazo[1,2-b]pyridazin-7-yl)-2-methoxyethyl)-5,5-difluorotetrahydropyrimidin-2(1H)-one

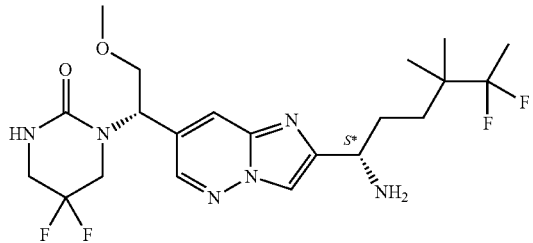 [SMILES: COC[C@H](c1cnn2cc([C@@H](N)CCC(C)(C)C(C)(F)F)nc2c1)N1CC(F)(F)CNC1=O]

Step A: 2-((S*)—(((S)-tert-Butylsulfinyl)amino)(7-((S)-1-(5,5-difluoro-2-oxotetrahydropyrimidin-1(2H)-yl)-2-methoxyethyl)imidazo[1,2-b]pyridazin-2-yl)methyl)-5,5-difluoro-4,4-dimethylhexanoic acid. The title compound was synthesized in a manner analogous to Intermediate 101 Step B using 5,5-difluoro-4,4-dimethylhexanoic acid in place of 3-(1-(trifluoromethyl)cyclopropyl)propanoic acid and was used without further purification.

Step B: 1,3-Dioxoisoindolin-2-yl 2-((S*)—(((S)-tert-butylsulfinyl)amino)(7-((S)-1-(5,5-difluoro-2-oxotetrahydropyrimidin-1(2H)-yl)-2-methoxyethyl)imidazo[1,2-b]pyridazin-2-yl)methyl)-5,5-difluoro-4,4-dimethylhexanoate. The title compound (8% yield over Steps A and B) was synthesized in a manner analogous to Intermediate 101 Step C using 2-((S*)—(((S)-tert-butylsulfinyl)amino)(7-((S)-1-(5,5-difluoro-2-oxotetrahydropyrimidin-1(2H)-yl)-2-methoxyethyl)imidazo[1,2-b]pyridazin-2-yl)methyl)-5,5-difluoro-4,4-dimethylhexanoic acid (Step A) in place of (2S*,3S*)-3-(((S)-tert-butylsulfinyl)amino)-3-(7-((R)-1-(5,5-difluoro-2-oxotetrahydropyrimidin-1(2H)-yl)-2-methoxyethyl)imidazo[1,2-b]pyridazin-2-yl)-2-((1-(trifluoromethyl)cyclopropyl)methyl)propanoic acid.

Step C: (S)—N—((S*)-1-(7-((S)-1-(5,5-Difluoro-2-oxotetrahydropyrimidin-1(2H)-yl)-2-methoxyethyl)imidazo[1,2-b]pyridazin-2-yl)-5,5-difluoro-4,4-dimethylhexyl)-2-methylpropane-2-sulfinamide. The title compound (89% yield) was synthesized in a manner analogous to Intermediate 101 Step D using 1,3-dioxoisoindolin-2-yl 2-((S*)—(((S)-tert-butylsulfinyl)amino)(7-((S)-1-(5,5-difluoro-2-oxotetrahydropyrimidin-1(2H)-yl)-2-methoxyethyl)imidazo[1,2-b]pyridazin-2-yl)methyl)-5,5-difluoro-4,4-dimethylhexanoate (Step B) in place of 1,3-dioxoisoindolin-2-yl 3-(((S)-tert-butylsulfinyl)amino)-3-(7-((S)-1-(5,5-difluoro-2-oxotetrahydropyrimidin-1(2H)-yl)-2-methoxyethyl)imidazo[1,2-b]pyridazin-2-yl)-2-((1-(trifluoromethyl)cyclopropyl)methyl)propanoate.

Step D: 1-((S)-1-(2-((S*)-1-Amino-5,5-difluoro-4,4-dimethylhexyl)imidazo[1,2-b]pyridazin-7-yl)-2-methoxyethyl)-5,5-difluorotetrahydropyrimidin-2(1H)-one. The title compound was synthesized in a manner analogous to Intermediate 101 Step E using (S)—N—((S*)-1-(7-((S)-1-(5,5-difluoro-2-oxotetrahydropyrimidin-1(2H)-yl)-2-methoxyethyl)imidazo[1,2-b]pyridazin-2-yl)-5,5-difluoro-4,4-dimethylhexyl)-2-methylpropane-2-sulfinamide (Step C) in place of (S)—N-(1-(7-((S)-1-(5,5-difluoro-2-oxotetrahydropyrimidin-1(2H)-yl)-2-methoxyethyl)imidazo[1,2-b]pyridazin-2-yl)-3-(1-(trifluoromethyl)cyclopropyl)propyl)-2-methylpropane-2-sulfinamide and was used without further purification.

Example 1: 4-Cyclopropyl-N—((S)-(4,4-difluorocyclohexyl)(7-(((R*)-5-fluoro-5-methyl-2-oxotetrahydropyrimidin-1(2H)-yl)methyl)imidazo[1,2-b]pyridazin-2-yl)methyl)-1,2,5-oxadiazole-3-carboxamide

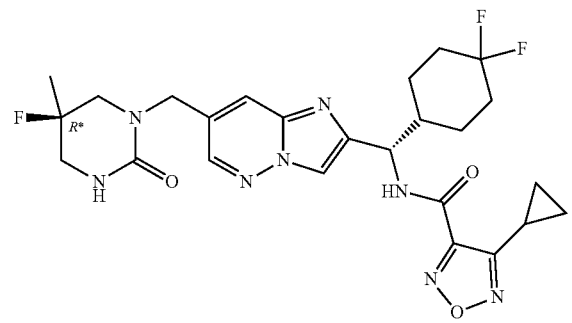 [SMILES: C[C@@]1(F)CNC(=O)N(Cc2cnn3cc([C@@H](NC(=O)c4nonc4C4CC4)C4CCC(F)(F)CC4)nc3c2)C1]

Example 2: 4-Cyclopropyl-N—((S)-(4,4-difluorocyclohexyl)(7-(((S*)-5-fluoro-5-methyl-2-oxotetrahydropyrimidin-1(2H)-yl)methyl)imidazo[1,2-b]pyridazin-2-yl)methyl)-1,2,5-oxadiazole-3-carboxamide

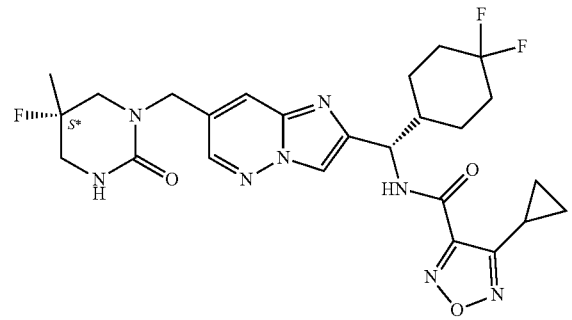 [SMILES: C[C@]1(F)CNC(=O)N(Cc2cnn3cc([C@@H](NC(=O)c4nonc4C4CC4)C4CCC(F)(F)CC4)nc3c2)C1]

Step A: tert-Butyl ((1S)-(7-(((3-amino-2-fluoro-2-methylpropyl)amino)methyl)imidazo[1,2-b]pyridazin-2-yl)(4,4-difluorocyclohexyl)methyl)carbamate. tert-Butyl (S)-((4,4-difluorocyclohexyl)(7-formylimidazo[1,2-b]pyridazin-2-yl)methyl)carbamate (500 mg, 1.27 mmol), 2-fluoro-2-methylpropane-1,3-diamine dihydrochloride (454 mg, 2.54 mmol, Intermediate 1), DCM (50 mL) and TEA (1.06 mL, 7.61 mmol) were added to a 100 mL three-neck round-bottomed flask. The resulting mixture was stirred for 16 h at 30° C. before it was treated with NaBH$_3$CN (239 mg, 3.80 mmol), methanol (10 mL) and AcOH (10 mL) in one portion. The resulting mixture stirred for another 16 h at 30° C. The reaction mixture was then poured into water (100 mL) and the pH was adjusted to pH 8 by the addition of saturated aqueous NaHCO$_3$, The resulting solution was extracted with DCM (50 mL×2). The combined organic extracts were washed with brine (50 mL), dried over anhydrous MgSO$_4$, filtered, and concentrated to dryness under reduced pressure to provide tert-butyl ((1S)-(7-(((3-amino-2-fluoro-2-methylpropyl)amino)methyl)imidazo[1,2-b]pyridazin-2-yl)(4,4-difluorocyclohexyl)methyl)carbamate as a brown solid, which was used without further purification.

Step B: tert-Butyl ((1S)-(4,4-difluorocyclohexyl)(7-((5-fluoro-5-methyl-2-oxotetrahydropyrimidin-1(2H)-yl)methyl)imidazo[1,2-b]pyridazin-2-yl)methyl)carbamate. tert-Butyl ((1S)-(7-(((3-amino-2-fluoro-2-methylpropyl)amino)methyl)imidazo[1,2-b]pyridazin-2-yl)(4,4-difluorocyclohexyl)methyl)carbamate (500 mg, 1.03 mmol, Step A), THF (50 mL) and CDI (334 mg, 2.06 mmol) were added to a 100 mL three-neck round-bottomed flask equipped with a condenser and a thermometer, and the resulting mixture was stirred for 4 h at 70° C. The reaction mixture was then concentrated to dryness to give a brown solid. The solid was initially purified by silica gel chromatography (0-100% EtOAc/petroleum ether followed by 0-20% MeOH/EtOAc). The resulting material was further purified by subjecting it to an additional silica gel chromatography using the same conditions to provide tert-butyl ((1S)-(4,4-difluorocyclohexyl)(7-((5-fluoro-5-methyl-2-oxotetrahydropyrimidin-1(2H)-yl)methyl)imidazo[1,2-b]pyridazin-2-yl)methyl)carbamate as a white solid that was used without further purification.

Step C: 1-((2-((S)-Amino(4,4-difluorocyclohexyl)methyl)imidazo[1,2-b]pyridazin-7-yl)methyl)-5-fluoro-5-methyltetrahydropyrimidin-2(1H)-one. tert-Butyl ((1S)-(4,4-difluorocyclohexyl)(7-((5-fluoro-5-methyl-2-oxotetrahydropyrimidin-1(2H)-yl)methyl)imidazo[1,2-b]pyridazin-2-yl)methyl)carbamate (400 mg, Step B) and HCl (12 mL, 4 M in MeOH) were added to a 50 mL round-bottomed flask, and the resulting mixture was stirred for 1 h at rt. The reaction mixture was then concentrated to dryness to afford a brown solid. The solid was then purified by preparative HPLC (Boston Green C18 column, 5 μm, 150×30 mm; 8-18% (v/v) H$_2$O (0.225% HCOOH)/CH$_3$CN) to provide, after lyophilization, 1-((2-((S)-amino(4,4-difluorocyclohexyl)methyl)imidazo[1,2-b]pyridazin-7-yl)methyl)-5-fluoro-5-methyltetrahydropyrimidin-2(1H)-one (62% yield) as a white solid.

Step D: 4-Cyclopropyl-N-((1S)-(4,4-difluorocyclohexyl)(7-((5-fluoro-5-methyl-2-oxotetrahydropyrimidin-1(2H)-yl)methyl)imidazo[1,2-b]pyridazin-2-yl)methyl)-1,2,5-oxadiazole-3-carboxamide. 4-Cyclopropyl-1,2,5-oxadiazole-3-carboxylic acid (75.1 mg, 0.487 mmol), 1-((2-((S)-amino(4,4-difluorocyclohexyl)methyl)imidazo[1,2-b]pyridazin-7-yl)methyl)-5-fluoro-5-methyltetrahydropyrimidin-2(1H)-one (200 mg, 0.487 mmol, Step C), TEA (0.260 mL, 1.46 mmol), 2-chloro-1-methylpyridinium iodide (373 mg, 0.731 mmol) and THF (40 mL) were added to a 100 mL round-bottomed flask, and the resulting mixture was stirred for 1 h at 30° C. The reaction mixture was then concentrated to dryness and partitioned between DCM (50 mL) and water (20 mL). The organic layer was dried over anhydrous MgSO$_4$, filtered, and concentrated to dryness to afford a white solid. The solid was initially purified by silica gel chromatography using (0-100% EtOAc/petroleum ether followed by second silica gel chromatography using 0-20% MeOH/EtOAc) to provide 4-cyclopropyl-N-((1S)-(4,4-difluorocyclohexyl)(7-((5-fluoro-5-methyl-2-oxotetrahydropyrimidin-1(2H)-yl)methyl)imidazo[1,2-b]pyridazin-2-yl)methyl)-1,2,5-oxadiazole-3-carboxamide (68% yield) as a white solid.

Step E: 4-Cyclopropyl-N—(S)-(4,4-difluorocyclohexyl)(7-(((R*)-5-fluoro-5-methyl-2-oxotetrahydropyrimidin-1(2H)-yl)methyl)imidazo[1,2-b]pyridazin-2-yl)methyl)-1,2,5-oxadiazole-3-carboxamide. The solid, 4-cyclopropyl-N-((1S)-(4,4-difluorocyclohexyl)(7-((5-fluoro-5-methyl-2-oxotetrahydropyrimidin-1(2H)-yl)methyl)imidazo[1,2-b]pyridazin-2-yl)methyl)-1,2,5-oxadiazole-3-carboxamide, from Step D was purified by chiral SFC (DAICEL CHIRALPAK IC column, 10 μm, 250×50 mm; 45% (v/v) EtOH (containing 0.1% of 25% aqueous NH$_3$)/CO$_2$) to afford two diastereomers. The first eluting isomer was designated as the (R*) isomer (Example 1) and the second eluting isomer was designated as the (S*) isomer (Example 2). The first eluting isomer, Example 1, was further purified by preparative HPLC (Phenomenex Gemini-NX C18 column, 3 μm, 75×30 mm; 35-65% (v/v) H$_2$O (0.05% aqueous NH$_3$ with 10 mM NH$_4$HCO$_3$)/CH$_3$CN) to provide, after lyophillization, 4-cyclopropyl-N—((S)-(4,4-difluorocyclohexyl)(7-(((R*)-5-fluoro-5-methyl-2-oxotetrahydropyrimidin-1(2H)-yl)methyl)imidazo[1,2-b]pyridazin-2-yl)methyl)-1,2,5-oxadiazole-3-carboxamide (Example 1, 13% yield) as a white solid. Example 1: $^1$H NMR (400 MHz, DMSO-d$_6$) δ 9.51 (d, J=8.8 Hz, 1H), 8.40 (d, J=2.0 Hz, 1H), 8.23 (s, 1H), 7.86 (s, 1H), 6.63 (d, J=4.4 Hz, 1H), 5.19 (t, J=8.8 Hz, 1H), 4.62-4.38 (m, 2H), 3.60-3.38 (m, 1H), 3.33-3.13 (m, 3H), 2.32-2.24 (m, 1H), 2.23-2.12 (m, 1H), 2.10-1.94 (m, 2H), 1.93-1.68 (m, 3H), 1.67-1.55 (m, 1H), 1.46-1.20 (m, 5H), 1.18-1.07 (m, 2H), 1.00-0.91 (m, 2H). MS (ESI) m/z: [M+H]$^+$ Found 547.3.

The second eluting isomer (Example 2) was further purified by preparative HPLC (Phenomenex Gemini-NX C18 column, 3 μm, 75×30 mm; 34-64% (v/v) H$_2$O (0.05% aqueous NH$_3$ with 10 mM NH$_4$HCO$_3$)/CH$_3$CN) to provide, after lyophillization, 4-cyclopropyl-N—((S)-(4,4-difluorocyclohexyl)(7-(((S*)-5-fluoro-5-methyl-2-oxotetrahydropyrimidin-1(2H)-yl)methyl)imidazo[1,2-b]pyridazin-2-yl)methyl)-1,2,5-oxadiazole-3-carboxamide (Example 2, 16% yield) as a white solid. Example 2: $^1$H NMR (400 MHz, DMSO-d$_6$) δ 9.52 (d, J=9.2 Hz, 1H), 8.40 (d, J=1.6 Hz, 1H), 8.23 (s, 1H), 7.85 (s, 1H), 6.63 (d, J=4.0 Hz, 1H), 5.18 (t, J=8.4 Hz, 1H), 4.61-4.52 (m, 1H), 4.47-4.39 (m, 1H), 3.57-3.42 (m, 1H), 3.32-3.10 (m, 3H), 2.32-2.23 (m, 1H), 2.23-2.12 (m, 1H), 2.11-1.96 (m, 2H), 1.94-1.69 (m, 3H), 1.67-1.56 (m, 1H), 1.46-1.23 (m, 5H), 1.18-1.08 (m, 2H), 1.00-0.92 (m, 2H). MS (ESI) m/z: [M+H]$^+$ Found 547.3.

Example 3 and Example 4: Diastereomeric Mixture of 4-cyclopropyl-N—((S)-(7-(((1R,7S)-8,8-difluoro-4-oxo-3,5-diazabicyclo[5.1.0]octan-3-yl)methyl)imidazo[1,2-b]pyridazin-2-yl)(4,4-difluorocyclohexyl)methyl)-1,2,5-oxadiazole-3-carboxamide and 4-cyclopropyl-N—((S)-(7-(((1R,7R)-8,8-difluoro-4-oxo-3,5-diazabicyclo[5.1.0]octan-3-yl)methyl)imidazo[1,2-b]pyridazin-2-yl)(4,4-difluorocyclohexyl)methyl)-1,2,5-oxadiazole-3-carboxamide

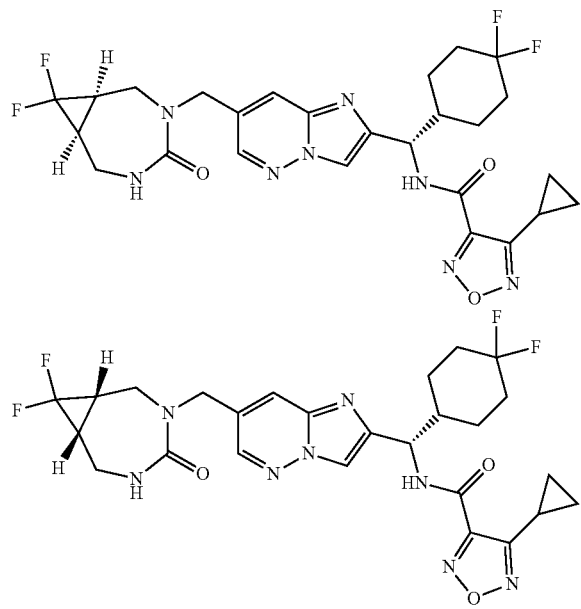

Step A: Diastereomeric mixture of tert-butyl ((S)-(7-(((((1R,3S)-3-(aminomethyl)-2,2-difluorocyclopropyl)methyl)amino)methyl)imidazo[1,2-b]pyridazin-2-yl)(4,4-difluorocyclohexyl)methyl)carbamate and tert-butyl ((S)-(7-(((((1S,3R)-3-(aminomethyl)-2,2-difluorocyclopropyl)methyl)amino)methyl)imidazo[1,2-b]pyridazin-2-yl)(4,4-difluorocyclohexyl)methyl)carbamate. tert-Butyl (S)-((4,4-difluorocyclohexyl)(7-formylimidazo[1,2-b]pyridazin-2-yl)methyl)carbamate (200 mg, 0.510 mmol), ((1R,2S)-3,3-difluorocyclopropane-1,2-diyl) dimethanamine (159 mg, 0.760 mmol), TEA (0.4 mL, 3.0 mmol) and anhydrous DCM (20 mL) were added to a 100 mL three-neck round-bottomed flask. The resulting mixture was stirred for 16 h at 30° C. before treating with NaBH₃CN (96 mg, 1.5 mmol), methanol (4 mL) and AcOH (4 mL) in one portion. The resulting mixture stirred for another 2 h at 30° C. The reaction mixture was then poured into water (30 mL) and extracted with DCM (30 mL). The pH of the aqueous layer was adjusted to pH 8 by the addition of saturated aqueous NaHCO₃ and then extracted with DCM (40 mL×3). The combined organic extracts were washed with brine (2×30 mL), dried over anhydrous Na₂SO₄, filtered, and concentrated to dryness under reduced pressure to provide the title compounds as a yellow oil, which were used without further purification.

Step B: Diastereomeric mixture of tert-butyl ((S)-(7-(((1R,7S)-8,8-difluoro-4-oxo-3,5-diazabicyclo[5.1.0]octan-3-yl)methyl)imidazo[1,2-b]pyridazin-2-yl)(4,4-difluorocyclohexyl)methyl)carbamate and tert-butyl ((S)-(7-(((1S,7R)-8,8-difluoro-4-oxo-3,5-diazabicyclo[5.1.0]octan-3-yl)methyl)imidazo[1,2-b]pyridazin-2-yl)(4,4-difluorocyclohexyl)methyl)carbamate. The diastereomeric mixture made in Step A (201 mg, 0.390 mmol), THF (40 mL) and CDI (127 mg, 0.780 mmol) were added to a 100 mL round-bottomed flask and the resulting mixture was stirred for 2 h at 70° C. The reaction mixture was then concentrated to dryness to give a colorless oil. This oil was then purified by preparative HPLC (Welch Xtimate C18 column, 5 μm, 150×25 mm; 36-66% (v/v) H₂O (0.225% HCOOH)/CH₃CN) to provide the title compounds (8% yield) as a white solid after lyophilization.

Step C: Diastereomeric mixture of (1R,7S)-3-((2-((S)-amino(4,4-difluorocyclohexyl)methyl)imidazo[1,2-b]pyridazin-7-yl)methyl)-8,8-difluoro-3,5-diazabicyclo[5.1.0]octan-4-one dihydrochloride and (1S,7R)-3-((2-((S)-amino(4,4-difluorocyclohexyl)methyl)imidazo[1,2-b]pyridazin-7-yl)methyl)-8,8-difluoro-3,5-diazabicyclo[5.1.0]octan-4-one dihydrochloride. The title compounds were prepared as described for the synthesis of Example 1 Step C using the diastereomeric mixture made in Step B in place of tert-butyl ((1S)-(4,4-difluorocyclohexyl)(7-((5-fluoro-5-methyl-2-oxotetrahydropyrimidin-1(2H)-yl)methyl)imidazo[1,2-b]pyridazin-2-yl)methyl)carbamate to provide the title compounds as a brown solid, which were used without further purification.

Step D: Diastereomeric mixture of 4-cyclopropyl-N—((S)-(7-(((1R,7S)-8,8-difluoro-4-oxo-3,5-diazabicyclo[5.1.0]octan-3-yl)methyl)imidazo[1,2-b]pyridazin-2-yl)(4,4-difluorocyclohexyl)methyl)-1,2,5-oxadiazole-3-carboxamide and 4-cyclopropyl-N—((S)-(7-(((1S,7R)-8,8-difluoro-4-oxo-3,5-diazabicyclo[5.1.0]octan-3-yl)methyl)imidazo[1,2-b]pyridazin-2-yl)(4,4-difluorocyclohexyl)methyl)-1,2,5-oxadiazole-3-carboxamide. The title compounds were prepared as described for the synthesis of Example 1 Step D using the diastereomeric mixture made in Step C in place of 1-((2-((S)-amino(4,4-difluorocyclohexyl)methyl)imidazo[1,2-b]pyridazin-7-yl)methyl)-5-fluoro-5-methyltetrahydropyrimidin-2(1H)-one. After stirring at 30° C. for 1 h, the reaction mixture was concentrated to dryness and the residue purified by preparative TLC (5% MeOH/DCM) to provide a white solid (36% yield). The diastereomeric mixture made in Step D was separated by chiral SFC (DAICEL CHIRALCEL OD-H column, 5 m, 250×30 mm; 45% (v/v) EtOH (containing 0.1% of 25% aqueous NH₃)/CO₂). The first eluting isomer was designated as isomer 1 (Example 3) and the second eluting isomer was designated as isomer 2 (Example 4). The first eluting isomer (Example 3, 13% yield) was isolated as a white solid after lyophilization. Example 3: $^1$H NMR (400 MHz, DMSO-$d_6$) δ 9.50 (d, J=8.8 Hz, 1H), 8.43 (d, J=1.6 Hz, 1H), 8.22 (s, 1H), 7.92 (s, 1H), 6.59 (d, J=7.6 Hz, 1H), 5.19 (t, J=8.4 Hz, 1H), 4.63 (d, J=15.6 Hz, 1H), 4.40 (d, J=15.6 Hz, 1H), 3.99-3.86 (m, 1H), 3.69-3.55 (m, 1H), 3.45-3.38 (m, 1H), 3.19-3.05 (m, 1H), 2.32-2.24 (m, 2H), 2.23-2.13 (m, 1H), 2.11-1.96 (m, 2H), 1.93-1.72 (m, 3H), 1.67-1.50 (m, 1H), 1.43-1.35 (m, 1H), 1.35-1.23 (m, 2H), 1.15-1.06 (m, 2H), 1.00-0.93 (m, 2H). MS (ESI) m/z: [M+H]⁺ Found 577.3.

The second eluting isomer (Example 4, 9.8% yield) was isolated as a white solid after lyophilization. Example 4: $^1$H NMR (400 MHz, DMSO-$d_6$) δ 9.51 (d, J=9.2 Hz, 1H), 8.44 (d, J=2.0 Hz, 1H), 8.22 (s, 1H), 7.93 (s, 1H), 6.59 (d, J=4.8 Hz, 1H), 5.19 (t, J=8.4 Hz, 1H), 4.64 (d, J=15.6 Hz, 1H), 4.40 (d, J=15.6 Hz, 1H), 4.00-3.89 (m, 1H), 3.68-3.55 (m, 1H), 3.48-3.38 (m, 1H), 3.18-3.01 (m, 1H), 2.34-2.25 (m, 2H), 2.24-2.13 (m, 1H), 2.11-1.96 (m, 2H), 1.93-1.72 (m, 3H), 1.68-1.51 (m, 1H), 1.46-1.20 (m, 3H), 1.15-1.08 (m, 2H), 1.00-0.93 (m, 2H). MS (ESI) m/z: [M+H]⁺ Found 577.3.

Example 5: 4-Cyclopropyl-N—((S)-(4,4-difluorocyclohexyl)(7-(((S*)-2-oxo-5-(trifluoromethyl)tetrahydropyrimidin-1(2H)-yl)methyl)imidazo[1,2-b]pyridazin-2-yl)methyl)-1,2,5-oxadiazole-3-carboxamide

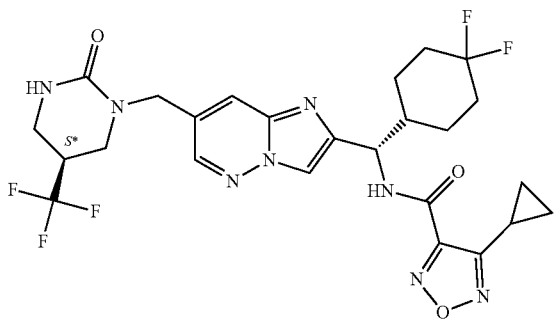 [SMILES: O=C(N[C@H](c1cn2ncc(CN3C[C@@H](C(F)(F)F)CNC3=O)cc2n1)C1CCC(F)(F)CC1)c1nonc1C1CC1]

Example 6: 4-Cyclopropyl-N—((S)-(4,4-difluorocyclohexyl)(7-(((R*)-2-oxo-5-(trifluoromethyl)tetrahydropyrimidin-1(2H)-yl)methyl)imidazo[1,2-b]pyridazin-2-yl)methyl)-1,2,5-oxadiazole-3-carboxamide

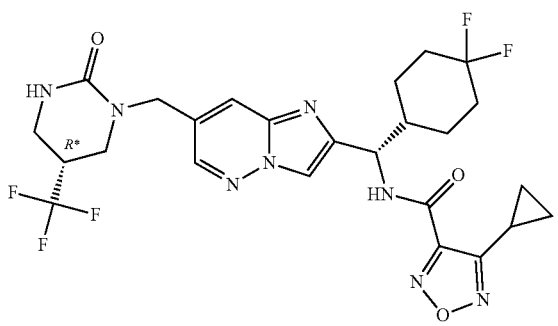 [SMILES: O=C(N[C@H](c1cn2ncc(CN3C[C@H](C(F)(F)F)CNC3=O)cc2n1)C1CCC(F)(F)CC1)c1nonc1C1CC1]

Step A: tert-Butyl ((1S)-(7-(((2-(((tert-butoxycarbonyl)amino)methyl)-3,3,3-trifluoropropyl)amino)methyl)imidazo[1,2-b]pyridazin-2-yl)(4,4-difluorocyclohexyl)methyl)carbamate. tert-Butyl (S)-((4,4-difluorocyclohexyl)(7-formylimidazo[1,2-b]pyridazin-2-yl)methyl)carbamate (500 mg, 1.27 mmol), tert-butyl (2-(aminomethyl)-3,3,3-trifluoropropyl) carbamate (461 mg, 1.90 mmol), TEA (1.06 mL, 7.61 mmol) and DCE (15 mL) were added to a 50 mL three-necked round-bottomed flask. The resulting mixture was stirred at 80° C. for 16 h. The reaction vessel was removed from the oil bath and allowed to gradually cool to rt. Then a mixture of NaBH$_3$CN (239 mg, 3.80 mmol), methanol (10 mL) and AcOH (2.5 mL) was added in one portion. The resulting mixture stirred for 2 h at rt. After that time, the reaction mixture was poured into water (20 mL) and extracted with CH$_2$Cl$_2$ (80 mL×2). The combined organic layers were washed with brine (50 mL), dried over anhydrous Na$_2$SO$_4$, filtered and concentrated to dryness to afford a yellow oil. This material was purified by silica gel chromatography (10-30% EtOAc/petroleum ether) to provide tert-butyl ((1S)-(7-(((2-(((tert-butoxycarbonyl)amino)methyl)-3,3,3-trifluoropropyl)amino)methyl)imidazo[1,2-b]pyridazin-2-yl)(4,4-difluorocyclohexyl)methyl)carbamate (76% yield) as a yellow oil.

Step B: N1-((2-((S)-Amino(4,4-difluorocyclohexyl)methyl)imidazo[1,2-b]pyridazin-7-yl)methyl)-2-(trifluoromethyl)propane-1,3-diamine. tert-Butyl ((1S)-(7-(((2-(((tert-butoxycarbonyl)amino)methyl)-3,3,3-trifluoropropyl)amino)methyl)imidazo[1,2-b]pyridazin-2-yl)(4,4-difluorocyclohexyl)methyl)carbamate (60 mg, 0.097 mmol, Step A) and anhydrous CH$_2$Cl$_2$ (1.5 mL) were added to a 10 mL round-bottomed flask. HCl (1.5 mL, 4 M in MeOH) was added in one portion at rt. The resulting mixture was stirred at rt for 2 h, after which it was concentrated to dryness to afford a colorless oil. The pH of this oil was adjusted to pH ~9-10 by the addition of 2 N aqueous NaOH (8 mL) dropwise, and then this mixture was extracted with EtOAc (20 mL×3). The combined organic extracts were washed with brine (50 mL), dried over anhydrous Na$_2$SO$_4$, filtered and concentrated to dryness to provide N1-((2-((S)-amino(4,4-difluorocyclohexyl)methyl)imidazo[1,2-b]pyridazin-7-yl)methyl)-2-(trifluoromethyl)propane-1,3-diamine (98% yield) as colorless oil.

Step C: 1-((2-((S)-Amino(4,4-difluorocyclohexyl)methyl)imidazo[1,2-b]pyridazin-7-yl)methyl)-5-(trifluoromethyl)tetrahydropyrimidin-2(1H)-one. N1-((2-((S)-Amino(4,4-difluorocyclohexyl)methyl)imidazo[1,2-b]pyridazin-7-yl)methyl)-2-(trifluoromethyl)propane-1,3-diamine (40 mg, 0.10 mmol, Step B) and anhydrous THF (11 mL) were combined and stirred at 65° for 5 min. Then, CDI (23 mg, 0.14 mmol) was added in one portion and the resulting mixture was stirred at 65° C. for 45 min. After that time, the mixture was treated with 2 N aqueous NaOH (3 mL) dropwise until the pH of the solution was pH 9-10 and then the resulting solution was extracted with EtOAc (20 mL×3). The combined organic extracts were washed with brine (30 mL), dried over anhydrous Na$_2$SO$_4$, filtered, and concentrated to dryness to afford a colorless oil. This oil was purified by preparative HPLC (Welch Xtimate C18 column, 5 μm, 150×25 mm, 13-43% (v/v) water (0.225% formic acid)/CH$_3$CN) to provide, after lyophilization, 1-((2-((S)-amino(4,4-difluorocyclohexyl)methyl)imidazo[1,2-b]pyridazin-7-yl)methyl)-5-(trifluoromethyl)tetrahydropyrimidin-2(1H)-one (57% yield) as a white solid.

Step D: 4-Cyclopropyl-N-((1S)-(4,4-difluorocyclohexyl)(7-((2-oxo-5-(trifluoromethyl)tetrahydropyrimidin-1(2H)-yl)methyl)imidazo[1,2-b]pyridazin-2-yl)methyl)-1,2,5-oxadiazole-3-carboxamide. 1-((2-((S)-Amino(4,4-difluorocyclohexyl)methyl)imidazo[1,2-b]pyridazin-7-yl)methyl)-5-(trifluoromethyl)tetrahydropyrimidin-2(1H)-one (24 mg, 0.050 mmol, Step C), 4-cyclopropyl-1,2,5-oxadiazole-3-carboxylic acid (12 mg, 0.080 mmol), HOBt (11 mg, 0.080 mmol), DIPEA (21 mg, 0.16 mmol) and CH$_3$CN (4 mL) were added to a 10 mL single-necked round-bottomed flask at rt. The mixture was stirred at 45° for 5 min, after which the mixture became homogeneous. Then, EDCI (15.5 mg, 0.080 mmol) was added in one portion and the resulting mixture was stirred at 50° C. for 2 h. The reaction was concentrated to dryness to afford a colorless oil, which was purified by preparative TLC (9% MeOH/DCM) to afford 4-cyclopropyl-N-((1S)-(4,4-difluorocyclohexyl)(7-((2-oxo-5-(trifluoromethyl)tetrahydropyrimidin-1(2H)-yl)methyl)imidazo[1,2-b]pyridazin-2-yl)methyl)-1,2,5-oxadiazole-3-carboxamide (96% yield) as colorless oil.

Step E: 4-Cyclopropyl-N—((S)-(4,4-difluorocyclohexyl)(7-(((S*)-2-oxo-5-(trifluoromethyl)tetrahydropyrimidin-1(2H)-yl)methyl)imidazo[1,2-b]pyridazin-2-yl)methyl)-1,2,5-oxadiazole-3-carboxamide. The colorless oil, 4-cyclopropyl-N-((1S)-(4,4-difluorocyclohexyl)(7-((2-oxo-5-(trifluoromethyl)tetrahydropyrimidin-1(2H)-yl)methyl)imidazo[1,2-b]pyridazin-2-yl)methyl)-1,2,5-oxadiazole-3- carboxamide, from Step D, was purified by chiral SFC (DAICEL CHIRALPAK AD column, 10 μm, 250×30 mm; 50% (v/v) EtOH (containing 0.1% of 25% aqueous NH$_3$)/CO$_2$) to afford two diastereomers. The first eluting isomer was designated as the (S*) isomer (Example 5) and the second eluting isomer was designated as the (R*) isomer (Example 6). The first eluting isomer was 4-cyclopropyl-N—((S)-(4,4-difluorocyclohexyl)(7-(((S*)-2-oxo-5-(trifluoromethyl)tetrahydropyrimidin-1(2H)-yl)methyl)imidazo[1,2-b]pyridazin-2-yl)methyl)-1,2,5-oxadiazole-3-carboxamide (Example 5, 8% yield) that was isolated as a white solid after lyophilization. Example 5: $^1$H NMR (400 MHz, DMSO-d$_6$) δ 9.50 (d, J=8.8 Hz, 1H), 8.42 (d, J=1.6 Hz, 1H), 8.23 (s, 1H), 7.93 (s, 1H), 6.73 (s, 1H), 5.19 (t, J=8.4 Hz, 1H), 4.57-4.45 (m, 2H), 3.56-3.48 (m, 1H), 3.42-3.39 (m, 1H), 3.29-3.25 (m, 1H), 3.20-3.12 (m, 1H), 2.31-2.23 (m, 1H), 2.23-2.13 (m, 1H), 2.08-1.95 (m, 2H), 1.92-1.70 (m, 3H), 1.66-1.57 (m, 1H), 1.44-1.22 (m, 3H), 1.14-1.06 (m, 2H), 1.00-0.91 (m, 2H). MS (ESI) m/z: [M+H]$^+$ Found 583.3.

The second eluting isomer was 4-cyclopropyl-N—((S)-(4,4-difluorocyclohexyl)(7-(((R*)-2-oxo-5-(trifluoromethyl)tetrahydropyrimidin-1(2H)-yl)methyl)imidazo[1,2-b]pyridazin-2-yl)methyl)-1,2,5-oxadiazole-3-carboxamide (Example 6, 7% yield) that was isolated as a white solid after lyophilization. Example 6: $^1$H NMR (400 MHz, DMSO-d$_6$) δ 9.50 (d, J=8.8 Hz, 1H), 8.42 (d, J=1.6 Hz, 1H), 8.23 (s, 1H), 7.93 (s, 1H), 6.73 (s, 1H), 5.19 (t, J=8.4 Hz, 1H), 4.57-4.49 (m, 2H), 3.55-3.48 (m, 1H), 3.42-3.39 (m, 1H), 3.29-3.24 (m, 1H), 3.20-3.12 (m, 1H), 2.31-2.24 (m, 1H), 2.23-2.13 (m, 1H), 2.08-1.95 (m, 2H), 1.92-1.69 (m, 3H), 1.67-1.57 (m, 1H), 1.51-1.19 (m, 3H), 1.16-1.08 (m, 2H), 0.99-0.92 (m, 4.8 Hz, 2H). MS (ESI) m/z: [M+H]$^+$ Found 583.3.

Example 7: 4-Cyclopropyl-N—((S)-(7-((R)-cyclopropyl(5,5-difluoro-2-oxotetrahydropyrimidin-1(2H)-yl)methyl)imidazo[1,2-b]pyridazin-2-yl)(4,4-difluorocyclohexyl)methyl)-1,2,5-oxadiazole-3-carboxamide

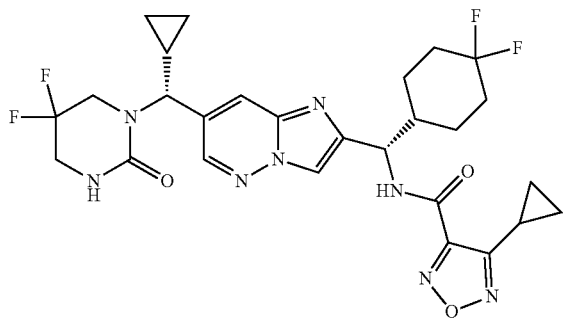 [SMILES: O=C(N[C@H](c1cn2ncc([C@@H](C3CC3)N3CC(F)(F)CNC3=O)cc2n1)C1CCC(F)(F)CC1)c1nonc1C1CC1]

A vial was charged with 1-((R)-(2-((S)-amino(4,4-difluorocyclohexyl)methyl)imidazo[1,2-b]pyridazin-7-yl)(cyclopropyl)methyl)-5,5-difluorotetrahydropyrimidin-2(1H)-one (53 mg, 0.12 mmol, Intermediate 2), 4-cyclopropyl-1,2,5-oxadiazole-3-carboxylic acid (20 mg, 0.13 mmol), MeCN (1.5 mL), HOBt (22 mg, 0.16 mmol), and Hunig's base (31 μL, 0.18 mmol). The solution was heated to 40° C. and stirred for 5 min. To the solution was added EDCI (30 mg 0.16 mmol) and the reaction was further stirred for 18 h at 40° C. Then the reaction mixture was diluted with MeCN and the material was purified directly by reverse phase basic HPLC (X-Bridge Prep C18 5 μm column 50×100 mm, 0-100% acetonitrile/water (with 20 nM NH$_4$OH). The purified fractions were concentrated to dryness to give the title compound as a white foam (74% yield). $^1$H NMR (400 MHz, DMSO-d$_6$) δ 9.47 (d, J=9.0 Hz, 1H), 8.38 (d, J=2.1 Hz, 1H), 8.24 (s, 1H), 8.07-7.93 (m, 1H), 6.91 (s, 1H), 5.26-5.13 (m, 1H), 4.60 (d, J=10.3 Hz, 1H), 3.92-3.74 (m, 1H), 3.67-3.45 (m, 3H), 2.37-2.13 (m, 2H), 2.13-1.47 (m, 7H), 1.47-1.20 (m, 2H), 1.19-1.07 (m, 2H), 1.01-0.93 (m, 2H), 0.86-0.73 (m, 1H), 0.72-0.59 (m, 1H), 0.59-0.48 (m, 1H), 0.46-0.33 (m, 1H). MS (ESI) m/z: [M+H]$^+$ Found 591.3.

Example 8: N—((S)-(7-((R)-Cyclopropyl(5,5-difluoro-2-oxotetrahydropyrimidin-1(2H)-yl)methyl)imidazo[1,2-b]pyridazin-2-yl)(4,4-difluorocyclohexyl)methyl)-4-methyl-1,2,5-oxadiazole-3-carboxamide

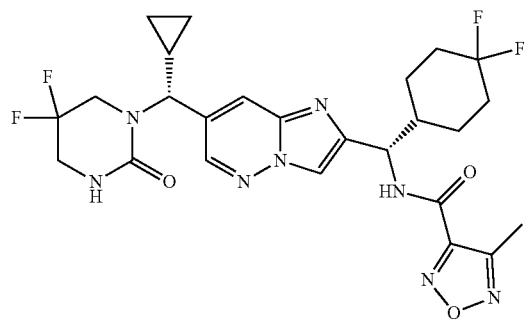 [SMILES: Cc1nonc1C(=O)N[C@H](c1cn2ncc([C@@H](C3CC3)N3CC(F)(F)CNC3=O)cc2n1)C1CCC(F)(F)CC1]

The title compound was prepared as described for the synthesis of Example 7, using 4-methyl-1,2,5-oxadiazole-3-carboxylic acid in place of 4-cyclopropyl-1,2,5-oxadiazole-3-carboxylic acid to afford the title compound as a white solid (70% yield). $^1$H NMR (400 MHz, DMSO-d$_6$) δ 9.40 (d, J=8.9 Hz, 1H), 8.38 (d, J=2.1 Hz, 1H), 8.25 (s, 1H), 8.07-8.00 (m, 1H), 6.91 (s, 1H), 5.23-5.13 (m, 1H), 4.64-4.54 (m, 1H), 3.92-3.75 (m, 1H), 3.68-3.46 (m, 3H), 2.48 (s, 3H), 2.29-2.14 (m, 1H), 2.12-1.69 (m, 5H), 1.69-1.47 (m, 2H), 1.47-1.20 (m, 2H), 0.86-0.74 (m, 1H), 0.72-0.60 (m, 1H), 0.59-0.48 (m, 1H), 0.45-0.33 (m, 1H). MS (ESI) m/z: [M+H]$^+$ Found 565.3.

Example 9: N—((S)-(7-((R)-Cyclopropyl(5,5-difluoro-2-oxotetrahydropyrimidin-1(2H)-yl)methyl)imidazo[1,2-b]pyridazin-2-yl)(4,4-difluorocyclohexyl)methyl)-1-(ethyl-d$_5$)-1H-pyrazole-5-carboxamide

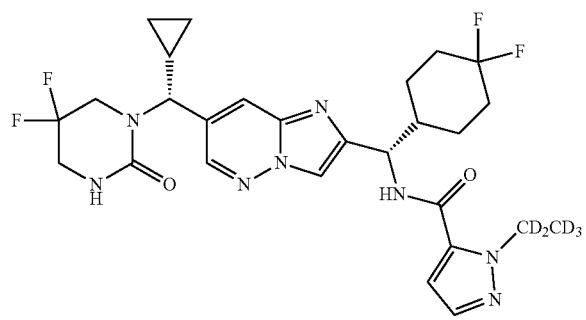

The title compound was prepared as described for the synthesis of Example 7, using 1-(ethyl-d₅)-1H-pyrazole-5-carboxylic acid in place of 4-cyclopropyl-1,2,5-oxadiazole-3-carboxylic acid to afford the title compound as a white solid (50% yield). ¹H NMR (400 MHz, DMSO-d₆) δ 8.72 (d, J=9.0 Hz, 1H), 8.37 (d, J=2.1 Hz, 1H), 8.22 (s, 1H), 8.04-7.98 (m, 1H), 7.47 (d, J=2.0 Hz, 1H), 6.99 (d, J=2.0 Hz, 1H), 6.91 (s, 1H), 5.21-5.12 (m, 1H), 4.64-4.55 (m, 1H), 3.93-3.76 (m, 1H), 3.65-3.46 (m, 3H), 2.26-2.13 (m, 1H), 2.12-1.58 (m, 6H), 1.58-1.47 (m, 1H), 1.46-1.20 (m, 2H), 0.85-0.75 (m, 1H), 0.69-0.60 (m, 1H), 0.58-0.49 (m, 1H), 0.44-0.33 (m, 1H). MS (ESI) m/z: [M+H]⁺ Found 582.3.

Example 10: N—((S)-(7-((R)-Cyclopropyl(5,5-difluoro-2-oxotetrahydropyrimidin-1(2H)-yl)methyl)imidazo[1,2-b]pyridazin-2-yl)(4,4-difluorocyclohexyl)methyl)-1-isopropyl-1H-pyrazole-5-carboxamide

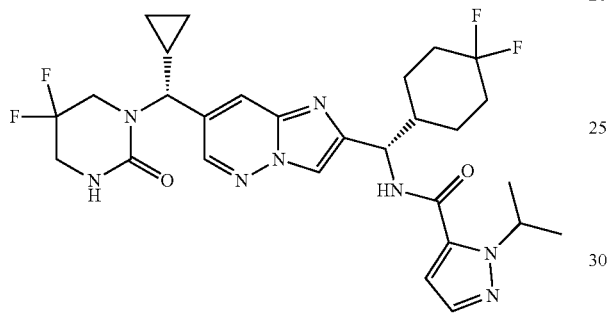

The title compound was prepared as described for the synthesis of Example 7, using 1-(propan-2-yl)-1H-pyrazole-5-carboxylic acid in place of 4-cyclopropyl-1,2,5-oxadiazole-3-carboxylic acid to afford the title compound as a white solid (47% yield). ¹H NMR (400 MHz, DMSO-d₆) δ 8.71 (d, J=9.0 Hz, 1H), 8.37 (d, J=2.1 Hz, 1H), 8.22 (s, 1H), 8.04-7.97 (m, 1H), 7.49 (d, J 2.0 Hz, 1H), 6.94-6.85 (m, 2H), 5.44-5.33 (m, 1H), 5.21-5.13 (m, 1H), 4.63-4.56 (m, 1H), 3.90-3.77 (m, 1H), 3.65-3.46 (m, 3H), 2.25-2.13 (m, 1H), 2.14-1.60 (m, 6H), 1.60-1.47 (m, 1H), 1.46-1.21 (m, 8H), 0.84-0.75 (m, 1H), 0.69-0.59 (m, 1H), 0.59-0.49 (m, 1H), 0.45-0.33 (m, 1H). MS (ESI) m/z: [M+H]⁺ Found 591.3.

Example 11: 4-Cyclopropyl-N—((S)-(7-((S)-1-(5,5-difluoro-2-oxotetrahydropyrimidin-1(2H)-yl)-2-methoxyethyl)imidazo[1,2-b]pyridazin-2-yl)(4,4-difluorocyclohexyl)methyl)-1,2,5-oxadiazole-3-carboxamide

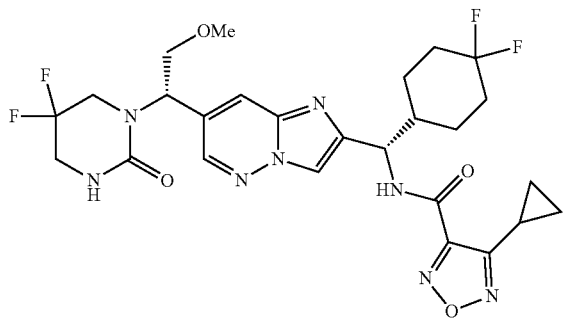 [SMILES: COC[C@H](c1cnn2cc([C@@H](NC(=O)c3nonc3C3CC3)C3CCC(F)(F)CC3)nc2c1)N1CC(F)(F)CNC1=O]

The title compound was prepared as described for the synthesis of Example 7, using 1-((S)-1-(2-((S)-amino(4,4-difluorocyclohexyl)methyl)imidazo[1,2-b]pyridazin-7-yl)-2-methoxyethyl)-5,5-difluorotetrahydropyrimidin-2(1H)-one (Intermediate 3) in place of 1-((R)-(2-((S)-amino(4,4-difluorocyclohexyl)methyl)imidazo[1,2-b]pyridazin-7-yl)(cyclopropyl)methyl)-5,5-difluorotetrahydropyrimidin-2(1H)-one and purification by preparative acidic HPLC (SunFire Prep C18 5 μm column 30×250 mm, 0-100% acetonitrile (0.05% TFA)/water (0.05% TFA)) followed by silica gel chromatography (0-100% (10% 2 M NH₃/MeOH in DCM)/DCM) afforded the title compound as a white foam (81% yield). ¹H NMR (400 MHz, DMSO-d₆) δ 9.48 (d, J=9.0 Hz, 1H), 8.39 (d, J=2.1 Hz, 1H), 8.25 (s, 1H), 7.96-7.91 (m, 1H), 6.96 (s, 1H), 5.61-5.54 (m, 1H), 5.24-5.16 (m, 1H), 3.96-3.86 (m, 2H), 3.77-3.63 (m, 1H), 3.62-3.47 (m, 3H), 3.35 (s, 3H), 2.33-2.25 (m, 1H), 2.25-2.13 (m, 1H), 2.12-1.69 (m, 5H), 1.68-1.58 (m, 1H), 1.47-1.26 (m, 2H), 1.17-1.09 (m, 2H), 0.99-0.93 (m, 2H). MS (ESI) m/z: [M+H]⁺ Found 595.2.

Example 12: N—((S)-(7-((S)-1-(5,5-Difluoro-2-oxotetrahydropyrimidin-1(2H)-yl)-2-methoxyethyl)imidazo[1,2-b]pyridazin-2-yl)(4,4-difluorocyclohexyl)methyl)-4-methyl-1,2,5-oxadiazole-3-carboxamide

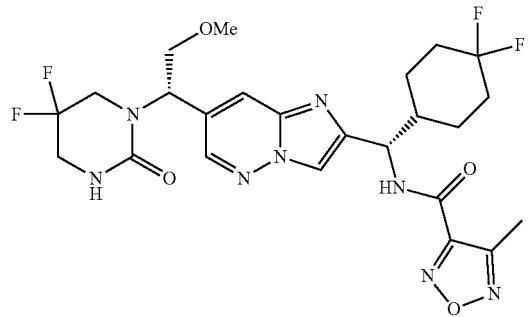 [SMILES: COC[C@H](c1cnn2cc([C@@H](NC(=O)c3nonc3C)C3CCC(F)(F)CC3)nc2c1)N1CC(F)(F)CNC1=O]

The title compound was prepared as described for the synthesis of Example 7, using 1-((S)-1-(2-((S)-amino(4,4-difluorocyclohexyl)methyl)imidazo[1,2-b]pyridazin-7-yl)-2-methoxyethyl)-5,5-difluorotetrahydropyrimidin-2(1H)-one (Intermediate 3) in place of 1-((R)-(2-((S)-amino(4,4-difluorocyclohexyl)methyl)imidazo[1,2-b]pyridazin-7-yl)(cyclopropyl)methyl)-5,5-difluorotetrahydropyrimidin-2(1H)-one and using 4-methyl-1,2,5-oxadiazole-3-carboxylic acid in place of 4-cyclopropyl-1,2,5-oxadiazole-3-carboxylic acid to give the title compound as a white foam (79% yield). ¹H NMR (400 MHz, DMSO-d₆) δ 9.50 (d, J=9.0 Hz, 1H), 8.47 (d, J=2.1 Hz, 1H), 8.34 (s, 1H), 8.03-7.98 (m, 1H), 7.05 (s, 1H), 5.70-5.62 (m, 1H), 5.33-5.20 (m, 1H), 4.04-3.92 (m, 2H), 3.85-3.71 (m, 1H), 3.71-3.52 (m, 3H), 3.43 (s, 3H), 2.56 (s, 3H), 2.36-2.21 (m, 1H), 2.21-1.76 (m, 5H), 1.76-1.65 (m, 1H), 1.56-1.29 (m, 2H). MS (ESI) m/z: [M+H]⁺ Found 569.2.

Example 13: N—((S)-(7-((S)-1-(5,5-Difluoro-2-oxotetrahydropyrimidin-1(2H)-yl)-2-methoxyethyl)imidazo[1,2-b]pyridazin-2-yl)(4,4-difluorocyclohexyl)methyl)-1-(ethyl-d₅)-1H-pyrazole-5-carboxamide

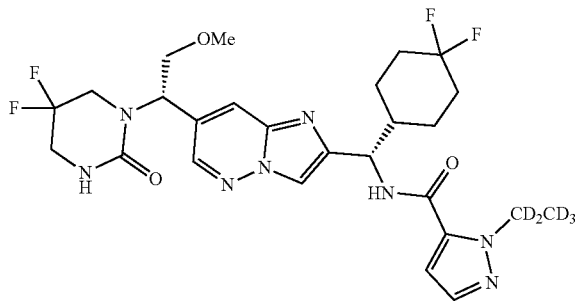

The title compound was prepared as described for the synthesis of Example 7, using 1-((S)-1-(2-((S)-amino(4,4-difluorocyclohexyl)methyl)imidazo[1,2-b]pyridazin-7-yl)-2-methoxyethyl)-5,5-difluorotetrahydropyrimidin-2(1H)-one (Intermediate 3) in place of 1-((R)-(2-((S)-amino(4,4-difluorocyclohexyl)methyl)imidazo[1,2-b]pyridazin-7-yl)(cyclopropyl)methyl)-5,5-difluorotetrahydropyrimidin-2(1H)-one and 1-(ethyl-d₅)-1H-pyrazole-5-carboxylic acid in place of 4-cyclopropyl-1,2,5-oxadiazole-3-carboxylic acid. Additional purifications by preparative acidic HPLC (SunFire Prep C18 5 μm column 30×250 mm, 0-100% acetonitrile (0.05% TFA)/water (0.05% TFA)) and by silica gel chromatography (0 to 100% (10% 2 M NH₃/MeOH in DCM)/DCM) were necessary to provide the title compound as a white foam (59% yield). ¹H NMR (400 MHz, DMSO-d₆) δ 8.73 (d, J=9.0 Hz, 1H), 8.38 (d, J=2.1 Hz, 1H), 8.23 (s, 1H), 7.98-7.86 (m, 1H), 7.47 (d, J=2.0 Hz, 1H), 7.06-6.87 (m, 2H), 5.63-5.53 (m, 1H), 5.22-5.11 (m, 1H), 3.96-3.86 (m, 2H), 3.77-3.64 (m, 1H), 3.64-3.47 (m, 3H), 3.34 (s, 3H), 2.26-2.13 (m, 1H), 2.13-1.68 (m, 5H), 1.68-1.58 (m, 1H), 1.47-1.19 (m, 2H). MS (ESI) m/z: [M+H]⁺ Found 586.3.

Example 14: N—((S)-(7-((S)-1-(5,5-Difluoro-2-oxotetrahydropyrimidin-1(2H)-yl)-2-methoxyethyl)imidazo[1,2-b]pyridazin-2-yl)(4,4-difluorocyclohexyl)methyl)-1-isopropyl-1H-pyrazole-5-carboxamide

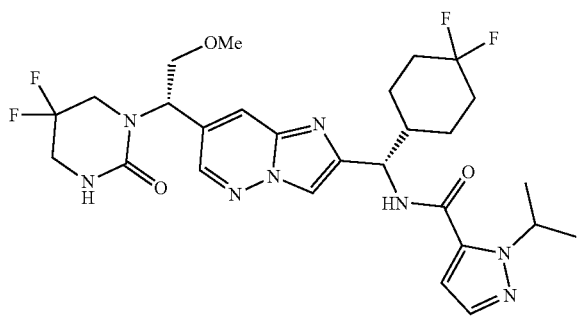 [SMILES: COC[C@H](c1cnn2cc([C@@H](NC(=O)c3ccnn3C(C)C)C3CCC(F)(F)CC3)nc2c1)N1CC(F)(F)CNC1=O]

The title compound was prepared as described for the synthesis of Example 7, using 1-((S)-1-(2-((S)-amino(4,4-difluorocyclohexyl)methyl)imidazo[1,2-b]pyridazin-7-yl)-2-methoxyethyl)-5,5-difluorotetrahydropyrimidin-2(1H)-one (Intermediate 3) in place of 1-((R)-(2-((S)-amino(4,4-difluorocyclohexyl)methyl)imidazo[1,2-b]pyridazin-7-yl)(cyclopropyl)methyl)-5,5-difluorotetrahydropyrimidin-2(1H)-one and 1-(propan-2-yl)-1H-pyrazole-5-carboxylic acid in place of 4-cyclopropyl-1,2,5-oxadiazole-3-carboxylic acid. Additional purifications by preparative acidic HPLC (SunFire Prep C18 5 μm column 30×250 mm, 0-100% acetonitrile (0.05% TFA)/water (0.05% TFA)) and by silica gel chromatography (0 to 100% (10% 2 M NH₃/MeOH in DCM)/DCM) provided the title compound (67% yield). ¹H NMR (400 MHz, DMSO-d₆) δ 8.72 (d, J=9.1 Hz, 1H), 8.38 (d, J=2.1 Hz, 1H), 8.22 (s, 1H), 7.92-7.89 (m, 1H), 7.49 (d, J=2.0 Hz, 1H), 6.95 (d, J=2.9 Hz, 1H), 6.92 (d, J=2.0 Hz, 1H), 5.62-5.55 (m, 1H), 5.42-5.33 (m, 1H), 5.20-5.13 (m, 1H), 3.95-3.86 (m, 2H), 3.76-3.64 (m, 1H), 3.61-3.45 (m, 3H), 3.34 (s, 3H), 2.24-2.13 (m, 1H), 2.10-1.94 (m, 2H), 1.93-1.69 (m, 3H), 1.67-1.59 (m, 1H), 1.44-1.22 (m, 8H). MS (ESI) m/z: [M+H]⁺ Found 595.3.

Example 15: N—((R)-1-(7-((S*)-1-(5,5-Difluoro-2-oxotetrahydropyrimidin-1(2H)-yl)-2-methoxyethyl)imidazo[1,2-b]pyridazin-2-yl)-2-((1,1,1-trifluoro-2-methylpropan-2-yl)oxy)ethyl)-4-methyl-1,2,5-oxadiazole-3-carboxamide

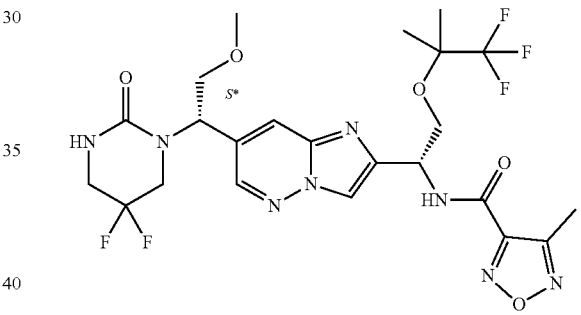

To a mixture of 1-((S*)-1-(2-((R)-1-amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one hydrochloride (73 mg, 0.15 mmol, Intermediate 11) and 4-methyl-1,2,5-oxadiazole-3-carboxylic acid (29 mg, 0.23 mmol) in CH₂Cl₂ (1.5 mL) was added DIPEA (0.13 mL, 0.76 mmol) then T₃P (0.14 mL, 0.23 mmol, 50% in EtOAc). The reaction mixture was stirred at rt for 1 h then DIPEA (0.13 mL, 0.76 mmol) and T₃P (0.14 mL, 0.23 mmol, 50% in EtOAc) were added. The reaction was stirred at rt for 1 h then concentrated under reduced pressure. Purification by silica gel chromatography (10-100% (10% MeOH in EtOAc)/hexanes) followed by SFC using a chiral stationary phase (Stationary phase: Chiralcel OD3 5 μm, 250×21 mm, Mobile phase: 20% Methanol, 80% CO₂) provided the title compound in 9% yield. ¹H NMR (500 MHz, DMSO-d₆) δ 9.43 (d, J=8.5 Hz, 1H), 8.39 (d, J=2.0 Hz, 1H), 8.23 (s, 1H), 7.95 (s, 1H), 6.99-6.92 (m, 1H), 5.64-5.53 (m, 1H), 5.46-5.34 (m, 1H), 4.04-4.01 (m, 1H), 3.99-3.87 (m, 3H), 3.76-3.63 (m, 1H), 3.61-3.48 (m, 3H), 3.35 (br s, 3H), 2.51 (s, 3H), 1.39-1.32 (m, 6H). MS (ESI) m/z: [M+H]⁺ Found 591.4.

Example 16: N—((S)-(7-((S)-2-Cyclopropoxy-1-(5,5-difluoro-2-oxotetrahydropyrimidin-1(2H)-yl)ethyl)imidazo[1,2-b]pyridazin-2-yl)(4,4-difluorocyclohexyl)methyl)-4-methyl-1,2,5-oxadiazole-3-carboxamide

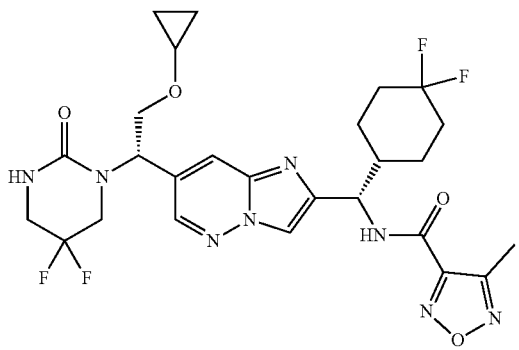 [SMILES: Cc1nonc1C(=O)N[C@H](c1cn2ncc([C@@H](COC3CC3)N3CC(F)(F)CNC3=O)cc2n1)C1CCC(F)(F)CC1]

To a mixture of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride (120 mg, 0.23 mmol, Intermediate 16) and 2,5-dioxopyrrolidin-1-yl 4-methyl-1,2,5-oxadiazole-3-carboxylate (78 mg, 0.35 mmol) in MeCN (2 mL) was added DIPLA (160 µL, 0.92 mmol). The reaction was stirred at rt for 10 min then quenched with H$_2$O. The resulting mixture was diluted with EtOAc then washed with saturated aqueous NaHCO$_3$, dried over anhydrous Na$_2$SO$_4$, filtered and concentrated under reduced pressure. Purification by silica gel chromatography (10-60% (10% MeOH in EtOAc)/hexanes) followed by SFC using a chiral stationary phase (Stationary phase: Whelk O1 SS 5 µm, 250×21 mm, Mobile phase: 25% Methanol, 75% CO$_2$) provided the title compound in 23% yield. $^1$H NMR (400 MHz, DMSO-d$_6$) δ 9.41 (d, J=9.0 Hz, 1H), 8.37 (d, J=2.0 Hz, 1H), 8.25 (s, 1H), 7.97-7.90 (m, 1H), 6.98-6.90 (m, 1H), 5.63-5.48 (m, 1H), 5.26-5.11 (m, 1H), 4.06-3.92 (m, 2H), 3.76-3.61 (m, 1H), 3.60-3.45 (m, 3H), 3.44-3.38 (m, 1H), 2.47 (s, 3H), 2.26-2.12 (m, 1H), 2.11-1.87 (m, 3H), 1.86-1.67 (m, 2H), 1.67-1.54 (m, 1H), 1.48-1.21 (m, 2H), 0.61-0.40 (m, 4H). MS (ESI) m/z: [M+H]$^+$ Found 595.3.

Example 17: (R)-4-Cyclopropyl-N-(1-(7-((5,5-difluoro-2-oxotetrahydropyrimidin-1(2H)-yl)methyl)imidazo[1,2-b]pyridazin-2-yl)-2-((1,1,1-trifluoro-2-methylpropan-2-yl)oxy)ethyl)-1,2,5-oxadiazole-3-carboxamide

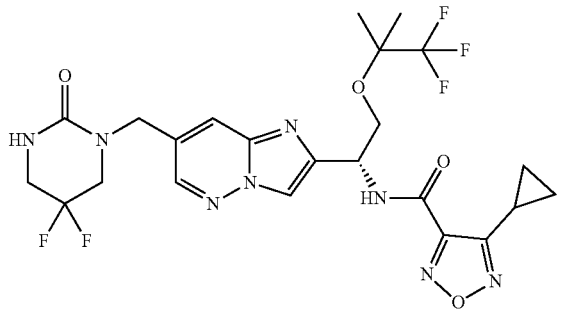

To a flask containing (R)-1-((2-(1-amino-2-((1,1,1-trifluoro-2-methylpropan-2-yl)oxy)ethyl)imidazo[1,2-b]pyridazin-7-yl)methyl)-5,5-difluorotetrahydropyrimidin-2(1H)-one (52.0 mg, 0.119 mmol, Intermediate 19) in EtOAc (1.5 mL) was added 4-cyclopropyl-1,2,5-oxadiazole-3-carboxylic acid (35.9 mg, 0.233 mmol), DIPEA (0.041 mL, 0.233 mmol) and HOBt (17.3 mg, 0.128 mmol). The mixture was stirred for 5 min and then EDCI (24.5 mg, 0.128 mmol) was added. The resulting mixture was stirred at 45° C. for 1.5 h. The reaction was then diluted with EtOAc and washed with saturated aqueous NH$_4$Cl followed by saturated aqueous NaHCO$_3$. The organic layer was washed with brine, dried over anhydrous Na$_2$SO$_4$, filtered, and concentrated under reduced pressure. Purification by silica gel chromatography (10-100% (10% MeOH in EtOAc)/hexanes) provided the title compound in 28% yield. $^1$H NMR (500 MHz, DMSO-d$_6$) δ 9.51-9.45 (m, 1H), 8.45-8.40 (m, 1H), 8.23-8.19 (m, 1H), 7.92-7.88 (m, 1H), 6.97-6.92 (m, 1H), 5.45-5.38 (m, 1H), 4.52-4.48 (m, 2H), 4.05-3.91 (m, 2H), 3.76-3.67 (m, 2H), 3.60-3.50 (m, 2H), 2.39-2.31 (m, 1H), 1.36-1.33 (m, 6H), 1.17-1.11 (m, 2H), 1.02-0.97 (m, 2H). MS (ESI) m/z: [M+H]$^+$ Found 573.2.

Example 18: (S)-4-Cyclopropyl-N-((4,4-difluorocyclohexyl)(7-((2-oxotetrahydropyrimidin-1(2H)-yl)methyl)imidazo[1,2-b]pyridazin-2-yl)methyl)-1,2,5-oxadiazole-3-carboxamide

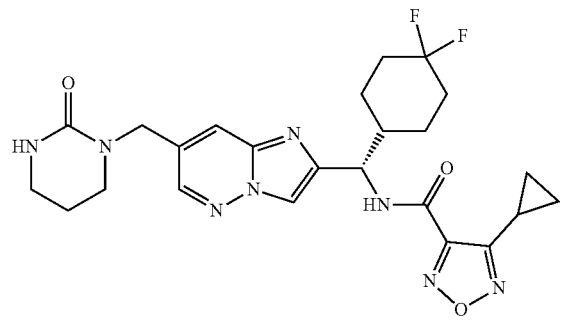

To a stirred solution of 4-cyclopropyl-1,2,5-oxadiazole-3-carboxylic acid (261 mg, 1.70 mmol) and 1-propanephosphonic anhydride (0.909 mL, 1.53 mmol, 50% in EtOAc) in EtOAc (4.24 mL) was added N,N-diisopropylethylamine (0.581 mL, 3.39 mmol). After 5 min, (S)-1-((2-(amino(4,4-difluorocyclohexyl)methyl)imidazo[1,2-b]pyridazin-7-yl)methyl)tetrahydropyrimidin-2(1H)-one (321 mg, 0.339 mmol, Intermediate 24) in DCM (3 mL) was added. After 12 h at rt, the reaction was diluted with aqueous HCl (15 mL, 0.05 M) and the aqueous layer was extracted with EtOAc (3×5 mL). The combined organic fractions were washed with saturated aqueous NaHCO$_3$ (10 mL), dried over anhydrous Na$_2$SO$_4$, filtered and concentrated to dryness. The residue was dissolved in DMSO and purified by preparative HPLC (C18, 5 µm, 50×250 mm, 10-100% MeCN/water (20 mM NH$_4$OH)) to give the title compound as a white solid (2.2% yield). $^1$H NMR (500 MHz, DMSO-d$_6$) δ 9.47 (d, J=9.0 Hz, 1H), 8.41 (d, J=2.0 Hz, 1H), 8.22 (s, 1H), 7.84 (d, J=1.3 Hz, 1H), 6.43 (s, 1H), 5.19 (t, J=8.6 Hz, 1H), 4.47 (s, 2H), 3.23 (t, J=5.8 Hz, 2H), 3.13 (dt, J=2.5, 5.6 Hz, 2H), 2.27 (tt, J=5.0, 8.4 Hz, 1H), 2.22-2.13 (m, 1H), 2.10-1.94 (m, 2H), 1.89 (d, J=13.3 Hz, 1H), 1.86-1.70 (m, 4H), 1.62 (d, J=13.1 Hz, 1H), 1.44-1.34 (m, 1H), 1.33-1.22 (m, 1H), 1.15-1.08 (m, 2H), 0.99-0.92 (m, 2H). MS (ESI) m/z: [M+H]+ Found 515.2.

Example 19: (S)—N-((4,4-Difluorocyclohexyl)(7-((2-oxotetrahydropyrimidin-1(2H)-yl)methyl)imidazo[1,2-b]pyridazin-2-yl)methyl)-1-isopropyl-1H-pyrazole-5-carboxamide

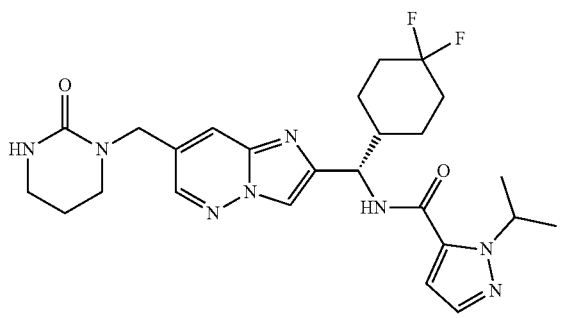

The title compound was synthesized in a manner analogous to Example 18 using 1-isopropyl-1H-pyrazole-5-carboxylic acid in place of 4-cyclopropyl-1,2,5-oxadiazole-3-carboxylic acid to provide the title compound as a white solid (2.9% yield). $^1$H NMR (500 MHz, DMSO-d$_6$) δ 8.71 (d, J=9.1 Hz, 1H), 8.40 (d, J=1.6 Hz, 1H), 8.19 (s, 1H), 7.82 (s, 1H), 7.49 (d, J=1.8 Hz, 1H), 6.91 (d, J=1.4 Hz, 1H), 6.43 (br s, 1H), 5.40-5.35 (m, 1H), 5.18-5.11 (m, 1H), 4.47 (s, 2H), 3.25-3.20 (m, 1H), 3.13 (d, J=2.5 Hz, 2H), 2.22-2.12 (m, 1H), 2.09-1.92 (m, 2H), 1.90-1.84 (m, 1H), 1.84-1.68 (m, 4H), 1.66-1.56 (m, 1H), 1.38 (s, 1H), 1.36 (d, J=6.5 Hz, 3H), 1.33 (d, J=6.6 Hz, 3H), 1.29-1.22 (m, 2H). MS (ESI) m/z: [M+H]+ Found 515.3.

Example 20: (S)-4-Cyclopropyl-N-((7-((5,5-difluoro-2-oxotetrahydropyrimidin-1(2H)-yl)methyl)imidazo[1,2-b]pyridazin-2-yl)(4,4-difluorocyclohexyl)methyl)-1,2,5-oxadiazole-3-carboxamide

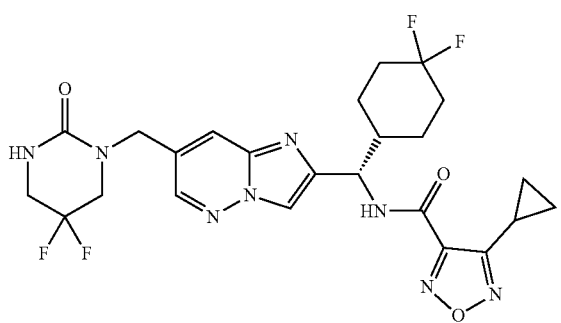

The title compound was synthesized in a manner analogous to Example 18 using (S)-1-((2-(amino(4,4-difluorocyclohexyl)methyl)imidazo[1,2-b]pyridazin-7-yl)methyl)-5,5-difluorotetrahydropyrimidin-2(1H)-one (Intermediate 20) in place of (S)-1-((2-(amino(4,4-difluorocyclohexyl)methyl)imidazo[1,2-b]pyridazin-7-yl)methyl)tetrahydropyrimidin-2(1H)-one to provide the title compound as a white solid (39.8% yield). $^1$H NMR (500 MHz, DMSO-d$_6$) δ 9.48 (d, J=8.9 Hz, 1H), 8.41 (d, J=2.0 Hz, 1H), 8.23 (s, 1H), 7.88 (d, J=1.1 Hz, 1H), 6.94 (br s, 1H), 5.19 (t, J=8.4 Hz, 1H), 4.50 (s, 2H), 3.72 (t, J=12.3 Hz, 2H), 3.54 (t, J=12.6 Hz, 2H), 2.33-2.23 (m, 1H), 2.22-2.13 (m, 1H), 2.09-1.94 (m, 2H), 1.90 (d, J=12.8 Hz, 1H), 1.85-1.69 (m, 2H), 1.62 (d, J=12.8 Hz, 1H), 1.45-1.34 (m, 1H), 1.33-1.24 (m, 1H), 1.16-1.05 (m, 2H), 1.00-0.92 (m, 2H). MS (ESI) m/z: [M+H]+ Found 551.2.

Example 21: (S)—N-((7-((5,5-Difluoro-2-oxotetrahydropyrimidin-1(2H)-yl)methyl)imidazo[1,2-b]pyridazin-2-yl)(4,4-difluorocyclohexyl)methyl)-1-isopropyl-1H-pyrazole-5-carboxamide

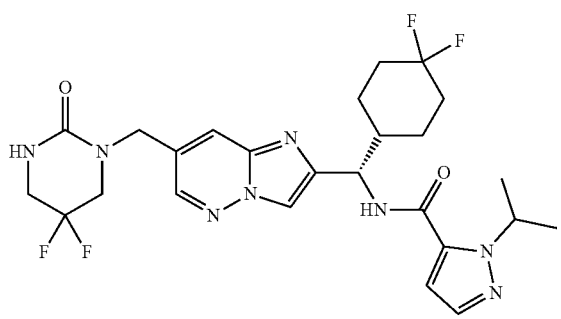

The title compound was synthesized in a manner analogous to Example 18 using (S)-1-((2-(amino(4,4-difluorocyclohexyl)methyl)imidazo[1,2-b]pyridazin-7-yl)methyl)-5,5-difluorotetrahydropyrimidin-2(1H)-one (Intermediate 20) in place of (S)-1-((2-(amino(4,4-difluorocyclohexyl)methyl)imidazo[1,2-b]pyridazin-7-yl)methyl)tetrahydropyrimidin-2(1H)-one and 1-isopropyl-1H-pyrazole-5-carboxylic acid in place of 4-cyclopropyl-1,2,5-oxadiazole-3-carboxylic acid to provide the title compound as a white solid (37.1% yield). $^1$H NMR (500 MHz, DMSO-d$_6$) δ 8.72 (d, J=9.1 Hz, 1H), 8.40 (d, J=2.1 Hz, 1H), 8.21 (s, 1H), 7.88-7.84 (m, 1H), 7.48 (d, J=1.9 Hz, 1H), 6.94 (br s, 1H), 6.91 (d, J=2.0 Hz, 1H), 5.37 (spt, J=6.6 Hz, 1H), 5.15 (t, J=8.6 Hz, 1H), 4.49 (s, 2H), 3.72 (t, J=12.3 Hz, 2H), 3.54 (t, J=12.7 Hz, 2H), 2.24-2.12 (m, 1H), 2.10-1.93 (m, 2H), 1.91-1.69 (m, 3H), 1.62 (d, J=13.5 Hz, 1H), 1.43-1.38 (m, 1H), 1.36 (d, J=6.6 Hz, 3H), 1.33 (d, J=6.6 Hz, 3H), 1.30-1.21 (m, 1H). MS (ESI) m/z: [M+H]+ Found 551.2.

Example 22: (S)—N-((7-((5,5-Difluoro-2-oxotetrahydropyrimidin-1(2H)-yl)methyl)imidazo[1,2-b]pyridazin-2-yl)(4,4-difluorocyclohexyl)methyl)-3-((difluoromethoxy)methyl)isoxazole-4-carboxamide

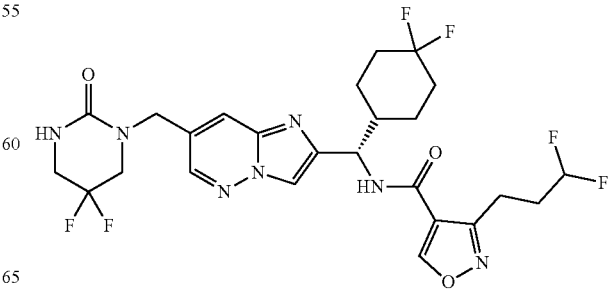

The title compound was synthesized in a manner analogous to Example 18 using (S)-1-((2-(amino(4,4-difluorocyclohexyl)methyl)imidazo[1,2-b]pyridazin-7-yl)methyl)-5,5-difluorotetrahydropyrimidin-2(1H)-one (Intermediate 20) in place of (S)-1-((2-(amino(4,4-difluorocyclohexyl)methyl) imidazo[1,2-b]pyridazin-7-yl)methyl)tetrahydropyrimidin-2(1H)-one and 3-((difluoromethoxy)methyl)isoxazole-4-carboxylic acid in place of 4-cyclopropyl-1,2,5-oxadiazole-3-carboxylic acid to provide the title compound as a white solid (40.3% yield). $^1$H NMR (500 MHz, DMSO-d$_6$) δ 9.55 (s, 1H), 8.84 (d, J=9.0 Hz, 1H), 8.40 (d, J=2.0 Hz, 1H), 8.22 (s, 1H), 7.86 (d, J=1.1 Hz, 1H), 6.96-6.60 (m, 2H), 5.23-5.13 (m, 3H), 4.49 (s, 2H), 3.72 (t, J=12.2 Hz, 2H), 3.54 (t, J=12.7 Hz, 2H), 2.20-2.10 (m, 1H), 2.08-1.92 (m, 2H), 1.90-1.68 (m, 3H), 1.60 (d, J=12.4 Hz, 1H), 1.43-1.33 (m, 1H), 1.32-1.22 (m, 1H). MS (ESI) m/z: [M+H]$^+$ Found 589.7.

Example 23: (S)—N-((7-((5,5-Difluoro-2-oxotetrahydropyrimidin-1(2H)-yl)methyl)imidazo[1,2-b]pyridazin-2-yl)(4,4-difluorocyclohexyl)methyl)-1-isopropyl-1H-1,2,4-triazole-5-carboxamide

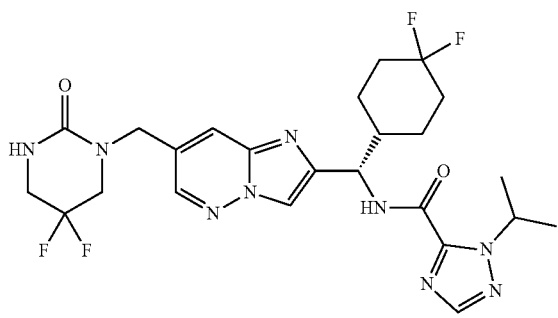

The title compound was synthesized in a manner analogous to Example 18 using (S)-1-((2-(amino(4,4-difluorocyclohexyl)methyl)imidazo[1,2-b]pyridazin-7-yl)methyl)-5,5-difluorotetrahydropyrimidin-2(1H)-one (Intermediate 20) in place of (S)-1-((2-(amino(4,4-difluorocyclohexyl)methyl) imidazo[1,2-b]pyridazin-7-yl)methyl)tetrahydropyrimidin-2(1H)-one and 1-isopropyl-1H-1,2,4-triazole-5-carboxylic acid in place of 4-cyclopropyl-1,2,5-oxadiazole-3-carboxylic acid to provide the title compound as a white solid (16.2% yield). $^1$H NMR (500 MHz, DMSO-d$_6$) δ 8.95-8.79 (m, 1H), 8.41 (br s, 1H), 8.27 (d, J=3.0 Hz, 1H), 8.14-8.04 (m, 1H), 7.90 (br s, 1H), 6.93 (br s, 1H), 5.64-5.45 (m, 1H), 5.22-5.04 (m, 1H), 4.49 (d, J=1.9 Hz, 2H), 3.79-3.65 (m, 2H), 3.55 (d, J=10.6 Hz, 2H), 2.15 (d, J=2.6 Hz, 1H), 2.08-1.84 (m, 3H), 1.84-1.67 (m, 2H), 1.66-1.54 (m, 1H), 1.48-1.30 (m, 7H), 1.25 (d, J=8.9 Hz, 1H). MS (ESI) m/z: [M+H]$^+$ Found 551.8.

Example 24: (S)-2-(Cyclopropylmethyl)-N-((7-((5,5-difluoro-2-oxotetrahydropyrimidin-1(2H)-yl)methyl)imidazo[1,2-b]pyridazin-2-yl)(4,4-difluorocyclohexyl)methyl)-2H-1,2,3-triazole-4-carboxamide

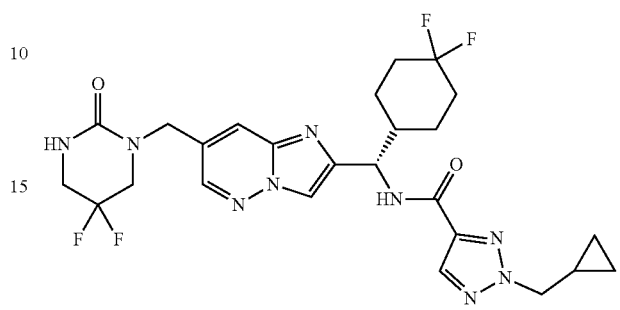

The title compound was synthesized in a manner analogous to Example 18 using (S)-1-((2-(amino(4,4-difluorocyclohexyl)methyl)imidazo[1,2-b]pyridazin-7-yl)methyl)-5,5-difluorotetrahydropyrimidin-2(1H)-one (Intermediate 20) in place of (S)-1-((2-(amino(4,4-difluorocyclohexyl)methyl) imidazo[1,2-b]pyridazin-7-yl)methyl)tetrahydropyrimidin-2(1H)-one and 2-(cyclopropylmethyl)-2H-1,2,3-triazole-4-carboxylic acid in place of 4-cyclopropyl-1,2,5-oxadiazole-3-carboxylic acid to provide the title compound as a white solid (30.2% yield). $^1$H NMR (500 MHz, DMSO-d$_6$) δ 8.49 (d, J=9.1 Hz, 1H), 8.40 (d, J=2.0 Hz, 1H), 8.25 (s, 1H), 8.18 (s, 1H), 7.88 (d, J=1.0 Hz, 1H), 6.93 (br s, 1H), 5.18 (t, J=8.8 Hz, 1H), 4.49 (s, 2H), 4.35 (d, J=7.4 Hz, 2H), 3.72 (t, J=12.3 Hz, 2H), 3.54 (t, J=12.6 Hz, 2H), 2.20-2.10 (m, 1H), 2.08-1.92 (m, 2H), 1.89 (d, J=12.4 Hz, 1H), 1.85-1.66 (m, 2H), 1.58 (d, J=12.8 Hz, 1H), 1.40-1.30 (m, 2H), 1.29-1.18 (m, 1H), 0.58-0.52 (m, 2H), 0.45-0.39 (m, 2H). MS (ESI) m/z: [M+H]$^+$ Found 563.8.

Example 25: (S)—N-((7-((5,5-Difluoro-2-oxotetrahydropyrimidin-1(2H)-yl)methyl)imidazo[1,2-b]pyridazin-2-yl)(4,4-difluorocyclohexyl)methyl)-1-(ethyl-d$_5$)-1H-pyrazole-5-carboxamide

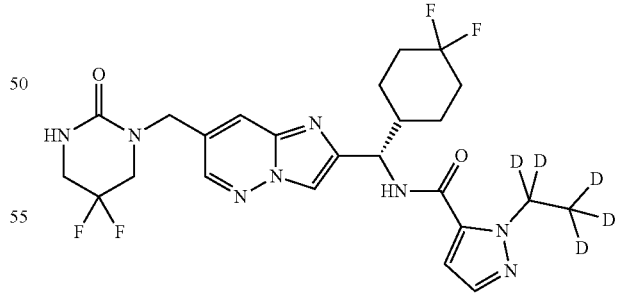

The title compound was synthesized in a manner analogous to Example 18 using (S)-1-((2-(amino(4,4-difluorocyclohexyl)methyl)imidazo[1,2-b]pyridazin-7-yl)methyl)-5,5-difluorotetrahydropyrimidin-2(1H)-one (Intermediate 20) in place of (S)-1-((2-(amino(4,4-difluorocyclohexyl)methyl) imidazo[1,2-b]pyridazin-7-yl)methyl)tetrahydropyrimidin-2(1H)-one and 1-(ethyl-d$_5$)-1H-pyrazole-5-carboxylic acid in place of 4-cyclopropyl-1,2,5-oxadiazole-3-carboxylic acid acid to provide the title compound as a white solid (38.1% yield). ¹H NMR (500 MHz, DMSO-d₆) δ 8.72 (d, J=9.1 Hz, 1H), 8.40 (d, J=2.0 Hz, 1H), 8.21 (s, 1H), 7.88-7.85 (m, 1H), 7.46 (d, J=2.0 Hz, 1H), 6.97 (d, J=2.0 Hz, 1H), 6.93 (br s, 1H), 5.16 (t, J=8.8 Hz, 1H), 4.49 (s, 2H), 3.71 (t, J=12.3 Hz, 2H), 3.54 (t, J=12.7 Hz, 2H), 2.23-2.14 (m, 1H), 2.10-1.93 (m, 2H), 1.92-1.68 (m, 3H), 1.61 (d, J=12.6 Hz, 1H), 1.43-1.19 (m, 2H). MS (ESI) m/z: [M+H]⁺ Found 541.8.

Example 26: (S)—N-((7-((5,5-Difluoro-2-oxotetra-hydropyrimidin-1(2H)-yl)methyl)imidazo[1,2-b]pyridazin-2-yl)(4,4-difluorocyclohexyl)methyl)-4-(2,2-difluoroethoxy)-1,2,5-oxadiazole-3-carboxamide

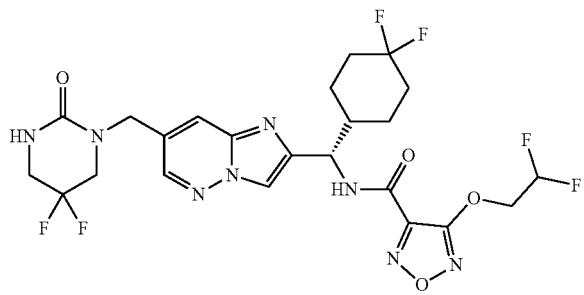 [SMILES: O=C(N[C@H](c1cn2ncc(CN3CC(F)(F)CNC3=O)cc2n1)C1CCC(F)(F)CC1)c1nonc1OCC(F)F]

The title compound was synthesized in a manner analogous to Example 18 using (S)-1-((2-(amino(4,4-difluorocyclohexyl)methyl)imidazo[1,2-b]pyridazin-7-yl)methyl)-5,5-difluorotetrahydropyrimidin-2(1H)-one (Intermediate 20) in place of (S)-1-((2-(amino(4,4-difluorocyclohexyl)methyl)imidazo[1,2-b]pyridazin-7-yl)methyl)tetrahydropyrimidin-2(1H)-one and 4-(2,2-difluoroethoxy)-1,2,5-oxadiazole-3-carboxylic acid in place of 4-cyclopropyl-1,2,5-oxadiazole-3-carboxylic acid to provide the title compound as a white solid (36.0% yield). ¹H NMR (500 MHz, DMSO-d₆) δ 9.36 (d, J=9.0 Hz, 1H), 8.41 (d, J=2.0 Hz, 1H), 8.20 (s, 1H), 7.87 (d, J=1.3 Hz, 1H), 6.94 (br s, 1H), 6.42 (tt, J=3.1, 53.6 Hz, 1H), 5.16 (t, J=8.3 Hz, 1H), 4.75-4.65 (m, 2H), 4.50 (s, 2H), 3.72 (t, J=12.3 Hz, 2H), 3.54 (t, J=12.6 Hz, 2H), 2.20-2.10 (m, 1H), 2.08-1.93 (m, 2H), 1.91-1.68 (m, 3H), 1.61 (d, J=13.1 Hz, 1H), 1.43-1.21 (m, 2H). MS (ESI) m/z: [M+H]⁺ Found 590.8.

Example 27: (S)—N-((7-((5,5-Difluoro-2-oxotetra-hydropyrimidin-1(2H)-yl)methyl)imidazo[1,2-b]pyridazin-2-yl)(4,4-difluorocyclohexyl)methyl)-2-(3,3,3-trifluoropropyl)-2H-1,2,3-triazole-4-carboxamide

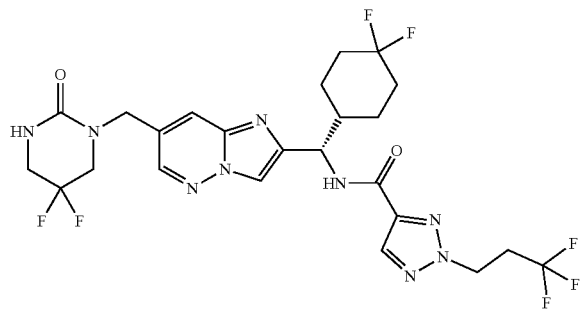 [SMILES: O=C(N[C@H](c1cn2ncc(CN3CC(F)(F)CNC3=O)cc2n1)C1CCC(F)(F)CC1)c1cnn(CCC(F)(F)F)n1]

The title compound was synthesized in a manner analogous to Example 18 using (S)-1-((2-(amino(4,4-difluorocyclohexyl)methyl)imidazo[1,2-b]pyridazin-7-yl)methyl)-5,5-difluorotetrahydropyrimidin-2(1H)-one (Intermediate 20) in place of (S)-1-((2-(amino(4,4-difluorocyclohexyl)methyl)imidazo[1,2-b]pyridazin-7-yl)methyl)tetrahydropyrimidin-2(1H)-one and 2-(3,3,3-trifluoropropyl)-2H-1,2,3-triazole-4-carboxylic acid in place of 4-cyclopropyl-1,2,5-oxadiazole-3-carboxylic acid to provide the title compound as a white solid (31.9% yield). ¹H NMR (500 MHz, DMSO-d₆) δ 8.55 (d, J=9.1 Hz, 1H), 8.40 (d, J=2.0 Hz, 1H), 8.25 (s, 1H), 8.23 (s, 1H), 7.88 (d, J=1.3 Hz, 1H), 6.93 (br s, 1H), 5.18 (t, J=8.8 Hz, 1H), 4.76 (t, J=6.7 Hz, 2H), 4.49 (s, 2H), 3.72 (t, J=12.4 Hz, 2H), 3.54 (t, J=12.7 Hz, 2H), 3.09-2.98 (m, 2H), 2.21-2.11 (m, 1H), 2.06-1.92 (m, 2H), 1.89 (d, J=13.3 Hz, 1H), 1.85-1.67 (m, 2H), 1.58 (d, J=12.0 Hz, 1H), 1.40-1.29 (m, 1H), 1.29-1.19 (m, 1H). MS (ESI) m/z: [M+H]⁺ Found 605.8.

Example 28: 4-Cyclopropyl-N—((S)-(4,4-difluoro-cyclohexyl)(7-(((S*)-5-methyl-2-oxotetrahydropy-rimidin-1(2H)-yl)methyl)imidazo[1,2-b]pyridazin-2-yl)methyl)-1,2,5-oxadiazole-3-carboxamide

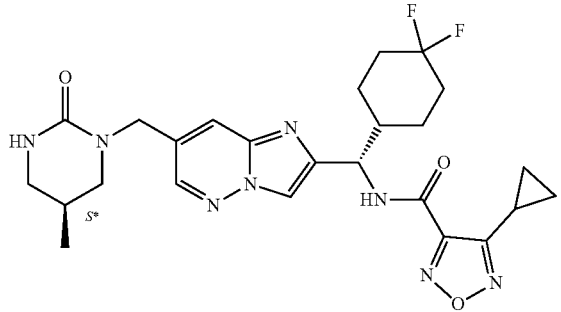 [SMILES: C[C@H]1CNC(=O)N(Cc2cnn3cc([C@@H](NC(=O)c4nonc4C4CC4)C4CCC(F)(F)CC4)nc3c2)C1]

Example 29: 4-Cyclopropyl-N—((S)-(4,4-difluoro-cyclohexyl)(7-(((R*)-5-methyl-2-oxotetrahydropy-rimidin-1(2H)-yl)methyl)imidazo[1,2-b]pyridazin-2-yl)methyl)-1,2,5-oxadiazole-3-carboxamide

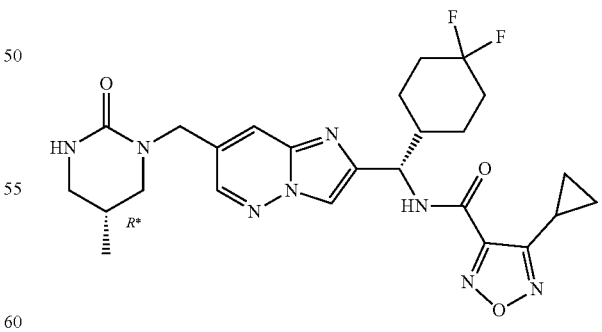

The title compounds were synthesized in a manner analogous to Example 18 using 1-((2-((S)-amino(4,4-difluorocyclohexyl)methyl)imidazo[1,2-b]pyridazin-7-yl)methyl)-5-methyltetrahydropyrimidin-2(1H)-one (Intermediate 21) in place of (S)-1-((2-(amino(4,4-difluorocyclohexyl)methyl)imidazo[1,2-b]pyridazin-7-yl)methyl)tetrahydropyrimidin- 2(1H)-one. The resulting mixture was purified by chiral SFC (DAICEL CHIRALPAK IB N3 column, 10 μm, 250×50 mm; 40% ACN:MeOH (9:1) 60% CO₂) to afford two diastereomers. The first eluting isomer was designated as the (S*) isomer (Example 28) and the second eluting isomer was designated as the (R*) isomer (Example 29). The first eluting isomer, 4-cyclopropyl-N—((S)-(4,4-difluorocyclohexyl)(7-(((S*)-5-methyl-2-oxotetrahydropyrimidin-1(2H)-yl)methyl)imidazo[1,2-b]pyridazin-2-yl)methyl)-1,2,5-oxadiazole-3-carboxamide, was isolated as a white solid (Example 28, 6.2% yield). The second eluting isomer, 4-cyclopropyl-N—((S)-(4,4-difluorocyclohexyl)(7-(((R*)-5-methyl-2-oxotetrahydropyrimidin-1(2H)-yl)methyl)imidazo[1,2-b]pyridazin-2-yl)methyl)-1,2,5-oxadiazole-3-carboxamide, was isolated as a white solid (Example 29, 6.0% yield). 4-Cyclopropyl-N—((S)-(4,4-difluorocyclohexyl)(7-(((S*)-5-methyl-2-oxotetrahydropyrimidin-1(2H)-yl)methyl)imidazo[1,2-b]pyridazin-2-yl)methyl)-1,2,5-oxadiazole-3-carboxamide. Example 28: ¹H NMR (500 MHz, DMSO-d₆) δ 9.47 (d, J=9.0 Hz, 1H), 8.40 (d, J=2.1 Hz, 1H), 8.22 (s, 1H), 7.85 (d, J=1.1 Hz, 1H), 6.44 (d, J=2.8 Hz, 1H), 5.19 (t, J=8.5 Hz, 1H), 4.51-4.40 (m, 2H), 3.25-3.15 (m, 1H), 3.15-3.05 (m, 1H), 2.91 (dd, J=9.5, 11.4 Hz, 1H), 2.85-2.77 (m, 1H), 2.32-2.23 (m, 1H), 2.22-2.13 (m, 1H), 2.09-1.95 (m, 3H), 1.90 (d, J=11.0 Hz, 1H), 1.85-1.70 (m, 2H), 1.62 (d, J=12.1 Hz, 1H), 1.45-1.35 (m, 1H), 1.33-1.24 (m, 1H), 1.15-1.08 (m, 2H), 0.99-0.92 (m, 2H), 0.88 (d, J=6.6 Hz, 3H). MS (ESI) m/z: [M+H]⁺ Found 529.2. 4-Cyclopropyl-N—((S)-(4,4-difluorocyclohexyl)(7-(((R*)-5-methyl-2-oxotetrahydropyrimidin-1(2H)-yl)methyl)imidazo[1,2-b]pyridazin-2-yl)methyl)-1,2,5-oxadiazole-3-carboxamide Example 29: ¹H NMR (500 MHz, DMSO-d₆) δ 9.47 (d, J=4.3 Hz, 1H), 8.40 (d, J=1.9 Hz, 1H), 8.27-8.15 (m, 1H), 7.85 (br s, 1H), 6.44 (br s, 1H), 5.26-5.10 (m, 1H), 4.46 (br s, 2H), 3.23 (br s, 1H), 3.12 (br s, 1H), 2.99-2.87 (m, 1H), 2.81 (d, J=1.5 Hz, 1H), 2.30-2.12 (m, 2H), 2.10-1.56 (m, 7H), 1.45-1.21 (m, 2H), 1.11 (d, J=3.1 Hz, 2H), 0.96 (br s, 2H), 0.88 (br s, 3H). MS (ESI) m/z: [M+H]⁺ Found 529.2.

Example 30: (S)-4-Cyclopropyl-N-((4,4-difluorocyclohexyl)(7-((2-oxo-1,3-diazepan-1-yl)methyl)imidazo[1,2-b]pyridazin-2-yl)methyl)-1,2,5-oxadiazole-3-carboxamide

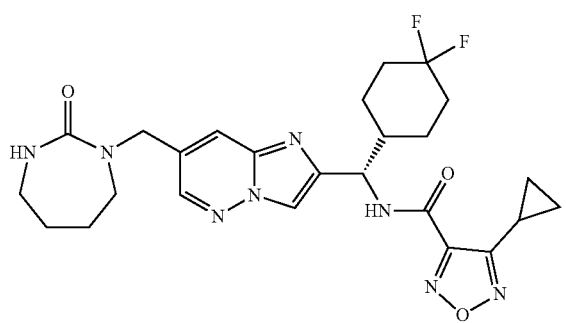

The title compound was synthesized in a manner analogous to Example 18 using (S)-1-((2-(amino(4,4-difluorocyclohexyl)methyl)imidazo[1,2-b]pyridazin-7-yl)methyl)-1,3-diazepan-2-one (Intermediate 22) in place of (S)-1-((2-(amino(4,4-difluorocyclohexyl)methyl)imidazo[1,2-b]pyridazin-7-yl)methyl)tetrahydropyrimidin-2(1H)-one to provide the title compound as a white solid (3.8% yield). ¹H NMR (500 MHz, DMSO-d₆) δ 9.48 (d, J=8.9 Hz, 1H), 8.51 (d, J=1.9 Hz, 1H), 8.22 (s, 1H), 7.92 (br s, 1H), 6.23 (d, J=4.1 Hz, 1H), 5.25-5.11 (m, 1H), 4.41 (s, 2H), 3.14 (d, J=3.3 Hz, 2H), 2.99 (br s, 2H), 2.32-2.23 (m, 1H), 2.22-2.11 (m, 1H), 2.09-1.94 (m, 2H), 1.90 (d, J=12.4 Hz, 1H), 1.85-1.67 (m, 2H), 1.62 (d, J=11.6 Hz, 1H), 1.55 (br s, 4H), 1.45-1.34 (m, 1H), 1.33-1.22 (m, 1H), 1.14-1.06 (m, 2H), 1.00-0.91 (m, 2H). MS (ESI) m/z: [M+H]⁺ Found 529.2.

Example 31: (S)—N-((4,4-Difluorocyclohexyl)(7-((2-oxo-1,3-diazepan-1-yl)methyl)imidazo[1,2-b]pyridazin-2-yl)methyl)-1-isopropyl-1H-pyrazole-5-carboxamide

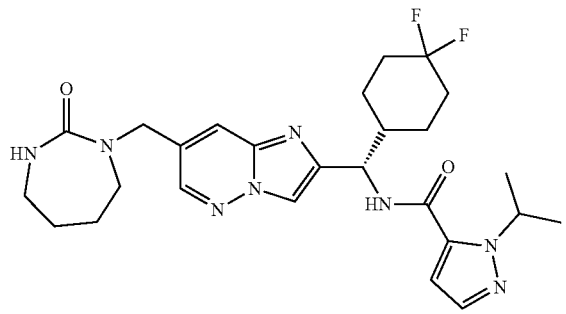 [SMILES: CC(C)n1nccc1C(=O)N[C@H](c1cn2ncc(CN3CCCCNC3=O)cc2n1)C1CCC(F)(F)CC1]

The title compound was synthesized in a manner analogous to Example 18 using (S)-1-((2-(amino(4,4-difluorocyclohexyl)methyl)imidazo[1,2-b]pyridazin-7-yl)methyl)-1,3-diazepan-2-one (Intermediate 22) in place of (S)-1-((2-(amino(4,4-difluorocyclohexyl)methyl)imidazo[1,2-b]pyridazin-7-yl)methyl)tetrahydropyrimidin-2(1H)-one and 1-isopropyl-1H-pyrazole-5-carboxylic acid in place of 4-cyclopropyl-1,2,5-oxadiazole-3-carboxylic acid to provide the title compound as a white solid (4.1% yield). ¹H NMR (500 MHz, DMSO-d₆) δ 8.71 (d, J=9.0 Hz, 1H), 8.49 (d, J=2.0 Hz, 1H), 8.19 (s, 1H), 7.91 (d, J=1.1 Hz, 1H), 7.48 (d, J=2.0 Hz, 1H), 6.91 (d, J=2.0 Hz, 1H), 6.22 (t, J=4.4 Hz, 1H), 5.37 (spt, J=6.6 Hz, 1H), 5.15 (t, J=8.6 Hz, 1H), 4.40 (s, 2H), 3.14 (d, J=5.8 Hz, 2H), 3.02-2.94 (m, 2H), 2.22-2.12 (m, 1H), 2.08-1.93 (m, 2H), 1.90-1.68 (m, 3H), 1.62 (d, J=12.0 Hz, 1H), 1.54 (br s, 4H), 1.43-1.38 (m, 1H), 1.36 (d, J=6.6 Hz, 3H), 1.33 (d, J=6.6 Hz, 3H), 1.30-1.22 (m, 1H). MS (ESI) m/z: [M+H]⁺ Found 529.2.

Example 32: (S)—N-((4,4-Difluorocyclohexyl)(7-((5,5-dimethyl-2-oxotetrahydropyrimidin-1(2H)-yl)methyl)imidazo[1,2-b]pyridazin-2-yl)methyl)-4-methyl-1,2,5-oxadiazole-3-carboxamide

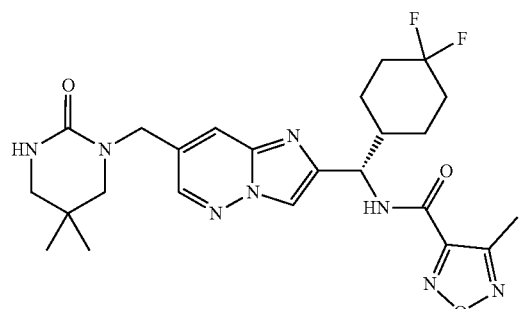

The title compound was synthesized in a manner analogous to Example 18 using (S)-1-((2-(amino(4,4-difluorocyclohexyl)methyl)imidazo[1,2-b]pyridazin-7-yl)methyl)-5,5-dimethyltetrahydropyrimidin-2(1H)-one (Intermediate 23) in place of (S)-1-((2-(amino(4,4-difluorocyclohexyl)methyl)imidazo[1,2-b]pyridazin-7-yl)methyl)tetrahydropyrimidin-2(1H)-one and 4-methyl-1,2,5-oxadiazole-3-carboxylic acid in place of 4-cyclopropyl-1,2,5-oxadiazole-3-carboxylic acid to provide the title compound as a white solid (39.6% yield). $^1$H NMR (500 MHz, DMSO-d$_6$) δ 9.35 (d, J=9.0 Hz, 1H), 8.34 (d, J=2.0 Hz, 1H), 8.16 (s, 1H), 7.80 (d, J=1.1 Hz, 1H), 6.40 (t, J=2.4 Hz, 1H), 5.10 (t, J=8.6 Hz, 1H), 4.39 (s, 2H), 2.87 (s, 2H), 2.76 (d, J=1.5 Hz, 2H), 2.40 (s, 3H), 2.16-2.06 (m, 1H), 2.03-1.87 (m, 2H), 1.83 (d, J=12.9 Hz, 1H), 1.79-1.62 (m, 2H), 1.54 (d, J=12.1 Hz, 1H), 1.37-1.26 (m, 1H), 1.25-1.16 (m, 1H), 0.85 (s, 6H). MS (ESI) m/z: [M+H]$^+$ Found 516.8.

Example 33: (S)-4-Cyclopropyl-N-((4,4-difluorocyclohexyl)(7-((5,5-dimethyl-2-oxotetrahydropyrimidin-1(2H)-yl)methyl)imidazo[1,2-b]pyridazin-2-yl)methyl)-1,2,5-oxadiazole-3-carboxamide

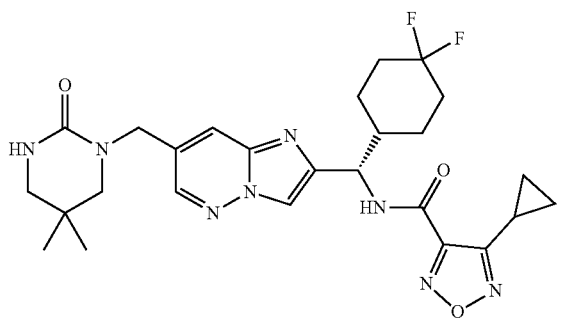 [SMILES: CC1(C)CNC(=O)N(Cc2cnn3cc([C@@H](NC(=O)c4nonc4C4CC4)C4CCC(F)(F)CC4)nc3c2)C1]

The title compound was synthesized in a manner analogous to Example 18 using (S)-1-((2-(amino(4,4-difluorocyclohexyl)methyl)imidazo[1,2-b]pyridazin-7-yl)methyl)-5,5-dimethyltetrahydropyrimidin-2(1H)-one (Intermediate 23) in place of (S)-1-((2-(amino(4,4-difluorocyclohexyl)methyl)imidazo[1,2-b]pyridazin-7-yl)methyl)tetrahydropyrimidin-2(1H)-one to provide the title compound as a white solid (22.7% yield). $^1$H NMR (500 MHz, DMSO-d$_6$) δ 9.48 (d, J=9.0 Hz, 1H), 8.41 (d, J=2.0 Hz, 1H), 8.22 (s, 1H), 7.87 (d, J=1.3 Hz, 1H), 6.46 (t, J=2.4 Hz, 1H), 5.19 (t, J=8.5 Hz, 1H), 4.46 (s, 2H), 2.94 (s, 2H), 2.83 (d, J=1.5 Hz, 2H), 2.32-2.23 (m, 1H), 2.22-2.13 (m, 1H), 2.10-1.94 (m, 2H), 1.90 (d, J=12.6 Hz, 1H), 1.86-1.69 (m, 2H), 1.62 (d, J=13.0 Hz, 1H), 1.44-1.34 (m, 1H), 1.33-1.23 (m, 1H), 1.14-1.08 (m, 2H), 0.98-0.93 (m, 2H), 0.92 (s, 6H). MS (ESI) m/z: [M+H]$^+$ Found 542.8.

Example 34: (S)—N-((4,4-Difluorocyclohexyl)(7-((5,5-dimethyl-2-oxotetrahydropyrimidin-1(2H)-yl)methyl)imidazo[1,2-b]pyridazin-2-yl)methyl)-1-isopropyl-1H-pyrazole-5-carboxamide

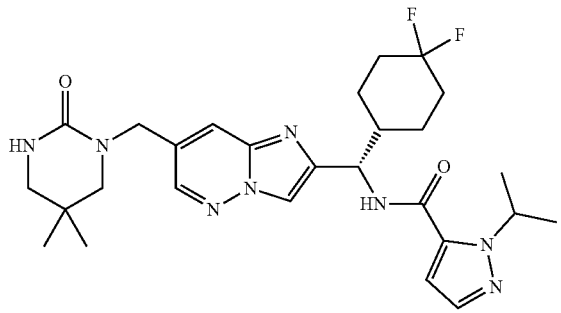 [SMILES: CC(C)n1nccc1C(=O)N[C@H](c1cn2ncc(CN3CC(C)(C)CNC3=O)cc2n1)C1CCC(F)(F)CC1]

The title compound was synthesized in a manner analogous to Example 18 using (S)-1-((2-(amino(4,4-difluorocyclohexyl)methyl)imidazo[1,2-b]pyridazin-7-yl)methyl)-5,5-dimethyltetrahydropyrimidin-2(1H)-one (Intermediate 23) in place of (S)-1-((2-(amino(4,4-difluorocyclohexyl)methyl)imidazo[1,2-b]pyridazin-7-yl)methyl)tetrahydropyrimidin-2(1H)-one and 1-isopropyl-1H-pyrazole-5-carboxylic acid in place of 4-cyclopropyl-1,2,5-oxadiazole-3-carboxylic acid to provide the title compound as a white solid (30.9% yield). $^1$H NMR (500 MHz, DMSO-d$_6$) δ 8.72 (d, J=8.9 Hz, 1H), 8.40 (d, J=1.6 Hz, 1H), 8.20 (s, 1H), 7.86 (br s, 1H), 7.49 (d, J=1.9 Hz, 1H), 6.91 (d, J=1.9 Hz, 1H), 6.46 (br s, 1H), 5.41-5.29 (m, 1H), 5.17-5.09 (m, 1H), 4.46 (s, 2H), 2.93 (br s, 2H), 2.83 (br s, 2H), 2.16 (br s, 1H), 2.09-1.92 (m, 2H), 1.90-1.66 (m, 3H), 1.65-1.54 (m, 1H), 1.35 (dd, J=6.6, 16.3 Hz, 6H), 1.29-1.20 (m, 2H), 0.92 (s, 6H). MS (ESI) m/z: [M+H]$^+$ Found 542.9.

Example 35: N—((S)-(7-((S*)-1-(5,5-Difluoro-2-oxotetrahydropyrimidin-1(2H)-yl)-2-ethoxyethyl)imidazo[1,2-b]pyridazin-2-yl)(4,4-difluorocyclohexyl)methyl)-4-methyl-1,2,5-oxadiazole-3-carboxamide

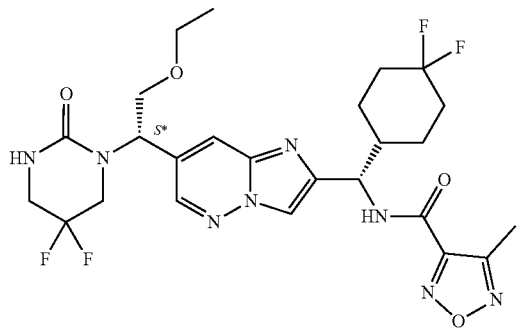 [SMILES: CCOC[C@H](c1cnn2cc([C@@H](NC(=O)c3nonc3C)C3CCC(F)(F)CC3)nc2c1)N1CC(F)(F)CNC1=O]

The title compound was prepared as described for the synthesis of Example 16, using 1-((S*)-1-(2-((S)-amino(4,4-difluorocyclohexyl)methyl)imidazo[1,2-b]pyridazin-7-yl)-2-ethoxyethyl)-5,5-difluorotetrahydropyrimidin-2(1H)-one hydrochloride (Intermediate 25) in place of 1-((S)-1-(2-((S*)-amino(4,4-difluorocyclohexyl)methyl)imidazo[1,2-b]pyridazin-7-yl)-2-cyclopropoxyethyl)-5,5- difluorotetrahydropyrimidin-2(1H)-one hydrochloride. Purification by silica gel chromatography (10-60% (10% MeOH in EtOAc)/hexanes) followed by SFC using a chiral stationary phase (Stationary phase: Whelk O1 SS 5 μm, 250×21 mm, Mobile phase: 30% Methanol, 70% $CO_2$) provided the title compound in 45% yield. $^1$H NMR (500 MHz, DMSO-d$^6$) δ 9.45-9.37 (m, 1H), 8.41-8.36 (m, 1H), 8.27-8.22 (m, 1H), 7.96-7.92 (m, 1H), 7.00-6.92 (m, 1H), 5.58-5.50 (m, 1H), 5.24-5.13 (m, 1H), 4.02-3.85 (m, 2H), 3.78-3.65 (m, 1H), 3.63-3.46 (m, 5H), 2.48-2.46 (m, 3H), 2.26-2.13 (m, 1H), 2.11-1.95 (m, 2H), 1.94-1.87 (m, 1H), 1.86-1.68 (m, 2H), 1.67-1.57 (m, 1H), 1.46-1.34 (m, 1H), 1.33-1.22 (m, 1H), 1.16-1.11 (m, 3H). MS (ESI) m/z: [M+H]+ Found 583.2.

Example 36: 4-Cyclopropyl-N—((S)-(7-((S*)-1-(5, 5-difluoro-2-oxotetrahydropyrimidin-1(2H)-yl)-2-ethoxyethyl)imidazo[1,2-b]pyridazin-2-yl)(4,4-difluorocyclohexyl)methyl)-1,2,5-oxadiazole-3-carboxamide

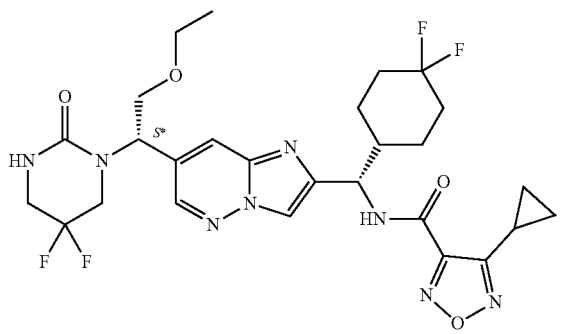 [SMILES: CCOC[C@H](c1cnn2cc([C@@H](NC(=O)c3nonc3C3CC3)C3CCC(F)(F)CC3)nc2c1)N1CC(F)(F)CNC1=O]

The title compound was prepared as described for the synthesis of Example 16, using 1-((S*)-1-(2-((S)-amino(4,4-difluorocyclohexyl)methyl)imidazo[1,2-b]pyridazin-7-yl)-2-ethoxyethyl)-5,5-difluorotetrahydropyrimidin-2(1H)-one hydrochloride (Intermediate 25) in place of 1-((S)-1-(2-((S*)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride) and 2,5-dioxopyrrolidin-1-yl 4-cyclopropyl-1,2,5-oxadiazole-3-carboxylate (Intermediate 31) in place of 2,5-dioxopyrrolidin-1-yl 4-methyl-1,2,5-oxadiazole-3-carboxylate. Purification by silica gel chromatography (10-60% (10% MeOH in EtOAc)/hexanes) followed by SFC using a chiral stationary phase (Stationary phase: Whelk O1 SS 5 pam, 250×21 mm, Mobile phase: 30% Methanol, 70% $CO_2$) provided the title compound in 45% yield. $^1$H NMR (500 MHz, DMSO-d$_6$) δ 9.54-9.42 (m, 1H), 8.42-8.36 (m, 1H), 8.26-8.22 (m, 1H), 7.96-7.92 (m, 1H), 6.98-6.92 (m, 1H), 5.57-5.50 (m, 1H), 5.24-5.16 (m, 1H), 4.00-3.87 (m, 2H), 3.77-3.65 (m, 1H), 3.62-3.47 (m, 5H), 2.32-2.25 (m, 1H), 2.24-2.14 (m, 1H), 2.12-1.94 (m, 2H), 1.94-1.87 (m, 1H), 1.86-1.69 (m, 2H), 1.67-1.58 (m, 1H), 1.46-1.35 (m, 1H), 1.34-1.22 (m, 1H), 1.16-1.09 (m, 5H), 1.00-0.93 (m, 2H). MS (ESI) m/z: [M+H]$^+$ Found 609.3.

Example 37: N—((S)-(7-((S)-2-Cyclopropoxy-1-(5,5-difluoro-2-oxotetrahydropyrimidin-1(2H)-yl)ethyl)imidazo[1,2-b]pyridazin-2-yl)(4,4-difluorocyclohexyl)methyl)-1-isopropyl-1H-pyrazole-5-carboxamide

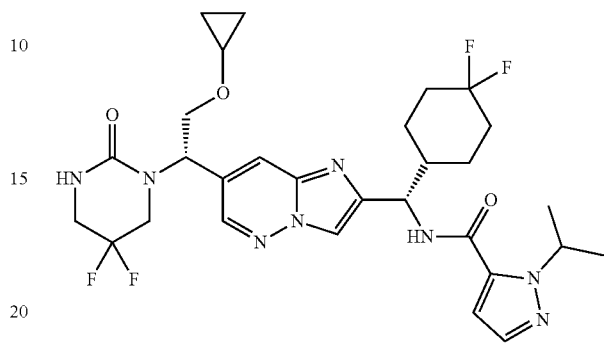

The title compound was prepared in a manner analogous to the synthesis of Example 16, using 2,5-dioxopyrrolidin-1-yl 1-isopropyl-1H-pyrazole-5-carboxylate (Intermediate 26) in place of 2,5-dioxopyrrolidin-1-yl 4-methyl-1,2,5-oxadiazole-3-carboxylate. In the course of the synthesis, Intermediate 15 was further purified by SFC using a chiral stationary phase (Stationary phase: Whelk O1 SS 5 μm 250×21 mm, Mobile phase: 30% methanol, 70% $CO_2$). Purification by silica gel chromatography (20-100% (10% MeOH in EtOAc)/DCM) provided the title compound in 61% yield. $^1$H NMR (500 MHz, DMSO-d$_6$) δ 8.72 (d, J=9.0 Hz, 1H), 8.40-8.34 (m, 1H), 8.22 (s, 1H), 7.94-7.89 (m, 1H), 7.49 (d, J=1.9 Hz, 1H), 6.96-6.93 (m, 1H), 6.91 (d, J=2.0 Hz, 1H), 5.56 (t, J=6.8 Hz, 1H), 5.37 (spt, J=6.6 Hz, 1H), 5.16 (t, J=8.6 Hz, 1H), 4.05-3.95 (m, 2H), 3.73-3.62 (m, 1H), 3.60-3.44 (m, 3H), 3.43-3.38 (m, 1H), 2.24-2.12 (m, 1H), 2.09-1.93 (m, 2H), 1.88 (br d, J=12.4 Hz, 1H), 1.84-1.68 (m, 2H), 1.62 (br d, J=12.4 Hz, 1H), 1.44-1.21 (m, 8H), 0.59-0.41 (m, 4H). MS (ESI) m/z: [M+H]$^+$ Found 621.3.

Example 38: N—((S)-(7-((S)-2-Cyclopropoxy-1-(5,5-difluoro-2-oxotetrahydropyrimidin-1(2H)-yl)ethyl)imidazo[1,2-b]pyridazin-2-yl)(4,4-difluorocyclohexyl)methyl)-3-methylisoxazole-4-carboxamide

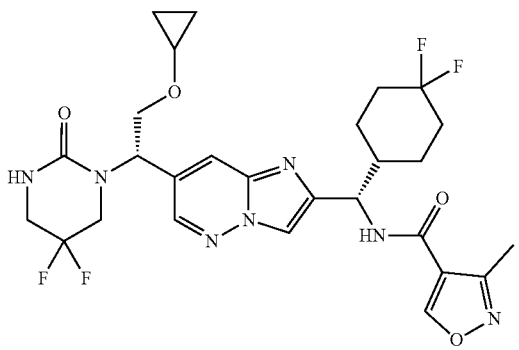

The title compound was prepared in a manner analogous to the synthesis of Example 17, using 1-((S)-1-(2-((S)-amino(4,4-difluorocyclohexyl)methyl)imidazo[1,2-b]pyridazin-7- yl)-2-cyclopropoxyethyl)-5,5-difluorotetrahydropyrimidin-2(1H)-one hydrochloride (Intermediate 16) in place of (R)-1-((2-(1-amino-2-((1,1,1-trifluoro-2-methylpropan-2-yl)oxy)ethyl)imidazo[1,2-b]pyridazin-7-yl)methyl)-5,5-difluorotetrahydropyrimidin-2(1H)-one and 3-methylisoxazole-4-carboxylic acid in place of 4-cyclopropyl-1,2,5-oxadiazole-3-carboxylic acid. In the course of the synthesis, Intermediate 15 was further purified by SFC using a chiral stationary phase (Stationary phase: Whelk O1 SS 5 μm 250×21 mm, Mobile phase: 30% methanol, 70% $CO_2$). Purification by silica gel chromatography (0-100% (10% MeOH in EtOAc)/DCM) provided the title compound in 62% yield. $^1$H NMR (500 MHz, DMSO-$d_6$) δ 9.41 (d, J=0.6 Hz, 1H), 8.66 (d, J=9.0 Hz, 1H), 8.38 (d, J=2.1 Hz, 1H), 8.22 (s, 1H), 7.92-7.88 (m, 1H), 6.95 (br s, 1H), 5.55 (t, J=6.8 Hz, 1H), 5.20-5.12 (m, 1H), 4.07-3.93 (m, 2H), 3.75-3.62 (m, 1H), 3.61-3.45 (m, 3H), 3.44-3.38 (m, 1H), 2.36 (s, 3H), 2.19-2.10 (m, 1H), 2.09-1.93 (m, 2H), 1.91-1.69 (m, 3H), 1.66-1.57 (m, 1H), 1.38 (qd, J=12.4, 3.5 Hz, 1H), 1.32-1.21 (m, 1H), 0.57-0.42 (m, 4H). MS (ESI) m/z: [M+H]$^+$ Found 594.3.

Example 39: 4-Cyclopropyl-N—((R)-1-(7-((S)-1-(5,5-difluoro-2-oxotetrahydropyrimidin-1(2H)-yl-4,4,6,6-$d_4$)-2-methoxyethyl)imidazo[1,2-b]pyridazin-2-yl)-2-((1,1,1-trifluoro-2-methylpropan-2-yl)oxy)ethyl)-1,2,5-oxadiazole-3-carboxamide

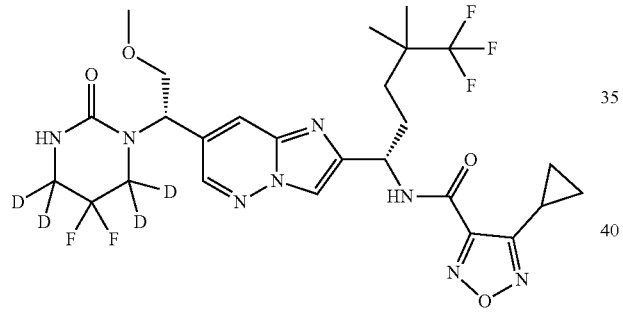

A vial was charged with 1-((5)-1-(2-((R)-1-amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one-4,4,6,6-$d_4$ (90 mg, 0.19 mmol, Intermediate 28), MeCN (3 mL), 2,5-dioxopyrrolidin-1-yl 4-cyclopropyl-1,2,5-oxadiazole-3-carboxylate (47 mg, 0.19 mmol, Intermediate 31), and DIPEA (42 μL, 0.24 mmol). The reaction was stirred for 15 min at rt, then poured over water and extracted with ethyl acetate (3×5 mL). The combined organic layers were washed with brine, dried over anhydrous MgSO$_4$, filtered, and condensed. The isolated material was purified by silica gel chromatography (0-100% ethyl acetate (w/10% MeOH) Hexane). The isolated material was further purified by SFC using a chiral stationary phase ((Stationary phase: Whelk O1 SS 5 μm 250×21 mm, Mobile phase: 35% methanol, 65% $CO_2$). The first eluting peak was lyophilized to yield the title compound as a white solid. $^1$H NMR (500 MHz, DMSO-$d_6$) δ 9.54-9.45 (m, 1H), 8.39 (d, J=2.1 Hz, 1H), 8.23 (s, 1H), 7.98-7.93 (m, 1H), 6.97-6.91 (m, 1H), 5.61-5.55 (m, 1H), 5.46-5.39 (m, 1H), 4.06-4.01 (m, 1H), 3.98-3.87 (m, 3H), 3.35 (s, 3H), 2.40-2.32 (m, 1H), 1.38-1.34 (m, 6H), 1.18-1.12 (m, 2H), 1.04-0.98 (m, 2H). MS (ESI) m/z: [M+H]$^+$ Found 621.20.

Example 40: N—((S)-(7-((S)-2-Cyclopropoxy-1-(5,5-difluoro-2-oxotetrahydropyrimidin-1(2H)-yl-4,4,6,6-$d_4$)ethyl)imidazo[1,2-b]pyridazin-2-yl)(4,4-difluorocyclohexyl)methyl)-4-methyl-1,2,5-oxadiazole-3-carboxamide

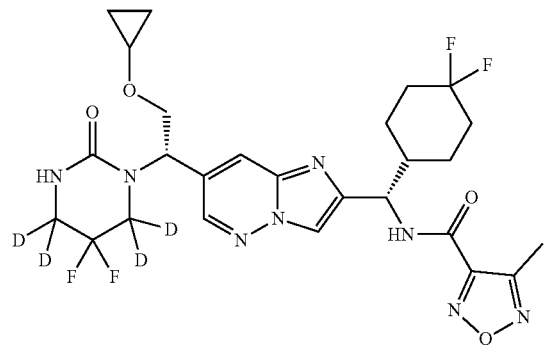 [SMILES: [2H]C1([2H])NC(=O)N([C@H](COC2CC2)c2cnn3cc([C@@H](NC(=O)c4nonc4C)C4CCC(F)(F)CC4)nc3c2)C([2H])([2H])C1(F)F]

The title compound was prepared as described for Example 16 using 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one-4,4,6,6-$d_4$ (Intermediate 30) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. The minor diastereomer was removed by SFC with a chiral stationary phase (Stationary phase: Whelk O1 SS 5 μm 250×21 mm, Mobile phase: 35% methanol, 65% $CO_2$). The first eluting was lyophilized to afford the title compound as a white solid. $^1$H NMR (500 MHz, DMSO-$d_6$) δ 9.42 (d, J=8.9 Hz, 1H), 8.38 (d, J=2.0 Hz, 1H), 8.25 (s, 1H), 7.96-7.92 (m, 1H), 6.93 (s, 1H), 5.59-5.54 (m, 1H), 5.21-5.15 (m, 1H), 4.06-3.94 (m, 2H), 3.44-3.39 (m, 1H), 2.48 (s, 3H), 2.24-2.15 (m, 1H), 2.11-1.95 (m, 2H), 1.94-1.88 (m, 1H), 1.86-1.70 (m, 2H), 1.66-1.58 (m, 1H), 1.44-1.23 (m, 2H), 0.57-0.43 (m, 4H). MS (ESI) m/z: [M+H]$^+$ Found 599.3.

Example 41: 4-Cyclopropyl-N—((S)-1-(7-((S)-1-(5,5-difluoro-2-oxotetrahydropyrimidin-1(2H)-yl)-2-methoxyethyl)imidazo[1,2-b]pyridazin-2-yl)-4,4,4-trifluoro-3,3-dimethylbutyl)-1,2,5-oxadiazole-3-carboxamide

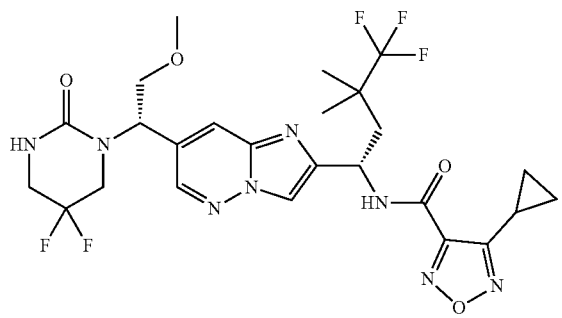

To a stirred solution of 1-((S)-1-(2-((S)-1-amino-4,4,4-trifluoro-3,3-dimethylbutyl)imidazo[1,2-b]pyridazin-7-yl)-

2-methoxyethyl)-5,5-difluorotetrahydropyrimidin-2(1H)-one (Intermediate 44, 42 mg, 0.09 mmol) in ACN (2.5 mL) was added DIPEA (234 uL, 1.36 mmol) and 2,5-dioxopyrrolidin-1-yl 4-cyclopropyl-1,2,5-oxadiazole-3-carboxylate (39 mg, 0.15 mmol, Intermediate 31). After 2 h, the reaction mixture was filtered and purified by reverse phase basic HPLC (X-Bridge Prep C18 5 μm column 50×250 mm, 5-100% acetonitrile/water (with 20 nM NH$_4$OH). The product containing fractions were lyophilized to give the title compound as a white solid (55% yield). $^1$H NMR (600 MHz, DMSO-d$_6$) δ 9.73 (d, J=8.8 Hz, 1H), 8.36 (d, J=2.1 Hz, 1H), 8.20 (s, 1H), 7.98-7.94 (m, 1H), 6.95 (br. s, 1H), 5.58 (t, J=6.8 Hz, 1H), 5.47 (dt, J=3.2, 9.0 Hz, 1H), 3.93-3.86 (m, 2H), 3.72-3.63 (m, 1H), 3.58-3.45 (m, 3H), 3.34 (s, 3H), 2.42-2.33 (m, 2H), 2.27 (dd, J=9.4, 14.6 Hz, 1H), 1.20 (s, 3H), 1.19 (s, 3H), 1.16-1.12 (m, 2H), 1.03-0.95 (m, 2H). MS (APCI/ESI) m/z: [M+H]$^+$ Found 601.3.

Example 42: 4-Cyclopropyl-N-((1R,2R)-1-(7-((S)-1-(5,5-difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propyl)-1,2,5-oxadiazole-3-carboxamide

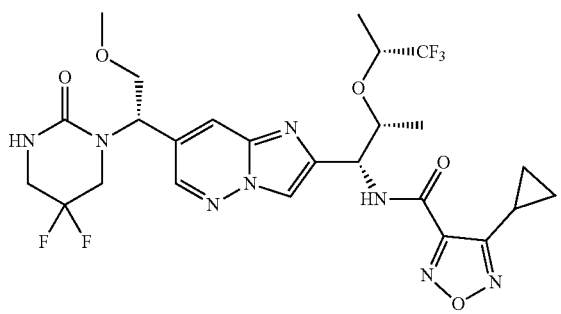 [SMILES: COC[C@H](c1cnn2cc([C@@H](NC(=O)c3nonc3C3CC3)[C@@H](C)O[C@H](C)C(F)(F)F)nc2c1)N1CC(F)(F)CNC1=O]

The title compound was prepared as described for the synthesis of Example 16, using 2,5-dioxopyrrolidin-1-yl 4-cyclopropyl-1,2,5-oxadiazole-3-carboxylate (Intermediate 31) in place of 2,5-dioxopyrrolidin-1-yl 4-methyl-1,2,5-oxadiazole-3-carboxylate and (1R,2R)-1-(7-((S)-1-(5,5-difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propan-1-aminium trifluoroacetate (Intermediate 41) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. The reaction was concentrated under reduced pressure and directly purified by preparative HPLC (XBridge Prep C18, 5 μm, 30×100 mm; 10-100% MeCN/water (20 mM NH$_4$OH) to afford the title compound as an amorphous solid. $^1$H NMR (600 MHz, DMSO-d$_6$) δ 9.42 (d, J=9.2 Hz, 1H), 8.40 (d, J=2.1 Hz, 1H), 8.29-8.23 (m, 1H), 7.97-7.89 (m, 1H), 7.00-6.88 (m, 1H), 5.62-5.55 (m, 1H), 5.29 (dd, J=9.2, 6.9 Hz, 1H), 4.31-4.22 (m, 2H), 3.96-3.87 (m, 2H), 3.76-3.63 (m, 1H), 3.62-3.43 (m, 3H), 3.34 (s, 3H), 2.35-2.26 (m, 1H), 1.18-1.08 (m, 8H), 1.04-0.88 (m, 2H). MS (ESI) m/z: [M+H]$^+$ Found 617.3.

Example 43: 4-Cyclopropyl-N-((1R,2R)-1-(7-((S)-1-(5,5-difluoro-2-oxotetrahydropyrimidin-1(2H)-yl)-2-methoxyethyl)imidazo[1,2-b]pyridazin-2-yl)-2-(((S)-1,1,1-trifluoropropan-2-yl)oxy)propyl)-1,2,5-oxadiazole-3-carboxamide

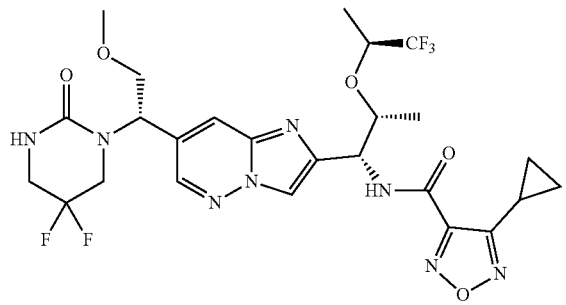 [SMILES: COC[C@H](c1cnn2cc([C@@H](NC(=O)c3nonc3C3CC3)[C@@H](C)O[C@@H](C)C(F)(F)F)nc2c1)N1CC(F)(F)CNC1=O]

The title compound was prepared as described for the synthesis of Example 16, using 2,5-dioxopyrrolidin-1-yl 4-cyclopropyl-1,2,5-oxadiazole-3-carboxylate (Intermediate 31) in place of 2,5-dioxopyrrolidin-1-yl 4-methyl-1,2,5-oxadiazole-3-carboxylate and (1R,2R)-1-(7-((S)-1-(5,5-difluoro-2-oxotetrahydropyrimidin-1(2H)-yl)-2-methoxyethyl)imidazo[1,2-b]pyridazin-2-yl)-2-(((S)-1,1,1-trifluoropropan-2-yl)oxy)propan-1-aminium trifluoroacetate (Intermediate 42) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. The reaction was purified by preparative HPLC (XBridge Prep C18, 5 μm, 30×100 mm; 10-100% MeCN/water (20 mM NH$_4$OH) to afford the title compound as an amorphous solid. $^1$H NMR (600 MHz, DMSO-d$_6$) δ 9.22 (d, J=9.1 Hz, 1H), 8.39 (d, J=2.1 Hz, 1H), 8.23 (s, 1H), 7.96-7.90 (m, 1H), 6.99-6.90 (m, 1H), 5.58 (t, J=6.8 Hz, 1H), 5.31 (dd, J=9.0, 6.7 Hz, 1H), 4.36-4.27 (m, 1H), 4.27-4.21 (m, 1H), 3.95-3.83 (m, 2H), 3.78-3.64 (m, 1H), 3.60-3.46 (m, 3H), 3.34 (s, 3H), 2.35-2.28 (m, 1H), 1.25 (d, J=6.5 Hz, 3H), 1.15-1.10 (m, 5H), 1.00-0.93 (m, 2H). MS (ESI) m/z: [M+H]$^+$ Found 617.3.

Example 44: N—((S)-1-(7-((S)-2-Cyclopropoxy-1-(5,5-difluoro-2-oxotetrahydropyrimidin-1(2H)-yl)ethyl)imidazo[1,2-b]pyridazin-2-yl)-4,4,4-trifluoro-3,3-dimethylbutyl)-4-cyclopropyl-1,2,5-oxadiazole-3-carboxamide

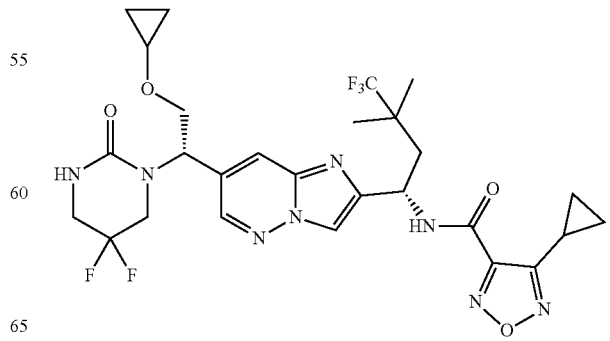

The title compound was prepared as described for the synthesis of Example 16, using 2,5-dioxopyrrolidin-1-yl 4-cyclopropyl-1,2,5-oxadiazole-3-carboxylate (Intermediate 31) in place of 2,5-dioxopyrrolidin-1-yl 4-methyl-1,2,5-oxadiazole-3-carboxylate and (S)-1-(7-((S)-2-cyclopropoxy-1-(5,5-difluoro-2-oxotetrahydropyrimidin-1(2H)-yl)ethyl)imidazo[1,2-b]pyridazin-2-yl)-4,4,4-trifluoro-3,3-dimethylbutan-1-aminium trifluoroacetate (Intermediate 43) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. The reaction was purified by preparative HPLC (XBridge Prep C18, 5 μm, 30×100 mm; 10-100% MeCN/water (20 mM NH$_4$OH) to afford the title compound as an amorphous solid. $^1$H NMR (500 MHz, DMSO-d$_6$) δ 9.74 (d, J=8.7 Hz, 1H), 8.36 (d, J=2.1 Hz, 1H), 8.20 (s, 1H), 7.99-7.92 (m, 1H), 6.99-6.90 (m, 1H), 5.57 (t, J=6.9 Hz, 1H), 5.47 (td, J=9.1, 3.4 Hz, 1H), 4.06-3.90 (m, 2H), 3.73-3.61 (m, 1H), 3.60-3.45 (m, 3H), 3.45-3.38 (m, 1H), 2.43-2.31 (m, 2H), 2.27 (dd, J=14.6, 9.4 Hz, 1H), 1.20 (s, 3H), 1.19 (s, 3H), 1.17-1.11 (m, 2H), 1.05-0.93 (m, 2H), 0.58-0.42 (m, 4H). MS (ESI) m/z: [M+H]$^+$ Found 627.3.

Example 45: N—((S*)-1-(7-((S)-1-(5,5-Difluoro-2-oxotetrahydropyrimidin-1(2H)-yl)-2-methoxyethyl)imidazo[1,2-b]pyridazin-2-yl)-5,5,5-trifluoro-4,4-dimethylpentyl)-4-methyl-1,2,5-oxadiazole-3-carboxamide

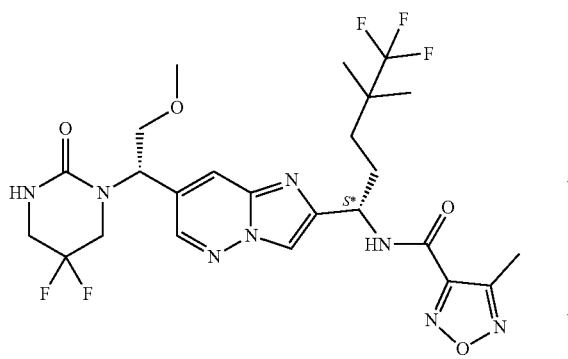

The title compound was synthesized in a manner analogous to Example 41 using 1-((S)-1-(2-((S*)-1-amino-5,5,5-trifluoro-4,4-dimethylpentyl)imidazo[1,2-b]pyridazin-7-yl)-2-methoxyethyl)-5,5-difluorotetrahydropyrimidin-2(1H)-one (Intermediate 47) in place of 1-((S)-1-(2-((S)-1-amino-4,4,4-trifluoro-3,3-dimethylbutyl)imidazo[1,2-b]pyridazin-7-yl)-2-methoxyethyl)-5,5-difluorotetrahydropyrimidin-2(1H)-one and 2,5-dioxopyrrolidin-1-yl 4-methyl-1,2,5-oxadiazole-3-carboxylate in place of 2,5-dioxopyrrolidin-1-yl 4-cyclopropyl-1,2,5-oxadiazole-3-carboxylate to provide the title compound as a white solid (21% yield). $^1$H NMR (600 MHz, DMSO-d$_6$) δ 9.50 (d, J=8.4 Hz, 1H), 8.37 (d, J=2.1 Hz, 1H), 8.19 (s, 1H), 7.96-7.94 (m, 1H), 6.95 (br s, 1H), 5.58 (t, J=6.8 Hz, 1H), 5.24-5.19 (m, 1H), 3.94-3.87 (m, 2H), 3.73-3.65 (m, 1H), 3.60-3.47 (m, 3H), 3.35 (s, 3H), 2.50 (s, 3H), 2.16-2.09 (m, 1H), 2.03-1.95 (m, 1H), 1.66 (dt, J=4.5, 13.2 Hz, 1H), 1.54 (dt, J=4.5, 13.1 Hz, 1H), 1.10 (m, 6H). MS (APCI/ESI) m/z: [M+H]$^+$ Found 589.2.

Example 46: 4-Cyclopropyl-N—((S*)-1-(7-((S)-1-(5,5-difluoro-2-oxotetrahydropyrimidin-1(2H)-yl)-2-methoxyethyl)imidazo[1,2-b]pyridazin-2-yl)-5,5,5-trifluoro-4,4-dimethylpentyl)-1,2,5-oxadiazole-3-carboxamide

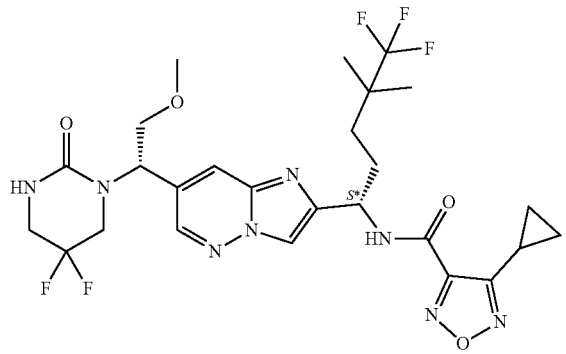 [SMILES: COC[C@H](c1cnn2cc([C@H](CCC(C)(C)C(F)(F)F)NC(=O)c3nonc3C3CC3)nc2c1)N1CC(F)(F)CNC1=O]

The title compound was synthesized in a manner analogous to Example 41 using 1-((S)-1-(2-((S*)-1-amino-5,5,5-trifluoro-4,4-dimethylpentyl)imidazo[1,2-b]pyridazin-7-yl)-2-methoxyethyl)-5,5-difluorotetrahydropyrimidin-2(1H)-one (Intermediate 47) in place of 1-((S)-1-(2-((S)-1-amino-4,4,4-trifluoro-3,3-dimethylbutyl)imidazo[1,2-b]pyridazin-7-yl)-2-methoxyethyl)-5,5-difluorotetrahydropyrimidin-2(1H)-one to provide the title compound as a white solid (39% yield). $^1$H NMR (600 MHz, DMSO-d$_6$) δ 9.54 (d, J=8.6 Hz, 1H), 8.39-8.36 (m, 1H), 8.19 (s, 1H), 7.96-7.92 (m, 1H), 6.95 (br s, 1H), 5.58 (t, J=6.9 Hz, 1H), 5.26-5.19 (m, 1H), 3.93-3.85 (m, 2H), 3.73-3.63 (m, 1H), 3.58-3.45 (m, 3H), 3.34 (s, 3H), 2.37-2.29 (m, 1H), 2.15-2.07 (m, 1H), 2.03-1.94 (m, 1H), 1.68-1.62 (m, 1H), 1.57-1.50 (m, 1H), 1.15-1.12 (m, 2H), 1.09 (s, 3H), 1.09 (s, 3H), 1.00-0.96 (m, 2H). MS (APCI/ESI) m/z: [M+H]$^+$ Found 614.8.

Example 47: N—[(S)-[7-[(R)-Cyclopropyl-(7-oxo-6,8-diazaspiro[2.5]octan-6-yl)methyl]imidazo[1,2-b]pyridazin-2-yl]-(4,4-difluorocyclohexyl)methyl]-4-methyl-1,2,5-oxadiazole-3-carboxamide

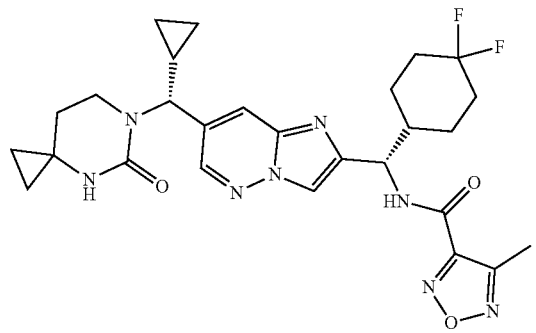 [SMILES: Cc1nonc1C(=O)N[C@H](c1cn2ncc([C@@H](C3CC3)N3CCC4(CC4)NC3=O)cc2n1)C1CCC(F)(F)CC1]

Step A. tert-Butyl ((S)-(7-((R)-cyclopropyl((2-(1-(1,3-dioxoisoindolin-2-yl)cyclopropyl)ethyl)amino)methyl)imidazo[1,2-b]pyridazin-2-yl)(4,4-difluorocyclohexyl)methyl) carbamate. To a mixture of 2-(1-(1,3-dioxoisoindolin-2-yl)cyclopropyl)acetaldehyde (342 mg, 1.49 mmol, Intermediate 49), tert-butyl ((S)-(7-((R)-amino(cyclopropyl)

methyl)imidazo[1,2-b]pyridazin-2-yl)(4,4-difluorocyclohexyl)methyl)carbamate (500 mg, 1.15 mmol), tetraethoxytitanium (524 mg, 2.3 mmol) and anhydrous MeOH (10 mL) was added NaBH₃CN (361 mg, 5.74 mmol) and the resulting mixture was stirred at rt for 1 h. The mixture was then diluted with water (20 mL) and extracted with EtOAc (3×50 mL). The organic layers were combined, washed with water (2×50 mL) and brine (50 mL), dried over anhydrous Na₂SO₄, filtered, and concentrated to dryness to give a light-yellow oil. The oil was purified by silica gel chromatography (0-80% EtOAc/petroleum ether) to provide the title compound as a light-yellow oil (30% yield).

Step B. tert-Butyl ((S)-(7-((R)-((2-(1-aminocyclopropyl)ethyl)amino)(cyclopropyl)methyl)imidazo[1,2-b]pyridazin-2-yl)(4,4-difluorocyclohexyl)methyl)carbamate. A mixture of tert-butyl ((S)-(7-((R)-cyclopropyl((2-(1-(1,3-dioxoisoindolin-2-yl)cyclopropyl)ethyl)amino)methyl)imidazo[1,2-b]pyridazin-2-yl)(4,4-difluorocyclohexyl)methyl)carbamate (450 mg, 0.69 mmol, Step A), hydrazine monohydrate (366 mg, 6.94 mmol) and anhydrous MeOH (5 mL) was stirred at rt for 1 h. The mixture was then filtered and concentrated to dryness to give a light-yellow oil. The oil was purified by silica gel chromatography (0-10% MeOH/DCM) to provide the title compound as a light-yellow oil (83% yield).

Step C. tert-Butyl ((S)-(7-((R)-cyclopropyl(5-oxo-4,6-diazaspiro[2.5]octan-6-yl)methyl)imidazo[1,2-b]pyridazin-2-yl)(4,4-difluorocyclohexyl)methyl)carbamate. A mixture of tert-butyl ((S)-(7-((R)-((2-(1-aminocyclopropyl)ethyl)amino)(cyclopropyl)methyl)imidazo[1,2-b]pyridazin-2-yl)(4,4-difluorocyclohexyl)methyl)carbamate (300 mg, 0.58 mmol, Step B), CDI (281 mg, 1.74 mmol) and anhydrous THF (2 mL) was heated at 65° C. for 2 h. After that time, the mixture was diluted with water (50 mL) and extracted with EtOAc (2×50 mL). The combined organic layers were washed with water (2×50 mL) and brine (50 mL), dried over anhydrous Na₂SO₄, filtered, and concentrated to dryness to give a light-yellow oil. The oil was purified by silica gel chromatography (0-80% EtOAc/petroleum ether) to provide the title compound as a light-yellow oil (63% yield).

Step D. 6-((R)-(2-((S)-Amino(4,4-difluorocyclohexyl)methyl)imidazo[1,2-b]pyridazin-7-yl)(cyclopropyl)methyl)-4,6-diazaspiro[2.5]octan-5-one hydrochloride. A mixture of tert-butyl ((S)-(7-((R)-cyclopropyl(5-oxo-4,6-diazaspiro[2.5]octan-6-yl)methyl)imidazo[1,2-b]pyridazin-2-yl)(4,4-difluorocyclohexyl)methyl)carbamate (200 mg, 0.37 mmol, Step C) and 4 M HCl in 1,4-dioxane (0.73 mL, 2.94 mmol) was stirred at rt for 90 min. After that time, the mixture was concentrated to dryness and lyophilized to provide the title compound as a yellow oil (86% yield).

Step E. N—[(S)-[7-[(R)-Cyclopropyl-(7-oxo-6,8-diazaspiro[2.5]octan-6-yl)methyl]imidazo[1,2-b]pyridazin-2-yl]-(4,4-difluorocyclohexyl)methyl]-4-methyl-1,2,5-oxadiazole-3-carboxamide. A mixture of 6-((R)-(2-((S)-amino(4,4-difluorocyclohexyl)methyl)imidazo[1,2-b]pyridazin-7-yl)(cyclopropyl)methyl)-4,6-diazaspiro[2.5]octan-5-one hydrochloride (140 mg, 0.31 mmol, Step D), 2,5-dioxypyrrolidin-1-yl 4-methyl-1,2,5-oxadiazole-3-carboxylate (106 mg, 0.47 mmol), TEA (0.22 mL, 1.57 mmol) and anhydrous DCM (2 mL) was stirred at rt for 6 h. The mixture was diluted with water (30 mL) and extracted with EtOAc (2×30 mL). The organic layers were combined, washed with water (2×50 mL) and brine (50 mL), dried over anhydrous Na₂SO₄, filtered, and concentrated to dryness to give a light-yellow oil. The oil was purified by silica gel chromatography (0-70% EtOAc/petroleum ether) and lyophilized to provide the title compound as a white solid (13% yield). ¹H NMR (400 MHz, DMSO-d₆) δ 9.41 (d, J=9.2 Hz, 1H), 8.35 (d, J=2.0 Hz, 1H), 8.23 (s, 1H), 8.00 (s, 1H), 6.58 (s, 1H), 5.16 (s, 1H), 4.67 (d, J=9.6 Hz, 1H), 3.15-3.05 (m, 1H), 2.46 (s, 3H), 2.22-2.13 (m, 1H), 2.11-1.86 (m, 4H), 1.84-1.67 (m, 3H), 1.65-1.48 (m, 3H), 1.41-1.31 (m, 1H), 1.30-1.25 (m, 1H), 0.83-0.77 (m, 1H), 0.73-0.67 (m, 1H), 0.67-0.59 (m, 2H), 0.57-0.50 (m, 2H), 0.49-0.42 (m, 1H), 0.41-0.31 (m, 1H). MS (ESI) m/z: [M+H]⁺ Found 555.0.

Example 48: N—((S)-(7-((R)-Cyclopropyl((S*)-2-oxo-4-(trifluoromethyl)tetrahydropyrimidin-1(2H)-yl)methyl)imidazo[1,2-b]pyridazin-2-yl)(4,4-difluorocyclohexyl)methyl)-4-methyl-1,2,5-oxadiazole-3-carboxamide

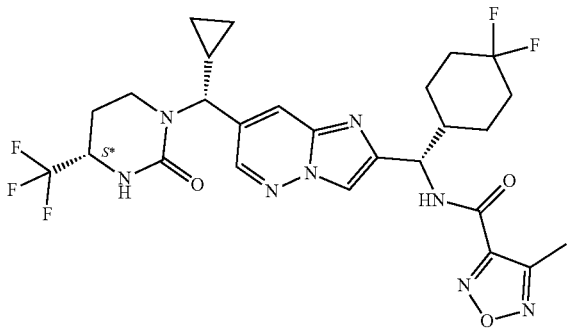 [SMILES: Cc1nonc1C(=O)N[C@H](c1cn2ncc([C@@H](C3CC3)N3CC[C@@H](C(F)(F)F)NC3=O)cc2n1)C1CCC(F)(F)CC1]

Example 49: N—((S)-(7-((R)-Cyclopropyl((R*)-2-oxo-4-(trifluoromethyl)tetrahydropyrimidin-1(2H)-yl)methyl)imidazo[1,2-b]pyridazin-2-yl)(4,4-difluorocyclohexyl)methyl)-4-methyl-1,2,5-oxadiazole-3-carboxamide

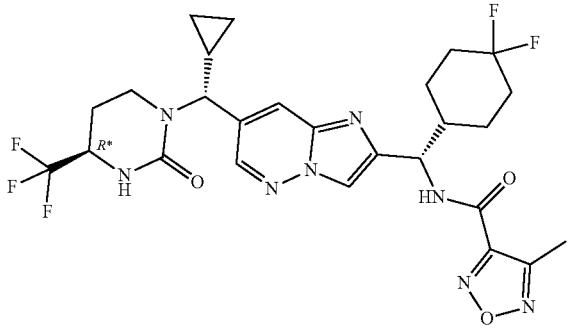 [SMILES: Cc1nonc1C(=O)N[C@H](c1cn2ncc([C@@H](C3CC3)N3CC[C@H](C(F)(F)F)NC3=O)cc2n1)C1CCC(F)(F)CC1]

Step A. tert-Butyl ((1S)-(7-((1R)-cyclopropyl((3-(1,3-dioxoisoindolin-2-yl)-4,4,4-trifluorobutyl)amino)methyl)imidazo[1,2-b]pyridazin-2-yl)(4,4-difluorocyclohexyl)methyl)carbamate. A mixture of 3-(1,3-dioxoisoindolin-2-yl)-4,4,4-trifluorobutanal (330 mg, 1.22 mmol, Intermediate 50), tert-butyl ((S)-(7-((R)-amino(cyclopropyl)methyl)imidazo[1,2-b]pyridazin-2-yl)(4,4-difluorocyclohexyl)methyl)carbamate (407 mg, 0.93 mmol), Ti(OiPr)₄ (532 mg, 1.87 mmol) and anhydrous MeOH (8 mL) was stirred at rt for 1 h, followed by the addition of NaBH₃CN (294 mg, 4.68 mmol). The resulting mixture was stirred at rt for 12 h. After that time, water (2 mL) was added and the mixture was extracted with EtOAc (2×40 mL). The organic layers were combined, washed with brine (30 mL), dried over anhydrous Na₂SO₄, filtered, and concentrated to dryness to give a yellow oil that was used without further purification (71% yield).

Step B. tert-Butyl ((1S)-(7-((1R)-((3-amino-4,4,4-trifluorobutyl)amino)(cyclopropyl)methyl)imidazo[1,2-b]pyridazin-2-yl)(4,4-difluorocyclohexyl)methyl)carbamate. The title compound was prepared in a manner analogous to Intermediate 10 Step B using tert-butyl ((1S)-(7-((1R)-cyclopropyl((3-(1,3-dioxoisoindolin-2-yl)-4,4,4-trifluorobutyl)amino)methyl)imidazo[1,2-b]pyridazin-2-yl)(4,4-difluorocyclohexyl)methyl)carbamate in place of tert-butyl ((R)-1-(7-((S*)-1-((3-(1,3-dioxoisoindolin-2-yl)-2,2-difluoropropyl)amino)-2-methoxyethyl)imidazo[1,2-b]pyridazin-2-yl)-2-((1,1,1-trifluoro-2-methylpropan-2-yl)oxy)ethyl) carbamate, and the mixture was heated at 70° C. for 4 h instead of 50° C. for 2 h. The yellow oil obtained was purified by preparative HPLC (Phenomenex C18, 3 μm, 30×75 mm, 43-73% MeCN/water (NH₄OH+NH₄HCO₃)) followed by lyophilization to provide the title compound as a yellow oil (53% yield).

Step C. tert-Butyl ((1S)-(7-((1R)-cyclopropyl(2-oxo-4-(trifluoromethyl)tetrahydropyrimidin-1(2H)-yl)methyl)imidazo[1,2-b]pyridazin-2-yl)(4,4-difluorocyclohexyl)methyl) carbamate. A stirred solution of tert-butyl ((1S)-(7-((1R)-((3-amino-4,4,4-trifluorobutyl)amino)(cyclopropyl)methyl)imidazo[1,2-b]pyridazin-2-yl)(4,4-difluorocyclohexyl) methyl)carbamate (260 mg, 0.46 mmol, Step B) and DIPEA (0.48 mL, 2.78 mmol) in CH₂Cl₂ (5 mL) was cooled to 0° C., then triphosgene (100 mg, 0.34 mmol) was added. The resulting mixture was stirred for 30 min at 0° C. then quenched with saturated aqueous NaHCO₃ (10 mL) and extracted with DCM (2×10 mL). The organic layers were combined, dried over anhydrous Na₂SO₄, filtered, and concentrated to dryness to afford a yellow oil. The oil was purified by silica gel chromatography (10-12% MeOH/DCM) to provide the title compound as a yellow oil (92% yield).

Step D. 1-((R)-(2-((S)-Amino(4,4-difluorocyclohexyl)methyl)imidazo[1,2-b]pyridazin-7-yl)(cyclopropyl)methyl)-4-(trifluoromethyl)tetrahydropyrimidin-2(1H)-one. A mixture of tert-butyl ((1S)-(7-((1R)-cyclopropyl(2-oxo-4-(trifluoromethyl)tetrahydropyrimidin-1(2H)-yl)methyl)imidazo[1,2-b]pyridazin-2-yl)(4,4-difluorocyclohexyl)methyl) carbamate (240 mg, 0.41 mmol, Step C) and 4 M HCl in 1,4-dioxane (3 mL, 12 mmol) was stirred at rt for 60 min. After that time, the pH of the mixture was adjusted by the addition of saturated aqueous NaHCO₃ (20 mL), and then extracted with EtOAc (3×30 mL). The organic layers were combined, washed with brine (20 mL), dried over anhydrous Na₂SO₄, filtered, and concentrated to dryness to provide the title compound as a yellow oil, which was used without further purification (100% yield).

Step E. N-((1S)-(7-((1R)-Cyclopropyl(2-oxo-4-(trifluoromethyl)tetrahydropyrimidin-1(2H)-yl)methyl)imidazo[1,2-b]pyridazin-2-yl)(4,4-difluorocyclohexyl)methyl)-4-methyl-1,2,5-oxadiazole-3-carboxamide. A mixture of 1-((R)-(2-((S)-amino(4,4-difluorocyclohexyl)methyl)imidazo[1,2-b]pyridazin-7-yl)(cyclopropyl)methyl)-4-(trifluoromethyl)tetrahydropyrimidin-2(1H)-one (150 mg, 0.31 mmol, Step D), 2,5-dioxopyrrolidin-1-yl 4-methyl-1,2,5-oxadiazole-3-carboxylate (139 mg, 0.62 mmol), TEA (0.21 mL, 1.54 mmol) and anhydrous DCM (3 mL) was stirred at rt for 1 h. After that time, the reaction mixture was concentrated to dryness and the resulting oil purified by silica gel chromatography (5-9% MeOH/DCM) to provide two diastereomers of the title compound as a yellow oil (92% yield).

Step F. N—((S)-(7-((R)-Cyclopropyl((S*)-2-oxo-4-(trifluoromethyl)tetrahydropyrimidin-1(2H)-yl)methyl)imidazo[1,2-b]pyridazin-2-yl)(4,4-difluorocyclohexyl)methyl)-4-methyl-1,2,5-oxadiazole-3-carboxamide. The two diastereomers of N-((1S)-(7-((1R)-cyclopropyl(2-oxo-4-(trifluoromethyl)tetrahydropyrimidin-1(2H)-yl)methyl)imidazo[1,2-b]pyridazin-2-yl)(4,4-difluorocyclohexyl)methyl)-4-methyl-1,2,5-oxadiazole-3-carboxamide, from Step E, were separated by chiral SFC (DAICEL CHIRALCEL OD column, 10 μm, 250×30 mm; 35% (v/v) EtOH (containing 0.1% aqueous NH₃)/CO₂). The first eluting isomer was designated as the (S*) isomer (Example 48) and the second eluting isomer was designated as the (R*) isomer (Example 49). The first eluting isomer, N—((S)-(7-((R)-cyclopropyl ((S*)-2-oxo-4-(trifluoromethyl)tetrahydropyrimidin-1(2H)-yl)methyl)imidazo[1,2-b]pyridazin-2-yl)(4,4-difluorocyclohexyl)methyl)-4-methyl-1,2,5-oxadiazole-3-carboxamide, (Example 48, 32% yield) was isolated as a white solid after lyophilization. Example 48: ¹H NMR (400 MHz, DMSO-d₆) δ 9.42 (d, J=8.8 Hz, 1H), 8.31-8.27 (m, 1H), 8.24 (s, 1H), 8.00 (s, 1H), 7.24 (d, J=3.2 Hz, 1H), 5.19-5.14 (m, 1H), 4.65-4.61 (m, 1H), 4.10 (s, 1H), 3.49-3.41 (m, 2H), 3.09-3.00 (m, 1H), 2.47 (s, 3H), 2.35-2.28 (m, 1H), 2.13-1.87 (m, 4H), 1.86-1.71 (m, 2H), 1.65-1.53 (m, 2H), 1.39-1.24 (m, 2H), 0.82-0.73 (m, 1H), 0.65-0.56 (m, 1H), 0.50-0.44 (m, 1H), 0.43-0.34 (m, 1H). MS (ESI) m/z: [M+H]⁺ Found 597.3.

The second eluting isomer, N—((S)-(7-((R)-cyclopropyl ((R*)-2-oxo-4-(trifluoromethyl)tetrahydropyrimidin-1(2H)-yl)methyl)imidazo[1,2-b]pyridazin-2-yl)(4,4-difluorocyclohexyl)methyl)-4-methyl-1,2,5-oxadiazole-3-carboxamide, (Example 49, 26% yield) was isolated as a white solid after lyophilization. Example 49: ¹H NMR (400 MHz, DMSO-d₆) δ 9.42 (d, J=9.2 Hz, 1H), 8.38-8.34 (m, 1H), 8.24 (s, 1H), 8.02 (s, 1H), 7.26 (d, J=4.4 Hz, 1H), 5.20-5.12 (m, 1H), 4.68-4.61 (m, 1H), 4.06 (s, 1H), 3.52-3.43 (m, 2H), 3.18-3.06 (m, 1H), 2.47 (s, 3H), 2.31-2.24 (m, 1H), 2.12-1.90 (m, 4H), 1.87-1.68 (m, 2H), 1.66-1.44 (m, 2H), 1.41-1.21 (m, 2H), 0.85-0.77 (m, 1H), 0.65-0.56 (m, 1H), 0.53-0.49 (m, 1H), 0.35-0.21 (m, 1H). MS (ESI) m/z: [M+H]⁺ Found 597.3.

Example 50: N—((S)-1-(7-((S)-2-Cyclopropoxy-1-(5,5-difluoro-2-oxotetrahydropyrimidin-1(2H)-yl) ethyl)imidazo[1,2-b]pyridazin-2-yl)-4,4,4-trifluoro-3,3-dimethylbutyl)-4-methyl-1,2,5-oxadiazole-3-carboxamide

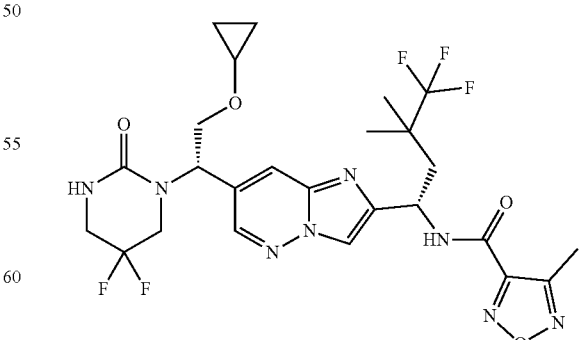

The title compound was synthesized in a manner analogous to Example 16 using (S)-1-(7-((S)-2-cyclopropoxy-1-(5,5-difluoro-2-oxotetrahydropyrimidin-1(2H)-yl)ethyl)

imidazo[1,2-b]pyridazin-2-yl)-4,4,4-trifluoro-3,3-dimethylbutan-1-aminium trifluoroacetate (Intermediate 43) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. The material was purified by preparative HPLC (XBridge Prep C18, 5 μm, 30×100 mm; 10-100% MeCN/water (20 mM NH$_4$OH)) to afford the title compound as an amorphous solid in 31% yield. $^1$H NMR (500 MHz, DMSO-d$_6$) δ 9.70 (d, J=8.7 Hz, 1H), 8.36 (d, J=2.1 Hz, 1H), 8.26-8.13 (m, 1H), 8.02-7.91 (m, 1H), 7.04-6.80 (m, 1H), 5.65-5.51 (m, 1H), 5.50-5.38 (m, 1H), 4.06-3.93 (m, 2H), 3.73-3.61 (m, 1H), 3.59-3.46 (m, 3H), 3.44-3.38 (m, 1H), 2.50 (s, 3H), 2.40 (dd, J=14.7, 3.4 Hz, 1H), 2.27 (dd, J=14.7, 9.5 Hz, 1H), 1.20 (s, 3H), 1.19 (s, 3H), 0.59-0.44 (m, 4H). MS (ESI) m/z: [M+H]$^+$ Found 601.3.

Example 51: 4-Cyclopropyl-N—((S*)-(7-((S)-1-(5,5-difluoro-2-oxotetrahydropyrimidin-1(2H)-yl)-2-methoxyethyl)imidazo[1,2-b]pyridazin-2-yl)((1R,5S,6r)-3,3-difluorobicyclo[3.1.0]hexan-6-yl)methyl)-1,2,5-oxadiazole-3-carboxamide

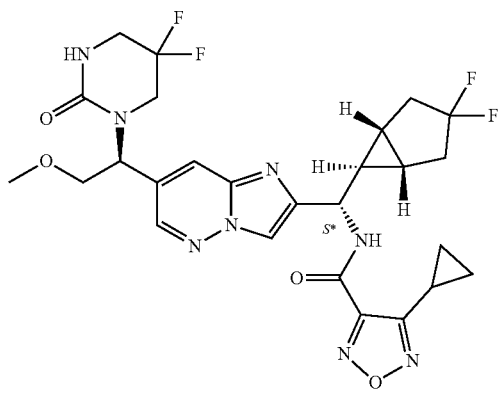 [SMILES: COC[C@H](c1cnn2cc([C@@H](NC(=O)c3nonc3C3CC3)[C@H]3[C@@H]4CC(F)(F)C[C@@H]43)nc2c1)N1CC(F)(F)CNC1=O]

The title compound was synthesized in a manner analogous to Example 16 using 2,5-dioxopyrrolidin-1-yl 4-cyclopropyl-1,2,5-oxadiazole-3-carboxylate (Intermediate 31) in place of 2,5-dioxopyrrolidin-1-yl 4-methyl-1,2,5-oxadiazole-3-carboxylate and (S*)-(7-((S)-1-(5,5-difluoro-2-oxotetrahydropyrimidin-1(2H)-yl)-2-methoxyethyl)imidazo[1,2-b]pyridazin-2-yl)((1R,5S,6r)-3,3-difluorobicyclo[3.1.0]hexan-6-yl)methanaminium 2,2,2-trifluoroacetate (Intermediate 51) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. The material was purified by preparative HPLC (XBridge Prep C18, 5 μm, 30×100 mm; 10-100% MeCN/water (20 mM NH$_4$OH)) to afford the title compound as an amorphous solid in 65% yield. $^1$H NMR (600 MHz, DMSO-d$_6$) δ 9.70 (d, J=8.2 Hz, 1H), 8.37 (d, J=2.1 Hz, 1H), 8.27-8.15 (m, 1H), 8.03-7.85 (m, 1H), 6.95 (s, 1H), 5.58 (t, J=6.8 Hz, 1H), 4.72 (t, J=8.7 Hz, 1H), 3.94-3.83 (m, 2H), 3.75-3.62 (m, 1H), 3.60-3.46 (m, 3H), 3.34 (s, 3H), 2.47-2.31 (m, 3H), 2.23-2.11 (m, 2H), 1.66-1.56 (m, 2H), 1.47-1.39 (m, 1H), 1.17-1.10 (m, 2H), 1.03-0.95 (m, 2H). MS (ESI) m/z: [M+H]$^+$ Found 593.3.

Example 52: 4-Cyclopropyl-N—((R*)-(7-((S)-1-(5,5-difluoro-2-oxotetrahydropyrimidin-1(2H)-yl)-2-methoxyethyl)imidazo[1,2-b]pyridazin-2-yl)((R*)-3,3-difluorocyclopentyl)methyl)-1,2,5-oxadiazole-3-carboxamide

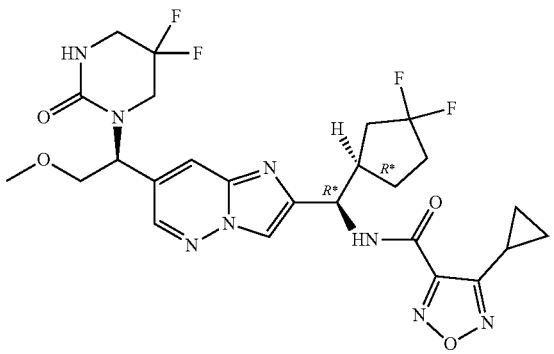 [SMILES: COC[C@H](c1cnn2cc([C@H](NC(=O)c3nonc3C3CC3)[C@@H]3CCC(F)(F)C3)nc2c1)N1CC(F)(F)CNC1=O]

The title compound was synthesized in a manner analogous to Example 16 using 2,5-dioxopyrrolidin-1-yl 4-cyclopropyl-1,2,5-oxadiazole-3-carboxylate (Intermediate 31) in place of 2,5-dioxopyrrolidin-1-yl 4-methyl-1,2,5-oxadiazole-3-carboxylate and (R*)-(7-((S)-1-(5,5-difluoro-2-oxotetrahydropyrimidin-1(2H)-yl)-2-methoxyethyl)imidazo[1,2-b]pyridazin-2-yl)((R*)-3,3-difluorocyclopentyl)methanaminium 2,2,2-trifluoroacetate (Intermediate 54) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. The material was purified by preparative HPLC (XBridge Prep C18, 5 μm, 30×100 mm; 10-100% MeCN/water (20 mM NH$_4$OH)) to afford the title compound as an amorphous solid in 42% yield. $^1$H NMR (600 MHz, DMSO-d$_6$) δ 9.58 (d, J=8.7 Hz, 1H), 8.38 (d, J=2.1 Hz, 1H), 8.25 (s, 1H), 7.97-7.83 (m, 1H), 6.97-6.89 (m, 1H), 5.57 (t, J=6.8 Hz, 1H), 5.24 (t, J=8.9 Hz, 1H), 3.95-3.83 (m, 2H), 3.75-3.63 (m, 1H), 3.61-3.46 (m, 3H), 3.34 (s, 3H), 2.98-2.88 (m, 1H), 2.37-2.27 (m, 2H), 2.21-1.98 (m, 3H), 1.78-1.68 (m, 1H), 1.66-1.55 (m, 1H), 1.16-1.09 (m, 2H), 1.01-0.92 (m, 2H). MS (ESI) m/z: [M+H]$^+$ Found 581.3.

Example 53: N-((1R,2R)-1-(7-((S)-1-(5,5-Difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propyl)-4-methyl-1,2,5-oxadiazole-3-carboxamide

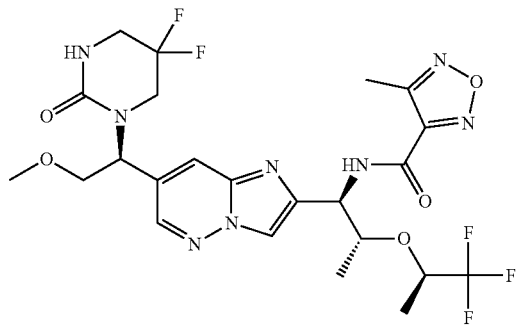 [SMILES: COC[C@H](c1cnn2cc([C@@H](NC(=O)c3nonc3C)[C@@H](C)O[C@H](C)C(F)(F)F)nc2c1)N1CC(F)(F)CNC1=O]

The title compound was synthesized in a manner analogous to Example 16 using (1R,2R)-1-(7-((S)-1-(5,5-difluoro-2-oxotetrahydropyrimidin-1(2H)-yl)-2-methoxyethyl)imidazo[1,2-b]pyridazin-2-yl)-2-(((R)-1,1,1-trifluoropropan-2-yl)oxy)propan-1-aminium trifluoroacetate (Intermediate 41) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. The material was purified by preparative HPLC (XBridge Prep C18, 5 μm, 30×100 mm; 10-100% MeCN/water (20 mM NH₄OH)) to afford the title compound as an amorphous solid in 48% yield. $^1$H NMR (600 MHz, DMSO-d$_6$) δ 9.34 (d, J=9.2 Hz, 1H), 8.39 (d, J=2.1 Hz, 1H), 8.26 (s, 1H), 7.99-7.84 (m, 1H), 7.03-6.90 (m, 1H), 5.57 (t, J=6.8 Hz, 1H), 5.27 (dd, J=9.1, 7.0 Hz, 1H), 4.35-4.22 (m, 2H), 3.96-3.83 (m, 2H), 3.77-3.65 (m, 1H), 3.64-3.45 (m, 3H), 3.34 (s, 3H), 2.48 (s, 3H), 1.11 (d, J=6.3 Hz, 3H), 1.09 (d, J=6.5 Hz, 3H). MS (ESI) m/z: [M+H]$^+$ Found 591.2.

Example 54: N-((1R*,2R*)-2-Cyclopropoxy-1-(7-((S)-1-(5,5-difluoro-2-oxotetrahydropyrimidin-1(2H)-yl)-2-methoxyethyl)imidazo[1,2-b]pyridazin-2-yl)propyl)-4-cyclopropyl-1,2,5-oxadiazole-3-carboxamide

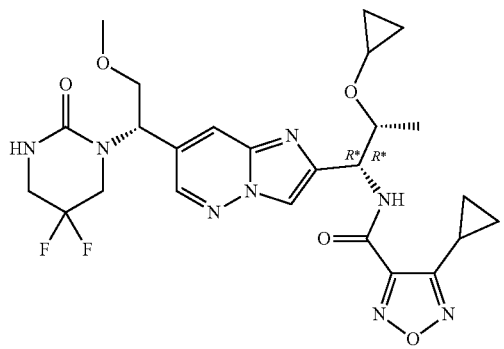 [SMILES: COC[C@H](c1cnn2cc([C@@H](NC(=O)c3nonc3C3CC3)[C@@H](C)OC3CC3)nc2c1)N1CC(F)(F)CNC1=O]

Example 55: N-((1R*,2S*)-2-cyclopropoxy-1-(7-((S)-1-(5,5-difluoro-2-oxotetrahydropyrimidin-1(2H)-yl)-2-methoxyethyl)imidazo[1,2-b]pyridazin-2-yl)propyl)-4-cyclopropyl-1,2,5-oxadiazole-3-carboxamide

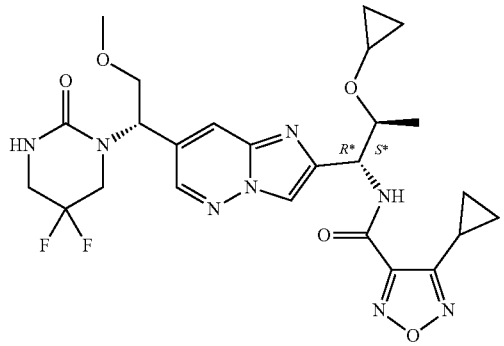 [SMILES: COC[C@H](c1cnn2cc([C@@H](NC(=O)c3nonc3C3CC3)[C@H](C)OC3CC3)nc2c1)N1CC(F)(F)CNC1=O]

The title compounds were synthesized in a manner analogous to Example 16 using 2,5-dioxopyrrolidin-1-yl 4-cyclopropyl-1,2,5-oxadiazole-3-carboxylate (Intermediate 31) in place of 2,5-dioxopyrrolidin-1-yl 4-methyl-1,2,5-oxadiazole-3-carboxylate and 1-((1S)-1-(2-((1R*)-1-amino-2-cyclopropoxypropyl)imidazo[1,2-b]pyridazin-7-yl)-2-methoxyethyl)-5,5-difluorotetrahydropyrimidin-2(1H)-one (Intermediate 57) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. The material was purified by silica gel chromatography (0-100% (10% MeOH) EtOAc/hexanes) to afford two diastereomers (Example 54 and Example 55). These diastereomers were separated by chiral SFC (Stationary phase: Lux Cellulose 1, 5 μm, 250×21 mm, Mobile phase: 25% IPA (0.2% i-PrNH₂), 75% CO₂) to afford Example 54 (18% yield) as the first eluting compound and Example 55 (14% yield) as the second eluting compound. Example 54: $^1$H NMR (600 MHz, DMSO-d$_6$) δ 9.23 (d, J=9.0 Hz, 1H), 8.39 (d, J=2.1 Hz, 1H), 8.20 (s, 1H), 7.93 (dt, J=2.0, 0.9 Hz, 1H), 6.95 (s, 1H), 5.57 (t, J=6.8 Hz, 1H), 5.27 (dd, J=9.0, 6.0 Hz, 1H), 4.13 (p, J=6.3 Hz, 1H), 3.96-3.86 (m, 2H), 3.74-3.65 (m, 1H), 3.60-3.45 (m, 3H), 3.39-3.33 (m, 1H), 3.34 (s, 3H), 2.28 (tt, J=8.4, 5.0 Hz, 1H), 1.19-1.12 (m, 5H), 1.03-0.93 (m, 2H), 0.48-0.41 (m, 2H), 0.41-0.30 (m, 2H). MS (ESI) m/z: [M+H]$^+$ Found 561.3. Example 55: $^1$H NMR (600 MHz, DMSO-d$_6$) δ 9.32 (d, J=9.2 Hz, 1H), 8.38 (d, J=2.1 Hz, 1H), 8.19 (s, 1H), 7.95-7.92 (m, 1H), 6.95 (s, 1H), 5.58 (t, J=6.8 Hz, 1H), 5.50 (dd, J=9.2, 5.2 Hz, 1H), 4.18-4.10 (m, 1H), 3.96-3.86 (m, 2H), 3.69 (ddd, J=19.5, 12.6, 7.1 Hz, 1H), 3.57-3.45 (m, 3H), 3.42 (tt, J=6.0, 3.2 Hz, 1H), 3.34 (s, 3H), 2.29 (tt, J=8.4, 5.0 Hz, 1H), 1.17-1.12 (m, 5H), 0.99 (dd, J=5.0, 2.5 Hz, 2H), 0.51-0.36 (m, 4H). MS (ESI) m/z: [M+H]$^+$ Found 561.3.

Example 56: N—((S)-1-(7-((S)-2-Cyclopropoxy-1-(5,5-difluoro-2-oxotetrahydropyrimidin-1(2H)-yl)ethyl)imidazo[1,2-b]pyridazin-2-yl)-5,5,5-trifluoro-4,4-dimethylpentyl)-4-methyl-1,2,5-oxadiazole-3-carboxamide

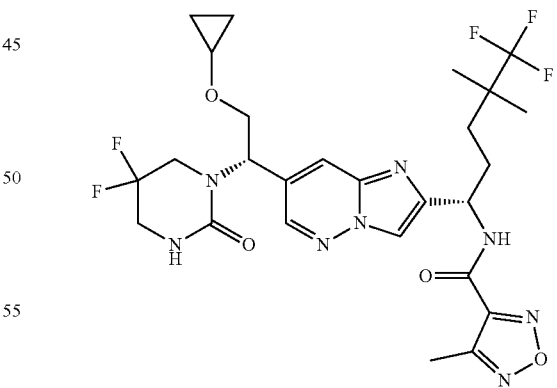

The title compound was synthesized in a manner analogous to Example 16 using (S)-1-(7-((S)-2-cyclopropoxy-1-(5,5-difluoro-2-oxotetrahydropyrimidin-1(2H)-yl)ethyl)imidazo[1,2-b]pyridazin-2-yl)-5,5,5-trifluoro-4,4-dimethylpentan-1-aminium 2,2,2-trifluoroacetate (Intermediate 58) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2

(1H)-one hydrochloride. The material was purified by preparative HPLC (XBridge Prep C18, 5 μm, 30×100 mm; 10-100% MeCN/water (20 mM NH₄OH)) to afford the title compound as an amorphous solid in 64% yield. ¹H NMR (500 MHz, DMSO-d₆) δ 9.50 (d, J=8.5 Hz, 1H), 8.36 (d, J=2.1 Hz, 1H), 8.19 (s, 1H), 8.01-7.83 (m, 1H), 6.94 (s, 1H), 5.56 (t, J=6.9 Hz, 1H), 5.31-5.10 (m, 1H), 4.11-3.92 (m, 2H), 3.73-3.59 (m, 1H), 3.59-3.45 (m, 3H), 3.44-3.36 (m, 1H), 2.49 (s, 3H), 2.16-2.07 (m, 1H), 2.03-1.94 (m, 1H), 1.69-1.60 (m, 1H), 1.58-1.48 (m, 1H), 1.09 (s, 6H), 0.58-0.41 (m, 4H). MS (ESI) m/z: [M+H]⁺ Found 615.3.

Example 57: N—((S)-(7-((S*)-2-Cyclobutoxy-1-(5,5-difluoro-2-oxotetrahydropyrimidin-1(2H)-yl)ethyl)imidazo[1,2-b]pyridazin-2-yl)(4,4-difluorocyclohexyl)methyl)-4-methyl-1,2,5-oxadiazole-3-carboxamide

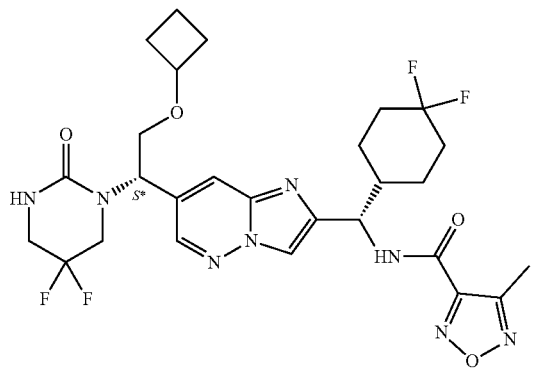 [SMILES: Cc1nonc1C(=O)N[C@H](c1cn2ncc([C@@H](COC3CCC3)N3CC(F)(F)CNC3=O)cc2n1)C1CCC(F)(F)CC1]

The title compound (23% yield) was synthesized in a manner analogous to Example 16 using 1-((S*)-1-(2-((S)-amino(4,4-difluorocyclohexyl)methyl)imidazo[1,2-b]pyridazin-7-yl)-2-cyclobutoxyethyl)-5,5-difluorotetrahydropyrimidin-2(1H)-one (Intermediate 61) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. ¹H NMR (500 MHz, DMSO-d₆) δ 9.41 (d, J=9.0 Hz, 1H), 8.38 (d, J=2.1 Hz, 1H), 8.24 (s, 1H), 7.98-7.90 (m, 1H), 6.97-6.90 (m, 1H), 5.54-5.46 (m, 1H), 5.21-5.14 (m, 1H), 4.06-3.97 (m, 1H), 3.92-3.85 (m, 1H), 3.84-3.78 (m, 1H), 3.76-3.66 (m, 1H), 3.62-3.44 (m, 3H), 2.47 (s, 3H), 2.25-2.12 (m, 3H), 2.11-1.94 (m, 2H), 1.93-1.70 (m, 5H), 1.67-1.58 (m, 2H), 1.52-1.33 (m, 2H), 1.33-1.23 (m, 1H). MS (ESI) m/z: [M+H]⁺ Found 609.3.

Example 58: N—((S)-(7-((S*)-1-(5,5-Difluoro-2-oxotetrahydropyrimidin-1(2H)-yl)-2-isopropoxyethyl)imidazo[1,2-b]pyridazin-2-yl)(4,4-difluorocyclohexyl)methyl)-4-methyl-1,2,5-oxadiazole-3-carboxamide

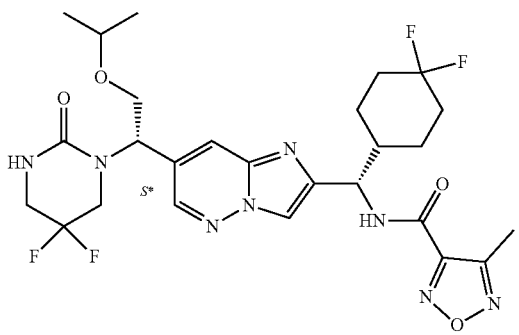 [SMILES: Cc1nonc1C(=O)N[C@H](c1cn2ncc([C@@H](COC(C)C)N3CC(F)(F)CNC3=O)cc2n1)C1CCC(F)(F)CC1]

The title compound (23% yield) was synthesized in a manner analogous to Example 16, using 1-((S*)-1-(2-((S)-amino(4,4-difluorocyclohexyl)methyl)imidazo[1,2-b]pyridazin-7-yl)-2-isopropoxyethyl)-5,5-difluorotetrahydropyrimidin-2(1H)-one (Intermediate 62) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. ¹H NMR (500 MHz, DMSO-d₆) δ 9.41 (d, J=9.0 Hz, 1H), 8.38 (d, J=2.1 Hz, 1H), 8.24 (s, 1H), 7.98-7.90 (m, 1H), 6.97-6.90 (m, 1H), 5.54-5.46 (m, 1H), 5.21-5.14 (m, 1H), 4.06-3.97 (m, 1H), 3.92-3.85 (m, 1H), 3.84-3.78 (m, 1H), 3.76-3.66 (m, 1H), 3.62-3.44 (m, 3H), 2.47 (s, 3H), 2.25-2.12 (m, 3H), 2.11-1.94 (m, 2H), 1.93-1.70 (m, 5H), 1.67-1.58 (m, 2H), 1.52-1.33 (m, 2H), 1.33-1.23 (m, 1H). MS (ESI) m/z: [M+H]⁺ Found 597.3.

Example 59: N—((S)-(7-((R*)-(5,5-Difluoro-2-oxotetrahydropyrimidin-1(2H)-yl)(tetrahydro-2H-pyran-4-yl)methyl)imidazo[1,2-b]pyridazin-2-yl)(4,4-difluorocyclohexyl)methyl)-4-methyl-1,2,5-oxadiazole-3-carboxamide

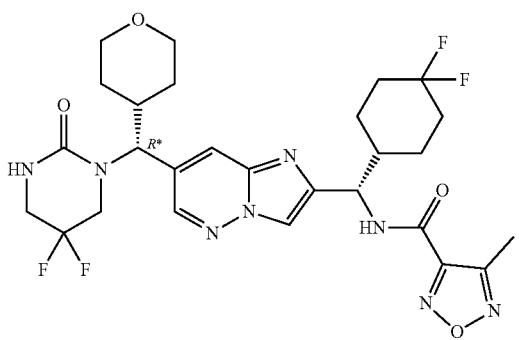 [SMILES: Cc1nonc1C(=O)N[C@H](c1cn2ncc([C@@H](C3CCOCC3)N3CC(F)(F)CNC3=O)cc2n1)C1CCC(F)(F)CC1]

To a solution of 1-((R*)-(2-((S)-amino(4,4-difluorocyclohexyl)methyl)imidazo[1,2-b]pyridazin-7-yl)(tetrahydro-2H-pyran-4-yl)methyl)-5,5-difluorotetrahydropyrimidin-2(1H)-one (45 mg, 0.09 mmol, Intermediate 63) and 2,5-dioxopyrrolidin-1-yl 4-methyl-1,2,5-oxadiazole-3-carboxylate (24 mg, 0.11 mmol) in MeCN (1 mL) was added DIPEA (0.037 mL, 0.22 mmol). The reaction was stirred at rt for 20 min then diluted with saturated aqueous NaHCO$_3$. The mixture was extracted three times with EtOAc. The combined organics were concentrated under reduced pressure and purification by silica gel chromatography (20-100% (10% MeOH in EtOAc)/(0.1% TEA in hexanes)) afforded the title compound in 61% yield. $^1$H NMR (500 MHz, DMSO-d$_6$) δ 9.40 (d, J=9.0 Hz, 1H), 8.41 (d, J=2.0 Hz, 1H), 8.25 (s, 1H), 8.08 (d, J=1.9 Hz, 1H), 6.87-6.81 (m, 1H), 5.21-5.13 (m, 2H), 3.97-3.89 (m, 1H), 3.81-3.73 (m, 1H), 3.73-3.63 (m, 1H), 3.47-3.38 (m, 2H), 3.38-3.32 (m, 2H), 3.30-3.27 (m, 1H), 2.62-2.53 (m, 1H), 2.47 (s, 3H), 2.25-2.13 (m, 1H), 2.10-1.95 (m, 2H), 1.95-1.88 (m, 1H), 1.86-1.67 (m, 3H), 1.66-1.56 (m, 1H), 1.44-1.33 (m, 1H), 1.33-1.21 (m, 3H), 1.20-1.09 (m, 1H). MS (ESI) m/z: [M+H]$^+$ Found 609.3.

Example 60: N-((1R*,2R*)-1-(7-((S)-1-(5,5-Difluoro-2-oxotetrahydropyrimidin-1(2H)-yl)-2-methoxyethyl)imidazo[1,2-b]pyridazin-2-yl)-2-((1,1,1-trifluoro-2-methylpropan-2-yl)oxy)propyl)-4-methyl-1,2,5-oxadiazole-3-carboxamide

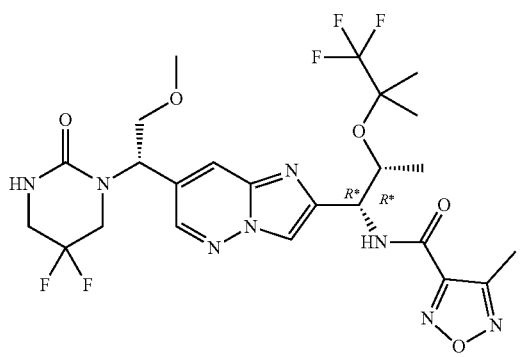 [SMILES: COC[C@H](c1cnn2cc([C@@H](NC(=O)c3nonc3C)[C@@H](C)OC(C)(C)C(F)(F)F)nc2c1)N1CC(F)(F)CNC1=O]

Example 61: N-((1R*,2S*)-1-(7-((S)-1-(5,5-Difluoro-2-oxotetrahydropyrimidin-1(2H)-yl)-2-methoxyethyl)imidazo[1,2-b]pyridazin-2-yl)-2-((1,1,1-trifluoro-2-methylpropan-2-yl)oxy)propyl)-4-methyl-1,2,5-oxadiazole-3-carboxamide

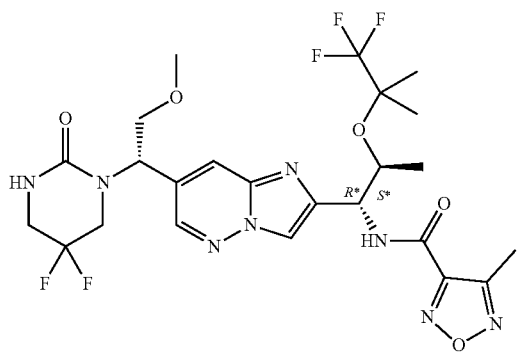 [SMILES: COC[C@H](c1cnn2cc([C@@H](NC(=O)c3nonc3C)[C@H](C)OC(C)(C)C(F)(F)F)nc2c1)N1CC(F)(F)CNC1=O]

The title compounds were synthesized in a manner analogous to Example 16 using 1-((1S)-1-(2-((1R*)-1-amino-2-((1,1,1-trifluoro-2-methylpropan-2-yl)oxy)propyl)imidazo[1,2-b]pyridazin-7-yl)-2-methoxyethyl)-5,5-difluorotetrahydropyrimidin-2(1H)-one (Intermediate 65) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. The reaction mixture was concentrated to dryness to afford two diastereomers (Example 60 and Example 61). Purification and separation of the two diastereomers was performed via chiral SFC (Stationary phase: Chiralpak IC 5 μm, 250×21 mm, Mobile phase: 20% MeOH, 80% CO$_2$) to afford Example 60 as the first eluting compound (10% yield) and Example 61 as the second eluting compound (17% yield). Example 60: $^1$H NMR (400 MHz, DMSO-d$_6$) δ 9.05-9.00 (m, 1H), 8.41-8.38 (m, 1H), 8.27-8.25 (m, 1H), 7.97-7.94 (m, 1H), 6.98-6.94 (m, 1H), 5.61-5.56 (m, 1H), 5.31-5.25 (m, 1H), 4.42-4.35 (m, 1H), 3.93-3.88 (m, 2H), 3.76-3.65 (m, 1H), 3.59-3.47 (m, 3H), 3.34-3.34 (m, 2H), 3.29-3.28 (m, 2H), 3.13-3.08 (m, 1H), 1.34-1.31 (m, 3H), 1.27-1.23 (m, 3H), 1.20-1.17 (m, 1H), 1.11-1.08 (m, 3H). MS (ESI) m/z: [M+H]$^+$ Found 604.9. Example 61: $^1$H NMR (400 MHz, DMSO-d$_6$) δ 9.32-9.29 (m, 1H), 8.37-8.36 (m, 1H), 8.22-8.21 (m, 1H), 7.95-7.94 (m, 1H), 6.96-6.93 (m, 1H), 5.59-5.55 (m, 1H), 5.44-5.40 (m, 1H), 4.49-4.45 (m, 1H), 3.92-3.88 (m, 2H), 3.74-3.64 (m, 1H), 3.59-3.46 (m, 4H), 3.34-3.33 (m, 3H), 3.28-3.27 (m, 1H), 1.36-1.35 (m, 3H), 1.24-1.23 (m, 3H), 1.12-1.10 (m, 3H), 0.94-0.93 (m, 1H). MS (ESI) m/z: [M+H]$^+$ Found 605.2.

Example 62: N—((R)-1-(7-((R)-Cyclopropyl(5,5-difluoro-2-oxotetrahydropyrimidin-1(2H)-yl)methyl)imidazo[1,2-b]pyridazin-2-yl)-2-((1,1,1-trifluoro-2-methylpropan-2-yl)oxy)ethyl)-4-methyl-1,2,5-oxadiazole-3-carboxamide

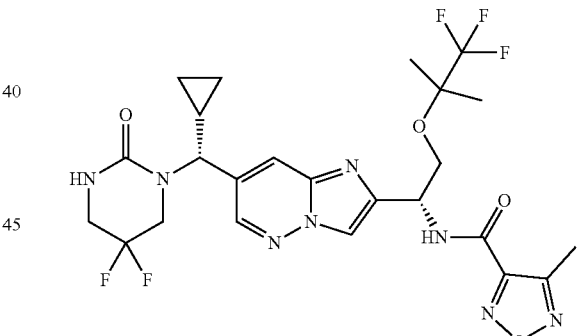

The title compound (19% yield) was synthesized in a manner analogous to Example 16 using 1-((R)-(2-((R)-1-amino-2-((1,1,1-trifluoro-2-methylpropan-2-yl)oxy)ethyl)imidazo[1,2-b]pyridazin-7-yl)(cyclopropyl)methyl)-5,5-difluorotetrahydropyrimidin-2(1H)-one (Intermediate 66) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. $^1$H NMR (600 MHz, DMSO-d$_6$) δ 9.41 (d, J=8.6 Hz, 1H), 8.39-8.36 (m, 1H), 8.21 (s, 1H), 8.06-8.02 (m, 1H), 6.90 (br s, 1H), 5.40 (dt, J=4.9, 8.4 Hz, 1H), 4.60 (d, J=10.3 Hz, 1H), 4.06-4.00 (m, 1H), 3.98-3.92 (m, 1H), 3.87-3.78 (m, 1H), 3.62-3.50 (m, 4H), 1.57-1.47 (m, 1H), 1.36 (s, 4H), 1.35 (s, 4H), 0.82-0.76 (m, 1H), 0.67-0.60 (m, 1H), 0.56-0.48 (m, 1H), 0.42-0.34 (m, 1H). MS (APCI/ESI) m/z: [M+H]$^+$ Found 587.2.

Example 63: 4-Cyclopropyl-N—((S)-(7-((R)-1-(5,5-difluoro-2-oxotetrahydropyrimidin-1(2H)-yl)ethyl)imidazo[1,2-b]pyridazin-2-yl)(4,4-difluorocyclohexyl)methyl)-1,2,5-oxadiazole-3-carboxamide

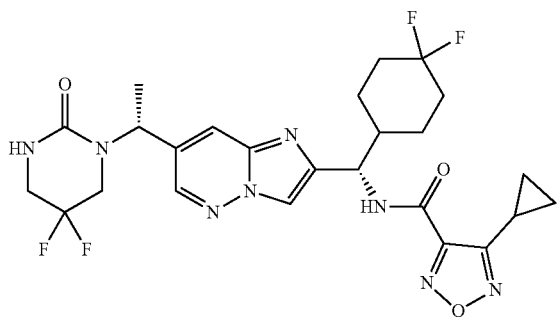 [SMILES: C[C@H](c1cnn2cc([C@@H](NC(=O)c3nonc3C3CC3)C3CCC(F)(F)CC3)nc2c1)N1CC(F)(F)CNC1=O]

The title compound (16% yield) was synthesized in a manner analogous to Example 16 using 1-((R)-1-(2-((S)-amino(4,4-difluorocyclohexyl)methyl)imidazo[1,2-b]pyridazin-7-yl)ethyl)-5,5-difluorotetrahydropyrimidin-2(1H)-one (Intermediate 67) in place of 1-((S)-1-(2-((S*)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride and 2,5-dioxopyrrolidin-1-yl 4-cyclopropyl-1,2,5-oxadiazole-3-carboxylate (Intermediate 31) in place of 2,5-dioxopyrrolidin-1-yl 4-methyl-1,2,5-oxadiazole-3-carboxylate). $^1$H NMR (600 MHz, DMSO-$d_6$) δ 9.46 (d, J=9.0 Hz, 1H), 8.35 (d, J=2.1 Hz, 1H), 8.22 (s, 1H), 7.91 (s, 1H), 6.91 (br s, 1H), 5.60 (q, J=6.9 Hz, 1H), 5.19 (t, J=8.6 Hz, 1H), 3.70-3.61 (m, 1H), 3.57-3.43 (m, 2H), 3.38-3.32 (m, 1H), 2.31-2.24 (m, 1H), 2.23-2.13 (m, 1H), 2.11-1.96 (m, 2H), 1.90 (d, J=12.2 Hz, 1H), 1.84-1.71 (m, 2H), 1.63 (d, J=13.2 Hz, 1H), 1.51 (d, J=7.1 Hz, 3H), 1.42-1.35 (m, 1H), 1.33-1.25 (m, 1H), 1.15-1.09 (m, 2H), 0.99-0.93 (m, 2H). MS (APCI/ESI) m/z: [M+H]$^+$ Found 565.2.

Example 64: 4-Cyclopropyl-N—((R)-1-(7-((S)-1-(5,5-difluoro-2-oxotetrahydropyrimidin-1(2H)-yl)-2-methoxyethyl)imidazo[1,2-b]pyridazin-2-yl)-2-((1,1,1-trifluoro-2-methylpropan-2-yl)oxy)ethyl)-1,2,5-oxadiazole-3-carboxamide

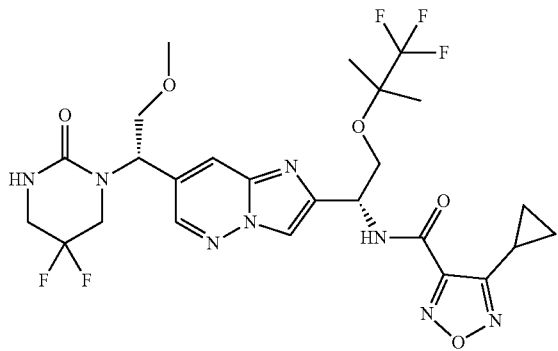 [SMILES: COC[C@H](c1cnn2cc([C@H](COC(C)(C)C(F)(F)F)NC(=O)c3nonc3C3CC3)nc2c1)N1CC(F)(F)CNC1=O]

The title compound (47% yield) was synthesized in a manner analogous to Example 16 using 1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one (Intermediate 68) in place of 1-((S)-1-(2-((S*)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride and 2,5-dioxopyrrolidin-1-yl 4-cyclopropyl-1,2,5-oxadiazole-3-carboxylate (Intermediate 31) in place of 2,5-dioxopyrrolidin-1-yl 4-methyl-1,2,5-oxadiazole-3-carboxylate). $^1$H NMR (600 MHz, DMSO-$d_6$) δ 9.48 (d, J=8.6 Hz, 1H), 8.38 (d, J=2.1 Hz, 1H), 8.22 (s, 1H), 7.96-7.93 (m, 1H), 6.95 (br s, 1H), 5.58 (t, J=6.8 Hz, 1H), 5.44-5.39 (m, 1H), 4.04-4.00 (m, 1H), 3.94 (t, J=9.1 Hz, 1H), 3.92-3.86 (m, 2H), 3.74-3.64 (m, 1H), 3.59-3.45 (m, 3H), 3.34 (s, 3H), 2.39-2.33 (m, 1H), 1.35 (s, 3H), 1.34 (s, 3H), 1.17-1.12 (m, 2H), 1.02-0.97 (m, 2H). MS (APCI/ESI) m/z: [M+H]$^+$ Found 617.2.

Example 65: N—((R)-1-(7-((S)-1-(5,5-Difluoro-2-oxotetrahydropyrimidin-1(2H)-yl)-2-methoxyethyl)imidazo[1,2-b]pyridazin-2-yl)-2-((1,1,1-trifluoro-2-methylpropan-2-yl)oxy)ethyl)-1-isopropyl-1H-pyrazole-5-carboxamide

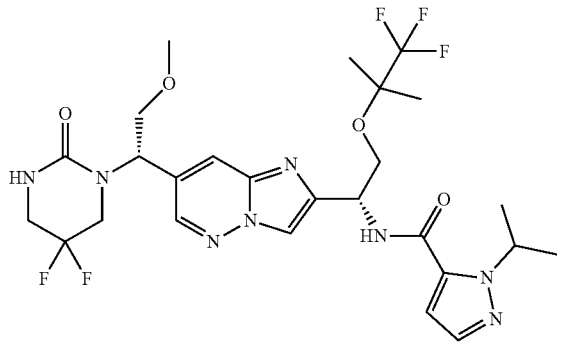 [SMILES: COC[C@H](c1cnn2cc([C@H](COC(C)(C)C(F)(F)F)NC(=O)c3ccnn3C(C)C)nc2c1)N1CC(F)(F)CNC1=O]

The title compound (56% yield) was synthesized in a manner analogous to Example 16 using 1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one (Intermediate 68) in place of 1-((S)-1-(2-((S*)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride and 2,5-dioxopyrrolidin-1-yl 1-isopropyl-1H-pyrazole-5-carboxylate (Intermediate 26) in place of 2,5-dioxopyrrolidin-1-yl 4-methyl-1,2,5-oxadiazole-3-carboxylate. $^1$H NMR (600 MHz, DMSO-$d_6$) δ 8.74 (d, J=8.6 Hz, 1H), 8.37 (d, J=2.1 Hz, 1H), 8.18 (s, 1H), 7.94-7.91 (m, 1H), 7.49 (d, J=1.9 Hz, 1H), 6.95 (br s, 1H), 6.85 (d, J=1.9 Hz, 1H), 5.58 (t, J=6.8 Hz, 1H), 5.44-5.35 (m, 2H), 4.03-3.99 (m, 1H), 3.93-3.86 (m, 3H), 3.73-3.64 (m, 1H), 3.59-3.45 (m, 3H), 3.34 (s, 3H), 1.38-1.36 (m, 6H), 1.35 (s, 3H), 1.34 (s, 3H). MS (APCI/ESI) m/z: [M+H]$^+$ Found 617.2.

Example 66: N—((S)-1-(7-((S)-1-(5,5-Difluoro-2-oxotetrahydropyrimidin-1(2H)-yl)-2-methoxyethyl)imidazo[1,2-b]pyridazin-2-yl)-4,4,4-trifluoro-3,3-dimethylbutyl)-4-methyl-1,2,5-oxadiazole-3-carboxamide

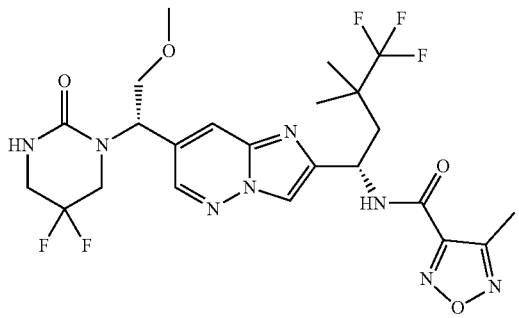 [SMILES: COC[C@H](c1cnn2cc([C@H](CC(C)(C)C(F)(F)F)NC(=O)c3nonc3C)nc2c1)N1CC(F)(F)CNC1=O]

The title compound (73% yield) was synthesized in a manner analogous to Example 16 using 1-((S)-1-(2-((S)-1-amino-4,4,4-trifluoro-3,3-dimethylbutyl)imidazo[1,2-b]pyridazin-7-yl)-2-methoxyethyl)-5,5-difluorotetrahydropyrimidin-2(1H)-one (Intermediate 44) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. $^1$H NMR (600 MHz, DMSO-$d_6$) δ 9.69 (d, J=8.8 Hz, 1H), 8.35 (d, J=2.1 Hz, 1H), 8.20 (s, 1H), 7.97-7.95 (m, 1H), 6.95 (br s, 1H), 5.58 (t, J=6.8 Hz, 1H), 5.47-5.42 (m, 1H), 3.93-3.85 (m, 2H), 3.72-3.63 (m, 1H), 3.60-3.45 (m, 3H), 3.34 (s, 3H), 2.50 (s, 3H), 2.43-2.39 (m, 1H), 2.30-2.24 (m, 1H), 1.20 (s, 3H), 1.19 (s, 3H). MS (APCI/ESI) m/z: [M+H]$^+$ Found 575.2.

Example 67: N—((R)-1-(7-((S)-1-(5,5-Difluoro-2-oxotetrahydropyrimidin-1(2H)-yl)-2-methoxyethyl)imidazo[1,2-b]pyridazin-2-yl)-5,5,5-trifluoro-4,4-dimethylpentyl)-4-methyl-1,2,5-oxadiazole-3-carboxamide

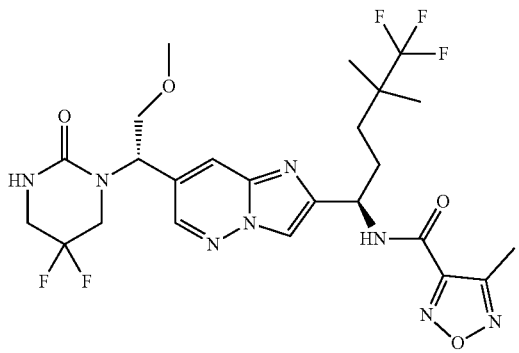 [SMILES: COC[C@H](c1cnn2cc([C@@H](CCC(C)(C)C(F)(F)F)NC(=O)c3nonc3C)nc2c1)N1CC(F)(F)CNC1=O]

The title compound (12% yield) was synthesized in a manner analogous to Example 16 using 1-((S)-1-(2-((R)-1-amino-5,5,5-trifluoro-4,4-dimethylpentyl)imidazo[1,2-b]pyridazin-7-yl)-2-methoxyethyl)-5,5-difluorotetrahydropyrimidin-2(1H)-one (Intermediate 71) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. $^1$H NMR (600 MHz, DMSO-$d_6$) δ 9.51 (d, J=8.4 Hz, 1H), 8.37 (d, J=2.3 Hz, 1H), 8.20 (s, 1H), 7.96-7.93 (m, 1H), 6.95 (br s, 1H), 5.58 (t, J=6.8 Hz, 1H), 5.21 (dt, J=5.3, 8.8 Hz, 1H), 3.94-3.86 (m, 2H), 3.74-3.64 (m, 1H), 3.60-3.47 (m, 3H), 3.34 (s, 3H), 2.50 (s, 3H), 2.16-2.06 (m, 1H), 2.03-1.95 (m, 1H), 1.66 (dt, J=4.4, 13.2 Hz, 1H), 1.54 (dt, J=4.4, 13.1 Hz, 1H), 1.10 (s, 6H). MS (APCI/ESI) m/z: [M+H]$^+$ Found 589.3.

Example 68: 4-Cyclopropyl-N—((S*)-1-(7-((S)-1-(5,5-difluoro-2-oxotetrahydropyrimidin-1(2H)-yl)-2-methoxyethyl)imidazo[1,2-b]pyridazin-2-yl)-4,4-difluoro-3,3-dimethylpentyl)-1,2,5-oxadiazole-3-carboxamide

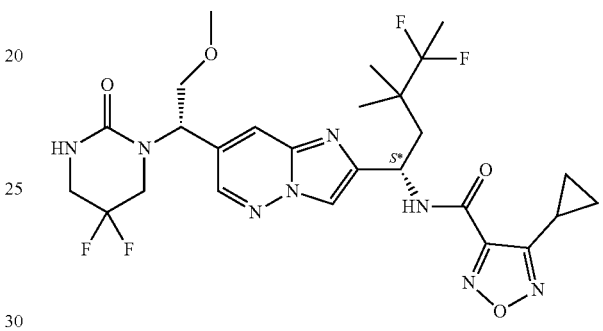

Step A: N—((S*)-1-(7-((S)-1-(5,5-Difluoro-2-oxotetrahydropyrimidin-1(2H)-yl)-2-methoxyethyl)imidazo[1,2-b]pyridazin-2-yl)-4,4-difluoro-3,3-dimethylpentyl)-2,4,6-trimethylbenzenesulfinamide. A mixture of (S)—N-((E)-(7-((S)-1-(5,5-difluoro-2-oxotetrahydropyrimidin-1(2H)-yl)-2-methoxyethyl)imidazo[1,2-b]pyridazin-2-yl)methylene)-2,4,6-trimethylbenzenesulfinamide (192 mg, 381 mmol, Intermediate 56), 1,3-dioxoisoindolin-2-yl 4,4-difluoro-3,3-dimethylpentanoate (474 mg, 1.52 mmol, Intermediate 72), zinc powder (149 mg, 2.3 mmol) and nickel (II) chloride ethylene glycol dimethyl ether complex (42 mg, 0.19 mmol) was sparged with $N_2$ and then DMF (1.1 mL) was added. The resulting mixture was heated at 40° C. for 8 h, then partitioned between brine (20 mL), saturated aqueous $NaHCO_3$ (15 mL) and EtOAc (20 mL). The aqueous layer was further extracted with EtOAc (4×20 mL). The organic layers were combined, dried over anhydrous $Na_2SO_4$, filtered through diatomaceous earth (e.g., Celite®), and the filtrate was concentrated to dryness. The residue was purified by silica gel chromatography (0-50% (25% EtOH in EtOAc)/EtOAc) to provide the title compound in 5% yield.

Step B: 1-((S)-1-(2-((S*)-1-Amino-4,4-difluoro-3,3-dimethylpentyl)imidazo[1,2-b]pyridazin-7-yl)-2-methoxyethyl)-5,5-difluorotetrahydropyrimidin-2(1H)-one. To a solution of N—((S*)-1-(7-((S)-1-(5,5-difluoro-2-oxotetrahydropyrimidin-1(2H)-yl)-2-methoxyethyl)imidazo[1,2-b]pyridazin-2-yl)-4,4-difluoro-3,3-dimethylpentyl)-2,4,6-trimethylbenzenesulfinamide (12.8 mg, 0.02 mmol, Step A) in 1,4-dioxane (3 mL) and MeOH (1 mL) was added HCl (0.1 mL, 0.41 mmol, 4 M in 1,4-dioxane) and the resulting mixture was heated at 55° C. for 75 min. The reaction was cooled to rt and concentrated to dryness. The residue was partitioned between water (4 mL) and hexanes (4 mL). The aqueous layer was then diluted with saturated aqueous $NaHCO_3$ (10 mL) and brine (10 mL) and extracted with DCM (4×4 mL). The DCM layers were combined, dried over anhydrous Na$_2$SO$_4$, filtered, and concentrated to dryness to provide the title compound (100% yield) that was used without further purification.

Step C: 4-Cyclopropyl-N—((S*)-1-(7-((S)-1-(5,5-difluoro-2-oxotetrahydropyrimidin-1(2H)-yl)-2-methoxyethyl)imidazo[1,2-b]pyridazin-2-yl)-4,4-difluoro-3,3-dimethylpentyl)-1,2,5-oxadiazole-3-carboxamide. The title compound (22% yield) was synthesized in a manner analogous to Example 16 using 1-((S)-1-(2-((S*)-1-amino-4,4-difluoro-3,3-dimethylpentyl)imidazo[1,2-b]pyridazin-7-yl)-2-methoxyethyl)-5,5-difluorotetrahydropyrimidin-2(1H)-one (Step B) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride and 2,5-dioxopyrrolidin-1-yl 4-cyclopropyl-1,2,5-oxadiazole-3-carboxylate (Intermediate 31) in place of 2,5-dioxopyrrolidin-1-yl 4-methyl-1,2,5-oxadiazole-3-carboxylate. $^1$H NMR (600 MHz, DMSO-d$_6$) δ 9.66 (d, J=8.6 Hz, 1H), 8.39-8.35 (m, 1H), 8.18 (s, 1H), 7.96 (d, J=1.0 Hz, 1H), 6.95 (s, 1H), 5.58 (t, J=6.8 Hz, 1H), 5.44 (dt, J=3.3, 8.9 Hz, 1H), 3.93-3.85 (m, 3H), 3.71-3.64 (m, 1H), 3.53-3.46 (m, 2H), 3.34 (s, 3H), 2.38-2.32 (m, 1H), 2.29-2.24 (m, 1H), 2.16 (dd, J=9.3, 14.6 Hz, 1H), 1.61 (t, J$_{(H-F)}$=19.6 Hz, 3H), 1.16-1.12 (m, 2H), 1.08 (s, 3H), 1.08 (s, 3H), 1.03-0.94 (m, 2H). MS (APCI/ESI) m/z: [M+H]$^+$ Found 597.3.

Example 69: N—((S)-(7-((S)-2-Cyclopropoxy-1-(5,5-difluoro-2-oxotetrahydropyrimidin-1(2H)-yl-4,4,6,6-d$_4$)ethyl)imidazo[1,2-b]pyridazin-2-yl)(4,4-difluorocyclohexyl)methyl)-4-methoxy-1,2,5-oxadiazole-3-carboxamide

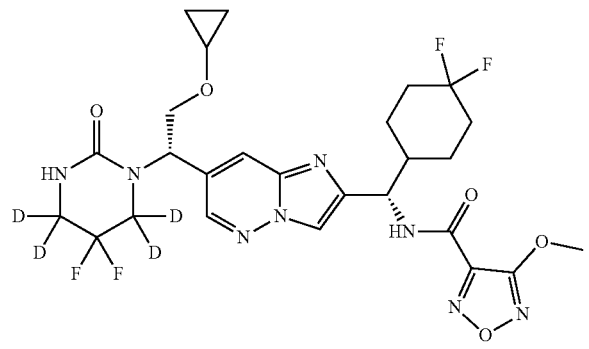 [SMILES: [2H]C1([2H])NC(=O)N([C@H](COC2CC2)c2cnn3cc([C@@H](NC(=O)c4nonc4OC)C4CCC(F)(F)CC4)nc3c2)C([2H])([2H])C1(F)F]

The title compound (57% yield) was synthesized in a manner analogous to Example 18 using 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one-4,4,6,6-d$_4$ (Intermediate 30) in place of (S)-1-((2-(amino(4,4-difluorocyclohexyl)methyl)imidazo[1,2-b]pyridazin-7-yl)methyl)tetrahydropyrimidin-2(1H)-one and 4-methoxy-1,2,5-oxadiazole-3-carboxylic acid in place of 4-cyclopropyl-1,2,5-oxadiazole-3-carboxylic acid. $^1$H NMR (500 MHz, DMSO-d$_6$) δ 9.28 (d, J=9.1 Hz, 1H), 8.39 (d, J=2.1 Hz, 1H), 8.21 (s, 1H), 7.95-7.91 (m, 1H), 6.92 (s, 1H), 5.55 (t, J=6.8 Hz, 1H), 5.16 (t, J=8.4 Hz, 1H), 4.08 (s, 3H), 4.05-3.93 (m, 2H), 3.44-3.38 (m, 1H), 2.20-2.10 (m, 1H), 2.08-1.91 (m, 2H), 1.90-1.68 (m, 3H), 1.60 (d, J=12.5 Hz, 1H), 1.43-1.21 (m, 2H), 0.58-0.43 (m, 4H). MS (APCI/ESI) m/z: [M+H]$^+$ Found 615.3.

Example 70: N—((S)-(7-((S)-2-Cyclopropoxy-1-(5,5-difluoro-2-oxotetrahydropyrimidin-1(2H)-yl-4,4,6,6-d$_4$)ethyl)imidazo[1,2-b]pyridazin-2-yl)(4,4-difluorocyclohexyl)methyl)-4-ethyl-1,2,5-oxadiazole-3-carboxamide

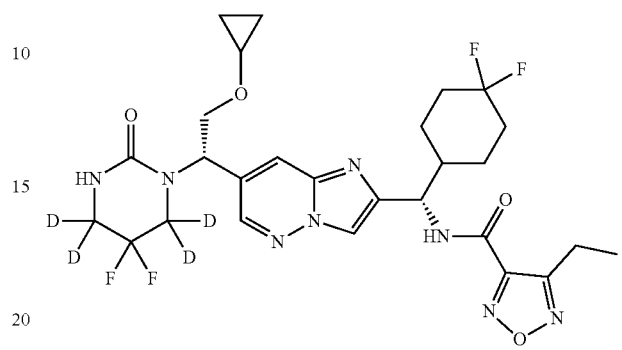

The title compound (46% yield) was synthesized in a manner analogous to Example 18 using 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one-4,4,6,6-d$_4$ (Intermediate 30) in place of (S)-1-((2-(amino(4,4-difluorocyclohexyl)methyl)imidazo[1,2-b]pyridazin-7-yl)methyl)tetrahydropyrimidin-2(1H)-one and 4-ethyl-1,2,5-oxadiazole-3-carboxylic acid in place of 4-cyclopropyl-1,2,5-oxadiazole-3-carboxylic acid. $^1$H NMR (500 MHz, DMSO-d$_6$) δ 9.44 (d, J=9.0 Hz, 1H), 8.38 (d, J=2.1 Hz, 1H), 8.24 (s, 1H), 7.95-7.92 (m, 1H), 6.92 (s, 1H), 5.55 (t, J=6.8 Hz, 1H), 5.18 (t, J=8.6 Hz, 1H), 4.04-3.93 (m, 2H), 3.44-3.38 (m, 1H), 2.93-2.86 (m, 2H), 2.23-2.13 (m, 1H), 2.08-1.93 (m, 2H), 1.89 (d, J=12.5 Hz, 1H), 1.85-1.69 (m, 2H), 1.62 (d, J=12.8 Hz, 1H), 1.43-1.25 (m, 2H), 1.22 (t, J=7.5 Hz, 3H), 0.57-0.42 (m, 4H). MS (APCI/ESI) m/z: [M+H]$^+$ Found 613.3.

Example 71: N—((S)-(7-((S)-2-Cyclopropoxy-1-(5,5-difluoro-2-oxotetrahydropyrimidin-1(2H)-yl-4,4,6,6-d$_4$)ethyl)imidazo[1,2-b]pyridazin-2-yl)(4,4-difluorocyclohexyl)methyl)-1-isopropyl-1H-pyrazole-5-carboxamide

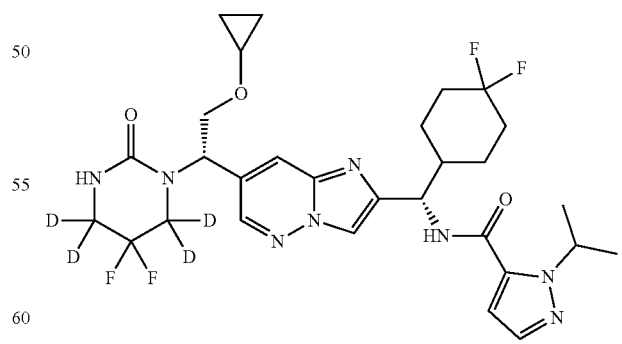

The title compound (51% yield) was synthesized in a manner analogous to Example 18 using 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one-4,4,6,6-d$_4$ (Intermediate 30) in place of (S)-1-((2-(amino(4,4-difluorocyclohexyl)methyl)imidazo[1,2-b]pyridazin-7-yl)methyl)tetrahydropyrimidin-2(1H)-one and 1-isopropyl-1H-pyrazole-5-carboxylic acid in place of 4-cyclopropyl-1,2,5-oxadiazole-3-carboxylic acid. $^1$H NMR (500 MHz, DMSO-d$_6$) δ 8.71 (d, J=9.1 Hz, 1H), 8.37 (d, J=2.1 Hz, 1H), 8.21 (s, 1H), 7.92-7.90 (m, 1H), 7.48 (d, J=1.9 Hz, 1H), 6.92 (br s, 1H), 6.91 (d, J=2.0 Hz, 1H), 5.55 (t, J=6.8 Hz, 1H), 5.41-5.32 (m, 1H), 5.16 (t, J=8.6 Hz, 1H), 4.04-3.93 (m, 2H), 3.43-3.38 (m, 1H), 2.22-2.13 (m, 1H), 2.08-1.93 (m, 2H), 1.88 (d, J=12.9 Hz, 1H), 1.84-1.68 (m, 2H), 1.62 (d, J=12.4 Hz, 1H), 1.39 (br s, 1H), 1.36 (d, J=6.6 Hz, 3H), 1.33 (d, J=6.6 Hz, 3H), 1.31-1.21 (m, 1H), 0.57-0.42 (m, 4H). MS (APCI/ESI) m/z: [M+H]$^+$ Found 625.3.

Example 72: 4-Cyclopropyl-N—((S)-(7-((S)-1-(5,5-difluoro-2-oxotetrahydropyrimidin-1(2H)-yl-4,4,6,6-d$_4$)-2-methoxyethyl)imidazo[1,2-b]pyridazin-2-yl)(4,4-difluorocyclohexyl)methyl)-1,2,5-oxadiazole-3-carboxamide

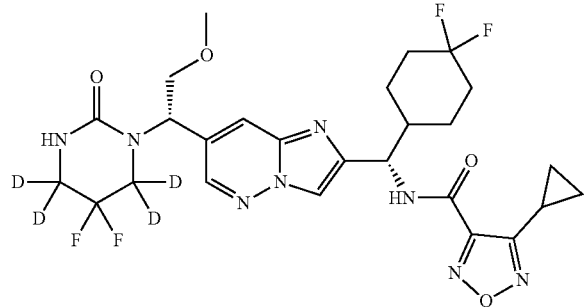 [SMILES: [2H]C1([2H])NC(=O)N([C@H](COC)c2cnn3cc([C@@H](NC(=O)c4nonc4C4CC4)C4CCC(F)(F)CC4)nc3c2)C([2H])([2H])C1(F)F]

Step A: tert-Butyl ((S)-(4,4-difluorocyclohexyl)(7-((S)-1-((3-(1,3-dioxoisoindolin-2-yl)-2,2-difluoropropyl-1,1,3,3-d$_4$)amino)-2-methoxyethyl)imidazo[1,2-b]pyridazin-2-yl)methyl)carbamate. The title compound was prepared as described in Intermediate 28 Step A using tert-butyl ((S)-(7-((S)-1-amino-2-methoxyethyl)imidazo[1,2-b]pyridazin-2-yl)(4,4-difluorocyclohexyl)methyl)carbamate (Intermediate 3, Step B) in place of tert-butyl ((R)-1-(7-((S)-1-amino-2-methoxyethyl)-6-chloroimidazo[1,2-b]pyridazin-2-yl)-2-((1,1,1-trifluoro-2-methylpropan-2-yl)oxy)ethyl)carbamate. The reaction was heated at 55° C. for 29 h instead of 60° C. for 48 h, then concentrated to dryness and purified by silica gel chromatography (10-60% acetone/hexanes (with 0.1% TEA)) to provide the title compound in 82% yield.

Step B: tert-Butyl ((S)-(7-((S)-1-((3-amino-2,2-difluoropropyl-1,1,3,3-d$_4$)amino)-2-methoxyethyl)imidazo[1,2-b]pyridazin-2-yl)(4,4-difluorocyclohexyl)methyl)carbamate. A flask was charged with tert-butyl ((S)-(4,4-difluorocyclohexyl)(7-((S)-1-((3-(1,3-dioxoisoindolin-2-yl)-2,2-difluoropropyl-1,1,3,3-d$_4$)amino)-2-methoxyethyl)imidazo[1,2-b]pyridazin-2-yl)methyl)carbamate (967 mg, 1.45 mmol, Step A), ethanol (5.8 mL), and hydrazine monohydrate (0.22 mL, 4.4 mmol), and the resulting mixture stirred at rt for 3.5 h. The reaction mixture was then heated at 35° C. for 2 h. After that time, the mixture was cooled to 0° C., filtered and washed with ice cold EtOH (2×5 mL). The filtrate was concentrated to dryness to provide the title compound in 90% yield.

Step C: tert-Butyl ((S)-(7-((S)-1-(5,5-difluoro-2-oxotetrahydropyrimidin-1(2H)-yl-4,4,6,6-d$_4$)-2-methoxyethyl)imidazo[1,2-b]pyridazin-2-yl)(4,4-difluorocyclohexyl)methyl)carbamate. The title compound was prepared as described in Intermediate 35 Step E using tert-butyl ((S)-(7-((S)-1-((3-amino-2,2-difluoropropyl-1,1,3,3-d$_4$)amino)-2-methoxyethyl)imidazo[1,2-b]pyridazin-2-yl)(4,4-difluorocyclohexyl)methyl)carbamate (Step B) in place of (S)—N$^1$-(1-(6-amino-3-chloropyridazin-4-yl)-2-methoxyethyl)-2,2-difluoropropane-1,3-diamine. The reaction was stirred at rt for 2 h and then heated at 55° C. for 2.5 h instead of rt for 12 h and 60° C. for 6 h. The residue was purified by silica gel chromatography (10-65% acetone/hexanes (with 0.1% TEA)) to provide the title compound in 61% yield.

Step D: 1-((S)-1-(2-((S)-Amino(4,4-difluorocyclohexyl)methyl)imidazo[1,2-b]pyridazin-7-yl)-2-methoxyethyl)-5,5-difluorotetrahydropyrimidin-2(1H)-one-4,4,6,6-d$_4$. The title compound (100% yield) was synthesized in a manner analogous to Intermediate 20 Step C using tert-butyl ((S)-(7-((S)-1-(5,5-difluoro-2-oxotetrahydropyrimidin-1(2H)-yl-4,4,6,6-d$_4$)-2-methoxyethyl)imidazo[1,2-b]pyridazin-2-yl)(4,4-difluorocyclohexyl)methyl)carbamate (Step C) in place of tert-butyl (S)-((7-((5,5-difluoro-2-oxotetrahydropyrimidin-1(2H)-yl)methyl)imidazo[1,2-b]pyridazin-2-yl)(4,4-difluorocyclohexyl)methyl)carbamate and was used without further purification.

Step E: 4-Cyclopropyl-N—((S)-(7-((S)-1-(5,5-difluoro-2-oxotetrahydropyrimidin-1(2H)-yl-4,4,6,6-d$_4$)-2-methoxyethyl)imidazo[1,2-b]pyridazin-2-yl)(4,4-difluorocyclohexyl)methyl)-1,2,5-oxadiazole-3-carboxamide. The title compound (89% yield) was synthesized in a manner analogous to Example 18 using 1-((S)-1-(2-((S)-amino(4,4-difluorocyclohexyl)methyl)imidazo[1,2-b]pyridazin-7-yl)-2-methoxyethyl)-5,5-difluorotetrahydropyrimidin-2(1H)-one-4,4,6,6-d$_4$ (Step D) in place of (S)-1-((2-(amino(4,4-difluorocyclohexyl)methyl)imidazo[1,2-b]pyridazin-7-yl)methyl)tetrahydropyrimidin-2(1H)-one. $^1$H NMR (500 MHz, DMSO-d$_6$) δ 9.47 (d, J=9.0 Hz, 1H), 8.38 (d, J=2.1 Hz, 1H), 8.24 (s, 1H), 7.94-7.90 (m, 1H), 6.93 (s, 1H), 5.57 (t, J=6.8 Hz, 1H), 5.19 (t, J=8.5 Hz, 1H), 3.95-3.85 (m, 2H), 3.34 (s, 3H), 2.32-2.25 (m, 1H), 2.23-2.13 (m, 1H), 2.10-1.94 (m, 2H), 1.90 (d, J=12.4 Hz, 1H), 1.86-1.68 (m, 2H), 1.62 (d, J=12.5 Hz, 1H), 1.44-1.34 (m, 1H), 1.34-1.24 (m, 1H), 1.14-1.09 (m, 2H), 0.98-0.94 (m, 2H). MS (APCI/ESI) m/z: [M+H]$^+$ Found 599.3.

Example 73: N—((S)-1-(7-((S)-1-(5,5-Difluoro-2-oxotetrahydropyrimidin-1(2H)-yl-4,4,6,6-d$_4$)-2-methoxyethyl)imidazo[1,2-b]pyridazin-2-yl)-5,5,5-trifluoro-4,4-dimethylpentyl)-4-methoxy-1,2,5-oxadiazole-3-carboxamide

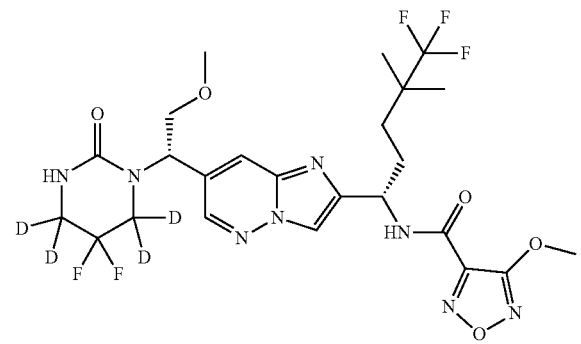 [SMILES: [2H]C1([2H])NC(=O)N([C@H](COC)c2cnn3cc([C@H](CCC(C)(C)C(F)(F)F)NC(=O)c4nonc4OC)nc3c2)C([2H])([2H])C1(F)F]

The title compound (65% yield) was synthesized in a manner analogous to Example 18 using 1-((S)-1-(2-((S)-1- amino-5,5,5-trifluoro-4,4-dimethylpentyl)imidazo[1,2-b]pyridazin-7-yl)-2-methoxyethyl)-5,5-difluorotetrahydropyrimidin-2(1H)-one-4,4,6,6-d₄ (Intermediate 73) in place of (S)-1-((2-(amino(4,4-difluorocyclohexyl)methyl)imidazo[1,2-b]pyridazin-7-yl)methyl)tetrahydropyrimidin-2(1H)-one and 4-methoxy-1,2,5-oxadiazole-3-carboxylic acid in place of 4-cyclopropyl-1,2,5-oxadiazole-3-carboxylic acid. ¹H NMR (500 MHz, DMSO-d₆) δ 9.36 (d, J=8.5 Hz, 1H), 8.37 (d, J=2.0 Hz, 1H), 8.16 (s, 1H), 7.94 (d, J=0.9 Hz, 1H), 6.93 (s, 1H), 5.57 (t, J=6.8 Hz, 1H), 5.21-5.15 (m, 1H), 4.09 (s, 3H), 3.93-3.86 (m, 2H), 3.34 (s, 3H), 2.13-2.04 (m, 1H), 1.99-1.89 (m, 1H), 1.67-1.59 (m, 1H), 1.55-1.47 (m, 1H), 1.08 (s, 6H). MS (APCI/ESI) m/z: [M+H]⁺ Found 609.3.

Example 74: N—((S)-1-(7-((S)-1-(5,5-Difluoro-2-oxotetrahydropyrimidin-1(2H)-yl-4,4,6,6-d₄)-2-methoxyethyl)imidazo[1,2-b]pyridazin-2-yl)-5,5,5-trifluoro-4,4-dimethylpentyl)-4-methyl-1,2,5-oxadiazole-3-carboxamide

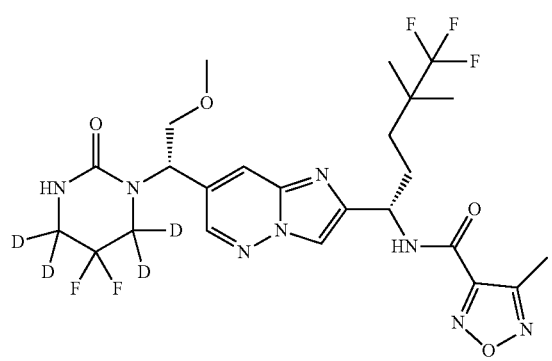 [SMILES: [2H]C1([2H])NC(=O)N([C@H](COC)c2cnn3cc([C@H](CCC(C)(C)C(F)(F)F)NC(=O)c4nonc4C)nc3c2)C([2H])([2H])C1(F)F]

The title compound (78% yield) was synthesized in a manner analogous to Example 18 using 1-((S)-1-(2-((S)-1-amino-5,5,5-trifluoro-4,4-dimethylpentyl)imidazo[1,2-b]pyridazin-7-yl)-2-methoxyethyl)-5,5-difluorotetrahydropyrimidin-2(1H)-one-4,4,6,6-d₄ (Intermediate 73) in place of (S)-1-((2-(amino(4,4-difluorocyclohexyl)methyl)imidazo[1,2-b]pyridazin-7-yl)methyl)tetrahydropyrimidin-2(1H)-one and 4-methyl-1,2,5-oxadiazole-3-carboxylic acid in place of 4-cyclopropyl-1,2,5-oxadiazole-3-carboxylic acid. ¹H NMR (500 MHz, DMSO-d₆) δ 9.50 (d, J=8.6 Hz, 1H), 8.36 (d, J=2.1 Hz, 1H), 8.19 (s, 1H), 7.94 (s, 1H), 6.93 (s, 1H), 5.57 (t, J=6.8 Hz, 1H), 5.24-5.17 (m, 1H), 3.93-3.85 (m, 2H), 3.34 (s, 3H), 2.49 (s, 3H), 2.16-2.06 (m, 1H), 2.04-1.92 (m, 1H), 1.69-1.61 (m, 1H), 1.57-1.49 (m, 1H), 1.09 (s, 6H). MS (APCI/ESI) m/z: [M+H]⁺ Found 593.3.

Example 75: N—((S)-1-(7-((S)-2-Cyclopropoxy-1-(5,5-difluoro-2-oxotetrahydropyrimidin-1(2H)-yl-4,4,6,6-d₄)ethyl)imidazo[1,2-b]pyridazin-2-yl)-5,5,5-trifluoro-4,4-dimethylpentyl)-4-methoxy-1,2,5-oxadiazole-3-carboxamide

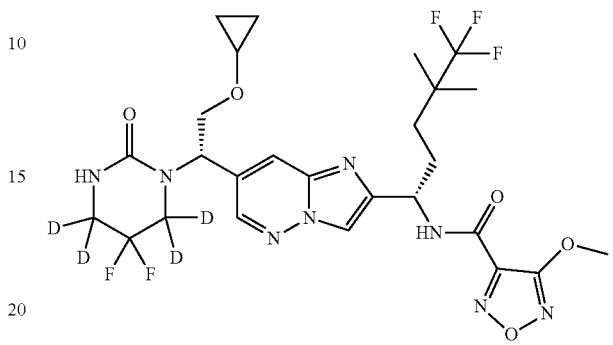

The title compound (69% yield) was synthesized in a manner analogous to Example 18 using 1-((S)-1-(2-((S)-1-amino-5,5,5-trifluoro-4,4-dimethylpentyl)imidazo[1,2-b]pyridazin-7-yl)-2-cyclopropoxyethyl)-5,5-difluorotetrahydropyrimidin-2(1H)-one-4,4,6,6-d₄ (Intermediate 74) in place of (S)-1-((2-(amino(4,4-difluorocyclohexyl)methyl)imidazo[1,2-b]pyridazin-7-yl)methyl)tetrahydropyrimidin-2(1H)-one and 4-methoxy-1,2,5-oxadiazole-3-carboxylic acid in place of 4-cyclopropyl-1,2,5-oxadiazole-3-carboxylic acid. ¹H NMR (500 MHz, DMSO-d₆) δ 9.37 (d, J=8.5 Hz, 1H), 8.38 (d, J=2.1 Hz, 1H), 8.16 (s, 1H), 7.97-7.93 (m, 1H), 6.92 (s, 1H), 5.56 (t, J=6.9 Hz, 1H), 5.22-5.14 (m, 1H), 4.09 (s, 3H), 4.04-3.95 (m, 2H), 3.44-3.38 (m, 1H), 2.13-2.03 (m, 1H), 1.99-1.89 (m, 1H), 1.68-1.58 (m, 1H), 1.56-1.47 (m, 1H), 1.08 (s, 6H), 0.57-0.42 (m, 4H). MS (APCI/ESI) m/z: [M+H]⁺ Found 635.3.

Example 76: N—((S)-1-(7-((S)-2-Cyclopropoxy-1-(5,5-difluoro-2-oxotetrahydropyrimidin-1(2H)-yl-4,4,6,6-d₄)ethyl)imidazo[1,2-b]pyridazin-2-yl)-5,5,5-trifluoro-4,4-dimethylpentyl)-4-methyl-1,2,5-oxadiazole-3-carboxamide

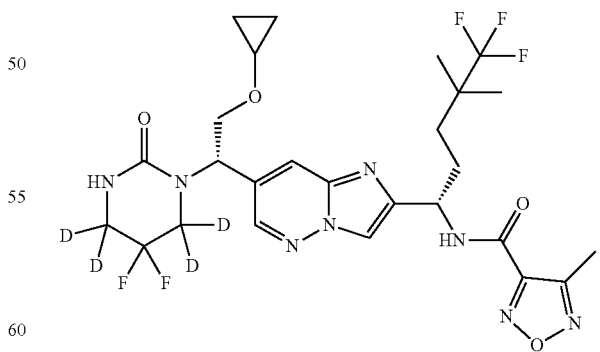

The title compound (69% yield) was synthesized in a manner analogous to Example 18 using 1-((S)-1-(2-((S)-1-amino-5,5,5-trifluoro-4,4-dimethylpentyl)imidazo[1,2-b]pyridazin-7-yl)-2-cyclopropoxyethyl)-5,5-difluorotetrahydropyrimidin-2(1H)-one-4,4,6,6-d₄ (Intermediate 74) in place of (S)-1-((2-(amino(4,4-difluorocyclohexyl)methyl) imidazo[1,2-b]pyridazin-7-yl)methyl)tetrahydropyrimidin-2(1H)-one and 4-methyl-1,2,5-oxadiazole-3-carboxylic acid in place of 4-cyclopropyl-1,2,5-oxadiazole-3-carboxylic acid. $^1$H NMR (500 MHz, DMSO-d$_6$) δ 9.51 (d, J=8.6 Hz, 1H), 8.36 (d, J=2.1 Hz, 1H), 8.19 (s, 1H), 7.97-7.93 (m, 1H), 6.92 (s, 1H), 5.56 (t, J=6.9 Hz, 1H), 5.24-5.17 (m, 1H), 4.04-3.94 (m, 2H), 3.44-3.39 (m, 1H), 2.49 (s, 3H), 2.16-2.07 (m, 1H), 2.03-1.94 (m, 1H), 1.69-1.61 (m, 1H), 1.57-1.49 (m, 1H), 1.09 (s, 6H), 0.58-0.42 (m, 4H). MS (APCI/ESI) m/z: [M+H]$^+$ Found 619.3.

Example 77: N—((S)-(7-((S)-2-Cyclopropoxy-1-(5,5-difluoro-2-oxotetrahydropyrimidin-1(2H)-yl)ethyl) imidazo[1,2-b]pyridazin-2-yl)(4,4-difluorocyclohexyl)methyl)-4-methoxy-1,2,5-oxadiazole-3-carboxamide The title compound (79% yield) was synthesized in a manner analogous to Example 18 using 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one (Intermediate 16A) in place of (S)-1-((2-(amino(4,4-difluorocyclohexyl)methyl)imidazo[1,2-b]pyridazin-7-yl)methyl)tetrahydropyrimidin-2(1H)-one and 4-methoxy-1,2,5-oxadiazole-3-carboxylic acid in place of 4-cyclopropyl-1,2,5-oxadiazole-3-carboxylic acid. $^1$H NMR (500 MHz, DMSO-d$_6$) δ 9.29 (d, J=9.0 Hz, 1H), 8.38 (d, J=2.1 Hz, 1H), 8.21 (s, 1H), 7.94-7.92 (m, 1H), 6.95 (br s, 1H), 5.56 (t, J=6.9 Hz, 1H), 5.16 (t, J=8.4 Hz, 1H), 4.08 (s, 3H), 4.04-3.94 (m, 2H), 3.73-3.63 (m, 1H), 3.60-3.45 (m, 3H), 3.44-3.38 (m, 1H), 2.20-2.10 (m, 1H), 2.09-1.93 (m, 2H), 1.90-1.69 (m, 3H), 1.60 (d, J=12.9 Hz, 1H), 1.42-1.23 (m, 2H), 0.57-0.42 (m, 4H). MS (APCI/ESI) m/z: [M+H]$^+$ Found 611.3.

Example 78: N—((S)-(7-((S)-2-Cyclopropoxy-1-(5,5-difluoro-2-oxotetrahydropyrimidin-1(2H)-yl)ethyl) imidazo[1,2-b]pyridazin-2-yl)(4,4-difluorocyclohexyl)methyl)-4-(difluoromethyl)-1,2,5-oxadiazole-3-carboxamide

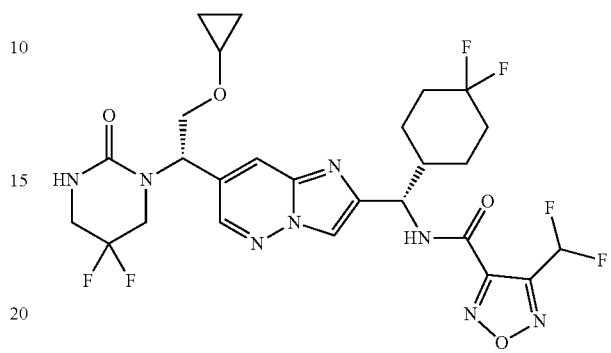

To a vial was added 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one (52 mg, 0.107 mmol, Intermediate 16A), ethyl 4-(difluoromethyl)-1,2,5-oxadiazole-3-carboxylate (62.0 mg, 0.322 mmol, Intermediate 75), and acetonitrile (0.14 mL). The vial was sparged with nitrogen gas for 1 min, sealed, and heated to 92° C. for 16 h. The reaction mixture was cooled to rt, diluted with DMSO, and purified by preparative HPLC (C18, 5 μm, 50×250 mm, 10-100% MeCN/water (20 mM NH$_4$OH)) to give the title compound as a white solid (35% yield). $^1$H NMR (500 MHz, DMSO-d$_6$) δ 9.70 (d, J=9.0 Hz, 1H), 8.38 (d, J=2.1 Hz, 1H), 8.24 (s, 1H), 7.95-7.91 (m, 1H), 7.48 (t, J=52.2 Hz, 1H), 6.94 (br s, 1H), 5.55 (t, J=6.9 Hz, 1H), 5.17 (t, J=8.6 Hz, 1H), 4.05-3.94 (m, 2H), 3.73-3.63 (m, 1H), 3.59-3.44 (m, 3H), 3.44-3.38 (m, 1H), 2.25-2.15 (m, 1H), 2.09-1.94 (m, 2H), 1.91 (d, J=13.0 Hz, 1H), 1.85-1.70 (m, 2H), 1.61 (d, J=13.4 Hz, 1H), 1.43-1.34 (m, 1H), 1.33-1.23 (m, 1H), 0.57-0.43 (m, 4H). MS (APCI/ESI) m/z: [M+H]$^+$ Found 631.2.

Example 79: N—((S)-(7-((S)-1-(5,5-Difluoro-2-oxotetrahydropyrimidin-1(2H)-yl)-2-methoxyethyl) imidazo[1,2-b]pyridazin-2-yl)(4,4-difluorocyclohexyl)methyl)-4-(difluoromethyl)-1,2,5-oxadiazole-3-carboxamide

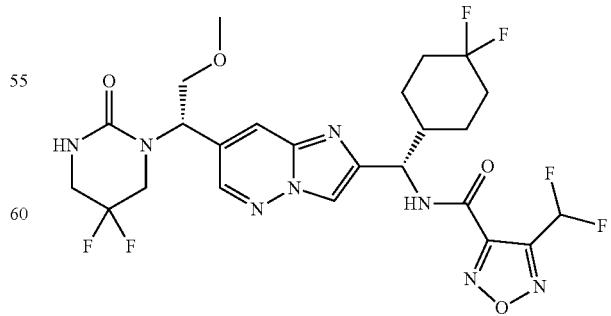

The title compound (23% yield) was prepared as described for the synthesis of Example 18 using 1-((S)-1-

(2-((S)-amino(4,4-difluorocyclohexyl)methyl)imidazo[1,2-b]pyridazin-7-yl)-2-methoxyethyl)-5,5-difluorotetrahydropyrimidin-2(1H)-one (Intermediate 3) in place of (S)-1-((2-(amino(4,4-difluorocyclohexyl)methyl)imidazo[1,2-b]pyridazin-7-yl)methyl)tetrahydropyrimidin-2(1H)-one and 4-(difluoromethyl)-1,2,5-oxadiazole-3-carboxylic acid (Intermediate 76) in place of 4-cyclopropyl-1,2,5-oxadiazole-3-carboxylic acid. ¹H NMR (500 MHz, DMSO-d₆) δ 9.70 (d, J=8.9 Hz, 1H), 8.38 (d, J=2.0 Hz, 1H), 8.24 (s, 1H), 7.94-7.90 (m, 1H), 7.48 (t, J=52.1 Hz, 1H), 6.95 (br s, 1H), 5.56 (t, J=6.8 Hz, 1H), 5.17 (t, J=8.6 Hz, 1H), 3.94-3.85 (m, 2H), 3.75-3.63 (m, 1H), 3.60-3.45 (m, 3H), 3.34 (s, 3H), 2.26-2.16 (m, 1H), 2.09-1.86 (m, 3H), 1.85-1.68 (m, 2H), 1.61 (d, J=13.4 Hz, 1H), 1.44-1.24 (m, 2H). MS (APCI/ESI) m/z: [M+H]⁺ Found 605.2.

Example 80: 4-Cyclopropyl-N—((S)-1-(7-((S)-1-(5,5-difluoro-2-oxotetrahydropyrimidin-1(2H)-yl-4,4,6,6-d₄)-2-methoxyethyl)imidazo[1,2-b]pyridazin-2-yl)-5,5,5-trifluoro-4,4-dimethylpentyl)-1,2,5-oxadiazole-3-carboxamide

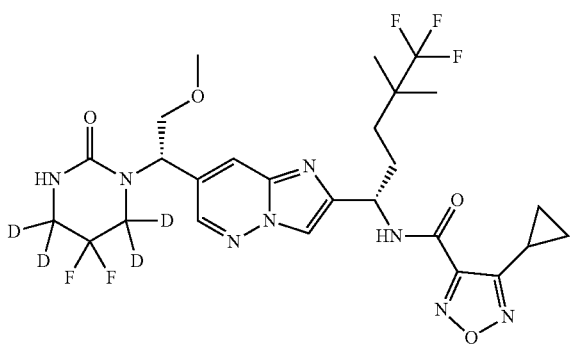 [SMILES: [2H]C1([2H])NC(=O)N([C@H](COC)c2cnn3cc([C@H](CCC(C)(C)C(F)(F)F)NC(=O)c4nonc4C4CC4)nc3c2)C([2H])([2H])C1(F)F]

The title compound (44% yield) was prepared as described for the synthesis of Example 18 using 1-((S)-1-(2-((S)-1-amino-5,5,5-trifluoro-4,4-dimethylpentyl)imidazo[1,2-b]pyridazin-7-yl)-2-methoxyethyl)-5,5-difluorotetrahydropyrimidin-2(1H)-one-4,4,6,6-d₄ (Intermediate 73) in place of 1-((S)-1-((2-(amino(4,4-difluorocyclohexyl)methyl)imidazo[1,2-b]pyridazin-7-yl)methyl)tetrahydropyrimidin-2(1H)-one. ¹H NMR (500 MHz, DMSO-d₆) δ 9.55 (d, J=8.5 Hz, 1H), 8.37 (d, J=2.1 Hz, 1H), 8.19 (s, 1H), 7.96-7.92 (m, 1H), 6.93 (s, 1H), 5.57 (t, J=6.8 Hz, 1H), 5.26-5.18 (m, 1H), 3.94-3.85 (m, 2H), 3.34 (s, 3H), 2.37-2.30 (m, 1H), 2.16-2.06 (m, 1H), 2.03-1.92 (m, 1H), 1.67-1.60 (m, 1H), 1.58-1.49 (m, 1H), 1.16-1.11 (m, 2H), 1.09 (s, 3H), 1.09 (s, 3H), 1.01-0.94 (m, 2H). MS (APCI/ESI) m/z: [M+H]⁺ Found 619.3.

Example 81: N—((S)-1-(7-((S)-1-(5,5-Difluoro-2-oxotetrahydropyrimidin-1(2H)-yl-4,4,6,6-d₄)-2-methoxyethyl)imidazo[1,2-b]pyridazin-2-yl)-5,5,5-trifluoro-4,4-dimethylpentyl)-4-(difluoromethyl)-1,2,5-oxadiazole-3-carboxamide

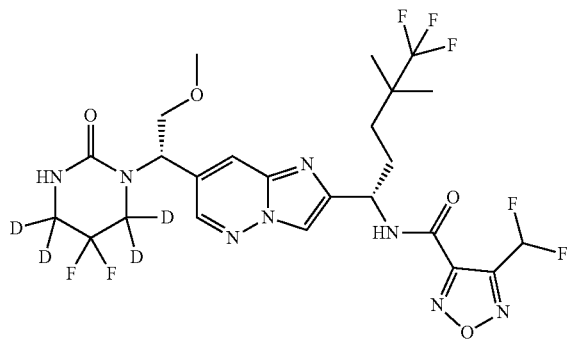 [SMILES: [2H]C1([2H])NC(=O)N([C@H](COC)c2cnn3cc([C@H](CCC(C)(C)C(F)(F)F)NC(=O)c4nonc4C(F)F)nc3c2)C([2H])([2H])C1(F)F]

The title compound (20% yield) was prepared as described for the synthesis of Example 78 using 1-((S)-1-(2-((S)-1-amino-5,5,5-trifluoro-4,4-dimethylpentyl)imidazo[1,2-b]pyridazin-7-yl)-2-methoxyethyl)-5,5-difluorotetrahydropyrimidin-2(1H)-one-4,4,6,6-d₄ (Intermediate 73) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one. ¹H NMR (500 MHz, DMSO-d₆) δ 9.79 (d, J=8.5 Hz, 1H), 8.37 (d, J=2.1 Hz, 1H), 8.19 (s, 1H), 7.94 (s, 1H), 7.50 (t, J=52.1 Hz, 1H), 6.93 (s, 1H), 5.57 (t, J=6.8 Hz, 1H), 5.24-5.15 (m, 1H), 3.94-3.85 (m, 2H), 3.34 (s, 3H), 2.18-2.08 (m, 1H), 2.05-1.94 (m, 1H), 1.70-1.62 (m, 1H), 1.58-1.49 (m, 1H), 1.09 (s, 3H), 1.09 (s, 3H). MS (APCI/ESI) m/z: [M+H]⁺ Found 629.3.

Example 82: N—((S)-(7-((S)-2-Cyclopropoxy-1-(5,5-difluoro-2-oxotetrahydropyrimidin-1(2H)-yl-4,4,6,6-d₄)ethyl)imidazo[1,2-b]pyridazin-2-yl)(4,4-difluorocyclohexyl)methyl)-4-(difluoromethyl)-1,2,5-oxadiazole-3-carboxamide

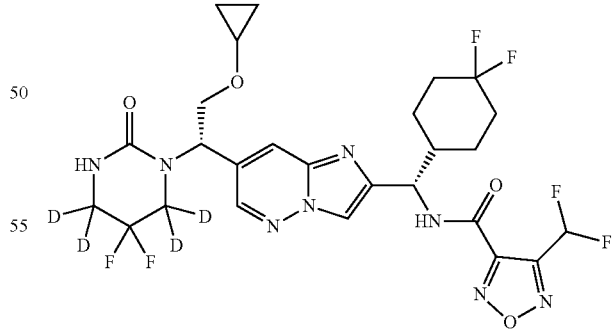

The title compound (23% yield) was prepared as described for the synthesis of Example 78 using 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one-4,4,6,6-d₄ (Intermediate 30) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one. ¹H NMR (500 MHz, DMSO-d₆) δ 9.64 (d, J=8.9 Hz, 1H), 8.31 (d, J=2.1 Hz, 1H), 8.17 (s, 1H), 7.86 (d, J=1.0 Hz, 1H), 7.42 (t, J=52.1 Hz, 1H), 6.85 (s, 1H), 5.48 (t, J=6.8 Hz, 1H), 5.10 (t, J=8.6 Hz, 1H), 3.97-3.87 (m, 2H), 3.37-3.31 (m, 1H), 2.19-2.09 (m, 1H), 2.03-1.80 (m, 3H), 1.79-1.62 (m, 2H), 1.54 (d, J=12.4 Hz, 1H), 1.37-1.15 (m, 2H), 0.50-0.34 (m, 4H). MS (APCI/ESI) m/z: [M+H]⁺ Found 635.3.

Example 83: N—((S)-1-(7-((S)-1-(5,5-Difluoro-2-oxotetrahydropyrimidin-1(2H)-yl-4,4,6,6-d₄)-2-methoxyethyl)imidazo[1,2-b]pyridazin-2-yl)-5,5,5-trifluoro-4,4-dimethylpentyl)-4-(trifluoromethyl)-1,2,5-oxadiazole-3-carboxamide

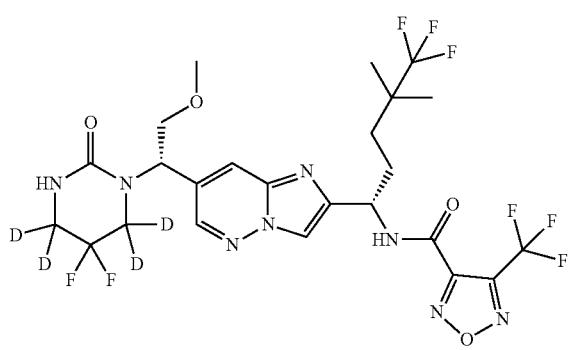 [SMILES: [2H]C1([2H])NC(=O)N([C@H](COC)c2cnn3cc([C@H](CCC(C)(C)C(F)(F)F)NC(=O)c4nonc4C(F)(F)F)nc3c2)C([2H])([2H])C1(F)F]

The title compound (23% yield) was prepared as described for the synthesis of Example 78 using 1-((S)-1-(2-((S)-1-amino-5,5,5-trifluoro-4,4-dimethylpentyl)imidazo[1,2-b]pyridazin-7-yl)-2-methoxyethyl)-5,5-difluorotetrahydropyrimidin-2(1H)-one-4,4,6,6-d₄ (Intermediate 73) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one and ethyl 4-(trifluoromethyl)-1,2,5-oxadiazole-3-carboxylate (Intermediate 77) in place of ethyl 4-(difluoromethyl)-1,2,5-oxadiazole-3-carboxylate. ¹H NMR (500 MHz, DMSO-d₆) δ 9.82 (d, J=8.5 Hz, 1H), 8.38 (d, J=2.1 Hz, 1H), 8.20 (s, 1H), 7.95-7.93 (m, 1H), 6.93 (s, 1H), 5.57 (t, J=6.8 Hz, 1H), 5.27-5.19 (m, 1H), 3.94-3.85 (m, 2H), 3.34 (s, 3H), 2.16-2.07 (m, 1H), 2.04-1.94 (m, 1H), 1.69-1.60 (m, 1H), 1.58-1.49 (m, 1H), 1.09 (s, 3H), 1.08 (s, 3H). MS (APCI/ESI) m/z: [M+H]⁺ Found 647.3.

Example 84: N—((S)-(7-((S)-1-(5,5-Difluoro-2-oxotetrahydropyrimidin-1(2H)-yl)-2-methoxyethyl)imidazo[1,2-b]pyridazin-2-yl)(4,4-difluorocyclohexyl)methyl)-4-(trifluoromethyl)-1,2,5-oxadiazole-3-carboxamide

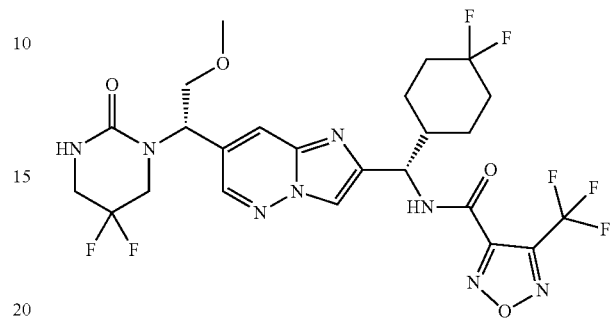

The title compound (22% yield) was prepared as described for the synthesis of Example 78 using 1-((S)-1-(2-((S)-amino(4,4-difluorocyclohexyl)methyl)imidazo[1,2-b]pyridazin-7-yl)-2-methoxyethyl)-5,5-difluorotetrahydropyrimidin-2(1H)-one (Intermediate 3) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one and ethyl 4-(trifluoromethyl)-1,2,5-oxadiazole-3-carboxylate (Intermediate 77) in place of ethyl 4-(difluoromethyl)-1,2,5-oxadiazole-3-carboxylate. ¹H NMR (500 MHz, DMSO-d₆) δ 9.75 (d, J=8.9 Hz, 1H), 8.39 (d, J=2.0 Hz, 1H), 8.24 (s, 1H), 7.92 (s, 1H), 6.95 (br s, 1H), 5.57 (t, J=6.8 Hz, 1H), 5.20 (t, J=8.5 Hz, 1H), 3.94-3.85 (m, 2H), 3.75-3.64 (m, 1H), 3.61-3.45 (m, 3H), 3.34 (s, 3H), 2.25-2.14 (m, 1H), 2.10-1.94 (m, 2H), 1.89 (d, J=12.1 Hz, 1H), 1.86-1.70 (m, 2H), 1.62 (d, J=12.4 Hz, 1H), 1.43-1.21 (m, 2H). MS (APCI/ESI) m/z: [M+H]⁺ Found 623.3.

Example 85: N—((S)-(7-((S)-(1-Cyanocyclobutyl)(5,5-difluoro-2-oxotetrahydropyrimidin-1(2H)-yl)methyl)imidazo[1,2-b]pyridazin-2-yl)(4,4-difluorocyclohexyl)methyl)-4-cyclopropyl-1,2,5-oxadiazole-3-carboxamide

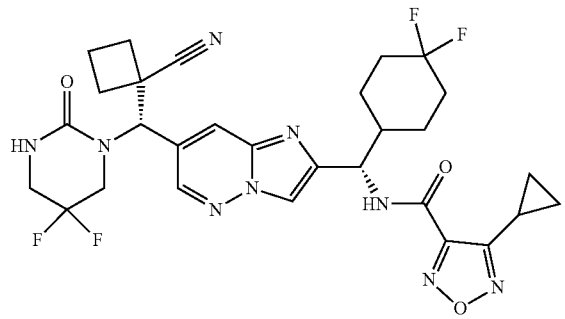 [SMILES: N#CC1([C@H](c2cnn3cc([C@@H](NC(=O)c4nonc4C4CC4)C4CCC(F)(F)CC4)nc3c2)N2CC(F)(F)CNC2=O)CCC1]

The title compound (21% yield) was prepared as described for Example 41 using 1-((S)-(2-((S)-amino(4,4-difluorocyclohexyl)methyl)imidazo[1,2-b]pyridazin-7-yl)(5,5-difluoro-2-oxotetrahydropyrimidin-1(2H)-yl)methyl)cyclobutane-1-carbonitrile hydrochloride (Intermediate 80)

in place of 1-((S)-1-(2-((S)-1-amino-4,4,4-trifluoro-3,3-dimethylbutyl)imidazo[1,2-b]pyridazin-7-yl)-2-methoxyethyl)-5,5-difluorotetrahydropyrimidin-2(1H)-one. $^1$H NMR (500 MHz, DMSO-d$_6$) δ 9.50 (d, J=9.0 Hz, 1H), 8.30 (s, 1H), 8.23 (d, J=2.3 Hz, 1H), 7.88-7.85 (m, 1H), 7.23 (s, 1H), 6.06-6.02 (m, 1H), 5.24-5.18 (m, 1H), 3.79-3.68 (m, 1H), 3.67-3.44 (m, 2H), 2.72-2.65 (m, 1H), 2.32-2.25 (m, 1H), 2.25-2.15 (m, 2H), 2.10-1.89 (m, 5H), 1.87-1.70 (m, 3H), 1.64 (d, J=13.6 Hz, 1H), 1.45-1.22 (m, 4H), 1.13-1.09 (m, 2H), 0.98-0.93 (m, 2H). MS (ESI) m/z: [M+H]$^+$ Found 630.3.

Example 86: (S)-4-Cyclopropyl-N-((4,4-difluorocyclohexyl)(7-((5,5,6,6-tetrafluoro-2-oxo-1,3-diazepan-1-yl)methyl)imidazo[1,2-b]pyridazin-2-yl)methyl)-1,2,5-oxadiazole-3-carboxamide

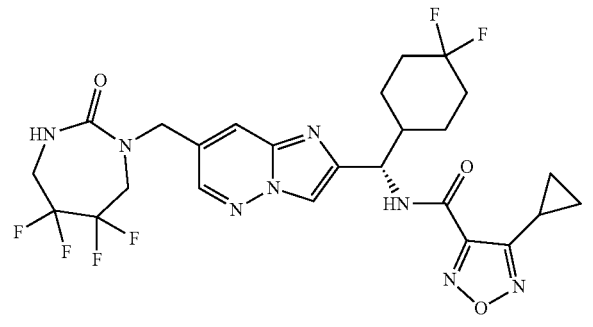 [SMILES: O=C(N[C@H](c1cn2ncc(CN3CC(F)(F)C(F)(F)CNC3=O)cc2n1)C1CCC(F)(F)CC1)c1nonc1C1CC1]

The title compound (30% yield) was prepared as described for Example 41 using (S)-1-((2-(amino(4,4-difluorocyclohexyl)methyl)imidazo[1,2-b]pyridazin-7-yl)methyl)-5,5,6,6-tetrafluoro-1,3-diazepan-2-one (Intermediate 81) in place of 1-((S)-1-(2-((S)-1-amino-4,4,4-trifluoro-3,3-dimethylbutyl)imidazo[1,2-b]pyridazin-7-yl)-2-methoxyethyl)-5,5-difluorotetrahydropyrimidin-2(1H)-one. $^1$H NMR (500 MHz, DMSO-d$_6$) δ 9.48 (d, J=9.0 Hz, 1H), 8.54 (d, J=2.0 Hz, 1H), 8.23 (s, 1H), 8.04-8.02 (m, 1H), 6.87 (t, J=4.7 Hz, 1H), 5.19 (t, J=8.5 Hz, 1H), 4.46 (s, 2H), 3.83-3.74 (m, 2H), 3.55-3.45 (m, 2H), 2.31-2.25 (m, 1H), 2.23-2.14 (m, 1H), 2.09-1.95 (m, 2H), 1.94-1.86 (m, 1H), 1.86-1.71 (m, 2H), 1.66-1.59 (m, 1H), 1.45-1.22 (m, 2H), 1.14-1.09 (m, 2H), 0.98-0.93 (m, 2H). MS (ESI) m/z: [M+H]$^+$ Found 601.2.

Example 87: 4-Cyclopropyl-N—((R)-1-(7-((R)-1-(5,5-difluoro-2-oxotetrahydropyrimidin-1(2H)-yl)ethyl)imidazo[1,2-b]pyridazin-2-yl)-2-((1,1,1-trifluoro-2-methylpropan-2-yl)oxy)ethyl)-1,2,5-oxadiazole-3-carboxamide

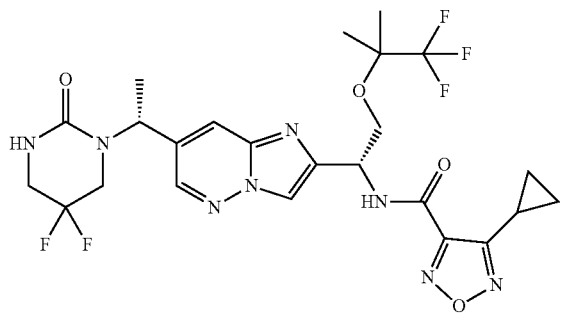 [SMILES: C[C@H](c1cnn2cc([C@H](COC(C)(C)C(F)(F)F)NC(=O)c3nonc3C3CC3)nc2c1)N1CC(F)(F)CNC1=O]

The title compound (30% yield) was prepared as described for Example 41 using 1-((R)-1-(2-((R)-1-amino-2-((1,1,1-trifluoro-2-methylpropan-2-yl)oxy)ethyl)imidazo[1,2-b]pyridazin-7-yl)ethyl)-5,5-difluorotetrahydropyrimidin-2(1H)-one (Intermediate 85) in place of 1-((S)-1-(2-((S)-1-amino-4,4,4-trifluoro-3,3-dimethylbutyl)imidazo[1,2-b]pyridazin-7-yl)-2-methoxyethyl)-5,5-difluorotetrahydropyrimidin-2(1H)-one. $^1$H NMR (500 MHz, DMSO-d$_6$) δ 9.48 (d, J=8.6 Hz, 1H), 8.35 (d, J=2.1 Hz, 1H), 8.21-8.19 (m, 1H), 7.93-7.95 (m, 1H), 6.93-6.90 (m, 1H), 5.65-5.57 (m, 1H), 5.45-5.38 (m, 1H), 4.05-4.00 (m, 1H), 3.97-3.91 (m, 1H), 3.70-3.60 (m, 1H), 3.58-3.42 (m, 2H), 3.36-3.26 (m, 1H, masked by H$_2$O peak), 2.39-2.32 (m, 1H), 1.51 (d, J=7.1 Hz, 3H), 1.35 (d, J=3.9 Hz, 6H), 1.17-1.12 (m, 2H), 1.02-0.98 (m, 2H). MS (ESI) m/z: [M+H]$^+$ Found 587.2.

Example 88: 4-Cyclopropyl-N—((S)-1-(7-((R)-1-(5,5-difluoro-2-oxotetrahydropyrimidin-1(2H)-yl)ethyl)imidazo[1,2-b]pyridazin-2-yl)-4,4,4-trifluoro-3,3-dimethylbutyl)-1,2,5-oxadiazole-3-carboxamide

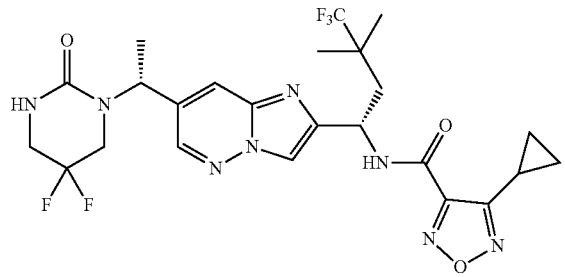 [SMILES: C[C@H](c1cnn2cc([C@H](CC(C)(C)C(F)(F)F)NC(=O)c3nonc3C3CC3)nc2c1)N1CC(F)(F)CNC1=O]

The title compound (37% yield) was prepared as described for Example 41 using 1-((R)-1-(2-((S)-1-amino-4,4,4-trifluoro-3,3-dimethylbutyl)imidazo[1,2-b]pyridazin-7-yl)ethyl)-5,5-difluorotetrahydropyrimidin-2(1H)-one (Intermediate 86) in place of 1-((S)-1-(2-((S)-1-amino-4,4,4-trifluoro-3,3-dimethylbutyl)imidazo[1,2-b]pyridazin-7-yl)-2-methoxyethyl)-5,5-difluorotetrahydropyrimidin-2(1H)-one. $^1$H NMR (500 MHz, DMSO-d$_6$) δ 9.73 (d, J=8.7 Hz, 1H), 8.33 (d, J=2.1 Hz, 1H), 8.18 (s, 1H), 7.97-7.95 (m, 1H), 6.94-6.88 (m, 1H), 5.64-5.58 (m, 1H), 5.49-5.43 (m, 1H), 3.70-3.58 (m, 1H), 3.57-3.42 (m, 2H), 3.36-3.26 (m, 1H, masked by H$_2$O peak), 2.43-2.33 (m, 2H), 2.30-2.23 (m, 1H), 1.50 (d, J=7.1 Hz, 3H), 1.20 (d, J=6.5 Hz, 6H), 1.16-1.12 (m, 2H), 1.04-0.93 (m, 2H). MS (ESI) m/z: [M+H]$^+$ Found 571.2.

Example 89: 4-Cyclopropyl-N—((S)-(7-((S)-1-(5,5-difluoro-2-oxotetrahydropyrimidin-1(2H)-yl)-2,2-difluoroethyl)imidazo[1,2-b]pyridazin-2-yl)(4,4-difluorocyclohexyl)methyl)-1,2,5-oxadiazole-3-carboxamide

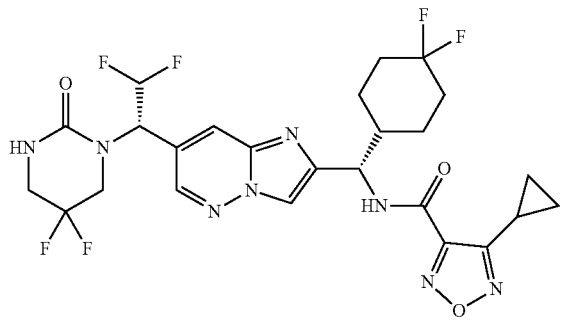 [SMILES: O=C(N[C@H](c1cn2ncc([C@@H](C(F)F)N3CC(F)(F)CNC3=O)cc2n1)C1CCC(F)(F)CC1)c1nonc1C1CC1]

The title compound (14% yield) was prepared as described for Example 41 using 1-((S)-1-(2-((S)-Amino(4,4-difluorocyclohexyl)methyl)imidazo[1,2-b]pyridazin-7-yl)-2,2-difluoroethyl)-5,5-difluorotetrahydropyrimidin-2(1H)-one (Intermediate 87) in place of 1-((S)-1-(2-((S)-1-amino-4,4,4-trifluoro-3,3-dimethylbutyl)imidazo[1,2-b]pyridazin-7-yl)-2-methoxyethyl)-5,5-difluorotetrahydropyrimidin-2(1H)-one. $^1$H NMR (500 MHz, DMSO-$d_6$) δ 9.51 (d, J=9.0 Hz, 1H), 8.45 (d, J=2.1 Hz, 1H), 8.32 (s, 1H), 8.14-8.11 (m, 1H), 7.17 (m, 1H), 7.03-6.77 (m, 1H), 5.63-5.54 (m, 1H), 5.21 (t, J=8.5 Hz, 1H), 3.89-3.79 (m, 1H), 3.71-3.46 (m, 3H), 2.31-2.25 (m, 1H), 2.24-2.14 (m, 1H), 2.07-1.95 (m, 2H), 1.95-1.87 (m, 1H), 1.87-1.70 (m, 2H), 1.66-1.58 (m, 1H), 1.45-1.35 (m, 1H), 1.35-1.25 (m, 1H), 1.14-1.09 (m, 2H), 0.98-0.94 (m, 2H). MS (ESI) m/z: [M+H]$^+$ Found 601.3.

Example 90: 4-Cyclopropyl-N-((1R*,2R*)-1-(7-((S)-1-(5,5-difluoro-2-oxotetrahydropyrimidin-1(2H)-yl)-2-methoxyethyl)imidazo[1,2-b]pyridazin-2-yl)-2-(1-(trifluoromethyl)cyclopropoxy)propyl)-1,2,5-oxadiazole-3-carboxamide

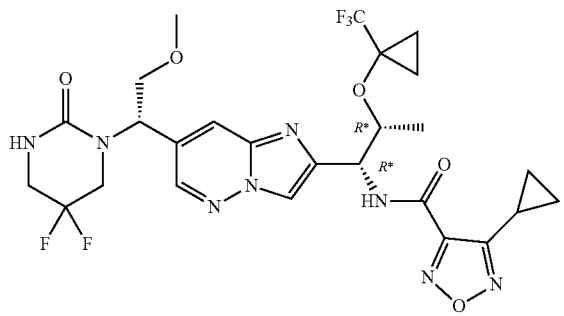 [SMILES: COC[C@H](c1cnn2cc([C@@H](NC(=O)c3nonc3C3CC3)[C@@H](C)OC3(C(F)(F)F)CC3)nc2c1)N1CC(F)(F)CNC1=O]

Example 91: 4-Cyclopropyl-N-((1R*,2S*)-1-(7-((S)-1-(5,5-difluoro-2-oxotetrahydropyrimidin-1(2H)-yl)-2-methoxyethyl)imidazo[1,2-b]pyridazin-2-yl)-2-(1-(trifluoromethyl)cyclopropoxy)propyl)-1,2,5-oxadiazole-3-carboxamide

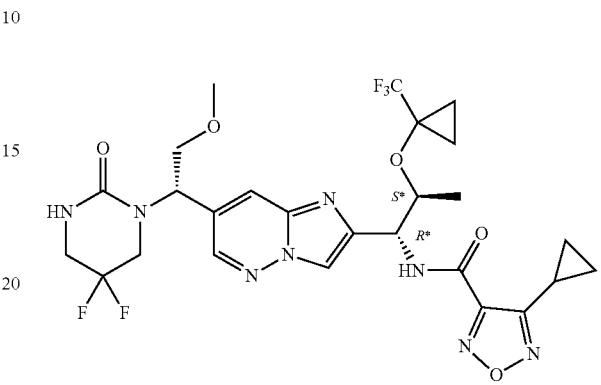

The title compounds were prepared as described for Example 39, using 1-((1S)-1-(2-((1R*)-1-amino-2-(1-(trifluoromethyl)cyclopropoxy)propyl)imidazo[1,2-b]pyridazin-7-yl)-2-methoxyethyl)-5,5-difluorotetrahydropyrimidin-2(1H)-one (Intermediate 89) in place of 1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one-4,4,6,6-$d_4$ to afford two diastereomers. The first eluting isomer was designated as the (1R*,2R*) isomer (Example 90) and the second eluting isomer was designated the (1R*,2S*) isomer (Example 91). 4-Cyclopropyl-N-((1R*,2R*)-1-(7-((S)-1-(5,5-difluoro-2-oxotetrahydropyrimidin-1(2H)-yl)-2-methoxyethyl)imidazo[1,2-b]pyridazin-2-yl)-2-(1-(trifluoromethyl)cyclopropoxy)propyl)-1,2,5-oxadiazole-3-carboxamide (Example 90, 10% yield) was isolated as a white solid after lyophilization. Example 90: $^1$H NMR (500 MHz, DMSO-$d_6$) δ 9.27 (d, J=9.1 Hz, 1H), 8.41 (d, J=2.1 Hz, 1H), 8.25 (s, 1H), 7.96-7.95 (m, 1H), 6.96 (s, 1H), 5.60-5.56 (m, 1H), 5.30-5.25 (m, 1H), 4.30-4.23 (m, 1H), 3.93-3.89 (m, 2H), 3.75-3.65 (m, 1H), 3.60-3.45 (m, 3H), 3.34 (s, 3H), 2.32-2.26 (m, 1H), 1.21 (d, J=6.3 Hz, 3H), 1.15-1.11 (m, 2H), 1.00-0.94 (m, 6H). MS (ESI) m/z: [M+H]$^+$ Found 629.3. 4-Cyclopropyl-N-((1R*,2S*)-1-(7-((S)-1-(5,5-difluoro-2-oxotetrahydropyrimidin-1(2H)-yl)-2-methoxyethyl)imidazo[1,2-b]pyridazin-2-yl)-2-(1-(trifluoromethyl)cyclopropoxy)propyl)-1,2,5-oxadiazole-3-carboxamide (Example 91, 13% yield) was isolated as a white solid after lyophilization. Example 91: $^1$H NMR (500 MHz, DMSO-$d_6$) δ 9.43 (d, J=9.3 Hz, 1H), 8.39 (d, J=2.1 Hz, 1H), 8.22 (d, J=0.7 Hz, 1H), 7.97-7.96 (m, 1H), 6.96 (s, 1H), 5.60-5.56 (m, 1H), 5.46-5.40 (m, 1H), 4.41-4.35 (m, 1H), 3.90 (dd, J=6.8, 3.1 Hz, 2H), 3.74-3.64 (m, 1H), 3.60-3.47 (m, 3H), 2.33-2.26 (m, 1H), 1.19 (d, J=6.4 Hz, 3H), 1.16-1.11 (m, 3H), 1.03-0.96 (m, 6H). MS (ESI) m/z: [M+H]$^+$ Found 629.2.

Example 92: 4-Cyclopropyl-N—((S)-(7-((S*)-1-(5,5-difluoro-2-oxotetrahydropyrimidin-1(2H)-yl)ethyl)imidazo[1,2-b]pyridazin-2-yl)(4,4-difluorocyclohexyl)methyl)-1,2,5-oxadiazole-3-carboxamide

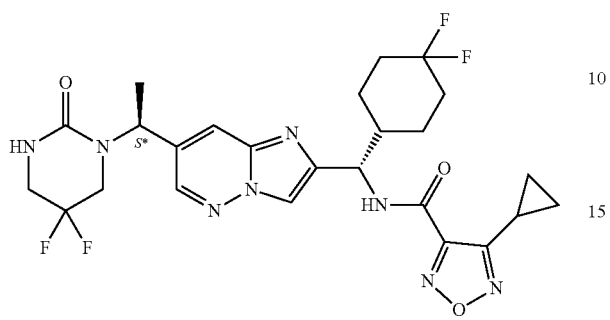

The title compound (58% yield) was prepared as described for Example 15 using 1-((S*)-1-(2-((S)-amino(4,4-difluorocyclohexyl)methyl)imidazo[1,2-b]pyridazin-7-yl)ethyl)-5,5-difluorotetrahydropyrimidin-2(1H)-one (Intermediate 90) in place of 1-((S*)-1-(2-((R)-1-amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one hydrochloride and 4-cyclopropyl-1,2,5-oxadiazole-3-carboxylic acid in place of 4-methyl-1,2,5-oxadiazole-3-carboxylic acid. $^1$H NMR (600 MHz, DMSO-d$_6$) δ 9.47 (d, J=8.9 Hz, 1H), 8.35 (d, J=2.1 Hz, 1H), 8.23 (s, 1H), 7.91 (dd, J=2.2, 1.1 Hz, 1H), 6.91 (d, J=3.0 Hz, 1H), 5.62-5.57 (m, 1H), 5.22-5.16 (m, 1H), 3.69-3.61 (m, 1H), 3.57-3.44 (m, 2H), 3.37-3.28 (m, 1H, masked by H$_2$O peak), 2.30-2.25 (m, 1H), 2.24-2.14 (m, 1H), 2.10-1.95 (m, 2H), 1.94-1.87 (m, 1H), 1.85-1.70 (m, 2H), 1.67-1.59 (m, 1H), 1.51 (d, J=7.2 Hz, 3H), 1.43-1.35 (m, 1H), 1.34-1.23 (m, 1H), 1.17-1.08 (m, 2H), 0.99-0.93 (m, 2H). MS (ESI) m/z: [M+H]$^+$ Found 565.3.

Example 93: N—((S)-(7-((S*)-1-(5,5-Difluoro-2-oxotetrahydropyrimidin-1(2H)-yl)ethyl)imidazo[1,2-b]pyridazin-2-yl)(4,4-difluorocyclohexyl)methyl)-4-methyl-1,2,5-oxadiazole-3-carboxamide

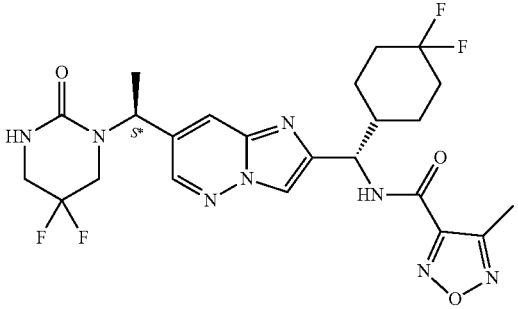 [SMILES: Cc1nonc1C(=O)N[C@H](c1cn2ncc([C@H](C)N3CC(F)(F)CNC3=O)cc2n1)C1CCC(F)(F)CC1]

The title compound (52% yield) was prepared as described for Example 15 using 1-((S*)-1-(2-((S)-amino(4,4-difluorocyclohexyl)methyl)imidazo[1,2-b]pyridazin-7-yl)ethyl)-5,5-difluorotetrahydropyrimidin-2(1H)-one (Intermediate 90) in place of 1-((S*)-1-(2-((R)-1-amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one hydrochloride. $^1$H NMR (600 MHz, DMSO-d$_6$) δ 9.41 (d, J=9.0 Hz, 1H), 8.35 (d, J=2.1 Hz, 1H), 8.23 (s, 1H), 7.92-7.90 (m, 1H), 6.93-6.90 (m, 1H), 5.63-5.57 (m, 1H), 5.19-5.15 (m, 1H), 3.67-3.62 (m, 1H), 3.38-3.28 (m, 1H, masked by H$_2$O peak), 3.58-3.44 (m, 2H), 2.46 (s, 3H), 2.22-2.14 (m, 1H), 2.07-1.95 (m, 2H), 1.94-1.88 (m, 1H), 1.84-1.70 (m, 2H), 1.65-1.58 (m, 1H), 1.51 (d, J=7.1 Hz, 3H), 1.43-1.35 (m, 1H), 1.32-1.23 (m, 1H). MS (ESI) m/z: [M+H]$^+$ Found 539.2.

Example 94: N—((S)-(4,4-Difluorocyclohexyl)(7-(((R*)-4-methyl-2-oxo-1,3-diazepan-1-yl)methyl)imidazo[1,2-b]pyridazin-2-yl)methyl)-1-isopropyl-1H-pyrazole-5-carboxamide

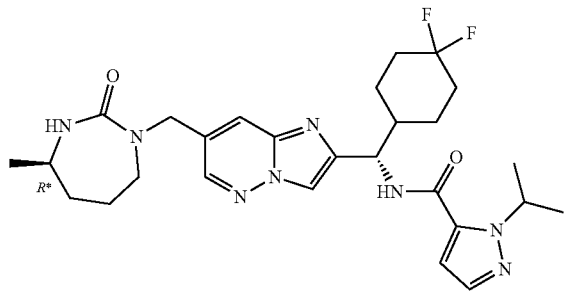 [SMILES: CC(C)n1nccc1C(=O)N[C@H](c1cn2ncc(CN3CCC[C@@H](C)NC3=O)cc2n1)C1CCC(F)(F)CC1]

Example 95: N—((S)-(4,4-Difluorocyclohexyl)(7-(((S*)-4-methyl-2-oxo-1,3-diazepan-1-yl)methyl)imidazo[1,2-b]pyridazin-2-yl)methyl)-1-isopropyl-1H-pyrazole-5-carboxamide

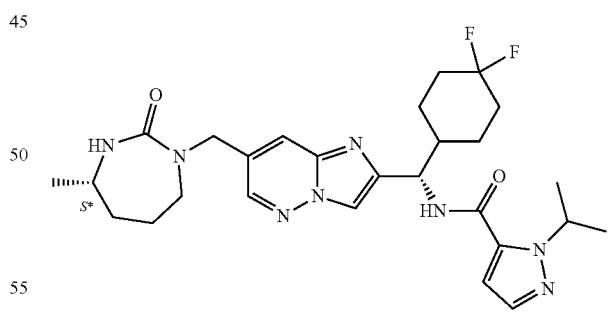

The title compounds were prepared as described for Example 15 using 1-((2-((S)-amino(4,4-difluorocyclohexyl)methyl)imidazo[1,2-b]pyridazin-7-yl)methyl)-4-methyl-1,3-diazepan-2-one (Intermediate 91) in place of 1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one-4,4,6,6-d$_4$ and 1-isopropyl-1H-pyrazole-5-carboxylic acid in place of 4-methyl-1,2,5-oxadiazole-3-carboxylic acid to afford two diastereomers, that were separated via SFC (Chiralpak IH Sum 250×21 mm, Mobile phase: 25% methanol:isopropanol (1:1) with 0.2% isopropylamine, 75% CO$_2$). During the separation of these diastereomers, a small amount of hexylene glycol was inadvertently introduced and may be seen in the $^1$H NMR spectra of the diastereomers. The first eluting isomer was designated as the (R*) isomer (Example 94) and the second eluting isomer was designated the (S*) isomer (Example 95). N—((S)-(4,4-Difluorocyclohexyl)(7-(((R*)-4-methyl-2-oxo-1,3-diazepan-1-yl)methyl)imidazo[1,2-b]pyridazin-2-yl)methyl)-1-isopropyl-1H-pyrazole-5-carboxamide (12% yield) was isolated as a white solid after lyophilization. Example 94: $^1$H NMR (600 MHz, DMSO-d$_6$) δ 8.71 (d, J=9.1 Hz, 1H), 8.48 (d, J=2.0 Hz, 1H), 7.91-7.89 (m, 1H), 7.48 (d, J=1.9 Hz, 1H), 6.91 (d, J=2.0 Hz, 1H), 5.81 (d, J=2.2 Hz, 1H), 5.40-5.34 (m, 1H), 5.18-5.12 (m, 1H), 4.62 (d, J=3.5 Hz, 1H), 4.56 (s, 1H), 4.46-4.35 (m, 2H), 3.95-3.89 (m, 1H), 3.30-3.23 (m, 3H), 3.06-3.00 (m, 1H), 2.21-2.13 (m, 1H), 2.08-1.93 (m, 2H), 1.91-1.84 (m, 1H), 1.84-1.59 (m, 6H), 1.51-1.38 (m, 3H), 1.36 (d, J=6.6 Hz, 4H), 1.33 (d, J=6.6 Hz, 3H), 1.31-1.22 (m, 2H), 1.14 (s, 2H), 1.12-1.10 (m, 6H), 1.05 (d, J=6.2 Hz, 2H). MS (ESI) m/z: [M+H]$^+$ Found 543.3.

N—((S)-(4,4-Difluorocyclohexyl)(7-(((S*)-4-methyl-2-oxo-1,3-diazepan-1-yl)methyl)imidazo[1,2-b]pyridazin-2-yl)methyl)-1-isopropyl-1H-pyrazole-5-carboxamide (14% yield) was isolated as a white solid after lyophilization. Example 95: $^1$H NMR (600 MHz, DMSO-d$_6$) δ 8.71 (d, J=9.1 Hz, 1H), 8.48 (d, J=2.0 Hz, 1H), 8.19 (s, 1H), 7.91-7.89 (m, 1H), 7.48 (d, J=1.9 Hz, 1H), 6.91 (d, J=2.0 Hz, 1H), 5.81 (d, J=2.3 Hz, 1H), 5.41-5.34 (m, 1H), 5.17-5.13 (m, 1H), 4.56 (s, 1H), 4.46-4.35 (m, 2H), 3.95-3.89 (m, 1H), 3.31-3.23 (m, 3H), 3.07-3.01 (m, 1H), 2.21-2.12 (m, 1H), 2.09-1.93 (m, 2H), 1.90-1.84 (m, 1H), 1.84-1.58 (m, 5H), 1.51-1.37 (m, 3H), 1.36 (d, J=6.6 Hz, 3H), 1.33 (d, J=6.6 Hz, 3H), 1.31-1.20 (m, 2H), 1.14 (s, 2H), 1.12-1.10 (m, 5H), 1.05 (d, J=6.2 Hz, 2H). MS (ESI) m/z: [M+H]$^+$ Found 543.3.

Example 96: 4-Cyclopropyl-N—((S)-(4,4-difluorocyclohexyl)(7-(((R*)-4-methyl-2-oxo-1,3-diazepan-1-yl)methyl)imidazo[1,2-b]pyridazin-2-yl)methyl)-1,2,5-oxadiazole-3-carboxamide Example 97: 4-Cyclopropyl-N—((S)-(4,4-difluorocyclohexyl)(7-(((S*)-4-methyl-2-oxo-1,3-diazepan-1-yl)methyl)imidazo[1,2-b]pyridazin-2-yl)methyl)-1,2,5-oxadiazole-3-carboxamide

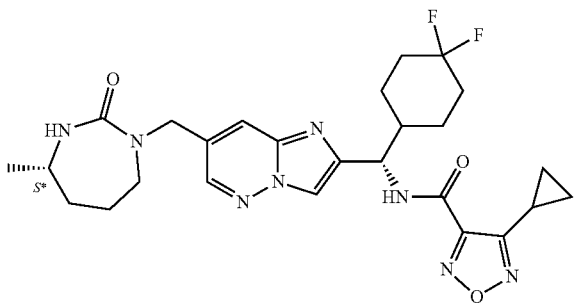 [SMILES: C[C@H]1CCCN(Cc2cnn3cc([C@@H](NC(=O)c4nonc4C4CC4)C4CCC(F)(F)CC4)nc3c2)C(=O)N1]

The title compounds were prepared as described for Example 15 using 1-((2-((S)-amino(4,4-difluorocyclohexyl)methyl)imidazo[1,2-b]pyridazin-7-yl)methyl)-4-methyl-1,3-diazepan-2-one (Intermediate 91) in place of 1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one-4,4,6,6-d$_4$ and 4-cyclopropyl-1,2,5-oxadiazole-3-carboxylic acid in place of 4-methyl-1,2,5-oxadiazole-3-carboxylic acid to afford two diastereomers that were separated via SFC (Chiralpak IH 5 um 250×21 mm, Mobile phase: 25% methanol:isopropanol (1:1) with 0.2% isopropylamine, 75% CO$_2$). During the separation of these diastereomers, a small amount of hexylene glycol was inadvertently introduced and may be seen in the $^1$H NMR spectra of the diastereomers. The first eluting isomer was designated as the (R*) isomer (Example 96) and the second eluting isomer was designated the (S*) isomer (Example 97). 4-Cyclopropyl-N—((S)-(4,4-difluorocyclohexyl)(7-(((R*)-4-methyl-2-oxo-1,3-diazepan-1-yl)methyl)imidazo[1,2-b]pyridazin-2-yl)methyl)-1,2,5-oxadiazole-3-carboxamide (10% yield) was isolated as a white solid after lyophilization. Example 96: $^1$H NMR (600 MHz, DMSO-d$_6$) δ 9.47 (d, J=9.0 Hz, 1H), 8.50 (d, J=2.0 Hz, 1H), 8.22 (s, 1H), 7.92-7.91 (m, 1H), 5.81 (d, J=2.2 Hz, 1H), 5.21-5.17 (m, 1H), 4.62 (d, J=3.6 Hz, 1H), 4.56 (s, 1H), 4.48-4.35 (m, 2H), 3.96-3.89 (m, 1H), 3.30-3.23 (m, 2H), 3.07-3.02 (m, 1H), 2.31-2.25 (m, 1H), 2.22-2.14 (m, 1H), 2.09-1.95 (m, 2H), 1.93-1.86 (m, 1H), 1.85-1.59 (m, 6H), 1.52-1.37 (m, 4H), 1.33-1.24 (m, 2H), 1.14 (s, 2H), 1.11 (d, J=6.0 Hz, 8H), 1.05 (d, J=6.1 Hz, 2H), 0.97-0.95 (m, 2H). MS (ESI) m/z: [M+H]$^+$ Found 543.3.

4-Cyclopropyl-N—((S)-(4,4-difluorocyclohexyl)(7-(((S*)-4-methyl-2-oxo-1,3-diazepan-1-yl)methyl)imidazo[1,2-b]pyridazin-2-yl)methyl)-1,2,5-oxadiazole-3-carboxamide (15% yield) was isolated as a white solid after lyophilization. Example 97: $^1$H NMR (600 MHz, DMSO-d$_6$) δ 9.47 (d, J=9.0 Hz, 1H), 8.50 (d, J=2.0 Hz, 1H), 8.22 (s, 1H), 7.92-7.91 (m, 1H), 5.81 (d, J=2.3 Hz, 1H), 5.21-5.17 (m, 1H), 4.62 (d, J=3.5 Hz, 1H), 4.56 (s, 1H), 4.47-4.36 (m, 2H), 3.95-3.89 (m, 1H), 3.30-3.24 (m, 3H), 3.08-3.02 (m, 1H), 2.30-2.24 (m, 1H), 2.22-2.14 (m, 1H), 2.09-1.93 (m, 2H), 1.93-1.87 (m, 1H), 1.86-1.59 (m, 5H), 1.53-1.35 (m, 4H), 1.33-1.24 (m, 2H), 1.14 (s, 2H), 1.13-1.10 (m, 7H), 1.05 (d, J=6.1 Hz, 2H), 0.97-0.94 (m, 2H). MS (ESI) m/z: [M+H]$^+$ Found 543.3.

Example 98 and Example 99: Diastereomeric Mixture of N—((S)-(7-(((1R,7S)-8,8-difluoro-4-oxo-3,5-diazabicyclo[5.1.0]octan-3-yl)methyl)imidazo[1,2-b]pyridazin-2-yl)(4,4-difluorocyclohexyl)methyl)-1-isopropyl-1H-pyrazole-5-carboxamide and N—((S)-(7-(((1S,7R)-8,8-difluoro-4-oxo-3,5-diazabicyclo[5.1.0]octan-3-yl)methyl)imidazo[1,2-b]pyridazin-2-yl)(4,4-difluorocyclohexyl)methyl)-1-isopropyl-1H-pyrazole-5-carboxamide

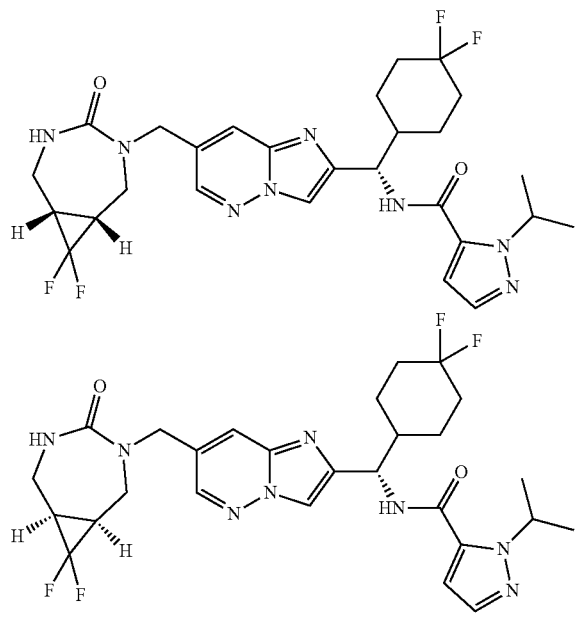

The title compounds were prepared as described for the synthesis of Example 15 using the diastereomeric mixture made in Intermediate 92 in place of 1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one-4,4,6,6-$d_4$ and 1-isopropyl-1H-pyrazole-5-carboxylic acid in place of 4-methyl-1,2,5-oxadiazole-3-carboxylic acid to afford two diastereomers. The diastereomeric mixture was separated via SFC (Chiralpak IB N3 5 μm, 250×21 mm, Mobile phase: 25% methanol:isopropanol (1:1) with 0.2% isopropylamine, 75% $CO_2$). During the separation of these diastereomers, a small amount of hexylene glycol was inadvertently introduced and may be seen in the $^1$H NMR spectra of the diastereomers. The first eluting isomer was designated as isomer 1 (Example 98) and the second eluting isomer was designated as isomer 2 (Example 99). The first eluting isomer (3% yield) was isolated as a white solid after lyophilization. Example 98: $^1$H NMR (600 MHz, DMSO-$d_6$) δ 8.70 (d, J=9.1 Hz, 1H), 8.42 (d, J=2.0 Hz, 1H), 8.18 (s, 1H), 7.91-7.89 (m, 1H), 7.48 (d, J=1.9 Hz, 1H), 6.90 (d, J=2.1 Hz, 1H), 6.58-6.54 (m, 1H), 5.40-5.33 (m, 1H), 5.17-5.13 (m, 1H), 4.65-4.60 (m, 2H), 4.41-4.38 (m, 1H), 3.96-3.88 (m, 2H), 3.64-3.56 (m, 1H), 3.44-3.38 (m, 1H), 3.15-3.07 (m, 1H), 2.37-2.28 (m, 2H), 2.21-2.13 (m, 1H), 2.09-1.94 (m, 2H), 1.90-1.84 (m, 1H), 1.84-1.70 (m, 2H), 1.66-1.59 (m, 1H), 1.47-1.38 (m, 2H), 1.36 (d, J=6.6 Hz, 3H), 1.33 (d, J=6.6 Hz, 3H), 1.14 (s, 3H), 1.11 (s, 3H), 1.05 (d, J=6.1 Hz, 3H). MS (ESI) m/z: [M+H]$^+$ Found 577.3.

The second eluting isomer (3% yield) was isolated as a white solid after lyophilization. Example 99: $^1$H NMR (600 MHz, DMSO-$d_6$) δ 8.70 (d, J=9.1 Hz, 1H), 8.42 (d, J=2.0 Hz, 1H), 8.18 (s, 1H), 7.91-7.89 (m, 1H), 7.48 (d, J=1.9 Hz, 1H), 6.91 (d, J=2.1 Hz, 1H), 6.58-6.55 (m, 1H), 5.40-5.33 (m, 1H), 5.17-5.13 (m, 1H), 4.64-4.60 (m, 2H), 4.42-4.38 (m, 1H), 3.95-3.88 (m, 2H), 3.64-3.56 (m, 1H), 3.44-3.38 (m, 1H), 3.15-3.07 (m, 1H), 2.36-2.28 (m, 2H), 2.21-2.13 (m, 1H), 2.09-1.94 (m, 2H), 1.90-1.84 (m, 1H), 1.84-1.70 (m, 2H), 1.66-1.59 (m, 1H), 1.47-1.38 (m, 2H), 1.36 (d, J=6.6 Hz, 3H), 1.33 (d, J=6.6 Hz, 3H), 1.14 (s, 3H), 1.11 (s, 3H), 1.05 (d, J=6.1 Hz, 3H). MS (ESI) m/z: [M+H]$^+$ Found 577.3.

Example 100 and Example 101: Diastereomeric Mixture of N—((S)-(7-(((1R,7S)-8,8-difluoro-4-oxo-3,5-diazabicyclo[5.1.0]octan-3-yl)methyl)imidazo[1,2-b]pyridazin-2-yl)(4,4-difluorocyclohexyl)methyl)-4-methyl-1,2,5-oxadiazole-3-carboxamide and N—((S)-(7-(((1S,7R)-8,8-difluoro-4-oxo-3,5-diazabicyclo[5.1.0]octan-3-yl)methyl)imidazo[1,2-b]pyridazin-2-yl)(4,4-difluorocyclohexyl)methyl)-4-methyl-1,2,5-oxadiazole-3-carboxamide

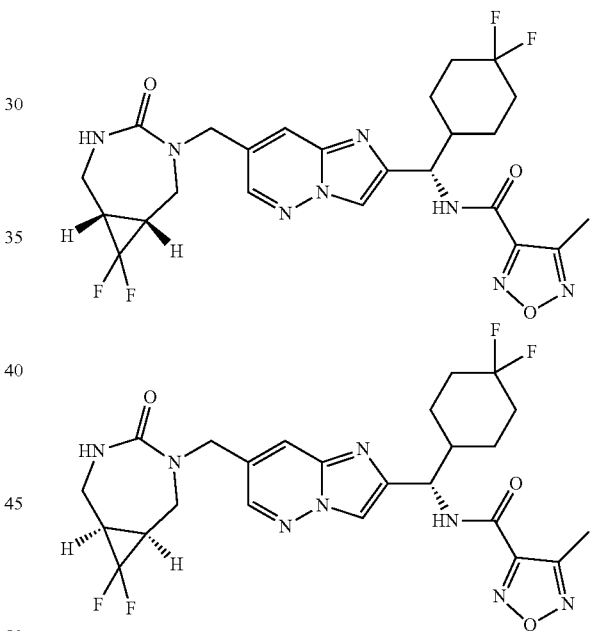

The title compounds were prepared as described for the synthesis of Example 15 using the diastereomeric mixture made in Intermediate 92 in place of 1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one-4,4,6,6-$d_4$ to afford two diastereomers. The diastereomeric mixture was separated via SFC (Chiralpak IB N3 5 μm, 250×21 mm, Mobile phase: 40% methanol:isopropanol (1:1) with 0.2% isopropylamine, 60% $CO_2$). During the separation of these diastereomers, a small amount of hexylene glycol was inadvertently introduced and may be seen in the $^1$H NMR spectra of the diastereomers. The first eluting isomer was designated as isomer 1 (Example 100) and the second eluting isomer was designated as isomer 2 (Example 101). The first eluting isomer (Example 100, 4% yield) was isolated as a white solid after lyophilization. Example 100: ¹H NMR (600 MHz, DMSO-d₆) δ 9.39 (d, J=9.0 Hz, 1H), 8.43 (d, J=2.0 Hz, 1H), 8.22 (s, 1H), 7.92-7.90 (m, 1H), 6.59-6.54 (m, 1H), 5.20-5.14 (m, 1H), 4.66-4.61 (m, 2H), 4.39 (d, J=15.7 Hz, 1H), 3.96-3.89 (m, 2H), 3.64-3.58 (m, 1H), 3.43-3.38 (m, 1H), 3.15-3.07 (m, 1H), 2.37-2.29 (m, 2H), 2.22-2.14 (m, 1H), 2.08-1.95 (m, 2H), 1.93-1.86 (m, 1H), 1.84-1.70 (m, 2H), 1.65-1.58 (m, 1H), 1.48-1.33 (m, 3H), 1.32-1.22 (m, 1H), 1.14 (s, 2H), 1.11 (s, 2H), 1.05 (d, J=6.1 Hz, 3H). MS (ESI) m/z: [M+H]⁺ Found 551.2.

The second eluting isomer (Example 101, 5% yield) was isolated as a white solid after lyophilization. Example 101: ¹H NMR (600 MHz, DMSO-d₆) δ 9.39 (d, J=9.0 Hz, 1H), 8.43 (d, J=2.1 Hz, 1H), 8.22 (s, 1H), 7.92-7.90 (m, 1H), 6.58-6.55 (m, 1H), 5.20-5.14 (m, 1H), 4.65-4.60 (m, 2H), 4.42-4.38 (m, 1H), 3.96-3.88 (m, 2H), 3.64-3.57 (m, 1H), 3.44-3.38 (m, 1H), 3.15-3.08 (m, 1H), 2.47 (s, 3H), 2.36-2.29 (m, 2H), 2.22-2.13 (m, 1H), 2.08-1.94 (m, 2H), 1.93-1.87 (m, 1H), 1.84-1.77 (m, 2H), 1.65-1.58 (m, 1H), 1.48-1.34 (m, 3H), 1.32-1.22 (m, 1H), 1.14 (s, 2H), 1.11 (s, 2H), 1.05 (d, J=6.1 Hz, 3H). MS (ESI) m/z: [M+H]⁺ Found 551.2.

Example 102: N—((S)-2,2-Dicyclopropyl-1-(7-((S)-1-(5,5-difluoro-2-oxotetrahydropyrimidin-1(2H)-yl)-2-methoxyethyl)imidazo[1,2-b]pyridazin-2-yl)ethyl)-4-methyl-1,2,5-oxadiazole-3-carboxamide

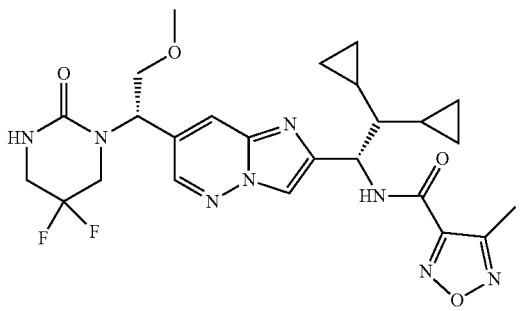 [SMILES: COC[C@H](c1cnn2cc([C@@H](NC(=O)c3nonc3C)C(C3CC3)C3CC3)nc2c1)N1CC(F)(F)CNC1=O]

The title compound (76% yield) was synthesized in a manner analogous to Example 16 using 1-((S)-1-(2-((S)-1-amino-2,2-dicyclopropylethyl)imidazo[1,2-b]pyridazin-7-yl)-2-methoxyethyl)-5,5-difluorotetrahydropyrimidin-2(1H)-one (Intermediate 93) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. ¹H NMR (500 MHz, Methanol-d₄) δ 8.41 (d, J=2.1 Hz, 1H), 8.17 (s, 1H), 8.01-7.86 (m, 1H), 5.78-5.68 (m, 1H), 5.65 (d, J=6.0 Hz, 1H), 4.10-3.97 (m, 2H), 3.89-3.74 (m, 1H), 3.74-3.52 (m, 3H), 3.39 (s, 3H), 2.57 (s, 3H), 1.09-0.95 (m, 1H), 0.87-0.74 (m, 2H), 0.59-0.46 (m, 2H), 0.46-0.35 (m, 2H), 0.35-0.25 (m, 2H), 0.24-0.17 (m, 1H), 0.15-0.05 (m, 1H). MS (APCI/ESI) m/z: [M+H]⁺ Found 545.4.

Example 103: 4-Cyclopropyl-N—((S)-2,2-dicyclopropyl-1-(7-((S)-1-(5,5-difluoro-2-oxotetrahydropyrimidin-1(2H)-yl)-2-methoxyethyl)imidazo[1,2-b]pyridazin-2-yl)ethyl)-1,2,5-oxadiazole-3-carboxamide

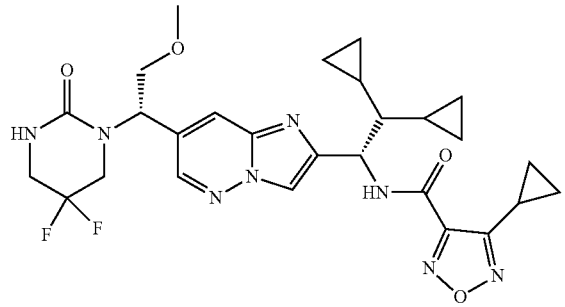 [SMILES: COC[C@H](c1cnn2cc([C@@H](NC(=O)c3nonc3C3CC3)C(C3CC3)C3CC3)nc2c1)N1CC(F)(F)CNC1=O]

The title compound (67% yield) was synthesized in a manner analogous to Example 16 using 1-((S)-1-(2-((S)-1-amino-2,2-dicyclopropylethyl)imidazo[1,2-b]pyridazin-7-yl)-2-methoxyethyl)-5,5-difluorotetrahydropyrimidin-2(1H)-one (Intermediate 93) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride and 2,5-dioxopyrrolidin-1-yl 4-cyclopropyl-1,2,5-oxadiazole-3-carboxylate (Intermediate 31) in place of 2,5-dioxopyrrolidin-1-yl 4-methyl-1,2,5-oxadiazole-3-carboxylate. ¹H NMR (500 MHz, Methanol-d₄) δ 8.42 (d, J=2.1 Hz, 1H), 8.17 (d, J=0.6 Hz, 1H), 7.98-7.88 (m, 1H), 5.77-5.69 (m, 1H), 5.67 (d, J=6.0 Hz, 1H), 4.10-3.97 (m, 2H), 3.92-3.75 (m, 1H), 3.75-3.52 (m, 3H), 3.49 (s, 3H), 3.38 (s, 1H), 2.45 (tt, J=8.4, 5.0 Hz, 1H), 1.24-1.12 (m, 2H), 1.12-1.06 (m, 2H), 1.06-0.95 (m, 1H), 0.89-0.74 (m, 2H), 0.60-0.47 (m, 2H), 0.46-0.35 (m, 2H), 0.33-0.26 (m, 2H), 0.26-0.16 (m, 1H), 0.15-0.06 (m, 1H). MS (APCI/ESI) m/z: [M+H]⁺ Found 571.4.

Example 104 and Example 105: Diastereomeric Mixture of N—((S)-(7-((S)-1-((1R,7S)-8,8-difluoro-4-oxo-3,5-diazabicyclo[5.1.0]octan-3-yl)-2-methoxyethyl)imidazo[1,2-b]pyridazin-2-yl)(4,4-difluorocyclohexyl)methyl)-4-methyl-1,2,5-oxadiazole-3-carboxamide and N—((S)-(7-((S)-1-((1S,7R)-8,8-difluoro-4-oxo-3,5-diazabicyclo[5.1.0]octan-3-yl)-2-methoxyethyl)imidazo[1,2-b]pyridazin-2-yl)(4,4-difluorocyclohexyl)methyl)-4-methyl-1,2,5-oxadiazole-3-carboxamide

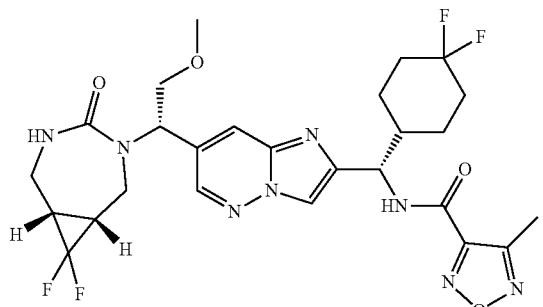

-continued

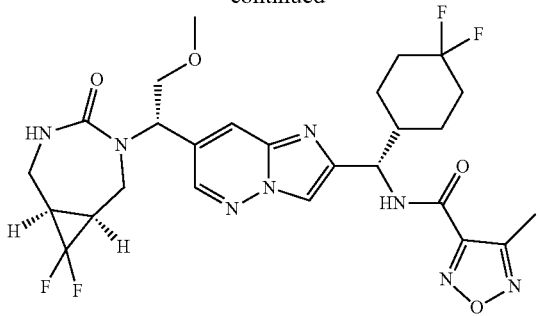

The title compounds were prepared as described for the synthesis of Example 16 using the diastereomeric mixture made in Intermediate 95 in place of 1-((S)-1-(2-((S)-amino (4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. The diastereomeric mixture was separated by SFC (Chiralpak IB N3 5 μm, 250×21 mm, Mobile phase: 30% methanol, 70% $CO_2$). The first-eluting isomer was designated as isomer 1 (Example 104, 39% yield) and the second-eluting isomer was designated as isomer 2 (Example 105, 24% yield). Example 104: $^1$H NMR (500 MHz, DMSO-$d_6$) δ 9.39 (d, J=9.0 Hz, 1H), 8.38 (d, J=2.1 Hz, 1H), 8.24 (s, 1H), 7.95-7.93 (m, 1H), 6.66-6.59 (m, 1H), 5.68-5.62 (m, 1H), 5.21-5.14 (m, 1H), 3.94-3.88 (m, 1H), 3.86-3.79 (m, 1H), 3.70-3.63 (m, 1H), 3.59-3.50 (m, 1H), 3.33 (s, 3H), 3.32-3.29 (m, 1H, masked by $H_2O$ peak) 3.16-3.07 (m, 1H), 2.47 (s, 3H), 2.37-2.26 (m, 1H), 2.23-2.13 (m, 1H), 2.09-1.69 (m, 6H), 1.66-1.58 (m, 1H), 1.44-1.33 (m, 1H), 1.33-1.21 (m, 1H). MS (APCI/ESI) m/z: [M+H]$^+$ Found 595.3. Example 105: $^1$H NMR (500 MHz, DMSO-$d_6$) δ 9.38 (d, J=9.0 Hz, 1H), 8.38 (d, J=2.1 Hz, 1H), 8.22 (s, 1H), 7.94-7.91 (m, 1H), 6.55-6.50 (m, 1H), 5.76-5.70 (m, 1H), 5.20-5.13 (m, 1H), 3.95-3.90 (m, 2H), 3.74-3.58 (m, 2H), 3.39-3.33 (m, 1H, masked by singlet at 3.36 ppm) 3.36 (s, 3H), 3.16-3.07 (m, 1H), 2.47 (s, 3H), 2.41-2.30 (m, 1H), 2.30-2.13 (m, 2H), 2.10-1.68 (m, 5H), 1.66-1.58 (m, 1H), 1.43-1.33 (m, 1H), 1.33-1.21 (m, 1H). MS (APCI/ESI) m/z: [M+H]$^+$ Found 595.3.

Example 106: N—((S)-(7-((S)-1-(5,5-Difluoro-2-oxotetrahydropyrimidin-1(2H)-yl)-2-methoxyethyl) imidazo[1,2-b]pyridazin-2-yl)(4,4-difluorocyclo-hexyl)methyl)-4-(2,2,2-trifluoroethyl)isoxazole-3-carboxamide

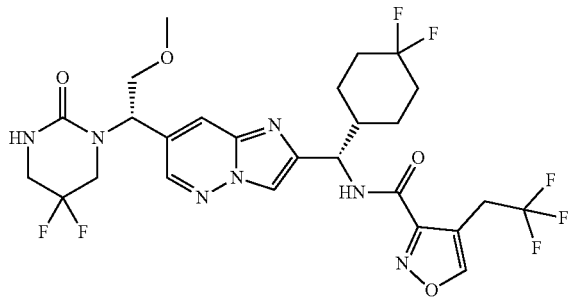 [SMILES: COC[C@H](c1cnn2cc([C@@H](NC(=O)c3nocc3CC(F)(F)F)C3CCC(F)(F)CC3)nc2c1)N1CC(F)(F)CNC1=O]

The title compound (59% yield) was synthesized in a manner analogous to Example 15 using 1-((S)-1-(2-((S)-amino(4,4-difluorocyclohexyl)methyl)imidazo[1,2-b] pyridazin-7-yl)-2-methoxyethyl)-5,5-difluorotetrahydropyrimidin-2(1H)-one (Intermediate 3) in place of 1-((S*)-1-(2-((R)-1-amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one hydrochloride and 4-(2,2,2-trifluoroethyl)isoxazole-3-carboxylic acid in place of 4-methyl-1,2,5-oxadiazole-3-carboxylic acid. $^1$H NMR (500 MHz, DMSO-$d_6$) δ 9.17-9.16 (m, 1H), 8.37-8.36 (m, 1H), 8.21-8.20 (m, 1H), 7.94-7.92 (m, 1H), 6.96-6.94 (m, 1H), 5.60-5.55 (m, 1H), 5.20-5.14 (m, 1H), 3.94-3.86 (m, 2H), 3.81-3.64 (m, 3H), 3.60-3.44 (m, 3H), 3.34-3.33 (m, 3H), 3.31-3.30 (m, 1H), 2.21-2.12 (m, 1H), 2.09-1.93 (m, 2H), 1.90-1.68 (m, 3H), 1.67-1.55 (m, 1H), 1.42-1.32 (m, 1H), 1.31-1.22 (m, 1H). MS (ESI) m/z: [M+H]$^+$ Found 636.7.

Example 107: N—((S)-(7-((S)-2-Cyclopropoxy-1-(5,5-difluoro-2-oxotetrahydropyrimidin-1(2H)-yl-4,4,6,6-$d_4$)ethyl)imidazo[1,2-b]pyridazin-2-yl)(4,4-difluorocyclohexyl)methyl)-4-(2,2,2-trifluoroethyl)isoxazole-3-carboxamide

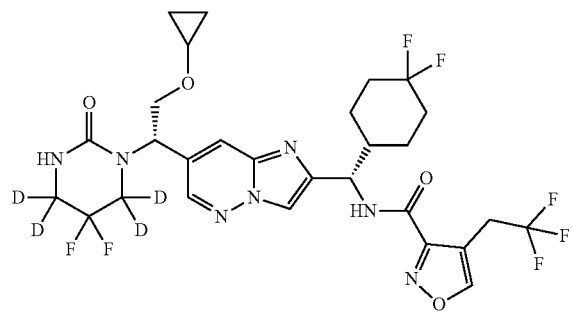 [SMILES: [2H]C1([2H])NC(=O)N([C@H](COC2CC2)c2cnn3cc([C@@H](NC(=O)c4nocc4CC(F)(F)F)C4CCC(F)(F)CC4)nc3c2)C([2H])([2H])C1(F)F]

The title compound (54% yield) was synthesized in a manner analogous to Example 15 using 1-((S)-1-(2-((S)-amino(4,4-difluorocyclohexyl)methyl)imidazo[1,2-b] pyridazin-7-yl)-2-cyclopropoxyethyl)-5,5-difluorotetrahydropyrimidin-2(1H)-one-4,4,6,6-$d_4$ (Intermediate 30) in place of 1-((S*)-1-(2-((R)-1-amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2 (1H)-one hydrochloride and 4-(2,2,2-trifluoroethyl) isoxazole-3-carboxylic acid in place of 4-methyl-1,2,5-oxadiazole-3-carboxylic acid. $^1$H NMR (500 MHz, DMSO-$d_6$) δ 9.18-9.14 (m, 2H), 8.37 (d, J=2.1 Hz, 1H), 8.21 (s, 1H), 7.94 (s, 1H), 6.92 (s, 1H), 5.56 (s, 1H), 5.17 (s, 1H), 4.04-3.94 (m, 2H), 3.76 (br dd, J=2.3, 11.1 Hz, 3H), 3.42 (s, 1H), 2.22-2.10 (m, 1H), 2.06-1.94 (m, 2H), 1.90-1.70 (m, 3H), 1.66-1.57 (m, 1H), 1.42-1.31 (m, 1H), 1.30-1.15 (m, 4H). MS (ESI) m/z: [M+H]$^+$ Found 666.4.

Example 108: N—((S)-(7-((S)-1-(5,5-Difluoro-2-oxotetrahydropyrimidin-1(2H)-yl)-2-methoxyethyl)imidazo[1,2-b]pyridazin-2-yl)(4,4-difluorocyclohexyl)methyl)-4-methoxy-1,2,5-oxadiazole-3-carboxamide

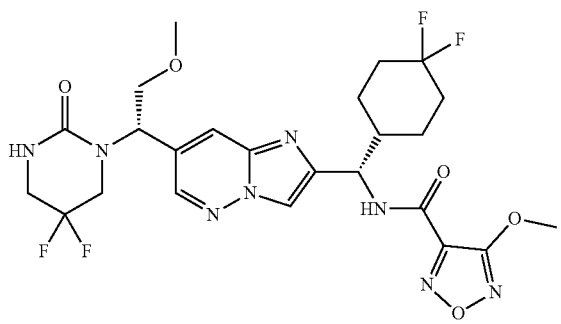 [SMILES: COC[C@H](c1cnn2cc([C@@H](NC(=O)c3nonc3OC)C3CCC(F)(F)CC3)nc2c1)N1CC(F)(F)CNC1=O]

The title compound (25% yield) was synthesized in a manner analogous to Example 15 using 1-((S)-1-(2-((S)-amino(4,4-difluorocyclohexyl)methyl)imidazo[1,2-b]pyridazin-7-yl)-2-methoxyethyl)-5,5-difluorotetrahydropyrimidin-2(1H)-one (Intermediate 3) in place of 1-((S*)-1-(2-((R)-1-amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one hydrochloride and 4-methoxy-1,2,5-oxadiazole-3-carboxylic acid in place of 4-methyl-1,2,5-oxadiazole-3-carboxylic acid. $^1$H NMR (500 MHz, DMSO-$d_6$) δ 9.31-9.27 (m, 1H), 8.40-8.38 (m, 1H), 8.22-8.21 (m, 1H), 7.94-7.92 (m, 1H), 6.98-6.95 (m, 1H), 5.60-5.56 (m, 1H), 5.19-5.14 (m, 1H), 4.10-4.08 (m, 3H), 3.94-3.87 (m, 2H), 3.74-3.65 (m, 1H), 3.61-3.47 (m, 3H), 3.35-3.34 (m, 3H), 2.20-2.12 (m, 1H), 2.06-1.96 (m, 2H), 1.90-1.71 (m, 3H), 1.65-1.59 (m, 1H), 1.43-1.24 (m, 2H). MS (ESI) m/z: [M+H]$^+$ Found 585.3.

Example 109: N—((S)-1-(7-((S)-1-(5,5-Difluoro-2-oxotetrahydropyrimidin-1(2H)-yl)-2-methoxyethyl)imidazo[1,2-b]pyridazin-2-yl)-5,5,5-trifluoro-4,4-dimethylpentyl)-4-methoxy-1,2,5-oxadiazole-3-carboxamide

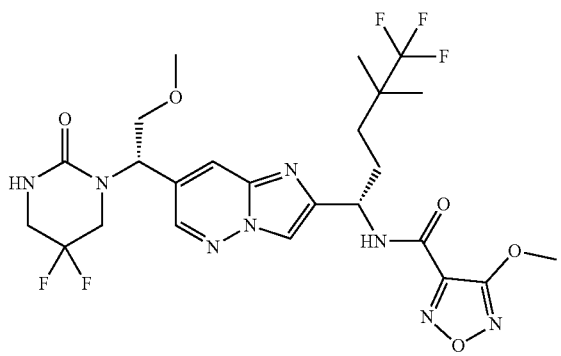 [SMILES: COC[C@H](c1cnn2cc([C@H](CCC(C)(C)C(F)(F)F)NC(=O)c3nonc3OC)nc2c1)N1CC(F)(F)CNC1=O]

The title compound (58% yield) was synthesized in a manner analogous to Example 15 using 1-((S)-1-(2-((S)-1-amino-5,5,5-trifluoro-4,4-dimethylpentyl)imidazo[1,2-b]pyridazin-7-yl)-2-methoxyethyl)-5,5-difluorotetrahydropyrimidin-2(1H)-one (Intermediate 47) in place of 1-((S*)-1-(2-((R)-1-amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one hydrochloride and 4-methoxy-1,2,5-oxadiazole-3-carboxylic acid in place of 4-methyl-1,2,5-oxadiazole-3-carboxylic acid. $^1$H NMR (500 MHz, DMSO-$d_6$) δ 9.37 (d, J=8.4 Hz, 1H), 8.38 (d, J=2.0 Hz, 1H), 8.17 (s, 1H), 7.94 (s, 1H), 6.96 (br s, 1H), 5.58 (s, 1H), 5.18 (br d, J=5.3 Hz, 1H), 4.09 (s, 3H), 3.90 (dd, J=3.4, 6.9 Hz, 2H), 3.72-3.64 (m, 1H), 3.60-3.46 (m, 3H), 3.35-3.34 (m, 3H), 2.13-2.04 (m, 1H), 2.00-1.89 (m, 1H), 1.68-1.59 (m, 1H), 1.55-1.46 (m, 1H), 1.12-1.07 (m, 6H). MS (ESI) m/z: [M+H]$^+$ Found 605.3.

Example 110: N—((S)-1-(7-((S)-1-(5,5-Difluoro-2-oxotetrahydropyrimidin-1(2H)-yl)-2-methoxyethyl)imidazo[1,2-b]pyridazin-2-yl)-5,5,5-trifluoro-4,4-dimethylpentyl)-4-(difluoromethyl)-1,2,5-oxadiazole-3-carboxamide

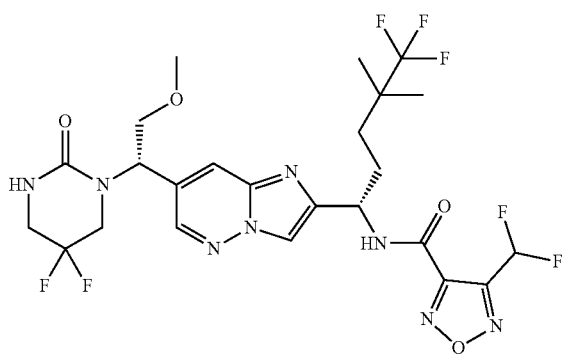 [SMILES: COC[C@H](c1cnn2cc([C@H](CCC(C)(C)C(F)(F)F)NC(=O)c3nonc3C(F)F)nc2c1)N1CC(F)(F)CNC1=O]

A mixture of ethyl 4-(difluoromethyl)-1,2,5-oxadiazole-3-carboxylate (161 mg, 0.836 mmol, Intermediate 75) and 1-((S)-1-(2-((S)-1-amino-5,5,5-trifluoro-4,4-dimethylpentyl)imidazo[1,2-b]pyridazin-7-yl)-2-methoxyethyl)-5,5-difluorotetrahydropyrimidin-2(1H)-one (160 mg, 0.334 mmol, Intermediate 47) in ACN (0.7 mL) was heated at 92° C. for 4 h. After that time, additional ethyl 4-(difluoromethyl)-1,2,5-oxadiazole-3-carboxylate (30 mg, 0.156 mmol, Intermediate 75) was then added and the mixture heated at 92° C. for 24 h. The mixture was then cooled to rt and allowed to stir for an additional 24 h at rt. The reaction mixture was concentrated to dryness, dissolved in DMF and purified by preparative HPLC (X-Bridge Prep C18 5 μm 50×100 mm, 0-100% acetonitrile/water (with 20 mM NH$_4$OH)) to afford the title compound in 8% yield. $^1$H NMR (500 MHz, DMSO-$d_6$) δ 9.80 (d, J=8.4 Hz, 1H), 8.37 (d, J=2.1 Hz, 1H), 8.20 (s, 1H), 7.95 (s, 1H), 7.62-7.40 (m, 1H), 6.96 (br s, 1H), 5.58 (s, 1H), 5.24-5.18 (m, 1H), 3.93-3.89 (m, 2H), 3.74-3.66 (m, 1H), 3.58-3.49 (m, 3H), 3.35-3.34 (m, 3H), 2.17-2.10 (m, 1H), 2.04-1.96 (m, 1H), 1.70-1.62 (m, 1H), 1.57-1.49 (m, 1H), 1.10-1.09 (m, 6H). MS (ESI) m/z: [M+H]$^+$ Found 625.2.

Example 111: N—((S)-1-(7-((S)-1-(5,5-Difluoro-2-oxotetrahydropyrimidin-1(2H)-yl)-2-methoxyethyl)imidazo[1,2-b]pyridazin-2-yl)-5,5,5-trifluoro-4,4-dimethylpentyl)-1-isopropyl-1H-1,2,4-triazole-5-carboxamide

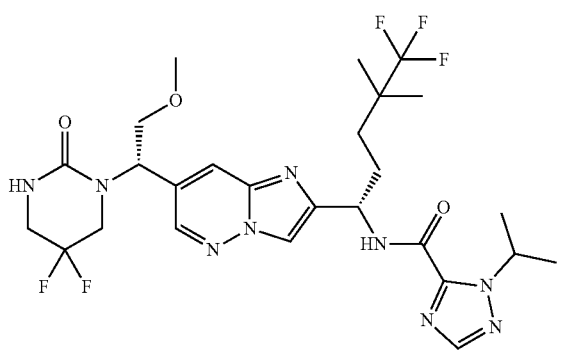 [SMILES: COC[C@H](c1cnn2cc([C@H](CCC(C)(C)C(F)(F)F)NC(=O)c3ncnn3C(C)C)nc2c1)N1CC(F)(F)CNC1=O]

A vial was charged with 1-((S)-1-(2-((S)-1-amino-4,4,4-trifluoro-3,3-dimethylbutyl)imidazo[1,2-b]pyridazin-7-yl)-2-methoxyethyl)-5,5-difluorotetrahydropyrimidin-2(1H)-one (60 mg, 0.125 mol, Intermediate 44), 1-isopropyl-1H-1,2,4-triazole-5-carboxylic acid (23 mg, 0.15 mmol), DIPEA (0.108 mL, 0.627 mmol), HATU (62 mg, 0.16 mmol) and DMF (1.2 mL). The resulting mixture was stirred at rt for 1 h. After that time, the reaction mixture was filtered and purified by preparative HPLC (X-Bridge Prep C18 column 5 μm, 50×250 mm, 5-100% acetonitrile/water (with 20 mM NH$_4$OH)) to afford the title compound as a white solid (43% yield) after lyophilization. $^1$H NMR (500 MHz, CDCl$_3$) δ 8.27 (d, J=2.2 Hz, 1H), 8.06 (d, J=8.6 Hz, 1H), 8.00-7.96 (m, 1H), 7.90 (s, 1H), 7.85 (d, J=0.7 Hz, 1H), 5.81-5.75 (m, 2H), 5.36-5.25 (m, 1H), 4.79 (s, 1H), 4.01-3.89 (m, 2H), 3.74-3.52 (m, 3H), 3.45 (d, J=1.0 Hz, 3H), 3.39-3.21 (m, 1H), 2.27-1.95 (m, 2H), 1.67-1.58 (m, 1H), 1.55-1.46 (m, 7H), 1.10 (d, J=11.1 Hz, 6H). MS (ESI) m/z: [M+H]$^+$ Found 616.3.

Example 112: N—((S)-1-(7-((S)-1-(5,5-Difluoro-2-oxotetrahydropyrimidin-1(2H)-yl-4,4,6,6-d$_4$)-2-methoxyethyl)imidazo[1,2-b]pyridazin-2-yl)-5,5,5-trifluoro-4,4-dimethylpentyl)-1-isopropyl-1H-1,2,4-triazole-5-carboxamide

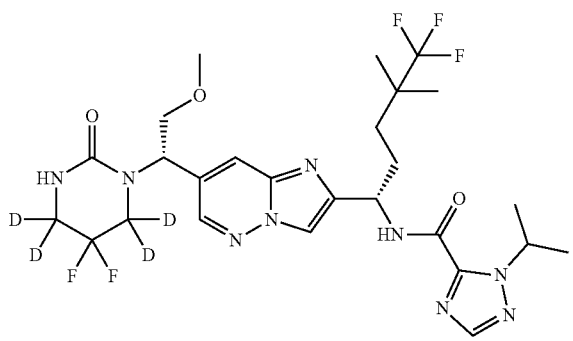 [SMILES: [2H]C1([2H])NC(=O)N([C@H](COC)c2cnn3cc([C@H](CCC(C)(C)C(F)(F)F)NC(=O)c4ncnn4C(C)C)nc3c2)C([2H])([2H])C1(F)F]

A mixture of 1-((S)-1-(2-((S)-1-amino-5,5,5-trifluoro-4,4-dimethylpentyl)imidazo[1,2-b]pyridazin-7-yl)-2-methoxyethyl)-5,5-difluorotetrahydropyrimidin-2(1H)-one-4,4,6,6-d$_4$ (55 mg, 0.11 mmol, Intermediate 73), 1-isopropyl-1H-1,2,4-triazole-5-carboxylic acid (23.3 mg, 0.150 mmol), DIPEA (0.108 mL, 0.627 mmol), HATU (62 mg, 0.16 mmol) and DMF (1.2 mL) was stirred at rt for 1 h. Then the reaction mixture was filtered and purified by preparative HPLC (X-Bridge Prep C18 column 5 μm, 50×250 mm, 5-100% acetonitrile/water (with 20 mM NH$_4$OH)) to afford the title compound as a white solid (47% yield) after lyophilization. $^1$H NMR (500 MHz, CDCl$_3$) δ 8.31 (d, J=2.2 Hz, 1H), 8.13 (d, J=8.7 Hz, 1H), 8.06 (s, 1H), 7.91 (s, 1H), 7.86 (s, 1H), 5.80-5.72 (m, 2H), 5.30 (s, 1H), 4.92 (s, 1H), 4.01-3.90 (m, 2H), 3.45 (s, 3H), 2.22-2.03 (m, 2H), 1.68-1.59 (m, 1H), 1.54-1.46 (m, 7H), 1.10 (d, J=11.0 Hz, 6H). MS (ESI) m/z: [M+H]$^+$ Found 620.3.

Example 113: (S)—N-(1-(7-((5,5-Difluoro-2-oxotetrahydropyrimidin-1(2H)-yl)methyl)imidazo[1,2-b]pyridazin-2-yl)-5,5,5-trifluoro-4,4-dimethylpentyl)-4-methoxy-1,2,5-oxadiazole-3-carboxamide

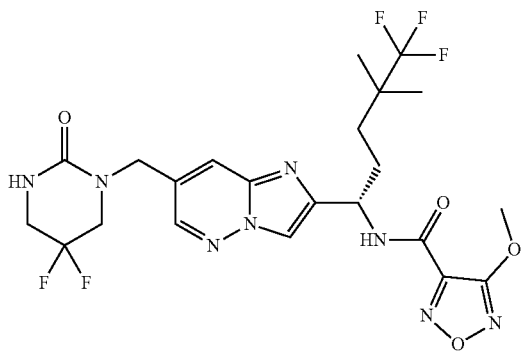 [SMILES: COc1nonc1C(=O)N[C@@H](CCC(C)(C)C(F)(F)F)c1cn2ncc(CN3CC(F)(F)CNC3=O)cc2n1]

The title compound was synthesized in a manner analogous to Example 15 using (S)-1-((2-(1-amino-5,5,5-trifluoro-4,4-dimethylpentyl)imidazo[1,2-b]pyridazin-7-yl)methyl)-5,5-difluorotetrahydropyrimidin-2(1H)-one (Intermediate 97) in place of 1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one-4,4,6,6-d$_4$ and 4-methoxy-1,2,5-oxadiazole-3-carboxylic acid in place of 4-methyl-1,2,5-oxadiazole-3-carboxylic acid. The material was purified by preparative HPLC (XBridge Prep C18 5 μm OBD 50×100 mm, 10-100% MeCN/water (20 mM NH$_4$OH)) to provide the title compound in 55% yield. $^1$H NMR (600 MHz, DMSO-d$_6$) δ 9.36 (d, J=8.5 Hz, 1H), 8.41 (d, J=2.0 Hz, 1H), 8.24-8.08 (m, 1H), 7.94-7.83 (m, 1H), 7.00-6.85 (m, 1H), 5.23-5.13 (m, 1H), 4.57-4.44 (m, 2H), 4.09 (s, 3H), 3.77-3.67 (m, 2H), 3.60-3.47 (m, 2H), 2.13-2.03 (m, 1H), 1.99-1.89 (m, 1H), 1.70-1.56 (m, 1H), 1.56-1.44 (m, 1H), 1.08 (s, 6H). MS (ESI) m/z: [M+H]$^+$ Found 561.3.

Example 114: (S)-4-Cyclopropyl-N-(1-(7-((5,5-difluoro-2-oxotetrahydropyrimidin-1(2H)-yl)methyl)imidazo[1,2-b]pyridazin-2-yl)-5,5,5-trifluoro-4,4-dimethylpentyl)-1,2,5-oxadiazole-3-carboxamide

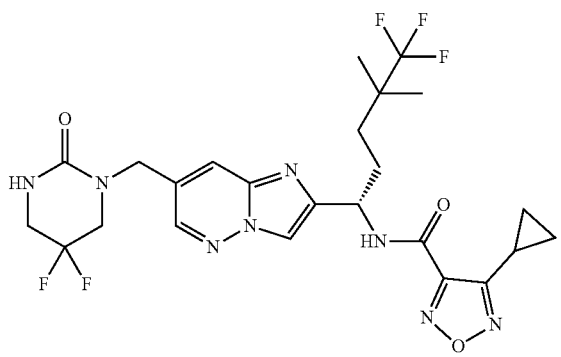 [SMILES: CC(C)(CC[C@H](NC(=O)c1nonc1C1CC1)c1cn2ncc(CN3CC(F)(F)CNC3=O)cc2n1)C(F)(F)F]

The title compound was synthesized in a manner analogous to Example 15 using (S)-1-((2-(1-amino-5,5,5-trifluoro-4,4-dimethylpentyl)imidazo[1,2-b]pyridazin-7-yl)methyl)-5,5-difluorotetrahydropyrimidin-2(1H)-one (Intermediate 97) in place of 1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one-4,4,6,6-d$_4$ and 4-cyclopropyl-1,2,5-oxadiazole-3-carboxylic acid in place of 4-methyl-1,2,5-oxadiazole-3-carboxylic acid. The material was purified by preparative HPLC (XBridge Prep C18 5 μm OBD 50×100 mm, 10-100% MeCN/water (20 mM NH$_4$OH)) to provide the title compound in 57% yield. $^1$H NMR (600 MHz, DMSO-d$_6$) δ 9.55 (d, J=8.5 Hz, 1H), 8.40 (d, J=2.0 Hz, 1H), 8.26-8.07 (m, 1H), 8.03-7.80 (m, 1H), 7.03-6.87 (m, 1H), 5.27-5.17 (m, 1H), 4.59-4.46 (m, 2H), 3.77-3.61 (m, 2H), 3.61-3.50 (m, 2H), 2.38-2.23 (m, 1H), 2.16-2.05 (m, 1H), 2.04-1.87 (m, 1H), 1.68-1.61 (m, 1H), 1.60-1.46 (m, 1H), 1.16-1.10 (m, 2H), 1.09 (s, 3H), 1.08 (s, 3H), 1.03-0.90 (m, 2H). MS (ESI) m/z: [M+H]$^+$ Found 571.3.

Example 115: (S)—N-(1-(7-((5,5-Difluoro-2-oxotetrahydropyrimidin-1(2H)-yl)methyl)imidazo[1,2-b]pyridazin-2-yl)-5,5,5-trifluoro-4,4-dimethylpentyl)-4-methyl-1,2,5-oxadiazole-3-carboxamide

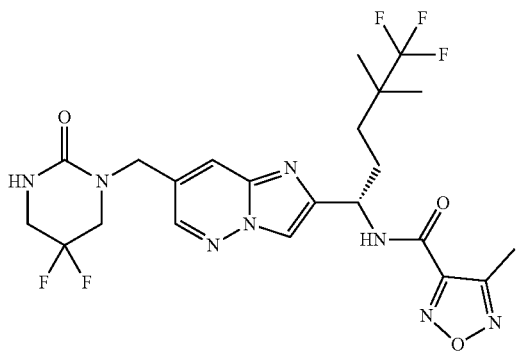 [SMILES: Cc1nonc1C(=O)N[C@@H](CCC(C)(C)C(F)(F)F)c1cn2ncc(CN3CC(F)(F)CNC3=O)cc2n1]

The title compound was synthesized in a manner analogous to Example 16 using (S)-1-((2-(1-amino-5,5,5-trifluoro-4,4-dimethylpentyl)imidazo[1,2-b]pyridazin-7-yl)methyl)-5,5-difluorotetrahydropyrimidin-2(1H)-one (Intermediate 97) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. The material was purified by preparative HPLC (XBridge Prep C18 5 μm OBD 50×100 mm, 10-100% MeCN/water (20 mM NH$_4$OH)) to provide the title compound in 69% yield. $^1$H NMR (600 MHz, DMSO-d$_6$) δ 9.50 (d, J=8.5 Hz, 1H), 8.40 (d, J=2.0 Hz, 1H), 8.18 (s, 1H), 7.92-7.84 (m, 1H), 7.06-6.84 (m, 1H), 5.42-5.06 (m, 1H), 4.50 (s, 2H), 3.83-3.60 (m, 2H), 3.61-3.47 (m, 2H), 2.49 (s, 3H), 2.18-2.05 (m, 1H), 2.04-1.94 (m, 1H), 1.69-1.59 (m, 1H), 1.57-1.47 (m, 1H), 1.09 (s, 3H), 1.09 (s, 3H). MS (ESI) m/z: [M+H]$^+$ Found 545.2.

Example 116: N—((S)-1-(7-(((1S*,7R*)-8,8-Difluoro-4-oxo-3,5-diazabicyclo[5.1.0]octan-3-yl)methyl)imidazo[1,2-b]pyridazin-2-yl)-5,5,5-trifluoro-4,4-dimethylpentyl)-4-methoxy-1,2,5-oxadiazole-3-carboxamide

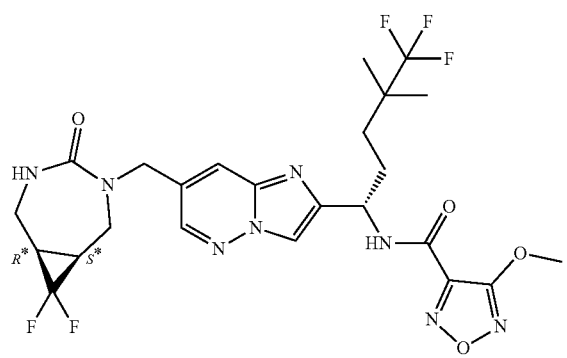 [SMILES: COc1nonc1C(=O)N[C@@H](CCC(C)(C)C(F)(F)F)c1cn2ncc(CN3C[C@@H]4[C@H](CNC3=O)C4(F)F)cc2n1]

Example 117: N—((S)-1-(7-(((1R*,7S*)-8,8-Difluoro-4-oxo-3,5-diazabicyclo[5.1.0]octan-3-yl)methyl)imidazo[1,2-b]pyridazin-2-yl)-5,5,5-trifluoro-4,4-dimethylpentyl)-4-methoxy-1,2,5-oxadiazole-3-carboxamide

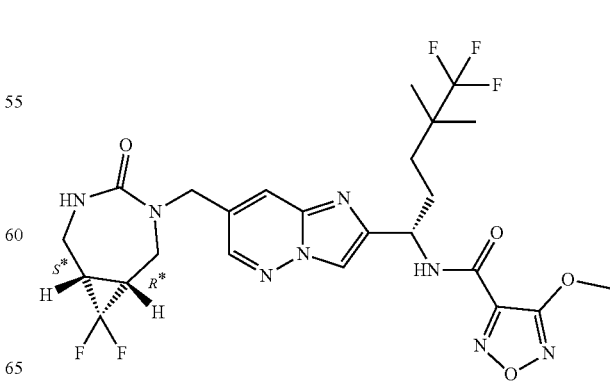

The title compounds were synthesized in a manner analogous to Example 15 using a diastereomeric mixture of (1S*,7R*)-3-((2-((S)-1-amino-5,5,5-trifluoro-4,4-dimethylpentyl)imidazo[1,2-b]pyridazin-7-yl)methyl)-8,8-difluoro-3,5-diazabicyclo[5.1.0]octan-4-one and (1R*,7S*)-3-((2-((S)-1-amino-5,5,5-trifluoro-4,4-dimethylpentyl)imidazo[1,2-b]pyridazin-7-yl)methyl)-8,8-difluoro-3,5-diazabicyclo[5.1.0]octan-4-one (Intermediate 98) in place of 1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one-4,4,6,6-d₄ and 4-methoxy-1,2,5-oxadiazole-3-carboxylic acid in place of 4-methyl-1,2,5-oxadiazole-3-carboxylic acid. The mixture was purified by silica gel chromatography (0-100% acetone/hexanes) followed by separation of the diastereomers by chiral SFC (Stationary phase: Chiralcel OJ-H 5 μm, 250×21 mm, Mobile phase: 30% methanol with 0.2% triethylamine, 70% CO₂). Example 116 was the first eluting isomer (11% yield) and Example 117 was the second eluting isomer (10% yield). Example 116: ¹H NMR (600 MHz, DMSO-d₆) δ 9.36 (d, J=8.5 Hz, 1H), 8.44 (d, J=2.0 Hz, 1H), 8.26-8.06 (m, 1H), 8.06-7.86 (m, 1H), 6.62-6.49 (m, 1H), 5.25-5.12 (m, 1H), 4.64 (d, J=15.8 Hz, 1H), 4.41 (d, J=15.6, 1.1 Hz, 1H), 4.10 (s, 3H), 4.00-3.89 (m, 1H), 3.67-3.57 (m, 1H), 3.49-3.37 (m, 1H), 3.18-3.05 (m, 1H), 2.38-2.26 (m, 2H), 2.12-2.03 (m, 1H), 2.03-1.89 (m, 1H), 1.68-1.58 (m, 1H), 1.56-1.46 (m, 1H), 1.09 (s, 6H). MS (ESI) m/z: [M+H]⁺ Found 587.4. Example 117: ¹H NMR (600 MHz, DMSO-d₆) δ 9.36 (d, J=8.5 Hz, 1H), 8.44 (d, J=2.1 Hz, 1H), 8.14 (s, 1H), 7.96-7.79 (m, 1H), 6.65-6.53 (m, 1H), 5.25-5.13 (m, 1H), 4.67-4.60 (m, 1H), 4.42 (d, J=15.8 Hz, 1H), 4.10 (s, 3H), 3.99-3.90 (m, 1H), 3.67-3.55 (m, 1H), 3.50-3.35 (m, 1H), 3.18-3.02 (m, 1H), 2.38-2.29 (m, 2H), 2.13-2.02 (m, 1H), 2.01-1.86 (m, 1H), 1.68-1.57 (m, 1H), 1.57-1.45 (m, 1H), 1.09 (s, 6H). MS (ESI) m/z: [M+H]⁺ Found 587.4.

Example 118: 4-Cyclopropyl-N—((S)-1-(7-(((1S*, 7R*)-8,8-difluoro-4-oxo-3,5-diazabicyclo[5.1.0]octan-3-yl)methyl)imidazo[1,2-b]pyridazin-2-yl)-5,5,5-trifluoro-4,4-dimethylpentyl)-1,2,5-oxadiazole-3-carboxamide

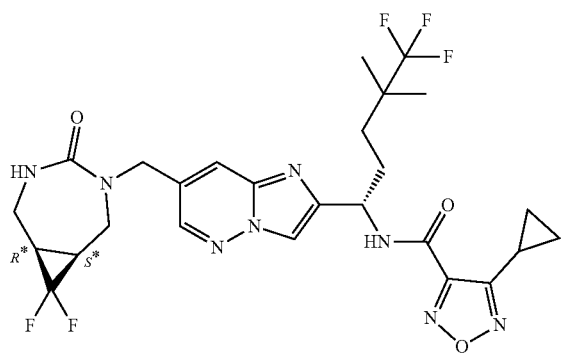 [SMILES: CC(C)(CC[C@H](NC(=O)c1nonc1C1CC1)c1cn2ncc(CN3C[C@@H]4[C@H](CNC3=O)C4(F)F)cc2n1)C(F)(F)F]

Example 119: 4-Cyclopropyl-N—((S)-1-(7-(((1R*, 7S*)-8,8-difluoro-4-oxo-3,5-diazabicyclo[5.1.0]octan-3-yl)methyl)imidazo[1,2-b]pyridazin-2-yl)-5,5,5-trifluoro-4,4-dimethylpentyl)-1,2,5-oxadiazole-3-carboxamide

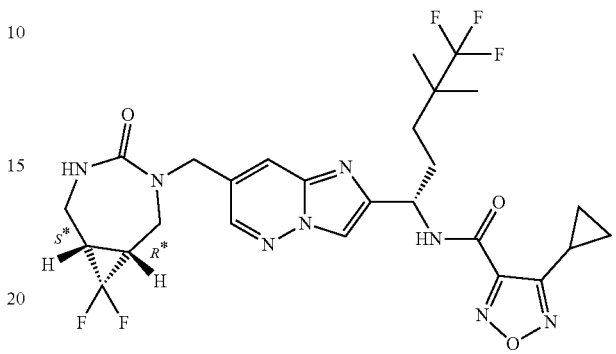

The title compounds were synthesized in a manner analogous to Example 15 using a diastereomeric mixture of (1S*,7R*)-3-((2-((S)-1-amino-5,5,5-trifluoro-4,4-dimethylpentyl)imidazo[1,2-b]pyridazin-7-yl)methyl)-8,8-difluoro-3,5-diazabicyclo[5.1.0]octan-4-one and (1R*,7S*)-3-((2-((S)-1-amino-5,5,5-trifluoro-4,4-dimethylpentyl)imidazo[1,2-b]pyridazin-7-yl)methyl)-8,8-difluoro-3,5-diazabicyclo[5.1.0]octan-4-one (Intermediate 98) in place of 1-((S)-1-(2-((R)-1-amino-2-((1,1,1-trifluoro-2-methylpropan-2-yl)oxy)ethyl)imidazo[1,2-b]pyridazin-7-yl)-2-methoxyethyl)-5,5-difluorotetrahydropyrimidin-2(1H)-one-4,4,6,6-d₄ and 4-cyclopropyl-1,2,5-oxadiazole-3-carboxylic acid in place of 4-methyl-1,2,5-oxadiazole-3-carboxylic acid. The mixture was purified by silica gel chromatography (0-100% acetone/hexanes) followed by separation of the diastereomers by chiral SFC (Stationary phase: Chiralcel OJ-H 5 μm, 250×21 mm, Mobile phase: 30% methanol with 0.2% triethylamine, 70% CO₂). Example 118 was the first eluting isomer (13% yield) and Example 119 was the second eluting isomer (11% yield). Example 118: ¹H NMR (600 MHz, DMSO-d₆) δ 9.54 (d, J=8.6 Hz, 1H), 8.44 (d, J=2.0 Hz, 1H), 8.21-8.13 (m, 1H), 7.96-7.92 (m, 1H), 6.61-6.55 (m, 1H), 5.27-5.19 (m, 1H), 4.69-4.60 (m, 1H), 4.45-4.37 (m, 1H), 3.97-3.90 (m, 1H), 3.66-3.57 (m, 1H), 3.46-3.37 (m, 1H), 3.18-3.08 (m, 1H), 2.38-2.29 (m, 3H), 2.16-2.06 (m, 1H), 2.03-1.95 (m, 1H), 1.70-1.59 (m, 1H), 1.60-1.50 (m, 1H), 1.16-1.12 (m, 2H), 1.10 (s, 3H), 1.09 (s, 3H), 1.01-0.97 (m, 2H). MS (ESI) m/z: [M+H]⁺ Found 597.3. Example 119: ¹H NMR (600 MHz, DMSO-d₆) δ 9.53 (d, J=8.5 Hz, 1H), 8.43 (d, J=2.0 Hz, 1H), 8.24-8.09 (m, 1H), 7.98-7.82 (m, 1H), 6.69-6.51 (m, 1H), 5.28-5.17 (m, 1H), 4.68-4.58 (m, 1H), 4.46-4.35 (m, 1H), 3.99-3.89 (m, 1H), 3.67-3.56 (m, 1H), 3.50-3.37 (m, 1H), 3.18-3.09 (m, 1H), 2.37-2.25 (m, 3H), 2.14-2.06 (m, 1H), 2.03-1.93 (m, 1H), 1.70-1.59 (m, 1H), 1.58-1.49 (m, 1H), 1.16-1.11 (m, 2H), 1.09 (s, 3H), 1.08 (s, 3H), 1.00-0.95 (m, 2H). MS (ESI) m/z: [M+H]⁺ Found 597.3.

Example 120: N—((S)-1-(7-(((1S*,7R*)-8,8-Difluoro-4-oxo-3,5-diazabicyclo[5.1.0]octan-3-yl)methyl)imidazo[1,2-b]pyridazin-2-yl)-5,5,5-trifluoro-4,4-dimethylpentyl)-4-methyl-1,2,5-oxadiazole-3-carboxamide

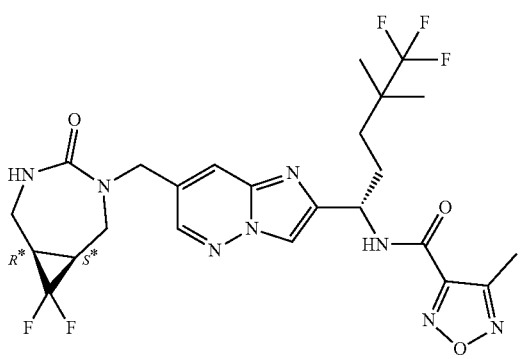 [SMILES: Cc1nonc1C(=O)N[C@@H](CCC(C)(C)C(F)(F)F)c1cn2ncc(CN3C[C@@H]4[C@H](CNC3=O)C4(F)F)cc2n1]

Example 121: N—((S)-1-(7-(((1R*,7S*)-8,8-Difluoro-4-oxo-3,5-diazabicyclo[5.1.0]octan-3-yl)methyl)imidazo[1,2-b]pyridazin-2-yl)-5,5,5-trifluoro-4,4-dimethylpentyl)-4-methyl-1,2,5-oxadiazole-3-carboxamide

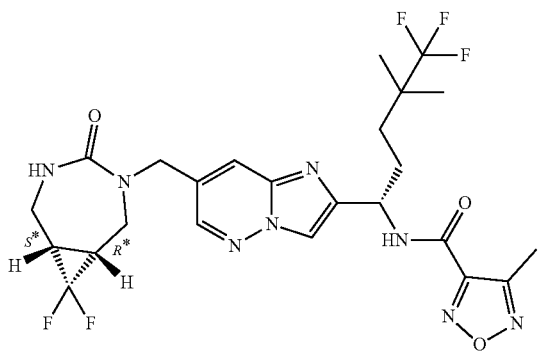

The title compounds were synthesized in a manner analogous to Example 16 using a diastereomeric mixture of (1S*,7R*)-3-((2-((S)-1-amino-5,5,5-trifluoro-4,4-dimethylpentyl)imidazo[1,2-b]pyridazin-7-yl)methyl)-8,8-difluoro-3,5-diazabicyclo[5.1.0]octan-4-one and (1R*,7S*)-3-((2-((S)-1-amino-5,5,5-trifluoro-4,4-dimethylpentyl)imidazo[1,2-b]pyridazin-7-yl)methyl)-8,8-difluoro-3,5-diazabicyclo[5.1.0]octan-4-one (Intermediate 98) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. The mixture was purified by silica gel chromatography (0-100% acetone/hexanes) followed by separation of the diastereomers by chiral SFC (Stationary phase: Chiralcel OJ-H 5 µm, 250×21 mm, Mobile phase: 25% methanol with 0.2% triethylamine, 75% $CO_2$). Example 120 was the first eluting isomer (20% yield) and Example 121 was the second eluting isomer (24% yield). Example 120: $^1$H NMR (600 MHz, DMSO-$d_6$) δ 9.49 (d, J=8.5 Hz, 1H), 8.42 (d, J=2.0 Hz, 1H), 8.22-8.12 (m, 1H), 7.93-7.91 (m, 1H), 6.59-6.54 (m, 1H), 5.23-5.17 (m, 1H), 4.63 (d, J=15.7 Hz, 1H), 4.40 (d, J=15.8 Hz, 1H), 3.97-3.90 (m, 1H), 3.64-3.58 (m, 1H), 3.43-3.37 (m, 1H), 3.16-3.08 (m, 1H), 2.49 (s, 3H), 2.37-2.27 (m, 2H), 2.15-2.07 (m, 1H), 2.04-1.93 (m, 1H), 1.68-1.60 (m, 1H), 1.58-1.49 (m, 1H), 1.09 (s, 3H), 1.09 (s, 3H). MS (ESI) m/z: [M+H]$^+$ Found 571.2. Example 121: $^1$H NMR (600 MHz, DMSO-$d_6$) δ 9.50 (d, J=8.5 Hz, 1H), 8.43 (d, J=2.0 Hz, 1H), 8.20-8.13 (m, 1H), 7.96-7.89 (m, 1H), 6.62-6.49 (m, 1H), 5.25-5.17 (m, 1H), 4.63 (d, J=15.8 Hz, 1H), 4.49-4.38 (m, 1H), 3.99-3.88 (m, 1H), 3.66-3.57 (m, 1H), 3.45-3.36 (m, 1H), 3.17-3.07 (m, 1H), 2.50 (s, 3H), 2.38-2.27 (m, 2H), 2.16-2.07 (m, 1H), 2.04-1.94 (m, 1H), 1.70-1.60 (m, 1H), 1.60-1.47 (m, 1H), 1.09 (s, 3H), 1.09 (s, 3H). MS (ESI) m/z: [M+H]$^+$ Found 571.2.

Example 122: N—((S)-1-(7-((S)-2-Cyclopropoxy-1-(5,5-difluoro-2-oxotetrahydropyrimidin-1(2H)-yl)ethyl)imidazo[1,2-b]pyridazin-2-yl)-5,5,5-trifluoro-4,4-dimethylpentyl)-4-methoxy-1,2,5-oxadiazole-3-carboxamide

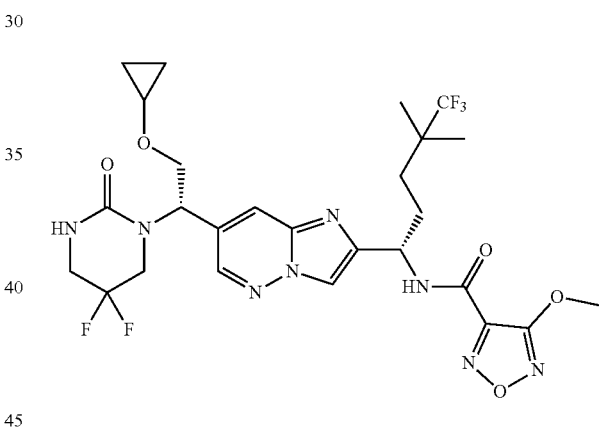

The title compound (56% yield) was synthesized in a manner analogous to Example 18 using (S)-1-(7-((S)-2-cyclopropoxy-1-(5,5-difluoro-2-oxotetrahydropyrimidin-1(2H)-yl)ethyl)imidazo[1,2-b]pyridazin-2-yl)-5,5,5-trifluoro-4,4-dimethylpentan-1-aminium 2,2,2-trifluoroacetate (Intermediate 58) in place of (S)-1-((2-(amino(4,4-difluorocyclohexyl)methyl)imidazo[1,2-b]pyridazin-7-yl)methyl)tetrahydropyrimidin-2(1H)-one and 4-methoxy-1,2,5-oxadiazole-3-carboxylic acid in place of 4-cyclopropyl-1,2,5-oxadiazole-3-carboxylic acid. $^1$H NMR (500 MHz, DMSO-$d_6$) δ 9.37 (d, J=8.5 Hz, 1H), 8.37 (d, J=2.0 Hz, 1H), 8.24-8.07 (m, 1H), 8.02-7.91 (m, 1H), 6.95 (s, 1H), 5.62-5.51 (m, 1H), 5.26-5.11 (m, 1H), 4.15-4.03 (m, 3H), 4.04-3.92 (m, 2H), 3.76-3.62 (m, 1H), 3.60-3.44 (m, 3H), 3.42-3.36 (m, 1H), 2.14-2.04 (m, 1H), 2.02-1.89 (m, 1H), 1.71-1.58 (m, 1H), 1.59-1.46 (m, 1H), 1.08 (s, 6H), 0.59-0.38 (m, 4H). MS (ESI) m/z: [M+H]$^+$ Found 631.3.

Example 123: N—((S)-(4,4-Difluorocyclohexyl)(7-((S)-2-methoxy-1-(5,5,6,6-tetrafluoro-2-oxo-1,3-diazepan-1-yl)ethyl)imidazo[1,2-b]pyridazin-2-yl)methyl)-4-methyl-1,2,5-oxadiazole-3-carboxamide

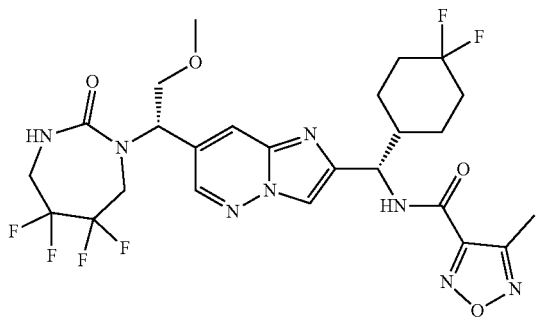 [SMILES: COC[C@H](c1cnn2cc([C@@H](NC(=O)c3nonc3C)C3CCC(F)(F)CC3)nc2c1)N1CC(F)(F)C(F)(F)CNC1=O]

The title compound (48% yield) was prepared as described for the synthesis of Example 16 using 1-((S)-1-(2-((S)-amino(4,4-difluorocyclohexyl)methyl)imidazo[1,2-b]pyridazin-7-yl)-2-methoxyethyl)-5,5,6,6-tetrafluoro-1,3-diazepan-2-one (Intermediate 100) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. $^1$H NMR (500 MHz, DMSO-$d_6$) δ 9.39 (d, J=9.0 Hz, 1H), 8.58 (d, J=2.1 Hz, 1H), 8.24 (s, 1H), 8.15-8.00 (m, 1H), 6.94 (t, J=4.7 Hz, 1H), 5.24-5.12 (m, 2H), 4.08-3.97 (m, 1H), 3.96-3.87 (m, 1H), 3.75-3.56 (m, 2H), 3.56-3.39 (m, 2H), 3.33 (s, 3H), 2.47 (s, 3H), 2.24-2.13 (m, 1H), 2.10-1.94 (m, 2H), 1.94-1.88 (m, 1H), 1.87-1.70 (m, 2H), 1.64-1.55 (m, 1H), 1.48-1.32 (m, 1H), 1.32-1.16 (m, 1H). MS (ESI) m/z: [M+H]$^+$ Found 619.2.

Example 124: N—((S)-(4,4-Difluorocyclohexyl)(7-((S)-2-methoxy-1-(5,5,6,6-tetrafluoro-2-oxo-1,3-diazepan-1-yl)ethyl)imidazo[1,2-b]pyridazin-2-yl)methyl)-4-methoxy-1,2,5-oxadiazole-3-carboxamide

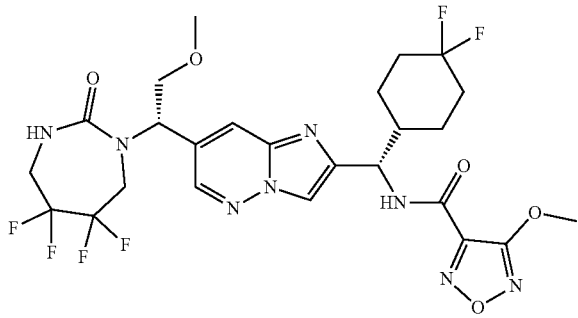 [SMILES: COC[C@H](c1cnn2cc([C@@H](NC(=O)c3nonc3OC)C3CCC(F)(F)CC3)nc2c1)N1CC(F)(F)C(F)(F)CNC1=O]

The title compound (53% yield) was synthesized in a manner analogous to Example 18 using 1-((S)-1-(2-((S)-amino(4,4-difluorocyclohexyl)methyl)imidazo[1,2-b]pyridazin-7-yl)-2-methoxyethyl)-5,5,6,6-tetrafluoro-1,3-diazepan-2-one (Intermediate 100) in place of (S)-1-((2-(amino(4,4-difluorocyclohexyl)methyl)imidazo[1,2-b]pyridazin-7-yl)methyl)tetrahydropyrimidin-2(1H)-one and 4-methoxy-1,2,5-oxadiazole-3-carboxylic acid in place of 4-cyclopropyl-1,2,5-oxadiazole-3-carboxylic acid. $^1$H NMR (500 MHz, DMSO-$d_6$) δ 9.21 (d, J=9.0 Hz, 1H), 8.52 (d, J=2.1 Hz, 1H), 8.14 (s, 1H), 8.09-7.89 (m, 1H), 7.00-6.75 (m, 1H), 5.19-4.97 (m, 2H), 4.02 (s, 3H), 3.99-3.91 (m, 1H), 3.89-3.78 (m, 1H), 3.67-3.50 (m, 2H), 3.50-3.31 (m, 2H), 3.26 (s, 3H), 2.18-2.03 (m, 1H), 2.03-1.85 (m, 2H), 1.85-1.61 (m, 3H), 1.60-1.45 (m, 1H), 1.38-1.12 (m, 2H). MS (ESI) m/z: [M+H]$^+$ Found 635.3.

Example 125: N—((R*)-1-(7-((S)-1-(5,5-Difluoro-2-oxotetrahydropyrimidin-1(2H)-yl)-2-methoxyethyl)imidazo[1,2-b]pyridazin-2-yl)-3-(1-(trifluoromethyl)cyclopropyl)propyl)-4-methyl-1,2,5-oxadiazole-3-carboxamide

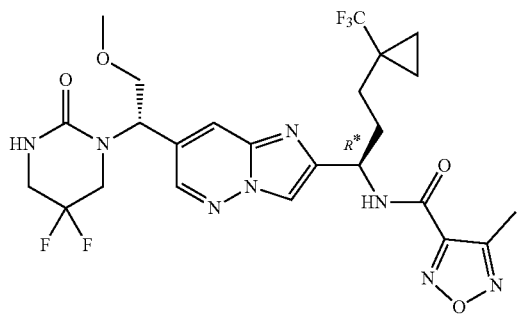 [SMILES: COC[C@H](c1cnn2cc([C@@H](CCC3(C(F)(F)F)CC3)NC(=O)c3nonc3C)nc2c1)N1CC(F)(F)CNC1=O]

Example 126: N—((S*)-1-(7-((S)-1-(5,5-Difluoro-2-oxotetrahydropyrimidin-1(2H)-yl)-2-methoxyethyl)imidazo[1,2-b]pyridazin-2-yl)-3-(1-(trifluoromethyl)cyclopropyl)propyl)-4-methyl-1,2,5-oxadiazole-3-carboxamide

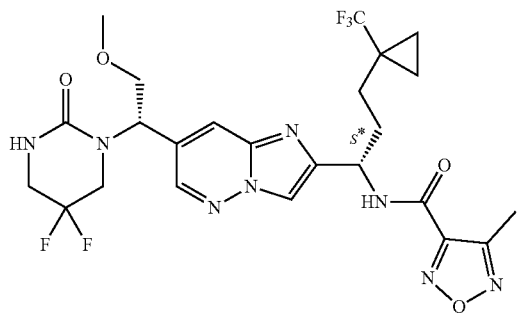 [SMILES: COC[C@H](c1cnn2cc([C@H](CCC3(C(F)(F)F)CC3)NC(=O)c3nonc3C)nc2c1)N1CC(F)(F)CNC1=O]

The title compounds were prepared as described for the synthesis of Example 16 using 1-((S)-1-(2-((S*)-1-amino-3-(1-(trifluoromethyl)cyclopropyl)propyl)imidazo[1,2-b]pyridazin-7-yl)-2-methoxyethyl)-5,5-difluorotetrahydropyrimidin-2(1H)-one (Intermediate 101) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. The resulting mixture was separated by chiral SFC (Whelk O1 SS, 5 µm, 250×30 mm, 25% methanol, 75% CO$_2$) to afford two diastereomers. The first eluting isomer was designated as the (R*) isomer (Example 125) and the second eluting isomer was designated as the (S*) isomer (Example 126) .The first eluting isomer, N—((R*)-1-(7-((S)-1-(5,5-difluoro-2-oxotetrahydropyrimidin-1(2H)-yl)-2-methoxyethyl) imidazo[1,2-b]pyridazin-2-yl)-3-(1-(trifluoromethyl) cyclopropyl)propyl)-4-methyl-1,2,5-oxadiazole-3-carboxamide (Example 125) was isolated as a white powder (9.9% yield). The second eluting isomer, N—((S*)-1-(7-((S)-1-(5,5-difluoro-2-oxotetrahydropyrimidin-1(2H)-yl)-2-methoxyethyl)imidazo[1,2-b]pyridazin-2-yl)-3-(1-(trifluoromethyl)cyclopropyl)propyl)-4-methyl-1,2,5-oxadiazole-3-carboxamide (Example 126), was isolated as a white powder (49.4% yield). Example 125: $^1$H NMR (500 MHz, DMSO-d$_6$) δ 9.48 (d, J=8.5 Hz, 1H), 8.36 (d, J=2.1 Hz, 1H), 8.16 (s, 1H), 7.99-7.85 (m, 1H), 6.95 (s, 1H), 5.58 (t, J=6.8 Hz, 1H), 5.31-5.12 (m, 1H), 3.97-3.80 (m, 2H), 3.76-3.62 (m, 1H), 3.62-3.44 (m, 3H), 3.34 (s, 3H), 2.49 (s, 3H), 2.27-2.13 (m, 1H), 2.12-1.98 (m, 1H), 1.77-1.59 (m, 2H), 0.96-0.85 (m, 2H), 0.84-0.66 (m, 2H). MS (ESI) m/z: [M+H]$^+$ Found 587.2. Example 126: $^1$H NMR (500 MHz, DMSO-d$_6$) δ 9.48 (d, J=8.5 Hz, 1H), 8.36 (d, J=2.2 Hz, 1H), 8.25-8.09 (m, 1H), 7.99-7.86 (m, 1H), 6.95 (s, 1H), 5.58 (t, J=6.8 Hz, 1H), 5.26-5.16 (m, 1H), 3.95-3.85 (m, 2H), 3.74-3.61 (m, 1H), 3.60-3.44 (m, 3H), 3.34 (s, 3H), 2.49 (s, 3H), 2.25-2.13 (m, 1H), 2.12-1.96 (m, 1H), 1.76-1.55 (m, 2H), 0.95-0.83 (m, 2H), 0.83-0.68 (m, 2H). MS (ESI) m/z: [M+H]$^+$ Found 587.2.

Example 127: N—((S)-(7-((S)-1-(5,5-Difluoro-2-oxotetrahydropyrimidin-1(2H)-yl)-2-methoxyethyl) imidazo[1,2-b]pyridazin-2-yl)(4,4-difluorocyclohexyl)methyl)-4-(1,1-difluoroethyl)-1,2,5-oxadiazole-3-carboxamide

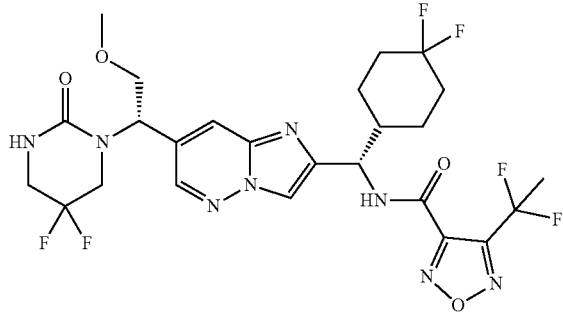 [SMILES: COC[C@H](c1cnn2cc([C@@H](NC(=O)c3nonc3C(C)(F)F)C3CCC(F)(F)CC3)nc2c1)N1CC(F)(F)CNC1=O]

To a solution of 1-((S)-1-(2-((S)-amino(4,4-difluorocyclohexyl)methyl)imidazo[1,2-b]pyridazin-7-yl)-2-methoxyethyl)-5,5-difluorotetrahydropyrimidin-2(1H)-one (119 mg, 0.240 mmol, Intermediate 3) and ethyl 4-(1,1-difluoroethyl)-1,2,5-oxadiazole-3-carboxylate (124 mg, 0.600 mmol) in ACN (0.48 mL) was added TEA (0.037 mL, 0.26 mmol). The mixture was transferred to a sealed pressure tube and heated at 90° C. for 15 h. The reaction mixture was cooled to rt, diluted with DMF, filtered, and purified by preparative HPLC (XBridge Prep C18, 5 μm, 50×150 mm; 10-100% MeCN/water (20 mM NH$_4$OH)) to afford the title compound as a white solid (8% yield). $^1$H NMR (500 MHz, DMSO-d$_6$) δ 9.69 (d, J=9.0 Hz, 1H), 8.39 (d, J=2.1 Hz, 1H), 8.19 (s, 1H), 8.03-7.77 (m, 1H), 6.95 (s, 1H), 5.68-5.48 (m, 1H), 5.34-5.17 (m, 1H), 3.98-3.85 (m, 2H), 3.76-3.62 (m, 1H), 3.61-3.44 (m, 4H), 3.34 (s, 3H), 2.16 (t, J=19.5 Hz, 3H), 2.08-1.96 (m, 2H), 1.90-1.70 (m, 3H), 1.66-1.57 (m, 1H), 1.45-1.21 (m, 2H). MS (ESI) m/z: [M+H]$^+$ Found 619.2.

Example 128: N—((S)-(7-((S)-1-(5,5-Difluoro-2-oxotetrahydropyrimidin-1(2H)-yl)-2-methoxyethyl) imidazo[1,2-b]pyridazin-2-yl)(4,4-difluorocyclohexyl)methyl)-4-((R*)-2,2-difluorocyclopropyl)-1,2,5-oxadiazole-3-carboxamide

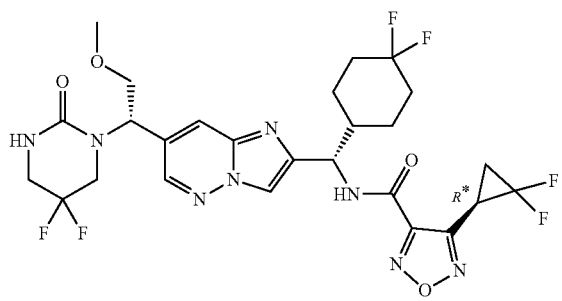 [SMILES: COC[C@H](c1cnn2cc([C@@H](NC(=O)c3nonc3[C@H]3CC3(F)F)C3CCC(F)(F)CC3)nc2c1)N1CC(F)(F)CNC1=O]

Example 129: N—((S)-(7-((S)-1-(5,5-Difluoro-2-oxotetrahydropyrimidin-1(2H)-yl)-2-methoxyethyl) imidazo[1,2-b]pyridazin-2-yl)(4,4-difluorocyclohexyl)methyl)-4-((S*)-2,2-difluorocyclopropyl)-1,2,5-oxadiazole-3-carboxamide

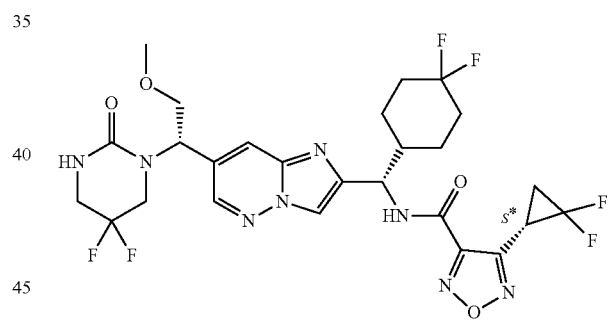

The title compounds were prepared as described for the synthesis of Example 127 using ethyl 4-(2,2-difluorocyclopropyl)-1,2,5-oxadiazole-3-carboxylate in place of ethyl 4-(1,1-difluoroethyl)-1,2,5-oxadiazole-3-carboxylate. The resulting mixture was separated by chiral SFC (Whelk O1 SS 5 μm, 250×21 mm, Mobile phase: 20% methanol, 80% CO$_2$) to afford two diastereomers. The first eluting isomer was designated as the (R*) isomer (Example 128) and the second eluting isomer was designated as the (S*) isomer (Example 129). The first eluting isomer, N—((S)-(7-((S)-1-(5,5-difluoro-2-oxotetrahydropyrimidin-1(2H)-yl)-2-methoxyethyl)imidazo[1,2-b]pyridazin-2-yl)(4,4-difluorocyclohexyl)methyl)-4-((R*)-2,2-difluorocyclopropyl)-1,2,5-oxadiazole-3-carboxamide, was isolated as a white solid (Example 128, 2.3% yield). The second eluting isomer, N—((S)-(7-((S)-1-(5,5-difluoro-2-oxotetrahydropyrimidin-1(2H)-yl)-2-methoxyethyl)imidazo[1,2b]pyridazin-2-yl)(4,4-difluorocyclohexyl)methyl)-4-((S*)-2,2-difluorocyclopropyl)-1,2,5-oxadiazole-3-carboxamide, was isolated as a white solid (Example 129, 2.0% yield). Example 128: $^1$H NMR (500 MHz, DMSO-d$_6$) δ 9.56 (d, J=8.9 Hz, 1H), 8.39 (d, J=2.1 Hz, 1H), 8.26 (s, 1H), 7.99-7.82 (m, 1H), 6.96 (s, 1H), 5.58 (t, J=6.8 Hz, 1H), 5.19 (t, J=8.6 Hz, 1H), 3.98-3.85 (m, 2H), 3.79-3.62 (m, 1H), 3.62-3.47 (m, 3H), 3.35 (s, 3H), 2.36-2.27 (m, 1H), 2.26-2.10 (m, 2H), 2.10-1.88 (m, 3H), 1.87-1.70 (m, 2H), 1.69-1.58 (m, 1H), 1.47-1.34 (m, 1H), 1.34-1.20 (m, 2H). MS (ESI) m/z: [M+H]$^+$ Found 631.2. Example 129: $^1$H NMR (500 MHz, DMSO-d$_6$) δ 9.58 (d, J=9.0 Hz, 1H), 8.38 (d, J=2.1 Hz, 1H), 8.26 (s, 1H), 7.93 (s, 1H), 6.96 (s, 1H), 5.58 (t, J=6.8 Hz, 1H), 5.19 (t, J=8.6 Hz, 1H), 3.97-3.86 (m, 2H), 3.77-3.63 (m, 1H), 3.60-3.48 (m, 3H), 3.34 (s, 3H), 2.35-2.26 (m, 1H), 2.26-2.17 (m, 1H), 2.17-2.10 (m, 1H), 2.09-1.95 (m, 2H), 1.95-1.88 (m, 1H), 1.87-1.69 (m, 2H), 1.68-1.58 (m, 1H), 1.46-1.35 (m, 1H), 1.33-1.22 (m, 2H). MS (ESI) m/z: [M+H]$^+$ Found 631.2.

Example 130: N—((S)-(7-((S)-1-(5,5-Difluoro-2-oxotetrahydropyrimidin-1(2H)-yl)-2-methoxyethyl)imidazo[1,2-b]pyridazin-2-yl)(4,4-difluorocyclohexyl)methyl)-4-(2,2,2-trifluoroethyl)-1,2,5-oxadiazole-3-carboxamide

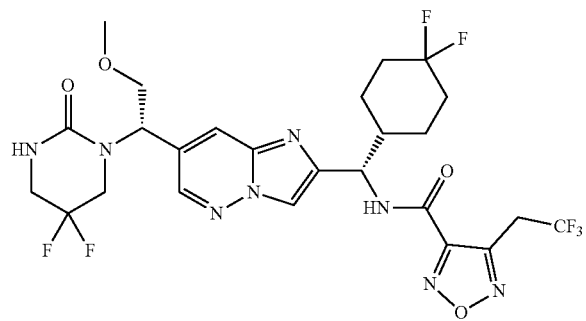 [SMILES: COC[C@H](c1cnn2cc([C@@H](NC(=O)c3nonc3CC(F)(F)F)C3CCC(F)(F)CC3)nc2c1)N1CC(F)(F)CNC1=O]

The title compound (58% yield) was synthesized in a manner analogous to Example 18 using 1-((S)-1-(2-((S)-amino(4,4-difluorocyclohexyl)methyl)imidazo[1,2-b]pyridazin-7-yl)-2-methoxyethyl)-5,5-difluorotetrahydropyrimidin-2(1H)-one (Intermediate 3 Step F) in place of (S)-1-((2-(amino(4,4-difluorocyclohexyl)methyl)imidazo[1,2-b]pyridazin-7-yl)methyl)tetrahydropyrimidin-2(1H)-one and 4-(2,2,2-trifluoroethyl)-1,2,5-oxadiazole-3-carboxylic acid (Intermediate 102) in place of 4-cyclopropyl-1,2,5-oxadiazole-3-carboxylic acid. $^1$H NMR (500 MHz, DMSO-d$_6$) δ 9.63 (d, J=9.0 Hz, 1H), 8.38 (d, J=2.1 Hz, 1H), 8.23 (s, 1H), 8.05-7.79 (m, 1H), 6.95 (s, 1H), 5.70-5.46 (m, 1H), 5.20-5.04 (m, 1H), 4.24 (q, J=10.8 Hz, 2H), 4.04-3.82 (m, 2H), 3.77-3.63 (m, 1H), 3.63-3.43 (m, 3H), 3.34 (s, 3H), 2.28-2.16 (m, 1H), 2.07-1.87 (m, 3H), 1.86-1.68 (m, 2H), 1.63-1.56 (m, 1H), 1.45-1.17 (m, 2H). MS (ESI) m/z: [M+H]$^+$ Found 637.2.

Example 131: N—((S)-1-(7-((S)-2-Cyclopropoxy-1-(5,5-difluoro-2-oxotetrahydropyrimidin-1(2H)-yl-4,4,6,6-d$_4$)ethyl)imidazo[1,2-b]pyridazin-2-yl)-5,5,5-trifluoro-4,4-dimethylpentyl)-1,2,5-oxadiazole-3-carboxamide trifluoroacetate

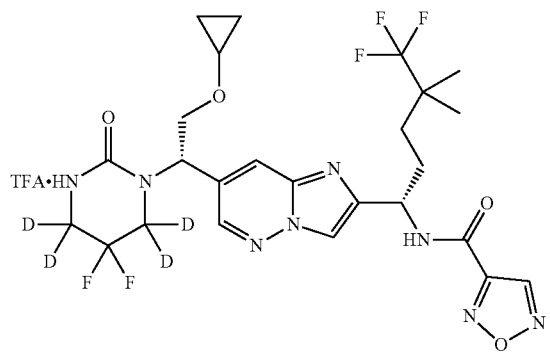

The title compound (24% yield) was synthesized in a manner analogous to Example 18 using 1-((S)-1-(2-((S)-1-amino-5,5,5-trifluoro-4,4-dimethylpentyl)imidazo[1,2-b]pyridazin-7-yl)-2-cyclopropoxyethyl)-5,5-difluorotetrahydropyrimidin-2(1H)-one-4,4,6,6-d$_4$ (Intermediate 74) in place of (S)-1-((2-(amino(4,4-difluorocyclohexyl)methyl)imidazo[1,2-b]pyridazin-7-yl)methyl)tetrahydropyrimidin-2(1H)-one and 1,2,5-oxadiazole-3-carboxylic acid in place of 4-cyclopropyl-1,2,5-oxadiazole-3-carboxylic acid. The material was further purified by preparative acidic HPLC to provide the title compound as a white solid. $^1$H NMR (500 MHz, DMSO-d$_6$) δ 9.62 (d, J=8.4 Hz, 1H), 9.37-9.29 (m, 1H), 8.46-8.38 (m, 1H), 8.32-8.24 (m, 1H), 7.97 (d, J=0.9 Hz, 1H), 6.94 (s, 1H), 5.56 (t, J=6.8 Hz, 1H), 5.27-5.18 (m, 1H), 4.04-3.95 (m, 2H), 3.46-3.36 (m, 1H), 2.21-2.07 (m, 1H), 2.07-1.92 (m, 1H), 1.69-1.61 (m, 1H), 1.59-1.47 (m, 1H), 1.09 (s, 6H), 0.62-0.37 (m, 4H). MS (ESI) m/z: [M+H]$^+$ Found 605.3.

Example 132: N-((1S*)-((1R,5S)-Bicyclo[3.2.0]heptan-3-yl)(7-((S)-1-(5,5-difluoro-2-oxotetrahydropyrimidin-1(2H)-yl)-2-methoxyethyl)imidazo[1,2-b]pyridazin-2-yl)methyl)-4-methyl-1,2,5-oxadiazole-3-carboxamide

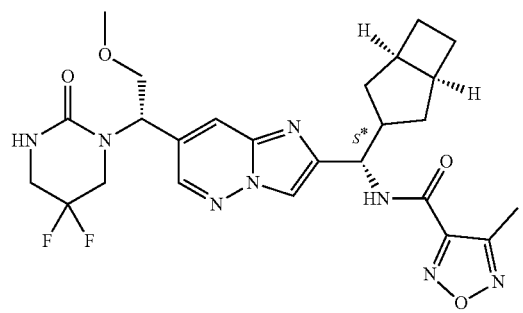 [SMILES: COC[C@H](c1cnn2cc([C@@H](NC(=O)c3nonc3C)C3C[C@H]4CC[C@H]4C3)nc2c1)N1CC(F)(F)CNC1=O]

Step A: 1,3-Dioxoisoindolin-2-yl (1R,5S)-bicyclo[3.2.0]heptane-3-carboxylate. The title compound was synthesized in a manner analogous to Intermediate 55 Step B using bicyclo[3.2.0]heptane-3-carboxylic acid in place of 2-cyclopropoxypropanoic acid. The material was purified by silica gel chromatography (0-60% EtOAc/hexanes) to provide the title compound in 46% yield.

Step B: (S)—N-((1S*)-((1R,5S)-Bicyclo[3.2.0]heptan-3-yl)(7-((S)-1-(5,5-difluoro-2-oxotetrahydropyrimidin-1(2H)-yl)-2-methoxyethyl)imidazo[1,2-b]pyridazin-2-yl)methyl)-2,4,6-trimethylbenzenesulfinamide. The title compound was synthesized in a manner analogous to Intermediate 57 Step A using 1,3-dioxoisoindolin-2-yl (1R,5S)-bicyclo[3.2.0]heptane-3-carboxylate (Step A) in place of 1,3-dioxoisoindolin-2-yl 2-cyclopropoxypropanoate.

Step C: 1-((1S)-1-(2-((1S*)-Amino((1R,5S)-bicyclo[3.2.0]heptan-3-yl)methyl)imidazo[1,2-b]pyridazin-7-yl)-2-methoxyethyl)-5,5-difluorotetrahydropyrimidin-2(1H)-one. The title compound was synthesized in a manner analogous to Intermediate 9 using (S)—N-((1S*)-((1R,5S)-bicyclo[3.2.0]heptan-3-yl)(7-((S)-1-(5,5-difluoro-2-oxotetrahydropyrimidin-1(2H)-yl)-2-methoxyethyl)imidazo[1,2-b]pyridazin-2-yl)methyl)-2,4,6-trimethylbenzenesulfinamide (Step B) in place of tert-butyl ((R)-1-(7-((S*)-1-(((R)-tert-butylsulfinyl)amino)-2-methoxyethyl)imidazo[1,2-b]pyridazin-2-yl)-2-((1,1,1-trifluoro-2-methylpropan-2-yl)oxy)ethyl)carbamate.

Step D: N-((1S*)-((1R,5S)-Bicyclo[3.2.0]heptan-3-yl)(7-((S)-1-(5,5-difluoro-2-oxotetrahydropyrimidin-1(2H)-yl)-2-methoxyethyl)imidazo[1,2-b]pyridazin-2-yl)methyl)-4-methyl-1,2,5-oxadiazole-3-carboxamide. The title compound was synthesized in a manner analogous to Example 16 using 1-((1S)-1-(2-((1S*)-amino((1R,5S)-bicyclo[3.2.0]heptan-3-yl)methyl)imidazo[1,2-b]pyridazin-7-yl)-2-methoxyethyl)-5,5-difluorotetrahydropyrimidin-2(1H)-one (Step C) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. The material was purified by preparative HPLC (XBridge BEH C18, 5 μm, 30×150 mm; 35-75% MeCN/water (0.16% of 28% aqueous NH₄OH)) to provide the title compound in 10% yield over Steps B, C and D. ¹H NMR (400 MHz, DMSO-d₆) δ 9.43 (d, J=8.8 Hz, 1H), 8.30 (d, J=2.1 Hz, 1H), 8.16 (s, 1H), 7.91-7.81 (m, 1H), 6.88 (s, 1H), 5.51 (t, J=6.8 Hz, 1H), 5.09 (t, J=8.9 Hz, 1H), 3.92-3.74 (m, 2H), 3.69-3.55 (m, 1H), 3.55-3.38 (m, 3H), 3.27 (s, 3H), 3.14-2.99 (m, 1H), 2.75-2.62 (m, 2H), 2.39 (s, 3H), 2.10-1.97 (m, 2H), 1.73-1.62 (m, 1H), 1.50-1.23 (m, 4H), 1.21-1.08 (m, 1H). MS (ESI) m/z: [M+H]⁺ Found 545.3.

Example 133: N—((S*)-1-(7-((S)-1-(5,5-Difluoro-2-oxotetrahydropyrimidin-1(2H)-yl)-2-methoxyethyl)imidazo[1,2-b]pyridazin-2-yl)-5,5-difluoro-4,4-dimethylhexyl)-4-methyl-1,2,5-oxadiazole-3-carboxamide The title compound was synthesized in a manner analogous to Example 16 using 1-((S)-1-(2-((S)-1-amino-5,5-difluoro-4,4-dimethylhexyl)imidazo[1,2-b]pyridazin-7-yl)-2-methoxyethyl)-5,5-difluorotetrahydropyrimidin-2(1H)-one (Intermediate 103) in place of 1-((S)-1-(2-((S)-amino(4,4-difluorocyclohexyl)methyl)imidazo[1,2-b]pyridazin-7-yl)-2-cyclopropoxyethyl)-5,5-difluorotetrahydropyrimidin-2(1H)-one hydrochloride. Purification was performed via SFC (Stationary phase: Chiralpak IC 5 μm, 250×30 mm, Mobile phase: 25% methanol, 75% CO₂) to afford the title compound in 8% yield. ¹H NMR (500 MHz, DMSO-d₆) δ 9.47 (d, J=8.6 Hz, 1H), 8.36 (d, J=2.2 Hz, 1H), 8.17 (s, 1H), 7.95-7.91 (m, 1H), 6.95 (s, 1H), 5.58 (t, J=6.8 Hz, 1H), 5.22-5.14 (m, 1H), 3.94-3.85 (m, 2H), 3.68 (m, 1H), 3.52 (m, 3H), 3.34 (s, 3H), 2.49 (s, 3H), 2.08 (m, 1H), 2.01-1.88 (m, 1H), 1.54 (t, J=19.7 Hz, 4H), 1.42 (td, J=13.0, 4.4 Hz, 1H), 0.97 (s, 6H). MS (ESI) m/z: [M+H]⁺ Found 585.3.

In Vitro Biological Data

IL-17A(FLAG-Tagged): IL-17RA(His-Tagged) Binding Disruption Eu-HTRF Assay

An antibody directed against the FLAG tag of IL-17A (SEQ ID NO: 1) is labeled with the HTRF donor chromophore (Europium-cryptate). IL-17A is present as a dimer that is "locked into" this quaternary structure due to the formation of loop-spanning intramolecular disulfide bridges. The construct of IL-17RA used in the assay excludes the outer-membrane portion of the receptor and is fused to a C-terminal 10×His tag (SEQ ID NO:2). An antibody directed against the His tag of the IL-17RA chimera is labeled with the HTRF acceptor chromophore ("D2"). The fluorescence-resonance energy transfer (FRET) depends on the vicinity of the donor chromophore to the acceptor, and interruption of the binding between the IL-17A and IL-17RA causes the reduction/loss of FRET. Therefore, this assay allows to evaluate the compound effect on the binding IL-17A and IL-17RA by monitoring the fluorescence intensity of donor vs acceptor. The assay was run using either Protocol 1 or Protocol 2 as described below.

Protocol 1. 40 nl of 2-fold serial diluted compound solution for total 22 dilution points is added into each well of a 1536-well, white, low-volume, non-binding plate (Greiner #782904), then 2 μl of FLAG tagged IL-17A at 2×final concentration (2.5 nM) in solution of PBS+0.01% Triton-X100 is added to each well. The assay plate is briefly centrifuged then incubated for 1 h at rt. A mixed solution is prepared containing 2×5 nM 10HIS×IL-17RA, 2×2.5 nM Eu-anti-FLAG (CISBIO), 2×5 nM D2-anti-HIS (CISBIO) in PBS+0.01% Triton-X100+200 mM Potassium Fluoride (Sigma 60238) and 2 μl of mix is added to each well of the assay plate. The plate is briefly centrifuged then incubated for 2 h at rt. The HTRF intensities at the wavelength of donor (620 nm) and acceptor (665 nm) are measured using BMG Pherastar. The ratio between intensities at two wavelengths is calculated and plotted against the compound concentration and the data is fitted to a one-site competition model to yield IC₅₀ of the compound.

Protocol 2. 40 nl of 2-fold serial diluted compound solution for total 22 dilution points is added into each well of a 1536-well, white, low-volume, non-binding plate (Greiner #782904), then 2 μl of FLAG tagged IL-17A at 2×final concentration (1 nM) in solution of PBS+0.01% Triton-X100 is added to each well. The assay plate is briefly centrifuged then incubated for 1 h at rt. A mixed solution is prepared containing 2×5 nM 10HIS×IL-17RA, 2×2.5 nM Eu-anti-FLAG (CISBIO), 2×5 nM D2-anti-HIS (CISBIO) in PBS+0.01% Triton-X100+200 mM Potassium Fluoride (Sigma 60238) and 2 μl of mix is added to each well of the

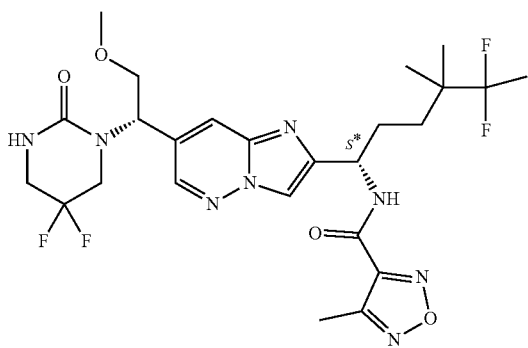 [SMILES: COC[C@H](c1cnn2cc([C@H](CCC(C)(C)C(C)(F)F)NC(=O)c3nonc3C)nc2c1)N1CC(F)(F)CNC1=O]

assay plate. The plate is briefly centrifuged then incubated for 2 h at rt. The HTRF intensities at the wavelength of donor (615 nm) and acceptor (665 nm) are measured using BMG Pherastar. The ratio between intensities at two wavelengths is calculated and plotted against the compound concentration and the data is fitted to a one-site competition model to yield $IC_{50}$ of the compound.

IL-17A acts directly on keratinocytes through binding to dimeric receptor IL-17RA/RC and drives the production of a number of inflammatory mediators known to be elevated in psoriasis lesional tissue. IL-17A small molecule inhibitors that block the IL-17A to interact with IL-17R would inhibit the IL-17A signaling in its targeted cells such as keratinocytes. The compound functional activity is evaluated for its impact on IL-17A-induced G-CSF production in human normal keratinocyte (NHK).

NHK Assay

Adult normal human keratinocytes are cultured in keratinocyte growth medium (Lonza) in a flask till reaching ~90% confluence, then cells are transferred to a 384-well plate at density of 3000-4000 cell/well. Recombinant human IL-17A (Gibco PHC9174) is pre-incubated with titrated compound or DMSO for 1 h at rt then added to the cell culture plate. The final concentration of IL-17A is 5 ng/mL and DMSO is 0.2%, in the culture containing 5% FBS. Cells are cultured/treated for 24 h at 37° C. Supernatants are collected and G-CSF production is measured through HTRF technology using Human G-CSF Kit (CisBio). G-CSF concentration was extrapolated from the standard curve and $IC_{50}$ is determined using GraphPad Prism. Cell viability is also evaluated using CellTiter-Glo kit (Promega) and effect of compound on cell viability is compared to DMSO control.

In cases where the compound was tested more than once, the $IC_{50}$ value shown is a simple average of the measured values.

A: $IC_{50} < 0.05$ μM; B: $0.05$ μM $\leq IC_{50} \leq 0.1$ μM; C: $IC_{50} > 0.1$ μM
—Not available

TABLE 3

| Example | HTRF IC$_{50}$ Protocol 1 | HTRF IC$_{50}$ Protocol 2 | NHK IC$_{50}$ |
|---|---|---|---|
| 1 | A | — | C |
| 2 | B | — | C |
| 3 | A | — | A |
| 4 | B | — | C |
| 5 | A | — | B |
| 6 | C | — | C |
| 7 | A | — | A |
| 8 | A | — | B |
| 9 | A | — | A |
| 10 | B | — | A |
| 11 | A | A | A |
| 12 | A | — | A |
| 13 | B | — | A |
| 14 | B | — | A |
| 15 | A | — | A |
| 16 | A | A | A |
| 17 | A | — | A |
| 18 | C | — | C |
| 19 | C | — | C |
| 20 | A | — | A |
| 21 | C | — | A |
| 22 | B | — | B |
| 23 | C | — | C |
| 24 | C | — | C |
| 25 | B | — | A |
| 26 | A | — | A |
| 27 | C | — | C |
| 28 | A | — | C |
| 29 | C | — | C |
| 30 | B | — | C |
| 31 | C | — | C |
| 32 | C | — | C |
| 33 | B | — | C |
| 34 | C | — | C |
| 35 | — | — | A |
| 36 | — | — | A |
| 37 | — | — | A |
| 38 | — | — | A |
| 39 | — | — | A |
| 40 | — | A | A |
| 41 | — | — | A |
| 42 | — | — | A |
| 43 | — | — | A |
| 44 | — | — | A |
| 45 | — | A | A |
| 46 | — | — | A |
| 47 | — | — | C |
| 48 | — | — | C |
| 49 | — | — | C |
| 50 | — | — | A |
| 51 | — | — | A |
| 52 | — | — | A |
| 53 | — | — | A |
| 54 | — | A | B |
| 55 | — | C | C |
| 56 | — | A | A |
| 57 | — | — | A |
| 58 | — | — | A |
| 59 | — | A | A |
| 60 | — | — | A |
| 61 | — | C | C |
| 62 | — | — | B |
| 63 | — | — | A |
| 64 | — | — | A |
| 65 | — | — | A |
| 66 | — | — | B |
| 67 | — | — | C |
| 68 | — | A | A |
| 69 | — | A | A |
| 70 | — | A | A |
| 71 | — | A | A |
| 72 | — | A | A |
| 73 | — | A | A |
| 74 | — | A | A |
| 75 | — | A | A |
| 76 | — | A | A |
| 77 | — | A | A |
| 78 | — | A | A |
| 79 | — | A | A |
| 80 | — | A | A |
| 81 | — | A | A |
| 82 | — | A | A |
| 83 | — | A | A |
| 84 | — | A | A |
| 85 | A | — | C |
| 86 | A | A | A |
| 87 | — | — | A |
| 88 | — | — | A |
| 89 | — | A | A |
| 90 | — | A | A |
| 91 | — | B | C |
| 92 | C | — | C |
| 93 | C | — | C |
| 94 | C | — | C |
| 95 | C | — | C |
| 96 | A | — | C |
| 97 | B | — | C |
| 98 | — | — | C |
| 99 | C | — | A |
| 100 | C | — | C |
| 101 | A | — | A |
| 102 | — | A | A |
| 103 | — | A | A |

TABLE 3-continued

| Example | HTRF IC$_{50}$ Protocol 1 | HTRF IC$_{50}$ Protocol 2 | NHK IC$_{50}$ |
|---|---|---|---|
| 104 | — | A | A |
| 105 | — | C | C |
| 106 | — | A | A |
| 107 | — | A | A |
| 108 | — | A | A |
| 109 | — | A | A |
| 110 | — | A | A |
| 111 | — | A | A |
| 112 | — | A | B |
| 113 | — | A | A |
| 114 | — | A | A |
| 115 | — | A | B |
| 116 | — | B | C |
| 117 | — | A | A |
| 118 | — | A | C |
| 119 | — | A | A |
| 120 | — | C | C |
| 121 | — | A | A |
| 122 | — | A | A |
| 123 | — | A | B |
| 124 | — | A | B |
| 125 | — | C | C |
| 126 | — | A | A |
| 127 | — | A | A |
| 128 | — | A | A |
| 129 | — | A | A |
| 130 | — | A | A |
| 131 | — | A | C |
| 132 | — | A | A |
| 133 | — | A | A |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

```
Name: IL-17A-Flag
                                            SEQ ID NO: 1
MATGSRTSLLLAFGLLCLPWLQEGSAGSDYKDDDDKGSGSGSLEVLFQGP

GITIPRNPGCPNSEDKNFPRTVMVNLNIHNRNTNTNPKRSSDYYNRSTSP

WNLHRNEDPERYPSVIWEAQCRHLGCINADGNVDYHMNSVPIQQEILVLR

REPPHCPNSFRLEKILVSVGCTCVTPIVHHVQ

Name: IL-17RA
                                            SEQ ID NO: 2
MKFLVNVALVFMVVYISYIYALRLLDHRALVCSQPGLNCTVKNSTCLDDS

WIHPRNLTPSSPKDLQIQLHFAHTQQGDLFPVAHIEWTLQTDASILYLEG

AELSVLQLNTNERLCVRFEFLSKLRHHHHRRWRFTFSHFVVDPDQEYEVTV

HHLPKPIPDGDPNHQSKNFLVPDCEHARMKVTTPCMSSGSLWDPNITVET

LEAHQLRVSFTLWNESTHYQILLTSFPHMENHSCFEHMHHIPAPRPEEFH

QRSNVTLTLRNLKGCCRHQVQIQPFFSSCLNDCLRHSATVSCPEMPDTPE

PIPDYMPLWGSGGHHHHHHHHHH*
```

---

We claim:
1. A compound or a pharmaceutically acceptable salt thereof, having a formula selected from the group consisting of:
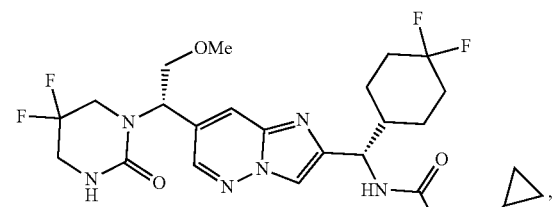,
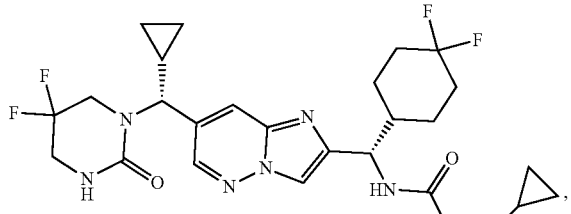,
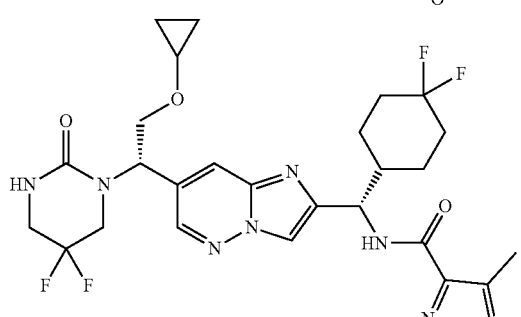,
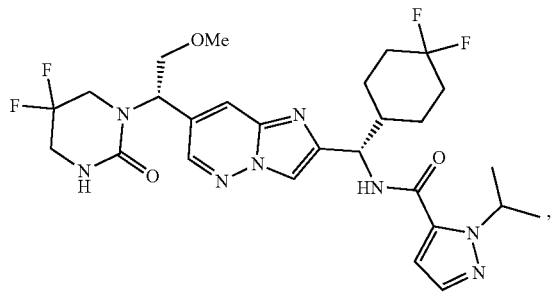,
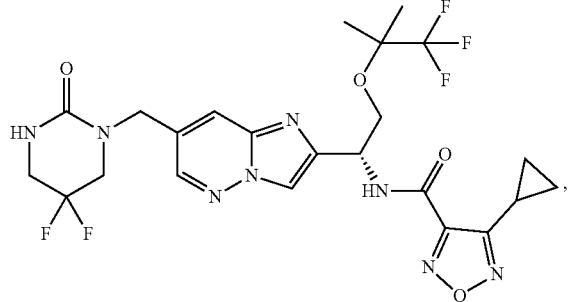,
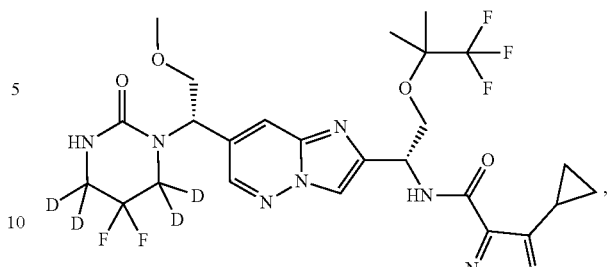,
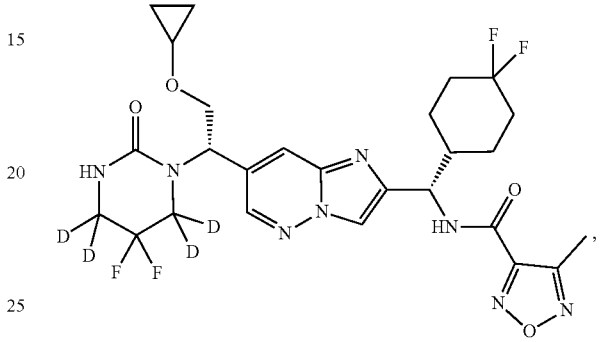,
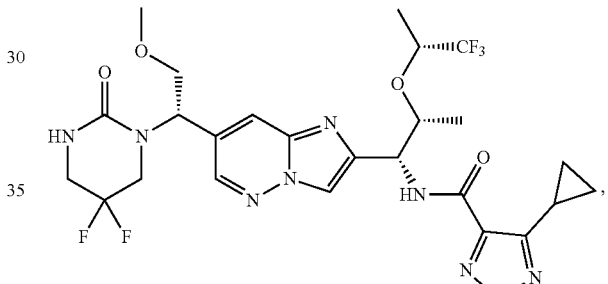,
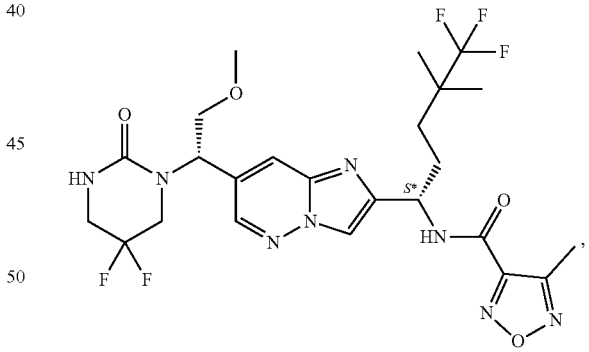,
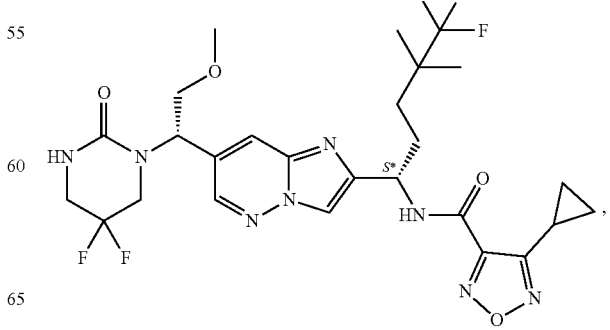,

323
-continued
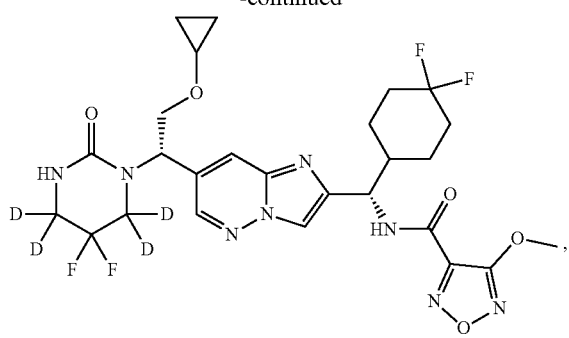
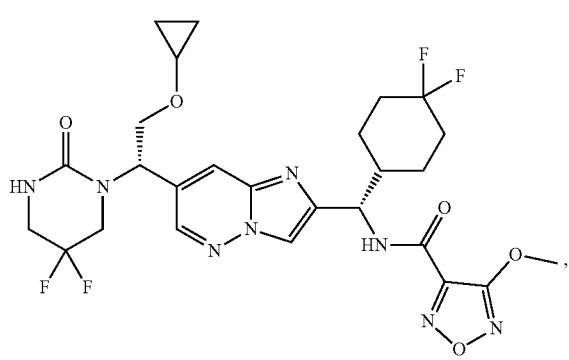
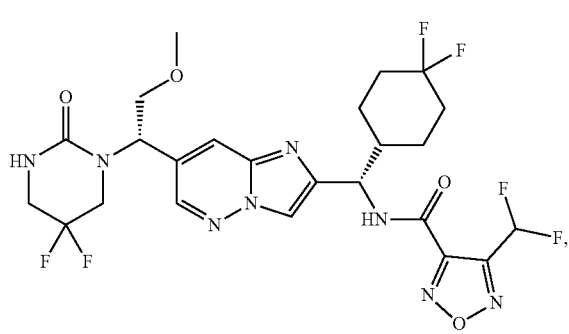
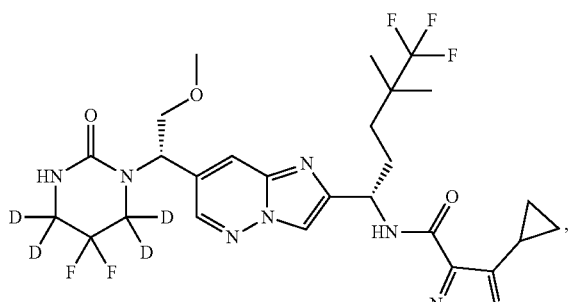
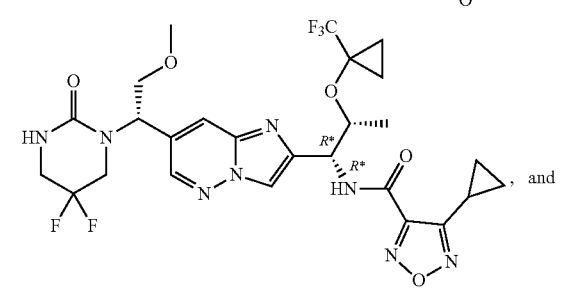, and
324
-continued
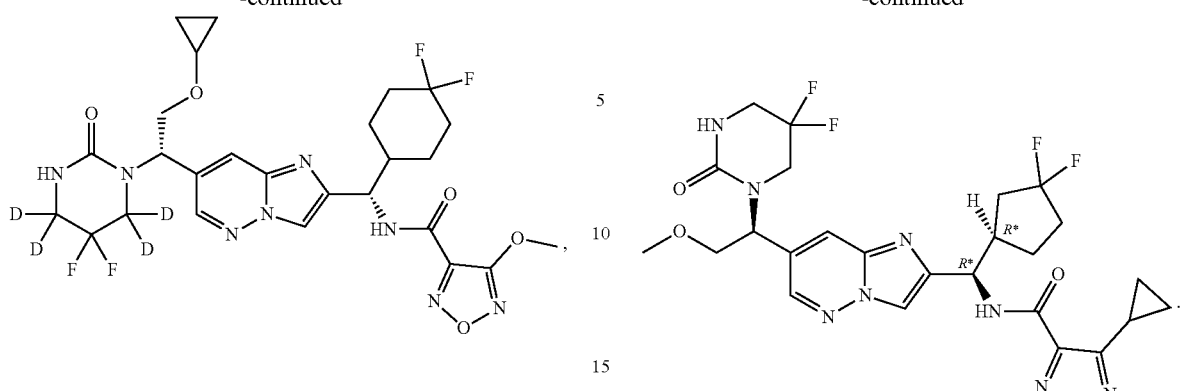
2. The compound of claim 1, or a pharmaceutically acceptable salt thereof, having the following formula:
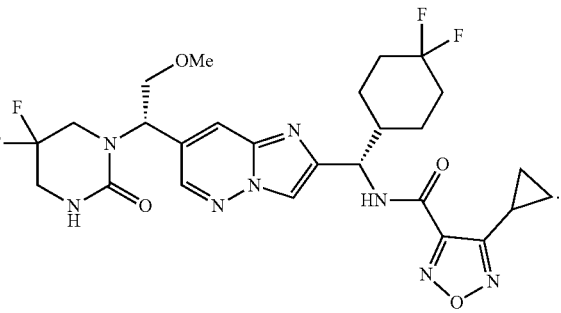
3. The compound of claim 1, or a pharmaceutically acceptable salt thereof, having the following formula:
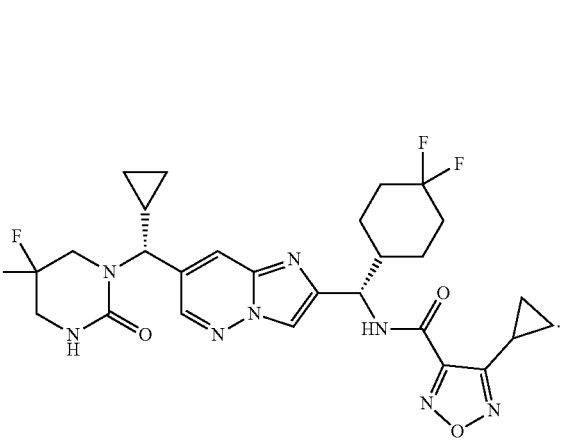

4. The compound of claim 1, or a pharmaceutically acceptable salt thereof, having the following formula:

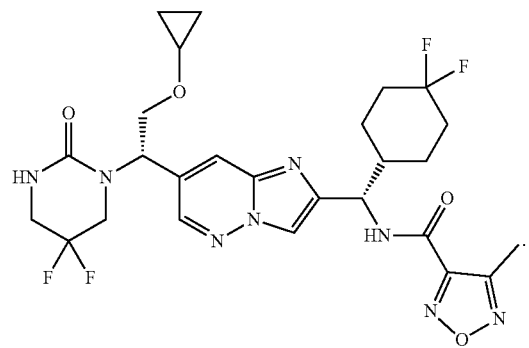 [SMILES: Cc1nonc1C(=O)N[C@H](c1cn2ncc([C@@H](COC3CC3)N3CC(F)(F)CNC3=O)cc2n1)C1CCC(F)(F)CC1]

5. The compound of claim 1 or a pharmaceutically acceptable salt thereof, having the following formula:

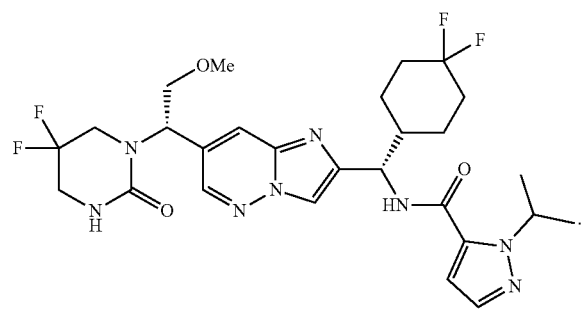 [SMILES: COC[C@H](c1cnn2cc([C@@H](NC(=O)c3ccnn3C(C)C)C3CCC(F)(F)CC3)nc2c1)N1CC(F)(F)CNC1=O]

6. The compound of claim 1 or a pharmaceutically acceptable salt thereof, having the following formula:

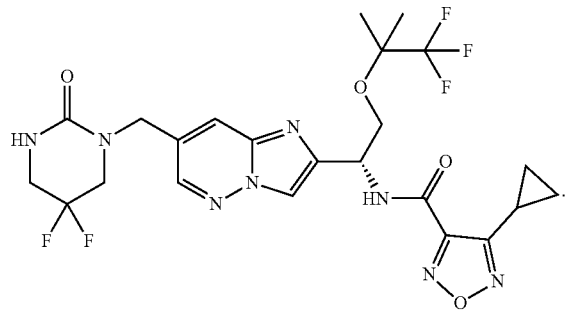 [SMILES: CC(C)(OC[C@H](NC(=O)c1nonc1C1CC1)c1cn2ncc(CN3CC(F)(F)CNC3=O)cc2n1)C(F)(F)F]

7. The compound of claim 1 or a pharmaceutically acceptable salt thereof, having the following formula:

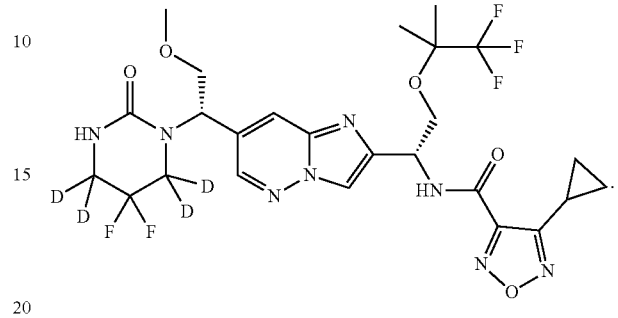

8. The compound of claim 1 or a pharmaceutically acceptable salt thereof, having the following formula:

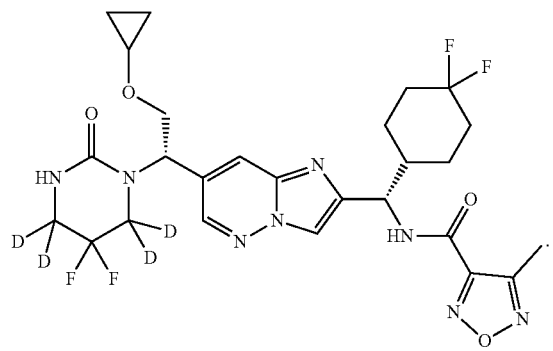 [SMILES: [2H]C1([2H])NC(=O)N([C@H](COC2CC2)c2cnn3cc([C@@H](NC(=O)c4nonc4C)C4CCC(F)(F)CC4)nc3c2)C([2H])([2H])C1(F)F]

9. The compound of claim 1 or a pharmaceutically acceptable salt thereof, having the following formula:

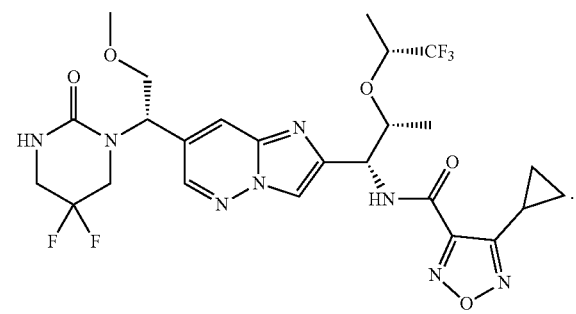 [SMILES: COC[C@H](c1cnn2cc([C@@H](NC(=O)c3nonc3C3CC3)[C@@H](C)O[C@H](C)C(F)(F)F)nc2c1)N1CC(F)(F)CNC1=O]

10. The compound of claim 1 or a pharmaceutically acceptable salt thereof, having the following formula:

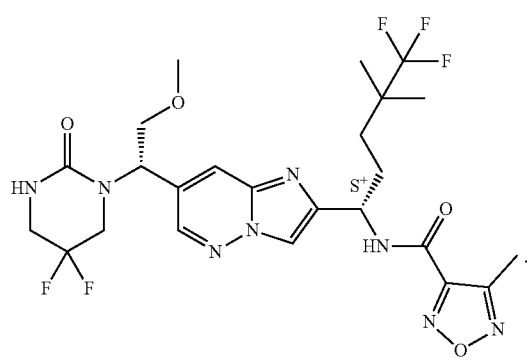

11. The compound of claim 1 or a pharmaceutically acceptable salt thereof, having the following formula:

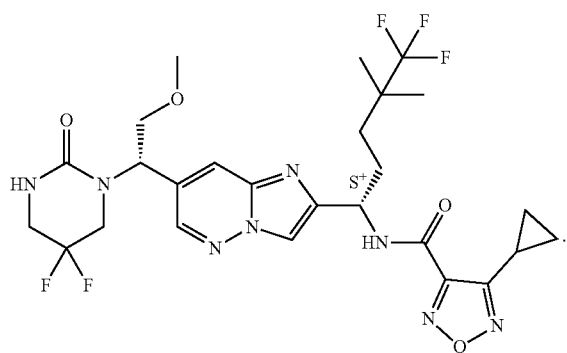

12. The compound of claim 1 or a pharmaceutically acceptable salt thereof, having the following formula:

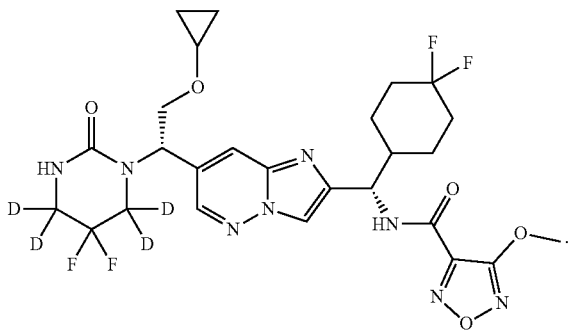 [SMILES: [2H]C1([2H])NC(=O)N([C@H](COC2CC2)c2cnn3cc([C@@H](NC(=O)c4nonc4OC)C4CCC(F)(F)CC4)nc3c2)C([2H])([2H])C1(F)F]

13. The compound of claim 1 or a pharmaceutically acceptable salt thereof, having the following formula:

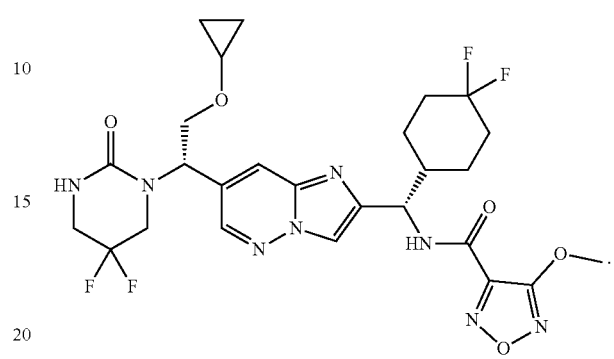

14. The compound of claim 1 or a pharmaceutically acceptable salt thereof, having the following formula:

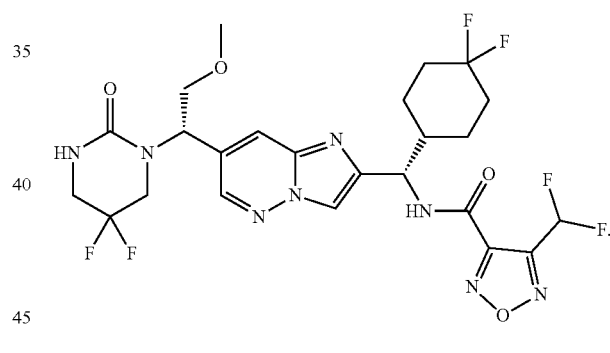

15. The compound of claim 1 or a pharmaceutically acceptable salt thereof, having the following formula:

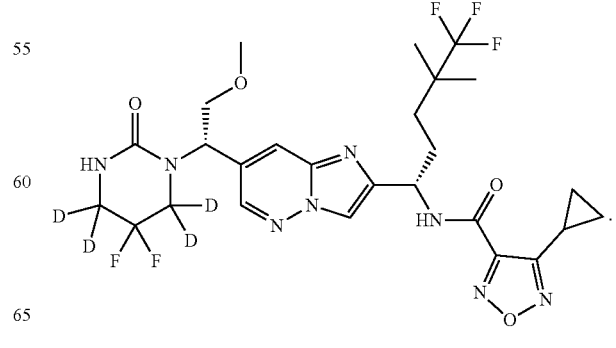

16. The compound of claim 1 or a pharmaceutically acceptable salt thereof, having the following formula:

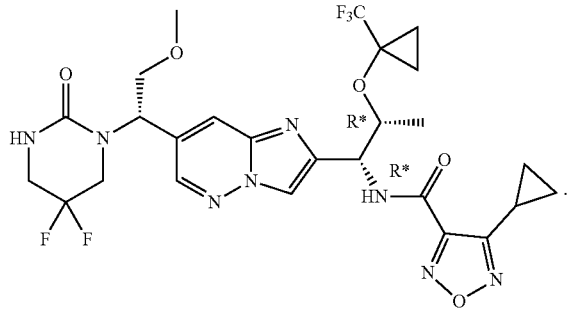 [SMILES: COC[C@H](c1cnn2cc([C@@H](NC(=O)c3nonc3C3CC3)[C@@H](C)OC3(C(F)(F)F)CC3)nc2c1)N1CC(F)(F)CNC1=O]

17. The compound of claim 1 or a pharmaceutically acceptable salt thereof, having the following formula:

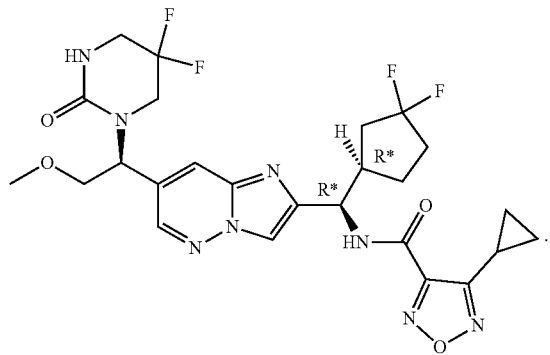 [SMILES: COC[C@H](c1cnn2cc([C@H](NC(=O)c3nonc3C3CC3)[C@@H]3CCC(F)(F)C3)nc2c1)N1CC(F)(F)CNC1=O]

18. A pharmaceutical composition made by combining a compound of claim 1, or a pharmaceutically acceptable salt thereof, and a pharmaceutically acceptable carrier.

19. The pharmaceutical composition of claim 18, or a pharmaceutically acceptable salt thereof, which is administered orally.

20. The pharmaceutical composition of claim 19, or a pharmaceutically acceptable salt thereof, which is administered as a tablet or a capsule.

21. The compound of claim 1 selected from the group consisting of:

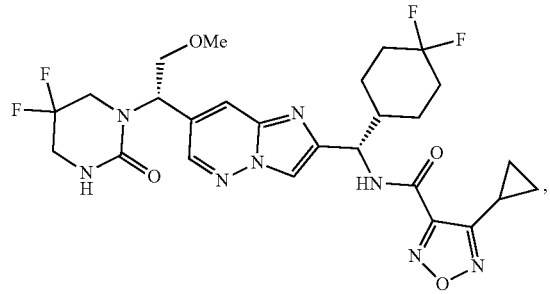

-continued

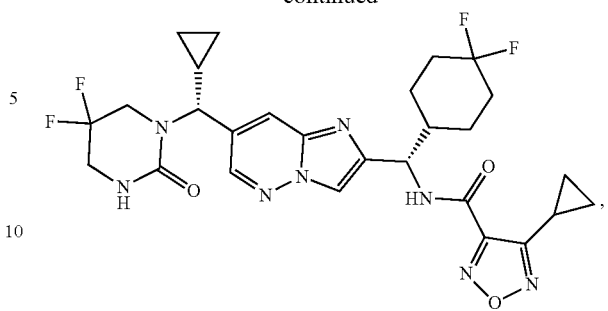

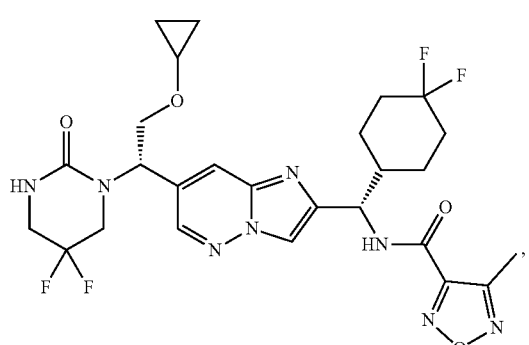

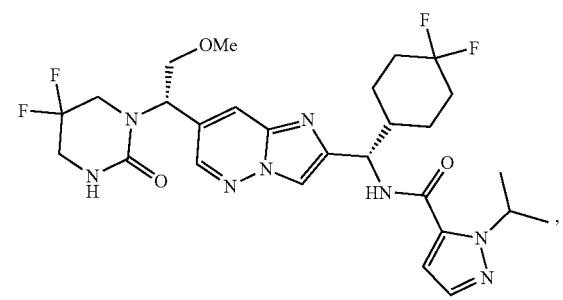

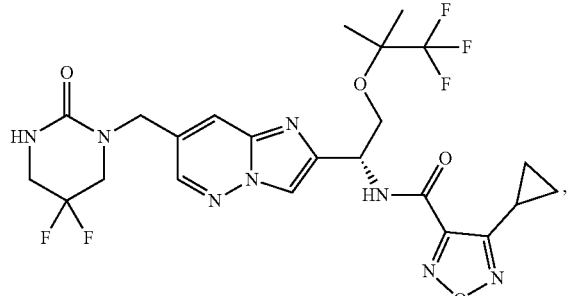

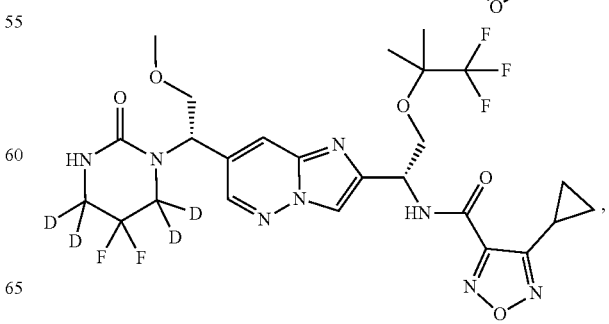

331
-continued
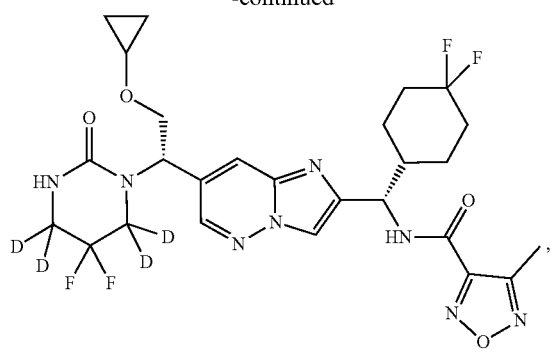
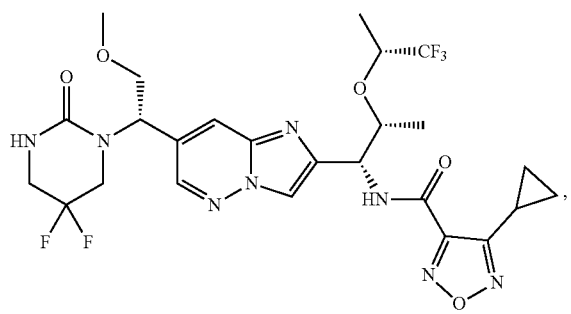
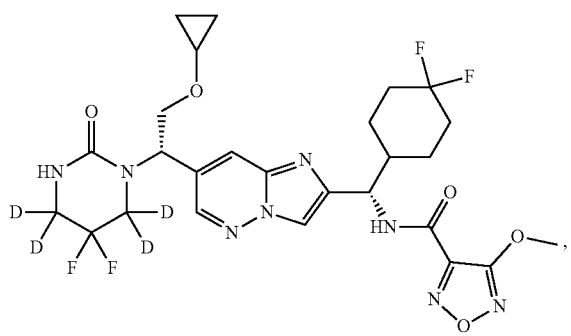
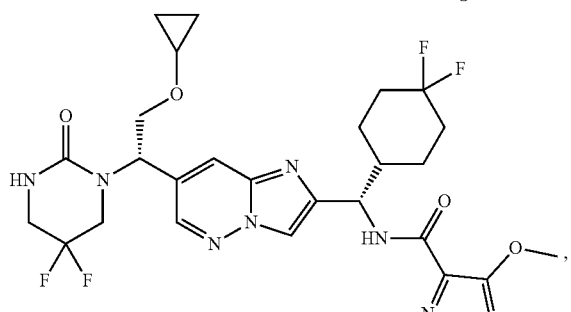
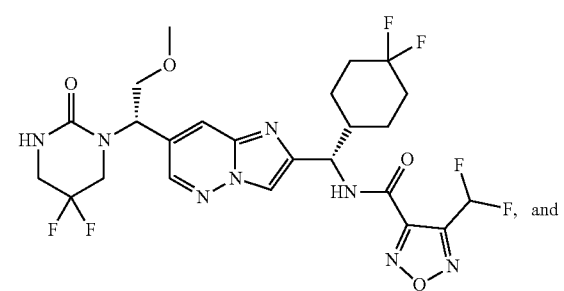, and
332
-continued
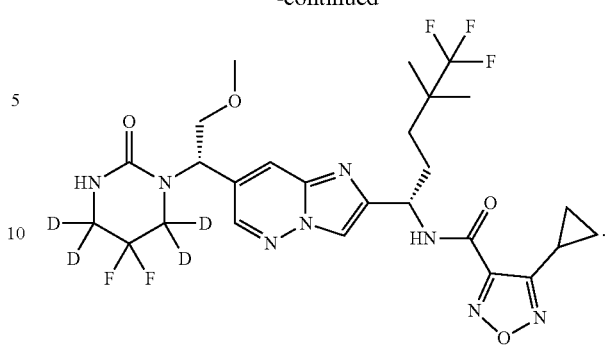
22. The compound of claim 21 having the following formula:
23. The compound of claim 21 having the following formula:
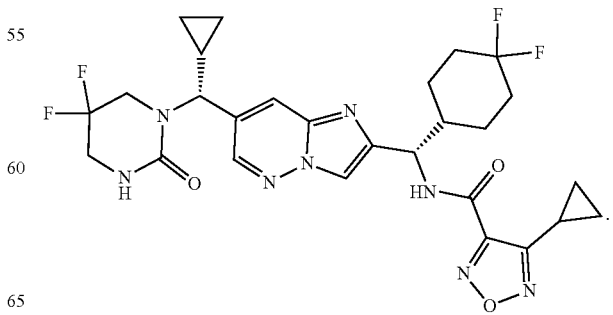

24. The compound of claim 21 having the following formula:
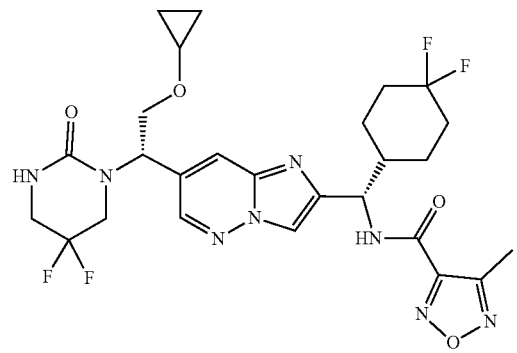 [SMILES: Cc1nonc1C(=O)N[C@H](c1cn2ncc([C@@H](COC3CC3)N3CC(F)(F)CNC3=O)cc2n1)C1CCC(F)(F)CC1]
25. The compound of claim 21 having the following formula:
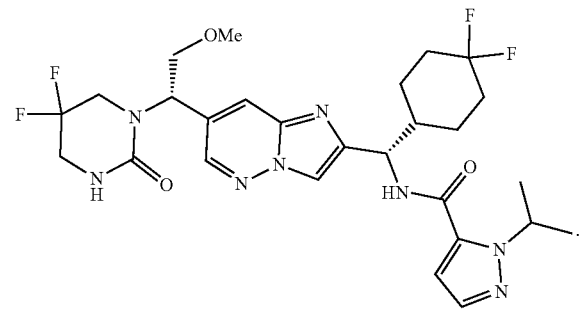 [SMILES: COC[C@H](c1cnn2cc([C@@H](NC(=O)c3ccnn3C(C)C)C3CCC(F)(F)CC3)nc2c1)N1CC(F)(F)CNC1=O]
26. The compound of claim 21 having the following formula:
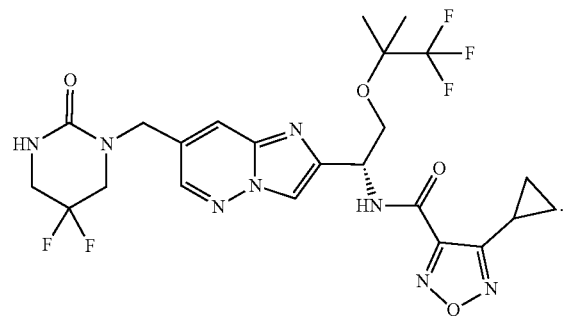 [SMILES: CC(C)(OC[C@H](NC(=O)c1nonc1C1CC1)c1cn2ncc(CN3CC(F)(F)CNC3=O)cc2n1)C(F)(F)F]
27. The compound of claim 21 having the following formula:
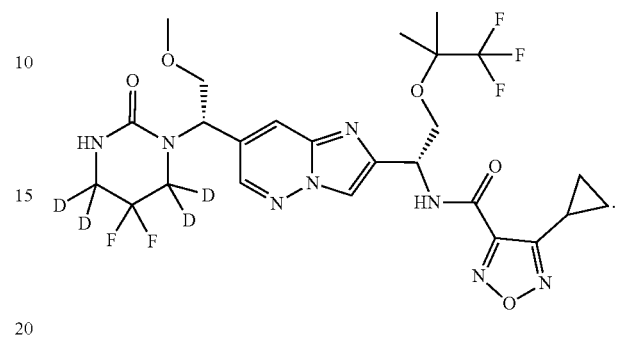
28. The compound of claim 21 having the following formula:
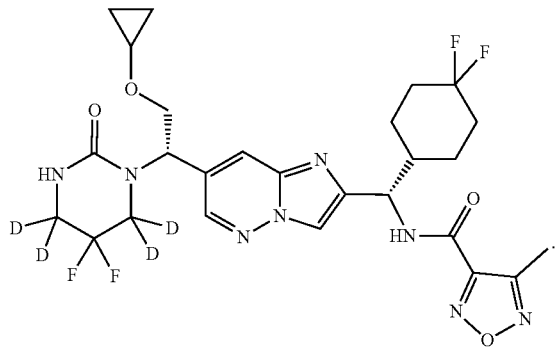 [SMILES: [2H]C1([2H])NC(=O)N([C@H](COC2CC2)c2cnn3cc([C@@H](NC(=O)c4nonc4C)C4CCC(F)(F)CC4)nc3c2)C([2H])([2H])C1(F)F]
29. The compound of claim 21 having the following formula:
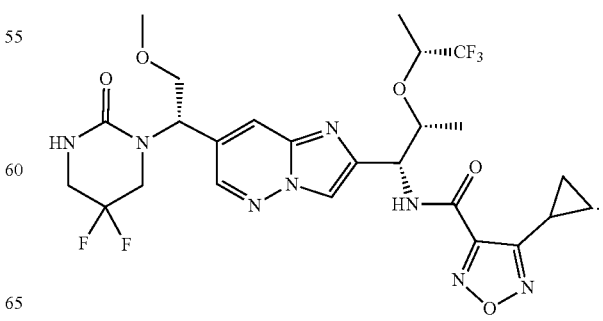

30. The compound of claim 21 having the following formula:
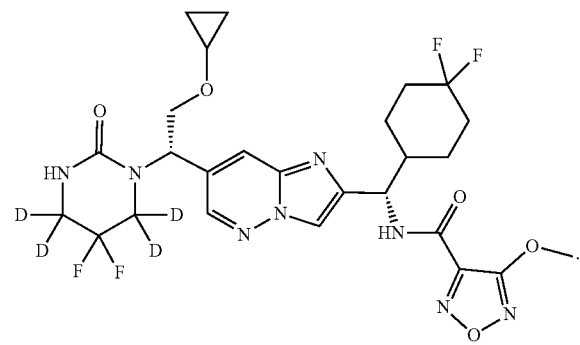 [SMILES: [2H]C1([2H])NC(=O)N([C@H](COC2CC2)c2cnn3cc([C@@H](NC(=O)c4nonc4OC)C4CCC(F)(F)CC4)nc3c2)C([2H])([2H])C1(F)F]
31. The compound of claim 21 having the following formula:
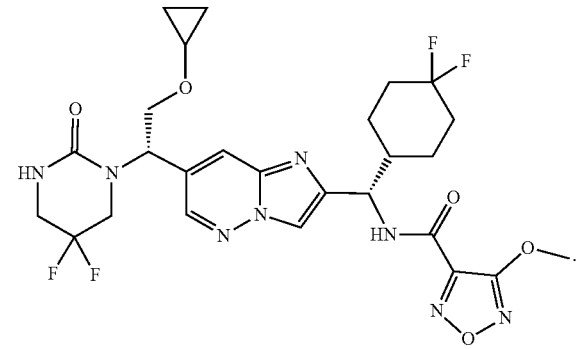 [SMILES: COc1nonc1C(=O)N[C@H](c1cn2ncc([C@@H](COC3CC3)N3CC(F)(F)CNC3=O)cc2n1)C1CCC(F)(F)CC1]
32. The compound of claim 21 having the following formula:
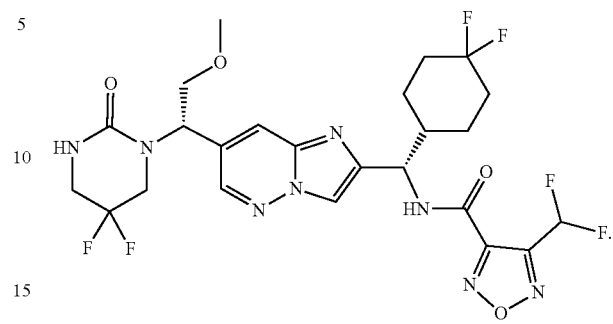
33. The compound of claim 21 having the following formula:
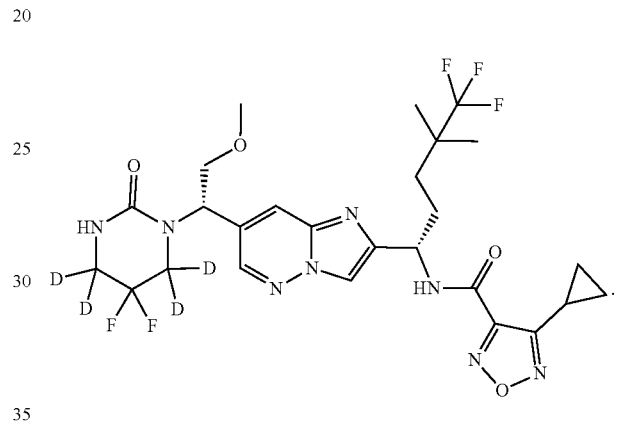
* * * * *

UNITED STATES PATENT AND TRADEMARK OFFICE
CERTIFICATE OF CORRECTION

| | | |
|---|---|---|
| PATENT NO. | : 12,173,007 B2 | Page 1 of 1 |
| APPLICATION NO. | : 17/935360 | |
| DATED | : December 24, 2024 | |
| INVENTOR(S) | : Steven D. Goldberg et al. | |

It is certified that error appears in the above-identified patent and that said Letters Patent is hereby corrected as shown below:

On the Title Page

Under Column 1, item (72), under Inventors: please delete "Dougas" and replace with --Douglas--.

Signed and Sealed this
Twenty-first Day of October, 2025

John A. Squires
*Director of the United States Patent and Trademark Office*